US008835617B2

(12) United States Patent
Luban et al.

(10) Patent No.: US 8,835,617 B2
(45) Date of Patent: Sep. 16, 2014

(54) POLYNUCLEOTIDES ENCODING A HUMAN TRIM-CYP FUSION POLYPEPTIDE, COMPOSITIONS THEREOF, AND METHODS OF USING SAME

(75) Inventors: Jeremy Luban, New York, NY (US); Martha Neagu, Gaithersburg, MD (US)

(73) Assignee: The Trustees of Columbia University in the City of New York, New York, NY (US)

( * ) Notice: Subject to any disclaimer, the term of this patent is extended or adjusted under 35 U.S.C. 154(b) by 429 days.

(21) Appl. No.: 13/128,143

(22) PCT Filed: Nov. 6, 2009

(86) PCT No.: PCT/US2009/063481
§ 371 (c)(1),
(2), (4) Date: Dec. 1, 2011

(87) PCT Pub. No.: WO2010/054141
PCT Pub. Date: May 14, 2010

(65) Prior Publication Data

US 2012/0095444 A1 Apr. 19, 2012

Related U.S. Application Data

(60) Provisional application No. 61/112,013, filed on Nov. 6, 2008, provisional application No. 61/240,505, filed on Sep. 8, 2009.

(51) Int. Cl.

| | |
|---|---|
| ***C07H 21/04*** | (2006.01) |
| ***C07K 19/00*** | (2006.01) |
| ***C12N 15/62*** | (2006.01) |
| ***C12N 15/63*** | (2006.01) |
| ***A61K 48/00*** | (2006.01) |
| ***C07K 14/47*** | (2006.01) |
| ***C12N 9/90*** | (2006.01) |
| *A61K 38/00* | (2006.01) |

(52) U.S. Cl.
CPC ............. *C07K 14/47* (2013.01); *C12N 2830/85* (2013.01); *A61K 48/005* (2013.01); *A01K 2217/15* (2013.01); *A61K 38/00* (2013.01); *C12N 2840/206* (2013.01); *A01K 2227/105* (2013.01); *C12N 9/90* (2013.01); *C07K 2319/00* (2013.01); *A01K 2207/12* (2013.01); *C12N 2740/16043* (2013.01); *C12N 2830/60* (2013.01); *A01K 2267/0337* (2013.01); *A01K 2217/052* (2013.01); *C12N 2740/16011* (2013.01)
USPC .... 536/23.4; 530/350; 530/387.9; 435/320.1; 435/325

(58) Field of Classification Search
CPC .. A61K 48/005; C07K 14/47; C07K 2319/00; C12N 15/00; C12N 15/63
See application file for complete search history.

(56) References Cited

U.S. PATENT DOCUMENTS

| | | | |
|---|---|---|---|
| 5,399,346 A | 3/1995 | Anderson et al. |
| 2006/0134663 A1 | 6/2006 | Harkin et al. |
| 2007/0105122 A1 | 5/2007 | Ota et al. |
| 2007/0141679 A1 | 6/2007 | Sodroski et al. |
| 2007/0185017 A1 | 8/2007 | Aggarwal et al. |
| 2008/0045454 A1 | 2/2008 | Luban et al. |

FOREIGN PATENT DOCUMENTS

| | | |
|---|---|---|
| EP | 336523 A1 | 10/1989 |
| WO | WO-9011092 A1 | 10/1990 |
| WO | WO-2006/014422 | 2/2006 |

OTHER PUBLICATIONS

Brennan et al. TRIMCyp expression in Old World primates *Macaca nemestrina* and *Macaca fascicularis*. PNAS, Mar. 4, 2008, vol. 105, No. 9, pp. 3569-3574.*
Liao et al. A novel fusion gene, TRIM5-Cyclophilin A in the pig-tailed macaque determines its susceptibility to HIV-1 infection. AIDS 2007, vol. 21, Suppl. 8, S19-S26.*
Extended European Search Report mailed Apr. 10, 2012 for European Application No. 09825443.6, filed Nov. 6, 2009 (9 pages).
Neagu et al., "Potent inhibition of HIV-1 by TRIM5-cyclophilin fusion proteins engineered from Human components," The Journal of Clinical Investigation, vol. 119, pp. 3035-3047 (Oct. 2009).
Nisole et al., "A Trim5-cycliphilin A fusion protein found in owl monkey kidney cells can restrict HIV-1," PNAS, vol. 101, pp. 13324-13328 (Sep. 7, 2004).
Sayah et al., "Cyclophilin A retrotransposition into TRIM5 explains owl monkey resistance to HIV-1," Nature, vol. 430, pp. 569-573 (Jul. 2004).
International Search Report mailed on May 27, 2010, for International Application No. PCT/US09/63481 filed Nov. 6, 2009.
Liao et al., Full = Trim5/ cyclophilin A V1 Fusion protein. Jan. 9, UniProt Accession No. A0SE27_MACNE.
Mortellaro et al., "Ex. vivo gene therapy with lentiviral vectors rescues adenosine deanimase (ADA)-deficient mice and corrects their immune and metabolic defects," Blood, vol. 108, pp. 2979-2988 (Nov. 1, 2006).
Written Opinion mailed on May 27, 2010, for International Application No. PCT/US09/63481 filed Nov. 6, 2009.
Ambrose, Z., KewalRamani, V. N., Bieniasz, P. D., and Hatziioannou, T. (2007). HIV/AIDS: in search of an animal model. Trends in biotechnology 25, 333-337.
An, D. S., et al. Stable reduction of CCR5 by RNAi through hematopoietic stem cell transplant in non-human primates. Proc Natl Acad Sci 104, 13110-13115 (2007).

(Continued)

*Primary Examiner* — Louise Humphrey
(74) *Attorney, Agent, or Firm* — Wilmer Cutler Pickering Hale and Dorr LLP

(57) ABSTRACT

A nucleic acid is provided which encodes a human TRIM-cyclophilin A fusion sequence encoding a human TRIM-CypA fusion protein which is active as an anti-viral agent, and in particular, as an anti-HIV-1 agent. Also provided is a nucleic acid encoding a polypeptide having both TRIM activity and cyclophilin activity. Also provided is an isolated polynucleotide encoding a human TRIM-CypA fusion protein, or variants thereof retaining the TRIM and cyclophilin A activities. Also provided are compositions thereof, antibodies that specifically bind thereto, and vectors and host cells comprising the nucleic acid or polypeptide. In addition, methods are provided for treating or preventing viral infection, or reducing viral load in a subject comprising administering the nucleic acid, polypeptide, vector, or composition to the subject in an amount effective to treat or prevent the viral infection. In some embodiments, the viral infection is HIV-I infection, hepatitis C infection, pox virus infection, vaccinia virus infection, or HTLV infection.

12 Claims, 75 Drawing Sheets

(56) References Cited

OTHER PUBLICATIONS

Anderson, J. and Akkina, R. Human immunodeficiency virus type 1 restriction by human-rhesus chimeric tripartite motif 5alpha (TRIM 5alpha) in CD34(+) cell-derived macrophages in vitro and in T cells in vivo in severe combined immunodeficient (SCID-hu) mice transplanted with human fetal tissue. Human Gene Therapy 9, 217-228 (2008).
Anderson, J. and Akkina, R. TRIM5alpharh expression restricts HIV-1 infection in lentiviral vector-transduced CD34+-cell-derived macrophages. Mol Ther 12, 687-696 (2005).
Anderson, J. L., Campbell, E. M., Wu, X., Vandegraaff, N., Engelman, A., and Hope, T. J. (2006). Proteasome inhibition reveals that a functional preintegration complex intermediate can be generated during restriction by diverse TRIM5 proteins. J Virol 80, 9754-9760.
Anderson, J., and Akkina, R. (2005). CXCR4 and CCR5 shRNA transgenic CD34+ cell derived macrophages are functionally normal and resist HIV-1 infection. Retrovirology 2, 53, 1-11.
Anderson, J., Li, M. J., Palmer, B., Remling, L., Li, S., Yam, P., Yee, J. K., Rossi, J., Zaia, J., and Akkina, R. (2007). Safety and efficacy of a lentiviral vector containing three anti-HIV genes—CCR5 ribozyme, tat-rev siRNA, and TAR decoy—in SCID-hu mouse-derived T cells. Mol Ther 15, 1182-1188.
Anderson, P., Phillips, K., Stoecklin, G., and Kedersha, N. (2004). Post-transcriptional regulation of proinflammatory proteins. J Leukoc Biol 76, 42-47.
Arthos, J., Cicala, C., Martinelli, E., Macleod, K., Van Ryk, D., Wei, D., Xiao, Z., Veenstra, T. D., Conrad, T. P., Lempicki, R. A., et al. (2008). HIV-1 envelope protein binds to and signals through integrin alpha4beta7, the gut mucosal homing receptor for peripheral T cells. Nature immunology 9, 301-309.
Asaoka, K., Ikeda, K., Hishinuma, T., Horie-lnoue, K., Takeda, S., and Inoue, S. (2005). A retrovirus restriction factor TRIM5 alpha is transcriptionally regulated by interferons. Biochemical and biophysical research communications 338, 1950-1956.
Baenziger, S., et al. Disseminated and sustained HIV infection in CD34+ cord blood cell-transplanted Rag2−/−gamma c−/− mice. Proc Natl Acad Sci 103, 15951-15956 (2006).
Barre-Sinoussi, F., Chemann, J. C., Rey, F., Nugeyre, M. T., Chamaret, S., Gruest, J., Dauguet, C., Axler-Blin, C., Vezinet-Brun, F., Rouzioux, C., et al. (1983). Isolation of a T-lymphotropic retrovirus from a patient at risk for acquired immune deficiency syndrome (AIDS). Science 220, 868-871.
Bartee, E., McCormack, A., and Fruh, K. (2006). Quantitative membrane proteomics reveals new cellular targets of viral immune modulators. PLoS pathogens 2, e107, 0975-0988.
Bassin, R. H., Duran-Troise, G., Gerwin, B. I., and Rein, A. (1978). Abrogation of Fv-1b restriction with murine leukemia viruses inactivated by heat or by gamma irradiation. J Virol 26, 306-315.
Benit, L., De Parseval, N., Casella, J. F., Callebaut, I., Cordonnier, A., and Heidmann, T. (1997). Cloning of a new murine endogenous retrovirus, MuERV-L, with strong similarity to the human HERV-L element and with a gag coding sequence closely related to the Fv1 restriction gene. J Virol 71, 5652-5657.
Berges, B. K., Akkina, S. R., Folkvord, J. M., Connick, E., and Akkina, R. (2008). Vaginal and rectal mucosal transmission of R5 and X4 tropic HIV-1 via vaginal and rectal routes in humanized Rag2−/−gammac−/− (RAG-hu) mice. Virology 373, 17 pgs.
Berthoux, L., Sebastian, S., Sayah, D. M. and Luban, J. Disruption of human TRIM5 alpha antiviral activity by nonhuman primate orthologues. Journal of Virology 79, 7883-7888 (2005).
Berthoux, L., Sebastian, S., Sokolskaja, E. and Luban, J. Lv1 inhibition of human immunodeficiency virus type 1 is counteracted by factors that stimulate synthesis or nuclear translocation of viral cDNA. Journal of Virology 78, 11739-11750 (2004).
Berthoux, L., Sebastian, S., Sokolskaja, E., and Luban, J. (2005). Cyclophilin A is required for TRIM5 {alpha}-mediated resistance to HIV-1 in Old World monkey cells. Proc Natl Acad Sci USA 102, 14849-14853.
Berthoux, L., Towers, G. J., Gurer, C., Salomoni, P., Pandolfi, P. P., and Luban, J. (2003). As(2)O(3) enhances retroviral reverse transcription and counteracts Ref1 antiviral activity. J Virol 77, 3167-3180.
Besnier, C., Takeuchi, Y., and Towers, G. (2002). Restriction of lentivirus in monkeys. Proc Natl Acad Sci USA 99, 11920-11925.
Besnier, C., Ylinen, L., Strange, B., Lister, A., Takeuchi, Y., Goff, S. P., and Towers, G. J. (2003). Characterization of murine leukemia virus restriction in mammals. J Virol 77, 13403-13406.
Bieniasz, P. D., "Restriction factors: a defense against retroviral infection," Trends Microbial 11:286-291 (2003).
Bishop, K. N., Bock, M., Towers, G., and Stoye, J. P. (2001). Identification of the regions of Fv1 necessary for murine leukemia virus restriction. J Virol 75, 5182-5188.
Blunt, T., Gell, D., Fox, M., Taccioli, G. E., Lehmann, A. R., Jackson, S. P., and Jeggo, P. A. (1996). Identification of a nonsense mutation in the carboxyl-terminal region of DNA-dependent protein kinase catalytic subunit in the scid mouse. Proc Natl Acad Sci USA 93, 10285-10290.
Boden, D., Pusch, O. and Ramratnam, B. Overcoming HIV-1 resistance to RNA interference. Front Biosci 12 (2007), 14 pgs.
Boden, D., Pusch, O., Lee, F., Tucker, L., and Ramratnam, B. (2003). Human immunodeficiency virus type 1 escape from RNA interference. J Virol 77, 11531-11535.
Bogerd, H. P., Doehle, B. P., Wiegand, H. L., and Cullen, B. R. (2004). A single amino acid difference in the host APOBEC3G protein controls the primate species specificity of HIV type 1 virion infectivity factor. Proc Natl Acad Sci USA 101, 3770-3774.
Boone, L. R., Innes, C. L., and Heitman, C. K. (1990). Abrogation of Fv-1 restriction by genome-deficient virions produced by a retrovirus packaging cell line. J Virol 64, 3376-3381.
Bosco, D. A., Eisenmesser, E. Z., Pochapsky, S., Sundquist, W. I., and Kern, D. (2002). Catalysis of cis/trans isomerization in native HIV-1 capsid by human cyclophilin A. Proc Natl Acad Sci USA 99, 5247-5252.
Bosma, G. C., Fried, M., Custer, R. P., Carroll, A., Gibson, D. M., and Bosma, M. J. (1988). Evidence of functional lymphocytes in some (leaky) scid mice. The Journal of experimental medicine 167, 1016-1033.
Bowerman et al., "A nucleoprotein complex mediates the integration of retroviral DNA," Genes Dev 3:469-478 (1989).
Braaten, D., Aberham, C., Franke, E. K., Yin, L., Phares, W., and Luban, J. (1996). Cyclosporine A-resistant human immunodeficiency virus type 1 mutants demonstrate that Gag encodes the functional target of cyclophilin A. J Virol 70, 5170-5176.
Braaten, D., and Luban, J. (2001). Cyclophilin A regulates HIV-1 infectivity, as demonstrated by gene targeting in human T cells. The EMBO journal 20, 1300-1309.
Braaten, D., Ansari, H. and Luban, J. The hydrophobic pocket of cyclophilin is the binding site for the human immunodeficiency virus type 1 Gag polyprotein. Journal of Virology 71, 2107-2113 (1997).
Brass, A. L., Dykxhoorn, D. M., Benita, Y., Yan, N., Engelman, A., Xavier, R. J., Lieberman, J., and Elledge, S. J. (2008). Identification of host proteins required for HIV infection through a functional genomic screen. Science 319, 921-926.
Brenchley, J. M., Price, D. A., Schacker, T. W., Asher, T. E., Silvestri, G., Rao, S., Kazzaz, Z., Bornstein, E., Lambotte, O., Altmann, D., et al. (2006). Microbial translocation is a cause of systemic immune activation in chronic HIV infection. Nature medicine 12, 1365-1371.
Brennan, G., Kozyrev, Y., and Hu, S. L. (2008). TRIMCyp expression in Old World primates *Macaca nemestrina* and *Macaca fascicularis*. Proc Natl Acad Sci USA 105, 3569-3574.
Brigham et al., "Rapid Communication: in vivo Transfection of Murine Lungs with a Functionin Prokaryotic Gene Usin a Li osome Vehicle," Am J. Med. Sci 298:278-281 (1989).
Brown, C. R., Czapiga, M., Kabat, J., Dang, Q., Ourmanov, I., Nishimura, Y., Martin, M. A., and Hirsch, V. M. (2007). Unique pathology in simian immunodeficiency virus-infected rapid progressor macaques is consistent with a pathogenesis distinct from that of classical AIDS. J Virol 81, 5594-5606.
Bushman, F. D. (2007). Retroviral integration and human gene therapy. The Journal of clinical investigation 117, 2083-2086.

(56) References Cited

OTHER PUBLICATIONS

Campbell, E. M., Dodding, M. P., Yap, M. W., Wu, X., Gallois-Montbrun, S., Malim, M. H., Stoye, J. P., and Hope, T. J. (2007). TRIM5 alpha cytoplasmic bodies are highly dynamic structures. Mol Biol Cell 18, 2102-2111.

Campbell, E. M., Perez, O., Anderson, J. L., and Hope, T. J. (2008). Visualization of a proteasome-independent intermediate during restriction of HIV-1 by rhesus TRIM5alpha. The Journal of cell biology 180, 549-561.

Canonico et al., "Expression of a CMV promoter driven Human a-1 antitrypsin gene in cultured lun endothelial cells and in the lun s ofrabbits," Clin Res 39:219A 1991.

Chatterji, U., Bobardt, M. D., Gaskill, P., Sheeter, D., Fox, H., and Gallay, P. A. (2006). Trim5alpha accelerates degradation of cytosolic capsid associated with productive HIV-1 entry. J Biol Chem 281, 37025-37033.

Chatterji, U., et al. Naturally occurring capsid substitutions render HIV-1 cyclophilin A independent in human cells and TRIM-cyclophilin-resistant in Owl monkey cells. J Biol Chem 280, 40293-40300 (2005).

Chen, B. K., Gandhi, R. T. and Baltimore, D. CD4 down-modulation during infection of human T cells with human immunodeficiency virus type 1 involves independent activities of vpu, env, and nef. Journal of Virology 70, 6044-6053 (1996).

Chiu, Y. L., and Greene, W. C. (2008). The APOBEC3 cytidine deaminases: an innate defensive network opposing exogenous retroviruses and endogenous retroelements. Annual review of immunology 26, 317-353.

Chiu, Y. L., Soros, V. B., Kreisberg, J. F., Stopak, K., Yonemoto, W., and Greene, W. C. (2005). Cellular APOBEC3G restricts HIV-1 infection in resting CD4+ T cells. Nature 435, 108-114.

Chiu, Y. L., Witkowska, H. E., Hall, S. C., Santiago, M., Soros, V. B., Esnault, C., Heidmann, T., and Greene, W. C. (2006). High-molecular-mass APOBEC3G complexes restrict Alu retrotransposition. Proc Natl Acad Sci USA 103, 15588-15593.

Ciuffi, A., Diamond, T. L., Hwang, Y., Marshall, H. M., and Bushman, F. D. (2006). Modulating target site selection during human immunodeficiency virus DNA integration in vitro with an engineered tethering factor. Human gene therapy 17, 960-967.

Coles, M. C., Veiga-Fernandes, H., Foster, K. E., Norton, T., Pagakis, S. N., Seddon, B., and Kioussis, D. (2006). Role of T and NK cells and IL7/IL7r interactions during neonatal maturation of lymph nodes. Proc Natl Acad Sci USA 103, 13457-13462.

Colgan et al., "Binding of the human immunodeficiency virus type 1 Gag poly protein to cyclophilin A is mediated by the central region of capsid and requires Gag dimerization," J. Virol. 70:4299-4310 1996.

Colgan, J., Asmal, M., and Luban, J. (2000). Isolation, characterization and targeted disruption of mouse ppia: cyclophilin A is not essential for mammalian cell viability. Genomics 68, 167-178.

Colgan, J., Asmal, M., Neagu, M., Yu, B., Schneidkraut, J., Lee, Y., Sokolskaja, E., Andreotti, A., and Luban, J. (2004). Cyclophilin A regulates TCR signal strength in CD4+ T cells via a proline-directed conformational switch in ltk. Immunity 21, 189-201.

Colgan, J., Asmal, M., Yu, B., and Luban, J. Cyclophilin A-deficient Mice are Resistant to Immunosuppresion by Cyclosporine. J Immunol 2005; 174:6030-6038.

Cowan, S., Hatziioannou, T., Cunningham, T., Muesing, M. A., Gottlinger, H. G., and Bieniasz, P. D. (2002). Cellular inhibitors with Fv1-like activity restrict human and simian immunodeficiency virus tropism. Proc Natl Acad Sci USA 99, 11914-11919.

Damert et al., "Leptin receptor isoform 219.1: an example protein evolution by LINE-1-mediated human-specific retrotransposition of a coding SVA element, " Mol. Biol. Evol. 21, 647-651 (2004).

Daniel, M. D., Kirchhoff, F., Czajak, S. C., Sehgal, P. K., and Desrosiers, R. C. (1992). Protective effects of a live attenuated SIV vaccine with a deletion in the nef gene. Science 258, 1938-1941.

Delebecque, F., Suspene, R., Calattini, S., Casartelli, N., Saib, A., Froment, A., Wain-Hobson, S., Gessain, A., Vartanian, J. P., and Schwartz, 0. (2006). Restriction of foamy viruses by APOBEC cytidine deaminases. J Virol 80, 605-614.

Denton, P. W., Estes, J. D., Sun, Z., Othieno, F. A., Wei, B. L., Wege, A. K., Powell, D. A., Payne, D., Haase, A. T., and Garcia, J. V. (2008). Antiretroviral Pre-exposure Prophylaxis Prevents Vaginal Transmission of HIV-1 in Humanized BLT Mice. PLoS Med 5, e16, 0079-0089.

Dewannieux et al., "LINE-mediated retrotransposition of marked Alu sequences," Nature Genet. 35, 41-48 (2003).

Diaz-Griffero, F., et al. Requirements for capsid-binding and an effector function in TRIMCyp-mediated restriction of HIV-1. Virology 351, 404-419 (2006).

Diaz-Griffero, F., Kar, A., Lee, M., Stremlau, M., Poeschla, E., and Sodroski, J. (2007). Comparative requirements for the restriction of retrovirus infection by TRIMs alpha and TRIMCyp. Virology 369, 24 pgs.

Diaz-Griffero, F., Li, X., Javanbakht, H., Song, B., Welikala, S., Stremlau, M., and Sodroski, J. (2006a). Rapid turnover and polyubiquitylation of the retroviral restriction factor TRIM5. Virology 349, 300-315.

Dimitrov, D. S., Willey, R. L., Sato, H., Chang, L. J., Blumenthal, R., and Martin, M. A. (1993). Quantitation of human immunodeficiency virus type 1 infection kinetics. J Virol 67, 2182-2190.

Dorfman, T., and Gottlinger, H. G. (1996). The human immunodeficiency virus type 1 capsid p2 domain confers sensitivity to the cyclophilin-binding drug SDZ NIM 811. J Virol 70, 5751-5757.

Douek, D. C., Picker, L. J., and Koup, R. A. (2003). T cell dynamics in HIV-1 infection. Annual review of immunology 21, 46 pgs.

Ejima et al., "Trans mobilization of genomic DNA as a mechanism for retrotransposon-mediated exon shuffling." Hum. Mol. Genet. 12, 1321-1328, 2003.

Esnault et al., "Human LINE retrotransposons generate processed pseudogenes," Nature Genet. 24, 363-367 (2000).

Esnault, C., Heidmann, O., Delebecque, F., Dewannieux, M., Ribet, D., Hance, A. J., Heidmann, T., and Schwartz, O. (2005). APOBEC3G cytidine deaminase inhibits retrotransposition of endogenous retroviruses. Nature 433, 430-433.

Fassati et al., "Characterization of intracellular reverse transcription complexes of Moloney murine leukemia virus," J Virol73:8919-8925 (1999).

Fehr et al., "A, B, C and D, novel cyclophilin-binding compounds isolated from Streptomyces sp. A92-30811 0. II. Structure elucidation, stereochemistry and physico-chemical properties," J. Antibiot. (Tokyo) 52, 474-479 (1999).

Feng et al., "Human L 1 retrotransposon encodes a conserved endonuclease required for retrotrans osition," Cell 87, 905-916 (1996).

Feng, Y., Broder, C. C., Kennedy, P. E., and Berger, E. A. (2011). HIV-1 entry cofactor: functional cDNA cloning of a seven-transmembrane, G protein-coupled receptor, Jlmmunol 186(11), 17 pgs.

Final Office Action mailed on Apr. 29, 2010 for co-pending U.S. Appl. No. 11/650,384; 17 pages.

Final Office Action mailed on Oct. 14, 2010 for co-pending U.S. Appl. No. 11/650,384; 11 pages.

Fisher, A. G., Ensoli, B., Ivanoff, L., Chamberlain, M., Petteway, S., Ratner, L., Gallo, R. C., and Wong-Staal, F. (1987). The sor gene of HIV-1 is required for efficient virus transmission in vitro. Science 237, 888-893.

Forshey, B. M., Shi, J., and Aiken, C. (2005). Structural requirements for recognition of the human immunodeficiency virus type 1 core during host restriction in owl monkey cells. J Virol 79, 869-875.

Forshey, B. M., von Schwedler, U., Sundquist, W. I., and Aiken, C. (2002). Formation of a human immunodeficiency virus type 1 core of optimal stability is crucial for viral replication. J Virol 76, 5667-5677.

Franke, E. K., and Luban, J. (1996). Inhibition of HIV-1 replication by cyclosporine A or related compounds correlates with the ability to disrupt the Gag-cyclophilin A interaction. Virology 222, 279-282.

Franke, E. K., Yuan, H. E., and Luban, J. (1994). Specific incorporation of cyclophilin A into HIV-1 virions. Nature 372, 359-362.

Freemont, P. S., "Ring for destruction?," Curr. Biol. 10:R84-R87 (2000).

(56) References Cited

OTHER PUBLICATIONS

Friend, C. (1957). Cell-free transmission in adult Swiss mice of a disease having the character of a leukemia. The Journal of experimental medicine 105, 307-318.
Galic, Z., Kitchen, S. G., Kacena, A., Subramanian, A., Burke, B., Cortado, R., and Zack, J. A. (2006). T lineage differentiation from human embryonic stem cells. Proc Natl Acad Sci USA 103, 11742-11747.
Geraghty, R. J., Talbot, K. J., Callahan, M., Harper, W., and Panganiban, A. T. (1994). Cell type-dependence for Vpu function. Journal of medical primatology 23, 146-150.
Gilbert, W., Why genes in pieces, Nature 271, 501 (1978).
Gimeno, R., Weijer, K., Voordouw, A., Uittenbogaart, C. H., Legrand, N., Alves, N. L., Wijnands, E., Blom, B., and Spits, H. (2004). Monitoring the effect of gene silencing by RNA interference in human CD34+ cells injected into newborn RAG2+/+ gammac /+ mice: functional inactivation of p53 in developing T cells. Blood 104, 3886-3893.
Glass, W. G., et al. CCR5 deficiency increases risk of symptomatic West Nile virus infection. The Journal of Experimental Medicine 203, 35-40 (2006).
Goff, S. P. (2004). Retrovirus restriction factors. Molecular cell 16, 849-859.
Goffinet, C., Allespach, I., and Keppler, O. T. (2007). HIV-susceptible transgenic rats allow rapid preclinical testing of antiviral compounds targeting virus entry or reverse transcription. Proc Natl Acad Sci USA 104, 1015-1020.
Goila-Gaur, R., and Strebel, K. (2008). HIV-1 Vif, APOBEC, and intrinsic immunity. Retrovirology 5, 51, 1-16.
Goldman, J. P., Blundell, M. P., Lopes, L., Kinnon, C., Di Santo, J. P., and Thrasher, A. J. (1998). Enhanced human cell engraftment in mice deficient in RAG2 and the common cytokine receptor gamma chain. British journal of haematology 103, 335-342.
Goldstein, H. Summary of presentations at the NIH/NIAID New Humanized Rodent Models 2007 Workshop. AIDS Research and Therapy 5, 3 (2008), 1-14.
Gottlinger, H. G. (2008). HIV/AIDS virus kept on a leash. Nature 451, 406-408.
Goujon, C., Jarrosson-Wuilleme, L., Bernaud, J., Rigal, D., Darlix, J. L., and Cimarelli, A. (2006). With a little help from a friend: increasing HIV transduction of monocyte-derived dendritic cells with virion-like particles of SIV(MAC). Gene therapy 13, 991-994.
Goujon, C., Riviere, L., Jarrosson-Wuilleme, L., Bernaud, J., Rigal, D., Darlix, J. L., and Cimarelli, A. (2007). SIVSM/HIV-2 Vpx proteins promote retroviral escape from a proteasome-dependent restriction pathway present in human dendritic cells. Retrovirology 4:2, 1-11.
Grant, A. D., and De Cock, K. M. (2001). ABC of AIDS. HIV infection and AIDS in the developing world. BMJ (Clinical research ed 322, 1475-1478.
Grutter, C., et al. Structure of the PRYSPRY-domain: implications for autoinflammatory diseases. FEBS Lett 580, 99-106 (2006).
Gyuris et al., "Cdi1, a human G1 and S phase protein phosphatase that associates with Cdk2," Cell 75:791-803 (1993).
Hacein-Bey-Abina, S., Garrigue, A., Wang, G. P., Soulier, J., Lim, A., Morillon, E., Clappier, E., Caccavelli, L., Delabesse, E., Beldjord, K., et al. (2008). Insertional oncogenesis in 4 patients after retrovirus-mediated gene therapy of SCID-X1. The Journal of clinical investigation 118, 3132-3142.
Handschumacher, R. E., Harding, M. W., Rice, J., Drugge, R. J., and Speicher, D. W. (1984). Cyclophilin: a specific cytosolic binding protein for cyclosporin A. Science 226, 544-547.
Hanna, Z., Kay, D. G., Cool, M., Jothy, S., Rebai, N., and Jolicoeur, P. (1998a). Transgenic mice expressing human immunodeficiency virus type 1 in immune cells develop a severe AIDS-like disease. J Virol 72, 121-132.
Hanna, Z., Kay, D. G., Rebai, N., Guimond, A., Jothy, S., and Jolicoeur, P. (1998b). Nef harbors a major determinant of pathogenicity for an AIDS-like disease induced by HIV-1 in transgenic mice. Cell 95, 163-175.
Harris, R. S., Bishop, K. N., Sheehy, A. M., Craig, H. M., Petersen-Mahrt, S. K., Watt, I. N., Neuberger, M. S., and Malim, M. H. (2003). DNA deamination mediates innate immunity to retroviral infection. Cell 113, 803-809.
Hartley, J. W., Rowe, W. P., and Huebner, R. J. (1970). Host-range restrictions of murine leukemia viruses in mouse embryo cell cultures. J Virol 5, 221-225.
Hatziioannou, T., Perez-Caballero, D., Yang, A., Cowan, S., and Bieniasz, P. D. (2004). Retrovirus resistance factors Ref1 and Lv1 are species-specific variants of TRIM5alpha. Proc Natl Acad Sci USA 101, 10774-10779.
Hatziioannou, T., Princiotta, M., Piatak, M., Jr., Yuan, F., Zhang, F., Lifson, J. D., and Bieniasz, P. D. (2006). Generation of simian-tropic HIV-1 by restriction factor evasion. Science 314, 95.
Hazinski et al., "Localization and induced Expression of Fusion Genes in the Rat Lung," Am. J. Res . Cell Mol. Biol. 4:206-209 (1991).
Himathongkham, S., and Luciw, P. A. (1996). Restriction of HIV-1 (subtype B) replication at the entry step in rhesus macaque cells. Virology 219, 485-488.
Ho, D. D., and Bieniasz, P. D. (2008). HIV-1 at 25. Cell 133, 561-565.
Hofer, U., Baenziger, S., Heikenwalder, M., Schlaepfer, E., Gehre, N., Regenass, S., Brunner, T. and Speck, R. F. (2008). RAG2+/+{gamma}c+/+ mice transplanted with human cord blood CD34+ cells show low intestinal engraftment and are resistant to rectal HIV transmission. J. Virol. 82(24):12145-12153.
Hofmann, W., Schubert, D., LaBonte, J., Munson, L., Gibson, S., Scammell, J., Ferrigno, P., and Sodroski, J. (1999). Species-specific, postentry barriers to primate immunodeficiency virus infection. J Virol 73, 10020-10028.
Howe, S. J., Mansour, M. R., Schwarzwaelder, K., Bartholomae, C., Hubank, M., Kempski, H., Brugman, M. H., Pike-Overzet, K., Chatters, S. J., de Ridder, D., et al. (2008). Insertional mutagenesis combined with acquired somatic mutations causes leukemogenesis following gene therapy of SCID-X1 patients. The Journal of clinical investigation 118, 3143-3150.
Hughes, A. L., and Yeager, M. (1998). Natural selection at major histocompatibility complex loci of vertebrates. Annual review of genetics 32, 415-435.
International Search report mailed on Apr. 29, 2008 for International Application No. PCT/US05/23803 filed Jul. 6, 2005, 4 pages.
Isaacs, A., and Lindenmann, J. (1957). Virus interference. I. The interferon. Proceedings of the Royal Society of London Series B, Containing papers of a Biological character 147, 258-267.
Ishikawa, F., Yasukawa, M., Lyons, B., Yoshida, S., Miyamoto, T., Yoshimoto, G., Watanabe, T., Akashi, K., Shultz, L. D., and Harada, M. (2005). Development of functional human blood and immune systems in NOD/SCID/IL2 receptor {gamma} chain (null) mice. Blood 106, 21 pgs.
Ito, M., Hiramatsu, H., Kobayashi, K., Suzue, K., Kawahata, M., Hioki, K., Ueyama, Y., Koyanagi, Y., Sugamura, K., Tsuji, K., et al. (2002). NOD/SCID/gamma(c)(null) mouse: an excellent recipient mouse model for engraftment of human cells. Blood 100, 3175-3182.
Iwatani, Y., Takeuchi, H., Strebel, K., and Levin, J. G. (2006). Biochemical activities of highly purified, catalytically active human APOBEC3G: correlation with antiviral effect. J Virol 80, 5992-6002.
Jackson, a. L. et al., "Expression profiling reveals off-target gene regulation by RNAi," Nature Biotechnol. 21, 635-637 (2003).
James, L. C., Keeble, a. H., Khan, Z., Rhodes, D. A., and Trowsdale, J. (2007). Structural basis for Pryspry-mediated tripartite motif (TRIM) protein function. Proc Natl Acad Sci USA 104, 6200-6205.
Javanbakht, H., Diaz-Griffero, F., Stremlau, M., Si, Z., and Sodroski, J. (2005). The contribution of Ring and B-box 2 domains to retroviral restriction mediated by monkey TRIM5alpha. J Biol Chem 280, 26933-26940.
Javanbakht, H., Diaz-Griffero, F., Yuan, W., Yeung, D. F., Li, X., Song, B., and Sodroski, J. (2007). The ability of multimerized cyclophilin a to restrict retrovirus infection. Virology. 367(1), 20 pgs.
Javanbakht, H., Yuan, W., Yeung, D. F., Song, B., Diaz-Griffero, F., Li, Y., Li, X., Stremlau, M., and Sodroski, J. (2006). Characterization of TRIM5alpha trimerization and its contribution to human immunodeficiency virus capsid binding. Virology 353, 234-246.

(56) References Cited

OTHER PUBLICATIONS

Jolicoeur, P., and Baltimore, D. (1976). Effect of Fv-1 gene product on proviral Dna formation and integration in cells infected with murine leukemia viruses. Proc Natl Acad Sci USA 73, 2236-2240.
Jolly, C., Kashefi, K., Hollinshead, M., and Sattentau, Q. J. (2004). Hiv-1 cell to cell transfer across an Env-induced, actin-dependent synapse. The Journal of experimental medicine 199, 283-293.
Kaiser, S. M., Malik, H. S., and Emerman, M. (2007). Restriction of an extinct retrovirus by the human Trims alpha antiviral protein. Science 316, 1756-1758.
Kao, S., Khan, M. A., Miyagi, E., Plishka, R., Buckler-White, a., and Strebel, K. (2003). The human immunodeficiency virus type 1 Vif protein reduces intracellular expression and inhibits packaging of APOBEC3G (CEM15), a cellular inhibitor of virus infectivity. J Virol 77, 1139811407.
Kazazian, H. H., Jr. (2004). Mobile elements: drivers of genome evolution. Science 303, 1626- 1632.
Keckesova, Z., Ylinen, L. M., and Towers, G. J. (2004). The human and African green monkey TRIM5 alpha genes encode Ref1 and Lv1 retroviral restriction factor activities. Proc Natl Acad Sci USA 101, 10780-10785.
Keele, B. F., Van Heuverswyn, F., Li, Y., Bailes, E., Takehisa, J., Santiago, M. L., Bibollet-Ruche, F., Chen, Y., Wain, L. V., Liegeois, F., et al. (2006). Chimpanzee reservoirs of pandemic and nonpandemic HIV-1. Science 313, 9 pgs.
Keppler, O. T., Welte, F. J., Ngo, T. A., Chin, P. S., Patton, K. S., Tsou, C. L., Abbey, N. W., Sharkey, M. E., Grant, R. M., You, Y., et al. (2002). Progress toward a human CD4/CCR5 transgenic rat model for de novo infection by human immunodeficiency virus type 1. The Journal of experimental medicine 195, 719-736.
Kerre, T. C., De Smet, G., De Smedt, M., Zippelius, A., Pittet, M. J., Langerak, A. W., De Bosscher, J., Offner, F., Vandekerckhove, B., and Plum, J. (2002). Adapted NOD/SCID model supports development of phenotypically and functionally mature T cells from human umbilical cord blood CD34(+) cells. Blood 99, 1620-1626.
Kirchhoff, F., Greenough, T. C., Brettler, D. B., Sullivan, J. L., and Desrosiers, R. C. (1995). Brief report: absence of intact nef sequences in a long-term survivor with nonprogressive HIV-1 infection. The New England journal of medicine 332, 228-232.
Klimkait, T., Strebel, K., Hoggan, M. D., Martin, M. A., and Orenstein, J. M. (1990). The human immunodeficiency virus type-specific protein Vpu is required for efficient virus maturation and release. J Virol 64, 621-629.
Konig, R., Zhou, Y., Elleder, D., Diamond, T. L., Bonamy, G. M., Irelan, J. T., Chiang, C. Y., Tu, B. P., De Jesus, P. D., Lilley, C. E., et al. (2008). Global analysis of host-pathogen interactions that regulate early-stage HIV-1 replication. Cell 135, 21 pgs.
Kootstra, N. A., Munk, C., Tonnu, N., Landau, N. R., and Verma, I. M. (2003). Abrogation of postentry restriction of HIV-1-based lentiviral vector transduction in simian cells. Proc Natl Acad Sci USA 100, 1298-1303.
Kozak, C. A., and Chakraborti, A. (1996). Single amino acid changes in the murine leukemia virus capsid protein gene define the target of Fv1 resistance. Virology 225, 300-305.
Kumar, P., Ban, H. S., Kim, S. S., Wu, H., Pearson, T., Greiner, D. L., Laouar, a., Yao, J., Haridas, V., Habiro, K., et al. (2008). T cell-specific siRNA delivery suppresses HIV-1 infection in humanized mice. Cell 134, 20 pgs.
Kunstman, K. J., Puffer, B., Korber, B. T., Kuiken, C., Smith, U. R., Kunstman, J., Stanton, J., Agy, M., Shibata, R., Yoder, A. D., et al. (2003). Structure and function of CC-chemokine receptor 5 homologues derived from representative primate species and subspecies of the taxonomic suborders Prosimii and Anthropoidea. J Virol 77, 12310-12318.
La Motte-Mohs, R. N., Herer, E., and Zuniga-Pflucker, J. C. (2005). Induction of T-cell development from human cord blood hematopoietic stem cells by Delta-like 1 in vitro. Blood 105, 1431-1439.
Labno, C. M., Lewis, C. M., You, D., Leung, D. W., Takesono, A., Kamberos, N., Seth, A., Finkelstein, L. D., Rosen, M. K., Schwartzberg, P. L., et al. (2003). ltk functions to control actin polymerization at the immune synapse through localized activation of Cdc42 and WASP. Curr Biol 13, 10 pgs.
LaBonte, J. A., Babcock, G. J., Patel, T., and Sodroski, J. (2002). Blockade of HIV-1 infection of New World monkey cells occurs primarily at the stage of virus entry. The Journal of experimental medicine 196, 431-445.
Lee et al., "In defense of the cell: TRIM Sa interception of mammalian retroviruses," Proc. Natl. Acad. Sci. USA 101: 10496-10497 2004.
Lee, Y. N., and Bieniasz, P. D. (2007). Reconstitution of an infectious human endogenous retrovirus. PLoS pathogens 3, e10, 0119-0130.
Lee, Y. N., Malim, M. H., and Bieniasz, P. D. (2008). Hypermutation of an ancient human retrovirus by APOBEC3G. J Virol 82, 8762-8770.
Legrand, N., Weijer, K., and Spits, H. (2006). Experimental models to study development and function of the human immune system in vivo. J Immunol 176, 2053-2058.
Levine, B. L., et al. Adoptive transfer of costimulated CD4+ T cells induces expansion of peripheral T cells and decreased CCR5 expression in HIV infection. Nature Medicine 8, 47-53 (2002).
Lewinski, M. K., Yamashita, M., Emerman, M., Ciuffi, A., Marshall, H., Crawford, G., Collins, F., Shinn, P., Leipzig, J., Hannenhalli, S., et al. (2006). Retroviral DNA integration: viral and cellular determinants of target-site selection. PLoS pathogens 2, e60, 0611-0622.
Li, X., Li, Y., Stremlau, M., Yuan, W., Song, B., Perron, M., and Sodroski, J. (2006a). Functional replacement of the RING, B-box 2, and coiled-coil domains of tripartite motif 5alpha (TRIM5alpha) by heterologous TRIM domains. J Virol 80, 6198-6206.
Li, Y., Li, X., Stremlau, M., Lee, M. and Sodroski, J. Removal of arginine 332 allows human TRIM5 alpha to bind human immunodeficiency virus capsids and to restrict infection. Journal of Virology 80, 6738-6744 (2006).
Lilly, F. (1967). Susceptibility to two strains of Friend leukemia virus in mice. Science 155, 461-462.
Lin, T. Y. and Emerman, M. Cyclophilin A interacts with diverse lentiviral capsids. Retrovirology 3, 70 (2006), 1-12.
Liu, J., Farmer, J. D., Jr., Lane, W. S., Friedman, J., Weissman, I., and Schreiber, S. L. (1991). Calcineurin is a common target of cyclophilin-cyclosporin A and FKBP-FK506 complexes. Cell 66, 807-815.
Lois, C., Hong, E. J., Pease, S., Brown, E. J. and Baltimore, D. Germline transmission and tissue-specific expression of transgenes delivered by lentiviral vectors. Science 295, 868-872 (2002).
Lombardo, A., Genovese, P., Beausejour, C. M., Colleoni, S., Lee, Y. L., Kim, K. A., Ando, D., Urnov, F. D., Galli, C., Gregory, P. D., et al. (2007). Gene editing in human stem cells using zinc finger nucleases and integrase-defective lentiviral vector delivery. Nature biotechnology 25, 9 pgs.
Long et al., "Natural selection and the origin of jingwei, a chimeric processed functional gene in Droso hila," Science 260, 91-95 (1993).
Luban, J. Cyclophilin A, TRIM5, and resistance to human immunodeficiency virus type 1 infection. Journal of Virology 81, 1054-1061 (2007).
Luban, J., Bossolt, K. L., Franke, E. K., Kalpana, G. V. and Goff, S. P. Human immunodeficiency virus type 1 Gag protein binds to cyclophilins A and B. Cell 73, 1067-1078 (1993).
Luo Z. et al (1998) "Roles in cell-to-cell fusion of two conserved hydrophobic regions in murine coronavirus spike protein" Virology, vol. 244, p. 483-494.
Madani, N., and Kabat, D. (1998). An endogenous inhibitor of human immunodeficiency virus in human lymphocytes is overcome by the viral Vif protein. J Virol 72, 10251-10255.
Maddon, P. J., Dagleish, A. G., McDougal, J. S., Clapham, P. R., Weiss, R. A., and Axel, R. (1986). The T4 gene encodes the AIDS virus receptor and is expressed in the immune system and the brain. Cell 47, 333-348.
Maertens, G., Cherepanov, P., Pluymers, W., Busschots, K., De Clercq, E., Debyser, Z., and Engelborghs, Y. (2003). LEDGF/p75 is essential for nuclear and chromosomal targeting of HIV-1 integrase in human cells. J Biol Chem 278, 33528-33539.
Malim, M. H., Freimuth, W. W., Liu, J., Boyle, T. J., Lyerly, H. K., Cullen, B. R., and Nabel, G. J. (1992). Stable expression of

(56) References Cited

OTHER PUBLICATIONS transdominant Rev protein in human T cells inhibits human immunodeficiency virus replication. The Journal of experimental medicine 176, 1197-1201.
Mangeat, B., Turelli, P., Caron, G., Friedli, M., Perrin, L., and Trono, D. (2003). Broad antiretroviral defence by human APOBEC3G through lethal editing of nascent reverse transcripts. Nature 424, 99-103.
Mangeot, P. E., et al. High levels of transduction of human dendritic cells with optimized SIV vectors. Mol Ther 5, 283-290 (2002).
Manz, M. G. (2007). Human-hemato-lymphoid-system mice: opportunities and challenges. Immunity 26, 537-541.
Marathe, J. G., and Wooley, D. P. (2007). Is gene therapy a good therapeutic approach for HIV-positive patients? Genet Vaccines Ther 5:5, 1-9.
Mariani, R., Chen, D., Schrofelbauer, B., Navarro, F., Konig, R., Bollman, B., Munk, C., Nymark-McMahon, H., and Landau, N. R. (2003). Species-specific exclusion of APOBEC3G from HIV-1 virions by Vif. Cell 114, 21-31.
Massiah, M. A., Simmons, B. N., Short, K. M., and Cox, T. C. (2006). Solution structure of the RBCC/TRIM B-box1 domain of human MIDI: B-box with a RING. Journal of molecular biology 358, 532-545.
McClintock, B., "The origin and behavior of mutable loci in maize," Proc. Natl Acad. Sci. USA 36, 44-355 (1950).
Mische, C. C., Javanbakht, H., Song, B., Diaz-Griffero, F., Stremlau, M., Strack, B., Si, Z., and Sodroski, J. (2005). Retroviral restriction factor TRIM5alpha is a trimer. J Virol 79, 14446-14450.
Mitchell, R. S., Beitzel, B. F., Schroder, A. R., Shinn, P., Chen, H., Berry, C. C., Ecker, J. R., and Bushman, F. D. (2004). Retroviral DNA integration: ASLV, HIV, and MLV show distinct target site preferences. PLoS biology 2, E234, 1127-1137.
Mitsuyasu, R. T., Anton, P. A., Deeks, S. G., Scadden, D. T., Connick, E., Downs, M. T., Bakker, A., Roberts, M. R., June, C. H., Jalali, S., et al. (2000). Prolonged survival and tissue trafficking following adoptive transfer of CD4zeta gene-modified autologous CD4(+) and CD8(+) T cells in human immunodeficiency virus-infected subjects. Blood 96, 785-793.
Moran et al. "Exon shuffling by L1 retrotransposition," Science 283, 1530-1534 (1999).
Morgan, R. A., Walker, R., Carter, C. S., Natarajan, V., Tavel, J. A., Bechtel, C., Herpin, B., Muul, L., Zheng, Z., Jagannatha, S., et al. (2005). Preferential survival of CD4+ T lymphocytes engineered with anti-human immunodeficiency virus (HIV) genes in HIV-infected individuals. Human gene therapy 16, 1065-1074.
Munk, C., Brandt, S. M., Lucero, G., and Landau, N. R. (2002). A dominant block to HIV-1 replication at reverse transcription in simian cells. Proc Natl Acad Sci USA 99, 13843-13848.
Nabel et al., "Site-Specific Gene Expression in vivo by Direct Gene Transfer into the Arterial Wall," Science 249:1285-1288 (1990).
Nakata, H., Maeda, K., Miyakawa, T., Shibayama, S., Matsuo, M., Takaoka, Y., Ito, M., Koyanagi, Y., and Mitsuya, H. (2005). Potent anti-R5 human immunodeficiency virus type 1 effects of a CCR5 antagonist, AK602/ONO4128/GW873140, in a novel human peripheral blood mononuclear cell nonobese diabetic-SCID, interleukin-2 receptor gamma-chain-knocked-out AIDS mouse model. J Virol 79, 2087-2096.
Nakayama EE, Miyoshi H, Nagai Y, Shioda T. "A specific region of 37 amino acid residues in the SPRY (830.2) domain of African green monkey TRIM5alpha determines species-specific restriction of simian immunodeficiency virus SIVmac infection." J Viral. Jul. 2005;79(14):8870-7.
Nath, B. M., Schumann, K. E., and Boyer, J. D. (2000). The chimpanzee and other non-human-primate models in HIV-1 vaccine research. Trends in microbiology 8, 426-431.
Neil, S. J., Eastman, S. W., Jouvenet, N., and Bieniasz, P. D. (2006). HIV-1 Vpu promotes release and prevents endocytosis of nascent retrovirus particles from the plasma membrane. PLoS pathogens 2, e39, 0354-0367.
Neil, S. J., Sandrin, V., Sundquist, W. I., and Bieniasz, P. D. (2007). An interferon-alpha-induced tethering mechanism inhibits HIV-1 and Ebola virus particle release but is counteracted by the HIV-1 Vpu protein. Cell host and microbe 2, 23 pgs.
Newman, R. M., and Johnson, W. E. (2007). A brief history of TRIM5alpha. AIDS Rev 9, 114-125.
Newman, R. M., Hall, L., Kirmaier, A., Pozzi, L. A., Pery, E., Farzan, M., O'Neil, S. P., and Johnson, W. (2008). Evolution of a TRIM5-CypA splice isoform in old world monkeys. PLoS pathogens 4, e1000003, 1-8.
Nisole et al., "A Trim5-cyclophilin A fusion protein found in owl monkey kidney cells can restrict HIV-1," Proc. Natl. Acad. Sci. USA 101:13324-13328 (2004).
Nisole, S., Lynch, C., Stoye, J. P. and Yap, M. W. A Trim5-cyclophilin A fusion protein found in owl monkey kidney cells can restrict HIV-1. Proc Natl Acad Sci 101, 13324-13328 (2004).
Nisole, S., Stoye, J. P., and Saib, A. (2005). TRIM family proteins: retroviral restriction and antiviral defence. Nature reviews 3, 799-808.
Non-Final Office Action mailed on Aug. 7, 2009 for co-pending U.S. Appl. No. 11/650,384; 17 pages.
Novembre, F. J., Saucier, M., Anderson, D. C., Klumpp, S. A., O'Neil, S. P., Brown, C. R., 2nd, Hart, C. E., Guenthner, P. C., Swenson, R. B., and McClure, H. M. (1997). Development of Aids in a chimpanzee infected with human immunodeficiency virus type 1. J Virol 71, 4086-4091.
Ohkura, S., Yap, M. W., Sheldon, T., and Stoye, J. P. (2006). All three variable regions of the TRIM5alpha B30.2 domain can contribute to the specificity of retrovirus restriction. J Virol 80, 8554-8565.
Opi, S., Kao, S., Goila-Gaur, R., Khan, M. A., Miyagi, E., Takeuchi, H., and Strebel, K. (2007). Human immunodeficiency virus type 1 Vif inhibits packaging and antiviral activity of a degradation-resistant APOBEC3G variant. J Virol 81, 8236-8246.
Owens, C. M., Yang, P. C., Gottlinger, H., and Sodroski, J. (2003). Human and simian immunodeficiency virus capsid proteins are major viral determinants of early, postentry replication blocks in simian cells. J Virol 77, 726-731.
Pandrea, I., Apetrei, C., Gordon, S., Barbercheck, J., Dufour, J., Bohm, R., Sumpter, B., Rogues, P., Marx, P. A., Hirsch, V. M., et al. (2007). Paucity of CD4+CCR5+T cells is a typical feature of natural SIV hosts. Blood 109, 1069-1076.
Pandrea, I., Sodora, D. L., Silvestri, G., and Apetrei, C. (2008). Into the wild: simian immunodeficiency virus (SIV) infection in natural hosts. Trends in immunology 29, 18 pgs.
Papkalla, A., Munch, J., Otto, C. and Kirchhoff, F. Nef enhances human immunodeficiency virus type 1 infectivity and replication independently of viral coreceptor tropism. Journal of Virology 76, 8455-8459 (2002).
Perez, E. E., et al. Establishment of HIV-1 resistance in CD4(+) T cells by genome editing using zinc-finger nucleases. Nat Biotechnol 26(7):808-816 (2008).
Perez-Caballero, D., Hatziioannou, T., Yang, A., Cowan, S. and Bieniasz, P. D. Human tripartite motif 5alpha domains responsible for retrovirus restriction activity and specificity. Journal of Virology 79, 8969-8978 (2005).
Perez-Caballero, D., Hatziioannou, T., Zhang, F., Cowan, S. and Bieniasz, P. D. Restriction of human immunodeficiency virus type 1 by TRIM-CypA occurs with rapid kinetics and independently of cytoplasmic bodies, ubiquitin, and proteasome activity. Journal of Virology 79, 15567-15572 (2005).
Perron, M. J., Stremlau, M., Lee, M., Javanbakht, H., Song, B., and Sodroski, J. (2007). The human TRIM5 alpha restriction factor mediates accelerated uncoating of the N-tropic murine leukemia virus capsid. J Virol 81, 2138-2148.
Perron, M. J., Stremlau, M., Song, B., Ulm, W., Mulligan, R. C., and Sodroski, J. (2004). TRIM5 alpha mediates the postentry block to N-tropic murine leukemia viruses in human cells. Proc Natl Acad Sci USA 101, 11827-11832.
Pincus, T., Hartley, J. W., and Rowe, W. P. (1971a). A major genetic locus affecting resistance to infection with murine leukemia viruses. I. Tissue culture studies of naturally occurring viruses. The Journal of experimental medicine 133, 1219-1233.

(56) References Cited

OTHER PUBLICATIONS

Pincus, T., Hartley, J. W., and Rowe, W. P. (1975). A major genetic locus affecting resistance to infection with murine leukemia viruses. IV. Dose-response relationships in Fv-1-sensitive and resistant cell cultures. Virology 65, 333-342.
Pincus, T., Rowe, W. P., and Lilly, F. (1971b). A major genetic locus affecting resistance to infection with murine leukemia viruses. II. Apparent identity to a major locus described for resistance to friend murine leukemia virus. The Journal of experimental medicine 133, 1234-1241.
Ponting et al., "SPRY domains in ryanodine receptors (Ca(2+)-release channels)," Trends Biochem Sci 22:193-194 (1997).
Potash, M. J., Chao, W., Bentsman, G., Paris, N., Saini, M., Nitkiewicz, J., Belem, P., Sharer, L. Brooks, A. I., and Volsky, D. J. (2005). A mouse model for study of systemic HIV-1 infection, antiviral immune responses, and neuroinvasiveness. Proc Natl Acad Sci USA 102, 3760-3765.
Pryciak, P. M., and Varmus, H. E. (1992). Fv-1 restriction and its effects on murine leukemia virus integration in vivo and in vitro. J Virol 66, 5959-5966.
Qi, C. F., Bonhomme, F., Buckler-White, A., Buckler, C., Orth, A., Lander, M. R., Chattopadhyay, S. K., and Morse, H. C., 3rd (1998). Molecular phylogeny of Fv1. Mamm Genome 9, 1049-1055.
Ranga, U., Woffendin, C., Verma, S., Xu, L., June, C. H., Bishop, D. K., and Nabel, G. J. (1998). Enhanced T cell engraftment after retroviral delivery of an antiviral gene in HIV-infected individuals. Proc Natl Acad Sci USA 95, 1201-1206.
Reymond, A., Meroni, G., Fantozzi, A., Merla, G., Cairo, S., Luzi, L., Riganelli, D., Zanaria, E., Messali, S., Cainarca, S., et al. (2001). The tripartite motif family identifies cell compartments. The EMBO journal 20, 2140-2151.
Ribeiro, I. P., et al. Evolution of cyclophilin A and TRIMCyp retrotransposition in New World primates. Journal of Virology 79, 14998-15003 (2005).
Richardson, M. W., Carroll, R. G., Stremlau, M., Korokhov, N., Humeau, L. M., Silvestri, G., Sodroski, J., and Riley, J. L. (2008). Mode of Transmission Affects the Sensitivity of HIV-1 to Restriction by Rhesus TRIM5 {alpha}. J. Virol. 82(22):11117-11128.
Riddell, S. R., et al. T-cell mediated rejection of gene-modified HIV-specific cytotoxic T lymphocytes in HIV-infected patients. Nature Medicine 2, 216-223 (1996).
Roberts, M. R., Qin, L., Zhang, D., Smith, D. H., Tran, A. C., Dull, T. J., Groopman, J. E., Capon, D. J., Byrn, R. A., and Finer, M. H. (1994). Targeting of human immunodeficiency virus-infected cells by CD8+ T lymphocytes armed with universal T-cell receptors. Blood 84, 2878-2889.
Rold, C. J., and Aiken, C. (2008). Proteasomal degradation of TRIM5 alpha during retrovirus restriction. PLoS pathogens 4, e1000074, 1-12.
Roy-Engel, A. M. et al.,"Non-traditional Alu evolution and primate genomic diversity," J. Mol. Bioi. 316, 1033-1040 (2002).
Ryffel, B., Woerly, G., Greiner, B., Haendler, B., Mihatsch, M. J., and Foxwell, B. M. (1991). Distribution of the cyclosporine binding protein cyclophilin in human tissues. Immunology 72, 399-404.
Saenz, D. T., Teo, W., Olsen, J. C. and Poeschla, E. M. Restriction of feline immunodeficiency virus by Ref1, Lv1, and primate TRIM5 alpha proteins. Journal of Virology 79, 15175-15188 (2005).
Sakuma, R., Noser, J. A., Ohmine, S., and Ikeda, Y. (2007). Rhesus monkey TRIM5alpha restricts HIV-1 production through rapid degradation of viral Gag polyproteins. Nature medicine 13, 631-635.
Santiago, M. L., Montano, M., Benitez, R., Messer, R. J., Yonemoto, W., Chesebro, B., Hasenkrug, K. J., and Greene, W. C. (2008). Apobec3 encodes Rfv3, a gene influencing neutralizing antibody control of retrovirus infection. Science 321, 13 pgs.
Santoni de Sio, F. R., Cascio, P., Zingale, A., Gasparini, M., and Naldini, L. (2006). Proteasome activity restricts lentiviral gene transfer into hematopoietic stem cells and is down-regulated by cytokines that enhance transduction. Blood 107, 4257-4265.
Saphire et al., "Host cyclophilin A mediates HIV-1 attachment to target via heparans," EMBO J, vol. 18,pp. 6771-6785 (1999).
Sarkar, I., Hauber, I., Hauber, J., and Buchholz, F. (2007). HIV-1 proviral DNA excision using an evolved recombinase. Science 316, 1912-1915.
Sawyer, S. L., Emerman, M., and Malik, H. S. (2004). Ancient adaptive evolution of the primate antiviral DNA-editing enzyme APOBEC3G. PLoS biology 2, E275, 1278-1285.
Sawyer, S. L., Wu, L. I., Akey, J. M., Emerman, M., and Malik, H. S. (2006). High-frequency persistence of an impaired allele of the retroviral defense gene TRIM5 alpha in humans. Curr Biot 16, 95-100.
Sawyer, S. L., Wu, L. I., Emerman, M. and Malik, H. S. Positive selection of primate Trims alpha identifies a critical species-specific retroviral restriction domain. Proc Natl Acad Sci 102, 2832-2837 (2005).
Sayah, D. M., and Luban, J. (2004). Selection for loss of Ref1 activity in human cells releases human immunodeficiency virus type 1 from cyclophilin A dependence during infection. J Virol 78, 12066-12070.
Sayah, D. M., Sokolskaja, E., Berthoux, L. and Luban, J. Cyclophilin A retrotransposition into TRIM5 explains owl monkey resistance to HIV-1. Nature 430, 569-573 (2004).
Schaller, T., Ylinen, L. M., Webb, B. L., Singh, S., and Towers, G. J. (2007). Fusion of cyclophilin a to fv1 enables cyclosporine-sensitive restriction of human and feline immunodeficiency viruses. J Virol 81, 10055-10063.
Schambach, A., Schiedlmeier, B., Kuhlcke, K., Verstegen, M., Margison, G. P., Li, Z., Kamino, K., Bohne, J., Alexandrov, A., Hermann, F. G., et al. (2006). Towards hematopoietic stem cell-mediated protection against infection with human immunodeficiency virus. Gene therapy 13, 1037-1047.
Schotte, R., Nagasawa, M., Weijer, K., Spits, H., and Blom, B. (2004). The ETS transcription factor Spi-B is required for human plasmacytoid dendritic cell development. The Journal of experimental medicine 200, 1503-1509.
Schrofelbauer, B., Chen, D., and Landau, N. R. (2004). A single amino acid of APOBEC3G controls its species-specific interaction with virion infectivity factor (Vif). Proc Natl Acad Sci USA 101, 3927-3932.
Schrofelbauer, B., Yu, Q., Zeitlin, S. G., and Landau, N. R. (2005). Human immunodeficiency virus type 1 Vpr induces the degradation of the UNG and SMUG uracil-DNA glycosylases. J Virol 79, 10978-10987.
Schwartz, O., Marechal, V., Friguet, B., Arenzana-Seisdedos, F., and Heard, J. M. (1998). Antiviral activity of the proteasome on incoming human immunodeficiency virus type 1. J Virol 72, 3845-3850.
Sebastian, S. and Luban, J. TRIM5alpha selectively binds a restriction-sensitive retroviral capsid. Retrovirology 2:40 (2005), 3 pages.
Sebastian, S., and Luban, J. (2007). The Retroviral Restriction Factor TRIM5alpha. Curr Infect Dis Rep 9, 167-173.
Sebastian, S., Sokolskaja, E. and Luban, J. Arsenic counteracts human immunodeficiency virus type 1 restriction by various Trims orthologues in a cell type-dependent manner. Journal of Virology 80, 2051-2054 (2006).
Sheehy, A. M., Gaddis, N. C., Choi, J. D., and Malim, M. H. (2002). Isolation of a human gene that inhibits HIV-1 infection and is suppressed by the viral Vif protein. Nature 418, 646-650.
Sherer, N. M., Lehmann, M. J., Jimenez-Soto, L. F., Horensavitz, C., Pypaert, M., and Mothes, W. (2007). Retroviruses can establish filopodial bridges for efficient cell-to-cell transmission. Nature cell biology 9, 12 pgs.
Shi, J., and Aiken, C. (2006). Saturation of TRIM5 alpha-mediated restriction of HIV-1 infection depends on the stability of the incoming viral capsid. Virology 350, 493-500.
Shi, M., Deng, W., Bi, E., Mao, K., Ji, Y., Lin, G., Wu, X., Tao, Z., Li, Z., Cai, X., et al. (2008). TRIM30 alpha negatively regulates TLR-mediated NF-kappa B activation by targeting TAB2 and TAB3 for degradation. Nature immunology 9, 369-377.
Shibata, R., Kawamura, M., Sakai, H., Hayami, M., Ishimoto, A., and Adachi, A. (1991). Generation of a chimeric human and simian immunodeficiency virus infectious to monkey peripheral blood mononuclear cells. J Virol 65, 3514-3520.
Shizuru, J. A., Weissman, I. L., Kernoff, R., Masek, M., and Scheffold, Y. C. (2000). Purified hematopoietic stem cell grafts induce

(56) References Cited

OTHER PUBLICATIONS tolerance to alloantigens and can mediate positive and negative T cell selection. Proc Natl Acad Sci USA 97, 9555-9560.
Shultz, L. D., Lyons, B. L., Burzenski, L. M., Gott, B., Chen, X., Chaleff, S., Kotb, M., Gillies, S. D. King, M., Mangada, J., et al. (2005). Human lymphoid and myeloid cell development in NOD/LtSz-scid IL2R gamma null mice engrafted with mobilized human hemopoietic stem cells. J Immunol 174, 6477-6489.
Simon, J. H., Gaddis, N. C., Fouchier, R. A., and Malim, M. H. (1998a). Evidence for a newly discovered cellular anti-HIV-1 phenotype. Nature medicine 4, 1397-1400.
Simon, J. H., Miller, D. L., Fouchier, R. A., Soares, M. A., Peden, K. W., and Malim, M. H. (1998). The regulation of primate immunodeficiency virus infectivity by Vif is cell species restricted: a role for Vif in determining virus host range and cross-species transmission. The EMBO journal 17, 1259-1267.
Simon, J. H., Southerling, T. E., Peterson, J. C., Meyer, B. E., and Malim, M. H. (1995). Complementation of vif-defective human immunodeficiency virus type 1 by primate, but not nonprimate, lentivirus vif genes. J Virol 69, 4166-4172.
Skowronski, J., Parks, D., and Mariani, R. (1993). Altered T cell activation and development in transgenic mice expressing the HIV-1 nef gene. The EMBO journal 12, 703-713.
Sokolskaja, E., Sayah, D. M., and Luban, J. (2004). Target cell cyclophilin a modulates human immunodeficiency virus type 1 infectivity. J Virol 78, 12800-12808.
Song et al., "Retrovirus restriction by TRIM5alpha variants from old world and new world primates," *J Virol* 79:3930-3937 (2005).
Song, B., Diaz-Griffero, F., Park, D. H., Rogers, T., Stremlau, M., and Sodroski, J. (2005a). TRIM5alpha association with cytoplasmic bodies is not required for antiretroviral activity. Virology 343, 201-211.
Song, B., et al. The B30.2(SPRY) domain of the retroviral restriction factor TRIM5alpha exhibits lineage-specific length and sequence variation in primates. Journal of Virology 79, 6111-6121 (2005).
Soros, V. B., Yonemoto, W., and Greene, W. C. (2007). Newly synthesized APOBEC3G is incorporated into HIV virions, inhibited by HIV RNA, and subsequently activated by RNase H. PLoS pathogens 3, e15, 0152-0167.
Sourisseau, M., Sol-Foulon, N., Porrot, F., Blanchet, F., and Schwartz, O. (2007). Inefficient human immunodeficiency virus replication in mobile lymphocytes. J Virol 81, 1000-1012.
Stegmeier, F., Hu, G., Rickles, R. J., Hannon, G. J., and Elledge, S. J. (2005). A lentiviral microRNA-based system for single-copy polymerase II-regulated RNA interference in mammalian cells. Proc Natl Acad Sci USA 102, 13212-13217.
Stern et al., "Five SWI genes are required for expression of the HO gene in yeast," J. Mol. Bioi. 178:853-868 (1984).
Stetson, D. B., Ko, J. S., Heidmann, T., and Medzhitov, R. (2008). Trex1 prevents cell-intrinsic initiation of autoimmunity. Cell 134, 21 pgs.
Stoddart, C. A., Bales, C. A., Bare, J. C., Chkhenkeli, G., Galkina, S. A., Kinkade, A. N., Moreno, M. E., Rivera, J. M., Ronquillo, R. E., Sloan, B., et al. (2007). Validation of the SCID-hu Thy/Liv mouse model with four classes of licensed antiretrovirals. PLoS ONE 2, e655, 1-11.
Stopak, K. S., Chiu, Y. L., Kropp, J., Grant, R. M., and Greene, W. C. (2007). Distinct patterns of cytokine regulation of APOBEC3G expression and activity in primary lymphocytes, macrophages, and dendritic cells. J Biol Chem 282, 3539-3546.
Stopak, K., de Noronha, C., Yonemoto, W., and Greene, W. C. (2003). HIV-1 Vif blocks the antiviral activity of APOBEC3G by impairing both its translation and intracellular stability. Molecular cell 12, 591-601.
Stoye, J. P. and Yap, M. W. Chance favors a prepared genome. Proc Natl Acad Sci 105, 3177-3178 (2008).
Stoye, J. P.,"An intracellular block to primate lentivirus replication," Proc. Natl. Acad. Sci. USA 99:11549-11551 (2002).
Strayer, D. S., et al. Current status of gene therapy strategies to treat HIV/AIDS. Mol Ther 11, 823-842 (2005).
Strebel, K. (2005). APOBEC3G and HTLV-1: inhibition without deamination. Retrovirology 2:37, 3 pages.
Strebel, K., Daugherty, D., Clouse, K., Cohen, D., Folks, T., and Martin, M. A. (1987). The HIV 'A' (sor) gene product is essential for virus infectivity. Nature 328, 728-730.
Strebel, K., Klimkait, T., Maldarelli, F., and Martin, M. A. (1989). Molecular and biochemical analysis of human immunodeficiency virus type 1 vpu protein. J Virol 63, 3784-3791.
Stremlau, M., et al. Specific recognition and accelerated uncoating of retroviral capsids by the TRIM5alpha restriction factor. Proc Natl Acad Sci 103, 5514-5519 (2006).
Stremlau, M., et al. The cytoplasmic body component TRIM5alpha restricts HIV-1 infection in Old World monkeys. Nature 427, 848-853 (2004).
Stremlau, M., Perron, M., Lee, M., Li, Y., Song, B., Javanbakht, H., Diaz-Griffero, F., Anderson, D. J., Sundquist, W. I., and Sodroski, J. (2006). Specific recognition and accelerated uncoating of retroviral capsids by the TRIM5 alpha restriction factor. Proc Natl Acad Sci USA 103, 5514-5519.
Stremlau, M., Perron, M., Welikala, S. and Sodroski, J. Species-specific variation in the B30.2(SPRY) domain of TRIM5alpha determines the potency of human immunodeficiency virus restriction. Journal of Virology 79, 3139-3145 (2005).
Sun, J., Soos, T., Kewalramani, V. N., Osiecki, K., Zheng, J. H., Falkin, L., Santambrogio, L., Littman, D. R., and Goldstein, H. (2006). CD4-specific transgenic expression of human cyclin T1 markedly increases human immunodeficiency virus type 1 (HIV-1) production by CD4+ T lymphocytes and myeloid cells in mice transgenic for a provirus encoding a monocyte-tropic HIV-1 isolate. J Virol 80, 1850-1862.
Sun, Z., Denton, P. W., Estes, J. D., Othieno, F. A., Wei, B. L., Wege, A. K., Melkus, M. W., Padgett-Thomas, A., Zupancic, M., Haase, A. T., et al. (2007). Intrarectal transmission, systemic infection, and CD4+ T cell depletion in humanized mice infected with HIV-1. The Journal of experimental medicine 204, 705-714.
Taylor, B. M., et al. An alteration of human immunodeficiency virus gp41 leads to reduced CCR5 dependence and CD4 independence. Journal of Virology 82, 5460-5471 (2008).
Terwilliger, E. F., Cohen, E. A., Lu, Y. C., Sodroski, J. G., and Haseltine, W. A. (1989). Functional role of human immunodeficiency virus type 1 vpu. Proc Natl Acad Sci U S A 86, 5163-5167.
Thali, M. et al. "Functional association of cyclophilin a with HIV-1 virions," Nature 372, 363-365 (1994).
Tissot, C., and Mechti, N. (1995). Molecular cloning of a new interferon-induced factor that represses human immunodeficiency virus type 1 long terminal repeat expression. J Biol Chem 270, 14891-14898.
Towers et al., "Abrogation of Ref1 retrovirus restriction in human cells," J Virol 76:2548-2550 (2002).
Towers, G. J., Hatziioannou, T., Cowan, S., Goff, S. P., Luban, J., and Bieniasz, P. D. (2003). Cyclophilin A modulates the sensitivity of HIV-1 to host restriction factors. Nature medicine 9, 1138-1143.
Towers, G., Bock, M., Martin, S., Takeuchi, Y., Stoye, J. P., and Danos, O. (2000). A conserved mechanism of retrovirus restriction in mammals. Proc Natl Acad Sci USA 97, 12295-12299.
Turelli, P., Vianin, S., and Trono, D. (2004b). The innate antiretroviral factor APOBEC3G does not affect human LINE-1 retrotransposition in a cell culture assay. J Biol Chem 279, 43371-43373.
Uchil, P. D., Quinlan, B. D., Chan, W. T., Luna, J. M., and Mothes, W. (2008). TRIM E3 ligases interfere with early and late stages of the retroviral life cycle. PLoS pathogens 4, e16, 1-13.
Unutmaz, D., KewalRamani, V. N., Marmon, S., and Littman, D. R. (1999). Cytokine signals are sufficient for HIV-1 infection of resting human T lymphocytes. The Journal of experimental medicine 189, 1735-1746.
Van Damme, N., Goff, D., Katsura, C., Jorgenson, R. L., Mitchell, R., Johnson, M. C., Stephens, E. B., and Guatelli, J. (2008). The interferon-induced protein BST-2 restricts HIV-1 release and is downregulated from the cell surface by the viral Vpu protein. Cell host and microbe 3, 17 pgs.

(56) References Cited

OTHER PUBLICATIONS van Rijn, R. S., et al. A new xenograft model for graft-versus-host disease by intravenous transfer of human peripheral blood mononuclear cells in RAG2-/- gammac-/- double-mutant mice. Blood 102, 2522-2531 (2003).
Varthakavi, V., Heimann-Nichols, E., Smith, R. M., Sun, Y., Bram, R. J., Ali, S., Rose, J., Ding, L., and Spearman, P. (2008). Identification of calcium-modulating cyclophilin ligand as a human host restriction to HIV-1 release overcome by Vpu. Nature medicine 14, 641-647.
Varthakavi, V., Smith, R. M., Bour, S. P., Strebel, K., and Spearman, P. (2003). Viral protein U counteracts a human host cell restriction that inhibits HICV-1 particle production. Proc Natl Acad Sci USA 100, 15154-15159.
Virgen, C. A., Kratovac, Z., Bieniasz, P. D., and Hatziioannou, T. (2008). Independent genesis of chimeric TRIM5-cyclophilin proteins in two primate species. Proc Natl Acad Sci U S A 105, 3563-3568.
von Laer, D., Hasselmann, S., and Hasselmann, K. (2006). Gene therapy for HIV infection: what does it need to make it work? J Gene Med 8, 658-667.
von Laer, D., Hasselmann, S., and Hasselmann, K. (2006). Impact of gene-modified T cells on HIV infection dynamics. J Theor Biol 238, 60-77.
Walker, R. E., Bechtel, C. M., Natarajan, V., Baseler, M., Hege, K. M., Metcalf, J. A., Stevens, R., Hazen, A., Blaese, R. M., Chen, C. C., et al. (2000). Long-term in vivo survival of receptor-modified modified syngeneic T cells in patients with human immunodeficiency virus infection. Blood 96, 467-474.
Wang, L., Menendez, P., Shojaei, F., Li, L., Mazurier, F., Dick, J. E., Cerdan, C., Levac, K., and Bhatia, M. (2005). Generation of hematopoietic repopulating cells from human embryonic stem cells independent of ectopic HOXB4 expression. The Journal of experimental medicine 201, 1603-1614.
Watanabe, S., Terashima, K., Ohta, S., Horibata, S., Yajima, M., Shiozawa, Y., Dewan, M. Z., Yu, Z., Ito, M., Mario, T., et al. (2007). Hematopoietic stem cell-engrafted NOD/SCID/IL2Rgamma null mice develop human lymphoid systems and induce long-lasting HIV-1 infection with specific humoral immune responses. Blood 109, 212-218.
Wei, W. et al., "Human L 1 retrotransposition: cis preference versus trans complementation," Mol. Cell. Bioi. 21, 1429-1439 (2001).
Welker et al,"Biochemical and structural analysis of isolated mature cores of human immunodeficiency virus type 1," J Virol 74:1168-1177 (2000).
Wilson, S. J., Webb, B. L., Ylinen, L. M., Verschoor, E., Heeney, J. L., and Towers, G. J. (2008). Independent evolution of an antiviral TRIMCyp in rhesus macaques. Proc Natl Acad Sci USA 105, 3557-3562.
Wolf, D., and Goff, S. P. (2008). Host Restriction Factors Blocking Retroviral Replication. Annu Rev Genet 42, 25 pgs.
Wolff et al., "Direct Gene Transfer in Mouse Muscle in vivo," Science 247:1465-1468 (1990).
Woo, J. S., et al. Structural and functional insights into the B30.2/SPRY domain. EMBO J 25, 1353-1363 (2006).
Wu et al., "Nup358, a cytoplasmically exposed nucleoporin with peptide repeats, Ran-GTP binding sites, zinc fingers, a cyclophilin A homologous domain, and a leucine-rich region," J. Biol. Chem. 270, 14209-14213 (1995).
Wu, X., Anderson, J. L., Campbell, E. M., Joseph, A. M., and Hope, T. J. (2006). Proteasome inhibitors uncouple rhesus TRIM5 alpha restriction of HIV-1 reverse transcription and infection. Proc Natl Acad Sci USA 103, 7465-7470.
Xu, L., Yang, L., Moitra, P. K., Hashimoto, K., Rallabhandi, P., Kaul, S., Meroni, G., Jensen, J. P., Weissman, a. M., and D'Arpa, P. (2003). BTBD1 and BTBD2 colocalize to cytoplasmic bodies with the RBCC/tripartite motif protein, TRIM5delta. Exp Cell Res 288, 84-93.
Yamashita, M., Perez, O., Hope, T. J., and Emerman, M. (2007). Evidence for direct involvement of the capsid protein in HIV infection of nondividing cells. PLoS pathogens 3, 1502-1510.
Yang, B., Chen, K., Zhang, C., Huang, S., and Zhang, H. (2007). Virion-associated uracil DNA glycosylase-2 and apurinic/apyrimidinic endonuclease are involved in the degradation of APOBEC3G-edited nascent HIV-1 DNA. J Biol Chem 282, 11667-11675.
Yang, L., Bailey, L., Baltimore, D., and Wang, P. (2006). Targeting lentiviral vectors to specific cell types in vivo. Proc Natl Acad Sci USA 103, 11479-11484.
Yap, M. W., Dodding, M. P., and Stoye, J. P. (2006). Trim-cyclophilin a fusion proteins can restrict human immunodeficiency virus type 1 infection at two distinct phases in the viral life cycle. J Virol 80, 4061-4067.
Yap, M. W., Mortuza, G. B., Taylor, I. A., and Stoye, J. P. (2007). The design of artificial retroviral restriction factors. Virology 365, 302-314.
Yap, M. W., Nisole, S. and Stoye, J. P. A single amino acid change in the SPRY domain of human Trim5alpha leads to HIV-1 restriction. Curr Biol 15, 73-78 (2005).
Yap, M. W., Nisole, S., Lynch, C., and Stoye, J. P. (2004). Trim5alpha protein restricts both HIV-1 and murine leukemia virus. Proc Natl Acad Sci USA 101, 10786-10791.
Yin, L., Braaten, D., and Luban, J. (1998). Human immunodeficiency virus type 1 replication is modulated by host cyclophilin a expression levels. J Virol 72, 6430-6436.
Yoneyama, M., Kikuchi, M., Matsumoto, K., Imaizumi, T., Miyagishi, M., Taira, K., Foy, E., Loo, Y. M., Gale, M., Jr., Akira, S., et al. (2005). Shared and unique functions of the DExD/H-box helicases RIG-I, MDA5, and LGP2 in antiviral innate immunity. J Immunol 175, 2851-2858.
Zennou et al., "Hiv-1 genome nuclear import is mediated by a central DNA flap," Cell 101:173-185 (2000).
Zennou, V., Perez-Caballero, D., Gottlinger, H., and Bieniasz, P. D. (2004). APOBEC3G incorporation into human immunodeficiency virus type 1 particles. J Virol 78, 12058-12061.
Zhang et al., "Millions of years of evolution preserved: a comprehensive catalog of the processed pseudogenes in the human genome," Genome Res. 13, 2541-2558 (2003).
Zhang, B. W., Zimmer, G., Chen, J., Ladd, D., Li, E., Alt, F. W., Wiederrecht, G., Cryan, J., O'Neill, E. A., Seidman, C. E., et al. (1996). T cell responses in calcineurin A alpha-deficient mice. The Journal of experimental medicine 183, 413-420.
Zhang, F., Hatziioannou, T., Perez-Caballero, D., Derse, D. and Bieniasz, P. D. Antiretroviral potential of human tripartite motif-5 and related proteins. Virology 353, 396-409 (2006).
Zhang, F., Perez-Caballero, D., Hatziioannou, T., and Bieniasz, P. D. (2008a). No effect of endogenous TRIM5alpha on HIV-1 production. Nature medicine 14, 235-236.
Zhang, H., Yang, B., Pomerantz, R. J., Zhang, C., Arunachalam, S. C., and Gao, L. (2003). The cytidine deaminase CEM15 induces hypermutation in newly synthesized HIV-1 DNA. Nature 424, 12 pgs.
Zhang, J. X., Diehl, G. E., and Littman, D. R. (2008b). Relief of preintegration inhibition and characterization of additional blocks for HIV replication in primary mouse T cells. PLoS ONE 3, e2035, 1-15.
Zhang, J., Scadden, D. T., and Crumpacker, C. S. (2007). Primitive hematopoietic cells resist HIV-1 infection via p21. The Journal of clinical investigation 117, 473-481.
Zielske, S. P., Reese, J. S., Lingas, K. T., Donze, J. R., and Gerson, S. L. (2003). In vivo selection of MGMT (P140K) lentivirus-transduced human NOD/SCID repopulating cells without pretransplant irradiation conditioning. The Journal of clinical investigation 112, 1561-1570.
Zinkernagel, R. M., and Althage, a. (1999). On the role of thymic epithelium vs. bone marrow-derived cells in repertoire selection of T cells. Proc Natl Acad Sci USA 96, 8092-8097.

* cited by examiner

```
   1 gcggttcctc taggaaaatt cctttgtgca gatcaggccc gtggattggt gagtgaatcc
  61 taaccacgtc ttccctggcc tgtcttcact cttctcccca gaatcaccac ttctgcactg
 121 gtgtctgaag gtgtattgag tgattttgtg gagggcagaa gtaggaagtc tttgggacaa
 181 aactgtattt accttgggat ctgtgaacaa gaggaacctc agcagccagg acaggcagga
 241 gcagtggaat agctactatg gcttctggaa tcctggttaa tgtaaaggag gaggtgacct
 301 gccccatctg cctggaactc ctgacacaac ccctgagcct ggactgcggc cacagcttct
 361 gccaagcatg cctcactgca aaccacaaga agtccatgct agacaaagga gagagtagct
 421 gccctgtgtg ccggatcagt taccagcctg agaacatacg gcctaatcgg catgtagcca
 481 acttagtgga gaagctcagg gaggtcaagt tgagcccaga ggggcagaaa gttgatcatt
 541 gtgcacgcca tggagagaaa cttctactct tctgtcagga ggacgggaag gtcatttgct
 601 ggctttgtga gcggtctcag gagcaccgtg gtcaccacac gttccccaca gaggaggttg
 661 cccaggagta ccaagtgaag ctccaggcag ctctggagat gctgaggcag aagcagcagg
 721 aagctgaaga gttggaagct gacatcagag aagagaaagc ttcctggaag actcaaatac
 781 agtatgacaa aaccaacgtc ttggcagatt ttgagcaact gagagacatc ctggactggg
 841 aggagagcaa tgagctgcaa aacctggaga aggaggagga agacattctg aaaagcctta
 901 cgaactctga aactgagatg gtgcagcaga cccagtccct gagagagctc atctcagatc
 961 tggagcatcg gctgcagggg tcagtgatgg agctgcttca gggtgtggat ggcgtcataa
1021 aaaggacgga gaacgtgacc ttgaagaagc cagaaacttt tccaaaaaat caaaggagag
1081 tgtttcgagc tcctgatctg aaaggaatgc tagaagtgtt tagagagctg acagatgtcc
1141 gacgctactg ggttgatgtg acagtggctc caaacaacat ttcatgtgct gtcatttctg
1201 aagataagag acaagtgagc tctccgaaac cacagataat atatggggca cgagggacaa
1261 gataccagac atttgtgaat ttcaattatt gtactggcat cctgggctct caaagtatca
1321 catcagggaa acattactgg gaggtagacg tgtccaagaa aactgcttgg atcctggggg
1381 tatgtgctgg cttccaacct gatgcaatgt gtaatattga aaaaaatgaa aattatcaac
1441 ctaaatacgg ctactgggtt atagggttag aggaaggagt taaatgtagt gctttccagg
1501 atagttcctt ccatactcct tctgttcctt tcattgtgcc cctctctgtg attatttgtc
1561 ctgatcgtgt tggagttttc ctagactatg aggcttgcac tgtctcattc ttcaatatca
1621 caaaccatgg atttctcatc tataagtttt ctcactgttc tttttctcag cctgtatttc
1681 catatttaaa tcctagaaaa tgtggagtcc ccatgactct gtgctcacca agctcttgaa
1741 ccttcttaca cactcagccc cttctgtaca gcacctcttg tccaggtgca tctcatacac
1801 ctgaactcat ttgcatcatt ttaaccatct tttccttgct gtctcccttc tttctatttg
1861 aacgtccttc actcatcagt aaaatgtaat aattgccttg tgccatattg tccccaatat
1921 tttattgaca tttgatagca atttttttca tcattttccg tactcctaag gaaaactgac
1981 ctatacctca taaaatgaga ccgctattta ggtattactt ctgccagata tttatcaccc
2041 aattgcctct gacactgact aagaagatga agaaaagctt ttcaacagcc tttctatatc
2101 atcgtgtgat aattgttcac caatgaatga gtccttagcc ctgtgtcagt ttaccctcga
2161 tgcccttatt tgtgagttaa agagaaaata tcataaatgg tatactctta agtatagagg
2221 ttttgtatct agaggatctc agttcaactc ctgtctctcc atataccagc agtgtaactg
2281 tgaataacat acttaaatgg ctgtgcttat ttccttttct tttctttttt cttttttttt
2341 tttttgaga tgaagttttg ctcttgttcc ccaggctgga gtgcaatggc acgatctcgg
2401 ttcactgcaa cctccacctc tcagattcaa gcaattctcc tgcctcagcc tcccaagtag
2461 ctgggattac aggtgcccac caccaccccct ggctaaattt gtattttcag tagagacggg
2521 gtttccccat gttggttagg ctcgtctaga acctctgacc tcaggtgatc cacccgcctc
2581 ggcctcccaa agtgctggga ttacaggcgt gagccacggc gcccagcctg tgcttatttt
2641 cttaaaataa tttttgtatt aaaaacttca cattaaataa gtgctaatgt tttattgcat
2701 agtagggtga ctagagttaa caataaccta ttgcatatat tttgaaatag ctagaagaga
2761 ggattttgaa agttctcaac acaaagaaac gacacatatt tgaggtgatg gatatgctaa
2821 ttaccctggt tcggttatta cgcaatgtat acatgtatca aaacatcaca ctgtaccaca
2881 taaatatgta tatttattat ttgtcaatta aaagcaaaat aaaacaaaaa accttcatct
2941 aatactttgg atcattgtga aaaaataaat tcctgaagta taaagcatct (SEQ ID NO:1)
```

FIG. 13

```
  1 masgilvnvk eevtcpicle lltqplsldc ghsfcqaclt anhkksmldk gesscpvcri
 61 syqpenirpn rhvanlvekl revklspegq kvdhcarhge klllfcqedg kvicwlcers
121 qehrghhtfp teevaqeyqv klqaalemlr qkqqeaeele adireekasw ktqiqydktn
181 vladfeqlrd ildweesnel qnlekeeedi lksltnsete mvqqtqslre lisdlehrlq
241 gsvmellqgv dgvikrtenv tlkkpetfpk nqrrvfrapd lkgmlevfre ltdvrrywvd
301 vtvapnnisc avisedkrqv sspkpqiiyg argtryqtfv nfnyctgilg sqsitsgkhy
361 wevdvskkta wilgvcagfq pdamcniekn enyqpkygyw vigleegvkc safqdssfht
421 psvpfivpls viicpdrvgv fldyeactvs ffnitnhgfl iykfshcsfs qpvfpylnpr
481 kcgvpmtlcs pss (SEQ ID NO:2)
```

FIG. 14

```
   1 gaacgtggta taaaaggggc gggaggccag gctcgtgccg ttttgcagac gccaccgccg
  61 aggaaaaccg tgtactatta gccatggtca accccaccgt gttcttcgac attgccgtcg
 121 acggcgagcc cttgggccgc gtctcctttg agctgtttgc agacaaggtc ccaaagacag
 181 cagaaaattt tcgtgctctg agcactggag agaaaggatt tggttataag ggttcctgct
 241 ttcacagaat tattccaggg tttatgtgtc agggtggtga cttcacacgc cataatggca
 301 ctggtggcaa gtccatctat ggggagaaat ttgaagatga gaacttcatc ctaaagcata
 361 cgggtcctgg catcttgtcc atggcaaatg ctggacccaa cacaaatggt tcccagtttt
 421 tcatctgcac tgccaagact gagtggttgg atggcaagca tgtggtgttt ggcaaagtga
 481 aagaaggcat gaatattgtg gaggccatgg agcgctttgg gtccaggaat ggcaagacca
 541 gcaagaagat caccattgct gactgtggac aactcgaata agtttgactt gtgttttatc
 601 ttaaccacca gatcattcct tctgtagctc aggagagcac ccctccaccc catttgctcg
 661 cagtatccta gaatctttgt gctctcgctg cagttccctt tgggttccat gttttccttg
 721 ttccctccca tgcctagctg gattgcagag ttaagtttat gattatgaaa taaaaactaa
 781 ataacaattg tcctcgtttg agttaagagt gttgatgtag gctttatttt aagcagtaat
 841 gggttacttc tgaaacatca cttgtttgct taattctaca cagtacttag attttttta
 901 ctttccagtc ccaggaagtg tcaatgtttg ttgagtggaa tattgaaaat gtaggcagca
 961 actgggcatg gtggctcact gtctgtaatg tattacctga ggcagaagac cacctgaggg
1021 taggagtcaa gatcagcctg ggcaacatag tgagacgctg tctctacaaa aaataattag
1081 cctggcctgg tggtgcatgc ctagtcctag ctgatctgga ggctgacgtg ggaggattgc
1141 ttgagcctag agtgagctat tatcatgcca ctgtacagcc tgggtgttca cagatcttgt
1201 gtctcaaagg taggcagagg caggaaaagc aaggagccag aattaagagg ttgggtcagt
1261 ctgcagtgag ttcatgcatt tagaggtgtt cttcaagatg actaatgtca aaaattgaga
1321 catctgttgc ggtttttttt tttttttttt cccctggaat gcagtggcgt gatctcagct
1381 cactgcagcc tccgcctcct gggttcaagt gattctagtg cctcagcctc ctgagtagct
1441 gggataatgg gcgtgtgcca ccatgcccag ctaatttttg tatttttagt atagatgggg
1501 tttcatcatt ttgaccaggc tggtctcaaa ctcttgacct cagctgatgc gcctgccttg
1561 gcctcccaaa ctgctgagat tacagatgtg agccaccgca ccctacctca ttttctgtaa
1621 caaagctaag cttgaacact gttgatgttc ttgagggaag catattgggc tttaggctgt
1681 aggtcaagtt tatacatctt aattatggtg gaattcctat gtagagtcta aaaagccagg
1741 tacttggtgc tacagtcagt ctccctgcag agggttaagg cgcagactac ctgcagtgag
1801 gaggtactgc ttgtagcata tagagcctct ccctagcttt ggttatggag gctttgaggt
1861 tttgcaaacc tgaccaattt aagccataag atctggtcaa agggataccc ttcccactaa
1921 ggacttggtt tctcaggaaa ttatatgtac agtgcttgct ggcagttaga tgtcaggaca
1981 atctaagctg agaaaacccc ttctctgccc accttaacag acctctaggg ttcttaaccc
2041 agcaatcaag tttgcctatc ctagaggtgg cggatttgat catttggtgt gttgggcaat
2101 ttttgtttta ctgtctggtt ccttctgcgt gaattaccac caccaccact tgtgcatctc
2161 agtcttgtgt gttgtctggt tacgtattcc ctgggtgata ccattcaatg tcttaatgta
2221 cttgtggctc agacctgagt gcaaggtgga aataaacatc aaacatcttt tcatta (SEQ
ID NO:3)
```

FIG. 15

```
   1 mvnptvffdi avdgeplgrv sfelfadkvp ktaenfrals tgekgfgykg scfhriipgf
  61 mcqggdftrh ngtggksiyg ekfedenfil khtgpgilsm anagpntngs qffictakte
 121 wldgkhvvfg kvkegmnive amerfgsrng ktskkitiad cgqle (SEQ ID NO:4)
```

FIG. 16 hT5-A331-Cyp-
ATGGCTTCTGGAATCCTGGTTAATGTAAAGGAGGAGGTGACCTGCCCCATCTGCCTGGAACT
CCTGACACAACCCCTGAGCCTGGACTGCGGCCACAGCTTCTGCCAAGCATGCCTCACTGCAA
ACCACAAGAAGTCCATGCTAGACAAAGGAGAGAGTAGCTGCCCTGTGTGCCGGATCAGTTAC
CAGCCTGAGAACATACGGCCTAATCGGCATGTAGCCAACTTAGTGGAGAAGCTCAGGGAGGT
CAAGTTGAGCCCAGAGGGGCAGAAAGTTGATCATTGTGCACGCCATGGAGAGAAACTTCTAC
TCTTCTGTCAGGAGGACGGGAAGGTCATTTGCTGGCTTTGTGAGCGGTCTCAGGAGCACCGT
GGTCACCACACGTTCCCCACAGAGGAGGTTGCCCAGGAGTACCAAGTGAAGCTCCAGGCAGC
TCTGGAGATGCTGAGGCAGAAGCAGCAGGAAGCTGAAGAGTTGGAAGCTGACATCAGAGAAG
AGAAAGCTTCCTGGAAGACTCAAATACAGTATGACAAAACCAACGTCTTGGCAGATTTTGAG
CAACTGAGAGACATCCTGGACTGGGAGGAGAGCAATGAGCTGCAAAACCTGGAGAAGGAGGA
GGAAGACATTCTGAAAAGCCTTACGAACTCTGAAACTGAGATGGTGCAGCAGACCCAGTCCC
TGAGAGAGCTCATCTCAGATCTGGAGCATCGGCTGCAGGGGTCAGTGATGGAGCTGCTTCAG
GGTGTGGATGGCGTCATAAAAAGGACGGAGAACGTGACCTTGAAGAAGCCAGAAACTTTTCC
AAAAAATCAAAGGAGAGTGTTTCGAGCTCCTGATCTGAAAGGAATGCTAGAAGTGTTTAGAG
AGCTGACAGATGTCCGACGCTACTGGGTTGATGTGACAGTGGCTCCAAACAACATTTCATGT
GCTGTCATTTCTGAAGATAAGAGACAAGTGAGCTCTCCGAAACCACAGATAATATATGGGGC
AGTCAACCCCACCGTGTTCTTCGACATTGCCGTCGACGGCGAGCCCTTGGGCCGCGTCTCCT
TTGAGCTGTTTGCGACAAGGTCCCAAAGACAGCAGAAAATTTTCGTGCTCTGAGCACTGGAG
AGAAAGGATTTGGTTATAAGGGTTCCTGCTTTCACAGAATTATTCCAGGGTTTATGTGTCAG
GGTGGTGACTTCACACGCCATAATGGCACTGGTGGCAAGTCCATCTATGGGGAGAAATTTGA
AGATGAGAACTTCATCCTAAAGCATACGGGTCCTGGCATCTTGTCCATGGCAAATGCTGGAC
CCAACACAAATGGTTCCCAGTTTTTCATCTGCACTGCCAAGACTGAGTGGTTGGATGGCAAG
CATGTGGTGTTTGGCAAAGTGAAAGAAGGCATGAATATTGTGGAGGCCATGGAGCGCTTTGG
GTCCAGGAATGGCAAGACCAGCAAGAAGATCACCATTGCTGACTGTGGACAACTCGAATAA
(SEQ ID NO:5)

M A S G I L V N V K E E V T C P I C L E L L T Q P L S L D C G H S F C Q A C L T A N
H K K S M L D K G E S S C P V C R I S Y Q P E N I R P N R H V A N I V E K L R E V K
L S P E G Q K V D H C A R H G E K L L L F C Q E D G K V I C W L C E R S Q E H R G
H H T F L T E E V A R E Y Q V K L Q A A L E M L R Q K Q Q E A E E L E A D I R E E
K A S W K T Q I Q Y D K T N V L A D F E Q L R D I L D W E E S N E L Q N L E K E E
E D I L K S L T N S E T E M V Q Q T Q S L R E L I S D L E H R L Q G S V M E L L Q G
V D G V I K R T E N V T L K K P E T F P K N Q R R V F R A P D L K G M L E V F R E
L T D V R R Y W V D V T V A P N N I S C A V I S E D K R Q V S S P K P Q I I Y G A V
N P T V F F D I A V D G E P L G R V S F E L F A D K V P K T A E N F R A L S T G E K
G F G Y K G S C F H R I I P G F M C Q G G D F T R H N G T G G K S I Y G E K F E D E
N F I L K H T G P G I L S M A N A G P N T N G S Q F F I C T A K T E W L D G K H V
V F G K V K E G M N I V E A M E R F G S R N G K T S K K I T I A D C G Q L E (SEQ
ID NO:10)

FIG. 17

>hTC_S309.fa -
ATGGCTTCTGGAATCCTGGTTAATGTAAAGGAGGAGGTGACCTGCCCCATCTGCCTGGAACT
CCTGACACAACCCCTGAGCCTGGACTGCGGCCACAGCTTCTGCCAAGCATGCCTCACTGCAA
ACCACAAGAAGTCCATGCTAGACAAAGGAGAGAGTAGCTGCCCTGTGTGCCGGATCAGTTAC
CAGCCTGAGAACATACGGCCTAATCGGCATGTAGCCAACATAGTGGAGAAGCTCAGGGAGGT
CAAGTTGAGCCCAGAGGGGCAGAAAGTTGATCATTGTGCACGCCATGGAGAGAAACTTCTAC
TCTTCTGTCAGGAGGACGGGAAGGTCATTTGCTGGCTTTGTGAGCGGTCTCAGGAGCACCGT
GGTCACCACACGTTCCTCACAGAGGAGGTTGCCCGGGAGTACCAAGTGAAGCTCCAGGCAGC
TCTGGAGATGCTGAGGCAGAAGCAGCAGGAAGCTGAAGAGTTGGAAGCTGACATCAGAGAAG
AGAAAGCTTCCTGGAAGACTCAAATACAGTATGACAAAACCAACGTCTTGGCAGATTTTGAG
CAACTGAGAGACATCCTGGACTGGGAGGAGAGCAATGAGCTGCAAAACCTGGAGAAGGAGGA
GGAAGACATTCTGAAAAGCCTTACGAACTCTGAAACTGAGATGGTGCAGCAGACCCAGTCCC
TGAGAGAGCTCATCTCAGATCTGGAGCATCGGCTGCAGGGGTCAGTGATGGAGCTGCTTCAG
GGTGTGGATGGCGTCATAAAAAGGACGGAGAACGTGACCTTGAAGAAGCCAGAAACTTTTCC
AAAAAATCAAAGGAGAGTGTTTCGAGCTCCTGATCTGAAAGGAATGCTAGAAGTGTTTAGAG
AGCTGACAGATGTCCGACGCTACTGGGTTGATGTGACAGTGGCTCCAAACAACATTTCAGTC
AACCCCACCGTGTTCTTCGACATTGCCGTCGACGGCGAGCCCTTGGGCCGCGTCTCCTTTGA
GCTGTTTGCAGACAAGGTCCCAAAGACAGCAGAAAATTTTCGTGCTCTGAGCACTGGAGAGA
AAGGATTTGGTTATAAGGGTTCCTGCTTTCACAGAATTATTCCAGGGTTTATGTGTCAGGGT
GGTGACTTCACACGCCATAATGGCACTGGTGGCAAGTCCATCTATGGGGAGAAATTTGAAGA
TGAGAACTTCATCCTAAAGCATACGGGTCCTGGCATCTTGTCCATGGCAAATGCTGGACCCA
ACACAAATGGTTCCCAGTTTTTCATCTGCACTGCCAAGACTGAGTGGTTGGATGGCAAGCAT
GTGGTGTTTGGCAAAGTGAAAGAAGGCATGAATATTGTGGAGGCCATGGAGCGCTTTGGGTC
CAGGAATGGCAAGACCAGCAAGAAGATCACCATTGCTGACTGTGGACAACTCGAATAA
(SEQ ID NO:6)

M A S G I L V N V K E E V T C P I C L E L L T Q P L S L D C G H S F C Q A C L T A N
H K K S M L D K G E S S C P V C R I S Y Q P E N I R P N R H V A N I V E K L R E V K
L S P E G Q K V D H C A R H G E K L L L F C Q E D G K V I C W L C E R S Q E H R G
H H T F L T E E V A R E Y Q V K L Q A A L E M L R Q K Q Q E A E E L E A D I R E E
K A S W K T Q I Q Y D K T N V L A D F E Q L R D I L D W E E S N E L Q N L E K E E
E D I L K S L T N S E T E M V Q Q T Q S L R E L I S D L E H R L Q G S V M E L L Q G
V D G V I K R T E N V T L K K P E T F P K N Q R R V F R A P D L K G M L E V F R E
L T D V R R Y W V D V T V A P N N I S V N P T V F F D I A V D G E P L G R V S F E
L F A D K V P K T A E N F R A L S T G E K G F G Y K G S C F H R I I P G F M C Q G G
D F T R H N G T G G K S I Y G E K F E D E N F I L K H T G P G I L S M A N A G P N T
N G S Q F F I C T A K T E W L D G K H V V F G K V K E G M N I V E A M E R F G S R
N G K T S K K I T I A D C G Q L E (SEQ ID NO:11)

FIG. 18

>hT-S322-Cyp.fa -
ATGGCTTCTGGAATCCTGGTTAATGTAAAGGAGGAGGTGACCTGCCCCATCTGCCTGGAACT
CCTGACACAACCCCTGAGCCTGGACTGCGGCCACAGCTTCTGCCAAGCATGCCTCACTGCAA
ACCACAAGAAGTCCATGCTAGACAAAGGAGAGAGTAGCTGCCCTGTGTGCCGGATCAGTTAC
CAGCCTGAGAACATACGGCCTAATCGGCATGTAGCCAACATAGTGGAGAAGCTCAGGGAGGT
CAAGTTGAGCCCAGAGGGGCAGAAAGTTGATCATTGTGCACGCCATGGAGAGAAACTTCTAC
TCTTCTGTCAGGAGGACGGGAAGGTCATTTGCTGGCTTTGTGAGCGGTCTCAGGAGCACCGT
GGTCACCACACGTTCCTCACAGAGGAGGTTGCCCGGGAGTACCAAGTGAAGCTCCAGGCAGC
TCTGGAGATGCTGAGGCAGAAGCAGCAGGAAGCTGAAGAGTTGGAAGCTGACATCAGAGAAG
AGAAAGCTTCCTGGAAGACTCAAATACAGTATGACAAAACCAACGTCTTGGCAGATTTTGAG
CAACTGAGAGACATCCTGGACTGGGAGGAGAGCAATGAGCTGCAAAACCTGGAGAAGGAGGA
GGAAGACATTCTGAAAAGCCTTACGAACTCTGAAACTGAGATGGTGCAGCAGACCCAGTCCC
TGAGAGAGCTCATCTCAGATCTGGAGCATCGGCTGCAGGGGTCAGTGATGGAGCTGCTTCAG
GGTGTGGATGGCGTCATAAAAAGGACGGAGAACGTGACCTTGAAGAAGCCAGAAACTTTTCC
AAAAAATCAAAGGAGAGTGTTTCGAGCTCCTGATCTGAAAGGAATGCTAGAAGTGTTTAGAG
AGCTGACAGATGTCCGACGCTACTGGGTTGATGTGACAGTGGCTCCAAACAACATTTCATGT
GCTGTCATTTCTGAAGATAAGAGACAAGTGAGCTCTGTCAACCCCACCGTGTTCTTCGACAT
TGCCGTCGACGGCGAGCCCTTGGGCCGCGTCTCCTTTGAGCTGTTTGCAGACAAGGTCCCAA
AGACAGCAGAAAATTTTCGTGCTCTGAGCACTGGAGAGAAAGGATTTGGTTATAAGGGTTCC
TGCTTTCACAGAATTATTCCAGGGTTTATGTGTCAGGGTGGTGACTTCACACGCCATAATGG
CACTGGTGGCAAGTCCATCTATGGGGAGAAATTTGAAGATGAGAACTTCATCCTAAAGCATA
CGGGTCCTGGCATCTTATCGATGGCAAATGCTGGACCCAACACAAATGGTTCCCAGTTTTTC
ATCTGCACTGCCAAGACTGAGTGGTTGGATGGCAAGCATGTGGTGTTTGGCAAAGTGAAAGA
AGGCATGAATATTGTGGAGGCGATGGAGCGCTTTGGGTCCAGGAATGGCAAGACCAGCAAGA
AGATCACCATTGCTGACTGTGGACAACTCGAATAA (SEQ ID NO:7)

M A S G I L V N V K E E V T C P I C L E L L T Q P L S L D C G H S F C Q A C L T A N
H K K S M L D K G E S S C P V C R I S Y Q P E N I R P N R H V A N I V E K L R E V K
L S P E G Q K V D H C A R H G E K L L L F C Q E D G K V I C W L C E R S Q E H R G
H H T F L T E E V A R E Y Q V K L Q A A L E M L R Q K Q Q E A E E L E A D I R E E
K A S W K T Q I Q Y D K T N V L A D F E Q L R D I L D W E E S N E L Q N L E K E E
E D I L K S L T N S E T E M V Q Q T Q S L R E L I S D L E H R L Q G S V M E L L Q G
V D G V I K R T E N V T L K K P E T F P K N Q R R V F R A P D L K G M L E V F R E
L T D V R R Y W V D V T V A P N N I S C A V I S E D K R Q V S S V N P T V F F D I A
V D G E P L G R V S F E L F A D K V P K T A E N F R A L S T G E K G F G Y K G S C
F H R I I P G F M C Q G G D F T R H N G T G G K S I Y G E K F E D E N F I L K H T G
P G I L S M A N A G P N T N G S Q F F I C T A K T E W L D G K H V V F G K V K E G
M N I V E A M E R F G S R N G K T S K K I T I A D C G Q L E (SEQ ID NO:12)

FIG. 19 scALPS-GFP vector

GTCGACGGATCGGGAGATCTCCCGATCCCCTATGGTGCACTCTCAGTACAATCTGCTCTGAT
GCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTA
GGGTTAGGCGTTTTGCGCTGCTTCGCGATGTACGGGCCAGATATACGCGCTGTGGAATGTGT
GTCAGTTAGGGTGTGGAAAGTCCCCAGGCTCCCCAGCAGGCAGAAGTATGCAAAGCATGCAT
CTCAATTAGTCAGCAACCAGGTGTGGAAAGTCCCCAGGCTCCCCAGCAGGCAGAAGTATGCA
AAGCATGCATCTCAATTAGTCAGCAACCATAGTCCCGCCCCTAACTCCGCCCATCCCGCCCC
TAACTCCGCCCAGTTCCGCCCATTCTCCGCCCCATGGCTGACTAATTTTTTTTATTTATGCA
GAGGCCGAGGCCGCCTCTGCCTCTGAGCTATTCCAGAAGTAGTGAGGAGGCTTTTTTGGAGG
CCTAGGCTTTTGCAAAAAGCTTTGACATTGATTATTGACTAGTTATTAATAGTAATCAATTA
CGGGGTCATTAGTTCATAGCCCATATATGGAGTTCCGCGTTACATAACTTACGGTAAATGGC
CCGCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGCCC
ACTTGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCAGTA
CATCTACGTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAATGGGAGT
TTGTTTTGGCACCAAAATCAACGGGACTTTCCAAAATGTCGTAACAACTCCGCCCCATTGAC
GCAAATGGGCGGTAGGCGTGTACGGTGGGAGGTCTATATAAGCAGCGCGTTTTGCCTGTACT
GGGTCTCTCTGGTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCGTCTGTTGTGTG
ACTCTGGTAACTAGAGATCCCTCAGACCCTTTTAGTCAGTGTGGAAAATCTCTAGCAGTGGC
GCCCGAACAGGGACTTGAAAGCGAAAGGGAAACCAGAGGAGCTCTCTCGACGCAGGACTCGG
CTTGCTGAAGCGCGCACGGCAAGAGGCGAGGGGCGGCGACTGGTGAGTACGCCAAAAATTTT
GACTAGCGGAGGCTAGAAGGAGAGAGATGGGTGCGAGAGCGTCAGTATTAAGCGGGGGAGAA
TTAGATCGCGATGGGAAAAAATTCGGTTAAGGCCAGGGGGAAAGAAAAAATATAAATTAAAA
CATATAGTATGGGCAAGCAGGGAGCTAGAACGATTCGCAGTTAATCCTGGCCTGTTAGAAAC
ATCAGAAGGCTGTAGACAAATACTGGGACAGCTACAACCATCCCTTCAGACAGGATCAGAAG
AACTTAGATCATTATATAATACAGTAGCAACCCTCTATTGTGTGCATCAAAGGATAGAGATA
AAAGACACCAAGGAAGCTTTAGACAAGATAGAGGAAGAGCAAAACAAAAGTAAGACCACCGC
ACAGCAAGCggccGGCCGCTGATCTTCAGACCTGGAGGAGGAGATATGAGGGACAATTGGAG
AAGTGAATTATATAAATATAAAGTAGTAAAAATTGAACCATTAGGAGTAGCACCCACCAAGG
CAAAGAGAAGAGTGGTGCAGAGAGAAAAAAGAGCAGTGGGAATAGGAGCTTTGTTCCTTGGG
TTCTTGGGAGCAGCAGGAAGCACTATGGGCGCAGCGTCAATGACGCTGACGGTACAGGCCAG
ACAATTATTGTCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAATCCTGGCTGTG
GAAAGATACCTAAAGGATCAACAGCTCCTGGGGATTTGGGGTTGCTCTGGAAAACTCATTTG
CACCACTGCTGTGCCTTGGAATGCTAGTTGGAGTAATAAATCTCTGGAACAGATTTGGAATC
ACACGACCTGGATGGAGTGGGACAGAGAAATTAACAATTACACAAGCTTAATACACTCCTTA
ATTGAAGAATCGCAAAACCAGCAAGAAAAGAATGAACAAGAATTATTGGAATTAGATAAATG
GGCAAGTTTGTGGAATTGGTTTAACATAACAAATTGGCTGTGGTATATAAAATTATTCATAA
TGATAGTAGGAGGCTTGGTAGGTTTAAGAATAGTTTTTGCTGTACTTTCTATAGTGAATAGA
GTTAGGCAGGGATATTCACCATTATCGTTTCAGACCCACCTCCCAACCCCGAGGGGACCCGA
CAGGCCCGAAGGAATAGAAGAAGAAGGTGGAGAGAGAGACAGAGACAGATCCATTCGATTAG
TGAACGGATCGGCACTGCGTGCGCCAATTCTGCAGACAAATGGCAGTATTCATCCACAATTT
TAAAAGAAAAGGGGGGATTGGGGGGTACAGTGCAGGGGAAAGAATAGTAGACATAATAGCAA

Fig. 20A

CAGACATACAAACTAAAGAATTACAAAAACAAATTACAAAAATTCAAAATTTTCGGGTTTAT
TACAGGGACAGCAGAGATCCAGTTTGGTTAATtaaCTGCAGCCCCGATAAAATAAAAGATTT
TATTTAGTCTCCAGAAAAAGGGGGGAATGAAAGACCCCACCTGTAGGTTTGGCAAGCTAGCT
GCAGTAACGCCATTTTGCAAGGCATGGAAAAATACCAAACCAAGAATAGAGAAGTTCAGATC
AAGGGCGGGTACATGAAAATAGCTAACGTTGGGCCAAACAGGATATCTGCGGTGAGCAGTTT
CGGCCCCGGCCCGGGGCCAAGAACAGATGGTCACCGCAGTTTCGGCCCCGGCCCGAGGCCAA
GAACAGATGGTCCCCAGATATGGCCCAACCCTCAGCAGTTTCTTAAGACCCATCAGATGTTT
CCAGGCTCCCCCAAGGACCTGAAATGACCCTGCGCCTTATTTGAATTAACCAATCAGCCTGC
TTCTCGCTTCTGTTCGCGCGCTTCTGCTTCCCGAGCTCTATAAAAGAGCTCACAACCCCTCA
CTCGGCGCGCCAGTCCTCCGACAGACTGAGTCGCCCGGGGGtCTAGAAGCGCTGGATCCGTT
TAAACGCGGCCGCCCAGCACAGTGGCTCGAGCCGCGGGTTAACTGGCCAGaattctcgacct
tgactggcggcgcgaccttgaggcctgcgttcgcctcagttgccccctctgtgcaatgggga
gacgcgcctcatcgcttgacaacggccgaagagccgccgcgcttccgtctcccgcgtgcgcg
cgccatgctgcccacccccgttccgcactgaccctcccccgtgccccgcgtcccgtactgcc
gccccgccccgagtcccatgccgcagccaccgcgacggagcccgcaggcgggaacctgcctc
cgcgcgttagcgcgcacgcgcgcctcatgtgtcgtccccatcagcgccggcttccgtctata
ggccagatgcactgtcactctggcgaagtcgcagacccgattggccgggacggaggcgcgag
accgggttgcgggcggggccGAACGTGGTATAAAAGGGGCGGGAGGCCAGGCTCGTGCCGTT
TTGCAGACGCCACCGCCGAGGAAAACCGTGTACTATTAGCCacgcgtgccaccATGGCCCAG
TCCAAGCACGGCCTGACCAAGGAGATGACCATGAAGTACCGCATGGAGGGCTGCGTGGACGG
CCACAAGTTCGTGATCACCGGCGAGGGCATCGGCTACCCCTTCAAGGGCAAGCAGGCCATCA
ACCTGTGCGTGGTGGAGGGCGGCCCCTTGCCCTTCGCCGAGGACATCTTGTCCGCCGCCTTC
ATGTACGGCAACCGCGTGTTCACCGAGTACCCCCAGGACATCGTCGACTACTTCAAGAACTC
CTGCCCCGCCGGCTACACCTGGGACCGCTCCTTCCTGTTCGAGGACGGCGCCGTGTGCATCT
GCAACGCCGACATCACCGTGAGCGTGGAGGAGAACTGCATGTACCACGAGTCCAAGTTCTAC
GGCGTGAACTTCCCCGCCGACGGCCCCGTGATGAAGAAGATGACCGACAACTGGGAGCCCTC
CTGCGAGAAGATCATCCCCGTGCCCAAGCAGGGCATCTTGAAGGGCGACGTGAGCATGTACC
TGCTGCTGAAGGACGGTGGCCGCTTGCGCTGCCAGTTCGACACCGTGTACAAGGCCAAGTCC
GTGCCCCGCAAGATGCCCGACTGGCACTTCATCCAGCACAAGCTGACCCGCGAGGACCGCAG
CGACGCCAAGAACCAGAAGTGGCACCTGACCGAGCACGCCATCGCCTCCGGCTCCGCCTTGC
CCTGAgcgatcgcTAATCAACCTCTGGATTACAAAATTTGTGAAAGATTGACTGGTATTCTT
AACTATGTTGCTCCTTTTACGCTATGTGGATACGCTGCTTTAATGCCTTTGTATCATGCTAT
TGCTTCCCGTATGGCTTTCATTTTCTCCTCCTTGTATAAATCCTGGTTGCTGTCTCTTTATG
AGGAGTTGTGGCCCGTTGTCAGGCAACGTGGCGTGGTGTGCACTGTGTTTGCTGACGCAACC
CCCACTGGTTGGGGCATTGCCACCACCTGTCAGCTCCTTTCCGGGACTTTCGCTTTCCCCCT
CCCTATTGCCACGGCGGAACTCATCGCCGCCTGCCTTGCCCGCTGCTGGACAGGGGCTCGGC
TGTTGGGCACTGACAATTCCGTGGTGTTGTCGGGGAAgctgaCGTCCTTTCCaTGGCTGCTC
GCCTGTGTTGCCACCTGGATTCTGCGCGGGACGTCCTTCTGCTACGTCCCTTCGGCCCTCAA
TCCAGCGGACCTTCCTTCCCGCGGCCTGCTGCCGGCTCTGCGGCCTCTTCCGCGTCTTCGCC
TTCGCCCTCAGACGAGTCGGATCTCCctttgggccgcctccccgcTTAATCGCGTCGAGACC
TAGAAAAACATGGAGCAATCACAAGTAGCAATACAGCAGCTACCAATGCTGATTGTGCCTGG
CTAGAAGCACAAGAGGAGGAGGAGGTGGGTTTTCCAGTCACACCTCAGGTACCTTTAAGACC
AATGACTTACAAGGCAGCTGTAGATCTTAGCCACTTTTTAAAAGAAAAGGGGGGACTGGAAG
GGCTAATTCACTCCCAACGAAGACAAGATATCCTTGATCTGTGGATCTACCACACACAAGGC
TACTTCCCTGATTGGCAGAACTACACACCAGGGCCAGGGATCAGATATCCACTGACCTTTGG
ATGGTGCTACAAGCTAGTACCAGTTGAGCAAGAGAAGGTAGAAGAAGCCAATGAAGGAGAGA
ACACCCGCTTGTTACACCCTGTGAGCCTGCATGGGATGGATGACCCGGAGAGAGAAGTATTA

Fig. 20B

GAGTGGAGGTTTGACAGCCGCCTAGCATTTCATCACATGGCCCGAGAGCTGCATCCGGACTG
TACTGGGTCTCTCTGGTTAGACCAGATCTGAGCCTGGGAGCTCTCTGGCTAACTAGGGAACC
CACTGCTTAAGCCTCAATAAAGCTTGCCTTGAGTGCTTCAAGTAGTGTGTGCCCGTCTGTTG
TGTGACTCTGGTAACTAGAGATCCCTCAGACCCTTTTAGTCAGTGTGGAAAATCTCTAGCAG
GGCCCGTTTCATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGTAACTA
TCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTAC
GGCTACACTAGAAGAACAGTATTTGGTATCTGCGCTCTGCTGAAGCCAGTTACCTTCGGAAA
AAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATACGGGA
GGGCTTACCATCTGGCCCCAGTGCTGCAATGATACCGCGAGACCCACGCTCACCGGCTCCAG
ATTTATCAGCAATAAACCAGCCAGCCGGAAGGGCCGAGCGCAGAAGTGGTCCTGCAACTTTA
TCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGTGC
AAAAAAGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCGAGT
TGCTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTT
TCTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCCGCGCACA
TTTCCCCGAAAAGTGCCACCTGAC (SEQ ID NO:8)

Fig. 20C scALPS-hT5Cyp-GFP
GTCGACGGATCGGGAGATCTCCCGATCCCCTATGGTGCACTCTCAGTACAATCTGCTCTGAT
GCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTA
GGGTTAGGCGTTTTGCGCTGCTTCGCGATGTACGGGCCAGATATACGCGCTGTGGAATGTGT
GTCAGTTAGGGTGTGGAAAGTCCCCAGGCTCCCCAGCAGGCAGAAGTATGCAAAGCATGCAT
CTCAATTAGTCAGCAACCAGGTGTGGAAAGTCCCCAGGCTCCCCAGCAGGCAGAAGTATGCA
AAGCATGCATCTCAATTAGTCAGCAACCATAGTCCCGCCCCTAACTCCGCCCATCCCGCCCC
TAACTCCGCCCAGTTCCGCCCATTCTCCGCCCCATGGCTGACTAATTTTTTTTATTTATGCA
GAGGCCGAGGCCGCCTCTGCCTCTGAGCTATTCCAGAAGTAGTGAGGAGGCTTTTTTGGAGG
CCTAGGCTTTTGCAAAAAGCTTTGACATTGATTATTGACTAGTTATTAATAGTAATCAATTA
CGGGGTCATTAGTTCATAGCCCATATATGGAGTTCCGCGTTACATAACTTACGGTAAATGGC
CCGCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGCCC
ACTTGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCAGTA
CATCTACGTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAATGGGAGT
TTGTTTTGGCACCAAAATCAACGGGACTTTCCAAAATGTCGTAACAACTCCGCCCCATTGAC
GCAAATGGGCGGTAGGCGTGTACGGTGGGAGGTCTATATAAGCAGCGCGTTTTGCCTGTACT
GGGTCTCTCTGGTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCGTCTGTTGTGTG
ACTCTGGTAACTAGAGATCCCTCAGACCCTTTTAGTCAGTGTGGAAAATCTCTAGCAGTGGC
GCCCGAACAGGGACTTGAAAGCGAAAGGGAAACCAGAGGAGCTCTCTCGACGCAGGACTCGG
CTTGCTGAAGCGCGCACGGCAAGAGGCGAGGGGCGGCGACTGGTGAGTACGCCAAAAATTTT
GACTAGCGGAGGCTAGAAGGAGAGAGATGGGTGCGAGAGCGTCAGTATTAAGCGGGGGAGAA
TTAGATCGCGATGGGAAAAAATTCGGTTAAGGCCAGGGGGAAAGAAAAAATATAAATTAAAA
CATATAGTATGGGCAAGCAGGGAGCTAGAACGATTCGCAGTTAATCCTGGCCTGTTAGAAAC
ATCAGAAGGCTGTAGACAAATACTGGGACAGCTACAACCATCCCTTCAGACAGGATCAGAAG
AACTTAGATCATTATATAATACAGTAGCAACCCTCTATTGTGTGCATCAAAGGATAGAGATA
AAAGACACCAAGGAAGCTTTAGACAAGATAGAGGAAGAGCAAAACAAAAGTAAGACCACCGC
ACAGCAAGCggccGGCCGCTGATCTTCAGACCTGGAGGAGGAGATATGAGGGACAATTGGAG
AAGTGAATTATATAAATATAAAGTAGTAAAAATTGAACCATTAGGAGTAGCACCCACCAAGG
CAAAGAGAAGAGTGGTGCAGAGAGAAAAAAGAGCAGTGGGAATAGGAGCTTTGTTCCTTGGG
TTCTTGGGAGCAGCAGGAAGCACTATGGGCGCAGCGTCAATGACGCTGACGGTACAGGCCAG
ACAATTATTGTCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAATCCTGGCTGTG
GAAAGATACCTAAAGGATCAACAGCTCCTGGGGATTTGGGGTTGCTCTGGAAAACTCATTTG
CACCACTGCTGTGCCTTGGAATGCTAGTTGGAGTAATAAATCTCTGGAACAGATTTGGAATC
ACACGACCTGGATGGAGTGGGACAGAGAAATTAACAATTACACAAGCTTAATACACTCCTTA
ATTGAAGAATCGCAAAACCAGCAAGAAAAGAATGAACAAGAATTATTGGAATTAGATAAATG
GGCAAGTTTGTGGAATTGGTTTAACATAACAAATTGGCTGTGGTATATAAAATTATTCATAA
TGATAGTAGGAGGCTTGGTAGGTTTAAGAATAGTTTTTGCTGTACTTTCTATAGTGAATAGA
GTTAGGCAGGGATATTCACCATTATCGTTTCAGACCCACCTCCCAACCCCGAGGGGACCCGA

Fig. 21A

CAGGCCCGAAGGAATAGAAGAAGAAGGTGGAGAGAGAGACAGAGACAGATCCATTCGATTAG
TGAACGGATCGGCACTGCGTGCGCCAATTCTGCAGACAAATGGCAGTATTCATCCACAATTT
TAAAAGAAAAGGGGGGATTGGGGGGTACAGTGCAGGGGAAAGAATAGTAGACATAATAGCAA
CAGACATACAAACTAAAGAATTACAAAAACAAATTACAAAAATTCAAAATTTTCGGGTTTAT
TACAGGGACAGCAGAGATCCAGTTTGGTTAATtaaCTGCAGCCCCGATAAAATAAAAGATTT
TATTTAGTCTCCAGAAAAAGGGGGGAATGAAAGACCCCACCTGTAGGTTTGGCAAGCTAGCT
GCAGTAACGCCATTTTGCAAGGCATGGAAAAATACCAAACCAAGAATAGAGAAGTTCAGATC
AAGGGCGGGTACATGAAAATAGCTAACGTTGGGCCAAACAGGATATCTGCGGTGAGCAGTTT
CGGCCCCGGCCCGGGGCCAAGAACAGATGGTCACCGCAGTTTCGGCCCCGGCCCGAGGCCAA
GAACAGATGGTCCCCAGATATGGCCCAACCCTCAGCAGTTTCTTAAGACCCATCAGATGTTT
CCAGGCTCCCCCAAGGACCTGAAATGACCCTGCGCCTTATTTGAATTAACCAATCAGCCTGC
TTCTCGCTTCTGTTCGCGCGCTTCTGCTTCCCGAGCTCTATAAAAGAGCTCACAACCCCTCA
CTCGGCGCGCCAGTCCTCCGACAGACTGAGTCGCCCGGGGGtctagagccaccATGGCTTCT
GGAATCCTGGTTAATGTAAAGGAGGAGGTGACCTGCCCCATCTGCCTGGAACTCCTGACACA
ACCCCTGAGCCTGGACTGCGGCCACAGCTTCTGCCAAGCATGCCTCACTGCAAACCACAAGA
AGTCCATGCTAGACAAAGGAGAGAGTAGCTGCCCTGTGTGCCGGATCAGTTACCAGCCTGAG
AACATACGGCCTAATCGGCATGTAGCCAACATAGTGGAGAAGCTCAGGGAGGTCAAGTTGAG
CCCAGAGGGGCAGAAAGTTGATCATTGTGCACGCCATGGAGAGAAACTTCTACTCTTCTGTC
AGGAGGACGGGAAGGTCATTTGCTGGCTTTGTGAGCGGTCTCAGGAGCACCGTGGTCACCAC
ACGTTCCTCACAGAGGAGGTTGCCCGGGAGTACCAAGTGAAGCTCCAGGCAGCTCTGGAGAT
GCTGAGGCAGAAGCAGCAGGAAGCTGAAGAGTTGGAAGCTGACATCAGAGAAGAGAAAGCTT
CCTGGAAGACTCAAATACAGTATGACAAAACCAACGTCTTGGCAGATTTTGAGCAACTGAGA
GACATCCTGGACTGGGAGGAGAGCAATGAGCTGCAAAACCTGGAGAAGGAGGAGGAAGACAT
TCTGAAAAGCCTTACGAACTCTGAAACTGAGATGGTGCAGCAGACCCAGTCCCTGAGAGAGC
TCATCTCAGATCTGGAGCATCGGCTGCAGGGGTCAGTGATGGAGCTGCTTCAGGGTGTGGAT
GGCGTCATAAAAAGGACGGAGAACGTGACCTTGAAGAAGCCAGAAACTTTTCCAAAAAATCA
AAGGAGAGTGTTTCGAGCTCCTGATCTGAAAGGAATGCTAGAAGTGTTTAGAGAGCTGACAG
ATGTCCGACGCTACTGGGTTGATGTGACAGTGGCTCCAAACAACATTTCATGTGCTGTCATT
TCTGAAGATAAGAGACAAGTGAGCTCTGTCAACCCCACCGTGTTCTTCGACATTGCCGTCGA
CGGCGAGCCCTTGGGCCGCGTCTCCTTTGAGCTGTTTGCAGACAAGGTCCCAAAGACAGCAG
AAAATTTTCGTGCTCTGAGCACTGGAGAGAAAGGATTTGGTTATAAGGGTTCCTGCTTTCAC
AGAATTATTCCAGGGTTTATGTGTCAGGGTGGTGACTTCACACGCCATAATGGCACTGGTGG
CAAGTCCATCTATGGGGAGAAATTTGAAGATGAGAACTTCATCCTAAAGCATACGGGTCCTG
GCATCTTATCGATGGCAAATGCTGGACCCAACACAAATGGTTCCCAGTTTTTCATCTGCACT
GCCAAGACTGAGTGGTTGGATGGCAAGCATGTGGTGTTTGGCAAAGTGAAAGAAGGCATGAA
TATTGTGGAGGCGATGGAGCGCTTTGGGTCCAGGAATGGCAAGACCAGCAAGAAGATCACCA
TTGCTGACTGTGGACAACTCGAATAAgGATCCGTTTAAACGCGGCCGCCCAGCACAGTGGCT
CGAGCCGCGGGTTAACTGGCCAGaattctcgaccttgactggcggcgcgaccttgaggcctg
cgttcgcctcagttgccccctctgtgcaatggggagacgcgcctcatcgcttgacaacggcc
gaagagccgccgcgcttccgtctcccgcgtgcgcgcgccatgctgcccacccccgttccgca
ctgaccctcccccgtgccccgcgtcccgtactgccgccccgccccgagtcccatgccgcagc
caccgcgacggagcccgcaggcgggaacctgcctccgcgcgttagcgcgcacgcgcgcctca
tgtgtcgtccccatcagcgccggcttccgtctataggccagatgcactgtcactctggcgaa
gtcgcagacccgattggccgggacggaggcgcgagaccgggttgcgggcggggccGAACGTG
GTATAAAAGGGGCGGGAGGCCAGGCTCGTGCCGTTTTGCAGACGCCACCGCCGAGGAAAACC
GTGTACTATTAGCCacgcgtgccaccATGGCCCAGTCCAAGCACGGCCTGACCAAGGAGATG

Fig. 21B

ACCATGAAGTACCGCATGGAGGGCTGCGTGGACGGCCACAAGTTCGTGATCACCGGCGAGGG
CATCGGCTACCCCTTCAAGGGCAAGCAGGCCATCAACCTGTGCGTGGTGGAGGGCGGCCCCT
TGCCCTTCGCCGAGGACATCTTGTCCGCCGCCTTCATGTACGGCAACCGCGTGTTCACCGAG
TACCCCCAGGACATCGTCGACTACTTCAAGAACTCCTGCCCCGCCGGCTACACCTGGGACCG
CTCCTTCCTGTTCGAGGACGGCGCCGTGTGCATCTGCAACGCCGACATCACCGTGAGCGTGG
AGGAGAACTGCATGTACCACGAGTCCAAGTTCTACGGCGTGAACTTCCCCGCCGACGGCCCC
GTGATGAAGAAGATGACCGACAACTGGGAGCCCTCCTGCGAGAAGATCATCCCCGTGCCCAA
GCAGGGCATCTTGAAGGGCGACGTGAGCATGTACCTGCTGCTGAAGGACGGTGGCCGCTTGC
GCTGCCAGTTCGACACCGTGTACAAGGCCAAGTCCGTGCCCCGCAAGATGCCCGACTGGCAC
TTCATCCAGCACAAGCTGACCCGCGAGGACCGCAGCGACGCCAAGAACCAGAAGTGGCACCT
GACCGAGCACGCCATCGCCTCCGGCTCCGCCTTGCCCTGAgcgatcgcTAATCAACCTCTGG
ATTACAAAATTTGTGAAAGATTGACTGGTATTCTTAACTATGTTGCTCCTTTTACGCTATGT
GGATACGCTGCTTTAATGCCTTTGTATCATGCTATTGCTTCCCGTATGGCTTTCATTTTCTC
CTCCTTGTATAAATCCTGGTTGCTGTCTCTTTATGAGGAGTTGTGGCCCGTTGTCAGGCAAC
GTGGCGTGGTGTGCACTGTGTTTGCTGACGCAACCCCCACTGGTTGGGGCATTGCCACCACC
TGTCAGCTCCTTTCCGGGACTTTCGCTTTCCCCCTCCCTATTGCCACGGCGGAACTCATCGC
CGCCTGCCTTGCCCGCTGCTGGACAGGGGCTCGGCTGTTGGGCACTGACAATTCCGTGGTGT
TGTCGGGGAAgctgaCGTCCTTTCCaTGGCTGCTCGCCTGTGTTGCCACCTGGATTCTGCGC
GGGACGTCCTTCTGCTACGTCCCTTCGGCCCTCAATCCAGCGGACCTTCCTTCCCGCGGCCT
GCTGCCGGCTCTGCGGCCTCTTCCGCGTCTTCGCCTTCGCCCTCAGACGAGTCGGATCTCCc
tttgggccgcctccccgcTTAATCGCGTCGAGACCTAGAAAAACATGGAGCAATCACAAGTA
GCAATACAGCAGCTACCAATGCTGATTGTGCCTGGCTAGAAGCACAAGAGGAGGAGGAGGTG
GGTTTTCCAGTCACACCTCAGGTACCTTTAAGACCAATGACTTACAAGGCAGCTGTAGATCT
TAGCCACTTTTTAAAAGAAAAGGGGGGACTGGAAGGGCTAATTCACTCCCAACGAAGACAAG
ATATCCTTGATCTGTGGATCTACCACACACAAGGCTACTTCCCTGATTGGCAGAACTACACA
CCAGGGCCAGGGATCAGATATCCACTGACCTTTGGATGGTGCTACAAGCTAGTACCAGTTGA
GCAAGAGAAGGTAGAAGAAGCCAATGAAGGAGAGAACACCCGCTTGTTACACCCTGTGAGCC
TGCATGGGATGGATGACCCGGAGAGAGAAGTATTAGAGTGGAGGTTTGACAGCCGCCTAGCA
TTTCATCACATGGCCCGAGAGCTGCATCCGGACTGTACTGGGTCTCTCTGGTTAGACCAGAT
CTGAGCCTGGGAGCTCTCTGGCTAACTAGGGAACCCACTGCTTAAGCCTCAATAAAGCTTGC
CTTGAGTGCTTCAAGTAGTGTGTGCCCGTCTGTTGTGTGACTCTGGTAACTAGAGATCCCTC
AGACCCTTTTAGTCAGTGTGGAAAATCTCTAGCAGGGCCCGTTTCATGTGAGCAAAAGGCCA
GCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGAACAGTATTTGGT
ATCTGCGCTCTGCTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAAAC
TCACGTTAAGGATTTTGGTCATGAGATTATCAAAAAGGATCTTCACCTAGATCCTTTTAAA

Fig. 21C

TTAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCG
AAAACTCTCAAGGATCTTACCGCTGTTGAGATCCAGTTCGATGTAACCCACTCGTGCACCCA
ACTGATCTTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTCTTCCTTTT
TCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTGAC
(SEQ ID NO:9)

Ring Finger

MASGILVNVKEEVTCPICLELLTQPLSLDCGHSFCQACLTANHKKSMLDK

GESSCPVCRISYQPENIRPNRHVANLVEKLREVKLSPEGQKVDHCARHGE

B Box 2 efgabcdefgabcdefgab

KLLLFCQEDGKVICWLCERSQEHRGHHTFPTEEVAQEYQVKLQAALEMLR cdefgabcdefgabcdefg

QKQQEAEELEADIREEKASWKTQIQYDKTNVLADFEQLRDILDWEESNEL gabcdefgabcdefgabcdefgabcdefgab M244

QNLEKEEEDILKSLTNSETEMVQQTQSLRELISDLEHRLQGSVMELLQGV

M284 W298

DGVIKRTENVTLKKPETFPKNQRRVFRAPDLKGMLEVFRELTDVRRYWVD

T302 S309 S314 S322 A331

VTVAPNNISCAVISEDKRQVSSPKPQIIYGARGTRYQTFVNFNYCTGILG

G357 T369 G398

SQSITSGKHYWEVDVSKKTAWILGVCAGFQPDAMCNIEKNENYQPKYGYW

VIGLEEGVKCSAFQDSSFHTPSVPFIVPLSVIICPDRVGVFLDYEACTVS

FFNITNHGFLIYKFSHCSFSQPVFPYLNPRKCGVPMTLCSPSS

B

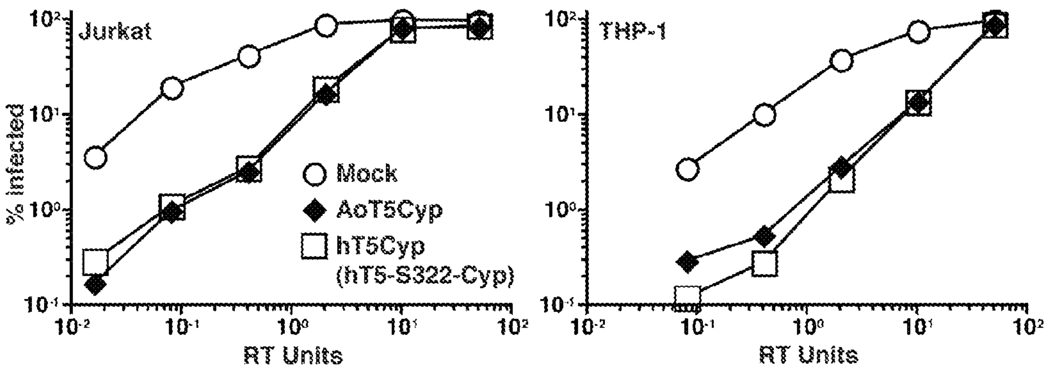

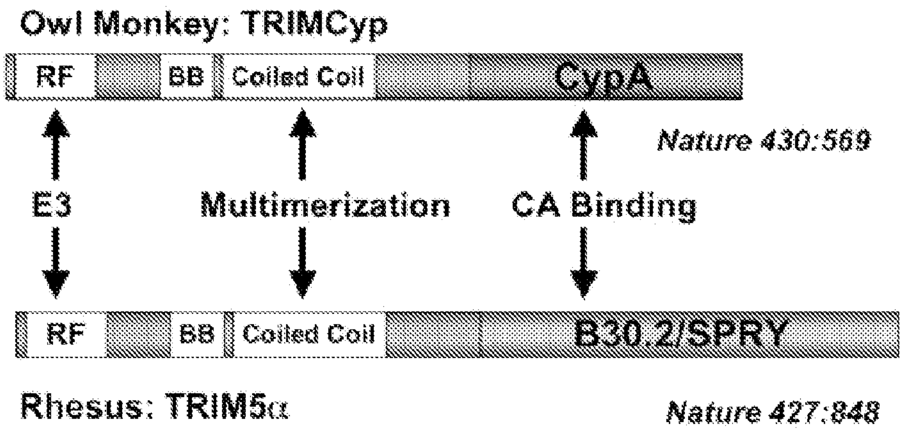

B

| Protein | Sequence at junction | HIV-1 block |
|---|---|---|
| MaT5Cyp | PR----------DAAAEESPVLLA-------------MVNPTVFFDIADGEPLGRVSFEL | - |
| AoT5Cyp | FKEPTEVQRENWDAAANDL-VASA-----------MVNPTVFFDIADGEPLGRVSFEL | +++ |
| hT5Cyp* | FRELTDVRRYWVDVTVAPNNISCAVISEDKRQVSS-VNPTVFFDIADGEPLGRVSFEL | +++ |
| hT5α | FRELTDVRRYWVDVTVAPNNISCAVISEDKRQVSSPKPQIIYGARGTRYQT--FVNFN | - |
| RhT5α | FRELTDVRRYWVDVTVAPNNISHAVIAEDKRQVSSRNPQIMYQAPGTLFTFPSLTNFN | ++ |
| hT5α$_{R332P}$* | FRELTDVRRYWVDVTVAPNNISCAVISEDKRQVSSRKPQIIYGARGTRYQT--FVNFN | + |
| hT5α$_{323-332}$* | FRELTDVRRYWVDVTVAPNNISCAVISEDKRQVSSRNPQIMYQAPGTRYQT--FVNFN | + |

FIG. 41

```
79.6% identity in 486 residues overlap; Score: 2002.0; Gap frequency: 2.7%

HsTRIMCyp,      1 MASGILVNVKEEVTCPICLELLTQPLSLDCGHSFCQACLTANHKKSMLDKGESSCPVCRI
AoTRIMCyp,      1 MASRILVNIKEEVTCPICLELLTEPLSLDCGHSFCQACITANHKKSMPHQGERSCPLCRI
                  *** **** ************** ************** ********   ** *** ***

HsTRIMCyp,     61 SYQPENIRPNRHVANIVEKLREVKLSPE-GQKVDHCARHGEKLLLFCQEDGKVICWLCER
AoTRIMCyp,     61 SYSSENLRPNRHLVNIVERLREVMLSPEEGQKVDHCAHHGEKLVLFCQQDGNVICWLCER
                  **  ** *****  **** **** **** ******** ***** **** ** ********

HsTRIMCyp,    120 SQEHRGHHTFLTEEVAREYQVKLQAALEMLRQKQQEAEELEADIREEKASWKTQIQYDKT
AoTRIMCyp,    121 SQEHRGHQTFLVEEVAQKYREKLQVALEMMRQKQKDAEKLEADVREEQASWKIQIQNDKT
                  ******* *** ****  *  *** **** ****  ** **** *** **** *** ***

HsTRIMCyp,    180 NVLADFEQLRDILDWEESNELQNLEKEEEDILKSLTNSETEMVQQTQSLRELISDLEHRL
AoTRIMCyp,    181 NIMAEFKKRRDILDCEESKELQNLEKEEKNILKRLVQSENDMVLQTQSVRVLISDLEHRL
                  *  * *   ***** *** *********  *** *  **  ** **** * *********

HsTRIMCyp,    240 QGSVMELLQGVDGVIKRTENVTLKKPETFPKNQRRVFRAPDLKGMLEVFRELTDVRRYWV
AoTRIMCyp,    241 QGSVMELLQGVDGVIKRIEKVTLQNPKTFLNEKRRIFQTPDLKGTLQVFKEPTEVQRYW-
                  ***************** * ***  * **    ** *  ***** * ** * * * ***

HsTRIMCyp,    300 DVTVAPNNISCAVISEDKRQVSSVNPTVFFDIAVDGEPLGRVSFELFADKVPKTAENFRA
AoTRIMCyp,    300 -----------DAAANDLVASAHVNPTVFFDIAVDGEPLGRVSFELFADKVPKTAENFRA
                                  *      *************************************

HsTRIMCyp,    360 LSTGEKGFGYKGSCFHRIIPGFMCQGGDFTRHNGTGGKSIYGEKFEDENFILKHTGPGIL
AoTRIMCyp,    349 LSTGEKGFGYKGSCFHRIIPGFMCQGGDFTRHNGTGGKSIYGEKFDDENFILKHTGPGIL
                  ********************************************* **************

HsTRIMCyp,    420 SMANAGPNTNGSQFFICTAKTEWLDGKHVVFGKVKEGMNIVEAMERFGSRNGKTSKKITI
AoTRIMCyp,    409 SMANAGPNTNGSQFFICTAKTEWLDGKHVVFGKVKEGMNVVEAMERFGCRYGKTSKKITI
                  *************************************** ******** * *********

HsTRIMCyp,    480 ADCGQL
AoTRIMCyp,    469 ADCGQL
                  ******
```

| Fusion protein | ....T5-linker residues-CypA | HIV-1 restriction |
|---|---|---|
| AoT5Cyp | ...RYW-DAAAWDLVASA-CypA | + |
| hT5αCyp | ...RYW-VDVTVAPNNISCAVIS-CypA | − |
| hT5γCyp | ...RYW-GKEKSHYHKPPCGLS-CypA | − |
| hT5δCyp | ...RYW-GWSAMARSRFTATSTS-CypA | − |
| hT5directCyp | ...RYW-CypA | − |
| hT5(SGG)$_4$Cyp | ...RYW-SGGSGGSGGSGG-CypA | + |

A

———————Ring Finger———————
MASGILVNVKEEVTCPICLELLTQPLSLDCGHSFCQACLTANHKKSMLDK

GESSCPVCRISYQPENIRPNRHVANLVEKLREVKLSPEGQKVDHCARHGE
          ———————B Box 2———————         efgabcdefgabcdefgab
KLLLFCQEDGKVICWLCERSQEHRGHHTFPTEEVAQEYQVKLQAALEMLR
cdefgabcdefgabcdefg
QKQQEAEELEADIREEKASWKTQIQYDKTNVLADFEQLRDILDWEESNEL
            gabcdefgabcdefgabcdefgabcdefgab    M264
QNLEKEEEDILKSLTNSETEMVQQTQSLRELISDLEHRLQGSVMELLQGV M284         W298
DGVIKRTENVTLKKPETFPKNQRRVFRAPDLKGMLEVFRELTDVRRYWVD
T302    S309 S314    S322      A331
VTVAPNNISCAVISEDKRQVSSPKPQIIYGARGTRYQTFVNFNYCTGILG
     G357      T369                              G398
SQSITSGKHYWEVDVSKKTAWILGVCAGFQPDAMCNIEKNENYQPKYGYW

VIGLEEGVKCSAFQDSSPHTPSVPFIVPLSVIICPDRVGVFLDYEACTVS

FFNITNHGFLIYKFSHCSFSQPVFPYLNPRKCGVPMTLCSPSS

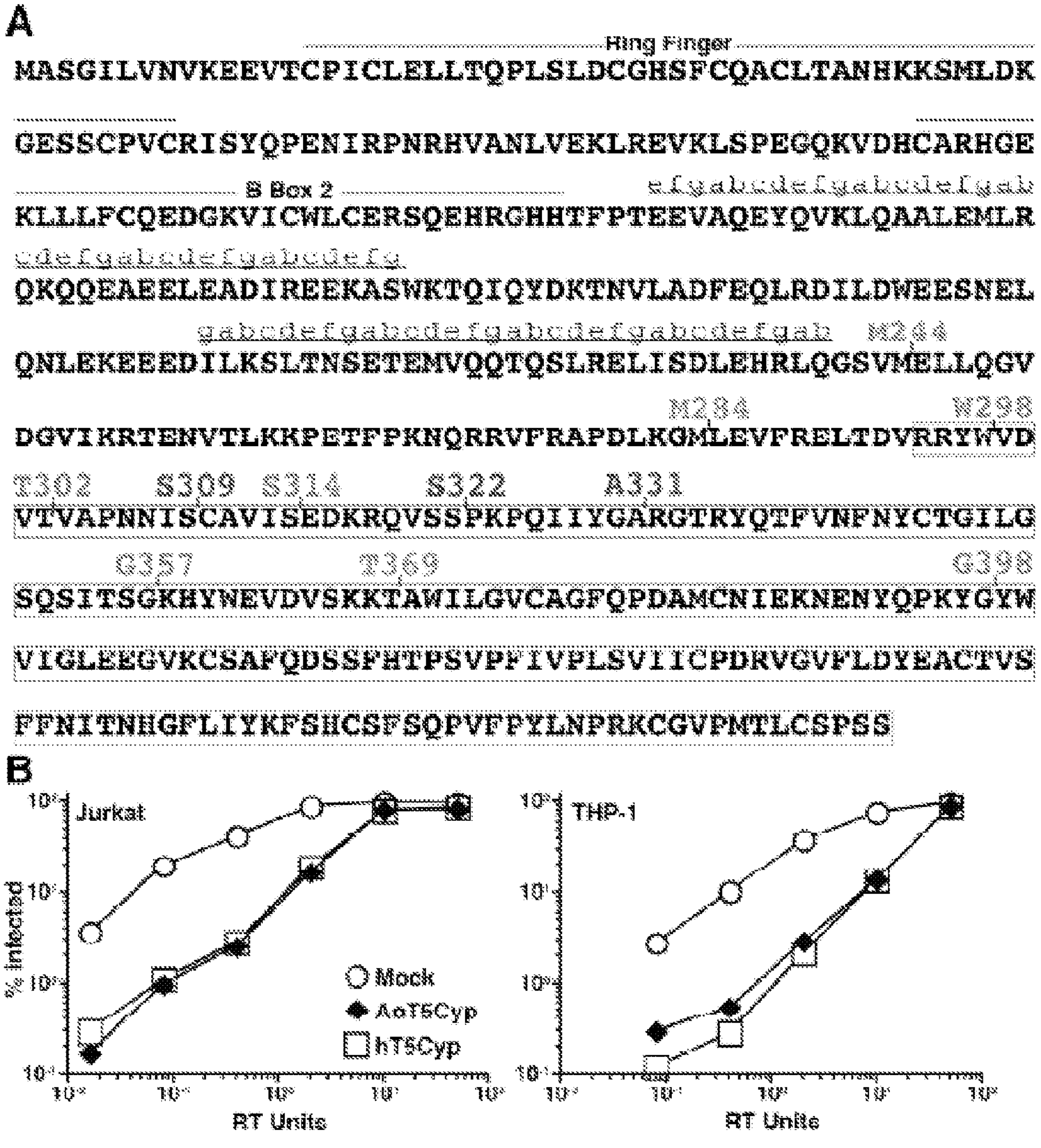

FIG. 44

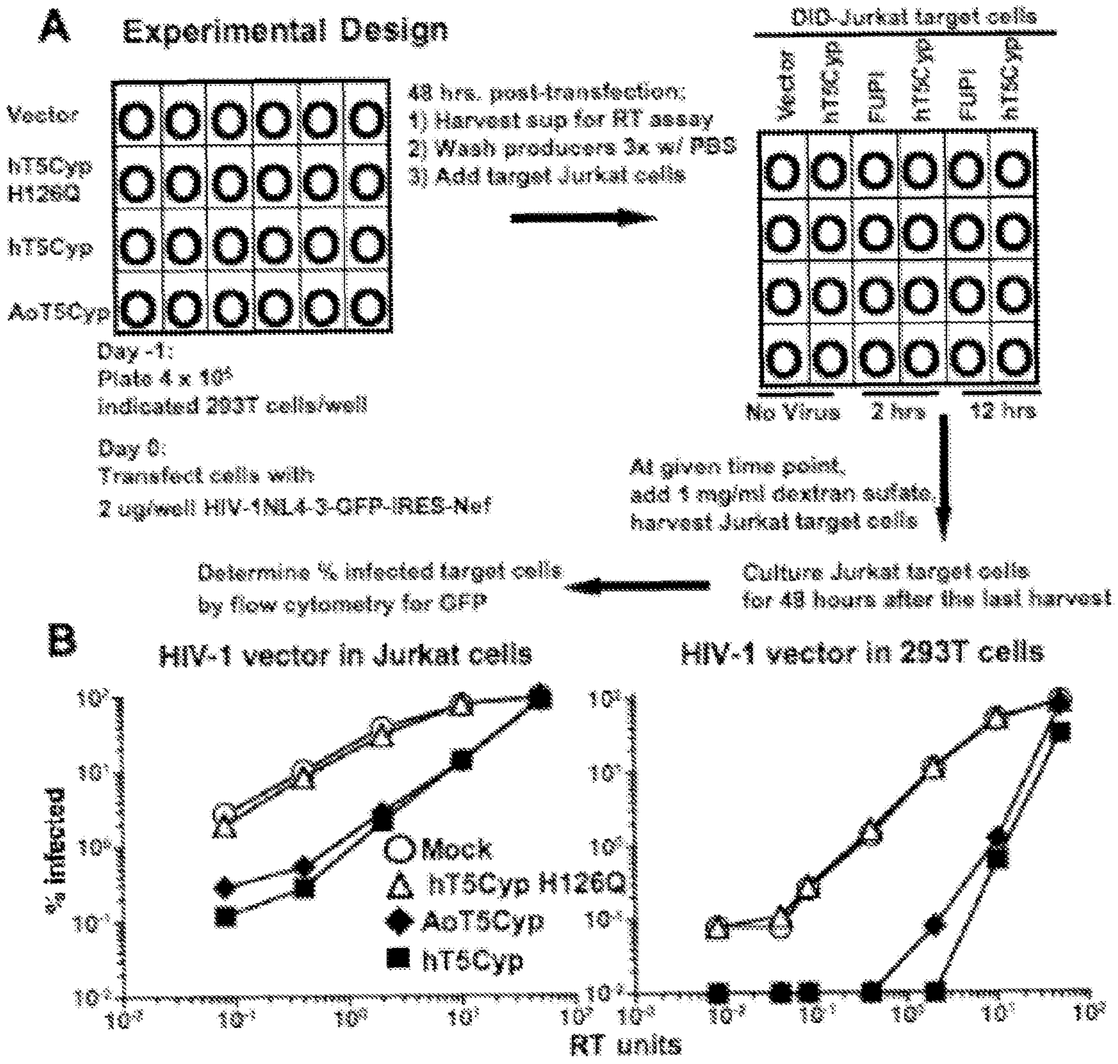
FIG. 53A-B

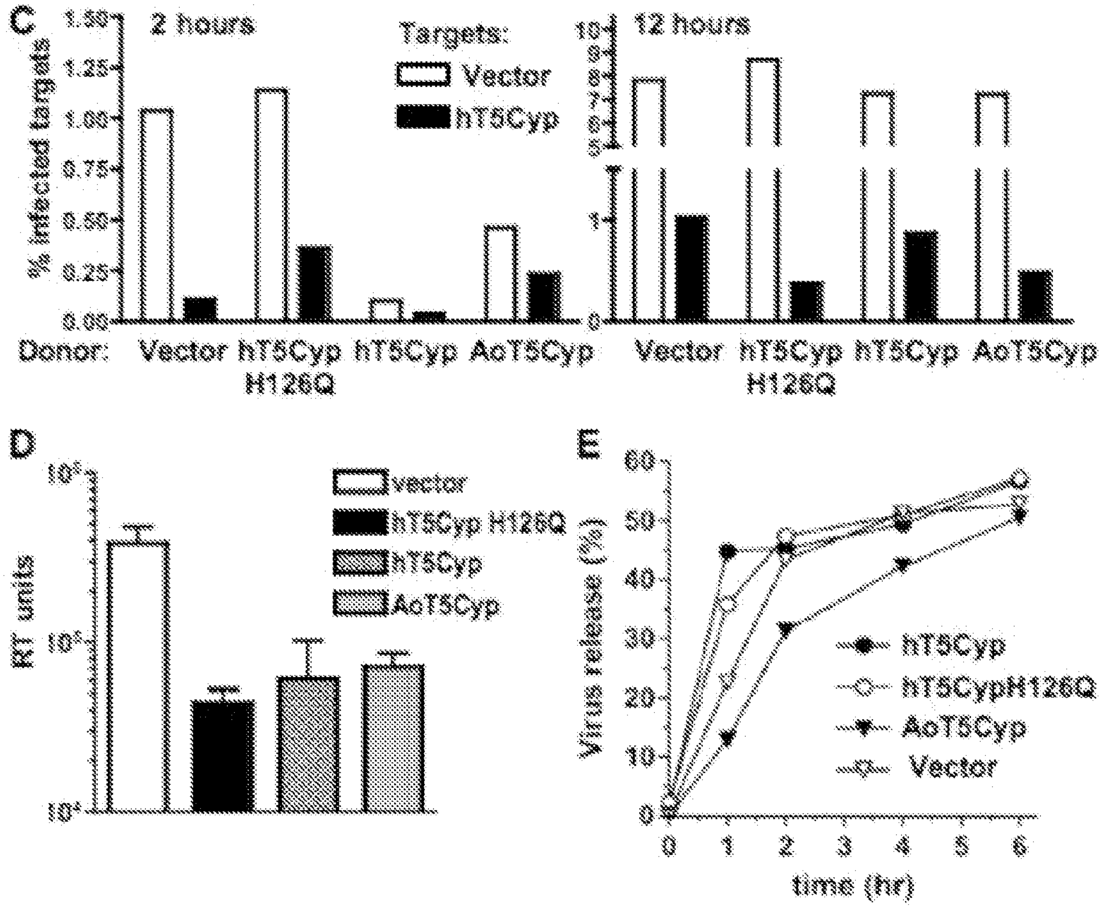
FIG. 53C-E

SEQUENCE LISTING

<160> NUMBER OF SEQ ID NOS: 149

<210> SEQ ID NO 1
<211> LENGTH: 2990
<212> TYPE: DNA
<213> ORGANISM: Homo sapiens

<400> SEQUENCE: 1
gcggttcctc taggaaaatt cctttgtgca gatcaggccc gtggattggt gagtgaatcc 60
taaccacgtc ttccctggcc tgtcttcact cttctcccca gaatcaccac ttctgcactg 120
gtgtctgaag gtgtattgag tgattttgtg gagggcagaa gtaggaagtc tttgggacaa 180
aactgtattt accttgggat ctgtgaacaa gaggaacctc agcagccagg acaggcagga 240
gcagtggaat agctactatg gcttctggaa tcctggttaa tgtaaaggag gaggtgacct 300
gccccatctg cctggaactc ctgacacaac ccctgagcct ggactgcggc cacagcttct 360
gccaagcatg cctcactgca aaccacaaga agtccatgct agacaaagga gagagtagct 420
gccctgtgtg ccggatcagt taccagcctg agaacatacg gcctaatcgg catgtagcca 480
acttagtgga gaagctcagg gaggtcaagt tgagcccaga ggggcagaaa gttgatcatt 540
gtgcacgcca tggagagaaa cttctactct tctgtcagga ggacgggaag gtcatttgct 600
ggctttgtga gcggtctcag gagcaccgtg gtcaccacac gttccccaca gaggaggttg 660
cccaggagta ccaagtgaag ctccaggcag ctctggagat gctgaggcag aagcagcagg 720
aagctgaaga gttggaagct gacatcagag aagagaaagc ttcctggaag actcaaatac 780
agtatgacaa aaccaacgtc ttggcagatt ttgagcaact gagagacatc ctggactggg 840
aggagagcaa tgagctgcaa aacctggaga aggaggagga agacattctg aaaagcctta 900
cgaactctga aactgagatg gtgcagcaga cccagtccct gagagagctc atctcagatc 960
tggagcatcg gctgcagggg tcagtgatgg agctgcttca gggtgtggat ggcgtcataa 1020
aaaggacgga gaacgtgacc ttgaagaagc cagaaacttt tccaaaaaat caaaggagag 1080
tgtttcgagc tcctgatctg aaaggaatgc tagaagtgtt tagagagctg acagatgtcc 1140
gacgctactg ggttgatgtg acagtggctc caaacaacat ttcatgtgct gtcatttctg 1200
aagataagag acaagtgagc tctccgaaac cacagataat atatggggca cgagggacaa 1260
gataccagac atttgtgaat ttcaattatt gtactggcat cctgggctct caaagtatca 1320
catcagggaa acattactgg gaggtagacg tgtccaagaa aactgcttgg atcctggggg 1380
tatgtgctgg cttccaacct gatgcaatgt gtaatattga aaaaaatgaa aattatcaac 1440
ctaaatacgg ctactgggtt atagggttag aggaaggagt taaatgtagt gctttccagg 1500
atagttcctt ccatactcct tctgttcctt tcattgtgcc cctctctgtg attatttgtc 1560
ctgatcgtgt tggagttttc ctagactatg aggcttgcac tgtctcattc ttcaatatca 1620
caaaccatgg atttctcatc tataagtttt ctcactgttc tttttctcag cctgtatttc 1680
catatttaaa tcctagaaaa tgtggagtcc ccatgactct gtgctcacca agctcttgaa 1740
ccttcttaca cactcagccc cttctgtaca gcacctcttg tccaggtgca tctcatacac 1800
ctgaactcat ttgcatcatt ttaaccatct tttccttgct gtctcccttc tttctatttg 1860
aacgtccttc actcatcagt aaaatgtaat aattgccttg tgccatattg tccccaatat 1920
tttattgaca tttgatagca attttttca tcattttccg tactcctaag gaaaactgac 1980
ctatacctca taaaatgaga ccgctattta ggtattactt ctgccagata tttatcaccc 2040
aattgcctct gacactgact aagaagatga agaaaagctt ttcaacagcc tttctatatc 2100

-continued

```
atcgtgtgat aattgttcac caatgaatga gtccttagcc ctgtgtcagt ttaccctcga   2160

tgcccttatt tgtgagttaa agagaaaata tcataaatgg tatactctta agtatagagg   2220

ttttgtatct agaggatctc agttcaactc ctgtctctcc atataccagc agtgtaactg   2280

tgaataacat acttaaatgg ctgtgcttat ttccttttct tttctttttt cttttttttt   2340

tttttgaga tgaagttttg ctcttgttcc ccaggctgga gtgcaatggc acgatctcgg   2400

ttcactgcaa cctccacctc tcagattcaa gcaattctcc tgcctcagcc tcccaagtag   2460

ctgggattac aggtgcccac caccacccct ggctaaattt gtattttcag tagagacggg   2520

gtttccccat gttggttagg ctcgtctaga acctctgacc tcaggtgatc cacccgcctc   2580

ggcctcccaa agtgctggga ttacaggcgt gagccacggc gcccagcctg tgcttatttt   2640

cttaaaataa tttttgtatt aaaaacttca cattaaataa gtgctaatgt tttattgcat   2700

agtagggtga ctagagttaa caataaccta ttgcatatat tttgaaatag ctagaagaga   2760

ggattttgaa agttctcaac acaaagaaac gacacatatt tgaggtgatg gatatgctaa   2820

ttaccctggt tcggttatta cgcaatgtat acatgtatca aaacatcaca ctgtaccaca   2880

taaatatgta tatttattat ttgtcaatta aaagcaaaat aaaacaaaaa accttcatct   2940

aatactttgg atcattgtga aaaaataaat tcctgaagta taaagcatct             2990
```

<210> SEQ ID NO 2
<211> LENGTH: 493
<212> TYPE: PRT
<213> ORGANISM: Homo sapiens

<400> SEQUENCE: 2

```
Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
```

-continued

```
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Ala Trp Ile Leu Gly Val Cys Ala Gly Phe Gln Pro Asp Ala Met
    370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
                405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
        435                 440                 445

Val Ser Phe Phe Asn Ile Thr Asn His Gly Phe Leu Ile Tyr Lys Phe
    450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                485                 490
```

<210> SEQ ID NO 3
<211> LENGTH: 2276
<212> TYPE: DNA
<213> ORGANISM: Homo sapiens

<400> SEQUENCE: 3

```
gaacgtggta taaaaggggc gggaggccag gctcgtgccg ttttgcagac gccaccgccg      60

aggaaaaccg tgtactatta gccatggtca accccaccgt gttcttcgac attgccgtcg     120

acggcgagcc cttgggccgc gtctcctttg agctgtttgc agacaaggtc ccaaagacag     180

cagaaaattt tcgtgctctg agcactggag agaaaggatt tggttataag ggttcctgct     240

ttcacagaat tattccaggg tttatgtgtc agggtggtga cttcacacgc cataatggca     300

ctggtggcaa gtccatctat ggggagaaat ttgaagatga gaacttcatc ctaaagcata     360

cgggtcctgg catcttgtcc atggcaaatg ctggacccaa cacaaatggt tcccagtttt     420

tcatctgcac tgccaagact gagtggttgg atggcaagca tgtggtgttt ggcaaagtga     480

aagaaggcat gaatattgtg gaggccatgg agcgctttgg gtccaggaat ggcaagacca     540
```

-continued

```
gcaagaagat caccattgct gactgtggac aactcgaata agtttgactt gtgttttatc    600

ttaaccacca gatcattcct tctgtagctc aggagagcac ccctccaccc catttgctcg    660

cagtatccta gaatctttgt gctctcgctg cagttccctt tgggttccat gttttccttg    720

ttccctccca tgcctagctg gattgcagag ttaagtttat gattatgaaa taaaaactaa    780

ataacaattg tcctcgtttg agttaagagt gttgatgtag gctttatttt aagcagtaat    840

gggttacttc tgaaacatca cttgtttgct taattctaca cagtacttag attttttta     900

ctttccagtc ccaggaagtg tcaatgtttg ttgagtggaa tattgaaaat gtaggcagca    960

actgggcatg gtggctcact gtctgtaatg tattacctga ggcagaagac cacctgaggg   1020

taggagtcaa gatcagcctg ggcaacatag tgagacgctg tctctacaaa aaataattag   1080

cctggcctgg tggtgcatgc ctagtcctag ctgatctgga ggctgacgtg ggaggattgc   1140

ttgagcctag agtgagctat tatcatgcca ctgtacagcc tgggtgttca cagatcttgt   1200

gtctcaaagg taggcagagg caggaaaagc aaggagccag aattaagagg ttgggtcagt   1260

ctgcagtgag ttcatgcatt tagaggtgtt cttcaagatg actaatgtca aaaattgaga   1320

catctgttgc ggtttttttt tttttttttt cccctggaat gcagtggcgt gatctcagct   1380

cactgcagcc tccgcctcct gggttcaagt gattctagtg cctcagcctc ctgagtagct   1440

gggataatgg gcgtgtgcca ccatgcccag ctaatttttg tatttttagt atagatgggg   1500

tttcatcatt ttgaccaggc tggtctcaaa ctcttgacct cagctgatgc gcctgccttg   1560

gcctcccaaa ctgctgagat tacagatgtg agccaccgca ccctacctca ttttctgtaa   1620

caaagctaag cttgaacact gttgatgttc ttgagggaag catattgggc tttaggctgt   1680

aggtcaagtt tatacatctt aattatggtg gaattcctat gtagagtcta aaaagccagg   1740

tacttggtgc tacagtcagt ctccctgcag agggttaagg cgcagactac ctgcagtgag   1800

gaggtactgc ttgtagcata tagagcctct ccctagcttt ggttatggag gctttgaggt   1860

tttgcaaacc tgaccaattt aagccataag atctggtcaa agggataccc ttcccactaa   1920

ggacttggtt tctcaggaaa ttatatgtac agtgcttgct ggcagttaga tgtcaggaca   1980

atctaagctg agaaaacccc ttctctgccc accttaacag acctctaggg ttcttaaccc   2040

agcaatcaag tttgcctatc ctagaggtgg cggatttgat catttggtgt gttgggcaat   2100

ttttgtttta ctgtctggtt ccttctgcgt gaattaccac caccaccact tgtgcatctc   2160

agtcttgtgt gttgtctggt tacgtattcc ctgggtgata ccattcaatg tcttaatgta   2220

cttgtggctc agacctgagt gcaaggtgga aataaacatc aaacatcttt tcatta       2276
```

<210> SEQ ID NO 4
<211> LENGTH: 165
<212> TYPE: PRT
<213> ORGANISM: Homo sapiens

<400> SEQUENCE: 4

```
Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Gly Lys Ser Ile Tyr Gly
```

-continued

```
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165


<210> SEQ ID NO 5
<211> LENGTH: 1487
<212> TYPE: DNA
<213> ORGANISM: Homo sapiens

<400> SEQUENCE: 5

atggcttctg gaatcctggt taatgtaaag gaggaggtga cctgccccat ctgcctggaa     60

ctcctgacac aacccctgag cctggactgc ggccacagct tctgccaagc atgcctcact    120

gcaaaccaca agaagtccat gctagacaaa ggagagagta gctgccctgt gtgccggatc    180

agttaccagc ctgagaacat acggcctaat cggcatgtag ccaacttagt ggagaagctc    240

agggaggtca agttgagccc agaggggcag aaagttgatc attgtgcacg ccatggagag    300

aaacttctac tcttctgtca ggaggacggg aaggtcattt gctggctttg tgagcggtct    360

caggagcacc gtggtcacca cacgttcccc acagaggagg ttgcccagga gtaccaagtg    420

aagctccagg cagctctgga gatgctgagg cagaagcagc aggaagctga agagttggaa    480

gctgacatca gagaagagaa agcttcctgg aagactcaaa tacagtatga caaaaccaac    540

gtcttggcag attttgagca actgagagac atcctggact gggaggagag caatgagctg    600

caaaacctgg agaaggagga ggaagacatt ctgaaaagcc ttacgaactc tgaaactgag    660

atggtgcagc agacccagtc cctgagagag ctcatctcag atctggagca tcggctgcag    720

gggtcagtga tggagctgct tcagggtgtg gatggcgtca taaaaaggac ggagaacgtg    780

accttgaaga agccagaaac ttttccaaaa aatcaaagga gagtgtttcg agctcctgat    840

ctgaaaggaa tgctagaagt gtttagagag ctgacagatg tccgacgcta ctgggttgat    900

gtgacagtgg ctccaaacaa catttcatgt gctgtcattt ctgaagataa gagacaagtg    960

agctctccga aaccacagat aatatatggg gcagtcaacc ccaccgtgtt cttcgacatt   1020

gccgtcgacg gcgagccctt gggccgcgtc tcctttgagc tgtttgcgac aaggtcccaa   1080

agacagcaga aaattttcgt gctctgagca ctggagagaa aggatttggt tataagggtt   1140

cctgctttca cagaattatt ccagggttta tgtgtcaggg tggtgacttc acacgccata   1200

atggcactgg tggcaagtcc atctatgggg agaaatttga agatgagaac ttcatcctaa   1260

agcatacggg tcctggcatc ttgtccatgg caaatgctgg acccaacaca aatggttccc   1320

agtttttcat ctgcactgcc aagactgagt ggttggatgg caagcatgtg gtgtttggca   1380

aagtgaaaga aggcatgaat attgtggagg ccatggagcg ctttgggtcc aggaatggca   1440

agaccagcaa gaagatcacc attgctgact gtggacaact cgaataa                 1487
```

<210> SEQ ID NO 6
<211> LENGTH: 1422
<212> TYPE: DNA
<213> ORGANISM: Homo sapiens

<400> SEQUENCE: 6

```
atggcttctg gaatcctggt taatgtaaag gaggaggtga cctgccccat ctgcctggaa     60
ctcctgacac aacccctgag cctggactgc ggccacagct tctgccaagc atgcctcact    120
gcaaaccaca agaagtccat gctagacaaa ggagagagta gctgccctgt gtgccggatc    180
agttaccagc ctgagaacat acggcctaat cggcatgtag ccaacatagt ggagaagctc    240
agggaggtca agttgagccc agaggggcag aaagttgatc attgtgcacg ccatggagag    300
aaacttctac tcttctgtca ggaggacggg aaggtcattt gctggctttg tgagcggtct    360
caggagcacc gtggtcacca cacgttcctc acagaggagg ttgcccggga gtaccaagtg    420
aagctccagg cagctctgga gatgctgagg cagaagcagc aggaagctga agagttggaa    480
gctgacatca gagaagagaa agcttcctgg aagactcaaa tacagtatga caaaaccaac    540
gtcttggcag attttgagca actgagagac atcctggact gggaggagag caatgagctg    600
caaaacctgg agaaggagga ggaagacatt ctgaaaagcc ttacgaactc tgaaactgag    660
atggtgcagc agacccagtc cctgagagag ctcatctcag atctggagca tcggctgcag    720
gggtcagtga tggagctgct tcagggtgtg gatggcgtca taaaaaggac ggagaacgtg    780
accttgaaga agccagaaac ttttccaaaa aatcaaagga gagtgtttcg agctcctgat    840
ctgaaaggaa tgctagaagt gtttagagag ctgacagatg tccgacgcta ctgggttgat    900
gtgacagtgg ctccaaacaa catttcagtc aaccccaccg tgttcttcga cattgccgtc    960
gacggcgagc ccttgggccg cgtctccttt gagctgtttg cagacaaggt cccaaagaca   1020
gcagaaaatt ttcgtgctct gagcactgga gagaaaggat ttggttataa gggttcctgc   1080
tttcacagaa ttattccagg gtttatgtgt cagggtggtg acttcacacg ccataatggc   1140
actggtggca agtccatcta tggggagaaa tttgaagatg agaacttcat cctaaagcat   1200
acgggtcctg gcatcttgtc catggcaaat gctggaccca acacaaatgg ttcccagttt   1260
ttcatctgca ctgccaagac tgagtggttg gatggcaagc atgtggtgtt tggcaaagtg   1320
aaagaaggca tgaatattgt ggaggccatg gagcgctttg ggtccaggaa tggcaagacc   1380
agcaagaaga tcaccattgc tgactgtgga caactcgaat aa                      1422
```

<210> SEQ ID NO 7
<211> LENGTH: 1461
<212> TYPE: DNA
<213> ORGANISM: Homo sapiens

<400> SEQUENCE: 7

```
atggcttctg gaatcctggt taatgtaaag gaggaggtga cctgccccat ctgcctggaa     60
ctcctgacac aacccctgag cctggactgc ggccacagct tctgccaagc atgcctcact    120
gcaaaccaca agaagtccat gctagacaaa ggagagagta gctgccctgt gtgccggatc    180
agttaccagc ctgagaacat acggcctaat cggcatgtag ccaacatagt ggagaagctc    240
agggaggtca agttgagccc agaggggcag aaagttgatc attgtgcacg ccatggagag    300
aaacttctac tcttctgtca ggaggacggg aaggtcattt gctggctttg tgagcggtct    360
caggagcacc gtggtcacca cacgttcctc acagaggagg ttgcccggga gtaccaagtg    420
aagctccagg cagctctgga gatgctgagg cagaagcagc aggaagctga agagttggaa    480
```

```
gctgacatca gagaagagaa agcttcctgg aagactcaaa tacagtatga caaaaccaac    540

gtcttggcag attttgagca actgagagac atcctggact gggaggagag caatgagctg    600

caaaacctgg agaaggagga ggaagacatt ctgaaaagcc ttacgaactc tgaaactgag    660

atggtgcagc agacccagtc cctgagagag ctcatctcag atctggagca tcggctgcag    720

gggtcagtga tggagctgct tcagggtgtg gatggcgtca taaaaaggac ggagaacgtg    780

accttgaaga agccagaaac ttttccaaaa aatcaaagga gagtgtttcg agctcctgat    840

ctgaaaggaa tgctagaagt gtttagagag ctgacagatg tccgacgcta ctgggttgat    900

gtgacagtgg ctccaaacaa catttcatgt gctgtcattt ctgaagataa gagacaagtg    960

agctctgtca accccaccgt gttcttcgac attgccgtcg acggcgagcc cttgggccgc   1020

gtctcctttg agctgtttgc agacaaggtc ccaaagacag cagaaaattt tcgtgctctg   1080

agcactggag agaaaggatt tggttataag ggttcctgct ttcacagaat tattccaggg   1140

tttatgtgtc agggtggtga cttcacacgc cataatggca ctggtggcaa gtccatctat   1200

ggggagaaat ttgaagatga gaacttcatc ctaaagcata cgggtcctgg catcttatcg   1260

atggcaaatg ctggacccaa cacaaatggt tcccagtttt tcatctgcac tgccaagact   1320

gagtggttgg atggcaagca tgtggtgttt ggcaaagtga aagaaggcat gaatattgtg   1380

gaggcgatgg agcgctttgg gtccaggaat ggcaagacca gcaagaagat caccattgct   1440

gactgtggac aactcgaata a                                               1461
```

<210> SEQ ID NO 8
<211> LENGTH: 7836
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgctgtg    240

gaatgtgtgt cagttagggt gtggaaagtc cccaggctcc ccagcaggca gaagtatgca    300

aagcatgcat ctcaattagt cagcaaccag gtgtggaaag tccccaggct ccccagcagg    360

cagaagtatg caaagcatgc atctcaatta gtcagcaacc atagtcccgc ccctaactcc    420

gcccatcccg cccctaactc cgcccagttc cgcccattct ccgccccatg gctgactaat    480

ttttttattt tatgcagagg ccgaggccgc ctctgcctct gagctattcc agaagtagtg    540

aggaggcttt tttggaggcc taggcttttg caaaaagctt tgacattgat tattgactag    600

ttattaatag taatcaatta cggggtcatt agttcatagc ccatatatgg agttccgcgt    660

tacataactt acggtaaatg gcccgcctgg ctgaccgccc aacgaccccc gcccattgac    720

gtcaataatg acgtatgttc ccatagtaac gccaataggg actttccatt gacgtcaatg    780

ggtggagtat ttacggtaaa ctgcccactt ggcagtacat caagtgtatc atatgccaag    840

tacgccccct attgacgtca atgacggtaa atggcccgcc tggcattatg cccagtacat    900

gaccttatgg gactttccta cttggcagta catctacgta ttagtcatcg ctattaccat    960

ggtgatgcgg ttttggcagt acatcaatgg gcgtggatag cggtttgact cacggggatt   1020
```

-continued

```
tccaagtctc caccccattg acgtcaatgg gagtttgttt tggcaccaaa atcaacggga   1080
ctttccaaaa tgtcgtaaca actccgcccc attgacgcaa atgggcggta ggcgtgtacg   1140
gtgggaggtc tatataagca gcgcgttttg cctgtactgg gtctctctgg ttagaccaga   1200
tctgagcctg ggagctctct ggctaactag ggaacccact gcttaagcct caataaagct   1260
tgccttgagt gcttcaagta gtgtgtgccc gtctgttgtg tgactctggt aactagagat   1320
ccctcagacc cttttagtca gtgtggaaaa tctctagcag tggcgcccga acagggactt   1380
gaaagcgaaa gggaaaccag aggagctctc tcgacgcagg actcggcttg ctgaagcgcg   1440
cacggcaaga ggcgaggggc ggcgactggt gagtacgcca aaaattttga ctagcggagg   1500
ctagaaggag agagatgggt gcgagagcgt cagtattaag cgggggagaa ttagatcgcg   1560
atgggaaaaa attcggttaa ggccaggggg aaagaaaaaa tataaattaa aacatatagt   1620
atgggcaagc agggagctag aacgattcgc agttaatcct ggcctgttag aaacatcaga   1680
aggctgtaga caaatactgg gacagctaca accatccctt cagacaggat cagaagaact   1740
tagatcatta tataatacag tagcaaccct ctattgtgtg catcaaagga tagagataaa   1800
agacaccaag gaagctttag acaagataga ggaagagcaa aacaaaagta agaccaccgc   1860
acagcaagcg gccggccgct gatcttcaga cctggaggag gagatatgag ggacaattgg   1920
agaagtgaat tatataaata taaagtagta aaaattgaac cattaggagt agcacccacc   1980
aaggcaaaga gaagagtggt gcagagagaa aaaagagcag tgggaatagg agctttgttc   2040
cttgggttct tgggagcagc aggaagcact atgggcgcag cgtcaatgac gctgacggta   2100
caggccagac aattattgtc tggtatagtg cagcagcaga acaatttgct gagggctatt   2160
gaggcgcaac agcatctgtt gcaactcaca gtctggggca tcaagcagct ccaggcaaga   2220
atcctggctg tggaaagata cctaaaggat caacagctcc tggggatttg gggttgctct   2280
ggaaaactca tttgcaccac tgctgtgcct tggaatgcta gttggagtaa taaatctctg   2340
gaacagattt ggaatcacac gacctggatg gagtgggaca gagaaattaa caattacaca   2400
agcttaatac actccttaat tgaagaatcg caaaaccagc aagaaaagaa tgaacaagaa   2460
ttattggaat tagataaatg ggcaagtttg tggaattggt ttaacataac aaattggctg   2520
tggtatataa aattattcat aatgatagta ggaggcttgg taggtttaag aatagttttt   2580
gctgtacttt ctatagtgaa tagagttagg cagggatatt caccattatc gtttcagacc   2640
cacctcccaa ccccgagggg acccgacagg cccgaaggaa tagaagaaga aggtggagag   2700
agagacagag acagatccat tcgattagtg aacggatcgg cactgcgtgc gccaattctg   2760
cagacaaatg gcagtattca tccacaattt taaaagaaaa ggggggattg gggggtacag   2820
tgcaggggaa agaatagtag acataatagc aacagacata caaactaaag aattacaaaa   2880
acaaattaca aaaattcaaa attttcgggt ttattacagg gacagcagag atccagtttg   2940
gttaattaac tgcagccccg ataaaataaa agattttatt tagtctccag aaaaaggggg   3000
gaatgaaaga ccccacctgt aggtttggca agctagctgc agtaacgcca ttttgcaagg   3060
catggaaaaa taccaaacca agaatagaga agttcagatc aagggcgggt acatgaaaat   3120
agctaacgtt gggccaaaca ggatatctgc ggtgagcagt ttcggccccg gcccggggcc   3180
aagaacagat ggtcaccgca gtttcggccc cggcccgagg ccaagaacag atggtcccca   3240
gatatggccc aaccctcagc agtttcttaa gacccatcag atgtttccag gctcccccaa   3300
ggacctgaaa tgaccctgcg ccttatttga attaaccaat cagcctgctt ctcgcttctg   3360
ttcgcgcgct tctgcttccc gagctctata aaagagctca caacccctca ctcggcgcgc   3420
```

-continued

```
cagtcctccg acagactgag tcgcccgggg gtctagaagc gctggatccg tttaaacgcg   3480
gccgcccagc acagtggctc gagccgcggg ttaactggcc agaattctcg accttgactg   3540
gcggcgcgac cttgaggcct gcgttcgcct cagttgcccc ctctgtgcaa tggggagacg   3600
cgcctcatcg cttgacaacg gccgaagagc cgccgcgctt ccgtctcccg cgtgcgcgcg   3660
ccatgctgcc cacccccgtt ccgcactgac cctcccccgt gccccgcgtc ccgtactgcc   3720
gccccgcccc gagtcccatg ccgcagccac cgcgacggag cccgcaggcg ggaacctgcc   3780
tccgcgcgtt agcgcgcacg cgcgcctcat gtgtcgtccc catcagcgcc ggcttccgtc   3840
tataggccag atgcactgtc actctggcga agtcgcagac ccgattggcc gggacggagg   3900
cgcgagaccg ggttgcgggc ggggccgaac gtggtataaa aggggcggga ggccaggctc   3960
gtgccgtttt gcagacgcca ccgccgagga aaaccgtgta ctattagcca cgcgtgccac   4020
catggcccag tccaagcacg gcctgaccaa ggagatgacc atgaagtacc gcatggaggg   4080
ctgcgtggac ggccacaagt tcgtgatcac cggcgagggc atcggctacc ccttcaaggg   4140
caagcaggcc atcaacctgt gcgtggtgga gggcggcccc ttgcccttcg ccgaggacat   4200
cttgtccgcc gccttcatgt acggcaaccg cgtgttcacc gagtaccccc aggacatcgt   4260
cgactacttc aagaactcct gccccgccgg ctacacctgg gaccgctcct tcctgttcga   4320
ggacggcgcc gtgtgcatct gcaacgccga catcaccgtg agcgtggagg agaactgcat   4380
gtaccacgag tccaagttct acggcgtgaa cttccccgcc gacggccccg tgatgaagaa   4440
gatgaccgac aactgggagc cctcctgcga gaagatcatc cccgtgccca agcagggcat   4500
cttgaagggc gacgtgagca tgtacctgct gctgaaggac ggtggccgct tgcgctgcca   4560
gttcgacacc gtgtacaagg ccaagtccgt gccccgcaag atgcccgact ggcacttcat   4620
ccagcacaag ctgacccgcg aggaccgcag cgacgccaag aaccagaagt ggcacctgac   4680
cgagcacgcc atcgcctccg gctccgcctt gccctgagcg atcgctaatc aacctctgga   4740
ttacaaaatt tgtgaaagat tgactggtat tcttaactat gttgctcctt ttacgctatg   4800
tggatacgct gctttaatgc ctttgtatca tgctattgct tcccgtatgg ctttcatttt   4860
ctcctccttg tataaatcct ggttgctgtc tctttatgag gagttgtggc ccgttgtcag   4920
gcaacgtggc gtggtgtgca ctgtgtttgc tgacgcaacc cccactggtt ggggcattgc   4980
caccacctgt cagctccttt ccgggacttt cgctttcccc ctccctattg ccacggcgga   5040
actcatcgcc gcctgccttg cccgctgctg gacaggggct cggctgttgg gcactgacaa   5100
ttccgtggtg ttgtcgggga agctgacgtc ctttccatgg ctgctcgcct gtgttgccac   5160
ctggattctg cgcgggacgt ccttctgcta cgtcccttcg gccctcaatc cagcggacct   5220
tccttcccgc ggcctgctgc cggctctgcg gcctcttccg cgtcttcgcc ttcgccctca   5280
gacgagtcgg atctcccttt gggccgcctc cccgcttaat cgcgtcgaga cctagaaaaa   5340
catggagcaa tcacaagtag caatacagca gctaccaatg ctgattgtgc ctggctagaa   5400
gcacaagagg aggaggaggt gggttttcca gtcacacctc aggtaccttt aagaccaatg   5460
acttacaagg cagctgtaga tcttagccac tttttaaaag aaaagggggg actggaaggg   5520
ctaattcact cccaacgaag acaagatatc cttgatctgt ggatctacca cacacaaggc   5580
tacttccctg attggcagaa ctacacacca gggccaggga tcagatatcc actgaccttt   5640
ggatggtgct acaagctagt accagttgag caagagaagg tagaagaagc caatgaagga   5700
gagaacaccc gcttgttaca ccctgtgagc ctgcatggga tggatgaccc ggagagagaa   5760
```

```
gtattagagt ggaggtttga cagccgccta gcatttcatc acatggcccg agagctgcat   5820
ccggactgta ctgggtctct ctggttagac cagatctgag cctgggagct ctctggctaa   5880
ctagggaacc cactgcttaa gcctcaataa agcttgcctt gagtgcttca agtagtgtgt   5940
gcccgtctgt tgtgtgactc tggtaactag agatccctca gaccctttta gtcagtgtgg   6000
aaaatctcta gcagggcccg tttcatgtga gcaaaaggcc agcaaaaggc caggaaccgt   6060
aaaaaggccg cgttgctggc gtttttccat aggctccgcc cccctgacga gcatcacaaa   6120
aatcgacgct caagtcagag gtggcgaaac ccgacaggac tataaagata ccaggcgttt   6180
ccccctggaa gctccctcgt gcgctctcct gttccgaccc tgccgcttac cggatacctg   6240
tccgcctttc tcccttcggg aagcgtggcg ctttctcata gctcacgctg taggtatctc   6300
agttcggtgt aggtcgttcg ctccaagctg ggctgtgtgc acgaaccccc cgttcagccc   6360
gaccgctgcg ccttatccgg taactatcgt cttgagtcca acccggtaag acacgactta   6420
tcgccactgg cagcagccac tggtaacagg attagcagag cgaggtatgt aggcggtgct   6480
acagagttct tgaagtggtg gcctaactac ggctacacta gaagaacagt atttggtatc   6540
tgcgctctgc tgaagccagt taccttcgga aaaagagttg gtagctcttg atccggcaaa   6600
caaaccaccg ctggtagcgg tggttttttt gtttgcaagc agcagattac gcgcagaaaa   6660
aaaggatctc aagaagatcc tttgatcttt tctacggggt ctgacgctca gtggaacgaa   6720
aactcacgtt aagggatttt ggtcatgaga ttatcaaaaa ggatcttcac ctagatcctt   6780
ttaaattaaa aatgaagttt taaatcaatc taaagtatat atgagtaaac ttggtctgac   6840
agttaccaat gcttaatcag tgaggcacct atctcagcga tctgtctatt tcgttcatcc   6900
atagttgcct gactccccgt cgtgtagata actacgatac gggagggctt accatctggc   6960
cccagtgctg caatgatacc gcgagaccca cgctcaccgg ctccagattt atcagcaata   7020
aaccagccag ccggaagggc cgagcgcaga agtggtcctg caactttatc cgcctccatc   7080
cagtctatta attgttgccg ggaagctaga gtaagtagtt cgccagttaa tagtttgcgc   7140
aacgttgttg ccattgctac aggcatcgtg gtgtcacgct cgtcgtttgg tatggcttca   7200
ttcagctccg gttcccaacg atcaaggcga gttacatgat cccccatgtt gtgcaaaaaa   7260
gcggttagct ccttcggtcc tccgatcgtt gtcagaagta agttggccgc agtgttatca   7320
ctcatggtta tggcagcact gcataattct cttactgtca tgccatccgt aagatgcttt   7380
tctgtgactg gtgagtactc aaccaagtca ttctgagaat agtgtatgcg gcgaccgagt   7440
tgctcttgcc cggcgtcaat acgggataat accgcgccac atagcagaac tttaaaagtg   7500
ctcatcattg gaaaacgttc ttcggggcga aaactctcaa ggatcttacc gctgttgaga   7560
tccagttcga tgtaacccac tcgtgcaccc aactgatctt cagcatcttt tactttcacc   7620
agcgtttctg ggtgagcaaa aacaggaagg caaaatgccg caaaaaaggg aataagggcg   7680
acacggaaat gttgaatact catactcttc ctttttcaat attattgaag catttatcag   7740
ggttattgtc tcatgagcgg atacatattt gaatgtattt agaaaaataa acaaataggg   7800
gttccgcgca catttccccg aaaagtgcca cctgac                              7836
```

<210> SEQ ID NO 9
<211> LENGTH: 9297
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgctgtg    240
gaatgtgtgt cagttagggt gtggaaagtc cccaggctcc ccagcaggca gaagtatgca    300
aagcatgcat ctcaattagt cagcaaccag gtgtggaaag tccccaggct ccccagcagg    360
cagaagtatg caaagcatgc atctcaatta gtcagcaacc atagtcccgc ccctaactcc    420
gcccatcccg cccctaactc cgcccagttc cgcccattct ccgccccatg gctgactaat    480
ttttttattt tatgcagagg ccgaggccgc ctctgcctct gagctattcc agaagtagtg    540
aggaggcttt tttggaggcc taggcttttg caaaaagctt tgacattgat tattgactag    600
ttattaatag taatcaatta cggggtcatt agttcatagc ccatatatgg agttccgcgt    660
tacataactt acggtaaatg gcccgcctgg ctgaccgccc aacgaccccc gcccattgac    720
gtcaataatg acgtatgttc ccatagtaac gccaataggg actttccatt gacgtcaatg    780
ggtggagtat ttacggtaaa ctgcccactt ggcagtacat caagtgtatc atatgccaag    840
tacgccccct attgacgtca atgacggtaa atggcccgcc tggcattatg cccagtacat    900
gaccttatgg gactttccta cttggcagta catctacgta ttagtcatcg ctattaccat    960
ggtgatgcgg ttttggcagt acatcaatgg gcgtggatag cggtttgact cacggggatt   1020
tccaagtctc caccccattg acgtcaatgg gagtttgttt tggcaccaaa atcaacggga   1080
ctttccaaaa tgtcgtaaca actccgcccc attgacgcaa atgggcggta ggcgtgtacg   1140
gtgggaggtc tatataagca gcgcgttttg cctgtactgg gtctctctgg ttagaccaga   1200
tctgagcctg ggagctctct ggctaactag ggaacccact gcttaagcct caataaagct   1260
tgccttgagt gcttcaagta gtgtgtgccc gtctgttgtg tgactctggt aactagagat   1320
ccctcagacc cttttagtca gtgtggaaaa tctctagcag tggcgcccga acagggactt   1380
gaaagcgaaa gggaaaccag aggagctctc tcgacgcagg actcggcttg ctgaagcgcg   1440
cacggcaaga ggcgaggggc ggcgactggt gagtacgcca aaaattttga ctagcggagg   1500
ctagaaggag agagatgggt gcgagagcgt cagtattaag cgggggagaa ttagatcgcg   1560
atgggaaaaa attcggttaa ggccaggggg aaagaaaaaa tataaattaa aacatatagt   1620
atgggcaagc agggagctag aacgattcgc agttaatcct ggcctgttag aaacatcaga   1680
aggctgtaga caaatactgg gacagctaca accatccctt cagacaggat cagaagaact   1740
tagatcatta tataatacag tagcaaccct ctattgtgtg catcaaagga tagagataaa   1800
agacaccaag gaagctttag acaagataga ggaagagcaa aacaaaagta agaccaccgc   1860
acagcaagcg gccggccgct gatcttcaga cctggaggag gagatatgag ggacaattgg   1920
agaagtgaat tatataaata taaagtagta aaaattgaac cattaggagt agcacccacc   1980
aaggcaaaga gaagagtggt gcagagagaa aaaagagcag tgggaatagg agctttgttc   2040
cttgggttct tgggagcagc aggaagcact atgggcgcag cgtcaatgac gctgacggta   2100
caggccagac aattattgtc tggtatagtg cagcagcaga acaatttgct gagggctatt   2160
gaggcgcaac agcatctgtt gcaactcaca gtctggggca tcaagcagct ccaggcaaga   2220
atcctggctg tggaaagata cctaaaggat caacagctcc tggggatttg gggttgctct   2280
ggaaaactca tttgcaccac tgctgtgcct tggaatgcta gttggagtaa taaatctctg   2340
```

-continued

```
gaacagattt ggaatcacac gacctggatg gagtgggaca gagaaattaa caattacaca   2400
agcttaatac actccttaat tgaagaatcg caaaaccagc aagaaaagaa tgaacaagaa   2460
ttattggaat tagataaatg ggcaagtttg tggaattggt ttaacataac aaattggctg   2520
tggtatataa aattattcat aatgatagta ggaggcttgg taggtttaag aatagttttt   2580
gctgtacttt ctatagtgaa tagagttagg cagggatatt caccattatc gtttcagacc   2640
cacctcccaa ccccgagggg acccgacagg cccgaaggaa tagaagaaga aggtggagag   2700
agagacagag acagatccat tcgattagtg aacggatcgg cactgcgtgc gccaattctg   2760
cagacaaatg gcagtattca tccacaattt taaaagaaaa ggggggattg gggggtacag   2820
tgcaggggaa agaatagtag acataatagc aacagacata caaactaaag aattacaaaa   2880
acaaattaca aaaattcaaa attttcgggt ttattacagg gacagcagag atccagtttg   2940
gttaattaac tgcagccccg ataaaataaa agattttatt tagtctccag aaaaaggggg   3000
gaatgaaaga ccccacctgt aggtttggca agctagctgc agtaacgcca ttttgcaagg   3060
catggaaaaa taccaaacca agaatagaga agttcagatc aagggcgggt acatgaaaat   3120
agctaacgtt gggccaaaca ggatatctgc ggtgagcagt ttcggccccg gcccggggcc   3180
aagaacagat ggtcaccgca gtttcggccc cggcccgagg ccaagaacag atggtcccca   3240
gatatggccc aaccctcagc agtttcttaa gacccatcag atgtttccag gctcccccaa   3300
ggacctgaaa tgaccctgcg ccttatttga attaaccaat cagcctgctt ctcgcttctg   3360
ttcgcgcgct tctgcttccc gagctctata aaagagctca caacccctca ctcggcgcgc   3420
cagtcctccg acagactgag tcgcccgggg gtctagagcc accatggctt ctggaatcct   3480
ggttaatgta aaggaggagg tgacctgccc catctgcctg gaactcctga cacaacccct   3540
gagcctggac tgcggccaca gcttctgcca agcatgcctc actgcaaacc acaagaagtc   3600
catgctagac aaaggagaga gtagctgccc tgtgtgccgg atcagttacc agcctgagaa   3660
catacggcct aatcggcatg tagccaacat agtggagaag ctcagggagg tcaagttgag   3720
cccagagggg cagaaagttg atcattgtgc acgccatgga gagaaacttc tactcttctg   3780
tcaggaggac gggaaggtca tttgctggct ttgtgagcgg tctcaggagc accgtggtca   3840
ccacacgttc ctcacagagg aggttgcccg ggagtaccaa gtgaagctcc aggcagctct   3900
ggagatgctg aggcagaagc agcaggaagc tgaagagttg gaagctgaca tcagagaaga   3960
gaaagcttcc tggaagactc aaatacagta tgacaaaacc aacgtcttgg cagattttga   4020
gcaactgaga gacatcctgg actgggagga gagcaatgag ctgcaaaacc tggagaagga   4080
ggaggaagac attctgaaaa gccttacgaa ctctgaaact gagatggtgc agcagaccca   4140
gtccctgaga gagctcatct cagatctgga gcatcggctg caggggtcag tgatggagct   4200
gcttcagggt gtggatggcg tcataaaaag gacggagaac gtgaccttga agaagccaga   4260
aacttttcca aaaaatcaaa ggagagtgtt tcgagctcct gatctgaaag gaatgctaga   4320
agtgtttaga gagctgacag atgtccgacg ctactgggtt gatgtgacag tggctccaaa   4380
caacatttca tgtgctgtca tttctgaaga taagagacaa gtgagctctg tcaaccccac   4440
cgtgttcttc gacattgccg tcgacggcga gcccttgggc cgcgtctcct ttgagctgtt   4500
tgcagacaag gtcccaaaga cagcagaaaa ttttcgtgct ctgagcactg gagagaaagg   4560
atttggttat aagggttcct gctttcacag aattattcca gggtttatgt gtcagggtgg   4620
tgacttcaca cgccataatg gcactggtgg caagtccatc tatggggaga aatttgaaga   4680
```

-continued

```
tgagaacttc atcctaaagc atacgggtcc tggcatctta tcgatggcaa atgctggacc   4740
caacacaaat ggttcccagt ttttcatctg cactgccaag actgagtggt tggatggcaa   4800
gcatgtggtg tttggcaaag tgaaagaagg catgaatatt gtggaggcga tggagcgctt   4860
tgggtccagg aatggcaaga ccagcaagaa gatcaccatt gctgactgtg gacaactcga   4920
ataaggatcc gtttaaacgc ggccgcccag cacagtggct cgagccgcgg gttaactggc   4980
cagaattctc gaccttgact ggcggcgcga ccttgaggcc tgcgttcgcc tcagttgccc   5040
cctctgtgca atggggagac gcgcctcatc gcttgacaac ggccgaagag ccgccgcgct   5100
tccgtctccc gcgtgcgcgc gccatgctgc ccaccccgt tccgcactga ccctccccg    5160
tgccccgcgt cccgtactgc cgccccgccc cgagtcccat gccgcagcca ccgcgacgga   5220
gcccgcaggc gggaacctgc ctccgcgcgt tagcgcgcac gcgcgcctca tgtgtcgtcc   5280
ccatcagcgc cggcttccgt ctataggcca gatgcactgt cactctggcg aagtcgcaga   5340
cccgattggc cgggacggag gcgcgagacc gggttgcggg cggggccgaa cgtggtataa   5400
aaggggcggg aggccaggct cgtgccgttt tgcagacgcc accgccgagg aaaaccgtgt   5460
actattagcc acgcgtgcca ccatggccca gtccaagcac ggcctgacca aggagatgac   5520
catgaagtac cgcatggagg gctgcgtgga cggccacaag ttcgtgatca ccggcgaggg   5580
catcggctac cccttcaagg gcaagcaggc catcaacctg tgcgtggtgg agggcggccc   5640
cttgcccttc gccgaggaca tcttgtccgc cgccttcatg tacggcaacc gcgtgttcac   5700
cgagtacccc caggacatcg tcgactactt caagaactcc tgccccgccg gctacacctg   5760
ggaccgctcc ttcctgttcg aggacggcgc cgtgtgcatc tgcaacgccg acatcaccgt   5820
gagcgtggag gagaactgca tgtaccacga gtccaagttc tacggcgtga acttccccgc   5880
cgacggcccc gtgatgaaga agatgaccga caactgggag ccctcctgcg agaagatcat   5940
ccccgtgccc aagcagggca tcttgaaggg cgacgtgagc atgtacctgc tgctgaagga   6000
cggtggccgc ttgcgctgcc agttcgacac cgtgtacaag gccaagtccg tgccccgcaa   6060
gatgcccgac tggcacttca tccagcacaa gctgacccgc gaggaccgca gcgacgccaa   6120
gaaccagaag tggcacctga ccgagcacgc catcgcctcc ggctccgcct tgccctgagc   6180
gatcgctaat caacctctgg attacaaaat ttgtgaaaga ttgactggta ttcttaacta   6240
tgttgctcct tttacgctat gtggatacgc tgctttaatg cctttgtatc atgctattgc   6300
ttcccgtatg gctttcattt tctcctcctt gtataaatcc tggttgctgt ctctttatga   6360
ggagttgtgg cccgttgtca ggcaacgtgg cgtggtgtgc actgtgtttg ctgacgcaac   6420
ccccactggt tggggcattg ccaccacctg tcagctcctt tccgggactt tcgctttccc   6480
cctccctatt gccacggcgg aactcatcgc cgcctgcctt gcccgctgct ggacaggggc   6540
tcggctgttg ggcactgaca attccgtggt gttgtcgggg aagctgacgt cctttccatg   6600
gctgctcgcc tgtgttgcca cctggattct gcgcgggacg tccttctgct acgtcccttc   6660
ggccctcaat ccagcggacc ttccttcccg cggcctgctg ccggctctgc ggcctcttcc   6720
gcgtcttcgc cttcgccctc agacgagtcg gatctccctt tgggccgcct ccccgcttaa   6780
tcgcgtcgag acctagaaaa acatggagca atcacaagta gcaatacagc agctaccaat   6840
gctgattgtg cctggctaga agcacaagag gaggaggagg tgggttttcc agtcacacct   6900
caggtacctt taagaccaat gacttacaag gcagctgtag atcttagcca ctttttaaaa   6960
gaaaaggggg gactggaagg gctaattcac tcccaacgaa gacaagatat ccttgatctg   7020
tggatctacc acacacaagg ctacttccct gattggcaga actacacacc agggccaggg   7080
```

atcagatatc cactgacctt tggatggtgc tacaagctag taccagttga gcaagagaag 7140
gtagaagaag ccaatgaagg agagaacacc cgcttgttac accctgtgag cctgcatggg 7200
atggatgacc cggagagaga agtattagag tggaggtttg acagccgcct agcatttcat 7260
cacatggccc gagagctgca tccggactgt actgggtctc tctggttaga ccagatctga 7320
gcctgggagc tctctggcta actagggaac ccactgctta agcctcaata aagcttgcct 7380
tgagtgcttc aagtagtgtg tgcccgtctg ttgtgtgact ctggtaacta gagatccctc 7440
agaccctttt agtcagtgtg gaaaatctct agcagggccc gtttcatgtg agcaaaaggc 7500
cagcaaaagg ccaggaaccg taaaaaggcc gcgttgctgg cgtttttcca taggctccgc 7560 cccccctgacg agcatcacaa aaatcgacgc tcaagtcaga ggtggcgaaa cccgacagga 7620
ctataaagat accaggcgtt tccccctgga agctccctcg tgcgctctcc tgttccgacc 7680
ctgccgctta ccggatacct gtccgccttt ctcccttcgg gaagcgtggc gctttctcat 7740
agctcacgct gtaggtatct cagttcggtg taggtcgttc gctccaagct gggctgtgtg 7800
cacgaacccc ccgttcagcc cgaccgctgc gccttatccg gtaactatcg tcttgagtcc 7860
aacccggtaa gacacgactt atcgccactg gcagcagcca ctggtaacag gattagcaga 7920
gcgaggtatg taggcggtgc tacagagttc ttgaagtggt ggcctaacta cggctacact 7980
agaagaacag tatttggtat ctgcgctctg ctgaagccag ttaccttcgg aaaaagagtt 8040
ggtagctctt gatccggcaa acaaaccacc gctggtagcg gtggtttttt tgtttgcaag 8100
cagcagatta cgcgcagaaa aaaaggatct caagaagatc ctttgatctt ttctacgggg 8160
tctgacgctc agtggaacga aaactcacgt taagggattt tggtcatgag attatcaaaa 8220
aggatcttca cctagatcct tttaaattaa aaatgaagtt ttaaatcaat ctaaagtata 8280
tatgagtaaa cttggtctga cagttaccaa tgcttaatca gtgaggcacc tatctcagcg 8340
atctgtctat ttcgttcatc catagttgcc tgactccccg tcgtgtagat aactacgata 8400
cgggagggct taccatctgg ccccagtgct gcaatgatac cgcgagaccc acgctcaccg 8460
gctccagatt tatcagcaat aaaccagcca gccggaaggg ccgagcgcag aagtggtcct 8520
gcaactttat ccgcctccat ccagtctatt aattgttgcc gggaagctag agtaagtagt 8580
tcgccagtta atagtttgcg caacgttgtt gccattgcta caggcatcgt ggtgtcacgc 8640
tcgtcgtttg gtatggcttc attcagctcc ggttcccaac gatcaaggcg agttacatga 8700
tcccccatgt tgtgcaaaaa agcggttagc tccttcggtc ctccgatcgt tgtcagaagt 8760
aagttggccg cagtgttatc actcatggtt atggcagcac tgcataattc tcttactgtc 8820
atgccatccg taagatgctt ttctgtgact ggtgagtact caaccaagtc attctgagaa 8880
tagtgtatgc ggcgaccgag ttgctcttgc ccggcgtcaa tacgggataa taccgcgcca 8940
catagcagaa ctttaaaagt gctcatcatt ggaaaacgtt cttcggggcg aaaactctca 9000
aggatcttac cgctgttgag atccagttcg atgtaaccca ctcgtgcacc caactgatct 9060
tcagcatctt ttactttcac cagcgtttct gggtgagcaa aaacaggaag gcaaaatgcc 9120
gcaaaaaagg gaataagggc gacacggaaa tgttgaatac tcatactctt cctttttcaa 9180
tattattgaa gcatttatca gggttattgt ctcatgagcg gatacatatt tgaatgtatt 9240
tagaaaaata aacaaatagg ggttccgcgc acatttcccc gaaaagtgcc acctgac 9297

<210> SEQ ID NO 10
<211> LENGTH: 495
<212> TYPE: PRT

<213> ORGANISM: Homo sapiens

<400> SEQUENCE: 10

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Val Asn Pro Thr Val
                325                 330                 335

Phe Phe Asp Ile Ala Val Asp Gly Glu Pro Leu Gly Arg Val Ser Phe
            340                 345                 350

Glu Leu Phe Ala Asp Lys Val Pro Lys Thr Ala Glu Asn Phe Arg Ala
        355                 360                 365

Leu Ser Thr Gly Glu Lys Gly Phe Gly Tyr Lys Gly Ser Cys Phe His
    370                 375                 380

Arg Ile Ile Pro Gly Phe Met Cys Gln Gly Gly Asp Phe Thr Arg His
385                 390                 395                 400

```
Asn Gly Thr Gly Gly Lys Ser Ile Tyr Gly Glu Lys Phe Glu Asp Glu
                405                 410                 415

Asn Phe Ile Leu Lys His Thr Gly Pro Gly Ile Leu Ser Met Ala Asn
            420                 425                 430

Ala Gly Pro Asn Thr Asn Gly Ser Gln Phe Phe Ile Cys Thr Ala Lys
        435                 440                 445

Thr Glu Trp Leu Asp Gly Lys His Val Val Phe Gly Lys Val Lys Glu
    450                 455                 460

Gly Met Asn Ile Val Glu Ala Met Glu Arg Phe Gly Ser Arg Asn Gly
465                 470                 475                 480

Lys Thr Ser Lys Lys Ile Thr Ile Ala Asp Cys Gly Gln Leu Glu
                485                 490                 495


<210> SEQ ID NO 11
<211> LENGTH: 473
<212> TYPE: PRT
<213> ORGANISM: Homo sapiens

<400> SEQUENCE: 11

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285
```

```
Arg Glu Leu Thr Asp Val Arg Arg Tyr Trp Val Asp Val Thr Val Ala
    290                 295                 300

Pro Asn Asn Ile Ser Val Asn Pro Thr Val Phe Phe Asp Ile Ala Val
305                 310                 315                 320

Asp Gly Glu Pro Leu Gly Arg Val Ser Phe Glu Leu Phe Ala Asp Lys
                325                 330                 335

Val Pro Lys Thr Ala Glu Asn Phe Arg Ala Leu Ser Thr Gly Glu Lys
            340                 345                 350

Gly Phe Gly Tyr Lys Gly Ser Cys Phe His Arg Ile Ile Pro Gly Phe
        355                 360                 365

Met Cys Gln Gly Gly Asp Phe Thr Arg His Asn Gly Thr Gly Gly Lys
    370                 375                 380

Ser Ile Tyr Gly Glu Lys Phe Glu Asp Glu Asn Phe Ile Leu Lys His
385                 390                 395                 400

Thr Gly Pro Gly Ile Leu Ser Met Ala Asn Ala Gly Pro Asn Thr Asn
                405                 410                 415

Gly Ser Gln Phe Phe Ile Cys Thr Ala Lys Thr Glu Trp Leu Asp Gly
            420                 425                 430

Lys His Val Val Phe Gly Lys Val Lys Glu Gly Met Asn Ile Val Glu
        435                 440                 445

Ala Met Glu Arg Phe Gly Ser Arg Asn Gly Lys Thr Ser Lys Lys Ile
    450                 455                 460

Thr Ile Ala Asp Cys Gly Gln Leu Glu
465                 470


<210> SEQ ID NO 12
<211> LENGTH: 486
<212> TYPE: PRT
<213> ORGANISM: Homo sapiens

<400> SEQUENCE: 12

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
```

-continued

```
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Val Asn Pro Thr Val Phe Phe Asp Ile Ala Val Asp Gly Glu
                325                 330                 335

Pro Leu Gly Arg Val Ser Phe Glu Leu Phe Ala Asp Lys Val Pro Lys
            340                 345                 350

Thr Ala Glu Asn Phe Arg Ala Leu Ser Thr Gly Glu Lys Gly Phe Gly
        355                 360                 365

Tyr Lys Gly Ser Cys Phe His Arg Ile Ile Pro Gly Phe Met Cys Gln
    370                 375                 380

Gly Gly Asp Phe Thr Arg His Asn Gly Thr Gly Gly Lys Ser Ile Tyr
385                 390                 395                 400

Gly Glu Lys Phe Glu Asp Glu Asn Phe Ile Leu Lys His Thr Gly Pro
                405                 410                 415

Gly Ile Leu Ser Met Ala Asn Ala Gly Pro Asn Thr Asn Gly Ser Gln
            420                 425                 430

Phe Phe Ile Cys Thr Ala Lys Thr Glu Trp Leu Asp Gly Lys His Val
        435                 440                 445

Val Phe Gly Lys Val Lys Glu Gly Met Asn Ile Val Glu Ala Met Glu
    450                 455                 460

Arg Phe Gly Ser Arg Asn Gly Lys Thr Ser Lys Lys Ile Thr Ile Ala
465                 470                 475                 480

Asp Cys Gly Gln Leu Glu
                485


<210> SEQ ID NO 13
<211> LENGTH: 298
<212> TYPE: PRT
<213> ORGANISM: Homo sapiens

<400> SEQUENCE: 13

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60
```

Glu Asn Ile Arg Pro Asn Arg His Val Ala Asn Leu Val Glu Lys Leu
65 70 75 80

Arg Glu Val Lys Leu Ser Pro Glu Gly Gln Lys Val Asp His Cys Ala
85 90 95

Arg His Gly Glu Lys Leu Leu Leu Phe Cys Gln Glu Asp Gly Lys Val
100 105 110

Ile Cys Trp Leu Cys Glu Arg Ser Gln Glu His Arg Gly His His Thr
115 120 125

Phe Pro Thr Glu Glu Val Ala Gln Glu Tyr Gln Val Lys Leu Gln Ala
130 135 140

Ala Leu Glu Met Leu Arg Gln Lys Gln Gln Glu Ala Glu Glu Leu Glu
145 150 155 160

Ala Asp Ile Arg Glu Glu Lys Ala Ser Trp Lys Thr Gln Ile Gln Tyr
165 170 175

Asp Lys Thr Asn Val Leu Ala Asp Phe Glu Gln Leu Arg Asp Ile Leu
180 185 190

Asp Trp Glu Glu Ser Asn Glu Leu Gln Asn Leu Glu Lys Glu Glu Glu
195 200 205

Asp Ile Leu Lys Ser Leu Thr Asn Ser Glu Thr Glu Met Val Gln Gln
210 215 220

Thr Gln Ser Leu Arg Glu Leu Ile Ser Asp Leu Glu His Arg Leu Gln
225 230 235 240

Gly Ser Val Met Glu Leu Leu Gln Gly Val Asp Gly Val Ile Lys Arg
245 250 255

Thr Glu Asn Val Thr Leu Lys Lys Pro Glu Thr Phe Pro Lys Asn Gln
260 265 270

Arg Arg Val Phe Arg Ala Pro Asp Leu Lys Gly Met Leu Glu Val Phe
275 280 285

Arg Glu Leu Thr Asp Val Arg Arg Tyr Trp
290 295

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(33)
<223> OTHER INFORMATION: Any amino acid and this region may encompass 12-33 residues

<400> SEQUENCE: 14

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa

<210> SEQ ID NO 15
<211> LENGTH: 164
<212> TYPE: PRT
<213> ORGANISM: Homo sapiens

<400> SEQUENCE: 15

Val Asn Pro Thr Val Phe Phe Asp Ile Ala Val Asp Gly Glu Pro Leu
1 5 10 15

```
Gly Arg Val Ser Phe Glu Leu Phe Ala Asp Lys Val Pro Lys Thr Ala
            20                  25                  30

Glu Asn Phe Arg Ala Leu Ser Thr Gly Glu Lys Gly Phe Gly Tyr Lys
        35                  40                  45

Gly Ser Cys Phe His Arg Ile Ile Pro Gly Phe Met Cys Gln Gly Gly
    50                  55                  60

Asp Phe Thr Arg His Asn Gly Thr Gly Gly Lys Ser Ile Tyr Gly Glu
65                  70                  75                  80

Lys Phe Glu Asp Glu Asn Phe Ile Leu Lys His Thr Gly Pro Gly Ile
                85                  90                  95

Leu Ser Met Ala Asn Ala Gly Pro Asn Thr Asn Gly Ser Gln Phe Phe
            100                 105                 110

Ile Cys Thr Ala Lys Thr Glu Trp Leu Asp Gly Lys His Val Val Phe
        115                 120                 125

Gly Lys Val Lys Glu Gly Met Asn Ile Val Glu Ala Met Glu Arg Phe
    130                 135                 140

Gly Ser Arg Asn Gly Lys Thr Ser Lys Lys Ile Thr Ile Ala Asp Cys
145                 150                 155                 160

Gly Gln Leu Glu


<210> SEQ ID NO 16
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (299)..(331)
<223> OTHER INFORMATION: Any amino acid and this region may encompass
      12-33 residues

<400> SEQUENCE: 16

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175
```

Asp Lys Thr Asn Val Leu Ala Asp Phe Glu Gln Leu Arg Asp Ile Leu
180 185 190

Asp Trp Glu Glu Ser Asn Glu Leu Gln Asn Leu Glu Lys Glu Glu Glu
195 200 205

Asp Ile Leu Lys Ser Leu Thr Asn Ser Glu Thr Glu Met Val Gln Gln
210 215 220

Thr Gln Ser Leu Arg Glu Leu Ile Ser Asp Leu Glu His Arg Leu Gln
225 230 235 240

Gly Ser Val Met Glu Leu Leu Gln Gly Val Asp Gly Val Ile Lys Arg
245 250 255

Thr Glu Asn Val Thr Leu Lys Lys Pro Glu Thr Phe Pro Lys Asn Gln
260 265 270

Arg Arg Val Phe Arg Ala Pro Asp Leu Lys Gly Met Leu Glu Val Phe
275 280 285

Arg Glu Leu Thr Asp Val Arg Arg Tyr Trp Xaa Xaa Xaa Xaa Xaa Xaa
290 295 300

Xaa Xaa Xaa Xaa Xaa Xaa Xaa Xaa Xaa Xaa Xaa Xaa Xaa Xaa Xaa Xaa
305 310 315 320

Xaa Xaa Xaa Xaa Xaa Xaa Xaa Xaa Xaa Xaa Xaa Val Asn Pro Thr Val
325 330 335

Phe Phe Asp Ile Ala Val Asp Gly Glu Pro Leu Gly Arg Val Ser Phe
340 345 350

Glu Leu Phe Ala Asp Lys Val Pro Lys Thr Ala Glu Asn Phe Arg Ala
355 360 365

Leu Ser Thr Gly Glu Lys Gly Phe Gly Tyr Lys Gly Ser Cys Phe His
370 375 380

Arg Ile Ile Pro Gly Phe Met Cys Gln Gly Gly Asp Phe Thr Arg His
385 390 395 400

Asn Gly Thr Gly Gly Lys Ser Ile Tyr Gly Glu Lys Phe Glu Asp Glu
405 410 415

Asn Phe Ile Leu Lys His Thr Gly Pro Gly Ile Leu Ser Met Ala Asn
420 425 430

Ala Gly Pro Asn Thr Asn Gly Ser Gln Phe Phe Ile Cys Thr Ala Lys
435 440 445

Thr Glu Trp Leu Asp Gly Lys His Val Val Phe Gly Lys Val Lys Glu
450 455 460

Gly Met Asn Ile Val Glu Ala Met Glu Arg Phe Gly Ser Arg Asn Gly
465 470 475 480

Lys Thr Ser Lys Lys Ile Thr Ile Ala Asp Cys Gly Gln Leu Glu
485 490 495

<210> SEQ ID NO 17
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Ala Ser Gly Ile Leu Val Asn Val Lys Glu Glu Val Thr Cys Pro
1 5 10 15

Ile Cys Leu Glu Leu Leu Thr Gln Pro Leu Ser Leu Asp Cys Gly His
20 25 30

Ser Phe Cys Gln Ala Cys Leu Thr Ala Asn His Lys Lys Ser Met Leu
35 40 45

-continued

```
Asp Lys Gly Glu Ser Ser Cys Pro Val Cys Arg Ile Ser Tyr Gln Pro
    50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Ser Gly Gly Ser Gly Gly
    290                 295                 300

Ser Gly Gly Ser Gly Gly Val Asn Pro Thr Val Phe Phe Asp Ile Ala
305                 310                 315                 320

Val Asp Gly Glu Pro Leu Gly Arg Val Ser Phe Glu Leu Phe Ala Asp
                325                 330                 335

Lys Val Pro Lys Thr Ala Glu Asn Phe Arg Ala Leu Ser Thr Gly Glu
            340                 345                 350

Lys Gly Phe Gly Tyr Lys Gly Ser Cys Phe His Arg Ile Ile Pro Gly
        355                 360                 365

Phe Met Cys Gln Gly Gly Asp Phe Thr Arg His Asn Gly Thr Gly Gly
    370                 375                 380

Lys Ser Ile Tyr Gly Glu Lys Phe Glu Asp Glu Asn Phe Ile Leu Lys
385                 390                 395                 400

His Thr Gly Pro Gly Ile Leu Ser Met Ala Asn Ala Gly Pro Asn Thr
                405                 410                 415

Asn Gly Ser Gln Phe Phe Ile Cys Thr Ala Lys Thr Glu Trp Leu Asp
            420                 425                 430

Gly Lys His Val Val Phe Gly Lys Val Lys Glu Gly Met Asn Ile Val
        435                 440                 445

Glu Ala Met Glu Arg Phe Gly Ser Arg Asn Gly Lys Thr Ser Lys Lys
    450                 455                 460
```

Ile Thr Ile Ala Asp Cys Gly Gln Leu Glu
465 470

<210> SEQ ID NO 18
<211> LENGTH: 894
<212> TYPE: DNA
<213> ORGANISM: Homo sapiens

<400> SEQUENCE: 18
atggcttctg gaatcctggt taatgtaaag gaggaggtga cctgccccat ctgcctggaa 60
ctcctgacac aacccctgag cctggactgc ggccacagct tctgccaagc atgcctcact 120
gcaaaccaca agaagtccat gctagacaaa ggagagagta gctgccctgt gtgccggatc 180
agttaccagc ctgagaacat acggcctaat cggcatgtag ccaacttagt ggagaagctc 240
agggaggtca agttgagccc agaggggcag aaagttgatc attgtgcacg ccatggagag 300
aaacttctac tcttctgtca ggaggacggg aaggtcattt gctggctttg tgagcggtct 360
caggagcacc gtggtcacca cacgttcccc acagaggagg ttgcccagga gtaccaagtg 420
aagctccagg cagctctgga gatgctgagg cagaagcagc aggaagctga agagttggaa 480
gctgacatca gagaagagaa agcttcctgg aagactcaaa tacagtatga caaaaccaac 540
gtcttggcag attttgagca actgagagac atcctggact gggaggagag caatgagctg 600
caaaacctgg agaaggagga ggaagacatt ctgaaaagcc ttacgaactc tgaaactgag 660
atggtgcagc agacccagtc cctgagagag ctcatctcag atctggagca tcggctgcag 720
gggtcagtga tggagctgct tcagggtgtg gatggcgtca taaaaaggac ggagaacgtg 780
accttgaaga agccagaaac ttttccaaaa aatcaaagga gagtgtttcg agctcctgat 840
ctgaaaggaa tgctagaagt gtttagagag ctgacagatg tccgacgcta ctgg 894

<210> SEQ ID NO 19
<211> LENGTH: 494
<212> TYPE: DNA
<213> ORGANISM: Homo sapiens

<400> SEQUENCE: 19
gtcaacccca ccgtgttctt cgacattgcc gtcgacggcg agcccttggg ccgcgtctcc 60
tttgagctgt ttgcgacaag gtcccaaaga cagcagaaaa ttttcgtgct ctgagcactg 120
gagagaaagg atttggttat aagggttcct gctttcacag aattattcca gggtttatgt 180
gtcagggtgg tgacttcaca cgccataatg gcactggtgg caagtccatc tatgggggaga 240 aatttgaaga tgagaacttc atcctaaagc atacgggtcc tggcatcttg tccatggcaa 300
atgctggacc caacacaaat ggttcccagt ttttcatctg cactgccaag actgagtggt 360
tggatggcaa gcatgtggtg tttggcaaag tgaaagaagg catgaatatt gtggaggcca 420
tggagcgctt tgggtccagg aatggcaaga ccagcaagaa gatcaccatt gctgactgtg 480
gacaactcga ataa 494

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Ser Gly Gly Ser Gly Gly Ser Gly Gly Ser Gly Gly 1 5 10

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Val Asp Val Thr Val Ala Pro Asn Asn Ile Ser Cys Ala Val Ile Ser
1 5 10 15

Glu Asp Lys Arg Gln Val Ser Ser Pro Lys Pro Gln Ile Ile Tyr Gly
20 25 30

Ala

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Val Asp Val Thr Val Ala Pro Asn Asn Ile Ser
1 5 10

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Val Asp Val Thr Val Ala Pro Asn Asn Ile Ser Cys Ala Val Ile Ser
1 5 10 15

Glu Asp Lys Arg Gln Val Ser Ser
20

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(12)
<223> OTHER INFORMATION: Any amino acid

<400> SEQUENCE: 24

Xaa Xaa Xaa Xaa Xaa Xaa Xaa Xaa Xaa Xaa Xaa Xaa
1 5 10

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic peptide
<220> FEATURE:

<221> NAME/KEY: MOD_RES
<222> LOCATION: (1)..(24)
<223> OTHER INFORMATION: Any amino acid

<400> SEQUENCE: 25

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa
20

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(33)
<223> OTHER INFORMATION: Any amino acid

<400> SEQUENCE: 26

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa

<210> SEQ ID NO 27
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (299)..(310)
<223> OTHER INFORMATION: Any amino acid

<400> SEQUENCE: 27

Met Ala Ser Gly Ile Leu Val Asn Val Lys Glu Glu Val Thr Cys Pro
1 5 10 15

Ile Cys Leu Glu Leu Leu Thr Gln Pro Leu Ser Leu Asp Cys Gly His
20 25 30

Ser Phe Cys Gln Ala Cys Leu Thr Ala Asn His Lys Lys Ser Met Leu
35 40 45

Asp Lys Gly Glu Ser Ser Cys Pro Val Cys Arg Ile Ser Tyr Gln Pro
50 55 60

Glu Asn Ile Arg Pro Asn Arg His Val Ala Asn Leu Val Glu Lys Leu
65 70 75 80

Arg Glu Val Lys Leu Ser Pro Glu Gly Gln Lys Val Asp His Cys Ala
85 90 95

Arg His Gly Glu Lys Leu Leu Leu Phe Cys Gln Glu Asp Gly Lys Val
100 105 110

Ile Cys Trp Leu Cys Glu Arg Ser Gln Glu His Arg Gly His His Thr
115 120 125

Phe Pro Thr Glu Glu Val Ala Gln Glu Tyr Gln Val Lys Leu Gln Ala
130 135 140

Ala Leu Glu Met Leu Arg Gln Lys Gln Gln Glu Ala Glu Glu Leu Glu
145 150 155 160

-continued

```
Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Xaa Xaa Xaa Xaa Xaa Xaa
    290                 295                 300

Xaa Xaa Xaa Xaa Xaa Xaa Val Asn Pro Thr Val Phe Phe Asp Ile Ala
305                 310                 315                 320

Val Asp Gly Glu Pro Leu Gly Arg Val Ser Phe Glu Leu Phe Ala Asp
                325                 330                 335

Lys Val Pro Lys Thr Ala Glu Asn Phe Arg Ala Leu Ser Thr Gly Glu
            340                 345                 350

Lys Gly Phe Gly Tyr Lys Gly Ser Cys Phe His Arg Ile Ile Pro Gly
        355                 360                 365

Phe Met Cys Gln Gly Gly Asp Phe Thr Arg His Asn Gly Thr Gly Gly
    370                 375                 380

Lys Ser Ile Tyr Gly Glu Lys Phe Glu Asp Glu Asn Phe Ile Leu Lys
385                 390                 395                 400

His Thr Gly Pro Gly Ile Leu Ser Met Ala Asn Ala Gly Pro Asn Thr
                405                 410                 415

Asn Gly Ser Gln Phe Phe Ile Cys Thr Ala Lys Thr Glu Trp Leu Asp
            420                 425                 430

Gly Lys His Val Val Phe Gly Lys Val Lys Glu Gly Met Asn Ile Val
        435                 440                 445

Glu Ala Met Glu Arg Phe Gly Ser Arg Asn Gly Lys Thr Ser Lys Lys
    450                 455                 460

Ile Thr Ile Ala Asp Cys Gly Gln Leu Glu
465                 470
```

<210> SEQ ID NO 28
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (299)..(322)
<223> OTHER INFORMATION: Any amino acid

<400> SEQUENCE: 28

```
Met Ala Ser Gly Ile Leu Val Asn Val Lys Glu Glu Val Thr Cys Pro
1               5                   10                  15
```

```
Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Val Asn Pro Thr Val Phe Phe Asp Ile Ala Val Asp Gly Glu
                325                 330                 335

Pro Leu Gly Arg Val Ser Phe Glu Leu Phe Ala Asp Lys Val Pro Lys
            340                 345                 350

Thr Ala Glu Asn Phe Arg Ala Leu Ser Thr Gly Glu Lys Gly Phe Gly
        355                 360                 365

Tyr Lys Gly Ser Cys Phe His Arg Ile Ile Pro Gly Phe Met Cys Gln
    370                 375                 380

Gly Gly Asp Phe Thr Arg His Asn Gly Thr Gly Gly Lys Ser Ile Tyr
385                 390                 395                 400

Gly Glu Lys Phe Glu Asp Glu Asn Phe Ile Leu Lys His Thr Gly Pro
                405                 410                 415

Gly Ile Leu Ser Met Ala Asn Ala Gly Pro Asn Thr Asn Gly Ser Gln
            420                 425                 430

Phe Phe Ile Cys Thr Ala Lys Thr Glu Trp Leu Asp Gly Lys His Val
```

```
        435                 440                 445

Val Phe Gly Lys Val Lys Glu Gly Met Asn Ile Val Glu Ala Met Glu
    450                 455                 460

Arg Phe Gly Ser Arg Asn Gly Lys Thr Ser Lys Lys Ile Thr Ile Ala
465                 470                 475                 480

Asp Cys Gly Gln Leu Glu
                485


<210> SEQ ID NO 29
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (299)..(331)
<223> OTHER INFORMATION: Any amino acid

<400> SEQUENCE: 29

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285
```

```
Arg Glu Leu Thr Asp Val Arg Arg Tyr Trp Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Val Asn Pro Thr Val
                325                 330                 335

Phe Phe Asp Ile Ala Val Asp Gly Glu Pro Leu Gly Arg Val Ser Phe
            340                 345                 350

Glu Leu Phe Ala Asp Lys Val Pro Lys Thr Ala Glu Asn Phe Arg Ala
        355                 360                 365

Leu Ser Thr Gly Glu Lys Gly Phe Gly Tyr Lys Gly Ser Cys Phe His
    370                 375                 380

Arg Ile Ile Pro Gly Phe Met Cys Gln Gly Gly Asp Phe Thr Arg His
385                 390                 395                 400

Asn Gly Thr Gly Gly Lys Ser Ile Tyr Gly Glu Lys Phe Glu Asp Glu
                405                 410                 415

Asn Phe Ile Leu Lys His Thr Gly Pro Gly Ile Leu Ser Met Ala Asn
            420                 425                 430

Ala Gly Pro Asn Thr Asn Gly Ser Gln Phe Phe Ile Cys Thr Ala Lys
        435                 440                 445

Thr Glu Trp Leu Asp Gly Lys His Val Val Phe Gly Lys Val Lys Glu
    450                 455                 460

Gly Met Asn Ile Val Glu Ala Met Glu Arg Phe Gly Ser Arg Asn Gly
465                 470                 475                 480

Lys Thr Ser Lys Lys Ile Thr Ile Ala Asp Cys Gly Gln Leu Glu
                485                 490                 495
```

<210> SEQ ID NO 30
<211> LENGTH: 473
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (299)..(309)
<223> OTHER INFORMATION: Any amino acid

<400> SEQUENCE: 30

```
Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125
```

Phe Pro Thr Glu Glu Val Ala Gln Glu Tyr Gln Val Lys Leu Gln Ala
130 135 140

Ala Leu Glu Met Leu Arg Gln Lys Gln Gln Glu Ala Glu Glu Leu Glu
145 150 155 160

Ala Asp Ile Arg Glu Glu Lys Ala Ser Trp Lys Thr Gln Ile Gln Tyr
165 170 175

Asp Lys Thr Asn Val Leu Ala Asp Phe Glu Gln Leu Arg Asp Ile Leu
180 185 190

Asp Trp Glu Glu Ser Asn Glu Leu Gln Asn Leu Glu Lys Glu Glu Glu
195 200 205

Asp Ile Leu Lys Ser Leu Thr Asn Ser Glu Thr Glu Met Val Gln Gln
210 215 220

Thr Gln Ser Leu Arg Glu Leu Ile Ser Asp Leu Glu His Arg Leu Gln
225 230 235 240

Gly Ser Val Met Glu Leu Leu Gln Gly Val Asp Gly Val Ile Lys Arg
245 250 255

Thr Glu Asn Val Thr Leu Lys Lys Pro Glu Thr Phe Pro Lys Asn Gln
260 265 270

Arg Arg Val Phe Arg Ala Pro Asp Leu Lys Gly Met Leu Glu Val Phe
275 280 285

Arg Glu Leu Thr Asp Val Arg Arg Tyr Trp Xaa Xaa Xaa Xaa Xaa Xaa
290 295 300

Xaa Xaa Xaa Xaa Xaa Val Asn Pro Thr Val Phe Phe Asp Ile Ala Val
305 310 315 320

Asp Gly Glu Pro Leu Gly Arg Val Ser Phe Glu Leu Phe Ala Asp Lys
325 330 335

Val Pro Lys Thr Ala Glu Asn Phe Arg Ala Leu Ser Thr Gly Glu Lys
340 345 350

Gly Phe Gly Tyr Lys Gly Ser Cys Phe His Arg Ile Ile Pro Gly Phe
355 360 365

Met Cys Gln Gly Gly Asp Phe Thr Arg His Asn Gly Thr Gly Gly Lys
370 375 380

Ser Ile Tyr Gly Glu Lys Phe Glu Asp Glu Asn Phe Ile Leu Lys His
385 390 395 400

Thr Gly Pro Gly Ile Leu Ser Met Ala Asn Ala Gly Pro Asn Thr Asn
405 410 415

Gly Ser Gln Phe Phe Ile Cys Thr Ala Lys Thr Glu Trp Leu Asp Gly
420 425 430

Lys His Val Val Phe Gly Lys Val Lys Glu Gly Met Asn Ile Val Glu
435 440 445

Ala Met Glu Arg Phe Gly Ser Arg Asn Gly Lys Thr Ser Lys Lys Ile
450 455 460

Thr Ile Ala Asp Cys Gly Gln Leu Glu
465 470

<210> SEQ ID NO 31
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Ala Ser Gly Ile Leu Val Asn Val Lys Glu Glu Val Thr Cys Pro
1 5 10 15

-continued

```
Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Val Asn Pro Thr Val Phe
305                 310                 315                 320

Phe Asp Ile Ala Val Asp Gly Glu Pro Leu Gly Arg Val Ser Phe Glu
                325                 330                 335

Leu Phe Ala Asp Lys Val Pro Lys Thr Ala Glu Asn Phe Arg Ala Leu
            340                 345                 350

Ser Thr Gly Glu Lys Gly Phe Gly Tyr Lys Gly Ser Cys Phe His Arg
        355                 360                 365

Ile Ile Pro Gly Phe Met Cys Gln Gly Gly Asp Phe Thr Arg His Asn
    370                 375                 380

Gly Thr Gly Gly Lys Ser Ile Tyr Gly Glu Lys Phe Glu Asp Glu Asn
385                 390                 395                 400

Phe Ile Leu Lys His Thr Gly Pro Gly Ile Leu Ser Met Ala Asn Ala
                405                 410                 415

Gly Pro Asn Thr Asn Gly Ser Gln Phe Phe Ile Cys Thr Ala Lys Thr
            420                 425                 430
```

-continued

```
Glu Trp Leu Asp Gly Lys His Val Val Phe Gly Lys Val Lys Glu Gly
        435                 440                 445

Met Asn Ile Val Glu Ala Met Glu Arg Phe Gly Ser Arg Asn Gly Lys
    450                 455                 460

Thr Ser Lys Lys Ile Thr Ile Ala Asp Cys Gly Gln Leu Glu
465                 470                 475


<210> SEQ ID NO 32
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Gly Lys Glu Lys Ser His
    290                 295                 300

Tyr His Lys Pro Pro Cys Gly Leu Ser Val Asn Pro Thr Val Phe Phe
305                 310                 315                 320
```

Asp Ile Ala Val Asp Gly Glu Pro Leu Gly Arg Val Ser Phe Glu Leu
325 330 335

Phe Ala Asp Lys Val Pro Lys Thr Ala Glu Asn Phe Arg Ala Leu Ser
340 345 350

Thr Gly Glu Lys Gly Phe Gly Tyr Lys Gly Ser Cys Phe His Arg Ile
355 360 365

Ile Pro Gly Phe Met Cys Gln Gly Gly Asp Phe Thr Arg His Asn Gly
370 375 380

Thr Gly Gly Lys Ser Ile Tyr Gly Glu Lys Phe Glu Asp Glu Asn Phe
385 390 395 400

Ile Leu Lys His Thr Gly Pro Gly Ile Leu Ser Met Ala Asn Ala Gly
405 410 415

Pro Asn Thr Asn Gly Ser Gln Phe Phe Ile Cys Thr Ala Lys Thr Glu
420 425 430

Trp Leu Asp Gly Lys His Val Val Phe Gly Lys Val Lys Glu Gly Met
435 440 445

Asn Ile Val Glu Ala Met Glu Arg Phe Gly Ser Arg Asn Gly Lys Thr
450 455 460

Ser Lys Lys Ile Thr Ile Ala Asp Cys Gly Gln Leu Glu
465 470 475

<210> SEQ ID NO 33
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Met Ala Ser Gly Ile Leu Val Asn Val Lys Glu Glu Val Thr Cys Pro
1 5 10 15

Ile Cys Leu Glu Leu Leu Thr Gln Pro Leu Ser Leu Asp Cys Gly His
20 25 30

Ser Phe Cys Gln Ala Cys Leu Thr Ala Asn His Lys Lys Ser Met Leu
35 40 45

Asp Lys Gly Glu Ser Ser Cys Pro Val Cys Arg Ile Ser Tyr Gln Pro
50 55 60

Glu Asn Ile Arg Pro Asn Arg His Val Ala Asn Leu Val Glu Lys Leu
65 70 75 80

Arg Glu Val Lys Leu Ser Pro Glu Gly Gln Lys Val Asp His Cys Ala
85 90 95

Arg His Gly Glu Lys Leu Leu Leu Phe Cys Gln Glu Asp Gly Lys Val
100 105 110

Ile Cys Trp Leu Cys Glu Arg Ser Gln Glu His Arg Gly His His Thr
115 120 125

Phe Pro Thr Glu Glu Val Ala Gln Glu Tyr Gln Val Lys Leu Gln Ala
130 135 140

Ala Leu Glu Met Leu Arg Gln Lys Gln Gln Glu Ala Glu Glu Leu Glu
145 150 155 160

Ala Asp Ile Arg Glu Glu Lys Ala Ser Trp Lys Thr Gln Ile Gln Tyr
165 170 175

Asp Lys Thr Asn Val Leu Ala Asp Phe Glu Gln Leu Arg Asp Ile Leu
180 185 190

Asp Trp Glu Glu Ser Asn Glu Leu Gln Asn Leu Glu Lys Glu Glu Glu

```
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Gly Trp Ser Ala Met Ala
    290                 295                 300

Arg Ser Arg Phe Thr Ala Thr Ser Thr Ser Val Asn Pro Thr Val Phe
305                 310                 315                 320

Phe Asp Ile Ala Val Asp Gly Glu Pro Leu Gly Arg Val Ser Phe Glu
                325                 330                 335

Leu Phe Ala Asp Lys Val Pro Lys Thr Ala Glu Asn Phe Arg Ala Leu
            340                 345                 350

Ser Thr Gly Glu Lys Gly Phe Gly Tyr Lys Gly Ser Cys Phe His Arg
        355                 360                 365

Ile Ile Pro Gly Phe Met Cys Gln Gly Gly Asp Phe Thr Arg His Asn
    370                 375                 380

Gly Thr Gly Gly Lys Ser Ile Tyr Gly Glu Lys Phe Glu Asp Glu Asn
385                 390                 395                 400

Phe Ile Leu Lys His Thr Gly Pro Gly Ile Leu Ser Met Ala Asn Ala
                405                 410                 415

Gly Pro Asn Thr Asn Gly Ser Gln Phe Phe Ile Cys Thr Ala Lys Thr
            420                 425                 430

Glu Trp Leu Asp Gly Lys His Val Val Phe Gly Lys Val Lys Glu Gly
        435                 440                 445

Met Asn Ile Val Glu Ala Met Glu Arg Phe Gly Ser Arg Asn Gly Lys
    450                 455                 460

Thr Ser Lys Lys Ile Thr Ile Ala Asp Cys Gly Gln Leu Glu
465                 470                 475


<210> SEQ ID NO 34
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80
```

-continued

```
Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Val Asn Pro Thr Val Phe Phe Asp Ile Ala Val Asp Gly Glu Pro
    370                 375                 380

Leu Gly Arg Val Ser Phe Glu Leu Phe Ala Asp Lys Val Pro Lys Thr
385                 390                 395                 400

Ala Glu Asn Phe Arg Ala Leu Ser Thr Gly Glu Lys Gly Phe Gly Tyr
                405                 410                 415

Lys Gly Ser Cys Phe His Arg Ile Ile Pro Gly Phe Met Cys Gln Gly
            420                 425                 430

Gly Asp Phe Thr Arg His Asn Gly Thr Gly Gly Lys Ser Ile Tyr Gly
        435                 440                 445

Glu Lys Phe Glu Asp Glu Asn Phe Ile Leu Lys His Thr Gly Pro Gly
    450                 455                 460

Ile Leu Ser Met Ala Asn Ala Gly Pro Asn Thr Asn Gly Ser Gln Phe
465                 470                 475                 480

Phe Ile Cys Thr Ala Lys Thr Glu Trp Leu Asp Gly Lys His Val Val
                485                 490                 495

Phe Gly Lys Val Lys Glu Gly Met Asn Ile Val Glu Ala Met Glu Arg
```

```
            500                 505                 510

Phe Gly Ser Arg Asn Gly Lys Thr Ser Lys Lys Ile Thr Ile Ala Asp
        515                 520                 525

Cys Gly Gln Leu Glu
    530


<210> SEQ ID NO 35
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Val Asn Pro Thr
        275                 280                 285

Val Phe Phe Asp Ile Ala Val Asp Gly Glu Pro Leu Gly Arg Val Ser
    290                 295                 300

Phe Glu Leu Phe Ala Asp Lys Val Pro Lys Thr Ala Glu Asn Phe Arg
305                 310                 315                 320
```

-continued

```
Ala Leu Ser Thr Gly Glu Lys Gly Phe Gly Tyr Lys Gly Ser Cys Phe
                325                 330                 335

His Arg Ile Ile Pro Gly Phe Met Cys Gln Gly Gly Asp Phe Thr Arg
            340                 345                 350

His Asn Gly Thr Gly Gly Lys Ser Ile Tyr Gly Glu Lys Phe Glu Asp
        355                 360                 365

Glu Asn Phe Ile Leu Lys His Thr Gly Pro Gly Ile Leu Ser Met Ala
    370                 375                 380

Asn Ala Gly Pro Asn Thr Asn Gly Ser Gln Phe Phe Ile Cys Thr Ala
385                 390                 395                 400

Lys Thr Glu Trp Leu Asp Gly Lys His Val Val Phe Gly Lys Val Lys
                405                 410                 415

Glu Gly Met Asn Ile Val Glu Ala Met Glu Arg Phe Gly Ser Arg Asn
            420                 425                 430

Gly Lys Thr Ser Lys Lys Ile Thr Ile Ala Asp Cys Gly Gln Leu Glu
        435                 440                 445
```

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ccctctagag ccaccatggc ttctggaatc ctggtta 37

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aaaagcggcc gctcaagagc ttggtgagca cagagt 36

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ccctctagag ccaccatggc ttctggaatc ctgctta 37

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
aaaagttaac tcaagagctt ggtgagcaca 30

<210> SEQ ID NO 40
<211> LENGTH: 35

<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
ccctctagag ccaccatggt caaccccacc gtgtt 35

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
aaaaggatcc ttattagagt tgtccacagt cagc 34

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
ccctctagag ccaccatggc ttctggaatc ctggtta 37

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
aaaaggatcc ttattcgagt tgtccacagt c 31

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
cggctgcagg ggtcagtgat ggtcaacccc accgtgttc 39

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
gaacacggtg gggttgacca tcactgaccc ctgcagccg 39

<210> SEQ ID NO 46
<211> LENGTH: 39
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 46

gctcctgatc tgaaaggaat ggtcaacccc accgtgttc                            39


<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

gaacacggtg gggttgacca ttcctttcag atcaggagc                            39


<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

cgctactggg ttgatgtgac agtcaacccc accgtgttc                            39


<210> SEQ ID NO 49
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

gaacacggtg gggttgactg tcacatcaac ccagtagc                             38


<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

gtggctccaa acaacatttc agtcaacccc accgtgttc                            39


<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

gaacacggtg gggttgactg aaatgttgtt tggagccac                            39


<210> SEQ ID NO 52
<211> LENGTH: 30
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 52
caagtgagct ctgtcaaccc caccgtgttc 30

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggggttgaca gagctcactt gtctcttatc ttcag 35

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccacagataa tatatggggc agtcaacccc accgtgttct tc 42

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cacggtgggg ttgactgccc catatattat ctgtggtttc g 41

<210> SEQ ID NO 56
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gctctcaaag tatcacatca ggggtcaacc ccaccgtgtt cttc 44

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gaagaacacg gtggggttga cccctgatgt gatactttga gagc 44

<210> SEQ ID NO 58
<211> LENGTH: 45
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 58
gaggtagacg tgtccaagaa aactgtcaac cccaccgtgt tcttc 45

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gaagaacacg gtggggttga cagttttctt ggacacgtct acctc 45

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gaaaattatc aacctaaata cggcgtcaac cccaccgtgt tcttc 45

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaagaacacg gtggggttga cgccgtattt aggttgataa ttttc 45

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctggattgca gagttaagtt ta 22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgccaagcat gcctcactgc aa 22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
tcgtgtgata attgttcacc aa 22

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gggtactagt agttcctg 18

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ggggcggccg ctggtgagag atgggtgcga gagcgtc 37

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
cggctaccac atccaaggaa 20

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
gctggaatta ccgcggct 18

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ccccgtgatg aagaagatga 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gtcagcttgt gctggatgaa 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ctgggttgat gtgacagtgg 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tctgctgtct ttgggacctt 20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 73
cggctaccac atccaaggaa 20

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 74
gctggaatta ccgcggct 18

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 75
tgctggcacc agacttgccc tc 22

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
acccactccc tcttagccaa tatt 24

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
gtagggctag gcccaccg 18

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 78
ctagtctttg ccgcctgcga agca 24

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
acaagctagt accagttgag ccagataag 29

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gccgtgcgcg cttcagcaag c 21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 81
cagtggcgcc cgaacaggga 20

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
aactagggaa cccactgctt aag 23

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
tccacagatc aaggatatct tgtc 24

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 84
acactacttg aagcactcaa ggcaagcttt 30

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
aactagggaa cccactgctt aag 23

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tgctgggatt acaggcgtga g 21

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 87
acactacttg aagcactcaa ggcaagcttt 30

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
cggctaccac atccaaggaa 20

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
gctggaatta ccgcggct 18

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
ccccgtgatg aagaagatga 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
gtcagcttgt gctggatgaa 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
ctgggttgat gtgacagtgg 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
tctgctgtct ttgggacctt 20

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
acccactccc tcttagccaa tatt 24

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
gtagggctag gcccaccg 18

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 96
ctagtctttg ccgcctgcga agca 24

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
acaagctagt accagttgag ccagataag 29

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
gccgtgcgcg cttcagcaag c 21

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 99
cagtggcgcc cgaacaggga 20

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
ccctctagag ccaccatggc ttctggaatc ctggtta 37

```
<210> SEQ ID NO 101
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

aaaaggatcc ttattcgagt tgtccacagt c                                  31


<210> SEQ ID NO 102
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102

cggctgcagg ggtcagtgat ggtcaacccc accgtgttc                          39


<210> SEQ ID NO 103
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103

gaacacggtg gggttgacca tcactgaccc ctgcagccg                          39


<210> SEQ ID NO 104
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104

gctcctgatc tgaaaggaat ggtcaacccc accgtgttc                          39


<210> SEQ ID NO 105
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105

gaacacggtg gggttgacca ttcctttcag atcaggagc                          39


<210> SEQ ID NO 106
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106

ggtggggttg acccagtagc gtcggacatc tgtc                               34
```

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 107
cgacgctact gggtcaaccc caccgtgttc 30

<210> SEQ ID NO 108
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 108
cgctactggg ttgatgtgac agtcaacccc accgtgttc 39

<210> SEQ ID NO 109
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 109
gaacacggtg gggttgactg tcacatcaac ccagtagc 38

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 110
gtggctccaa acaacatttc agtcaacccc accgtgttc 39

<210> SEQ ID NO 111
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 111
gaacacggtg gggttgactg aaatgttgtt tggagccac 39

<210> SEQ ID NO 112
<211> LENGTH: 65
<212> TYPE: DNA
<213> ORGANISM: Artificial Sequence
<220> FEATURE:
<223> OTHER INFORMATION: Description of Artificial Sequence: Synthetic
primer

<400> SEQUENCE: 112
tgggttgatg tgacagtggc tccaaacaac atttcatgtg ctgtcatttc gtcaacccca 60
ccgtg 65

<210> SEQ ID NO 113
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
gttgacagaa atgacagcac atgaaatgtt gtttggagcc actgtcacat caacccagta 60
gcgtcggac 69

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
caagtgagct ctgtcaaccc caccgtgttc 30

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
ggggttgaca gagctcactt gtctcttatc ttcag 35

<210> SEQ ID NO 116
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
ccacagataa tatatggggc agtcaacccc accgtgttct tc 42

<210> SEQ ID NO 117
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
cacggtgggg ttgactgccc catatattat ctgtggtttc g 41

<210> SEQ ID NO 118
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
gctctcaaag tatcacatca ggggtcaacc ccaccgtgtt cttc 44

<210> SEQ ID NO 119
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
gaagaacacg gtggggttga cccctgatgt gatactttga gagc 44

<210> SEQ ID NO 120
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gaggtagacg tgtccaagaa aactgtcaac cccaccgtgt tcttc 45

<210> SEQ ID NO 121
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
gaagaacacg gtggggttga cagttttctt ggacacgtct acctc 45

<210> SEQ ID NO 122
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
gaaaattatc aacctaaata cggcgtcaac cccaccgtgt tcttc 45

<210> SEQ ID NO 123
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
gaagaacacg gtggggttga cgccgtattt aggttgataa ttttc 45

<210> SEQ ID NO 124
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
ccctctagag ccaccatggc ttctggaatc ctgctta 37

-continued

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
aaaagttaac tcaagagctt ggtgagcaca 30

<210> SEQ ID NO 126
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
ccctctagag ccaccatggc ttctggaatc ctggtta 37

<210> SEQ ID NO 127
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
aaaagttaac tcaagagctt ggtgagcaca gagt 34

<210> SEQ ID NO 128
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(31)
<223> OTHER INFORMATION: Any amino acid and this region may encompass 23-28 residues
<220> FEATURE:
<221> NAME/KEY: MOD_RES
<222> LOCATION: (34)..(37)
<223> OTHER INFORMATION: Any amino acid and this region may encompass 2-4 residues

<400> SEQUENCE: 128

```
His Xaa Glu Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Pro
            20                  25                  30

Cys Xaa Xaa Xaa Xaa Cys
        35
```

<210> SEQ ID NO 129
<211> LENGTH: 14
<212> TYPE: PRT
<213> ORGANISM: Artificial Sequence
<220> FEATURE:

<223> OTHER INFORMATION: Description of Artificial Sequence: Synthetic peptide

<400> SEQUENCE: 129

Arg Tyr Trp Asp Ala Ala Ala Trp Asp Leu Val Ala Ser Ala
1 5 10

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Arg Tyr Trp Val Asp Val Thr Val Ala Pro Asn Asn Ile Ser Cys Ala
1 5 10 15

Val Ile Ser

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Arg Tyr Trp Gly Lys Glu Lys Ser His Tyr His Lys Pro Pro Cys Gly
1 5 10 15

Leu Ser

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Arg Tyr Trp Gly Trp Ser Ala Met Ala Arg Ser Arg Phe Thr Ala Thr
1 5 10 15

Ser Thr Ser

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Arg Tyr Trp Ser Gly Gly Ser Gly Gly Ser Gly Gly Ser Gly Gly
1 5 10 15

<210> SEQ ID NO 134
<211> LENGTH: 493
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 134

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Leu Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Ala Trp Ile Leu Gly Val Cys Ala Gly Phe Gln Pro Asp Ala Met
    370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
                405                 410                 415
```

-continued

```
Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
        435                 440                 445

Val Ser Phe Phe Asn Ile Thr Asn His Gly Phe Leu Ile Tyr Lys Phe
    450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                485                 490


<210> SEQ ID NO 135
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Glu Leu Thr Asp Val Arg Arg Tyr Trp Ser Gly Gly Ser Gly Gly
1               5                   10                  15

Ser Gly Gly Ser Gly Gly
            20


<210> SEQ ID NO 136
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Glu Leu Thr Asp Val Arg Arg Tyr Trp Gly Trp Ser Ala Met Ala
1               5                   10                  15

Arg Ser Arg Phe Thr Ala Thr Ser Thr Ser
            20                  25


<210> SEQ ID NO 137
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Glu Leu Thr Asp Val Arg Arg Tyr Trp Gly Lys Glu Lys Ser His
1               5                   10                  15

Tyr His Lys Pro Pro Cys Gly Leu Ser
            20                  25


<210> SEQ ID NO 138
<211> LENGTH: 37
<212> TYPE: PRT
<213> ORGANISM: Macacca sp.

<400> SEQUENCE: 138

Phe Arg Asp Ala Ala Ala Glu Glu Ser Pro Val Leu Leu Ala Met Val
1               5                   10                  15

Asn Pro Thr Val Phe Phe Asp Ile Ala Asp Gly Glu Pro Leu Gly Arg
```

```
            20                  25                  30

Val Ser Phe Glu Leu
        35


<210> SEQ ID NO 139
<211> LENGTH: 45
<212> TYPE: PRT
<213> ORGANISM: Aotus sp.

<400> SEQUENCE: 139

Phe Lys Glu Pro Thr Glu Val Gln Arg Tyr Trp Asp Ala Ala Ala Trp
1               5                   10                  15

Asp Leu Val Ala Ser Ala Met Val Asn Pro Thr Val Phe Phe Asp Ile
            20                  25                  30

Ala Asp Gly Glu Pro Leu Gly Arg Val Ser Phe Glu Leu
        35                  40                  45


<210> SEQ ID NO 140
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Phe Arg Glu Leu Thr Asp Val Arg Arg Tyr Trp Val Asp Val Thr Val
1               5                   10                  15

Ala Pro Asn Asn Ile Ser Cys Ala Val Ile Ser Glu Asp Lys Arg Gln
            20                  25                  30

Val Ser Ser Val Asn Pro Thr Val Phe Phe Asp Ile Ala Asp Gly Glu
        35                  40                  45

Pro Leu Gly Arg Val Ser Phe Glu Leu
    50                  55


<210> SEQ ID NO 141
<211> LENGTH: 56
<212> TYPE: PRT
<213> ORGANISM: Homo sapiens

<400> SEQUENCE: 141

Phe Arg Glu Leu Thr Asp Val Arg Arg Tyr Trp Val Asp Val Thr Val
1               5                   10                  15

Ala Pro Asn Asn Ile Ser Cys Ala Val Ile Ser Glu Asp Lys Arg Gln
            20                  25                  30

Val Ser Ser Pro Lys Pro Gln Ile Ile Tyr Gly Ala Arg Gly Thr Arg
        35                  40                  45

Tyr Gln Thr Phe Val Asn Phe Asn
    50                  55


<210> SEQ ID NO 142
<211> LENGTH: 58
<212> TYPE: PRT
<213> ORGANISM: Macacca mulatta

<400> SEQUENCE: 142

Phe Arg Glu Leu Thr Asp Val Arg Arg Tyr Trp Val Asp Val Thr Val
1               5                   10                  15

Ala Pro Asn Asn Ile Ser His Ala Val Ile Ala Glu Asp Lys Arg Gln
            20                  25                  30
```

```
Val Ser Ser Arg Asn Pro Gln Ile Met Tyr Gln Ala Pro Gly Thr Leu
        35                  40                  45

Phe Thr Phe Pro Ser Leu Thr Asn Phe Asn
    50                  55


<210> SEQ ID NO 143
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Phe Arg Glu Leu Thr Asp Val Arg Arg Tyr Trp Val Asp Val Thr Val
1               5                   10                  15

Ala Pro Asn Asn Ile Ser Cys Ala Val Ile Ser Glu Asp Lys Arg Gln
            20                  25                  30

Val Ser Ser Arg Lys Pro Gln Ile Ile Tyr Gly Ala Pro Gly Thr Arg
        35                  40                  45

Tyr Gln Thr Phe Val Asn Phe Asn
    50                  55


<210> SEQ ID NO 144
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Phe Arg Glu Leu Thr Asp Val Arg Arg Tyr Trp Val Asp Val Thr Val
1               5                   10                  15

Ala Pro Asn Asn Ile Ser Cys Ala Val Ile Ser Glu Asp Lys Arg Gln
            20                  25                  30

Val Ser Ser Arg Asn Pro Gln Ile Met Tyr Gln Ala Pro Gly Thr Arg
        35                  40                  45

Tyr Gln Thr Phe Val Asn Phe Asn
    50                  55


<210> SEQ ID NO 145
<211> LENGTH: 485
<212> TYPE: PRT
<213> ORGANISM: Homo sapiens

<400> SEQUENCE: 145

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
            20                  25                  30

Ser Phe Cys Gln Ala Cys Leu Thr Ala Asn His Lys Lys Ser Met Leu
        35                  40                  45

Asp Lys Gly Glu Ser Ser Cys Pro Val Cys Arg Ile Ser Tyr Gln Pro
    50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
```

-continued

```
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
    290                 295                 300

Pro Asn Asn Ile Ser Cys Ala Val Ile Ser Glu Asp Lys Arg Gln Val
305                 310                 315                 320

Ser Ser Val Asn Pro Thr Val Phe Phe Asp Ile Ala Val Asp Gly Glu
                325                 330                 335

Pro Leu Gly Arg Val Ser Phe Glu Leu Phe Ala Asp Lys Val Pro Lys
            340                 345                 350

Thr Ala Glu Asn Phe Arg Ala Leu Ser Thr Gly Glu Lys Gly Phe Gly
        355                 360                 365

Tyr Lys Gly Ser Cys Phe His Arg Ile Ile Pro Gly Phe Met Cys Gln
    370                 375                 380

Gly Gly Asp Phe Thr Arg His Asn Gly Thr Gly Gly Lys Ser Ile Tyr
385                 390                 395                 400

Gly Glu Lys Phe Glu Asp Glu Asn Phe Ile Leu Lys His Thr Gly Pro
                405                 410                 415

Gly Ile Leu Ser Met Ala Asn Ala Gly Pro Asn Thr Asn Gly Ser Gln
            420                 425                 430

Phe Phe Ile Cys Thr Ala Lys Thr Glu Trp Leu Asp Gly Lys His Val
        435                 440                 445

Val Phe Gly Lys Val Lys Glu Gly Met Asn Ile Val Glu Ala Met Glu
    450                 455                 460

Arg Phe Gly Ser Arg Asn Gly Lys Thr Ser Lys Lys Ile Thr Ile Ala
465                 470                 475                 480

Asp Cys Gly Gln Leu
                485
```

<210> SEQ ID NO 146
<211> LENGTH: 474
<212> TYPE: PRT
<213> ORGANISM: Aotus sp.

<400> SEQUENCE: 146

```
Met Ala Ser Arg Ile Leu Val Asn Ile Lys Glu Glu Val Thr Cys Pro
1               5                   10                  15

Ile Cys Leu Glu Leu Leu Thr Glu Pro Leu Ser Leu Asp Cys Gly His
            20                  25                  30

Ser Phe Cys Gln Ala Cys Ile Thr Ala Asn His Lys Lys Ser Met Pro
        35                  40                  45

His Gln Gly Glu Arg Ser Cys Pro Leu Cys Arg Ile Ser Tyr Ser Ser
    50                  55                  60

Glu Asn Leu Arg Pro Asn Arg His Leu Val Asn Ile Val Glu Arg Leu
65                  70                  75                  80

Arg Glu Val Met Leu Ser Pro Glu Glu Gly Gln Lys Val Asp His Cys
                85                  90                  95

Ala His His Gly Glu Lys Leu Val Leu Phe Cys Gln Gln Asp Gly Asn
            100                 105                 110

Val Ile Cys Trp Leu Cys Glu Arg Ser Gln Glu His Arg Gly His Gln
        115                 120                 125

Thr Phe Leu Val Glu Glu Val Ala Gln Lys Tyr Arg Glu Lys Leu Gln
    130                 135                 140

Val Ala Leu Glu Met Met Arg Gln Lys Gln Lys Asp Ala Glu Lys Leu
145                 150                 155                 160

Glu Ala Asp Val Arg Glu Glu Gln Ala Ser Trp Lys Ile Gln Ile Gln
                165                 170                 175

Asn Asp Lys Thr Asn Ile Met Ala Glu Phe Lys Lys Arg Arg Asp Ile
            180                 185                 190

Leu Asp Cys Glu Glu Ser Lys Glu Leu Gln Asn Leu Glu Lys Glu Glu
        195                 200                 205

Lys Asn Ile Leu Lys Arg Leu Val Gln Ser Glu Asn Asp Met Val Leu
    210                 215                 220

Gln Thr Gln Ser Val Arg Val Leu Ile Ser Asp Leu Glu His Arg Leu
225                 230                 235                 240

Gln Gly Ser Val Met Glu Leu Leu Gln Gly Val Asp Gly Val Ile Lys
                245                 250                 255

Arg Ile Glu Lys Val Thr Leu Gln Asn Pro Lys Thr Phe Leu Asn Glu
            260                 265                 270

Lys Arg Arg Ile Phe Gln Thr Pro Asp Leu Lys Gly Thr Leu Gln Val
        275                 280                 285

Phe Lys Glu Pro Thr Glu Val Gln Arg Tyr Trp Asp Ala Ala Ala Trp
    290                 295                 300

Asp Leu Val Ala Ser Ala Met Val Asn Pro Thr Val Phe Phe Asp Ile
305                 310                 315                 320

Ala Val Asp Gly Glu Pro Leu Gly Arg Val Ser Phe Glu Leu Phe Ala
                325                 330                 335

Asp Lys Val Pro Lys Thr Ala Glu Asn Phe Arg Ala Leu Ser Thr Gly
            340                 345                 350

Glu Lys Gly Phe Gly Tyr Lys Gly Ser Cys Phe His Arg Ile Ile Pro
        355                 360                 365

Gly Phe Met Cys Gln Gly Gly Asp Phe Thr Arg His Asn Gly Thr Gly
```

-continued

```
    370                 375                 380

Gly Lys Ser Ile Tyr Gly Glu Lys Phe Asp Asp Glu Asn Phe Ile Leu
385                 390                 395                 400

Lys His Thr Gly Pro Gly Ile Leu Ser Met Ala Asn Ala Gly Pro Asn
                405                 410                 415

Thr Asn Gly Ser Gln Phe Phe Ile Cys Thr Ala Lys Thr Glu Trp Leu
            420                 425                 430

Asp Gly Lys His Val Val Phe Gly Lys Val Lys Glu Gly Met Asn Val
        435                 440                 445

Val Glu Ala Met Glu Arg Phe Gly Cys Arg Tyr Gly Lys Thr Ser Lys
    450                 455                 460

Lys Ile Thr Ile Ala Asp Cys Gly Gln Leu
465                 470


<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Asp Val Thr Val Ala Pro Asn Asn Ile Ser Cys Ala Val Ile Ser
1               5                   10                  15


<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Lys Glu Lys Ser His Tyr His Lys Pro Pro Cys Gly Leu Ser
1               5                   10                  15


<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Trp Ser Ala Met Ala Arg Ser Arg Phe Thr Ala Thr Ser Thr Ser
1               5                   10                  15
```

POLYNUCLEOTIDES ENCODING A HUMAN TRIM-CYP FUSION POLYPEPTIDE, COMPOSITIONS THEREOF, AND METHODS OF USING SAME

This application is a U.S. National Phase application under 35 U.S.C. X371 of International Patent Application No. PCT/US2009/063481 filed Nov. 6, 2009, which claims priority to Application Ser. No. 61/112,013 filed Nov. 6, 2008 and Application Ser. No. 61/240,505 filed Sep. 8, 2009, the contents of which applications are hereby incorporated in their entirety.

The invention disclosed herein was made with Government support under NIH Grant Nos. RO1AI36199 and RO1AI59159 from the Department of Health and Human Services. Accordingly, the U.S. Government has certain rights in this invention.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

Throughout this application, patent applications, published patent applications, issued and granted patents, texts, and literature references are cited. The disclosures of these publications in their entireties are hereby incorporated by reference into this application.

BACKGROUND

Several million people die each year as a consequence of HIV-1 infection. Currently used antiviral therapies suppress HIV-1 replication and resultant disease but these antiviral therapies are plagued with complications and cannot eliminate the virus. Gene therapy is an alternative to life-long pharmacotherapy. Ideally, gene therapy should potently suppress HIV-1 replication without eliciting viral resistance. While all steps of the viral life cycle are potential gene therapy targets, blocking the virus before reverse transcription (RT) would preclude the genetic diversity that permits emergence of viral resistance. Additionally, targeting the virus before HIV-1 cDNA is ligated into host chromosomal DNA would prevent the virus from becoming a heritable genetic element in that cellular lineage. The discovery that certain TRIM5 (T5) orthologues inhibit HIV-1 infection immediately after the virus enters otherwise susceptible cells raised the prospect that these host factors might be exploited in HIV-1 gene therapy.

HIV-1 infection is a serious problem throughout the world and there is a great need for a composition that will prevent infection of a subject by HIV-1 and for a composition that treats or ameliorates the effects of HIV-1 infection in humans. There is a need for life-long anti-HIV-1 pharmacotherapy, and therapies that treat or prevent HIV-1 associated morbidity and mortality.

SUMMARY

Provided herein is a nucleic acid which comprises a sequence selected from the group consisting of: SEQ ID NO:1, SEQ ID NO:3, SEQ ID NO:5, SEQ ID NO:6, SEQ ID NO:7 and a variant having at least about 50% identity to SEQ ID NO:1, SEQ ID NO:3, SEQ ID NO:5, SEQ ID NO:6, or SEQ ID NO:7, wherein the nucleic acid encodes a polypeptide having both TRIM activity and cyclophilin activity. In one embodiment, the variant has at least about 55%, 60%, 70%, 75%, 80%, 85%, 90%, 95% or 99% identity to SEQ ID NO:1, SEQ ID NO:3, SEQ ID NO:5, SEQ ID NO:6, or SEQ ID NO:7. Another embodiment provides a nucleic acid which comprises a sequence complementary to a nucleic acid provided by an embodiment of the invention.

Provided herein is a nucleic acid encoding a polypeptide comprising SEQ ID NO:4 and SEQ ID NO:2, or a polypeptide comprising SEQ ID NO:10, 11, or 12.

Provided herein is a nucleic acid encoding a human TRIM5-cyclophilin A fusion protein. In one embodiment, the polynucleotide encodes a polypeptide comprising SEQ ID NO:2 and SEQ ID NO:4, wherein the last amino acid of SEQ ID NO:2 is serine at position 309, serine at position 322, or alanine at position 331. In another embodiment, the nucleic acid encodes a polypeptide consisting essentially of SEQ ID NO:4 and SEQ ID NO:2, wherein the last amino acid of SEQ ID NO:2 is serine at position 309, serine at position 322, or alanine at position 331. In one embodiment, the last amino acid of SEQ ID NO:2 is serine at position 309, serine at position 322, or alanine at position 331. In one embodiment, the last amino acid of SEQ ID NO:2 is any one amino acid residue from about residue 280 to about residue 400, or from about residue 280 to about residue 290, or from about residue 308 to about residue 311; or from about residue 321 to about residue 346; or from about residue 366 to about residue 371; or from about residue 381 to about residue 393. In one embodiment, the last residue of SEQ ID NO:2 is residue 493. The last residue of SEQ ID NO:2 can be fused to Cyp A (for example, at residue 2 of SEQ ID NO:4). In another embodiment, the nucleic acid encodes a polypeptide comprising a sequence that is at least 60%, 65%, 70%, 75%, 80%, 85%, 90%, 95%, or 99% identical to SEQ ID NO:4 and a sequence that is at least 60%, 65%, 70%, 75%, 80%, 85%, 90%, 95%, or 99% identical to SEQ ID NO:2, or a sequence that is at least 60%, 65%, 70%, 75%, 80%, 85%, 90%, 95%, or 99% identical to SEQ ID NO:10, or a sequence that is at least 60%, 65%, 70%, 75%, 80%, 85%, 90%, 95%, or 99% identical to SEQ ID NO:11, or a sequence that is at least 60%, 65%, 70%, 75%, 80%, 85%, 90%, 95%, or 99% identical to SEQ ID NO:12, and the polypeptide has the function of TRIM5 and specifically binds a capsid protein of HIV.

In another embodiment, the fusion protein comprises a polypeptide linker sequence, wherein (i) TRIM5 is located upstream of the linker sequence, so that the N-terminal amino acid of the linker sequence is attached to the C-terminal amino acid of TRIM5, and (ii) cyclophilin A is located downstream of the linker sequence, so that the C-terminal amino acid residue of the linker sequence is attached to the N-terminal amino acid residue of cyclophilin A. In one embodiment, the linker sequence comprises from about 10 to about 20 amino acids. In one embodiment, wherein the linker sequence comprises the consecutive amino acids SGGSGGSGGSGG.

Provided herein is a polypeptide encoded by a nucleic acid of the invention. Also provided is a polypeptide comprising SEQ ID NO:4 and SEQ ID NO:2, or a polypeptide comprising SEQ ID NO:10, 11, or 12. In one embodiment, the last (C-terminal) amino acid of SEQ ID NO:2, which can be fused to cyclophilin, is serine at position 309, serine at position 322, or alanine at position 331. In one embodiment, the last amino acid of SEQ ID NO:2 is any one amino acid residue from about residue 280 to about residue 400, or from about residue 280 to about residue 290, or from about residue 308 to about residue 311; or from about residue 321 to about residue 346; or from about residue 366 to about residue 371; or from about residue 381 to about residue 393. In one embodiment, the last residue of SEQ ID NO:2 is residue 493. In one embodiment, the last residue of SEQ ID NO:2 is 280, 281, 282, 283, 284, 285, 286, 287, 288, 289, 290, 308, 309, 310, 311, 321, 322, 323, 324, 325, 326, 327, 328, 329, 330, 331, 332, 333, 334, 335, 336, 337, 338, 339, 340, 341, 342, 343, 344, 345, 346, 366, 367, 368, 369, 370, 371, 381, 382, 383, 384, 385, 386, 387, 388, 389, 390, 391, 392, 393, or 493. The last residue of SEQ ID NO:2 can be fused to Cyp A (for example, at residue 2 of SEQ ID NO:4). Also provided is a polypeptide comprising a sequence that is at least 60%, 65%, 70%, 75%, 80%, 85%, 90%, 95%, or 99% identical to SEQ ID NO:4 and a sequence that is at least 60%, 65%, 70%, 75%, 80%, 85%, 90%, 95%, or 99% identical to SEQ ID NO:2, or a sequence that is at least 60%, 65%, 70%, 75%, 80%, 85%, 90%, 95%, or 99% identical to SEQ ID NO:10, or a sequence that is at least 60%, 65%, 70%, 75%, 80%, 85%, 90%, 95%, or 99% identical to SEQ ID NO:11, or a sequence that is at least 60%, 65%, 70%, 75%, 80%, 85%, 90%, 95%, or 99% identical to SEQ ID NO:12.

Provided herein is an antibody that specifically binds to a polypeptide of the invention. Also provided is an antibody that specifically binds to a polypeptide encoded by a nucleic acid provided by the invention. In one embodiment, the antibody is a polyclonal antibody, a monoclonal antibody, or a chimeric antibody.

Provided herein is a method of producing a polypeptide of the invention, which comprises: (a) introducing a nucleic acid encoding the polypeptide into a host cell under conditions that are compatible with expression of the polypeptide by the host cell, and (b) recovering the polypeptide.

Provided herein is a nucleic acid vector, which comprises a nucleic acid of the invention. In one embodiment, the vector comprises a viral vector. In one embodiment, the vector is a lentiviral vector, an adenovirus vector, a retroviral vector, or an adeno-associated viral (AAV) vector. Also provided is a lentiviral vector comprising a nucleic acid of the invention.

Also provided is a lentiviral vector encoding a human TRIM5-cyclophilin A fusion protein, wherein the vector comprises a promoter from a spleen focus-forming virus (SFFV) long terminal repeat (LTR), a promoter from a human cyclophilin A gene, or both. Provided herein is a nucleic acid vector having SEQ ID NO:8 or SEQ ID NO:9.

Provided herein is a host organism comprising a vector of the invention. In one embodiment, the host is a prokaryote, a eukaryote or a fungus.

Provided herein is a method for preparing a pharmaceutical composition which comprises admixing a polypeptide of the invention or a fragment thereof, thereby preparing the pharmaceutical composition. Also provided is a pharmaceutical composition comprising a nucleic acid of the invention, a polypeptide of the invention, or a vector of the invention, and a carrier.

Provided herein is a method for treating a subject suffering from a disease or condition, the method comprising administering to the subject a nucleic acid of the invention, a polypeptide of the invention, or a vector of the invention. Also provided is a method for treating a subject suffering from a disease or a condition, the method comprising administering to the subject a polypeptide or a fragment thereof of the invention, so as to treat the subject.

Provided herein is a method for preventing retroviral infection of a subject, or for treating a subject with retroviral infection, the method comprising administering to the subject a pharmaceutical composition of the invention. Also provided is a method for treating or preventing a viral infection of a cell, the method comprising introducing a human TRIM5-Cyp A fusion polypeptide into the cell. In one embodiment, the introducing comprises transfection, transduction, viral-mediated introduction, or liposome-mediated introduction of a polynucleotide encoding a human TRIM5-Cyp A fusion polypeptide. In one embodiment, the vial infection is an HIV infection, an HTLV infection, a pox virus infection, a retrovirus infection, a malaria infection, a hepatitis C virus infection, a hepatitis B virus infection, or a vaccinia virus infection.

Provided herein is a method for treating HIV infection or preventing HIV infection of a subject which comprises introducing into cells of the subject a human TRIM5-Cyp A fusion polypeptide. In one embodiment, the human TRIM5-Cyp A fusion polypeptide binds to a capsid protein of the HIV and subsequently degrades the HIV, thereby treating or preventing HIV infection in the subject.

Provided herein is a peptidomimetic comprising an amino acid sequence substantially identical to the amino acid sequence of a polypeptide of the invention and wherein the peptidomimetic comprises TRIM5 function and cyclophilin A function.

Provided herein is a cell comprising a nucleic acid of the invention. In one embodiment, the cell is a stem cell. In another embodiment, the cell is a T cell.

Provided herein is a method for imparting resistance to HIV to a subject or to cells of a subject, the method comprising administering to the cells of the subject a nucleic acid of the invention, a vector of the invention, or a polypeptide of the invention. Provided herein is a method for reducing or inhibiting lentiviral replication, including but not limited to HIV replication, to a subject or to cells of a subject, the method comprising administering to the cells of the subject a nucleic acid of the invention, a vector of the invention, or a polypeptide of the invention. Provided herein is a method for reducing viral load, including but not limited to HIV, to a subject or to cells of a subject, the method comprising administering to the cells of the subject a nucleic acid of the invention, a vector of the invention, or a polypeptide of the invention. Also provided is a therapeutic composition comprising a nucleic acid of the invention, a polypeptide of the invention, or a peptidomimetic of the invention, and a therapeutically acceptable carrier. In one embodiment, the carrier comprises a vector, a liposome, or a viral vector.

Provided herein is a method for ex vivo gene therapy, the method comprising: (a) removing bone marrow cells from a subject; (b) transfecting the removed bone marrow cells with a nucleic acid of the invention in vitro; and (c) transplanting the transfected bone marrow back into the subject. Also provided is a method for reducing viral burden or load in a subject infected by a virus, the method comprising administering to the subject a nucleic acid of the invention, a polypeptide of the invention, or a vector of the invention.

Provided herein is a topical composition for prevention or treatment of a viral infection which comprises a nucleic acid of the invention or a polypeptide of the invention, and a topical carrier. In one embodiment, the composition is for use on the skin, in the vagina, in the nose, in the mouth, or on any skin or muscosal surface.

Provided herein is a method for delivering a therapeutically effective amount of a human TRIM5-cyclophilin A fusion protein systemically to a subject, comprising administering to the subject a vector of the invention under conditions that are compatible with expression of the nucleic acid in the subject. In one embodiment, the vector comprises a nonviral vector. In another embodiment, the vector comprises a gold or tungsten particle and the coated particle is administered to the subject using a gene gun. In another embodiment, the vector comprises a liposome. In another embodiment, the vector comprises a viral vector. In another embodiment, the vector is an adenovirus vector, a lentiviral vector, a retroviral vector, or an adeno-associated viral (AAV) vector.

Provided herein is a method for delivering a therapeutically effective amount of a human TRIM5-cyclophilin A fusion protein systemically to a subject, comprising transfecting cells of said subject with a vector of the invention, under conditions that permit the expression of the nucleic acid and production of a human TRIM5-cyclophilin A fusion protein. In one embodiment, the transfecting occurs ex vivo and the transfected cells are reintroduced into the subject.

In certain embodiments the invention provides a fusion polypeptide comprising the following consecutive amino acids in N- to C-terminus orientation: (i) SEQ ID NO: 13, which consists of amino acids at position 1-298 from hTRIM5α (SEQ ID NO:2) or a variant of SEQ ID NO: 13; (ii) a linker of 12 to 33 amino acids linking SEQ ID NO: 13 and SEQ ID NO: 15 or the variants thereof; and (iii) SEQ ID NO:15, which consists of amino acid at positions 2 to 166 from hCypA (SEQ ID NO: 4) or a variant of SEQ ID NO: 15, wherein the polypeptide has lentiviral restriction activity.

In certain embodiments the invention provides a fusion polypeptide comprising the following consecutive amino acids in N- to C-terminus orientation: (i) SEQ ID NO: 13, which consists of amino acids at position 1-298 from hTRIM5α (SEQ ID NO:2) or a variant of SEQ ID NO: 13; (ii) a linker of 11-33 amino acids linking SEQ ID NO: 13 and SEQ ID NO: 15 or the variants thereof; and (iii) SEQ ID NO:15, which consists of amino acid at positions 2 to 166 from hCypA (SEQ ID NO: 4) or a variant of SEQ ID NO: 15, wherein the polypeptide has lentiviral restriction activity.

In certain embodiments the invention provides a fusion polypeptide comprising the following consecutive amino acids in N- to C-terminus orientation: (i) SEQ ID NO: 13, which consists of amino acids at position 1-298 from hTRIM5α (SEQ ID NO:2) or a variant of SEQ ID NO:13; (ii) a linker of 11, 12, 24 or 33 amino acids linking SEQ ID NO: 13 and SEQ ID NO: 15 or the variants thereof; and (iii) SEQ ID NO:15, which consists of amino acid at positions 2 to 166 from hCypA (SEQ ID NO: 4) or a variant of SEQ ID NO:15, wherein the polypeptide has lentiviral restriction activity. The linker of 11, 12, 24, or 33 amino acids may consist of any amino acid, or have the specific amino acid as described herein, including conservative variants of the specific linker as described herein.

In certain embodiments the invention provides a fusion polypeptide comprising the following consecutive amino acids in N- to C-terminus orientation: (i) SEQ ID NO: 13, which consists of amino acids at position 1-298 from hTRIM5α (SEQ ID NO:2); (ii) a linker of 11, 12, 24 or 33 amino acids linking SEQ ID NO: 13 and SEQ ID NO: 15; and (iii) SEQ ID NO:15, which consists of amino acid at positions 2 to 166 from hCypA (SEQ ID NO: 4), wherein the polypeptide has lentiviral restriction activity.

In certain embodiments, the lentiviral restriction activity is HIV-1 restriction activity. In other embodiments, the lentiviral restriction activity includes TRIM5 and Cyclophilin activity as described herein and known in the art.

In certain embodiments, the fusion polypeptides of the invention are recombinant polypeptides. In certain embodiments, the fusion polypeptides are not naturally occurring. In certain embodiments, the fusion polypeptides of the invention are isolated polypeptides. In certain embodiments, the nucleic acids which encode the fusion polypeptide are isolated. In certain embodiments, the nucleic acids which encode the fusion polypeptides are not naturally occurring.

In certain embodiments the variants of SEQ ID NO: 13 or 15 have at least about 55%, 60%, 70%, 75%, 80%, 85%, 90%, 95% or 99% identity to SEQ ID NO: 13 or 15. In certain embodiments, variants include any of the variants described herein. In certain embodiments the variants of SEQ ID NO: 13 or 15 have conservative substitutions, as described herein or known in the art. In certain embodiments, the conservative variants of SEQ ID NO: 13 or 15 have at least about 85%, 90%, 95% or 99% identity to SEQ ID NO: 13 or 15.

In certain embodiments the invention provides polypeptide comprising SEQ ID NO: 10, 11, 12, or 17 or a variant of SEQ ID NOS: 10, 11, 12, or 17 having about 55%, 60%, 70%, 75%, 80%, 85%, 90%, 95% or 99% identity to SEQ ID NO: 10, 11, 12, or 17. In certain embodiments, the variant have conservative substations as described herein or known in the art. In certain embodiments the conservative variants have about 85%, 90%, 95% or 99% identity to SEQ ID NO: 10, 11, 12, or 17.

In certain embodiments, the linker linking the TRIM5 and Cyclophilin portions of the fusion polypeptide has SEQ ID NO: 20, 21, 22 or 23 or a variant of SEQ ID NO: 20, 21, 22 or 23 having about 55%, 60%, 70%, 75%, 80%, 85%, 90%, 95% or 99% identity to SEQ ID NO: 20, 21, 22 or 23. In certain embodiments, the linker has SEQ ID NO: 20, 21, 22 or 23 or a conservative variant of SEQ ID NO: 20, 21, 22 or 23. In certain embodiments the conservative variants have about 85%, 90%, 95% or 99% identity to SEQ ID NO: 20, 21, 22 or 23.

In certain aspects, the invention provides an isolated nucleic acid encoding any of the polypeptides of the invention. In certain aspects, the invention provides a vector comprising any one of the nucleic acids of the invention. In certain aspects, the invention provides use of any of the inventive nucleic acids or variants thereof, and/or protein encoded by these nucleic acids or variants thereof, in any of the methods of the invention.

In certain aspects the invention provides use of the nucleic acid and the polypeptides encoded by these nucleic acids in any of the methods of the invention, including but not limited to methods of treatment of lentiviral infection, methods of reducing viral loads, methods of restricting viral replication, and so forth.

BRIEF DESCRIPTION OF THE FIGURES

FIG. 14. Human TRIM5alpha protein (SEQ ID NO:2) (*Homo sapiens* tripartite motif protein TRIM5 isoform alpha amino acid sequence). GenBank Accession No. NP_149023.

FIG. 15. Human cyclophilin A mRNA (SEQ ID NO:3) (*Homo sapiens* peptidylprolyl isomerase A (PPIA; cyclophilin A) mRNA). GenBank Accession No. NM_021130.

FIG. 16. Human cyclophilin A protein (SEQ ID NO:4) (*Homo sapiens* peptidylprolyl isomerase A). GenBank Accession No. NP_066953.

FIG. 17. Nucleotide sequence (SEQ ID NO:5) encoding human hTSCyp fusion polypeptide (SEQ ID NO:10) where Cyp is fused to TRIM5 at alanine 331 (underlined) of TRIM5 (hT5-A331-Cyp).

FIG. 18. Nucleotide sequence (SEQ ID NO:6) encoding human hTSCyp fusion polypeptide (SEQ ID NO:11) where Cyp is fused to TRIM5 at serine 309 (underlined) of TRIM5 (hT5-5309-Cyp).

FIG. 19. Nucleotide sequence (SEQ ID NO:7) encoding human hT5Cyp fusion polypeptide (SEQ ID NO:12) where Cyp is fused to TRIM5 at serine 322 (underlined) of TRIM5 (hT5-S322-Cyp).

FIGS. 20A-20C. Nucleotide sequence (SEQ ID NO:8) of vector scALPS-GFP.

FIGS. 21A-21D. Nucleotide sequence (SEQ ID NO:9) of vector scALPS-GFP containing a nucleotide sequence encoding hT5Cyp.

FIG. 24A-24B. Identification of human TSCyp proteins that potently restrict HIV-1. (A) The sequence of hT5α protein. Horizontal lines indicate the RING finger and B-box domains. The register of the predicted coiled-coils is indicated with lower case letters. PRYSPRY residues are boxed. Vertical lines indicate the site of fusion of CypA to T5. Numbers indicate the T5 amino acid to which CypA is fused and are color-coded for restriction phenotype: red, potently restrictive; green, permissive; orange, variably restrictive. (B) Jurkat T cells (left panel) and THP-1 monocytes (right panel) were transduced with vectors encoding puromycin-resistance and either AoT5Cyp or hT5Cyp (hT5-S222-Cyp) fusion proteins. Pools of puromycin-resistant cells were infected with increasing amounts of a single-cycle, HIV-1 vector encoding GFP (left to right on X-axis). The percentage of $GFP^+$ cells (Y-axis) was determined 48 hrs later.

FIG. 41A-41B. (A.) Organization of functional domains along the linear TRIM5 sequence; BB=B box, RF=RING finger, E3=E3 ubiquitin ligase activity, CA=capsid (B.) Alignment of amino acid sequences at the fusion junction (SEQ ID NOs: 138-144); Ma=*Macacca* (sequence identical for *mulatta, nemestrina*, and *fascicularis*), Ao=*Aotus*, h=human, Rh=rhesus (*macacca mulatta*); * indicates engineered not naturally-occurring protein. Color coded for domains: Blue=RBCC, Green=PRYSPRY, Red=Cyclophilin A, underlined residues represent amino-acid changes between human and rhesus PRYSPRY domains, black=Rhesus-inspired amino-acid changes in the human T5α PRYSPRY domain.

FIG. 42. Alignment of AoT5Cyp (SEQ ID NO: 146) and hT5Cyp amino-acid sequences (SEQ ID NO: 145).

FIGS. 44A-B. (A.) The sequence of hT5α protein. Horizontal lines indicate the RING finger and B-box domains. The register of the predicted coiled-coils is indicated with lower case letters. PRYSPRY residues are boxed. Vertical lines indicate the site of fusion of CypA to T5. Numbers indicate the T5 amino acid to which CypA is fused and are color-coded for restriction phenotype: red, potently restrictive; green, permissive; orange, variably restrictive. (B.) Jurkat T cells (left panel) and THP-1 monocytes (right panel) were transduced with vectors encoding puromycin-resistance and the indicated T5Cyp fusion proteins. Pools of puromycin-resistant cells were infected with increasing amounts of an HIV-1 vector encoding GFP (left to right on X-axis). The percentage of GFP$^+$ cells (Y-axis) was determined 48 hrs later.

FIGS. 53A-E. (A) Schematic of experimental layout for analysis of cell-to-cell spread in a single cycle of infection. (B) Jurkat T cells (target, left panel) and 293T cells (donor, right panel) stably transduced with lentiviral vectors coding for indicated T5Cyps or controls were challenged with increasing doses of an HIV-1 GFP vectors (X-axis). The percentage of infected cells (Y-axis) was determined 48 hours later. (C) Donor 293T cell lines shown in FIG. 53B were transfected with HIV-$1_{NL4-3-GFP-IRES-Nef}$ proviral DNA. 48 hours post-transfection cells were washed and target DiD-labelled Jurkat T control or hT5Cyp-expressing cell lines shown in FIG. 53B were co-cultured with donor 293T cell lines for 2 hours (left panel) or 12 hours. The percentage of infected target Jurkat cells (Y-axis) was assessed by flow cytometry 48 hours later. T5-expression in donor 293T cell lines is indicated on the X-axis. (D) Prior to addition of target cells, relative concentration of virus produced by donor 293T cells was determined by RT assay of the supernatant. (E) Release of $^{35}$S-labelled Gag from indicated donor T cells (Y-axis) was measured at given time points (X-axis) following addition of pulse.

DETAILED DESCRIPTION

Figure 1:
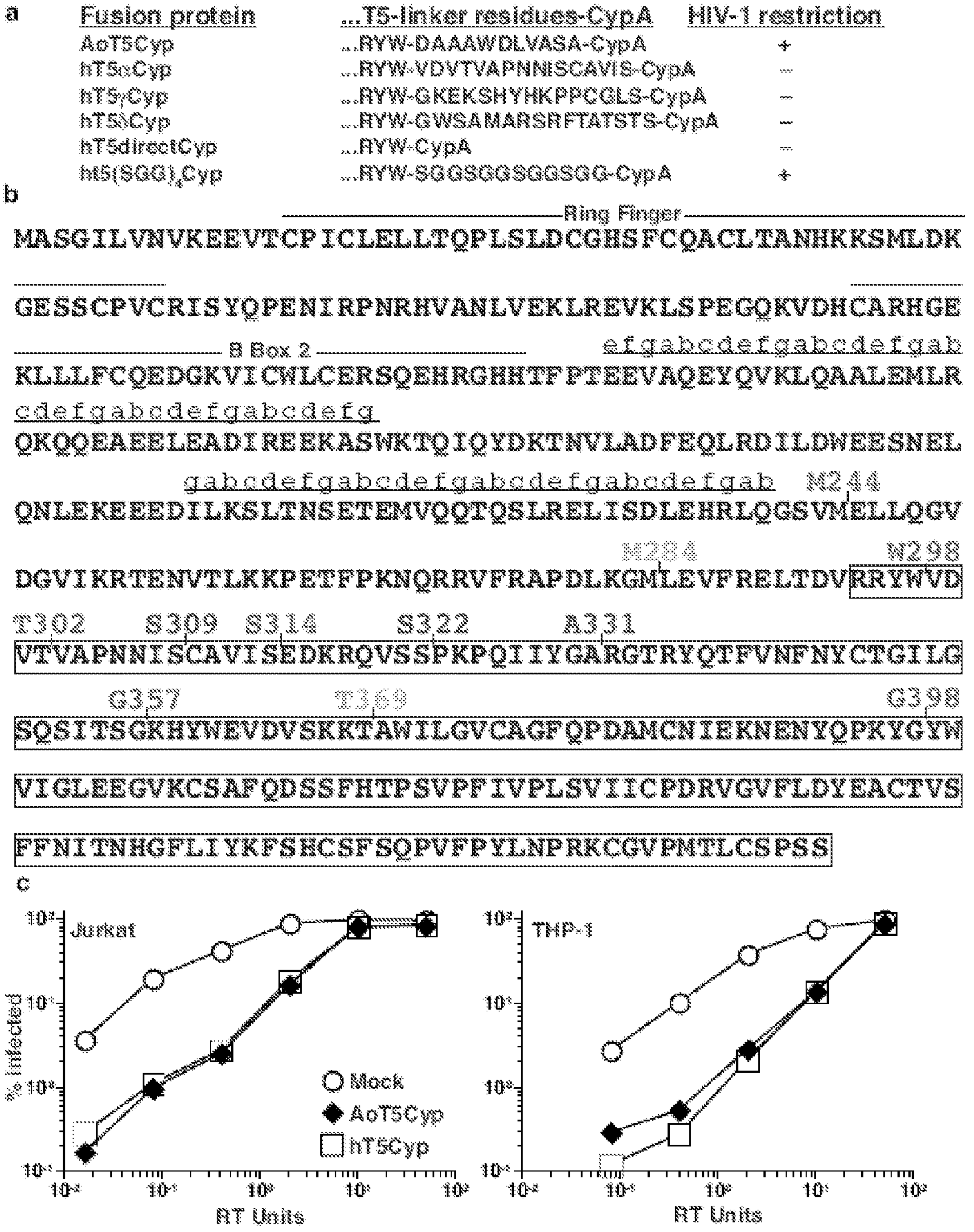
FIGS. 1_a_-1_c_. Identification of human T5Cyp proteins that potently restrict HIV-1. (a) Amino acid sequence at the junction (SEQ ID NOs: 129-133) of the indicated T5Cyp fusion proteins and the corresponding anti-HIV-1 activity. (b) The sequence of hT5α protein (SEQ ID NO: 134). Horizontal lines indicate the RING finger and B-box domains. The register of the predicted coiled-coils is indicated with lower case letters. PRYSPRY residues are boxed. Vertical lines indicate the site of fusion of CypA to T5. Numbers indicate the T5 amino acid to which CypA is fused and are color-coded for restriction phenotype: red, potently restrictive (S309, 5322, A331); green, permissive (M244, W298, T302, 5314, G357, G398); orange, variably restrictive (M284, T369). (c) Jurkat T cells (left panel) and THP-1 monocytes (right panel) were transduced with vectors encoding puromycin-resistance and the indicated T5Cyp fusion proteins. Pools of puromycin-resistant cells were infected with increasing amounts of an HIV-1 vector encoding GFP (left to right on X-axis). The percentage of $GFP^+$ cells (Y-axis) was determined 48 hrs later.

As used herein the term "lentiviral restriction activity" of a fusion protein or polypeptide is defined as binding and degradation of a lentivirus, wherein the cyclophilin A part of the fusion protein specifically binds to the lentiviral capsid protein, while the TRIM5 part of the fusion protein acts as TRIM5 alone has been characterized, causing the degradation of the substance bound to the cyclophilin A portion of the fusion protein. Thus, the fusion protein has coupled a specific binding tropism, i.e., the binding of cyclophilin portion to capsid of a lentivirus, with the degradation activity of TRIM5. The term "lentiviral restriction activity" of a fusion protein or polypeptide may be used interchangeably with the term "both TRIM activity and cyclophilin activity."

In certain embodiments the term "lentiviral restriction activity" specifically includes the term "HIV-1 restriction activity" of a fusion protein or polypeptide, which is defined as binding and degradation of HIV-1, wherein the cyclophilin A part of the fusion protein specifically binds to the HIV-1 capsid protein once HIV-1 enters the cell, while the TRIM5 part of the fusion protein acts as TRIM5 alone has been characterized, causing the degradation of the substance bound to the cyclophilin A portion of the fusion protein. Thus, the fusion protein has coupled a specific binding tropism, i.e., the binding of cyclophilin portion to capsid of HIV-1, with the degradation activity of TRIM5.

As used herein, "administration" means any of the standard methods of administering a pharmaceutical composition known to those skilled in the art. Examples include, but are not limited to, intravenous, intraperitoneal or intramuscular administration, in vitro gene therapy via adenoviral vector or other vector (liposome), ex vivo gene therapy, oral, and inhalation. In another embodiment of the invention, the administering is carried out via injection, oral administration, or topical administration. In another embodiment, administration is intramuscularly, intramucosally, intranasally, subcutaneously, intradermally, transdermally, intravaginally, intrarectally, orally or intravenously. In one embodiment of this invention, the subject is a mammal, e.g., a mouse or a human. Preferably, the mammal is a human. In another embodiment of the invention, the "introducing" or administering is carried out by a means selected from the group consisting of transduction, viral-mediated introduction, adenovirus infection, liposome-mediated transfer, topical application to the cell, and microinjection. In another embodiment of the invention, the carrier is an aqueous carrier, a liposome, a vector, a viral vector, or a lipid carrier.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

Two DNA or polypeptide sequences are "substantially homologous" when at least about 80% (preferably at least about 90%, and most preferably at least about 95%) of the nucleotides or amino acids match over a defined length of the molecule. As used herein, "substantially homologous" also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Cold Springs Harbor Laboratory, 2nd ed., Cold Springs Harbor, N. Y. (1989).

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, prokaryotic sequences, cDNA from eukaryotic mRNA, genomic DNA sequences from eukaryotic (e.g., mammalian) sources, viral RNA or DNA, and even synthetic nucleotide sequences. A transcription termination sequence will usually be located 3' to the coding sequence.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. In eukaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eukaryotic cell to establish cell lines or clones comprised of a population of daughter cells containing the exogenous DNA.

As used herein, a "variant", refers to a nucleic acid or a protein of the invention differing in sequence from a "reference" molecule, for example a sequence specifically described herewith, but retaining function, activity and/or therapeutic property of the inventive fusion proteins or inventive nucleic acids which encode the inventive fusion proteins with lentiviral restriction activity, which activity is described elsewhere herein or otherwise known in the art. In certain embodiments, the lentiviral restriction activity is HIV-1 restriction activity. Generally, variants are overall very similar, and, in many regions, identical to the amino acid sequence of the inventive proteins or the nucleic acid sequences encoding the same.

As used herein, "mutation" with reference to a polynucleotide or polypeptide, refers to a naturally-occurring, synthetic, recombinant, or chemical change or difference to the primary, secondary, or tertiary structure of a polynucleotide or polypeptide, as compared to a reference polynucleotide or polypeptide, respectively (e.g., as compared to sequences of polynucleotide or polypeptide as described herein). Mutations include such changes as, for example, deletions, insertions, or substitutions. Polynucleotides and polypeptides having such mutations can be isolated or generated using methods well known in the art.

As used herein, "deletion" is defined as a change in either polynucleotide or amino acid sequences in which one or more polynucleotides or amino acid residues, respectively, are absent.

As used herein, "insertion" or "addition" is that change in a polynucleotide or amino acid sequence which has resulted in the addition of one or more polynucleotides or amino acid residues, respectively, as compared to a reference polynucleotide or amino acid sequence.

As used herein, "substitution" results from the replacement of one or more polynucleotides or amino acids by different polynucleotides or amino acids, respectively.

The present invention is also directed to proteins which comprise, or consist of, or consist essentially of an amino acid sequence which is at least 80%, 81%, 82%, 83%, 84%, 85%, 86%, 87%, 88%, 90%, 91%, 92%, 93%, 94%, 95%, 96%, 97%, 98%, 99%, 99.5% or 100%, or which is 80%, 81%, 82%, 83%, 84%, 85%, 86%, 87%, 88%, 90%, 91%, 92%, 93%, 94%, 95%, 96%, 97%, 98%, 99%, 99.5% or 100% identical to, for example, the amino acid and nucleic acids sequences of the invention.

Further polypeptides encompassed by the invention are polypeptides encoded by polynucleotides which hybridize to the complement of a nucleic acid molecule encoding a fusion protein of the invention under stringent hybridization conditions (e.g., hybridization to filter bound DNA in 6× Sodium chloride/Sodium citrate (SSC) at about 45 degrees Celsius, followed by one or more washes in 0.2×SSC, 0.1% SDS at about 50-65 degrees Celsius), under highly stringent conditions (e.g., hybridization to filter bound DNA in 6× sodium chloride/Sodium citrate (SSC) at about 45 degrees Celsius, followed by one or more washes in 0.1×SSC, 0.2% SDS at about 68 degrees Celsius), or under other stringent hybridization conditions which are known to those of skill in the art (see, for example, Ausubel, F. M. et al., eds., 1989 Current protocol in Molecular Biology, Green publishing associates, Inc., and John Wiley & Sons Inc., New York, at pages 6.3.1-6.3.6 and 2.10.3). Polynucleotides encoding these polypeptides are also encompassed by the invention.

By a polypeptide having an amino acid sequence at least, for example, 95% "identical" to a query amino acid sequence, it is intended that the amino acid sequence of the subject polypeptide is identical to the query sequence except that the subject/reference polypeptide sequence may in a non-limiting example include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 81%, 82%, 83%, 84%, 85%, 86%, 87%, 88%, 90%, 91%, 92%, 93%, 94%, 95%, 96%, 97%, 98%, 99%, 99.5% or 100% identical to, for instance, the amino acid sequence of a fusion protein of the invention or a fragment thereof, can be determined conventionally using known computer programs. A non-limiting example of a method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. In certain embodiments, no other manual corrections are to made for the purposes of the present invention.

The variants of the invention will usually have at least 75%, 80%, 81%, 82%, 83%, 84%, 85%, 86%, 87%, 88%, 90%, 91%, 92%, 93%, 94%, 95%, 96%, 97%, 98%, 99%, 99.5% or 100% or 75%, 80%, 81%, 82%, 83%, 84%, 85%, 86%, 87%, 88%, 90%, 91%, 92%, 93%, 94%, 95%, 96%, 97%, 98%, 99%, 99.5% or 100% sequence identity with any length or the full length of any of the inventive sequences provided herein. Homology or identity at the nucleotide or amino acid sequence level maybe determined by BLAST (Basic Local Alignment Search Tool) analysis using the algorithm employed by the programs blastp, blastn, blastx, tblastn and tblastx (Karlin et al., Proc. Natl. Acad. Sci. USA 87: 2264-2268 (1990) and Altschul, J. Mol. Evol. 36: 290-300 (1993), fully incorporated by reference) which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., Proc. Natl. Acad. Sci. USA 89: 10915-10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively. Four blastn parameters may be adjusted as follows: Q=10 (gap creation penalty); R=10 (gap extension penalty); wink=1 (generates word hits at every position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2. Other sequence analysis programs and algorithms are known and used in the art. Non-limiting examples of programs for sequence analysis include DNAStar®Lasergene® and MacVector.

The polynucleotide variants of the invention may contain alterations in the coding regions, non-coding regions, or both. The invention provides polynucleotide variants containing alterations which produce silent substitutions, additions, or deletions, but do not alter the properties or activities of the encoded polypeptide. The invention provides nucleotide variants produced by silent substitutions due to the degeneracy of the genetic code. Moreover, polypeptide variants in which less than 50, less than 40, less than 30, less than 20, less than 10, or 5-50, 5-25, 5-15, 5-10, 1-5, 1-3, 1-2 or 10, 9, 8, 7, 6, 5, 4, 3, 2, or 1 amino acids are substituted, deleted, or added in any combination are also preferred. Polynucleotide variants can be produced for a variety of reasons, e.g., to optimize codon expression for a particular host, for example but not limited to yeast or mammalian cells.

In certain embodiments, the invention provides naturally occurring variants which are called "allelic variants," and refer to one of several alternate forms of a gene occupying a given locus on a chromosome of an organism. (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis as described herein and known in the art. See Sambrook et al. In certain embodiments, the invention contemplates allelic variants of the TRIM5 and/or CyclophilinA portion of the nucleic acids which encode the fusion proteins of the invention. Using known methods of protein engineering and recombinant DNA technology, variants may be generated to improve or alter the characteristics of the polypeptides of the present invention. For instance, one or more amino acids can be deleted from the N-terminus or C-terminus of the polypeptide of the present invention without substantial loss of biological function. It is well known in the art that variants often retain a biological activity similar to that of the reference protein. In certain embodiments, variants of proteins of the invention or nucleic acids encoding proteins of the invention retain HIV-1 restriction activity as described herein. The HIV-1 restriction activity of variants may be comparable, increased or reduced compared to the HIV-1 restriction activity of the reference polypeptides. Furthermore, even if deleting one or more amino acids from the N-terminus or C-terminus of a polypeptide results in modification or loss of one or more biological activities, other biological activities may still be retained. For example, the ability of a variant to bind to HIV-1 may be reduced compared to a reference polypeptide of the invention, while the variant maintains the HIV-1 degradation activity, or vice versa, thus preserving the "HIV-1 restriction activity," which can readily be determined by methods described herein and otherwise known in the art.

In certain embodiments, the variants of the invention have conservative substitutions. The term "conservative substitutions" refers to substitution of an amino acid residue for a different amino acid residue that has similar chemical properties as known and understood by a person of ordinary skill in the art. Non-limiting examples are replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. The term "nonconservative"

refers to substituting an amino acid residue for a different amino acid residue that has different chemical properties. In certain embodiments the invention provides non-conservative variants which have substantially the same HIV-1 restriction activity compared to the reference polypeptides. The invention contemplates conservative and/or nonconservative variants, so long as these variants retain HIV-1 restriction activity.

In certain embodiments the invention provides variants which modify the nucleic acids or amino acids of the linker between the TRIM5 and Cyclophilin portion of the fusion proteins of the invention. Without being bound by theory, the linker between the TRIM5 and Cyclophilin portions of the fusion proteins of the invention may tolerate a larger % variation in the number and/or types of modifications, including different length of the linker, while maintaining the HIV-1 restriction activity. In certain embodiments, the invention contemplates modifications of the linker which result in larger % variation in the linker sequence and thus lower % identity as compared to the % identity between the TRIM5 and/or Cyclophilin portions of the variants and the fusion protein of the invention. A non-limiting example includes variants wherein the identity between the TRIM5 and/or Cyclophilin portions of a variant and the fusion proteins of the invention is at least 50%, 55%, 60%, 65%, 70%, 75%, 80%, 81%, 82%, 83%, 84%, 85%, 86%, 87%, 88%, 90%, 91%, 92%, 93%, 94%, 95%, 96%, 97%, 98%, 99%, 99.5% or 100%, or 50%, 55%, 60%, 65%, 70%, 75%, 80%, 81%, 82%, 83%, 84%, 85%, 86%, 87%, 88%, 90%, 91%, 92%, 93%, 94%, 95%, 96%, 97%, 98%, 99%, 99.5% or 100%, while the identity between the linker of the variant and the fusion proteins of the invention is at least 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 90%, 91%, 92%, 93%, 94%, 95%, 96%, 97%, 98%, 99%, 99.5% or 100%, or 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 90%, 91%, 92%, 93%, 94%, 95%, 96%, 97%, 98%, 99%, 99.5% or 100%, or any combination there of.

Guidance concerning how to make phenotypically silent amino acid substitutions is provided, for example, in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein. The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. See Cunningham and Wells, Science 244:1081-1085 (1989). The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) polypeptides containing substitutions of one or more of the non-conserved amino acid residues, where the substituted amino acid residues may or may not be one encoded by the genetic code, or (ii) polypeptides containing substitutions of one or more of the amino acid residues having a substituent group, or (iii) polypeptides which have been fused with or chemically conjugated to another compound, such as a compound to increase the stability and/or solubility of the polypeptide (for example, polyethylene glycol), (iv) polypeptide containing additional amino acids, such as, for example, an IgG Fc fusion region peptide. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. See Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).

In specific embodiments, the polypeptides of the invention comprise, or alternatively, consist of, or consist essentially of fragments or variants of the amino acid sequences of the invention wherein the fragments or variants have 1, 2, 3, 4, 5, 6, 7, 8, 9, 10, 11, 12, 13, 14, 15, or 1-5, 5-10, 5-15, 5-25, 5-50, 10-50 or 50-150, amino acid residue additions, substitutions, and/or deletions when compared to the reference amino acid sequence. In preferred embodiments, the amino acid substitutions are conservative. Nucleic acids encoding these polypeptides are also encompassed by the invention.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GP1 anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N. Y. Acad. Sci. 663:48-62 (1992)).

The invention further provides a stem cell comprising a nucleic acid of the invention, wherein the nucleic acid is part of the genome of the stem cell. As used herein a "stem cell" refers to an undifferentiated cell in the bone marrow that has the ability both to multiply and to differentiate into a specific, specialized cell, such as a blood cell. In one embodiment, human hematopoietic stem cells are mobilized from the bone marrow of an HIV-1 infected subject, the cells are transduced in vitro with vectors expressing human TRIMCyp, and the cells are injected back into the patient as an auto-transplant.

As used in this specification and the appended claims, the singular forms "a," "an" and "the" include plural references unless the content clearly dictates otherwise.

Provided herein is a novel fusion between human TRIM5alpha (TRIM5α; T5; TRIM) and human cyclophilin A (CypA; Cyp; Cyp A). A fully human nucleic acid fusion sequence and polypeptide fusion sequence comprising a human TRIM5 sequence and a human CypA sequence are provided. Such fusion molecules are referred to as human TRIM5-CypA (or hT5-CypA or TRIM-Cyp or hTRIMCyp, or similar variations). Also provided are methods of using the fusion molecules.

The discovery that certain TRIM5 (T5) orthologues inhibit HIV-1 infection immediately after the virus enters otherwise susceptible cells (Diaz-Griffero et al., 2006b; Perez-Caballero et al., 2005a; Sayah et al., 2004; Stremlau et al., 2004) raised the prospect that these host factors might be exploited in HIV-1 gene therapy. The α-isoform of TRIM5 (T5α) contains a C-terminal PRYSPRY domain that is required for T5α binding to the capsid (CA) of restriction-sensitive retroviruses (Sebastian and Luban, 2005; Stremlau et al., 2006). The specificity of the PRYSPRY-CA interaction determines which retrovirus a given T5α orthologue inhibits (Luban, 2007). While human T5α (hTSα) weakly blocks HIV-1, it potently blocks N-tropic murine leukemia virus (N-MLV). In contrast, rhesus T5α (RhT5α) inhibits HIV-1 but N-MLV only weakly. The specificity of retroviral restriction and the modular nature of the T5 components are further demonstrated by the enhanced HIV-1 restriction activity that results when the hT5α PRYSPRY domain is replaced with that from RhT5α (Perez-Caballero et al., 2005a; Sawyer et al., 2005; Stremlau et al., 2005; Yap et al., 2005).

The T5 gene in the New World owl monkey (genus *Aotus*) is unusual. It resulted from retrotransposition of the cyclophilin A (CypA) cDNA into intron 7 (Nisole et al., 2004; Sayah et al., 2004). CypA is a CA-binding protein (Luban et al., 1993) and the *Aotus* TRIM5Cyp fusion (AoT5Cyp) prevents HIV-1 infection (Nisole et al., 2004; Sayah et al., 2004). AoT5Cyp has several properties that make it appealing for gene therapy. It potently inhibits HIV-1 infection when expressed in human cells (Nisole et al., 2004; Sayah et al., 2004), acting on the virus within minutes of entry (Diaz-Griffero et al., 2006b; Perez-Caballero et al., 2005a). Furthermore, AoT5Cyp is the only TRIM5 allele in 10 *Aotus* species (Ribeiro et al., 2005), indicating that cells bearing AoT5Cyp retain functionality. One drawback of AoT5Cyp is that it is not a human protein and if employed as gene therapy it might elicit an immune response (Riddell et al., 1996). Provided herein is an engineered fully human TRIM5-cyclophilin A fusion proteins (hTSCyp) exhibiting HIV-1 restriction activity comparable to AoT5Cyp and possessing all the properties desired of anti-HIV-1 gene therapy.

In Old World primates, TRIM5-α confers a potent block to HIV-1 infection that acts after virus entry into cells. Cyp A binding to viral capsid protects HIV-1 from a similar activity in human cells. Among New World primates, owl monkeys exhibit post-entry restriction of HIV-1. Paradoxically, the barrier to HIV-1 in owl monkey cells is released by capsid mutants or drugs that disrupt capsid interaction with CypA.

U.S. Patent Application Publication No. 2008/0045454, incorporated herein by reference, describes a fusion protein between TRIM5 and cyclophilin A which was discovered and isolated from Owl monkey, which is a species of primate from South America that are resistant to HIV-1 infection. The TRIM-cyclophilin fusion protein provides the Owl monkey with its resistance to HIV. The cyclophilin A part of the fusion protein specifically binds to the HIV-1 capsid protein once HIV-1 enters the cell. The TRIM5 part of the fusion protein acts as TRIM5 alone has been characterized, causing the degradation of the substance bound to the cyclophilin A portion of the fusion protein, namely the degradation of HIV-1. Thus, the fusion protein has coupled a specific binding tropism, i.e., the binding of cyclophilin to capsid of HIV-1, with the degradation activity of TRIM5. The cyclophilin part of the fusion protein is highly conserved among different species. Cyclophilin is a protein that is present in yeast and in humans. It plays a role in protein-folding and in the biological response to the immunosuppressive drug cyclosporine. The TRIM5 part of the fusion protein is highly variable from one species to another.

The α-isoform of TRIM5 (T5α) contains a C-terminal PRYSPRY domain that is required for T5α binding to the capsid (CA) of restriction-sensitive retroviruses[6,7]. The specificity of the PRYSPRY-CA interaction determines which retrovirus a given T5α orthologue inhibits[8]. While human T5α (hT5α) weakly blocks HIV-1, it potently blocks N-tropic murine leukemia virus (N-MLV). In contrast, rhesus T5α (rhT5α) inhibits HIV-1 but not N-MLV. Restriction specificity and the modular nature of the T5 components are further demonstrated by the enhanced HIV-1 restriction activity that results when the hT5α PRYSPRY domain is replaced with that from rhT5α[9-12].

The potency of a human TRIM-Cyp fusion has been demonstrated in vitro and in vivo in a humanized mouse model of HIV-1. The use of TRIM-Cyp provides several benefits and improvements over current anti-HIV-1 technologies, such as recombinant RevM10 protein, RNAi approaches, and disruption of the CCR5 co-receptor. The high efficacy of human TRIM-Cyp would enable its use as a monotherapy, which is a significant benefit over the use of combination therapies required by the current technologies. Also, the potency of human TRIM-Cyp minimizes the emergence of viral resistance, a recurrent problem with current technologies. Human TRIMCyp acts early in the viral life cycle conferring true protection and blocking the ligation of HIV-1 into host chromosomal DNA, thus minimizing viral persistence and potential mutagenic effects of HIV-1 infection.

Provided herein is an HIV-1 inhibitor modeled after AoT5Cyp generated by fusing human CypA to hT5 (hT5Cyp). As further described in Example 1, of 13 fusions, three were as potent as AoT5Cyp. Antiviral activity of the human fusions required capsid (CA)-binding by hCypA, linkage of hCypA to the capsid-specificity determinant in hT5, and the ability to form cytoplasmic bodies. CXCR4- and CCR5-tropic HIV-1 clones and primary isolates, a circulating HIV-1 isolate previously reported as AoT5Cyp-resistant, HIV-2, $SIV_{AGM}$tan, and FIV were all inhibited by hT5Cyp. hT5Cyp blocked HIV-1 infection of primary $CD4^+$ T cells and macrophages, and conferred selective advantage after HIV-1 infection, without selection for resistant virus or disruption of host cell function. Moreover, hT5Cyp preserved $hCD4^+$ T cells after adoptive transfer to $Rag2^{-/-}\gamma_c^{-/-}$ mice and challenge with HIV-1; viremia and productive infection in lymphoid organs were markedly reduced. Thus, hT5Cyp is a robust candidate for HIV-1 gene therapy.

The more successful anti-HIV-1 gene therapy approaches to date have followed two main strategies: either modification of host-cell factors required for viral replication or inhibition of essential viral elements (Strayer et al., 2005). As described herein, a third approach was adopted: the exploitation of natural inhibitors that evolved over millions of years in primates in response to retroviral attack (Li, 2006b; Sawyer, 2005; Stremlau, 2005; Yap, 2005). The potent block to HIV-1 observed with AoT5Cyp inspired the design of a human equivalent, hT5Cyp, that robustly blocks HIV-1 in vitro and in vivo. The strict structural requirements for engineering a functional hT5Cyp emphasize the remarkable nature of the fusion gene that was generated by retrotransposition in New World owl monkeys (Sayah et al., 2004). A distinct T5Cyp fusion gene was generated by an independent retrotransposition event in Old World macaques. In this case, restriction activity was detected against HIV-2 and FIV, but not against HIV-1 (Stove and Yap, 2008). The convergent evolution of T5Cyp fusion proteins with distinct retroviral specificities indicates a strong selection for these potent restriction factors. While the specific force behind selection remains to be elucidated for individual T5 orthologues, in each case the selective pressure is likely to have been a retrovirus (Sawyer et al., 2005).

Since T5α and T5Cyp are modular proteins, it was expected that the engineering of a restrictive hT5Cyp would be trivial. Surprisingly, only three of 13 hT5Cyp fusions inhibited HIV-1 comparably to AoT5Cyp. No correlation was observed between protein levels and antiviral activity, and CA-binding activity was not sufficient to restrict HIV-1 (See FIG. 47). Structural modeling showed that anti-HIV-1 activity was observed when hCypA was fused at the apex of the hT5α PRYSPRY domain (See FIG. 47C). Analysis of non-synonymous mutations indicates that this region undergoes some of the strongest selective pressure in the primate lineage and functional experiments pinpoint it as a specificity determinant for CA recognition (Sawyer et al., 2005; Song et al., 2005b; Yap et al., 2005). CypA fusion to this site may have antiviral activity because this apical loop is uniquely situated for coordinating CA recognition and effector domains of T5. Correlation between restriction activity and the ability of hT5Cyp fusion proteins to form cytoplasmic bodies suggests that activity requires particular spatial constraints or association with cofactors.

Optimal gene therapy candidates should provide high efficacy and low antigenicity. Hematopoietic progenitors transduced with rhesus macaque T5α or human-rhesus T5α chimeras differentiate into HIV-1-resistant macrophages and T cells (Anderson and Akkina, 2005a, 2008). These proteins, however, are potentially antigenic, which could lead to the elimination of modified cells in vivo (Riddell et al., 1996). By substituting only critical amino acids within the hT5α PRYSPRY domain one can reduce the risk of antigenicity but this also decreases anti-HIV-1 efficacy (hT5αR332P; See FIG. 5, A and B). hT5Cyp potently inhibits HIV-1 and, being composed of human components, is of low antigenic potential.

Figure 46:
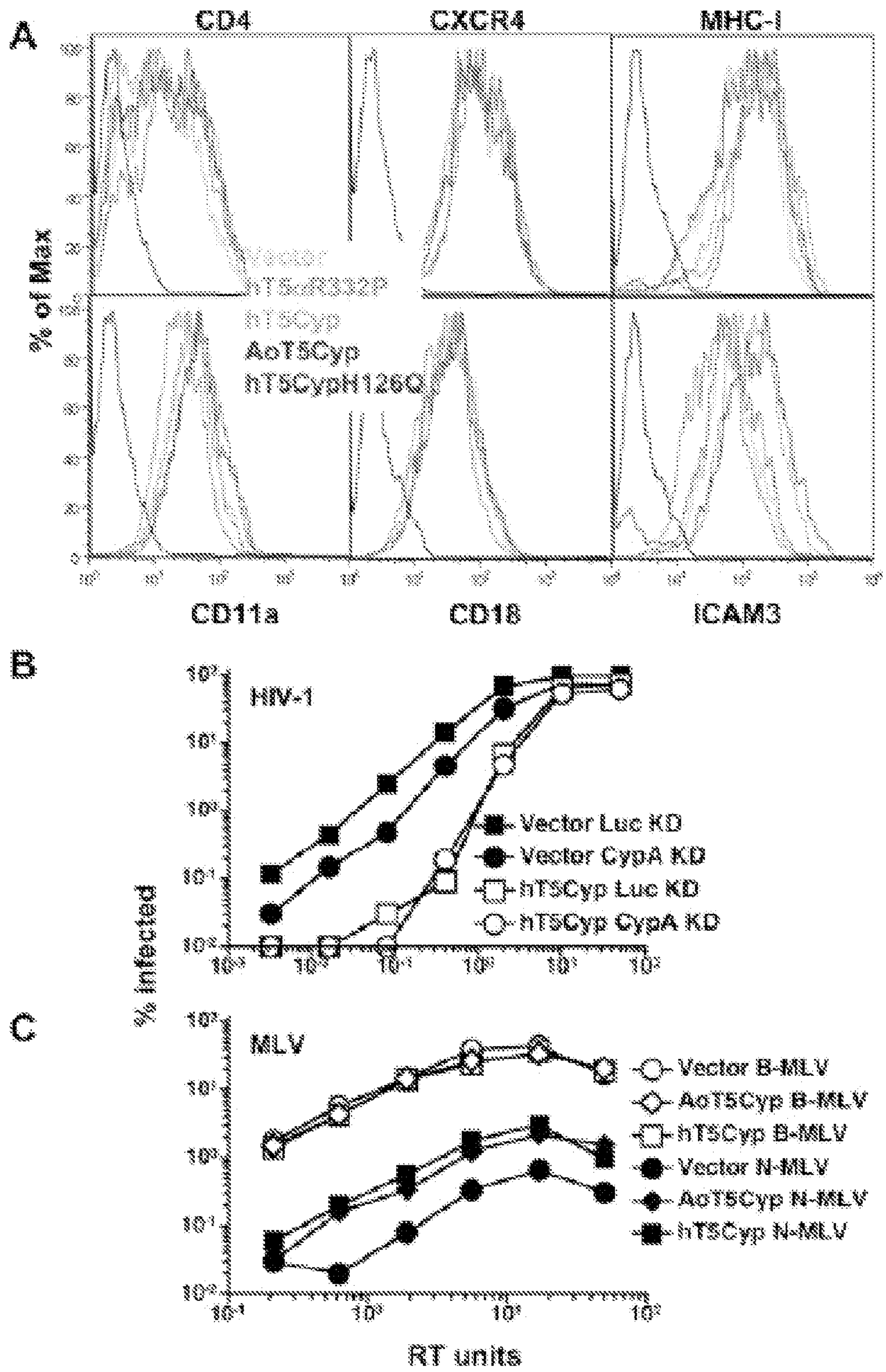
FIGS. 46A-C. (A.) Staining of indicated cell-surface markers in stable Jurkat T cell lines expressing the indicated T5. (B.) Anti-HIV-1 activity of hT5Cyp in Jurkat T cell lines with stable CypA knockdown. (C.) B- and N-MLV titration in Jurkat T cell lines stably expressing the indicated T5 or control. For B and C increasing viral doses were used (X-axis) and infected, GFP$^+$ cells were measured (Y-axis) 48 hours post-infection.
Figure 48:
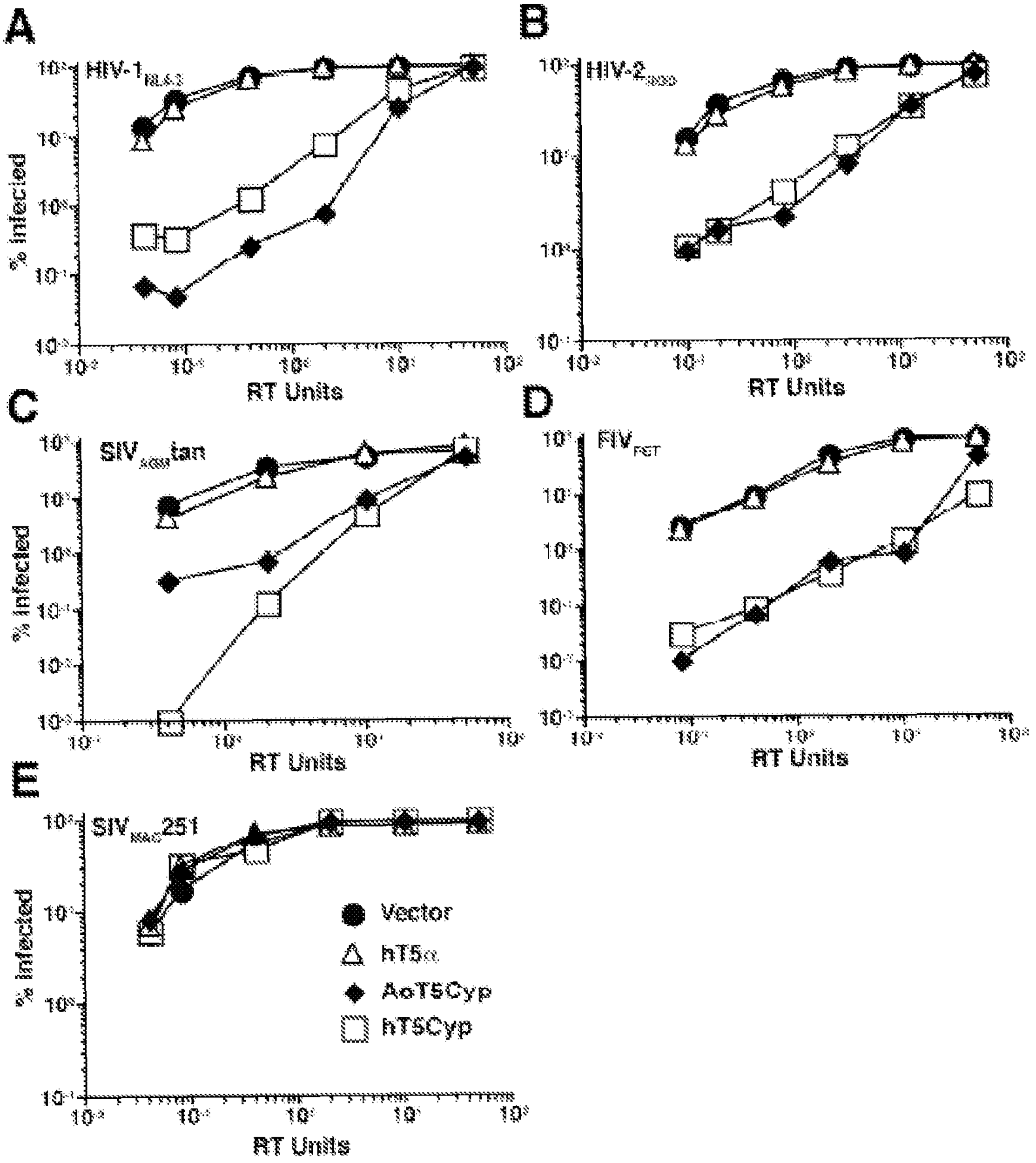
FIGS. 48A-E. T5Cyp restricts lentiviruses that encode Capsid with CypA-binding activity. CRFK cells stably expressing the indicated T5 proteins were transduced with increasing amounts (X-axis) of GFP vectors derived from HIV-$1_{NL4\text{-}3}$ (A), HIV-$2_{ROD}$ (B), $SIV_{AGM}$ tan (C), $FIV_{PET}$ (D), or $SIV_{MAC}$251 (E). The percentage of GFP$^+$ (infected) cells was determined at 48 hrs (Y-axis).
Figure 49:
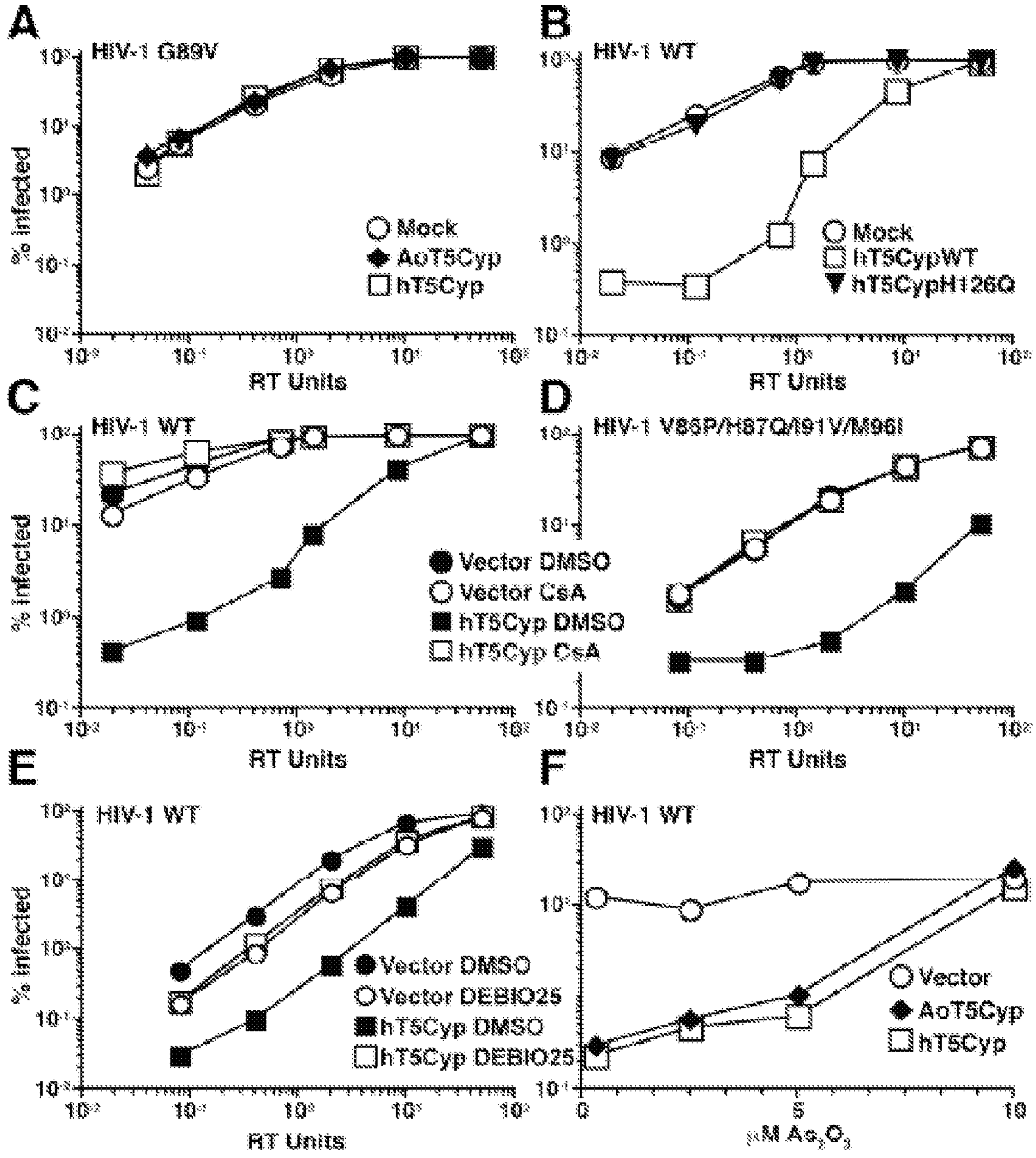
FIGS. 49A-F. (A-C) Disruption of the CA-CypA interaction by the G89V mutation in HIV-1 CA (A), the H126Q mutation in CypA (B), or the competitive inhibitor cyclosporine (CsA) at 2.5 μM (C), blocks HIV-1 restriction activity in CRFK cells stably expressing the indicated T5 proteins or controls. Cells were challenged with increasing amounts (X-axis) of HIV-1 GFP vector bearing the G89V mutation in CA (A) or wild-type HIV-1 GFP vector (B,C). (D) Introduction of a naturally-occurring quadruple mutation flanking the CA-CypA binding site in CA does not abrogate hT5Cyp-mediated restriction of HIV-1 in Jurkat T cells (E) Disruption of the CA-CypA interaction using the competitive, non-immunosuppressive inhibitor DEBIO-025 blocks HIV-1 restriction in Jurkat T cells. (F) Disruption of T5 by $As_2O_3$ blocks HIV-1 restriction activity by TSCyp. CRFK cells stably expressing the indicated TSCyp were infected with HIV-1 GFP vector in the presence of increasing amounts of $As_2O_3$ (X-axis). In each case (A-F) the percentage of GFP+ cells was measured by flow cytometry 48 hrs post-infection.
Figure 56:
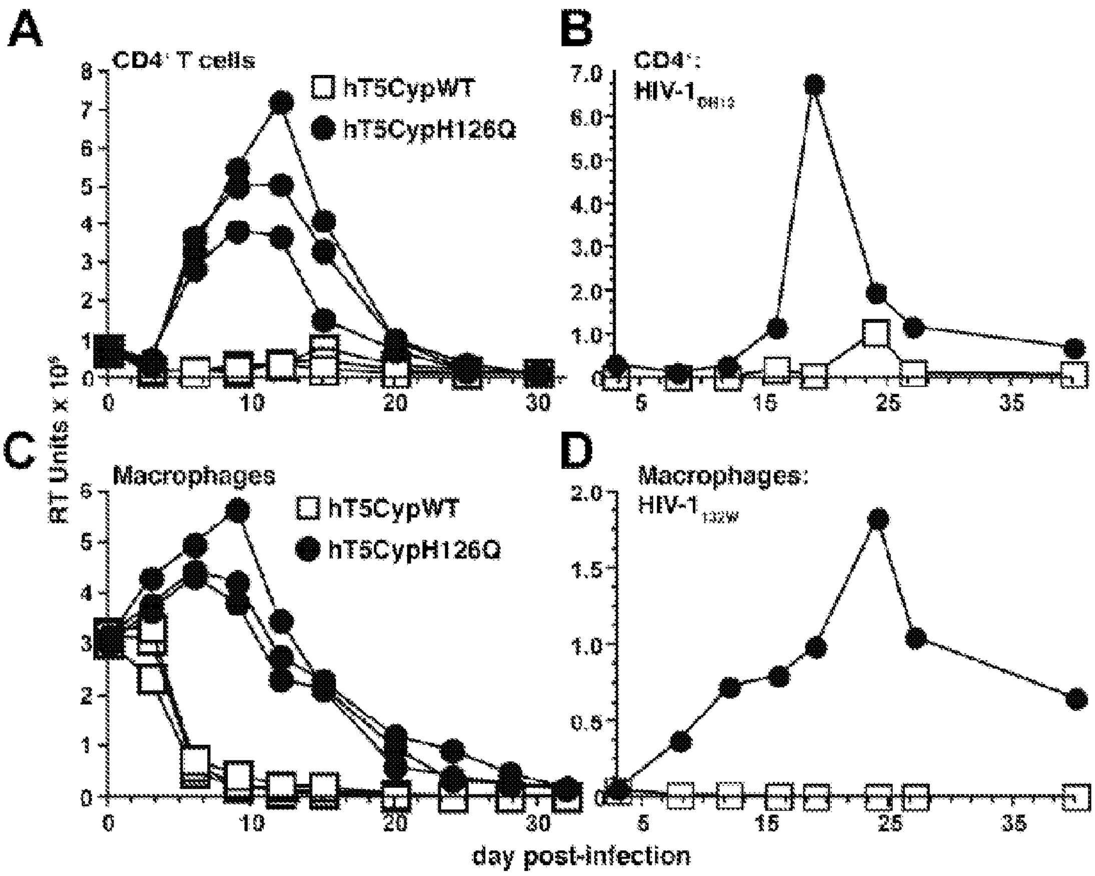
FIGS. 56A-D. hT5Cyp inhibits HIV-1 in primary human CD4$^+$ T cells. CD4$^+$ T cells transduced with scALPS encoding the indicated hT5Cyp proteins were sorted for GFP, infected with HIV-$1_{NL4-3}$ (A) or the primary isolate HIV-$1_{DH12}$ (B), and supernatant RT activity was measured. (C, D) hT5Cyp inhibits HIV-1 in monocyte-derived macrophages. (C) CD14$^+$ monocytes differentiated with GM-CSF were transduced, sorted for GFP, and challenged with HIV-$1_{NL4-3}$ as in (A) except that the viral envelope was modified to be CCR5-tropic or with the primary isolate HIV-$1_{132W}$ (D).

HIV-1 rev, tat, and gag (Boden et al., 2007; Strayer et al., 2005), as well as the HIV-1 co-receptor CCR5 (An et al., 2007; Perez et al., 2008), have been targeted by various means including siRNAs (Boden et al., 2007; Strayer et al., 2005) and zinc-finger endonucleases (Perez et al., 2008). With either approach there are concerns regarding toxicity[34], off-target effects[35], and viral resistance (Boden et al., 2007; Strayer et al., 2005). For siRNA approaches, escape mutants arise readily, since single point mutations are sufficient to escape the siRNA-mediated blocks to HIV-1 replication (Boden et al., 2007). CCR5 disruption could select for CCR5-independent viruses (Taylor et al., 2008) and is not without consequence, as the CCR5Δ32 allele is a risk factor for symptomatic West Nile Virus infection (Glass et al., 2006).

hT5Cyp is a broadly acting, anti-lentiviral agent that blocks CCR5- and CXCR4-tropic HIV-1 clones and primary isolates, as well as some HIV-2, SIV, and FIV clones (See FIGS. 48, 49, 56). T5 isoforms form hetero-multimers and hT5Cyp might interfere with endogenous hT5α function (Berthoux et al., 2005a). However, no significant decrease in hT5α-mediated restriction of N-MLV, and no alteration in cell surface markers or cytokine secretion, was observed in hT5Cyp-transduced cells (See FIG. 46). hT5Cyp-resistant viruses were not detected, perhaps due to the potency of the antiviral activity and the fact that hT5Cyp blocks HIV-1 prior to reverse transcription. hT5Cyp additionally blocked a natural HIV-1 CA variant reported to be resistant to AoT5Cyp (Chatterji et al., 2005) (See FIG. 49D). These results suggest that, if hT5Cyp were utilized as anti-HIV-1 gene therapy in people, viral resistance would not emerge and host cell function would remain intact.

Figure 54:
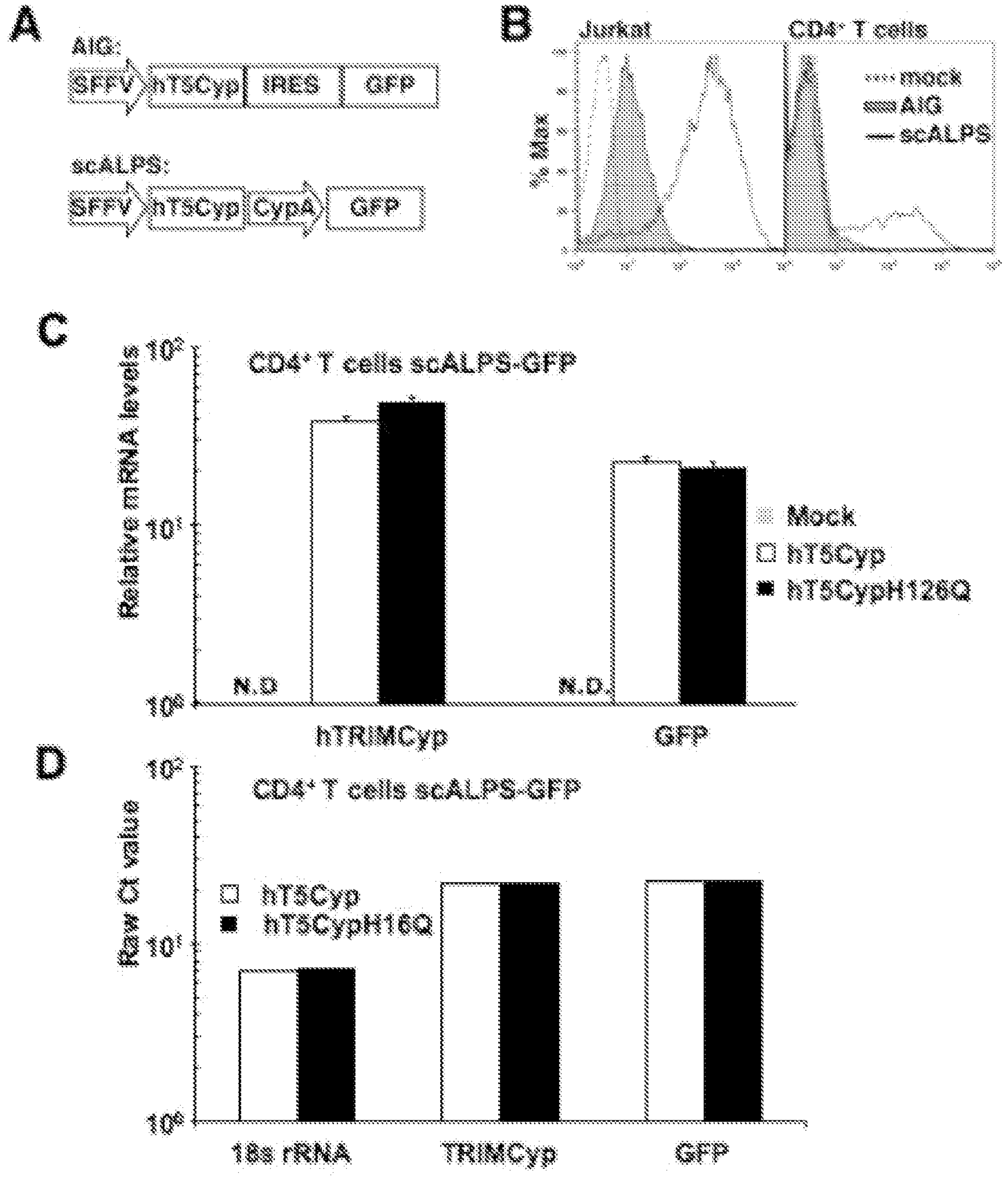
FIGS. 54A-D. (A) Design of bicistronic (AIG) and dual promoter (scALPS) lentiviral vectors. (B) GFP expression by flow cytometry 48 hrs after transduction of Jurkat T cells (left) or primary CD4$^+$ T cells (right) with the indicated vectors. (C, D) Quantitative RT-PCR for GFP and hT5Cyp wt or H126Q mRNA expression in CD4$^+$ T cells stably transduced with scAPLS vectors.

The evaluation of HIV-1 therapies is limited by a lack of adequate animal models for HIV-1 replication and pathogenesis. The $hCD4^+$-$Rag2^{-/-}\gamma_c^{-/-}$ mouse described in Example 2 is a robust model for assessing inhibition of HIV-1 infection and $CD4^+$ T cell protection by lentiviral transduction with hT5Cyp (See FIGS. 69, 70, 71). Autotransfusion of ex vivo expanded $CD4^+$ T cells is of clinical benefit to HIV-1-infected people (Levine et al., 2002). Thus, given that hT5Cyp-transduced $CD4^+$ cells can be expanded in vitro and in vivo (See FIGS. 54, 69), and that these cells exhibit a selective advantage during HIV-1 infection (See FIG. 57), an impressive effect of hT5Cyp-transduction on autologous $CD4^+$ T cell gene therapy in the clinical setting is expected. $CD34^+$ hematopoietic stem cells transduced with state-of-the-art lentiviral vectors (see FIGS. 65,66 (Amendola et al., 2005)) achieve long-term engraftment of $Rag2^{-/-}\gamma_c^{-/-}$ mice, but transgene expression in the mature $CD4^+$ T cells that develop within these animals has not yet been consistently detected. One could examine the effect of stem cell transduction with hT5Cyp on subsequent immune cell development and HIV-1 infection with a humanized mouse models currently under development (Goldstein, 2008).

Human TRIM5 and CypA sequences have been deposited in GenBank (accession numbers NM_033034 (human TRIM5alpha mRNA; FIG. 13; SEQ ID NO:1), NP_149023 (human TRIM5alpha protein; FIG. 14; SEQ ID NO:2), NM_021130 (human CypA mRNA; FIG. 15; SEQ ID NO:3) and NP_066953 (human CypA protein; FIG. 16; SEQ ID NO:4)).

The invention provides for a newly engineered nucleic acids and polynucleotides that comprise the nucleotide sequence of SEQ ID NO:1, 3, 5, 6 or 7. The encoded polypeptide is a fusion between human TRIM and cyclophilin, i.e., hTRIMCyp, which acts as an anti-HIV-1 factor.

The invention also provides for nucleic acid variants of any of SEQ ID NO: 1, 3, 5, 6 or 7 having at least about 50% identity to the SEQ ID NO, and encoding a polypeptide having both TRIM activity and cyclophilin activity. The variants may have at least about 55%, 60%, 70%, 75%, 80%, 85%, 90%, 95%, or 99% identity to the SEQ ID NO. Techniques for determining sequence identity are well known to one skilled in the art, and include, for example, analysis with a sequence comparison algorithm or FASTA version 3.0t78 using default parameters.

The invention also provides for an isolated nucleic acid which comprises consecutive nucleotides having a sequence complementary to the nucleic acids comprising the nucleotide sequence of SEQ ID NO:1, 3, 5, 6 or 7 or variants of at least about 50% identity thereof. The invention also provides for an isolated nucleic acid encoding a polypeptide comprising SEQ ID NO:4 (human Cyp A), and SEQ ID NO:2 (human TRIM5), wherein the last amino acid of SEQ ID NO:2 is alanine 331 (SEQ ID NO:5; FIG. 17), serine 309 (SEQ ID NO:6; FIG. 18), or serine 322 (SEQ ID NO:7; FIG. 19). Also provided by the invention is an isolated nucleic acid that hybridizes to a nucleic acid of the invention under conditions of high stringency, moderate stringency, or low stringency.

The invention further provides for an isolated polypeptide encoded by an isolated nucleic acid of the invention. Purified polypeptides substantially identical to the isolated polypeptide, as determined by analysis with a sequence comparison algorithm or FASTA version 3.0t78 using default parameters, are also included in the invention.

The invention also provides a human TRIM-cyclophilin fusion protein, and nucleic acids encoding such fusion proteins, where the N-terminus of human CypA (SEQ ID NO:4) is fused to the C-terminus of human TRIM5 (SEQ ID NO:5). Fusion proteins with anti-HIV-1 activity include hT5-S309-Cyp (SEQ ID NO:11), hT5-S322-Cyp (SEQ ID NO:12), hT5-A331-Cyp (SEQ ID NO:10), hT5-M284-Cyp, hT5-T369-Cyp, where the indicated amino acid is the C-terminal residue of TRIM5 (SEQ ID NO:2) to which the N-terminal amino acid (for example, residue 2 of SEQ ID NO:4) of CypA is directly attached or fused. Embodiments of the invention include a polypeptide comprising SEQ ID NO:4 and SEQ ID NO:2, or a polypeptide comprising SEQ ID NO:10, 11, or 12. The invention provides a polypeptide comprising a sequence that is at least 60%, 65%, 70%, 75%, 80%, 85%, 90%, 95%, or 99% identical to SEQ ID NO:4 and a sequence that is at least 60%, 65%, 70%, 75%, 80%, 85%, 90%, 95%, or 99% identical to SEQ ID NO:2, or a sequence that is at least 60%, 65%, 70%, 75%, 80%, 85%, 90%, 95%, or 99% identical to SEQ ID NO:10, or a sequence that is at least 60%, 65%, 70%, 75%, 80%, 85%, 90%, 95%, or 99% identical to SEQ ID NO:11, or a sequence that is at least 60%, 65%, 70%, 75%, 80%, 85%, 90%, 95%, or 99% identical to SEQ ID NO:12.

FIGS. 7A and 7C show amino acid residues depicted in red (308-311, 321-346, 366-371 and 381-393) indicating residues that comprise loops in the PRYSPRY domain that contain S309, S322 and A331. Thus fusion of CypA to any residue in these regions would be predicted to generate a hTRIM-Cyp fusion that has HIV-1 restrictive activity. Additionally, fusion of CypA at M285 generates a fusion protein that is variably restrictive, thus fusing to amino acid residues 280-290 would be predicted to have anti-HIV-1 activity. In one embodiment, the last (C-terminal) amino acid of SEQ ID NO:2, which is fused to CypA, is serine at position 309, serine at position 322, or alanine at position 331. In one embodiment, the last amino acid of SEQ ID NO:2 is any one amino acid residue from about residue 280 to about residue 435, or from about residue 280 to about residue 400, or from about residue 280 to about residue 290, or from about residue 308 to about residue 311; or from about residue 321 to about residue 346; or from about residue 366 to about residue 371; or from about residue 381 to about residue 393. In one embodiment, the last residue of SEQ ID NO:2 is residue 493, the end of the TRIM5 PRYSPRY domain, thus generating a fusion protein where a sequence encoding cyclophilin A replaces the stop codon of the PRYSPRY domain of TRIM5. In one embodiment, the last residue of SEQ ID NO:2 is 280, 281, 282, 283, 284, 285, 286, 287, 288, 289, 290, 308, 309, 310, 311, 321, 322, 323, 324, 325, 326, 327, 328, 329, 330, 331, 332, 333, 334, 335, 336, 337, 338, 339, 340, 341, 342, 343, 344, 345, 346, 366, 367, 368, 369, 370, 371, 381, 382, 383, 384, 385, 386, 387, 388, 389, 390, 391, 392, 393, or 493. The last amino acid of SEQ ID NO:2 can be fused to Cyp A (for example, at residue 2 of SEQ ID NO:4) by experimental methods known in the art and described in the Examples.

The polynucleotides provided by the invention may further comprise a sequence encoding a linker located between the TRIM sequence and the Cyp sequence. In one embodiment, the linker comprises from about 10 to about 20 amino acids. In other embodiments the linker comprises, consists of or consists essentially of from about 11 to about 20, from about 12 to about 20, from about 11 to about 24, from about 12 to about 24, 11 to about 33, from about 12 to about 33, 11 to about 43, from about 12 to about 43, 11 to about 59, from about 12 to about 59 amino acids. In other embodiments the linker comprises, consists of or consists essentially of from 11 to 20, from 12 to 20, from 11 to 24, from 12 to 24, 11 to 33, from 12 to 33, 11 to 43, from 12 to 43, 11 to 59, from 12 to 59 amino acids. In other embodiments the linker comprises, consists of or consists essentially of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 59, 71, or up to 100 amino acids. In another embodiment, the linker comprises the amino acid sequence SGGSGGSGGSGG (SEQ ID NO: 20) or a variant thereof. In one embodiment, the linker consists essentially of the amino acid sequence SGGSGGSGGSGG (SEQ ID NO: 20) or a variant thereof. In certain embodiments the linker comprises or consists of a synthetic sequence. In other embodiments the linker comprises, consists essentially of or consists of sequences from hTRIM5, for example as described herein. In certain embodiments the fusion proteins, which comprise linkers as described herein, are not naturally occurring. In certain embodiments, the fusion proteins of the invention do not encompass the naturally occurring protein AoT5Cyp.

It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., *Molecular Cloning: A Laboratory Manual*, Cold Springs Harbor Laboratory, 2nd ed., Cold Springs Harbor, N.Y. (1989).

The invention further provides for a purified antibody that specifically binds to a polypeptide of the invention or to a protein encoded by a polynucleotide of the invention. The antibody may be a polyclonal antibody, a monoclonal antibody, or a chimeric antibody. Polyclonal antibodies may be obtained by procedures which are well known to the skilled artisan, including injecting purified fusion protein into various animals and isolating the antibodies produced in the blood serum. The antibodies may be monoclonal antibodies whose method of production is well known to the art, including, for example, injecting purified fusion protein into a mouse, isolating the spleen cells producing the anti-serum, fusing the cells with tumor cells to form hybridomas and screening the hybridomas.

Methods for producing the polypeptides of the invention include introducing a nucleic acid encoding the polypeptide into a host cell under conditions that permit expression of the polypeptide by the host cell, and recovering the peptide. A nucleic acid may be introduced into a host cell, for example, with a replicable nucleic acid vector, such as a viral vector, a retroviral vector, a lentiviral vector, an adenovirus vector, or an adeno-associated viral (AAV) vector. Provided for in the invention is a replicable nucleic acid vector comprising a nucleic acid of the invention, and a host organism comprising the replicable nucleic acid vector. Suitable host organisms include a prokaryote, a eukaryote, or a fungus.

The invention provides for a host cell comprising the recombinant expression construct encoding the human TRIMCyp fusion protein as described herein. In another embodiment of the invention, the host cell is stably transformed with the recombinant expression construct described herein. In one embodiment the host cell is a bone marrow cell of a subject. In another embodiment of the invention, the cell is an immortalized cell. In another embodiment, the cell is a stem cell, a blood cell, a bone marrow cell or an immune cell. In one embodiment, the cell is a T cell or a B cell. In one embodiment, the cell is a CD4+ T cell.

A nucleic acid, a polypeptide, host cell or a nucleic acid vector of the invention may be used to prepare pharmaceutical compositions of the invention. Methods for preparing a pharmaceutical composition include admixing a polypeptide of the invention or a fragment thereof.

The pharmaceutical composition further comprises a pharmaceutically acceptable carrier. The carrier comprises a diluent. The carrier may also comprise an appropriate adjuvant, a herpes virus, an adenovirus, a liposome, a microencapsule, a polymer encapsulated cell or a retroviral vector. The pharmaceutically acceptable carrier may be an aerosol, intravenous, oral or topical carrier.

A nucleic acid, a polypeptide, a nucleic acid vector, or a pharmaceutical composition of the invention is suitable for treating a subject suffering from a disease or condition, such as a retroviral infection. In one embodiment, the invention provides for methods of preventing retroviral infection in a subject, or for treating a subject with a retroviral infection, by administering to the subject a pharmaceutical composition of the invention. In another embodiment, the invention provides for methods of reducing viral burden, or load, in a subject infected by a virus by administration of a nucleic acid, a polypeptide, or a nucleic acid vector of the invention, to the subject.

The invention also provides for a peptidomimetic comprising an amino acid sequence substantially identical to the amino acid sequence of a polypeptide of the invention. As used herein, a "peptidomimetic" refers to a chemical compound that mimics the biological activity of a peptide. In one embodiment of the invention, a peptidomimetic comprises TRIM function and cyclophilin function.

A peptidomimetic, a nucleic acid, or a polypeptide of the invention is suitable for preparing a therapeutic composition of the invention. The therapeutic composition further comprises a therapeutically acceptable carrier. The carrier may comprise a vector, a liposome, or a viral vector.

Provided by the invention is a topical composition for prevention or treatment of a viral infection which comprises a nucleic acid or a polypeptide of the invention. The topical composition further comprises a topical carrier, and may be used on the skin, in the vagina, in the nose, in the mouth, or on any skin or mucosal surface.

The present invention encompasses use of virus based vectors for transformation or transfection of the TRIMCyp coding region into a cell. In the case of eukaryotic cells, retrovirus, adenovirus or lentiviral based vectors are preferred. Such vectors contain all or a part of a viral genome, such as long term repeats ("LTRs"), promoters (e.g., CMV promoters, SV40 promoter, RSV promoter), enhancers, and other sequences known in the art. When the host cell is a prokaryote, bacterial viruses or phages may be used. Exemplary of such vectors are vectors based upon, e.g., lambda phage. The vector may comprise elements of more than one virus. The resulting vectors are transfected or transformed into a host cell, which may be eukaryotic or prokaryotic. The gene transfer vector may additionally comprise a gene encoding a marker or reporter molecule to more easily trace expression of the vector. The gene transfer vector may contain more than one gene encoding the same or different foreign polypeptides or RNAs. The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

Adenoviruses can be used for transformation or transfection of the nucleic acids of the present invention into cells. Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, in: Adenovirus DNA, Doerfler, Ed., Martinus Nijhoff Publishing, Boston, pp. 408-441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.). Methods for producing adenovirus vectors are well-known in the art (Berkner et al, Nucleic Acids Res., 11:6003-6020 (1983); van Doren et al, Mol. Cell. Biol., 4:1653-1656 (1984); Ghosh-Choudhury et al, Biochem. Biophys. Res. Commun., 147:964-973 (1987); McGrory et al, Virol., 163:614-617 (1988); and Gluzman et al, in: Eurkaryotic Viral Vectors, Ed. Gluzman, Y. pages 187-192, Cold Spring Harbor Laboratory (1982)). Vectors which can be used in the methods of the present invention include adenoviruses, retroviral vectors, and adeno-associated viral (AAV) vectors. Other virus vectors that may be used for gene transfer into cells include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses. Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216-4220; Rungold et al. (1981) J. Mol. and Appl. Genet. 1:165-175.

A novel vector is provided which can be used for expression of a human T5Cyp, for example, in primary T cells. The vector (SEQ ID NO:8; FIG. 20), scALPS, was engineered using two promoters, one from the SFFV LTR and the other from the hCypA gene. As described in Example 2, $CD4^+$ T cells were transduced with scALPS encoding either hT5Cyp (SEQ ID NO:9; FIG. 21). The novel vector compares favorably to previously published dual-promoter lentiviral gene-delivery systems that fail to lead to efficient reporter gene expression in primary T cells. Indeed the engineering of the novel vector was an advance that enabled direct assessment of T5Cyp-mediated inhibition of HIV-1 spreading infection in primary human cells (see Example 2).

The invention provides for methods of gene therapy of subjects for the prevention or treatment of viral infection comprising administering to the subject an effective amount of a pharmaceutical composition comprising, or consisting essentially of, a polynucleotide encoding a fusion protein having cyclophilin fused to a TRIM polypeptide, wherein the subject's cells takes up the polynucleotide or polypeptide such that the fusion protein is present in cells of the subject, so as to prevent or treat viral infection in the subject. In one embodiment, the treated subject has a reduced viral load, or burden. In one embodiment of this invention, the administering is via an autologous bone marrow transplant to the subject, where the polynucleotides coding for the fusion protein is transfected into the bone marrow cells ex vivo and then replaced into the subject. In this case, the bone marrow cells returned to the subject will have taken up (been transduced) the nucleic acid encoding the fusion protein.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO 90/11092; and Wolff et al., (1990) Science 247:1465-1468). Liposome-mediated gene transfer can also be accomplished using known methods. See, e.g., Hazinski et al., (1991) Am. J. Respir. Cell Mol. Biol. 4:206-209; Brigham et al. (1989) Am. J. Med. Sci. 298:278-281; Canonico et al. (1991) Clin. Res. 39:219 A; and Nabel et al. (1990) Science 249:1285-1288. Targeting agents, such as antibodies directed against surface antigens expressed on specific cell types, can be covalently conjugated to the liposomal surface so that the nucleic acid can be delivered to specific tissues and cells for local administration.

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Serial No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9-10 days before reinfusion (Culver et al., 1991). As the length of time the target cells are left in culture increases, the possibility of contamination also increases, therefore a shorter protocol would be more beneficial.

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stpyridis J. C., et al., Construction of transferrin-coated liposomes for in vivo transport of exogenous DNA to bone marrow erythroblasts in rabbits. Exp Cell Res 1986; 164:568-572).

A vesicle can be constructed in such a way that its membrane will fuse with the outer membrane of a target cell. The vector of the invention in vesicles can home into the cancer cells. The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation. Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, and allows multiple administrations simultaneously in several different sites or the same site using the same viral suspension. Multiple injections may consist of a mixture of therapeutic genes.

Viral infections that may be treated or prevented by introducing a human TRIM-Cyp fusion polypeptide into the subject's cells include an HIV infection, a human T-cell lymphotrophic virus (HTLV) infection, a pox virus infection, a retrovirus infection, a malaria infection, a hepatitis C virus infection, a hepatitis B virus infection, or a vaccinia virus infection.

The present invention provides for a human TRIMCyp fusion protein which combines a specific binding activity (specific for HIV-1 capsid protein) and a killing activity (TRIM activity, like ubiquitin). In this way, the HIV-1 is degraded in the cell.

The invention provides methods for treating HIV infection or preventing HIV infection of a subject by introducing a human TRIM-Cyp fusion polypeptide into the subject's cells. The human TRIM-Cyp polypeptide binds to a capsid protein of the HIV and subsequently degrades the HIV, thereby treating or preventing the HIV infection in the subject. Resistance to HIV may also be imparted to a subject or to the cells of a subject by administering to the cells of the subject a nucleic acid, a polypeptide, or a nucleic acid vector of the invention.

Embodiments of the invention are illustrated in the Examples that follow. These sections are set forth to aid in an understanding of the invention but are not intended to, and should not be construed to, limit in any way the invention as set forth in the claims which follow thereafter.

EXAMPLES

Example 1

Design and In Vitro Testing of Human TRIM5Cyp Fusion Proteins

The Antiviral Response and Restriction Factors

Mammalian cells have engaged in a host-pathogen arms race for millions of years and developed both broad and specific defense mechanisms. The most notable broad-range response in higher organisms is the type I interferon (IFN) response (Isaacs and Lindenmann, 1957). Type I IFNs are ubiquitous and most cells respond via the IFN alpha receptor, leading to both a broad antiviral state through effectors molecules such as PKR, eIF2a kinases, and RNAseL, as well as to a specific antiviral state through the upregulation of specialized antiviral restriction factors (Pichlmair and Reis e Sousa, 2007). The IFN-induced antiviral state is characterized by translational shutdown, RNA degradation and de-amination with the potential for causing apoptosis of the responding cell. IFN-dependent effectors are not constitutively active and their expression is therefore tightly controlled (Samuel, 2001). To this end, cells distinguish between self and non-self through pattern recognition receptors (PRRs). These include Toll-like receptors (TLRs) (Takeda et al., 2003) located on the cell surface and within endosomes, and cytosolic PRRs which detect double-stranded DNA (e.g. DNA-dependent activator of IRFs; DAI, (Takaoka et al., 2007)), double stranded and 5' triphosphate single stranded RNA (e.g. melanoma differentiation factor 5 (MDA-5) and retinoic acid inducible gene (RIG-I)) (Yoneyama et al., 2005), and unusual protein structures (e.g. TRIM5 family members recognizing in-coming retroviral capsid (CA) (Sayah et al., 2004; Stremlau et al., 2004)).

Figure 40:
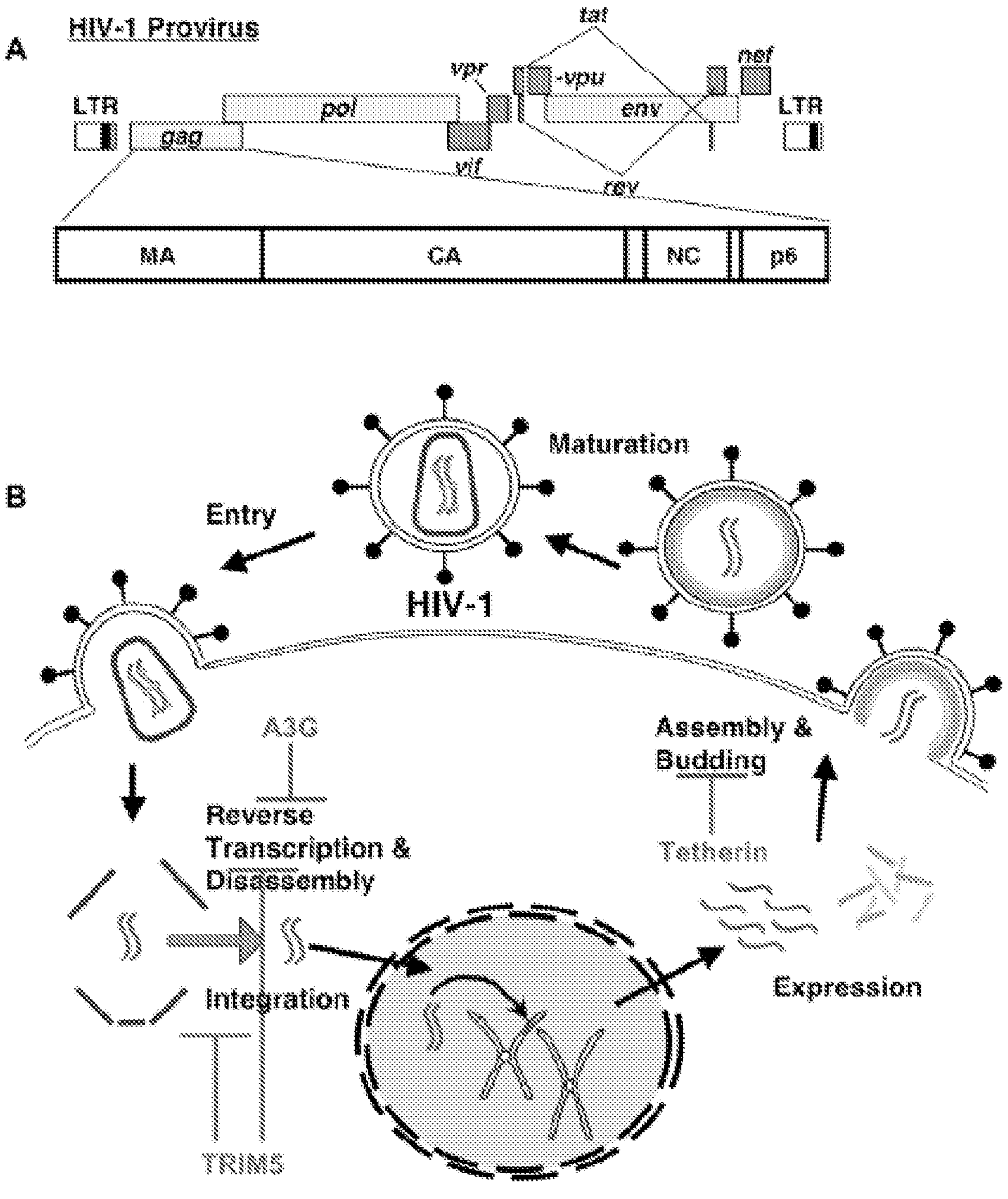
FIG. 40A-40B. (A.) Organization of HIV-1 provirus genome (top panel), Gag polyprotein components (bottom panel). MA=matrix; CA=capsid; NC=nucleocapsid. (B.) Simplified schematic of retroviral life cycle and site of action of HIV-1 restriction factors.

A virus not cleared by either the innate or adaptive immune response is the human immunodeficiency virus (HIV). HIV infects immune cells leading to fatal immune suppression (AIDS) in infected patients (Barre-Sinoussi et al., 1983; Popovic et al., 1984), with HIV-1 being responsible for the majority of worldwide lethalities each year while the HIV-2 epidemic is concentrated in western Africa (Grant and De Cock, 2001). Zoonotic transmission of the chimpanzee simian immunodeficiency virus ($SIV_{cpz}$) to humans is the likely cause of the HIV-1 pandemic (Keele et al., 2006). Like its relative, SIV, HIV is a complex retrovirus. In addition to the genes encoded by gag, pol, and env (FIG. 40A) common to all retroviruses, HIV-1 possesses several accessory genes: vif, vpr, vpu, tat, rev, and nef (FIG. 40A) (Muesing et al., 1985). The HIV life cycle begins with HIV binding to its receptor CD4 and its co-receptor CCR5 or CXCR4 via its envelope glycoprotein complex gp120 and gp41 encoded by env (Feng et al., 1996; Maddon et al., 1986). Recently, the mucosal homing receptor for peripheral T cells, a4b7 integrin, has been identified as another receptor for CCR5-topic HIV-1 (Arthos et al., 2008). Following receptor and co-receptor binding, the viral envelope fuses with the cellular envelope and delivers the virion core (composed of a capsid (CA) encoded by gag protecting the viral double-stranded genome and associated proteins) to the cytoplasm (FIG. 40A, B). There, the virion core uncoats and the RNA genome is reverse-transcribed by the reverse transcriptase (RT) encoded by pol into cDNA. Viral cDNA present in a pre-integration complex (PIC) is imported into the nucleus and ligated into the host chromosomal DNA with the help of integrase (IN) encoded by pol. This renders the virus a stable heritable element in the infected cell. The viral promoter (the 5' long terminal repeat; LTR) then directs transcription of viral proteins and genomic RNA. Together these assemble into progeny virions in the cytoplasm that bud from the infected cell. Upon viral protease-mediated maturation, progeny virus is capable of infecting target cells in a fresh infection cycle (FIG. 40B) (Ho and Bieniasz, 2008).

Clearly, such a complex life-cycle is dependent on intricate interactions with host cells. The most obvious determinant of retroviral tropism is lack of host co-factors essential for infection and replication (HIV-1 dependency factors, HDFs). As discussed in Example 3, rodents, for instance lack the receptors required for HIV-1 entry. More than 250 candidate HDFs have been identified or confirmed recently in a large-scale functional siRNA-based genomic screen (Brass et al., 2008). More recently, a similar screen identifying 213 likely HDFs was combined with the 11 HIV-1 genes and data from the human interactome database to create a human-pathogen biochemical network (Konig et al., 2008). Aside from lack of HDFs, natural, dominantly-acting, restriction factors (FIG. 40B) determine retroviral tropism and protect the host from the deleterious effects of retroviral replication: the alteration of gene expression, the transduction of toxic genes, and the risk of insertional mutagenesis (Luban, 2007). Three HIV-1 restriction factors (APOBEC3G, tetherin, and TRIM5) will be described in further detail and one served as a model to design a human equivalent with therapeutic potential.

APOBEC3G (A3G)

Several observations led to the identification of APOBEC3G (A3G; apolipoprotein B mRNA-editing catalytic polypeptide) as an HIV-1 restriction factor. For one, production of infectious HIV-1 virions was dependent on the accessory protein Vif in a cell-type specific manner (Fisher et al., 1987; Strebel et al., 1987). Also, when fusion of permissive and non-permissive cells resulted in a heterokaryon non-permissive for vif-deleted HIV-1(Madani and Kabat, 1998; Simon et al., 1998a); the search began for a dominant restriction factor counteracted by Vif. This factor was isolated by subtractive cloning using the nearly isogenic cell lines CEM-S(permissive) and CEM-SS (non-permissive) and identified as the cytidine deaminase A3G (Sheehy et al., 2002). Expression of A3G correlated with restrictive phenotype. Moreover, expression of A3G into permissive cells rendered them non-permissive and enforced Vif-dependency (Sheehy et al., 2002). A3G belongs to a large family of cytidine deaminases with a conserved zinc-coordinating catalytic motif (H-x-E-$x_{23-28}$-P-C-$x_{2-4}$-C) (SEQ ID NO: 128) (Jarmuz et al., 2002), which bind to nucleic acid and hydrolytically deaminate (deoxy)-cytidines at the C4 position into (deoxy)-uridines (Chiu and Greene, 2008; Wolf and Goff, 2008). Two other famous members of the APOBEC family are APOBEC1 (the prototypical member) and AID. APOBEC1 is required to deaminate C6666 in the extensive apolipoprotein B mRNA. This leads to an in-frame stop codon and, upon translation, a truncated protein with cellular functions distinct from the full-length protein (Teng et al., 1993). AID (activation-induced cytidine deaminase) is expressed in germinal center B cells and is required for B cell maturation events such as class-switch recombination and somatic hypermutation (Goff, 2004; Muramatsu et al., 2000).

A3G selectively deaminates deoxycytidines into deoxyuridines on single-stranded (ss) DNA (Iwatani et al., 2006; Yu et al., 2004); for HIV-1 this is the minus strand of the viral genome. Other viruses that go through ssDNA intermediates during genome replication can also be attacked by A3G; examples include other retroviruses like MLV, SIV, EAIV, foamy viruses, and HTLV (Delebecque et al., 2006; Harris et al., 2003; Mangeat et al., 2003; Sasada et al., 2005; Strebel, 2005), but also hepatitis B where A3G interferes with packaging of the pregenomic RNA into particles (Turelli et al., 2004a). In the case of HIV, minus strand deamination has two major effects: DNA base-repair enzymes degrade the destabilized minus strand resulting in reduction of nascent cDNA production (Schrofelbauer et al., 2005; Yang et al., 2007); the cDNA surviving this first attack is fatally hypermutated, leading to non-infectious progeny (Mangeat et al., 2003; Zhang et al., 2003).

A3G is a cytoplasmic protein and despite its selective ssDNA deamination activity, it also binds to single- and double-stranded DNA and RNA complexes, DNA:RNA hybrids, and thus to viral RNA (Iwatani et al., 2006; Yu et al., 2004). Consequently, A3G is packaged into nascent virions in the donor cell as part of a RNA-protein complex with the NC-portion of the Gag polyprotein awaiting attack during the next reverse transcription cycle in new target cells (Iwatani et al., 2006; Soros et al., 2007; Zennou et al., 2004). Vif binds to A3G and counteracts its antiviral effect by inhibiting its encapsidation into virions (Kao et al., 2003; Opi et al., 2007), potentially interfering with A3G translation (Stopak et al., 2003), and by targeting A3G for proteasomal degradation via the ElonginB/C, Cullin5, and Ring Box 1 E3 ubiquitin ligase complex (Goila-Gaur and Strebel, 2008; Sheehy et al., 2003; Yu et al., 2003). Vif inhibits A3G in a species-specific manner with narrow range limited to A3Gs from closely related primates (Mariani et al., 2003; Simon et al., 1998b; Simon et al., 1995). Mapping the Vif-A3G interaction identified one critical amino acid at position 128 in A3G required for the interaction and acting as the viral tropism determinant (Bogerd et al., 2004; Schrofelbauer et al., 2004).

Aside from driving species-specific retroviral tropism, A3G also determines cell-specific tropism in a permissive organism through a distinct anti-HIV-1 activity. A3G can recruit nascent, viral mRNA into intracellular low molecular mass (LMM) complexes; an effect that is not counteracted by Vif. This activity partly explains why monocytes and naïve or resting T cells are non-permissive for HIV-1 infection, while mitogen-activated $CD4^+$ T cells and macrophages, in which A3G is predominantly found in catalytically inactive high molecular weight (HMM) complexes, are permissive (Chiu et al., 2005; Stopak et al., 2007). siRNA-based knockdown of LMM hA3G in non-permissive T cells renders them permissive (Chiu et al., 2005).

Cells of the immune system are exquisitely sensitive to outside cues expressed by cytokines. Upon stimulation with IL-2, -7, and 15, A3G shifts from the active LMM to the inactive HMM complexes, rendering resting T cells permissive for HIV-1 infection after cytokine priming (Stopak et al., 2007; Unutmaz et al., 1999). In contrast, type I IFN release during DC-maturation leads to an increase in A3G expression, with A3G localization to restrictive LMM complexes and loss of HIV-1 permissivity in mature DCs (Stopak et al., 2007). As seen with APOBEC1, expression level and intracellular localization may be of maximal importance for orchestrating the different aspects of A3G. Intriguingly, upon HIV-1 infection, Pin-1, a petidyl-prolyl isomerase, has been shown to directly associate with A3G and reduce both its expression levels and its incorporation into virions in a Vif-independent manner (Watashi et al., 2008).

The host-retrovirus interactions observed in the lab now are the result of millions of years of co-evolution. The A3 gene cluster has been undergoing positive selection (Sawyer et al., 2004) long before the birth HIV-1 like viruses. Most likely, the force behind A3G-selection and evolution were ancient retroviruses. Their fossils now make up nearly 10% percent of our genomes as retroelements: endogenous retroviruses or non-LTR retrotransposons (Chiu and Greene, 2008; Kazazian, 2004). These are mobile DNA sequences that are characterized by the ability to insert into the genome of host cells and replicate first by transcription and then reverse transcription. The nascent cDNA then inserts itself back into the genome at novel locations (Chiu and Greene, 2008; Kazazian, 2004). Mobilization of retroelements is associated with the obvious risk of insertional mutagenesis, putting strong evolutionary pressure on the host to develop defenses. Recently, accumulation of extragenomic retroelement DNA due to disruption of the DNA nuclease Trex1, has been shown to increase the risk of fatal autoimmunity in mice (Stetson et al., 2008).

Indeed, both mouse and human A3 have been shown to inhibit retrotransposition of the murine retroelements MusD and IAP (intracisternal A particle) both by reducing the overall number of retrotransposition events as well as by editing inserted cDNA (Esnault et al., 2005). While replication-competent human endogenous retroviruses have not been derived to date, a reconstituted ancestral human retrovirus based on fossil records of HERV-K-family proviruses in the human genome was efficiently restricted by A3F (Lee and Bieniasz, 2007). Furthermore, analysis of the mutational footprint in two other HERV-K family members fixed in the human genome indicates that they have undergone A3G-mediated hypermutation (Lee et al., 2008). While A3G does not affect the retrotransposition of LINE1 (L1) retroelement (Turelli et al., 2004b), it strongly inhibits the retrotransposition of the non-autonomous L1-dependent Alu retroelements (Chiu et al., 2006). Alu inhibition does not depend on A3G catalytic activity. A3G sequesters Alu RNA in cytoplasmic HMM A3G-containing complexes and thus prohibits access to the nuclear retrotransposition machinery provided by L1 (Chiu et al., 2006). Unlike A3G, other A3 family members have access to the nucleus and there block L1 retrotransposition (Chiu and Greene, 2008).

Ultimately restriction factors are innate immune-system effectors involved in complex and finely-tuned, specific responses to retroviral attack. Indeed such an intriguing orchestration of the innate immune system, A3G, and the adaptive immune system was recently reported. Mouse A3 was identified as the susceptibility determinant encoded by Rfv3 (Recovery from friend virus (FV) 3), an autosomal genetic locus known to regulate retroviral neutralizing antibody responses and viremia (Santiago et al., 2008). Genetic inactivation of mA3 in FV-resistant mice was linked to significantly enhanced viremia, reduced neutralizing antibody titers, and increased mortality. Furthermore, FV-susceptible strains showed alternative splicing of the mA3 RNA leading to excision of exon 2 correlating with reduced antiviral activity against FV in vitro (Santiago et al., 2008). While acting as a FV restriction factor, functional mA3 leads to reduced viremia in vivo and enhances production of neutralizing antibodies—effectors of the adaptive immune system—essential for viral control in vivo (Santiago et al., 2008).

Tetherin

In a success story reminiscent to that of A3G, Tetherin was identified based on the differential Vpu requirement for efficient release of HIV-1 particles from certain cell lines (Gottlinger et al., 1993; Klimkait et al., 1990; Neil et al., 2008; Strebel et al., 1989; Terwilliger et al., 1989). When HeLa cells (Vpu-dependent phenotype) were fused with COS-7 cells (Vpu-independent phenotype) the resulting heterokaryon had a Vpu-dependent phenotype. This experiment pointed to Vpu as a factor protecting HIV-1 from a dominant retroviral restriction factor (Geraghty et al., 1994; Neil et al., 2006; Varthakavi et al., 2003). In cells with a Vpu-dependent phenotype, vpu-deleted HIV-1 virions fail to be released from infected cells. Instead, they accumulate at the cell surface from where they are subsequently internalized to endosomes (Neil et al., 2006). The particles themselves are fully mature and infectious upon proteolytic release from the cell surface (Neil et al., 2006; Neil et al., 2007), prompting the search for a protein "tether" at the plasma membrane that inhibits particle release in the absence of Vpu (Neil et al., 2008; Nomaguchi et al., 2008). CD317, now renamed tetherin, has been recently shown to fulfill all the requirements for the dominant, particle-tethering restriction factor counteracted by Vpu (Neil et al., 2008; Van Damme et al., 2008).

Tetherin is highly expressed in cell lines with the Vpu-dependent phenotype as well as strongly induced in cells that acquire this phenotype upon IFNα treatment. Overexpression of tetherin in cells with low endogenous levels and no Vpu-dependency, enforced a Vpu-requirement for HIV-1 particle release (Neil et al., 2008). Conversely, reducing endogenous mRNA levels via siRNA-targeting in cells with high endogenous levels of tetherin abolishes the Vpu-requirement for HIV-1 particle release (Neil et al., 2008; Van Damme et al., 2008). Moreover, in the absence of Vpu, Gag and tetherin co-localize both at the plasma membrane and in endosomes. When present, Vpu itself co-localizes with tetherin, an association that is required for efficient HIV-1 particle release (Neil et al., 2008; Van Damme et al., 2008). How Vpu interferes with tetherin-mediated HIV-1 restriction is unclear. One group did not observe a change in intracellular tetherin levels in the presence of Vpu, indicating that it sterically hinders a Gag:tetherin association, rather than causing a degradation of tetherin reminiscent of the effects of Vpu on CD4 (Neil et al., 2008). Another group showed that the KSHV protein K5 functions as an ubiquitin ligase and reduces levels of tetherin. They observed similar drops in tetherin concentrations in the presence of Vpu (Bartee et al., 2006; Gottlinger, 2008).

Tetherin has an N-terminal cytoplasmic domain, followed by a single transmembrane domain, a cytoplasmic coiled-coil domain and a C-terminal GPI-anchor implying that it directly traps the budding virions via the GPI-anchor (Gottlinger, 2008; Neil et al., 2006). Since tetherin tethers a budding membrane to the plasma membrane, it is a potent antiviral of fairly broad specificity targeting enveloped viruses (e.g. Ebola, HIV-1, MLV) that is strongly upregulated upon IFNα treatment (Neil et al., 2008; Van Damme et al., 2008).

Calcium modulating cyclophilin ligand (CAML) was identified as a Vpu interaction partner in a yeast two hybrid screen (Varthakavi et al., 2008). The interaction was confirmed by co-immunoprecipitation of endogenous CAML with Vpu in HIV-1 infected cells. Vpu and CAML were further seen to colocalize by immunofluorescence in HeLa cells. Like tetherin, expression of CAML in cells permissive to vpu-deleted HIV-1 enforced Vpu dependence. On the other hand, RNAi-mediated disruption of CAML expression in cells with a Vpu-dependent phenotype rescued particle release of vpu-deleted HIV-1. Like tetherin, CAML causes accumulation of mature particles at the plasma membrane. Given the strikingly similar Vpu-sensitive restriction observed with both CAML and tetherin, CAML may represent a required co-factor for tetherin-mediated HIV-1 restriction (Varthakavi et al., 2008).

FV1, LV1 and Cyp A

The field of retroviral restriction factors began, in 1957, with Charlotte Friend's description of a leukemia-like illness in mice whose causative agent was found to be the Friend murine leukemia virus (MLV) (Friend, 1957). Interestingly, two strains of mice showed different susceptibility (Friend, 1957; Lilly, 1967) to the etiologic agent, an observation upon which the on-going search for the host resistance genetic loci was based. The first such genetic locus recognized was named Fv1 (Friend virus susceptibility 1). The inbred mouse strains NIH Swiss and Balb-c showed different susceptibilities to MLV isolates; one MLV isolate capable of infecting NIH Swiss but not Balb-c mice or cells derived from the mice was termed N-MLV and the predicted resistance locus in NIH Swiss mice $Fv1^b$; while a strain infecting Balb-c but not NIH Swiss mice and cells derived from them was termed B-MLV and the resistance locus in Balb-c mice $Fv1^n$ (Hartley et al., 1970; Pincus et al., 1971b). The offspring of NIH Swiss and Balb-c crosses, while susceptible to NB-tropic viruses, were not susceptible to either N- or B-MLV, implying that each parent contributed a dominant restriction factor to offspring (Pincus et al., 1971a).

A series of experiments demonstrated CA-specificity of Fv1. MLV containing CA from both N and B-tropic strains are restricted by both $FV1^n$ and $Fv1^b$ (Rein et al., 1976). Furthermore, a single amino acid at position 110 of CA is sufficient to modulate N- or B-tropsim of MLV (Kozak and Chakraborti, 1996) showing the exquisite specificity of restriction. Another essential concept derived from the studies of Fv1 is that of saturability: restriction of MLV by Fv1 can be overcome either by high multiplicities of infection or by pre-treatment of cells with restricted virions or virus-like particles (protease-matured virions without genome) derived from restricted viruses (Bassin et al., 1978; Boone et al., 1990; Pincus et al., 1975). This shows that the restriction factor can be "titered out" and thus saturated. Expression of CA-protein alone in cells was unable to saturate restriction. Saturation of Fv1-mediated restriction consequently requires maintenance of the three-dimensional CA-structure. This points to a direct association of the incoming virion CA with the restriction machinery (Duran-Troise et al., 1981). After years of intense effort Fv1 was cloned by a positional cloning strategy and found to encode a Gag protein closely related to those found in the HERV-L and Mu-ERV-L endogenous retroviruses (Benit et al., 1997; Best et al., 1996; Qi et al., 1998).

Expression of the appropriate Fv1 protein in otherwise susceptible cells is sufficient to block the corresponding MLV-strain (Bishop et al., 2001). Fv1 blocks MLV after entry into the cell and before integration of the viral cDNA into the host genome. Since isolation of the pre-integration complex (PIC) from restrictive but infected cells contains integration-competent virus when assayed in vitro, the restriction step can be narrowed down to a point after reverse transcription and before nuclear translocation of the PIC (Pryciak and Varmus, 1992). This type of restriction is termed "post-entry" restriction to differentiate it from the earlier "entry" restriction or later inhibition following integration into the host-genome, such as suppression of viral gene expression or particle release (Jolicoeur and Baltimore, 1976). Thus, Fv1 serves as the prototypical post-entry retroviral restriction factor and fulfills the classical requirements of this class of retroviral inhibitors: it provides a genetic host-determinant for retroviral susceptibility, it is CA-specific, it is dominant, and it is saturable.

TRIM5α (T5) and TRIMCyp

Human and monkey cells have an activity to block N-MLV similar to the $Fv1^b$-encoded activity termed ref1 activity (Towers et al., 2000). Ref-1 activity causes post-entry restriction at the level of reverse transcription (albeit at a slightly earlier time-point than Fv-1), is CA-dependent, saturable, and dominant (Besnier et al., 2003; Towers et al., 2000). Ref1 activity, however, had to be due to a factor distinct from Fv1, since the human genome does not encode the Fv1 locus (Best et al., 1996). Finally, cells from both new world and old world monkeys exhibit a potent post-entry block to HIV-1 replication (Hofmann et al., 1999); which has hampered efforts of creating an adequate animal model for HIV-1. This restriction activity, termed Lv-1, shares striking similarities with Fv1 and Ref-1 restriction, blocking HIV-1 (but not SIVs) at the time of reverse transcription (Besnier et al., 2002; Cowan et al., 2002; Himathongkham and Luciw, 1996; Munk et al., 2002). Analysis of SIV-HIV-1 chimeras showed that viral Lv1 susceptibility determinates (as for Fv1) were found in CA. (Cowan et al., 2002; Kootstra et al., 2003; Owens et al., 2003). Like with Fv1, restriction was saturable (Besnier et al., 2002; Cowan et al., 2002) and cell-fusion experiments demonstrated that restriction was due to a dominant factor (Cowan et al., 2002; Munk et al., 2002).

Cells from the new world owl monkey (*Aotus* ss) and the old-world rhesus macaques *Macacca mulatta*) showed an especially strong HIV-1 restriction and were used in independent screens to clone the factors responsible for Lv1 activity (Besnier et al., 2002; Hofmann et al., 1999). The factor responsible for Lv1 activity in rhesus macaques was cloned by introduction of a rhesus macaque cDNA library into HIV-1 susceptible HeLa cells. Subsequent screening for HIV-1-resistant cells using HIV-1 GFP vectors led to the cloning of rhesus macaque TRIM5α (RhT5α) as the factor responsible for Lv1 activity in rhesus macaque cells (Stremlau et al., 2004). Further investigations demonstrated that both Ref1 and Lv-1 activity were encoded by different orthologs of primate T5α (Hatziioannou et al., 2004; Keckesova et al., 2004; Perron et al., 2004; Yap et al., 2004).

The cloning of Lv1 from new world owl monkey cells was based on a different strategy involving cyclophilin A (CypA). Although much remains to be elucidated about CypA, it is functionally a peptidyl-prolyl isomerase (PPiase) which catalyses the rate-limiting cis-trans interconversion of peptide bonds N-terminal to proline (Fischer et al., 1984; Liu et al., 1991; Schmid, 1995). CypA is known for its interaction with cyclosporine (CsA), an immunosuppressive agent used to prevent allograft rejection, with which it forms a complex at subnanomolar affinity. This complex inhibits T cell function by binding to the serine/threonine phosphatase calcineurin and blocking downstream signaling events (Handschumacher et al., 1984; Liu et al., 1991). In one of the first yeast two-hybrid screens designed to isolate CA-specific retroviral restriction factors like Fv-1, CypA was found to bind to HIV-1 CA affecting HIV-1 replication and infectivity (Braaten and Luban, 2001; Franke et al., 1994; Luban et al., 1993). Furthermore, CypA has a paradoxical effect on HIV-1 replication in human and non-human primate cells.

CypA is incorporated into HIV-1 virions and binds to CA via a hydrophobic pocket associating with glycine 89 and proline 90 in the conserved cyclophilin-binding loop of CA, which can serve as the catalytic substrate for CypA (Bosco et al., 2002; Braaten et al., 1997; Franke et al., 1994). Disruption of the CypA:CA interaction through genetic (mutations in CypA or CA) or pharmacologic (uses of competitive inhibitors like CsA) means inhibits viral replication in human cells at the stage of viral cDNA synthesis; the same stage as Ref1 and Lv1 activity leading to viral escape mutants in serial passage of HIV-1 in the presence of CsA (Braaten et al., 1996; Braaten and Luban, 2001; Dorfman and Gottlinger, 1996; Franke and Luban, 1996). Furthermore, it is neither the producer cell nor the virion-associated CypA but the target cell CypA that is responsible for this effect, again indicating an involvement of CypA early in the viral life cycle (Sokolskaja et al., 2004). Stunningly, exactly the opposite effect is observed in owl monkey cells.

In non-permissive owl monkey cells the disruption of the CA-CypA interaction increases HIV-1 titers over 100-fold (Towers et al., 2003). This observation together with the intriguing relationship of CypA, CA-binding, and HIV-1 tropism ultimately led to identification of the factor conferring Lv-1 activity to Owl monkey cells: a TRIM5-Cyp fusion protein (AoT5Cyp) (Sayah et al., 2004). It was noted, as before, that reducing the levels of CypA expression in Owl monkey cells by siRNA increased HIV-1 titers. Re-introduction of non-targetable CypA, however, did not restore the restrictive phenotype. This sparked the search for variant CypA mRNA sequences that could explain this phenotype (Sayah et al., 2004). Another group cloned the same factor by searching for owl monkey genes homologous to RhT5α (Nisole et al., 2004). Like RhT5α, AoT5Cyp is a member of the T5 family of tripartite motif proteins. In AoT5Cyp, however, the C-terminal PRYSPRY domain is replaced by the CA-binding protein CypA (FIG. 1-2A); a fusion resulting from the retrotransposition of the entire owl monkey CypA cDNA into the owl monkey T5 locus (Sayah et al., 2004).

Mechanism of T5-Mediated Retroviral Restriction

Structure and Tropism

RhT5α as well as AoT5Cyp are both members of the TRIM (TRIpartite Motif) protein family. This large (over 68 members) and disparate family of proteins includes PML (TRIM19), TRIM1, TRIM28, TRIM21, and TRIM22, which all have unrelated antiviral activities against a broad range of viruses (Nisole et al., 2005; Yap et al., 2006). TRIM28, for instance, acts as a primer binding site-specific transcriptional repressor inhibiting MLV replication in ES and EC cells (Wolf et al., 2007). TRIM22 blocks HIV-1 LTR-driven transcription (Tissot and Mechti, 1995). TRIM1, on the other hand, exhibits a moderate post-entry restriction of N-MLV at a step before reverse transcription, reminiscent of the more potent T5 (Zhang et al., 2006). Over 20 TRIM family members with antiretroviral activities have recently been identified in a comprehensive functional screen of 55 candidate TRIMs (Uchil et al., 2008). Noteworthy among them are TRIM11 and 31 which affect HIV-1 entry, TRIM11 which interferes with ref 1 activity indicating that heterologous TRIMs act in concert to modulate and fine-tune an antiretroviral response, and TRIM 25, 31, and 62 that inhibit viral release (Uchil et al., 2008).

TRIM proteins possess a cysteine-rich RING finger zinc-coordinating domain, a B-box zinc-coordinating domain, and a coiled-coil domain (Nisole et al., 2005; Reymond et al., 2001) and are also named RBCC proteins. The RING domain is often found in E3 ubiquitin ligases and T5 itself can act as an ubiquitin ligase (Xu et al., 2003). Since neither mutations in the RING domain nor the use of proteasome inhibitors fully abolish T5-mediated restriction activity, it is unclear whether ubiquitin ligase activity is required for retroviral restriction (Javanbakht et al., 2005; Perez-Caballero et al., 2005b). The B-Box domain may be a protein-protein interaction domain that regulates substrate specificity of the RING E3 ubiquitin ligase domain (Massiah et al., 2006). The T5 B-box is required for retroviral restriction and its deletion results in lack of antiviral activity (Javanbakht et al., 2005; Perez-Caballero et al., 2005a). Homo- and hetero-multimerization of T5 is achieved by the coiled-coil domain (Reymond et al., 2001) (FIG. 41A). Replacement of this domain with a heterologous trimeric coiled-coil in RhT5α did not support anti-HIV-1 function, despite efficient trimer formation and CA-binding, indicating that the coiled-coil domain in T5 may accomplish more than multimerization (Li et al., 2006a).

The T5 gene in the New World owl monkey (genus *Aotus*) has an unusual structure that resulted from retrotransposition of the complete cyclophilin A (CypA) cDNA into intron 7 (Nisole et al., 2004; Sayah et al., 2004), thus replacing the PRYSPRY domain and fusing CypA C-terminal to RBCC. Since CypA is a CA-binding protein (Luban et al., 1993), the fusion protein AoT5Cyp binds directly to CA (Nisole et al., 2004; Sayah et al., 2004). This implied that T5 retroviral restriction factors from other species may function similarly by binding to CA. Indeed, the C-terminal PRYSPRY domain the T5α is required for T5α binding to the CA of restriction-sensitive retroviruses (Sebastian and Luban, 2005; Stremlau et al., 2006). Restriction activity requires recognition of CA by multimerized T5 (Javanbakht et al., 2006; Mische et al., 2005) in context of intact viral cores (Forshey et al., 2005; Shi and Aiken, 2006).

The specificity of the PRYSPRY-CA interaction determines which retrovirus a given T5α orthologue inhibits. Human T5α (hT5α), for instance, weakly blocks HIV-1, but potently blocks N-tropic murine leukemia virus (N-MLV) (Hatziioannou et al., 2004; Keckesova et al., 2004; Perron et al., 2004; Yap et al., 2004). RhT5α potently blocks HIV-1 as well as N-MLV weakly, but fails to restrict SIV (Newman and Johnson, 2007). The specificity of this restriction, as well as the modular nature of the T5 components, is further demonstrated by the HIV-1 restriction activity that results when the hT5α PRYSPRY domain is replaced with that from RhT5α (Perez-Caballero et al., 2005a; Sawyer et al., 2005; Stremlau et al., 2005; Yap et al., 2005). Thus, T5, like A3G, is a major host determinant of retroviral tropism.

Restriction Mechanism

T5-mediated retroviral restriction occurs within minutes of viral entry, attacking the incoming virus at a step post-entry but prior to or during reverse transcription (Diaz-Griffero et al., 2006b; Perez-Caballero et al., 2005a). While much about the restriction mechanism remains unknown, restriction occurs in two steps. One step targets reverse transcription itself and a second step targets nuclear import of the pre-integration complex (PIC) (Berthoux et al., 2004; Wu et al., 2006). These distinct steps are sensitive to inhibition by different methods: the inhibition of reverse transcription requires proteasome function and is blocked by proteasome inhibitors as well as $As_2O_3$ and other drugs affecting mitochondrial membrane potential. Proteasome inhibitors, rescue reverse transcription in the presence of a restrictive T5 but fail to rescue nuclear import of PICs (Anderson et al., 2006). It is noteworthy that proteasome inhibitors, even in non-restricting environments, can modestly increase viral titers (Schwartz et al., 1998). Furthermore, mutation of the RING-domain residues required for E3 ubiquitin ligase activity diminishes, but does not fully abolish restriction (Diaz-Griffero et al., 2006a). Most surprisingly, however, even ubiquitin itself may be dispensable for restriction activity (Perez-Caballero et al., 2005b).

The CA-binding requirement for retroviral restriction indicates a model in which T5 binds to CA and targets it for proteasomal degradation. Indeed, T5 promotes the premature uncoating of incoming viruses as has been shown in CA-sedimentation assays (Perron et al., 2007; Stremlau et al., 2006). This could disturb the optimal coordination of the poorly understood uncoating process and reverse transcription; a disturbance that has been observed with destabilizing CA-mutants as well (Forshey et al., 2002). Proteasome inhibitors prevented T5-mediated loss of particulate CA, indicating that T5-mediated uncoating is a proteasome dependent process (Diaz-Griffero et al., 2007). Intriguingly, restrictive T5 itself is polyubiquitinated and, in the presence of restriction-sensitive CAs, T5 is targeted for proteasomal degradation. Thus, an entire T5-CA protein complex may be targeted for proteasomal degradation (Diaz-Griffero et al., 2006a; Rold and Aiken, 2008).

Even before the discovery of T5, it was observed that reverse transcription could be stimulated with $As_2O_3$ and other drugs perturbing mitochondrial membrane potential (Berthoux et al., 2004; Berthoux et al., 2003). By an unknown mechanism, $As_2O_3$ counteracts a HIV-1 restriction by all T5 orthologs tested in a cell-type specific manner (Sebastian et al., 2006). Nuclear import of PICs, on the other hand, can be inhibited by disruption of the CA-CypA interaction through genetic or pharmacologic means (Berthoux et al., 2004). While both $As_2O_3$ and proteasome inhibitors rescue reverse transcription, T5-mediated inhibition of PIC nuclear translocation can account for the proteasome-independent mechanism of T5-mediated CA degradation (Chatterji et al., 2006). Fusion of heterologous TRIM-family member RBCC domains with CypA leads to novel TRIMCyp fusion proteins with distinct blocks to HIV-1 replication depending on the RBCC domain used: either at reverse transcription or PIC nuclear import, or both (Yap et al., 2006). Aside from highlighting the modularity of T5 restriction factors (i.e. as long as the C-terminal PRYSPRY or Cyp domain target RBCC to CA, most RBCCs will be able to restrict retroviruses); these findings reaffirm the concept of a two-step restriction mechanism.

Evolution

In humans, T5 is located on chromosome 11 Between TRIM22, TRIM34, and TRIM6, in a cluster of SPRY domain containing, IFN-inducible TRIMs (Newman and Johnson, 2007). Since T5α has been evolving under extreme positive selection in the primate lineage for the last 30 million years (Sawyer et al., 2005), T5 exhibits significant sequence diversity between primate species. The most significant finding in regard to co-evolution with viral pathogens is the detection of footprints of positive selection in which sequence diversity is concentrated. These are located mainly in the PRYSPRY domain, which by binding to retroviral CA, directs retroviral tropism (Sawyer et al., 2005). Evolutionary hot-spots occur in what have become termed variable regions V1-V4 of the PRYSPRY domain (Song et al., 2005b) and were further predicted to correspond to retroviral tropism determinants. The most impressive evidence of positive selection was found in a 14 amino acid patch in the PRYSPRY domain. Phylogenetic data were backed up beautifully in tissue culture experiments that analyzed anti-HIV 1 activity of different simian-human chimeras containing this 14 amino acid patch. Indeed, this patch proved to be the key determinant of retroviral tropism (Sawyer et al., 2005). Independent experimental mapping intended to reveal restriction specificity determinants reinforced this finding (Perez-Caballero et al., 2005a; Stremlau et al., 2005; Yap et al., 2005). The pattern of specific positive-selection hotspots forming variable regions anchored in more constant domains is reminiscent of the selection of peptide binding regions in the major histocompatability (MHC) loci (Hughes and Yeager, 1998).

Analysis of polymorphisms in the hT5α gene revealed several with a high allelic frequency, mainly found in the RBCC domain. Strikingly, none have been reported for the variable regions of the PRYPSRY domain; those regions undergoing the strongest positive selection and comprising the greatest inter-species sequence diversity (Sawyer et al., 2006). This points to the possibility that hT5α in its current form is the likely result of a selective sweep exerted on the human genome by an ancient retroviral epidemic (Newman and Johnson, 2007). One reported candidate retrovirus is the chimpanzee endogenous retrovirus ptERV (Kaiser et al., 2007). Our closest relative, the chimpanzee, contains about 150 copies of ptERV in its genome, that are completely absent from the human genome. The absence of any trace of ptERV in the human genome suggests active elimination of ptERV or its parent virus from the human species. hT5α could indeed efficiently block an MLV-based vectors engineered to express the ptERV CA (Kaiser et al., 2007).

Another indication of the immense evolutionary pressure on the primate T5 locus is the discovery of additional T5Cyp fusion proteins. The generation of AoT5Cyp, the first such fusion protein discovered, seemed unique. It resulted from a Line-1 mediated retrotransposition of the CypA cDNA between Exon 7 and 8 of the *aotus* TRIM5 locus thus fully replacing the PRYPSRY domain encoded by exon 8 with CypA (Sayah et al., 2004). The fixation of the AoT5Cyp gene as the only T5 allele in more than 10 *Aotus* species speaks for an extremely strong positive selection force on this gene (Ribeiro et al., 2005). The discovery of a second TRIMCyp fusion protein (MaT5Cyp) in three species (*rhesus, nemestrina*, and *fascicularis*) of the macaque genus is a stunning example of convergent evolution (Brennan et al., 2008; Newman et al., 2008; Virgen et al., 2008; Wilson et al., 2008) (FIG. 41B). In MaT5Cyp the CypA insertion occurred within Exon 8 leading to a splicing-out of exon 7. Together with some amino-acid differences in the CypA moiety, this distinct retrotransposition event leads to a retroviral specificity different from that of AoTSyp. MaT5Cyp does not inhibit HIV-1 but potently blocks infection by HIV-2, $SIV_{AGM}$tan, and FIV (Virgen et al., 2008). The T5Cyp fusion was generated by Line-1 mediated retrotransposition on two separate occasions in old world and new world monkeys. Evolutionary pressure then drove fixation of these potent retroviral restriction factors in the owl monkey and macaque lineages. What the driving force in each case was remains to be determined, but there is a high likelihood that the genesis and maintenance of these genes is a result of an ancient battle against retroviruses.

T5Cyp, a natural anti-retroviral created by evolution, has several properties that would make it appealing for anti-HIV-1 therapy. In the case of AoT5Cyp, it potently blocks HIV-1 infection when expressed in human cells (Nisole et al., 2004; Sayah et al., 2004) and it acts on the virus within minutes of entry (Diaz-Griffero et al., 2006b; Perez-Caballero et al., 2005a) protecting the host from potentially deleterious insertional mutagenesis. Since AoT5Cyp is the single TRIM5 allele present in the *Aotus* genus (Ribeiro et al., 2005), cells bearing AoT5Cyp retain functionality. AoT5Cyp is not a human protein, and if expressed in patients may lead to an immune response. This Example focuses on generating a hT5Cyp fusion protein with reduced antigenic potential but equal anti-HIV-1 potency. T5 proteins are modular with the C-terminal PRYSPRY or CypA domain targeting the proteins to CA of restriction-sensitive viruses and RBCC acting as an effector domain. Fusion of the hT5α RBCC domain to AoCypA resulted in a fusion with anti-HIV-1 activity (Nisole et al., 2004). Similarly, addition of RBCC from different TRIM family members to the RhT5α PRYSPRY (Li et al., 2006a) domain or AoCypA (Yap et al., 2006) yielded chimeras with restriction activity. This Example will focus on design and in vitro testing of a hT5Cyp fusion protein with activity against HIV-1. Example 2 will discuss testing hT5Cyp in primary human cells and developing required gene therapy methodology. Example 3 will concentrate on testing the anti-HIV-1 activity of hT5Cyp in vivo, and on the establishment of humanized mouse models for HIV-1 infection necessary for this aim.

Design of hT5Cyp Fusions with Anti-HIV-1 Activity

While hCypA and AoCypA are highly conserved, the RBCC domains of human and owl monkey T5 have a substantial number of amino acid changes (FIG. 42). Therefore, AoT5Cyp could generate an immune response if expressed in $hCD4^+$ T in vivo, and experiments were designed to make a human T5Cyp with reduced antigenic potential. Given the significant sequence dissimilarities between the owl monkey and human T5 RBCC domains, the approach of "humanizing" AoT5Cyp by single amino acid substitution was not used here (FIG. 42). Instead, a human T5Cyp was generated de novo by fusion of hT5 to hCypA.

Figure 43:
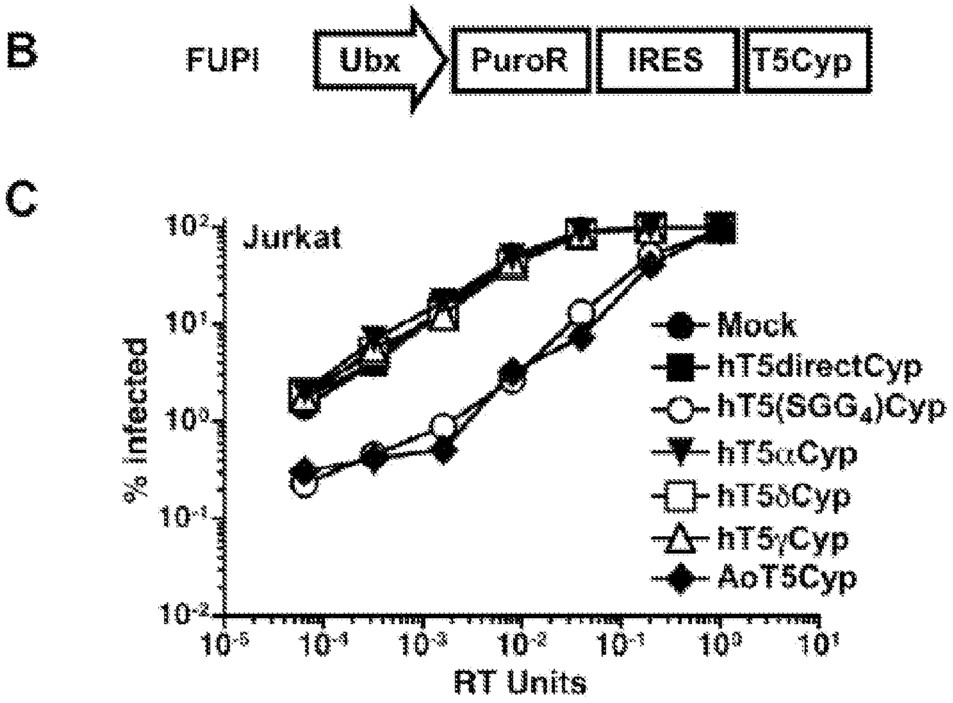
FIGS. 43A-C. (A.) Amino acid sequence at the junction of the indicated T5Cyp fusion proteins and the corresponding anti-HIV-1 activity. (B.) Schematic of lentiviral vector used for generation of stable cell lines; Ubx=Ubiquitin promoter, PuroR=puromycin-N-acetyl-transferase, IRES=internal ribosome entry site from encephalomyocarditis virus (ECMV) (C.) Jurkat T cells were transduced with vectors encoding puromycin-resistance and the indicated T5Cyp fusion proteins. Pools of puromycin-resistant cells were infected with increasing amounts of an HIV-1 vector encoding GFP (left to right on X-axis). The percentage of GFP$^+$ cells (Y-axis) was determined 48 hrs later.

A cryptic splice acceptor at the AoT5Cyp fusion junction results in the synthesis of 12 amino acids derived from the CypA 5'UTR (Sayah et al., 2004). An equivalent human fusion protein cannot be engineered due to lack of sequence homology in the CypA 5'UTR and the fact that the human 5'UTR, most likely remains untranslated. hT5Cyp was generated using only components normally expressed in human cells. Consequently, hT5-direct-Cyp was engineered with hCypA fused to a position in the linear sequence of hT5 analogous to that of the AoT5Cyp retrotransposition event (FIG. 43A). Since the 12 amino acids encoded by the AoCypA 5'UTR might be an essential spacer between the AoT5 and AoCypA moieties, sequences from the hT5α, γ, and δ isoforms, and a synthetic 12 amino acid spacer were used to generate linkers of similar length and character: SEQ ID NO:31 is hT5-α-Cyp (VDVTVAPNNISCAVIS (SEQ ID NO: 147)), SEQ ID NO:32 is hT5-γ-Cyp (GKEKSHYHKPPCGLS (SEQ ID NO: 148)), SEQ ID NO:33 is hT5-δ-Cyp (GWSAMARSRFTATSTS (SEQ ID NO: 149)), and SEQ ID NO:17 is $hT5(SGG)_4Cyp$ (SGGSGGSGGSGG (SEQ ID NO: 20)) (FIG. 43A). Jurkat T cells were transduced with a bicistronic lentiviral vector coding for puromycin resistance and the indicated T5Cyp fusion protein (FIG. 43B). Transduced Jurkat cells were then selected as pools using puromycin and challenged with serial dilutions of an HIV-1-GFP vector. $hT5(SGG)_4Cyp$ (SEQ ID NO:17) blocked HIV-1 comparably to AoT5Cyp but none of the other constructs exhibited detectable HIV-1 restriction activity (FIG. 43A,C).

Figure 45:
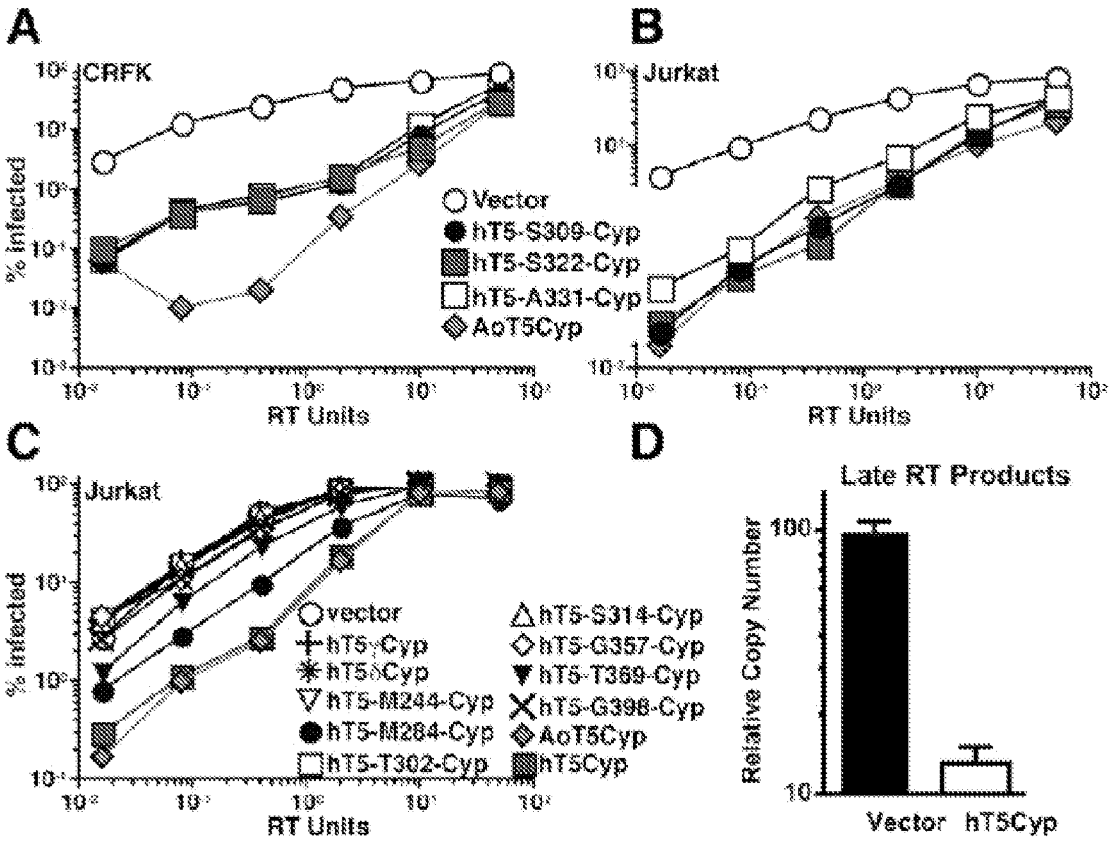
FIGS. 45A-D. Comparison of restrictive T5Cyp fusions in CRFK (A.) and Jurkat (B.) cells. (C.) Comparison of all designed fusions with reduced anti-HIV-1 activity to restrictive hT5Cyp and AoT5Cyp in Jurkat T cells. In all cases, cells were transduced with vectors encoding puromycin-resistance and the indicated T5Cyp fusion proteins. Pools of puromycin-resistant cells were infected with increasing amounts of an HIV-1 GFP (left to right on X-axis). The percentage of GFP$^+$ positive cells (Y-axis) was determined 48 hrs later. (D.) Total cellular DNA was purified from Jurkat cell lines and late RT products were quantified by PCR. Values were normalized to mitochondrial DNA content.

Since the objective was to engineer a fully human HIV-1 restriction factor, hCypA was the fused at 10 different positions along the length of hT5α (FIG. 44A). Of the hT5Cyp constructs tested for HIV-1 restriction activity in Jurkat T cells and THP-1 monocytes, three had activity comparable to AoT5Cyp (hT5-A331-Cyp (SEQ ID NO:5 and corresponding amino acid sequence of SEQ ID NO:10); hT5-5309-Cyp (SEQ ID NO:6 and corresponding amino acid sequence of SEQ ID NO:11); and hT5-5322-Cyp (SEQ ID NO:7 and corresponding amino acid sequence of SEQ ID NO:12)), one (hT5-T369-Cyp) with SEQ ID NO: 34 was moderately restrictive, while another (hT5-M284-Cyp) with SEQ ID NO:35 exhibited variable restriction activity based on cell-type and activation status (FIG. 44B, FIG. 45, Table 1). hT5-5322-Cyp with SEQ ID NO:12, consistently the strongest HIV-1-inhibitor, became the focus of subsequent experiments, and for simplicity will be referred to in the Examples as hT5Cyp (FIG. 45, Table 1). hT5Cyp also restricted HIV-1 in promonocytic U937 cells, the CEM-SS, SUP-T1, H9 T cell lines, HUH-7 human hepatoma cells, CRFK feline kidney cells, and the 293T embryonic kidney cell line (Table 1). Like AoT5Cyp (Diaz-Griffero et al., 2006b), hT5Cyp blocked the accumulation of viral cDNA, as measured by quantitative PCR in stable Jurkat T cell lines (FIG. 45D).

When compared to Jurkat T cells transduced with control vectors, Jurkat T cells transduced with hT5Cyp or AoT5Cyp grew with the same kinetics and expressed similar levels of cell surface CD4, CXCR4, CD11a, CD18, and ICAM3; members of the virological synapse which includes the HIV-1 receptor and co-receptor (Jolly et al., 2004); as well as MHC-I (FIG. 46A). Since CypA is highly abundant in the cytoplasm of most eukaryotic cells, endogenous CypA may inhibit hT5Cyp function by acting as a competitive inhibitor for CA-binding. hT5Cyp potency may be increased by modulating endogenous CypA levels. To investigate this, stable CypA KD Jurkat T cell lines were generated using a lentiviral vector with a CypA shRNA targeting the 3'UTR embedded in miR-30 downstream of the SFFV promoter driving hygromycin resistance. The control was a Luciferase shRNA (Luc KD). Hygromycin resistant cells were then stably transduced with bicistronic lentiviral vectors coding for the control or hT5Cyp and puromycin resistance. Cells resistant to both puromycin and hygromycin were then challenged with an HIV-1 GFP vector. The magnitude of hT5Cyp-mediated restriction was unexpectedly lower in the absence of CypA (FIG. 46B). Equivalent results were obtained for AoT5Cyp in Jurkat T cells and for both T5Cyps in H9 cells. Since T5 proteins form homo- and heteromultimers (Mische et al., 2005), T5 γ, a splice-isoform of T5α, which lacks the PRYPSRY domain, acts as a dominant negative inhibitor of T5α antiretroviral activity (Stremlau et al., 2004). While gross defects were not observed in proliferation or morphology of Jurkat T cells expressing T5Cyp, it was tested whether expression of exogenous T5Cyp analogously affects N-MLV inhibition by endogenous hT5α. Jurkat T cells stably expressing control vector or T5Cyps were challenged with B- and N-MLV. Cells expressing T5Cyp restricted N-MLV 4-10 fold less than cells transduced with empty vector, but continued to robustly restrict N-MLV 20-40 fold compared to B-MLV (FIG. 46C).

TABLE 1

HIV-1 inhibition by hT5Cyp

| T5 | HIV-1 Inhibition<br>Jurkat | THP-1 | PMA treated THP-1 | CRFK |
|---|---|---|---|---|
| hT5-M244-Cyp | – | – | – | – |
| hT5-M284-Cyp | +++ | – | + | +++ |
| hT5-T302-Cyp | – | – | – | – |
| hT5-S309-Cyp | +++ | +++ | +++ | +++ |
| hT5-S314(α)-Cyp | – | – | – | – |
| hT5-S322-Cyp | +++ | ++++ | +++ | +++ |
| hT5-A331-Cyp | ++ | ND | ND | +++ |
| hT5-G357-Cyp | – | ND | ND | ND |
| hT5-T369-Cyp | + | ND | ND | ND |
| hT5-G398-Cyp | – | ND | ND | – |
| hT5directCyp | – | ND | ND | ND |
| hT5($SGG_4$)Cyp | +++ | +++ | +++ | +++ |
| hT5δCyp* | – | – | – | –* |
| hT5γCyp* | – | – | – | –* |
| RhT5a | + | ND | ND | +++? |
| AoT5Cyp | +++ | +++ | +++ | ++++ |

*Despite lacking anti-HIV-1 activity, both hT5δCyp* and hT5γCyp* restrict $SIV_{AGM}$tan 6- and 15-fold in CRFK cells.

Structural Requirements for hT5Cyp-Mediated HIV-1 Restriction Activity

Despite the apparent modularity of TRIM5 (Perez-Caballero et al., 2005a; Sawyer et al., 2005; Stremlau et al., 2005; Yap et al., 2005), most hT5Cyp fusions lacked anti-HIV-1 activity. Steady-state protein level in stably-transduced Jurkat T cells did not correlate with restriction activity: AoT5Cyp and restrictive hT5Cyp fusions were undetectable by immunoblot while inactive or variable hT5Cyps (hT5-M244-Cyp and hT5-M284-Cyp) were highly expressed. Treatment with sodium butyrate, which is known to increase T5 protein levels (Perez-Caballero et al., 2005b), did not reveal expression of additional hT5Cyp fusion proteins in stably transduced Jurkat cell lines by western blot. To increase the possibility of detection, hT5Cyp proteins were then expressed as triple-FLAG-tagged fusions by plasmid transfection of 293T cells. Anti-FLAG immunoprecipitates were probed in immunoblots with anti-CypA antibody. Two fusions with no detectable restriction activity, hT5-M244-Cyp and hT5-T302-Cyp, were expressed at high-level, whereas fusions with potent anti-HIV-1 activity, hT5-A331-Cyp and AoT5Cyp, were expressed at low-level (FIG. 47A). Again, restriction activity did not correlate with protein level.

Lack of activity could result from failure to bind HIV-1 CA. Glutathione S-transferase (GST)-CA fusion protein was used to test CA-binding activity of hT5Cyp proteins produced in 293T cells. Among hT5Cyp fusions with no anti-HIV-1 activity, hT5-T302-Cyp bound HIV-1 CA as well as the potently restrictive hT5-S322-Cyp (FIG. 47B). Specificity of binding was demonstrated by blocking the CypA:CA interaction with the competitive inhibitor cyclosporine A (CsA) (FIG. 47B). Thus, the ability to bind CA was required but not sufficient for restriction activity.

To visualize the sites of CypA linkage to hT5, a three-dimensional model of the T5α PRYSPRY domain was generated using crystal structure coordinates from the C-terminal B30.2/SPRY domains of three homologues: GUSTAVUS, Pyrin, and TRIM21 (Grutter et al., 2006; James et al., 2007; Woo et al., 2006) (FIG. 47C). hT5Cyp fusions with potent anti-HIV-1 activity clustered near the main specificity determinant for HIV-1 restriction activity (Ohkura et al., 2006; Sawyer et al., 2005; Yap et al., 2005); a proposed protein interaction surface (Grutter et al., 2006; Woo et al., 2006) (FIG. 47C). No inactive hT5Cyp proteins mapped to this region (FIG. 47C). The inactive insertions, in fact, map on the "opposite" side of the proposed protein-protein interaction surface. One exception, hT5Cyp-M285-Cyp, is located in the linker region (linker 2) between the coiled-coil and the PRYSPRY domains of hT5α (N-terminal α-helix), and shows variable restriction activity based on cell type (FIG. 47C, Table 1).

T5, like some other TRIM-family members, can form aggregates in the cytoplasm called cytoplasmic bodies (Reymond et al., 2001). The exact function and the requirement of cytoplasmic body formation for lentiviral restriction is unclear and under debate (Campbell et al., 2007; Perez-Caballero et al., 2005b; Song et al., 2005a; Wu et al., 2006). In stable CRFK cell lines, visualization of hT5Cyp fusions by static immunofluorescence showed that AoT5Cyp and all three hT5Cyps with potent anti-HIV-1 activity formed distinct cytoplasmic bodies (FIG. 47D). In contrast, diffuse cytoplasmic staining was observed for hT5Cyp fusions that lacked restriction activity. Taken together, these results demonstrate strict conformational requirements for antiviral activity that are determined by the site of CypA fusion and correlate with the ability of the fusion proteins to form cytoplasmic bodies.

hT5Cyp Restricts Multiple Lentiviruses

AoT5Cyp restricts HIV-$1_{NL4-3}$, HIV-$2_{ROD}$, $SIV_{AGM}$tan, and $FIV_{PET}$, all viruses encoding a CA that binds CypA (Diaz-Griffero et al., 2006b; Lin and Emerman, 2006; Luban et al., 1993; Nisole et al., 2004; Saenz et al., 2005; Sayah et al., 2004; Zhang et al., 2006). To evaluate whether hT5Cyp blocked infection by these lentiviruses, stable cell lines were generated using CRFK cells. AoT5Cyp and hT5Cyp restricted all four lentiviruses (FIG. 48; A-D). in these cells, AoT5Cyp blocked HIV-1 infection about 10-fold more effectively at low multiplicities of infection (MOI) (FIG. 48A; Table 1); an effect that is lost in Jurkat T cell line and THP-1 monocytes where Ao- and hT5Cyp have comparable effects on HIV-1 infection (FIG. 43B, Table 1). In contrast, hT5Cyp inhibits $SIV_{AGM}$tan infection impressively, and significantly better than AoT5Cyp at low MOI (FIG. 48C). Interestingly, hT5γCyp and hT5δCyp, which lack detectable restriction activity against HIV-1 and FIV, show a maximal 15- and 6-fold restriction of $SIV_{AGM}$tan. HIV-$2_{ROD}$ and $FIV_{PET}$ are blocked comparably by AoT5Cyp and hT5Cyp (FIG. 48; B, D). Since CypA does not bind to $SIV_{MAC}$251 CA, neither AoT5Cyp nor hT5Cyp can restrict this virus (FIG. 48E).

hT5Cyp Restriction Activity Depends on Both the hCypA and hT5 Components

To confirm that hT5Cyps have the same CA-binding requirements as AoT5Cyp, the CRFK stable cell lines were challenged with HIV-1-G89V, a CA mutant that disrupts interaction with CypA (Sayah et al., 2004). Both AoT5Cyp and hT5Cyp failed to restrict HIV-1-G89V (FIG. 49A). The H126Q mutation in CypA also disrupts the CA-CypA interaction (Braaten et al., 1997) and hT5Cyp bearing the H126Q mutation in its CypA domain had no detectable anti-HIV-1 restriction activity (FIG. 49B). Since this single amino acid change in hT5Cyp leads to complete loss of HIV-1 restriction activity, hT5CypH126Q provides an attractive control for hT5Cyp and will be used in further studies. Finally, cyclosporine, a competitive inhibitor of the CypA-CA interaction (Luban et al., 1993), abrogated HIV-1 restriction by AoT5Cyp and hT5Cyp (FIG. 49C). Equivalent results were obtained when DEBIO-025, a non-immunosuppressive competitor of CypA, was used in place of CsA (FIG. 49E). A previous study searched the database for CA-variants circulating in HIV-1-infected people that are resistant to cyclosporine and to AoT5Cyp-mediated HIV-1-restriction (Chatterji et al., 2005). V86P/H87Q/I91V/M96I HIV-1, the CA-variant with the strongest cyclosporine resistance in vitro (Chatterji et al., 2005), an effect confirmed here (FIG. 49D). Both hT5Cyp and AoT5Cyp, however, blocked infection by viruses bearing this sequence as efficiently as they block standard HIV-1 clones (FIG. 49D).

To assess the contribution of the T5 domain to T5Cyp-mediated restriction, CRFK cell lines expressing AoT5Cyp or hT5Cyp were treated with arsenic trioxide ($As_2O_3$). This drug was previously shown to inhibit T5-mediated restriction (Sebastian et al., 2006). AoT5Cyp and hT5Cyp restriction activity was blocked to the same extent by $As_2O_3$ (FIG. 49F). These results show that, with respect to CA-recognition by the CypA domain, and effector function by the T5 domain, AoT5Cyp and hT5Cyp behave nearly identically.

hT5Cyp and AoT5Cyp have the Highest Anti-HIV Activity Among Characterized T5 Proteins Since the discovery of T5, its potential as anti-HIV-1 therapy has been in sight. While a protein modeled after AoT5Cyp is described here, other groups are considering proteins based on RhT5α. In contrast to hT5α, rhT5α restricts HIV-1 (Stremlau et al., 2004). Chimeric T5 proteins in which the PRYSPRY specificity determinant from the rhesus orthologue replaces the corresponding human residues ($hT5\alpha_{R323-332}$ (Sawyer et al., 2005; Stremlau et al., 2005)), or even in which a single, critical amino acid was substituted ($hT5\alpha_{R332P}$ (Li, et al. 2006b; Yap et al., 2005)), exhibit HIV-1 restriction activity approaching that of RhT5α in HeLa and CRFK cells, respectively. Since these molecules are nearly identical to the human protein (FIG. 41B), it has been proposed that they may have therapeutic utility (Anderson et al, 2008; Li et al, 2006b; Stremlau et al, 2005; Yap, 2005).

Anti-HIV-1 potency is an essential consideration in any potential therapy, so a direct comparison of hT5Cyp and other candidates was undertaken. $hT5\alpha_{R323-332}$ and $hT5\alpha_{R332P}$ caused moderate inhibition of HIV-1 (10-fold) in single-cycle infection of CRFK cells approaching RhT5α restriction activity. hT5Cyp, however, was ~10-fold more potent than either, with AoT5Cyp inhibiting HIV-1 infection the strongest by almost 1000-fold (FIG. 50A). CRFK, feline kidney fibroblast cells, lack endogenous T5 and are commonly used in the field as they have large T5-restriction phenotypes in single-cycle assays. In 293T human embryonic kidney cells, however, hT5Cyp and AoT5Cyp were equivalent in their anti-HIV 1 activity and over 10-fold more potent than RhT5α (FIG. 50B). In human Jurkat T cell lines, hT5α-R332P and hT5α-R323-332 have a negligible (maximum two-fold) effect on HIV-1 infection and RhT5α a modest one compared to AoT5Cyp and hT5Cyp (FIG. 50C).

Discussion

The potent block to HIV-1 infection observed with AoT5Cyp inspired the design of a human equivalent: hT5Cyp. Since T5α and T5Cyp are modular proteins, generation of an hT5Cyp fusion with anti-HIV-1 activity was expected to be trivial. Surprisingly, only three of 14 hT5Cyp fusions exhibited HIV-1 restriction activity comparable to AoT5Cyp. No correlation was observed between protein levels and antiviral activity (FIG. 47A). In fact, in stable Jurkat T cell lines, restricting hT5Cyp fusion proteins could not be detected by western blot while the only two fusion proteins that were highly expressed both lacked anti-HIV activity. Since T5 itself is polyubiquitinated and rapidly degraded when it encounters a restriction-sensitive CA (Rold and Aiken, 2008), rapid turnover may in fact be of physiological relevance and correlate with restriction activity.

The unexpectedly rare frequency with which restrictive fusion proteins were obtained suggests that there are strict spatial requirements for anti-HIV-1 activity. Structural modeling showed that the best anti-HIV-1 activity was obtained when hCypA was fused at the apex of the hT5α PRYSPRY domain. Interestingly, analysis of nonsynonymous mutations in T5α indicates that this region undergoes some of the strongest selective pressure in the primate lineage and functional experiments pinpoint this hypervariable region as a specificity determinant for CA recognition (Sawyer et al., 2005; Song et al., 2005b; Yap et al., 2005). CypA fusions 309, 322, and 332 may have the greatest antiviral activity simply because this region is especially tolerant of sequence variation. More likely, this apical loop is uniquely situated for coordinating the CA recognition and effector domains of T5.

T5-mediated restriction occurs by a two-pronged mechanism leading to reduction of viral cDNA (FIG. 45D) as well as inhibition of its nuclear import (Anderson et al., 2006; Wu et al., 2006). The presence of a restrictive T5 orthologue results in reduction of particulate CA in the target cell cytosol by promoting the premature uncoating of retroviral capsids (Diaz-Griffero et al., 2007; Stremlau et al., 2006). Proteasome inhibitors restore retroviral cDNA synthesis and the amount of cytosolic particulate CA without eliminating restriction (Anderson et al., 2006; Berthoux et al., 2004; Diaz-Griffero et al., 2007; Sebastian and Luban, 2007). In contrast, a B-box mutation in T5Cyp restricts HIV-1 while not reducing amount of particulate cytoplasmic CA, indicating that restriction can be observed even in the presence of particulate CA (Diaz-Griffero et al., 2007). The results presented here add to these observations by identifying a hT5Cyp-fusion (hT5-T302-Cyp) that does not restrict HIV-1 despite its ability to bind to CA (FIG. 47B). This indicates that simple CA-binding is not sufficient for HIV-1 restriction, either due to particular spatial constraints or a requirement for restriction cofactors. Due to its unique attribute of CA-binding in the absence of restriction activity, hT5-T302-Cyp could be used in a proteomics approach side by side with a restrictive T5Cyp in an effort to isolate and verify potential co-factors for restriction. Closer analysis of the level of reverse transcription, the amount of particulate CA, and the efficiency of nuclear import in the presence of the permissive hT5-T302-Cyp in comparison to restrictive hT5Cyp may lead to more detailed insights into the mechanism of T5-mediated restriction of HIV-1. Similarly, hT5-γ-Cyp and hT5-α-Cyp show no restriction activity against either HIV-1 or FIV, yet inhibit $SIV_{AGM}$tant in CRFK. They could also prove useful tools in further analysis of requirements for CA-interaction and effector functions.

Figure 47:
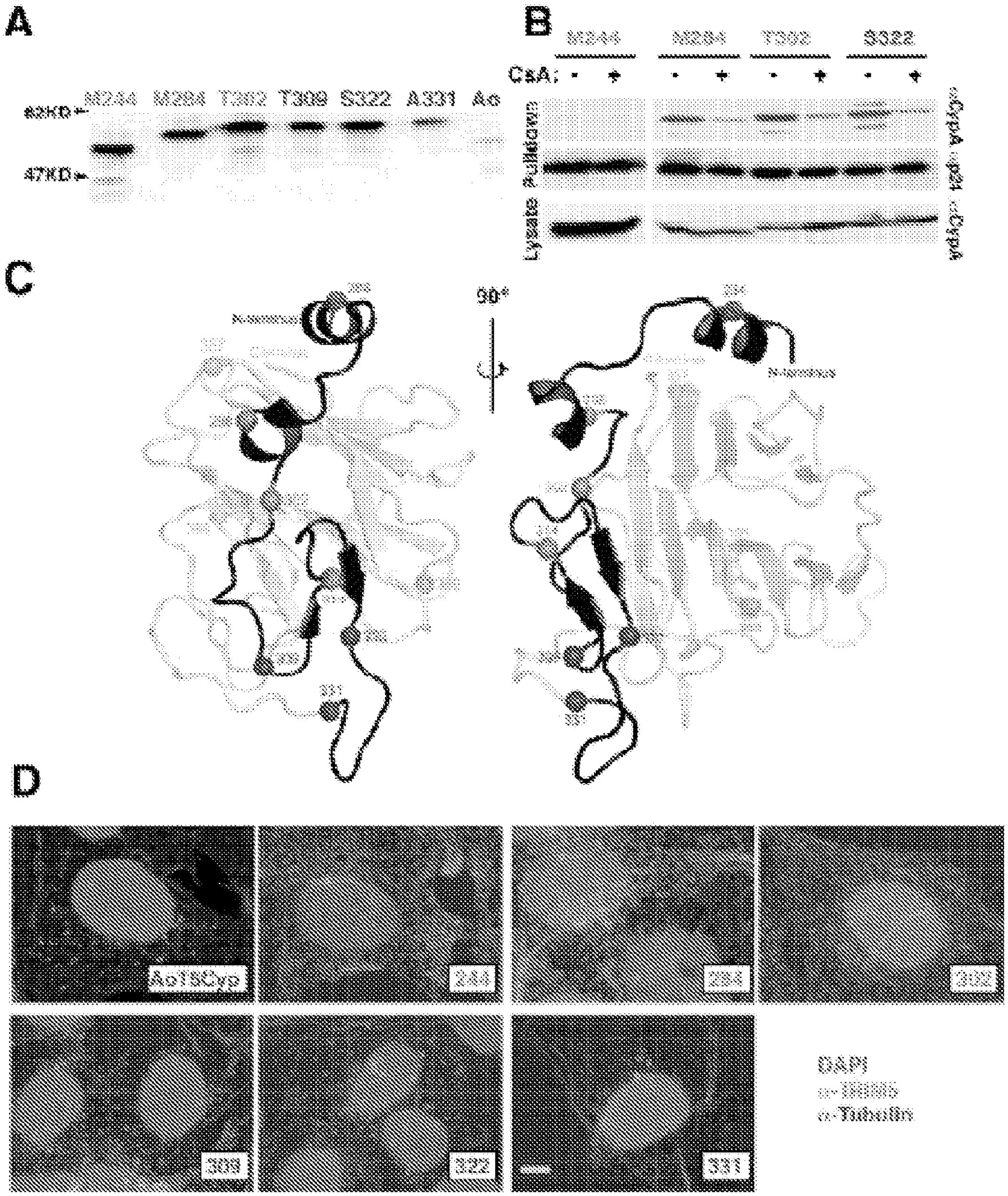
FIG. 47A-D. (A.) FLAG-hT5Cyp fusion proteins synthesized in 293T cells were immunoprecipitated and immunoblotted with anti-CypA antibodies. (B.) FLAG-hT5Cyp and GST-CA fusion proteins were co-expressed in 293T cells, pulled down with glutathione-sepharose beads in the presence or absence of 20 mM CsA, and immunoblotted. (C.) Model of the hT5α PRYSPRY domain based on crystal structures of PYRIN, GUSTAVUS and TRIM21. Ribbon representations show the position of hCypA fusions (spheres) to the hT5α PRYSPRY domain. The grey ribbon indicates regions of the model that would be replaced by CypA in hT5-A331-Cyp. (D.) Indirect immunofluorescence images of CRFK cells stably expressing the indicated T5Cyp fusions. Fixed samples were stained with anti-T5 antibody (green) and anti-tubulin antibody (red), followed by counter-stain with DAPI (blue) to visualize the nuclear DNA. Images represent three-color overlays. Bar: 5 μm. All panels are color-coded for restriction phenotype: red, restrictive; green, permissive; orange, variably restrictive.

While there seems to be no requirement for localization of restrictive T5 orthologues in pre-existing cytoplasmic bodies (Perez-Caballero et al., 2005b; Song et al., 2005a), T5 orthologs, much like their family member TRIM19, can form these highly dynamic structures (Campbell et al., 2007). Furthermore, T5-containing cytoplasmic bodies often form de novo, surrounding incoming viral complexes, and are better visualized by live rather than static immunofluorescence (Campbell et al., 2008). Proteasome inhibitors, which rescue cDNA synthesis and levels of particulate CA, induce the stable accumulation of viral complexes in cytoplasmic bodies. Thus cytoplasmic bodies could represent the visualization of a restriction-intermediate (Campbell et al., 2008). Static immunofluorescence of stable CRFK lines showed that the highly restrictive T5Cyp fusions 309, 322, and 332 (FIG. 45) all showed a punctate cytoplasmic staining also seen for AoT5Cyp, whereas non-restricting hT5Cyp fusions stained diffusely cytoplasmic (FIG. 47). Live imaging of hT5Cyp would be worth undertaking with a particular focus on whether permissive hT5-T302-Cyp which binds CA has the ability to form de novo cytoplasmic bodies surrounding HIV-1 complexes only to fail at a later point in the restriction pathway.

hT5Cyp fusion proteins with HIV-1 restriction activity behave comparably to AoT5Cyp. They are able to restrict the same range of lentiviruses (HIV-1, HIV-2, FIV, and $SIV_{AGM}$tant) at similar magnitudes of inhibition as AoT5Cyp (FIG. 48). Lentiviruses sensitive to T5Cyp-mediated restriction all have CA that bind CypA. Disruption of the CypA:CA interaction using pharmacologic or genetic means abolishes T5Cyp restriction activity, as does $As_2O_3$ (FIG. 49). This confirms for hT5Cyp that CA binding is necessary if not sufficient for restriction activity. There are few naturally occurring HIV-1 CA variants with amino acid substitutions surrounding the CypA binding loop that have lost CsA sensitivity in human cells (Chatterji et al., 2005). This may be due to reduced affinity of CypA to these CA variants. The same group reported a partial resistance of these variant viruses to T5Cyp restriction in owl monkey cells (Chatterji et al., 2005). T5Cyp-expressing Jurkat T cells lines were challenged with such a CA variant, confirming the CsA insensitivity. T5Cyp, however, retained the ability to inhibit this CA variant. CypA is hypothesized to protect HIV-1 against an unknown restriction factor ("factor x") in human cells. Treatment with CsA disrupts the CypA:CA interaction allowing for access of factor x to CA. One explanation for loss of CsA sensitivity together with retention of T5Cyp restriction sensitivity, is that CA-mutations affect the binding site for factor x to a greater extent that the CypA binding loop. Therefore, even when the CypA:CA interaction is blocked by CsA, factor x cannot access the variant CA. T5Cyp, however, retains the ability to bind the variant CA and restricts this virus (FIG. 49D).

Jurkat T cells expressing hT5Cyp proliferate at the same rate and express similar levels of cell surface markers involved in HIV-1 spread (FIG. 46A). T5γ, a shorter isoform of T5 interferes with T5α-mediated restriction in a dominant negative manner (Stremlau et al., 2004). Despite the apparent health of T5Cyp-transduced Jurkat T cells, T5Cyp could affect endogenous T5α akin to T5γ. To evaluate this possibility, T5Cyp was expressed in CypA KD and control cells and challenged with N- or B-MLV (FIG. 46C). In the presence of T5Cyp, there was a reduction in Ref-1 activity; which is still robust. While this is unlikely to cause wide-spread N-MLV infections in humans, the function of T5α in human T cells is unknown. Furthermore, endogenous T5α expression is upregulated upon IFNα treatment (Asaoka et al., 2005). One could investigate whether different T5 isoforms are differentially expressed upon IFNα stimulation and how constant expression of T5Cyp from a heterologous promoter may affect the immune function of T5α in the face of viral infection.

Since CypA binds to CA, as does T5Cyp, high levels of endogenous CypA could compete with hT5Cyp for CA-binding, thus reducing restriction activity. Intriguingly, this was not the case, and endogenous CypA has no effect on restriction by hT5Cyp in T cell lines (FIG. 46B). This could be simply because low levels of T5Cyp suffice for potent restriction of HIV-1. Indeed, expression of restricting T5Cyp fusion proteins could not be detected in Jurkat cell lines. Alternatively, T5Cyp and cytoplasmic CypA may not encounter CA in the same compartments. For instance, CypA concentration in cytoplasmic bodies may be significantly lower than in the rest of the cytoplasm. A rapid association of HIV-1 with cytoplasmic bodies in which T5Cyp is concentrated is observed in live imaging of cells expressing fluorescently-labeled restriction-competent T5 (Campbell et al., 2008). One question is whether CypA affects the formation of cytoplasmic bodies, warranting live imaging of T5Cyp-expressing CypA KD and control cells during HIV-1 infection. CypA is required for T5α-mediated resistance to HIV-1 infection in old world monkey cells (Berthoux et al., 2005b). A further possibility is that CypA is, in fact, required for T5Cyp-mediated restriction as well. Consistent with this possibility, an actual reduction in magnitude of HIV-1 restriction is observed in CypA KD cells compared to Luc KD cells. CypA could be specifically knocked down in a context where T5Cyp is expressed at physiologic levels such as in owl monkey kidney cell (OMK) cells, without affecting expression of T5Cyp. This should enable a clear assessment whether HIV-1 infection in OMK cells is enhanced in the absence of CypA, implicating CypA as a co-factor for T5Cyp-mediated restriction.

Figure 50:
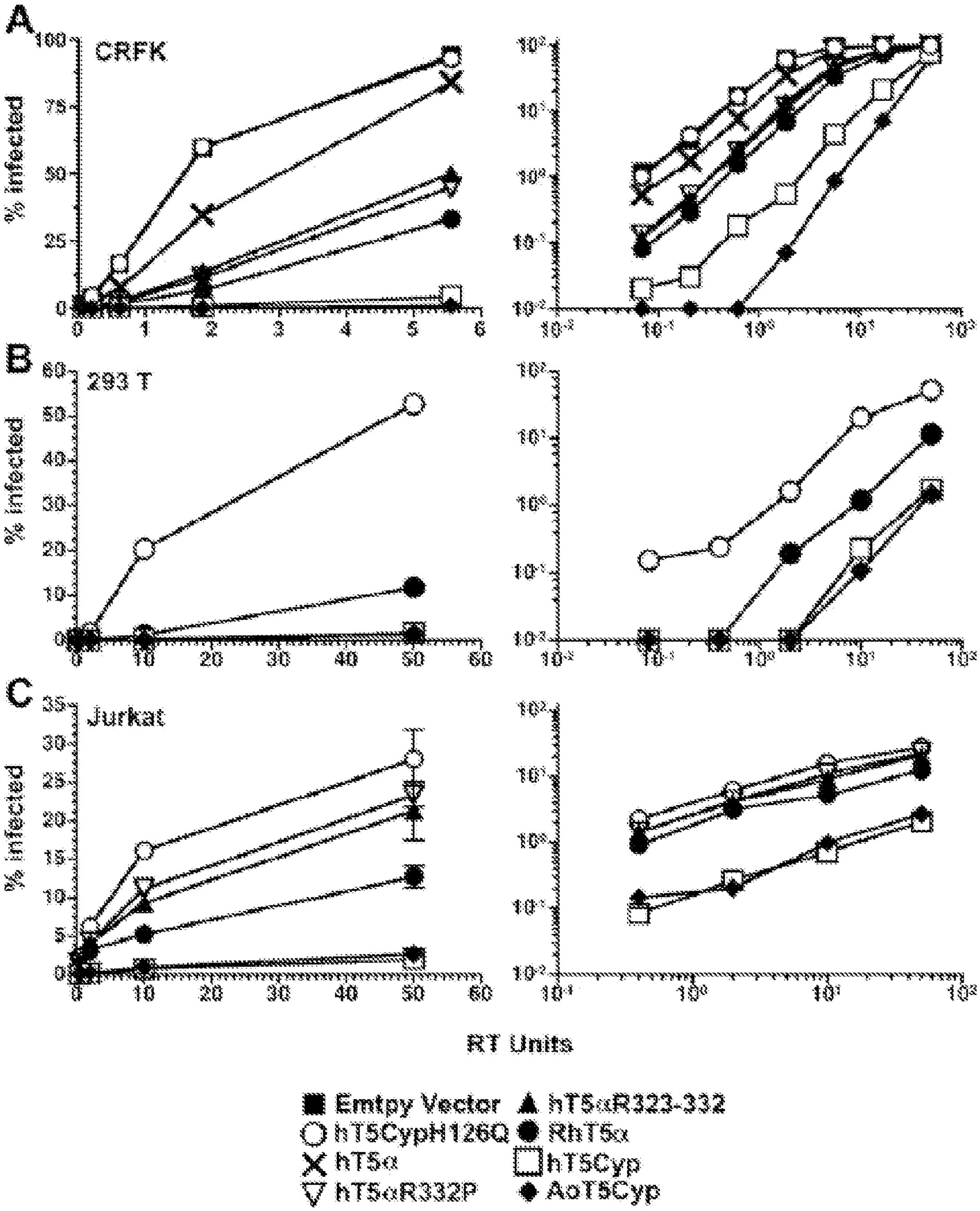
FIGS. 50A-C. Comparison of T5 restriction activity in CRFK cells, (A.) 293T cells (B.), and Jurkat T cells (C.) In A-C, cells were transduced with vectors encoding puromycin-resistance and the indicated T5 proteins. Pools of puromycin-resistant cells were infected with increasing amounts of an HIV-1 GFP (left to right on X-axis). The percentage of GFP$^+$ positive cells (Y-axis) was determined 48 hrs later.

One consistent finding has been that the magnitude of T5-mediated restriction depends on the cell-type in which exogenous T5Cyp is expressed. The most potent restriction is observed in CRFK cells, feline kidney fibroblasts that lack endogenous T5. Next, adherent cells such as 239T or TE671 have large T5-mediated HIV-1 restriction phenotypes. Lymphocytic cells in suspension such as Jurkat and THP-1 have consistently shown the smallest magnitude with 10-20 fold restriction of HIV-1 both by hT5Cyp and AoT5Cyp (FIGS. 43, 5, 6, 11). Potent HIV-1 inhibitors lower the risk of emerging viral resistance. Consequently, efficiency of HIV-1 inhibition is an essential consideration for any candidate therapy. The efficiency of HIV-1 inhibition by hT5Cyp was compared to that of RhT5α and modified hT5α with substitutions in the PRYSPRY domain. In all cell lines, T5Cyp was consistently 10-fold more potent than RhT5α. The largest, >10-fold inhibition of HIV-1 by RhT5α observed in CRFK and 293T cells (FIG. 50). In Jurkat T cells RhT5α is more than 4-fold less potent than T5Cyp. The effect of modified hT5α in T cell lines, however, is minimal (FIG. 50).

Most data published on potency of T5-based restriction factors were obtained in CRFK or HeLa cells that allow for large HIV-1 restriction phenotypes. Furthermore, in published reports, constructs are most commonly HA-tagged at the N-terminus; a modification that seems to enhance restriction activity (Stremlau et al., 2004). Published data are often represented on a linear scale that obscures effects on HIV-1 at low MOI, where T5 activity is the strongest (FIG. 50). This is the optimal experimental system and data representation when analyzing T5 function and small modulations of T5 restriction. In CRFK and Cf2Th cells even multimerized CypA alone (Javanbakht et al., 2007) and fusions of CypA to Fv1 or afpartin, a protein known to form extended dimers, were reported to block HIV-1 infection when visualized on a linear scale, albeit with lower potency than T5Cyp (Schaller et al., 2007; Yap et al., 2007). Notwithstanding, other models may be useful for the analysis of physiological potency. Here a first side-by-side comparison is shown of untagged T5-based restriction factors in T cell lines, a model system that is more physiologically relevant for treatment of HIV-1 infection than feline fibroblasts. T5Cyp is a significantly more potent HIV-1 inhibitor than RhT5α in T cells, which may be due to the high CA-binding affinity of CypA combined with distinct interactions of the exogenous T5-restriction factor with endogenous hT5α. To address the latter, one could assess the HIV-1 inhibition efficiency of various T5 proteins in T5α KD T cells and see if the magnitude of HIV-1 inhibition now approaches that seen in CRFK cells.

The strict structural requirements for engineering a functional hT5Cyp fusion emphasize that the generation of the fusion gene by retrotransposition within New World owl monkeys (*Aotus* sp.) was truly a remarkable event. As it turns out, a TRIMCyp fusion gene was independently generated by retrotransposition in Old World macaques, though in the case of the latter, restriction activity is detected against HIV-2 and FIV, but not HIV-1 (Brennan et al., 2008; Newman et al., 2008; Virgen et al., 2008; Wilson et al., 2008). The convergent evolution of TRIMCyp fusion proteins with distinct retroviral specificities indicates a strong selection for these potent restriction factors. While the force behind the selection remains to be elucidated for each T5 orthologue, it is likely to have been exerted by challenge with a retrovirus (Sawyer et al., 2005). Here a fully human restriction factor, hT5Cyp, was engineered that potently blocks HIV-1 in vitro and in vivo.

Example 2

Assessment of hT5Cyp Effects on HIV-1 Spreading Infection in Primary $CD4^+$ T Cells and Macrophages Current Anti-HIV-1 Gene Therapy Approaches Recently, gene- and stem cell therapies in the treatment of HIV-1 have come into renewed focus. Furthermore, life-long pharmacotherapy is associated with serious long-term health risks and cannot lead to clearance of HIV-1 in infected patients due to persisting reservoirs of latently-infected cells (Han et al., 2007). The ideal gene therapy candidate should have high efficacy as well as low toxicity and antigenicity. The following anti-HIV-1 gene therapy approaches have been put forward: at the cellular level, modification of host-cell factors required for viral replication or inhibition of essential viral elements at all steps of the viral life cycle; and systemically, accelerated destruction of infected cells (Strayer et al., 2005). To block HIV-1 entry, the HIV-1 co-receptor CCR5 has been targeted by various means including siRNA (An et al., 2007; Kumar et al., 2008) and zinc-finger endonucleases (Perez et al., 2008) with success in vitro and in vivo. In rhesus macaques, transplant of autologous $CD34^+$ cells transduced with a lentiviral vector coding for GFP and CCR5-targeting shRNAs led to stable maintenance of transduced PBMCs for the 12-month duration of the experiment in vivo. Furthermore, transduced PBLs derived from monkeys were SIV-resistant upon ex vivo challenge in contrast to untransduced PBLs from the same animal. This approach revealed a dose-dependent toxicity of shRNA expression in T cells (An et al., 2007).

An elegant adaptation of the CCR5-knockdown approach is the targeting of CCR5-specific siRNAs in combination with siRNAs against tat and vif directly to T cells in vivo (Kumar et al., 2008). This was achieved by non-covalently linking siRNAs to a single-chain antibody against IL-7, which is rapidly internalized to deliver the siRNAs to T cells. The approach efficiently blocked established HIV-1 replication in a humanized NOD/SCIDI12rg$^{-/-}$ mouse model. More impressive results were obtained in a huPBL-NOD/SCIDI12rg$^{-/-}$ model with significant T cell protection and >4-fold reduction in plasma viral load following HIV-1 infection. Transplant of $HIV^+$ PBMCs into NOD/SCIDI12rg$^{-/-}$ mice leads to re-activation of viral replication due to T cell activation in the xenogeneic context. With triple siRNA-targeting to T cells in vivo reactivation fails to occur, viral loads remain below detection, and T cell destruction is not apparent. Notably, the triple-treatment was significantly more efficient than anti-CCR5 siRNA alone. Furthermore, since the siRNAs are transiently expressed, it is unclear how frequently treatment would be required (Kumar et al., 2008). Recently, a novel approach using a zinc-finger nuclease targeting CCR5 has been described that protects $CD4^+$ T cells and reduces viral load in a hPBL-NOD/SCIDI12rg$^{-/-}$ mouse model for HIV-1 infection. While this approach was quite effective at blocking spread of CCR5-tropic HIV-1 strains, there was a concern of off-target effects specifically with CCR2 excision (Perez et al., 2008). For all strategies targeting CCR5, disruption could select for CCR5-independent viruses (Taylor et al., 2008) and is not without consequence, as the CCR5Δ32 allele is a risk factor for symptomatic West Nile Virus infection (Glass et al., 2006).

$CD34^+$ human hematopoietic progenitor cells expressing RhT5α can be differentiated into HIV-1-resistant macrophages (Anderson and Akkina, 2005b). RhT5α, however, is a simian protein and potentially antigenic. This could lead to the elimination of modified cells in vivo as was observed for the introduction of the suicide gene thymidine kinase into gag-specific $CD8^+$ T cells in clinical trials (Riddell et al., 1996). To minimize antigenic potential, a chimeric rhesus-human $T5\alpha_{R323\text{-}332}$ with improved anti-HIV activity was introduced into $hCD34^+$ HSCs. Upon maturation in SCID thy/liv mice, T cells showed reduced infectability with HIV-1 ex vivo (Anderson and Akkina, 2008). RhT5α, however, is not as potent a restriction factor as hT5Cyp in T cells (FIG. 50), and $hT5\alpha_{R323\text{-}332}$ is indeed quite weak in T cell lines, raising the risk of in vivo selection for T5-resistant viruses.

One protein-based gene therapy strategy is delivery of a transdominant rev (Malim et al., 1992). RevM10 contains point mutations in the transactivation domain and retains the ability to bind the RRE and form multimers with wildtype rev, but can no longer facilitate transfer of immature RNAs to the cytoplasm. RevM10 reduces viral load in vitro and is safe in vivo, providing cells with a selective advantage in HIV-1 infected patients without, however, reducing viral load (Ranga et al., 1998). The major difficulty in this study was efficient retroviral delivery of RevM10 to patient-autologous T cells ex vivo combined with their short life-span (~6 months, compared to 3 weeks for controls) upon re-infusion into patients (Ranga et al., 1998). Equally poor maintenance of transduced cells was observed upon transduction of autologous $CD34^+$ cells derived from bone marrow with retroviral vectors directing the expression of a codon-optimized RevM10 in two $HIV\text{-}1^+$ children. RevM10 expression was lost in PBMCs at three months post-infusion (Marathe and Wooley, 2007). Other transdominant proteins used are tat, tat-rev fusions, and transdominant gag (Strayer et al., 2005).

Essential viral factors, such as rev, tat, gag, and nef have also been targeted by siRNA (Boden et al., 2003; Boden et al., 2007). Escape mutants arise easily in vitro, as single point mutations suffice to escape the siRNA-mediated block to HIV-1 replication (Boden et al., 2007). Thus, few siRNA approaches have been clinically tested. Consequently, siRNAs are commonly used in combination with each other or other strategies to synergize in increasing the block to HIV-1 replication and to reduce the potential of viral escape mutants (Anderson et al., 2007). The retroviral delivery of transdominant rev combined with TAR anitsense sequence, for example, was tested in 10 sets of twins with discordant HIV-1 status (Morgan et al., 2005). $CD4^+$ cells from the uninfected twin were transduced with retroviruses coding for RevM10 and anti-sense elements directed against HIV-2 TAR. Transduction efficiency was dependent on envelope used and ranged between 9-20%. Soon after transfer into patients, increased survival of modified T cells was observed by PCR and cells persisted over two years. (Morgan et al., 2005) Although data are insufficient, combination therapies could be associated with increased risk of toxicity (off-target effects of siRNAs, induction of the type I interferon response, or global changes of mRNA expression profiles) (An et al., 2007).

The accelerated destruction of infected cells includes approaches such as the tat-dependent expression of herpes simplex thymidine kinase (HSV-TK) causing conditional suicide of HIV-1 infected cells treated with acyclovir (Marathe and Wooley, 2007). As pointed out previously, expression of foreign proteins can lead to elimination of transplanted cells in vivo. Similarly, direct transduction of Jurkat T cells with a HIV-1 protease-dependent caspase 3 causes efficient apoptosis of infected cells without harming non-infected cells (Vocero-Akbani et al., 1999). A "suicide"-strategy that has been tested in clinical trials is the use of a CD3/CD4 chimeric receptor termed CD4ζ. CD4ζ has the transmembrane and extracellular domains of CD4, enabling attachment of HIV-1, and the cytoplasmic domain of CD3 (ζ chain), enabling TCR-like signaling in transduced cells upon HIV-1 binding (Roberts et al., 1994). CD4ζ has been expressed in autologous $CD4^+$ and $CD8^+$ T cells, generating HIV-1-specific T cells with the ability to enhance or execute killing of infected cells (Marathe and Wooley, 2007). Transfer of $\sim 10^{10}$ autologous $CD4^+$ and $CD8^+$ T cells expressing CD4ζ is safe and leads to persistence of $CD4\zeta^+$ T cells for more than 1 year post-transfer in the blood. Additionally, there was early evidence of mucosal seeding following ex vivo stimulation of T cells with αCD3/αCD28 beads ex vivo. Nevertheless, there was no significant change in viral burden and clear therapeutic effect was not obtained (Mitsuyasu et al., 2000). Similarly, assessment of CD4ζ autologous T cell therapy in twins with discordant HIV-1 status (gene modified cells are $HIV\text{-}1^-$ prior to infusion into the $HIV\text{-}1^+$ twin), showed no reduction of viral load or significant therapeutic effect. Transferred T cells could be maintained at 0.1-1% of peripheral blood lymphocytes for more than 1 year, showing long-term maintenance of transferred cells in the host after appropriate prior stimulation (Walker et al., 2000). Overall, enhancing the destruction of infected cells is a strategy that has failed to produce a therapeutic benefit. Possibly, killing HIV-1 infected targets occurs too late in the viral life cycle, thus allowing production of sufficient progeny virus for sustained viremia (Mitsuyasu et al., 2000; Walker et al., 2000).

Instead of accelerated destruction of infected cells, an actual cure of HIV-1 infection at the cellular level would be preferable. "Cure" can be achieved in tissue culture by the excision of integrated provirus from infected cells using a "molecular scissor": tre, a cre-recombinases evolved in vitro to be LTR-specific (Sarkar et al., 2007). In general, gene therapies that act early and potently in the viral life cycle would block the virus from becoming a heritable genetic element and would protect cells from CTL-mediated killing. If these therapies additionally act before reverse transcription they preclude genetic diversity acquisition required for development of resistance. Mathematical modeling predicts a therapeutic benefit only for approaches targeting HIV-1 before integration in the context of autologous T cell therapy (von Laer et al., 2006b). Approaches targeting viral gene expression (most of the approaches tested to date) would require a much higher inhibitory activity to promote regeneration of T cells and viral load reduction, whereas approaches targeting viral assembly and release would not have a clinical benefit in isolation (von Laer et al., 2006b). According to this mathematical prediction, using tre-therapy alone would be unlikely to have much immediate therapeutic benefit. Given that it takes more than 3 months to cure tissue culture cells of provirus (Sarkar et al., 2007), curing latently-infected, resting primary cells in vivo will be a great challenge. Nonetheless, excision of integrated provirus, may cure previously infected memory T cells including those found in GALT. In combination with other early-acting therapies, tre could assist in T cell regeneration while maintaining the established memory T cell repertoire including HIV-1 specific T cells; an exciting prospect indeed.

Delivery of Candidate Gene Therapy to Target Cells

Efficient and safe delivery of gene therapy vectors is crucial for any potential clinical treatment. The deleterious potential of insertional mutagenesis in humans was sadly highlighted following the activation of the LMO2 proto-oncogene by proximal insertion of gammaretroviral vectors carrying the IL-2 receptor gamma chain to treat X-linked SCID in patients (Hacein-Bey-Abina et al., 2008; Howe et al., 2008), marring an otherwise impressive success (Cavazzana-Calvo et al., 2000). Retroviruses are a preferred vector for gene delivery due to their ability to integrate into the host genome and provide heritable gene modification in progeny cells (Bushman, 2007). Regarding integration target site preference not all retroviruses are created equal. Gammaretroviruses like MLV, which have been used in human trials, have a preference for the 5' ends of transcriptional units (TUs) and associated CpG islands, particularly near promoters of active genes (Bushman, 2007; Wu et al., 2003). Lentiviruses, of which HIV-based vectors are most frequently used, prefer to integrate within active transcription units (Mitchell et al., 2004). Integrase (IN) is the principle viral determinant of integration specificity as chimeric HIV-1 containing MLV-IN integrates at MLV-preferred sites (Lewinski et al., 2006).

Efforts are underway to modulate integration site specificity for increased safety of retroviral vectors. LEDGF/p75 is known to tightly bind HIV-1 IN and target provirus integration (Maertens et al., 2003). siRNA-mediated knockdown of LEDGF/p75 altered the insertion profile of HIV-1 indicating that LEDGF/p75 tethers IN to DNA and promotes HIV-1 insertion into active TUs (Ciuffi et al., 2006). While LEGF/p75 binds DNA relatively non-specifically, a proof-of-principle in vitro experiment showed that a LEGFP/p75 fusion to the DNA-binding domain of the λ repressor directed integration of HIV-1 provirus close to λ repressor binding sites in target λ phage DNA (Ciuffi et al., 2006). Another approach to controlling integration target sites takes advantage of the homologous recombination pathway. Lentiviral vectors defective for IN are used to ensure nuclear import of a site-specific integration system bearing desired sequences (Lombardo et al., 2007). The benefit of such a strategy is both directed integration and physiologic expression control (Lombardo et al., 2007). By combining a zinc-finger-endonuclease and IL2Rγ sequences flanked with homologous arms in an IN-defective lentiviral vector, removal of the endogenous IL2Rγ segment and replacement with a trackable donor IL2Rγ sequence in the IL2Rγ locus (gene editing) was achieved (Lombardo et al., 2007). Both T cells and $CD34^+$ HSCs are targets of candidate gene therapy. While only CD34-based therapy has the potential to regenerate the entire T cell repertoire and with it anti-HIV-1 immune responses, it clearly has greater therapeutic potential. At the same time, it is a difficult procedure prone to complications and high toxicity as patients need to be conditioned prior to transplant. Additionally, safe retroviral vectors for HSC-based therapy are still under development. Autologous T cell therapy is less toxic, easier to perform and administer, and may lead to improvement in disease progression upon repeated administration even in the absence of restoring the T cell repertoire (Strayer et al., 2005; von Laer et al., 2006a).

To date, therapeutic levels of transgene expression were not achieved in clinical gene therapy trials despite some encouraging effects on T cell survival (von Laer et al., 2006a). Problems arise at two levels: one is high-efficiency gene delivery to T cells or $CD34^+$ hHSCs, and the other is design of early-acting HIV-1 inhibitors potent enough to allow for T cell regeneration in the context of viral load reduction. hT5Cyp has several properties that make it appealing for gene therapy. It inhibits HIV-1 infection even more potently that RhT5α when expressed in human cells, acting early in the viral life cycle. Furthermore, AoT5Cyp, after which hT5Cyp is modeled, is the only TRIM5 allele in 10 *Aotus* species (Ribeiro et al., 2005), indicating that cells bearing AoT5Cyp retain functionality. Similarly, no deleterious effects of hT5Cyp-expression were observed in T cell lines. This Example analyzes the anti-HIV-1 activity of hT5Cyp in spreading infection of HIV-1 as well as primary human T cells and macrophages.

hT5Cyp Eliminates Spreading Infection of HIV-1

While Example 1 dealt with the design and characterization of a hT5Cyp with potent anti-HIV-1 activity in single cycle assays, this Example assesses the effects of hT5Cyp on HIV-1 spreading infection. Jurkat T cells stably transduced with T5-expression vectors were infected with replication-competent HIV-$1_{NL4\text{-}3\text{-}GFP\text{-}IRES\text{-}Nef}$. No HIV-1 replication was detected in cells transduced with hT5Cyp or AoT5Cyp for the two-month observation period (FIG. 51A,B). HIV-1 replication in cells transduced with hT5Cyp bearing a mutation that blocks binding to HIV-1 CA (CypA-H126Q, see FIG. 49B), hT5CypH126Q, was as rapid as in cells transduced with empty vector (FIG. 51A,B).

In contrast to hT5α, RhT5α restricts HIV-1 (Stremlau et al., 2004). Chimeric T5 protein in which the PRYSPRY specificity determinant from the rhesus orthologue replaces the corresponding human residues (hT5α-R323-332 (Stremlau et al., 2005) (Sawyer et al., 2005)), or even in which a single, critical amino acid was substituted (R332P (Li et al., 2006b)), exhibit HIV-1 restriction activity approaching that of RhT5α in HeLa and CRFK cell lines. Since these molecules are nearly identical to the human protein it has been proposed that they may have therapeutic utility (Anderson, 2008; Li, 2006; Stremlau, 2005; Yap, 2005). As reported in Example 1, hT5α-R323-332 and hT5α-R332P caused moderate inhibition of HIV-1 transduction in single-cycle infection, each behaving similarly to the other, though neither was as potent as hT5Cyp or AoT5Cyp (FIG. 50). When the effect of hT5αR332P was tested in a spreading infection, there was a delay in the peak of HIV-1 that was inversely proportional to initial viral dose, but in contrast to hT5Cyp or AoT5Cyp, it failed to prevent HIV-1 infection (FIG. 51A,B). Similarly, when compared to T5Cyp, RhT5α inhibited HIV-1 spread over 5-fold 12 days post-infection (FIG. 51C). Furthermore, peak viral replication was delayed by 24 days in Jurkat T cells transduced with lentiviral vectors coding for RhT5α. In stark contrast to hT5cyp and AoT5Cyp, RhT5α was unable to block spread of HIV-1 in these cells (FIG. 51C).

Figure 51:
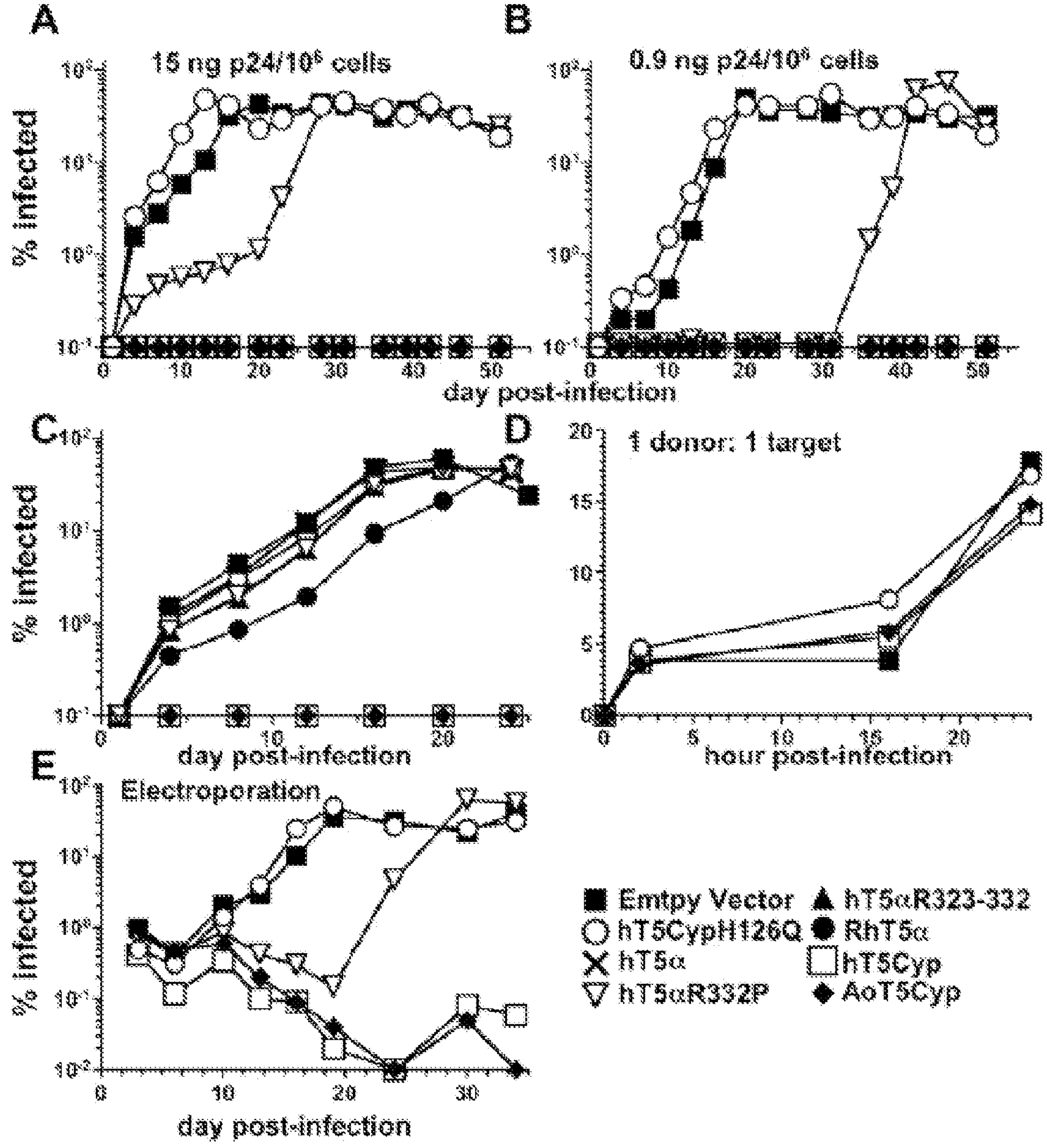
FIGS. 51A-E. hT5Cyp potently blocks replication-competent HIV-1. (A,B,C) Jurkat T cells expressing the indicated proteins were infected with cell-free HIV-$1_{NL4-3-GFP-IRES-Nef}$, 15 ng p24/$10^6$ cells (A, C) or 1 ng p24/$10^6$ cells (B) and the percentage of infected cells was recorded on indicated days. (D) Indicated DiD-labelled target T cell lines were infected with HIV-$1_{NL4-3}$-infected Jurkat donor cells. The percentages of infected target cells were analyzed at the 4, 16, and 24 hours post initiation of co-culture by intracellular p24 staining. (E) Jurkat T cell lines were electroporated with HIV-$1_{NL4-3-GFP-IRES-Nef}$ and the percentage of infected cells was recorded on indicated days. A-E: time post-infection is depicted on the X-axis, and % infected cells on the Y-axis.

HIV-1 has the capacity to acquire resistance to many antivirals during the step of reverse transcription, which allows for accumulation of genetic diversity in progeny. One focus was to see whether a hT5Cyp-resistant virus could be generated, with the purpose of studying its pathogenicity further. hT5Cyp and AoT5Cyp-resistant HIV-1 could not be isolated on 10 separate occasions (representative data FIG. 51, A-C), despite initiation of infection with a wide-range of HIV-1 inocula. Similarly, addition of untransduced cells and their subsequent removal using puromycin (the Jurkat T cell lines are puromycin resistant) failed to yield resistant virus. Furthermore, T5-mediated restriction in our Jurkat T cell lines can be overcome by using cell-associated rather than cell-free virus. To this end Jurkat T cell lines expressing the indicated T5Cyp or control were labeled with the fluorescent dye DiD (target) and mixed with Jurkat T cells previously infected with HIV-$1_{NL4-3}$ (donor) at a 1:1 ratio. All cell lines were equally infectible by cell-associated virus (FIG. 51D). Similar results were obtained by another group in primary $CD4^+$ T cells expressing RhT5α and in $CD4^+$ T cells from rhesus macaques (Richardson et al., 2008).

Studies were designed to see whether a similar system could be exploited in order to select for a T5Cyp-resistant virus. One approach was to introduce HIV-$1_{NL4-3-GFP-IRES-Nef}$ proviral DNA into Jurkat T cell lines expressing T5 or control by electroporation, to ensure that spreading infection was initiated by cell associated virus in the absence of free virus. The transfection efficiency was comparable for all cell lines analyzed and remained constant at about 1% of total cells in culture for the first 10 days post-electroporation (FIG. 51E). In Jurkat T cells expressing AoT5Cyp and hT5Cyp the infection was self-limiting and the percentages of infected cells had dropped to background levels by 34 days post-electroporation, without evidence for spread of HIV-$1_{NL4-3-GFP-IRES-Nef}$ (FIG. 51E). hT5α-R332P, in contrast, was able to delay peak viral replication by 10 days but failed to ultimately control spread (FIG. 51E). Again no T5Cyp-resistant HIV-1 could be derived in this experimental setting.

Figure 52:
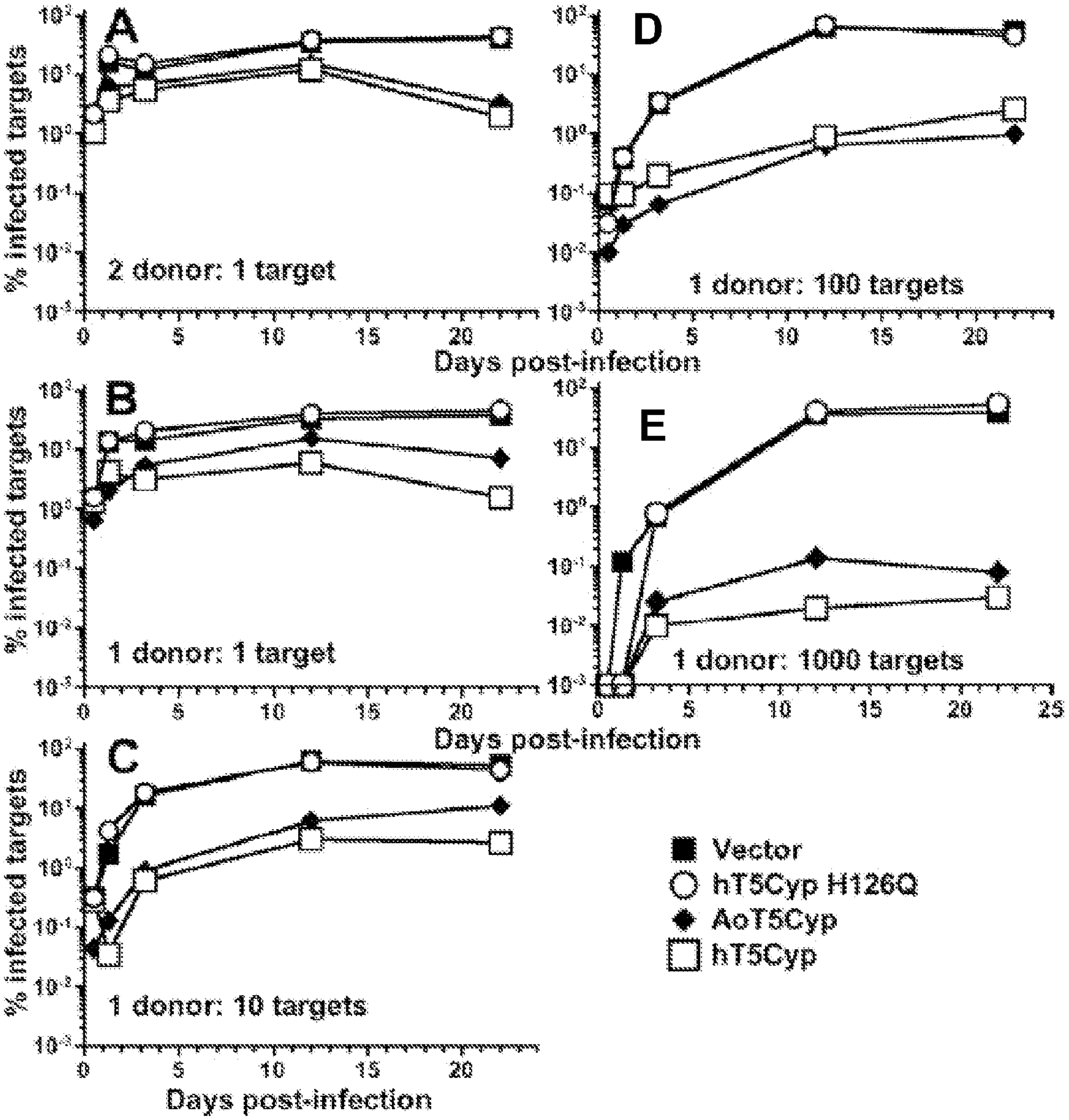
FIGS. 52A-E. Indicated DiD-labelled target T cell lines were infected with HIV-$1_{NL4-3-GFP-IRES-Nef}$-infected Jurkat donor cells. The percentages of infected target cells were analyzed at the indicated times post initiation of co-culture by flow cytometry for GFP expression. Puromycin was added at day 4 of co-culture to eliminate donor cells. Donor (D) and target (T) cells were mixed at a D:T ratio of (A) 2:1, (B) 1:1, (C) 1:10, (D) 1:100, (E) 1:1000.

Regardless of how spreading infection is initiated, cell-associated virus is essential and mechanical disruption of cell-to-cell association blocks spread of virus in vitro (Sourisseau et al., 2007). Furthermore, it represents the main method of transmission in vivo (Haase, 1999). In an attempt to reconcile that T5Cyp-mediated HIV-1 restriction is overcome by cell-associated virus in the first 24 hours post-infection (FIG. 51D) but concomitantly T5Cyp blocks spread when a long-term spreading infection was initiated with cell-associated virus (FIG. 51E), further experiments were undertaken. Spreading infections were initiated by co-culturing HIV-$1_{NL4-3-GFP-IRES-Nef}$-infected Jurkat T cells (donors) with DiD-labeled Jurkat T cell lines stably transduced with bicistronic lentiviral vectors coding for T5Cyp and puromycin resistance (targets). Donors (D) and targets (T) were mixed at different ratios: 2D:1T, 1D:1T, 1D:10T, 1D:100T, and 1D:1000T (FIG. 52, A-E). Unlike the pervious experiment (FIG. 52D), where infected target cells were monitored for only 24 hours, here infected target cells were monitored for 24 days (FIG. 52, A-E). Since DiD is a fluorescent membrane dye and is diluted out with cell division, puromycin was added on day 3 of the co-culture to ensure continued monitoring of target cells only.

For all donor to target ratios, initial infection of T5Cyp-expressing cells was comparable to control and proportional to infecting dose (FIG. 52, A-E). HIV-1 spread in T5Cyp-expressing cells is less efficient, however, resulting in control of infection over time (FIG. 52, A-E). The largest difference in levels of infection between control and T5Cyp-expressing Jurkat T cells were observed at the lowest D:T ratios of 1D:100T and 1D:1000T with a respective 400- and 100-fold difference at day 22 (FIG. 52D,E). At the highest D:T ratios of 2D:1T and 1D:1T, this difference was reduced to 20-fold at day 22 (FIG. 52A,B). Combined, these results indicate that while T5Cyp-transduced cells can be infected by cell-associated HIV-1, over time a T5Cyp-mediated inhibition of HIV-1 spread is apparent.

The mechanism underlying these observations has not yet been determined. Overexpression of RhT5α reduced HIV-1 production without affecting infectivity (Sakuma et al., 2007; Zhang et al., 2008a). This would implicate T5-mediated restriction both at post-entry and at a much later step in the viral life cycle (Sakuma et al., 2007; Zhang et al., 2008a). These observations may be an artifact due to overexpression of an exogenous protein, while knockdown of endogenous RhT5α seems to have no effect on HIV-1 production (Zhang et al., 2008a). To assess the effects of donor and target cell T5Cyp on cell-to-cell spread of HIV-1, a single-cycle cell-to-cell spreading assay for HIV-1 infection was designed. 293T donor cell lines expressing control or indicated T5Cyp were transfected with HIV-$1_{NL4-3-IRES-GFP-Nef}$ provirus and supernatant was harvest during the first 48 hours to measure production of virus by RT activity. 48 hours post-transfection, donor cells were washed three times with PBS and then DiD-labeled target Jurkat T cells transduced with control vector or vector coding for hT5Cyp were added to the 239T donor cells (FIG. 53A). At the indicated time points dextran sulfate was added to the co-culture to block further infection and cells were harvested. 48 hours later the percentage of infected target Jurkat T cells was measured by flow cytometry (FIG. 53A). The magnitude of HIV-1 restriction in single cycle assays using cell-free virus is shown for recipient Jurkat T cell lines and donor 293 T cell lines is shown (FIG. 53B).

In this single-cycle cell-to-cell infection it became clear that for short co-culture time (2 hours) both donor and target cell-T5Cyp cooperate to inhibit infection of donor cells (FIG. 53C, left panel). Infection of control target cells is 10-fold and 3-fold lower when the donor cells expressed hT5Cyp or AoT5Cyp, respectively, as compared to donor cells transduced with empty vector (FIG. 53C, left panel). Similarly, donor and target cell hT5Cyp cooperate to reduce infection of hT5Cyp-expressing targets further than when donor cells contain empty vector (FIG. 53C, left panel). With increased time of co-culture, the effects of donor T5Cyp are lost. When target cells transduced with empty vector were co-cultured with donor cells for 12 hours, the percentage of infected cells approached similar values regardless of donor cell phenotype (FIG. 53C, right panel). Similarly, after 12 hours of co-culture, target cells containing hT5Cyp inhibit infection to the same degree whether donor cells contained control vector or hT5Cyp (FIG. 53C, right panel). This effect is not due to an effect of T5Cyp on viral production in the 293T donor cells, as quantification of relative RT units 48 hours post-transfection showed comparable viral production in cells transduced with T5Cyp or control hT5CypH126Q and higher viral production in cells transduced with empty vector alone (FIG. 53D). Similarly, virus release was similar in all target cells (FIG. 53E). The effects observed for T5Cyp in donor cells during short co-cultures could account for our observation that, once initiated, spreading infection of HIV-1 dwindles and is controlled over time.

hT5Cyp Blocks HIV-1 Infection of Primary Human $CD4^+$ T Cells and Macrophages

To assess the feasibility of hT5Cyp as a viable HIV-1 therapy, hT5Cyp-mediated restriction of HIV-1 in primary human $CD4^+$ T cells and macrophages was assessed. To identify cells transduced with T5, a bicistronic lentiviral vector was used that directs synthesis of GFP from an internal ribosome entry site (FIG. 54A). These vectors failed to generate GFP in primary $CD4^+$ T cells (FIG. 54B) although they functioned efficiently in Jurkat T cell lines. Next, hT5Cyp was cloned into a bidirectional dual-promoter vector (BiD) in which the PGK promoter and a minimal CMV promoter drive transcription of hT5Cyp and GFP, respectively (Amendola et al., 2005). GFP production and hT5Cyp function in a single cycle assay using an HIV dsRed vector were efficient in Jurkat T cell lines transduced with BiD encoding hT5Cyp or hT5CypH126Q. BiD, however, failed to yield $GFP^+$ primary $CD4^+$ T cells. Better results were obtained when a vector, scALPS, was engineered using two promoters, one from the SFFV LTR and the other from the hCypA gene (SEQ ID NO:8) (FIG. 54A,B). $CD4^+$ T cells were transduced with scALPS encoding either hT5Cyp (SEQ ID NO:9) or the non-restrictive hT5CypH126Q. Cells were then sorted based on GFP-expression. Relative quantification of GFP, hT5Cyp, and hT5CypH126Q mRNA showed that all were efficiently transcribed at comparable levels in $CD4^+$ T cells (FIG. 54C, D). Expression of hT5Cyp and hT5CypH126Q was not detectable in these cells by western blot, corresponding to our previous experience in Jurkat T cell lines. To test for equivalent protein synthesis from both promoters, dsRed was cloned into scAPLS, such that the SFFV and hCypA promoters drive transcription of dsRed and GFP, respectively (FIG. 55A). While dsRed fluorescence was too weak in $CD4^+$ T cells to obtain reliable data, in transduced Jurkat T cells the majority of $GFP^+$ cells also expressed dsRed efficiently compared to mock-transduced cells (FIG. 55B). Also, expression of dsRed did not interfere with GFP expression as GFP-expression was equally efficient when scALPS-GFP or scAPLS-GFPdsRED vectors were used to transduce Jurkat T cells (FIG. 55B).

$CD4^+$ T cells were enriched from PBMCs using MACS, and activated using irradiated allo-PBMC and IL-2. Activated $CD4^+$ T cells were then transduced with dual-promoter vectors encoding either hT5Cyp or the non-restrictive hT5CypH126Q. Cells were sorted based on GFP-expression and then challenged with replication-competent, CXCR4-tropic, HIV-$1_{NL4-3}$. Viral replication in hT5CypH126Q-transduced cells peaked on day 12 and infection was not established in hT5Cyp-transduced cells (FIG. 56A). The same hT5Cyp-mediated block to infection was observed with the CXCR4-tropic primary isolate HIV-$1_{DH12}$ (FIG. 56B). To test hT5Cyp activity in human macrophages, $CD14^+$ cells were enriched from PBMCs using MACS and differentiated for 10 days in the presence of GM-CSF. Monocyte-derived macrophages were pre-treated with $SIV_{MAC}251$ virus-like particles (VLPs) (Goujon et al., 2006) and transduced with vectors encoding hT5Cyp or hT5CypH126Q and sorted based on GFP-expression four days after transduction. Cells were infected with HIV-$1_{NL4-3}$, modified to be CCR5-tropic. While input virus decays in cells transduced with hT5Cyp and infection is not established, infection peaks on day 10 post-infection in cells transduced with the non-restrictive hT5CypH126Q (FIG. 56C). Similar results were obtained when transduced macrophages were challenged with the CCR5-tropic primary isolate HIV-$1_{132W}$ (FIG. 56D). Both $CD4^+$ T cells and monocyte-derived macrophages transduced with hT5Cyp were resistant to HIV-1 infection (FIG. 56).

hT5Cyp Confers Selective Advantage to $CD4^+$ T Cells Challenged with HIV-1

The previous experiments showed that HIV-1 infection is blocked when all cells in the culture have been transduced with the hT5Cyp vector. Next anti-HIV-1 efficacy was evaluated under suboptimal conditions, in which <25% of cells were transduced with hT5Cyp. These conditions would be more realistic of hT5Cyp therapy in patients. In the absence of HIV-1 infection, the percent transduced cells persisting in the culture over the course of a month was equivalent for hT5Cyp and hT5CypH126Q. In the face of HIV-1 infection, the hT5CypH126Q cells declined to <10% of the cells in the culture. hT5Cyp cells, in contrast, had a distinct advantage, expanding to 75% of the cells in the population after re-stimulation of the $CD4^+$ T cell cultures using irradiated allo-PBMC and IL-2 (FIG. 57A). Consistent with these data, viral replication as assessed by RT activity in the culture supernatant was significantly lower in cultures transduced with hT5Cyp than in those transduced with hT5CypH126Q (FIG. 57A). Furthermore, while high viral replication is already apparent on day 12 post-infection in $CD4^+$ T cells transduced with hT5CypH126Q, viral replication does not peak until day 28 of the culture in $CD4^+$ T cells transduced with hT5Cyp; the first time-point after re-stimulation of the culture (FIG. 57A). The survival advantage of $CD4^+$ T cell becomes apparent when analyzing the viability of the cells by forward versus side-scatter and gating on live lymphocytes; a method that had to be adopted since the cells were fixed in paraformaldehyde for flow cytometry analysis. While transduced $CD4^+$ T cells were equally viable at the beginning of the experiment, throughout the course of the experiment $CD4^+$ T cells transduced with hT5Cyp had a viability advantage (FIG. 57B). After restimulation of the cultures, viable cells were rescued in $CD4^+$ T cell cultures transduced with hT5Cyp while there was no rescue of cells transduced with hT5CypH126Q (FIG. 57B, day 34). Representative plots are shown in FIG. 57C. Both the GFP selection and survival advantage observed for $CD4^+$ T cells transduced with hT5Cyp were most likely due to the antiviral activity of hT5Cyp, since HIV-1 replication was reduced in cultures containing hT5Cyp cells (FIG. 57A). Thus, even when a minority of cells are transduced in culture conditions where HIV-1 can spread directly from cell-to-cell, hT5Cyp is potent enough to block HIV-1 infection.

Effects of hT5Cyp on $CD4^+$ T Cell Function

While hT5Cyp efficiently blocks HIV-1 infection, in view of a potential therapeutic use, is essential that this occurs without perturbing primary $CD4^+$ T cell function. Primary $CD4^+$ T cells transduced with scAPLS bearing hT5Cyp (SEQ ID NO:9) were sorted based on GFP-expression. Transduced cells proliferated at the same rate as untransduced cells as untransduced cells as seen by thymidine incorporation (FIG. 58A). When stimulated with PMA and ionomycin, scAPLS-hT5Cyp transduced $CD4^+$ T cells produced comparable amounts of IL-2 as untransduced cell (FIG. 58B). Similarly, untransduced and scAPLS-transduced $CD4^+$ T cells expressed the same level of cell-surface CD4, CXCR4, and MHC I (FIG. 58C) as well as CD11a, CD18, ICAM3, CCR5, CD25, CD69, and PD-1. The functions of endogenous CypA and T5 in $hCD4^+$ T cells remain largely uncharacterized. Addressing these functions could improve predictions regarding the potential impact of introducing hT5Cyp into $CD4^+$ T cells. CypA is known to interact at subnanomolar affinity with cyclosporine (CsA), an immunosuppressive agent used to prevent allograft rejection. This complex inhibits T cell function by binding to the serine/threonine phosphatase calcineurin and blocking downstream signaling events (Handschumacher et al., 1984; Liu et al., 1991). Functionally, CypA is a peptidyl-prolyl isomerase (PPiase) which catalyses the rate-limiting cis-trans interconversion of peptide bonds N-terminal to proline, an enzymatic activity not required for immunosuppression via CsA (Fischer et al., 1984; Liu et al., 1991; Schmid, 1995). The peptidyl-prolyl isomerases are represented by three structurally distinct families: cyclophilins, FKBPs, and parvulins. Given their astounding evolutionary persistence, from some archeabacteria to all mammals, cyclophilins are not well understood (Colgan et al., 2000; Gothel and Marahiel, 1999).

Despite ubiquitous, high-level expression, CypA is not essential for viability in mice (Colgan et al., 2000; Ryffel et al., 1991). $CypA^{-/-}$ mice show hallmarks of allergic disease, such as allergic belpharitis, tissue infiltration by mast cells and eosinophils and elevation of serum IgE, IgG1, and IL-4 (Colgan, 2004). CypA is a negative regulator of the tec kinase itk which, primarily expressed in Th2 cells, potentiates signals downstream of the T cell receptor. Disruption of CypA in mice thus results in a hypersensitive Th2 response (Colgan, 2004). Consistent with the allergic phenotype, in vivo- and in vitro-generated $CypA^{-/-}$ effector and memory Th2 cells produced 2-4 fold higher IL-4 than wildtype cells accompanied by a comparable increase in IL-4 mRNA (Colgan, 2004).

IL-2 production, however, was also found to be consistently elevated in effector and memory $CD4^+$ T cells derived from $CypA^{-/-}$ mice, following stimulation with plate-bound αCD3 and αCD28 antibodies (Colgan et al., 2004). Similar results were obtained with in vitro differentiated Th2 effector or memory cells (FIG. 59A). The magnitude of this effect ranges from 5-30 fold (FIG. 59A). Surprisingly, unlike IL-4 elevation, increase in IL-2 production cannot be correlated with increased transcription of IL-2 mRNA (FIG. 59B), indicating that CypA regulates IL-2 expression post-transcriptionally. Furthermore, in vivo IL-2 capture shows that following TCR-stimulation, serum IL-2 levels are elevated more than 2-fold at time of peak production (FIG. 59C).

To evaluate if CypA had similar effects in human primary $CD4^+$ T cells, a lentiviral vector was generated to efficiently knock down target mRNAs in primary human $CD4^+$ T cells. APM contains a promoter derived from the SFFV LTR to drive puromycin-N-acetylase and sequence coding for the desired shRNA flanked on each side by miR-30 (FIG. 60A). $CD4^+$ T cells were enriched from PBMCs of healthy donors using MACS, stimulated with irradiated allo-PBMC and IL-2, and transduced with APM containing shRNA targeting luciferase (Luc) as a control, or either CypA or T5 (see below). After puromycin selection, knockdown efficiency was assessed at the mRNA-level by quantitative RT-PCR (FIG. 60B) and at the protein level by Western blot (FIG. 60B). Given efficient knockdown of CypA in primary human $CD4^+$ T cells, infectability of these cells was assessed by VSVG-pseudotyped HIV-$1_{NL4-3}$ GFP, HIV-$2_{ROD}$-GFP, and $SIV_{mac}$239-GFP vectors, primarily to see whether phenotypes previously reported in human cell lines were preserved in primary $CD4^+$ T cells (FIG. 60D).

Indeed, as observed in cell lines, CypA promotes HIV-1 infection in primary $CD4^+$ T cells, presumably by protection of HIV-1 from an unknown restriction factor. In the absence of CypA, HIV-1 infection is reduced by more than 2-fold (FIG. 60D). CypA did not have an effect on HIV-$2_{ROD}$ or $SIV_{mac}$239 infection. A more than 100-fold restriction of $SIV_{mac}$239 in $CD4^+$ T cells that was previously noted in Jurkat T cells and PBMCs was confirmed (FIG. 60D). Furthermore, an association of either CypA or T5 with restriction of $SIV_{mac}$239 in $CD4^+$ T cells was ruled out (FIG. 60D). Knockdown of T5 in primary $CD4^+$ T cells had no effect on HIV-$1_{NL4-3}$, HIV-$2_{ROD}$, and $SIV_{mac}$239 infection (FIG. 60D).

The most consistent and impressive phenotype observed in CypA KD $CD4^+$ T cells was on proliferation. At steady state, 4 days after secondary stimulation with irradiated allo-PBMC and IL-2, CypA KD bulk, non-polarized $CD4^+$ T cells incorporated 4-fold more thymidine than Luc KD control cells (FIG. 61A). This effect was even greater (close to 10-fold higher thymidine incorporation in CypA KD cells compared with Luc KD control) when proliferation was assessed in a Th2 memory T cell population isolated from a healthy donor based on CD4 and CrTh2 expression (Messi et al., 2003) (FIG. 61A). Consistent with increased cell cycling, staining CypA KD $CD4^+$ T cells for RNA content by Pyronin Y and DNA content by 7-AAD showed the majority of cells in the G2/M/S phase in CypA KD cells while control Luc KD cells had the expected majority in the G1 phase of the cell cycles (FIG. 61B). Similarly, CypA KD $CD4^+$ T cells are dividing faster than Luc KD control $CD4^+$ T cells as visualized by CFSE dilution 48 hours after staining (FIG. 61C). These results are consistent with a T cell hyperactivtion in the absence of CypA through loss of itk regulation as described for the $CypA^{-/-}$ mouse (Colgan et al., 2004). As observed for murine Th2 cells, human $CD4^+$ Th2 memory cells produce almost 10-fold more IL-2 in the absence of CypA compared to Luc KD cells; in this case at steady state without stimulation (FIG. 61D). By staining for intracellular cytokines, both IL-2 and IL-4 production are increased two-fold in CypA KD, non-polarized human $CD4^+$ T cells compared to the Luc KD controls following PMA/ionomycin stimulation (FIG. 61E).

Since T5 has no mouse homolog, little is known about its functions in human T cells outside of modulation of HIV-1 infection than is the case for CypA. When T5 expression was knocked down as previously described (FIG. 60A,B), there was a strong reduction in thymidine incorporation of $CD4^+$ T cells compared to control Luc KD $CD4^+$ T cells (FIG. 62A). T5 seems required for sustained proliferation of $CD4^+$ T cells. Consistent with cell cycle arrest, staining T5 KD $CD4^+$ T cells for RNA content by Pyronin Y and DNA content by 7-AAD showed that only 16% of T5 KD cells were cycling (G1/S/G2/M phase) while 84% were quiescent, compared with 89% cycling LucKD and 98% cycling CypA KD $CD4^+$ T cells (FIG. 62A,B). Similarly, T5 KD $CD4^+$ T cells failed to divide in comparison to Luc KD $CD4^+$ T cells as visualized by CFSE dilution 48 hours after staining (FIG. 61C). Interestingly, T5 affects steady-state proliferation but not an immediate response to stimulation. When T5 KD and Luc KD cells are synchronized by serum starvation and stimulated either using plate-bound α-CD3 and α-CD28 antibodies or irradiated allo-PBMC with IL-2, proliferation in the first 48 hours is similar in T5 and Luc KD T cells.

Differences in proliferation become increasingly apparent by 10 days post-stimulation with T5 KD cells reaching a quiescent state earlier than Luc KD control cells (FIG. 61) and dying in the absence of re-stimulation. The effects of T5 on steady-state proliferation posed some technical difficulties, and information could not be obtained on Th1 or Th2-skewed memory cells (Messi et al., 2003) that are significantly more difficult to handle than non-polarized bulk $CD4^+$ T cells. Notwithstanding, intracellular cytokine staining for IL-2, IL-4, IFNγ, and TNFα did not reveal any significant differences between T5 KD and Luc KD $CD4^+$ T cells despite stimulus titration. Similarly, neither CypA nor T5 KD cells showed any difference in steady-state expression of the cell-surface markers CD3, TCRαβ, CD4, CXCR4, CCR5, CD25, CD69, MHCI, and PD1 compared to Luc KD $CD4^+$ T cells at steady state.

Discussion

The more successful gene therapy approaches to date have followed two main strategies: either modification of host-cell factors required for viral replication or inhibition of essential viral elements (Strayer et al., 2005). Here, a third approach was adopted: the exploitation of natural inhibitors that evolved over millions of years in primates in response to retroviral attack (Li, 2006; Sawyer, 2005; Stremlau, 2005; Yap, 2005). The potent block to HIV-1 observed with AoT5Cyp inspired the design of a human equivalent, hT5Cyp, that robustly blocks HIV-1 in single cycle assay in vitro. This Example assesses the anti-HIV function of hT5Cyp under more physiological conditions, including spreading infection of HIV-1 in primary human cells. An optimal gene therapy candidate should provide a broad-range high efficacy combined with low antigenic potential. It should further preclude the emergence of viral resistance while not perturbing host cell function.

hT5Cyp is a potent HIV-1 inhibitor and acts early in the viral life cycle (FIG. 44). Since it targets reverse transcription it precludes the accumulation of genetic diversity during this stage of the viral life cycle. Therefore, viral escape mutants to T5Cyp are not expected to arise easily. Indeed, when stably expressed in Jurkat T cells, T5Cyp blocked spread if HIV-1 for the nearly two-month duration of the experiment, while the modified hT5$\alpha_{R332P}$ gene therapy candidate only delayed spread of HIV-1 (FIG. 51A, B). Furthermore, a comparison of various T5s stably expressed in Jurkat T cells, showed that even while RhT5α reduced the level of HIV-1 infection, it was not sufficient to block spread. In this assay, hT5$\alpha_{R332P}$ and hT5$\alpha_{R323-332}$ had little effect on magnitude of HIV-1 infection and kinetics of spread, while hT5Cyp completely blocked HIV-1 spread (FIG. 51C). This points to hT5Cyp as the most efficient HIV-1 inhibitor in this new class of candidates.

Viruses resistant to T5Cyp-mediated restriction could not be obtained in more than 10 separate long-term spreading infections initiated with a broad range of viral inocula. To allow for improved accumulation of genetic diversity and increase the probability of obtaining T5Cyp resistant HIV-1 in culture, untransduced Jurkat cells were co-cultured in spreading infection with T5Cyp-expressing Jurkat cells. Untransduced cells were efficiently infected, however, no hT5Cyp-resistant virus could be obtained upon their removal from co-culture using puromycin. The generation and characterization of a hT5Cyp resistant virus would have allowed its pathogenic potential to be gauged. Example 1, for instance, shows that HIV-1 bearing the G89V mutation in CA is resistant to T5Cyp-mediated restriction. This virus, however, replicates poorly in tissue culture (Sayah and Luban, 2004) as do other CA-mutants with reduced CypA binding affinity (Yin et al., 1998). Should a T5Cyp resistant virus arise in vivo it is likely to bear mutations in the CypA binding loop of CA. Given attenuated infectivity of such CA variants, a hT5Cyp resistant virus may act to boost an immune response to HIV-1 rather than cause HIV-1 related pathogenicity.

A naturally-occurring CA mutant, resistant to CsA treatment, was nonetheless susceptible to T5Cyp-mediated restriction (FIG. 49D) (Chatterji et al., 2005). This CA-variant is reportedly partially sensitive to AoT5Cyp-mediated restriction in OMK cells and bears 4 amino acid substitutions surrounding the CypA binding loop (Chatterji et al., 2005). Initiation of spreading infection using this CA-variant HIV-1 may allow for in vitro generation of hT5Cyp resistant HIV-1. Similarly, initiation of spreading infection in the presence of low levels of a pharmacologic inhibitor of the CA-CypA interaction may promote such emergence of T5Cyp-resistant viruses.

During co-culture of hT5Cyp-expressing cells with untransduced cells, it was noted that T5Cyp-bearing cells can be infected by cell-associated HIV-1, despite their resistance to cell-free virus. Especially at early time-points after initiation of co-culture, there was no difference in infectability of T5Cyp-expressing cells and controls (FIG. 51D). Since T5-mediated restriction is saturable, and cell-to-cell transmission of HIV-1 is 2-3 orders of magnitude more efficient than infection with cell-free virions (Dimitrov et al., 1993), this is likely a saturation of T5-mediated restriction. Similar results were obtained by a group assessing the potential for RhT5α and modified hT5α as candidate HIV-1 gene therapy in primary human $CD4^+$ T cells (Richardson et al., 2008). Given the resistance of cell-associated HIV-1 to T5α-mediated restriction, modified hT5$\alpha_{R323-332}$ was considered unlikely to have therapeutic benefit in vivo (Richardson et al., 2008). T5Cyp, however, is a significantly stronger HIV-1 inhibitor than hT5$\alpha_{R323-332}$ and even RhT5α (FIG. 51C). When the duration of spreading infections initiated with cell-associated HIV-1 was extended, a control of HIV-1 spread over time by hT5Cyp was observed (FIG. 52,A-E).

The mechanism underlying the gradual control of HIV-1 cell-to-cell transmission by hT5Cyp is unclear. A system was designed to clarify the effects of T5Cyp on cell-to-cell spread in a single cycle of infection (FIG. 53). During short time of co-culture both donor and target cell T5Cyp had an effect on HIV-1 infection of targets. Longer coculture times eliminated the effect of donor cell T5Cyp, while target cell T5Cyp still reduced level of HIV-1 infection. Both RT activity in donor cell supernatant as well and gag-production assayed by pulse-chase are similar in T5Cyp-expressing and control cells. Consequently, T5Cyp has no effect on viral production in donor cells (FIG. 53D, E). One possibility is that some T5Cyp is transferred from donor cell to the target cell either through filopodial bridges formed during cell to cell transfer (Sherer et al., 2007) or through encapsidation of T5Cyp into nascent virions (Sakuma et al., 2007). These possibilities could be distinguished by a thorough biochemical analysis as well as imaging the fate of T5Cyp during cell to cell transfer. Following prolonged cell-to-cell contact, the concentration of transferred virus may be high enough to saturate an effect of transferred T5Cyp. During each viral life cycle the effects of donor and target cell T5Cyp can accumulate, ultimately leading to T5Cyp-mediated control of spreading infection despite initial productive infection of T5Cyp-expressing cells.

Figure 55:
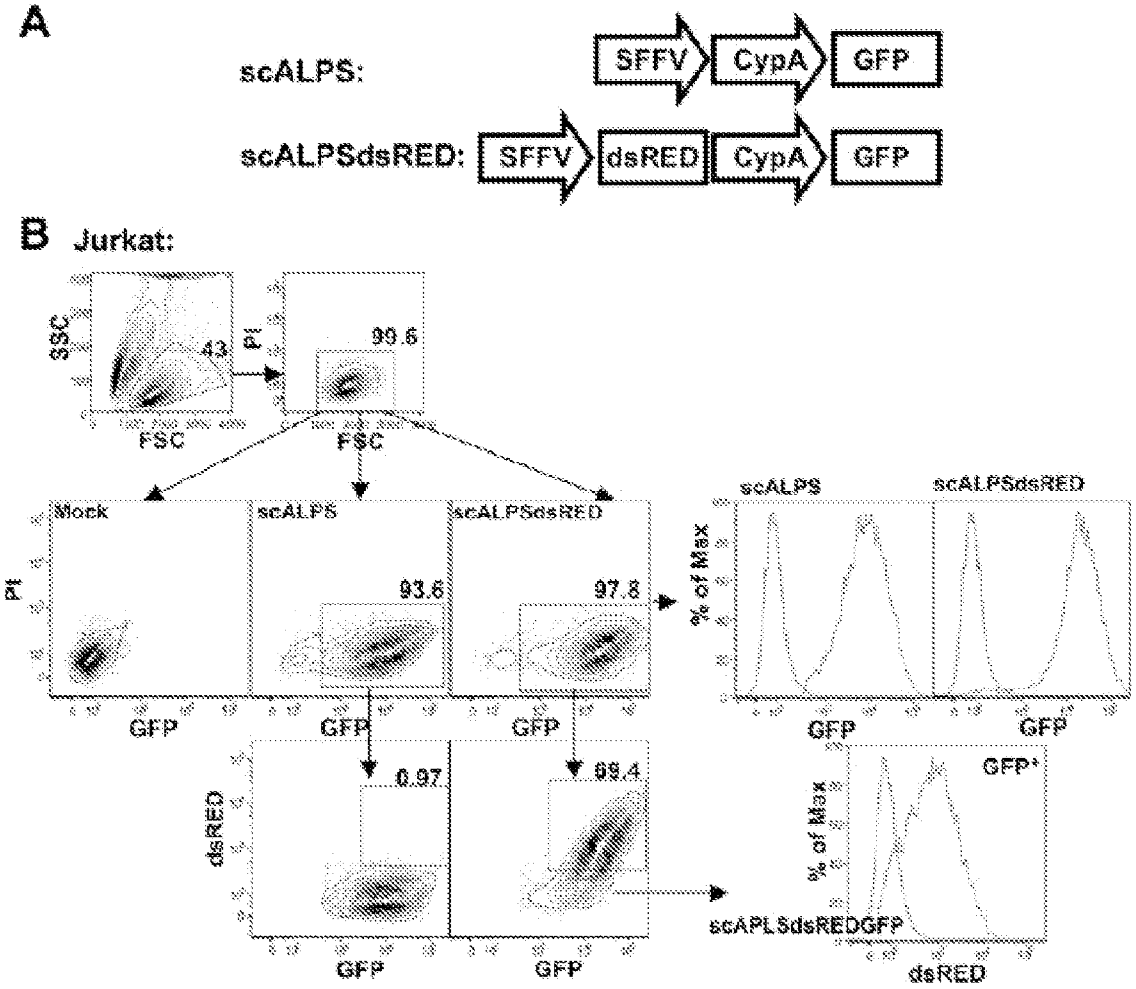
FIGS. 55A-B. (A) Schematic of dual-promoter lentiviral vectors (scALPS and scALPSdsRed) used to transduce Jurkat T cells. (B) Representative plots of GFP and dsRed expression in scALPS-transduced Jurkat T cells.

We wished to assess hT5Cyp-mediated inhibition of HIV-1 in primary $CD4^+$ T cells and macrophages. Ideally, it would be possible to co-express hT5Cyp and a reporter in primary human cells to eventually enable in vivo tracking of transduced cells. Since pre-existing gene-delivery vectors available failed to express GFP at satisfactory levels, a new dual-promoter lentiviral vector, scAPLS, was designed which routinely yielded 20-80% $GFP^+$ $CD4^+$ T cells post-transduction. While hT5Cyp in $CD4^+$ T cells was undetectable by western blot in $CD4^+$ T cells transduced with scAPLS-hT5Cyp, robust mRNA levels of both GFP and hT5Cyp could be detected in these cells indicating that both promoters were driving transgene transcription. scALPS compares favorably to previously published dual-promoter lentiviral gene-delivery systems that fail to lead to efficient reporter gene expression in primary T cells (Amendola et al., 2005). To assess whether the promoters chosen based on optimization experiments in $CD34^+$ HSCs and $CD4^+$ T led to similar levels of protein expression, Jurkat T cells were transduced with scAPLS coding for GFP and dsRed. The majority of transduced T cells expressed both GFP and dsRed (FIG. 55). Indeed the engineering of scAPLS was an advance that enabled direct assessment of T5Cyp-mediated inhibition of HIV-1 spreading infection in primary human cells. Another successful method to express T5 together with a GFP-reporter in primary human T cells is the use of multicistronic lentiviral vectors using the self-cleaving picorna-virus 2A peptides and 2A-like peptides to successfully translate up to four cistrons (Richardson et al., 2008; Szymczak et al., 2004).

Figure 57:
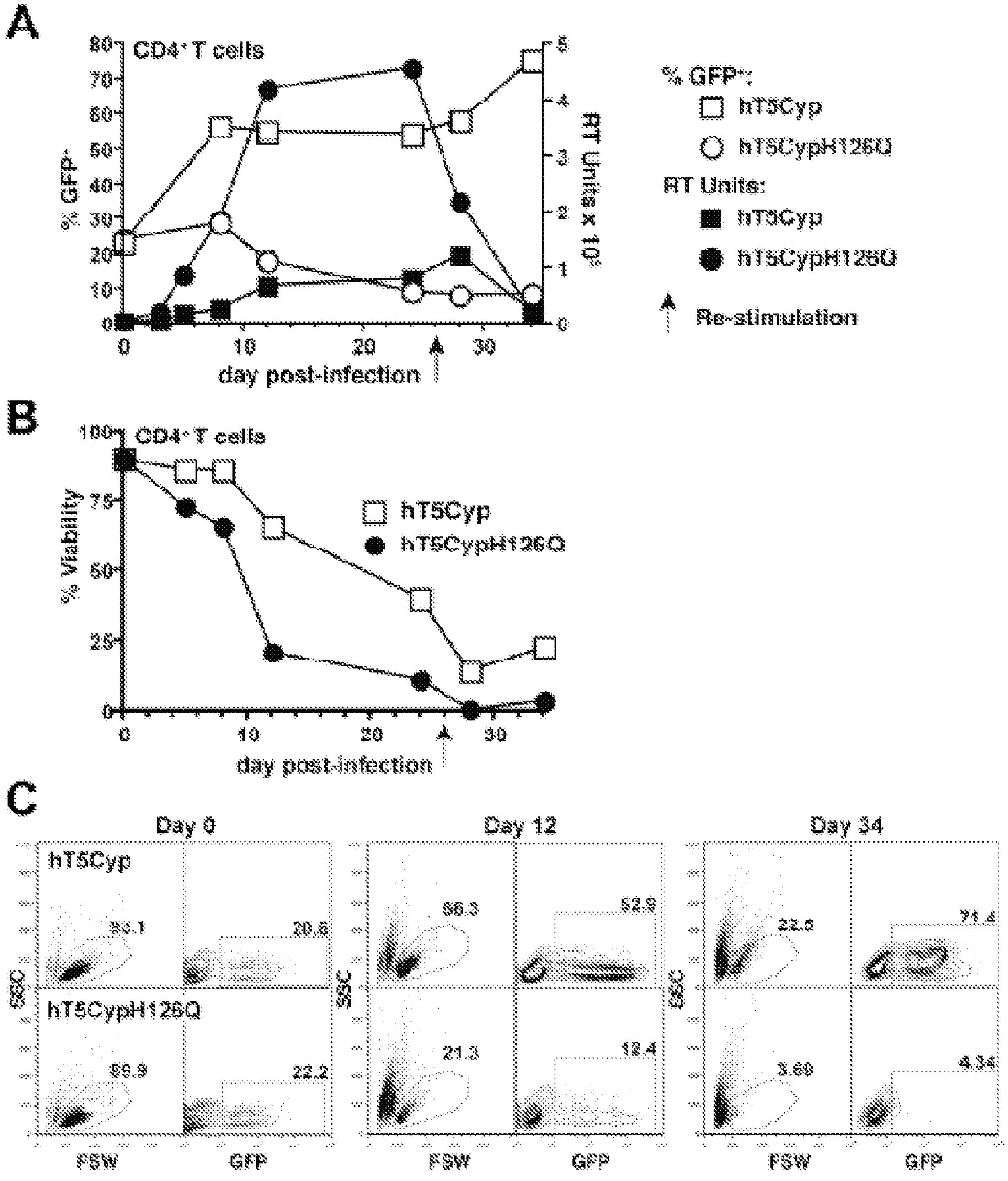
FIGS. 57A-C. Selective advantage of hT5Cyp-bearing CD4$^+$ T cells in the presence of HIV-1. (A) CD4$^+$ T cells were transduced with scALPS encoding the indicated T5Cyp proteins. Cultures containing 23% GFP$^+$ cells were challenged with 15 ng/$10^6$ cells HIV-$1_{NL4-3}$ and monitored for percentage GFP$^+$ cells (left Y-axis, open symbols). Supernatant RT activity was measured (right Y-axis, filled symbols). Cultures were re-stimulated using allogeneic-PBMC, IL-2, and PHA on day 26 post-infection (arrow). (B) % viable cells (Y-axis) was assessed as a function of time (X-axis) in the mixed cultures described in (A). (C) Representative FACS plots showing viability (left panels) and GFP expression (right panels) are shown for three time points plotted in (B).

Expression of hT5Cyp in $hCD4^+$ T cells and monocyte-derived macrophages inhibited spread of CCR5- and CXCR4-tropic HIV-1 strains as well as primary isolates (FIG. 56). When hT5Cyp-scAPLS transduced cells were infected in a competition assay containing untransduced T cells, there was selection for $GFP^+$ T cells previously transduced with hT5Cyp-scAPLS compared to a selection against $GFP^+$ T cells previously transduced with the permissive scAPLS-hT5CypH126Q (FIG. 57). Furthermore, mixed cultures containing hT5Cyp-expressing $CD4^+$ T cells showed a reduction in viral burden. This led to an overall protection of viability in these cultures (FIG. 57). As with spreading infection in T cell lines, infection of primary human cells failed to generate viral escape mutants resistant to T5Cyp-mediated restriction in vitro. T5Cyp could be considered as a candidate monotherapy in the autologous T cell or hematopoietic progenitor transplant context. Few other gene therapy approaches are as potent as T5Cyp, with the possible exception of CCR5 disruption. Notwithstanding, advances in gene delivery combined with intriguing new gene therapy approaches could yield highly effective future combination therapies. For instance, one could envision in vivo delivery of bicistronic P2A-based lentiviral vector (Szymczak et al., 2004) coding for hT5Cyp to block de novo HIV-1 infection and tre to "cure" infected cells (Sarkar et al., 2007), flanked by homologous sequences allowing for concomitant gene replacement of CCR5 (Lombardo et al., 2007) targeted specifically to T cells (Kumar et al., 2008) or $CD34^+$ HSCs (Yang et al., 2006).

So far, treatment with as much as $3\times10^{10}$ transduced, ex vivo expanded autologous T cells has been proven safe in phase II clinical trials (Mitsuyasu et al., 2000; Walker et al., 2000). This number of scAPLS-transduced $CD4^+$ T cells can be readily expanded ex vivo. Furthermore, autotransfusion of ex vivo expanded $CD4^+$ T cells is of clinical benefit to HIV-1-infected people partly because these cells are $CCR5^{lo}$ (Levine et al., 2002). This is consistent with the observation that in non-pathogenic SIV-infection of natural hosts T cells are predominantly $CCR5^{lo}$, especially in the gut, (Pandrea et al., 2007). Thus, given that hT5Cyp-transduced $CD4^+$ cells can be expanded in vitro acquiring a $CCR5^{lo}$ phenotype and exhibit a selective advantage during HIV-1 infection (FIG. 57), an impressive therapeutic effect could potentially be obtained using hT5Cyp in autologous $CD4^+$ T cell gene therapy.

Figure 2:
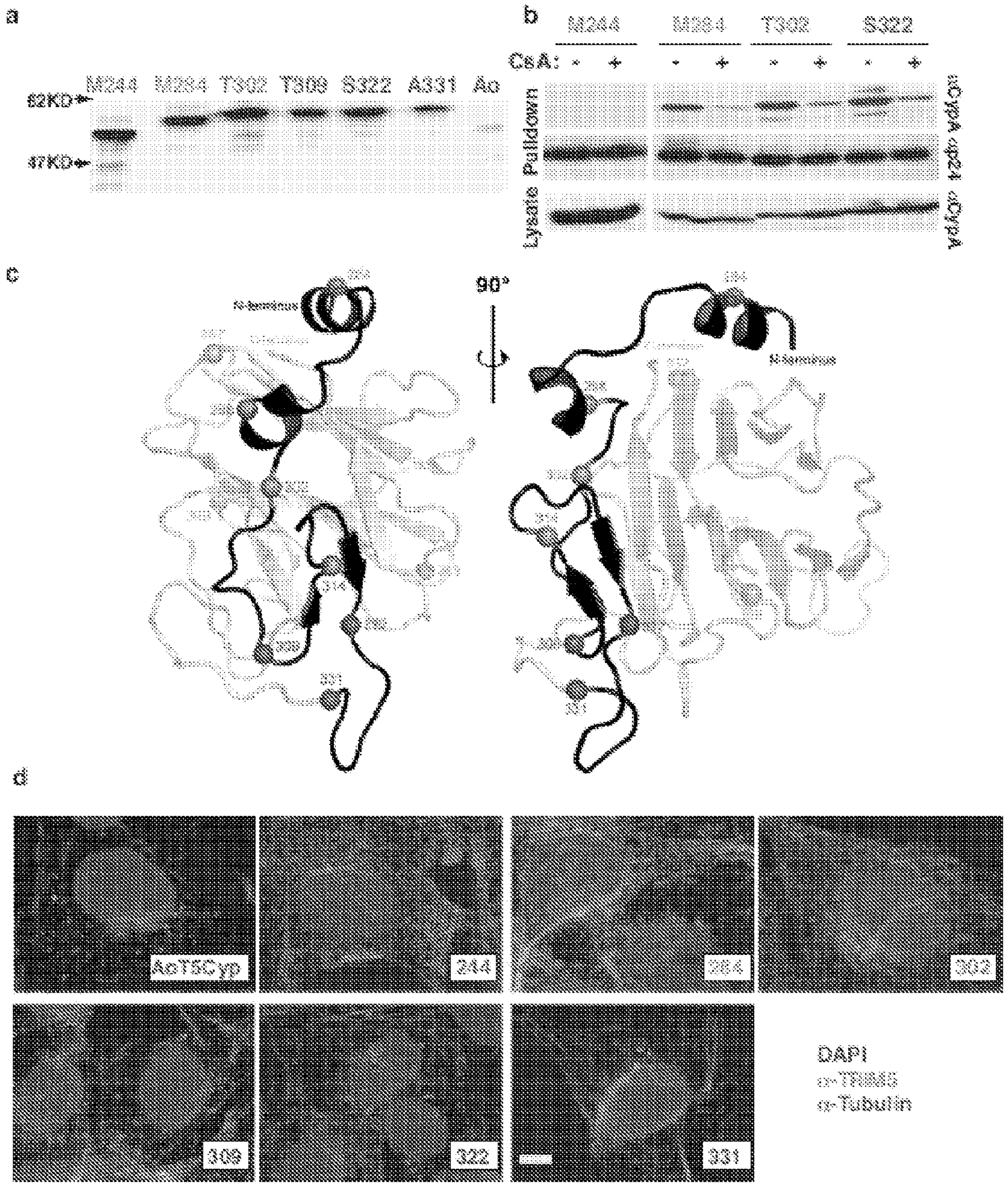
FIGS. 2_a_-2_d_. HIV-1 restriction activity correlates with CypA fusion to the T5α specificity determinant and the ability to form cytoplasmic bodies. (a) Expression of hT5-Cyp fusion proteins. FLAG-hT5Cyp fusion proteins synthesized in 293T cells were immunoprecipitated and immunoblotted with anti-CypA antibodies. (b) HIV-1 CA binding activity of hT5Cyp fusion proteins. FLAG-hT5Cyp and GST-CA fusion proteins were co-expressed in 293T cells, pulled out on glutathione-sepharose beads in the presence or absence of 20 μM CsA, and immunoblotted with anti-CypA and anti-p24-CA antibodies. (c) Model of the PRYSPRY domain of human T5α based on crystal structures of PRYSPRY, GUSTAVUS and TRIM21. Two ribbon representations showing the position of hCypA fusions (spheres) to the hT5α PRYSPRY domain. The grey transparent ribbon indicates regions of the model that would be replaced by CypA in hT5-S331-Cyp. (d) Restrictive T5Cyp fusion proteins form discrete puncta in the cytoplasm. Indirect immunofluorescence images of CRFK cells stably expressing the indicated T5Cyp fusions. Fixed samples were stained with anti-T5 antibody (green) and anti-tubulin antibody (red), followed by counter-stain with DAPI (blue) to visualize the nuclear DNA. For each color, one individual stack of 20 0.35 μm optical sections was acquired and subjected to maximum intensity projection along the optical axis. Images represent three-color overlays. Bar: 5 μm. All panels are color-coded for restriction phenotype: red, restrictive; green, permissive; orange, variably restrictive.
Figure 3:
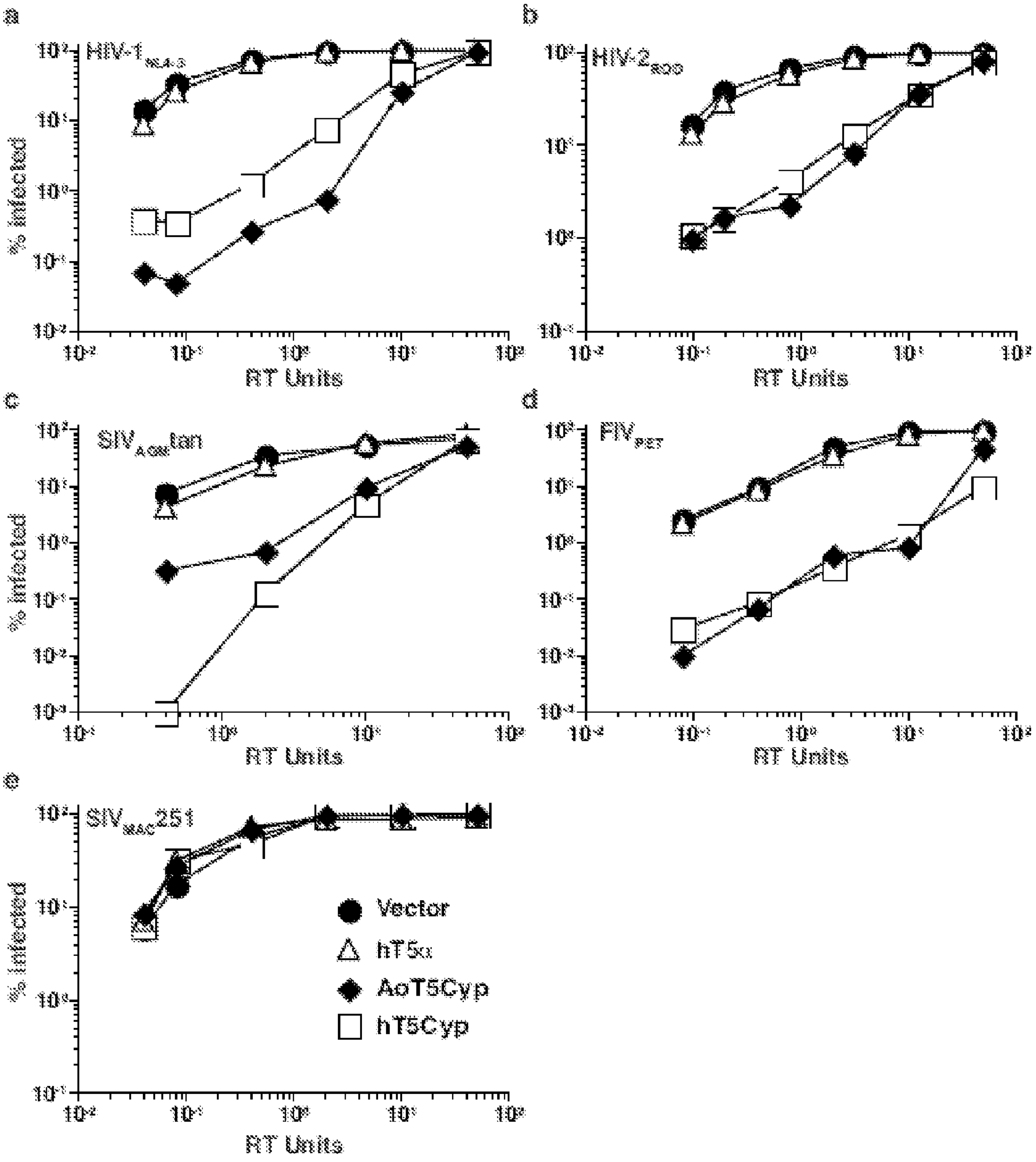
FIGS. 3*a*-3*e*. T5Cyp restricts lentiviruses that encode Capsid with CypA-binding activity. CRFK cells stably expressing the indicated T5 proteins were transduced with increasing amounts (X-axis) of GFP vectors derived from HIV-$1_{NL4-3}$ (a), HIV-$2_{ROD}$ (b), $SIV_{AGM}$tan (c), $FIV_{PET}$ (d), or $SIV_{MAC}$251 (e). The percentage of $GFP^+$ (infected) cells was determined at 48 hrs (Y-axis).
Figure 58:
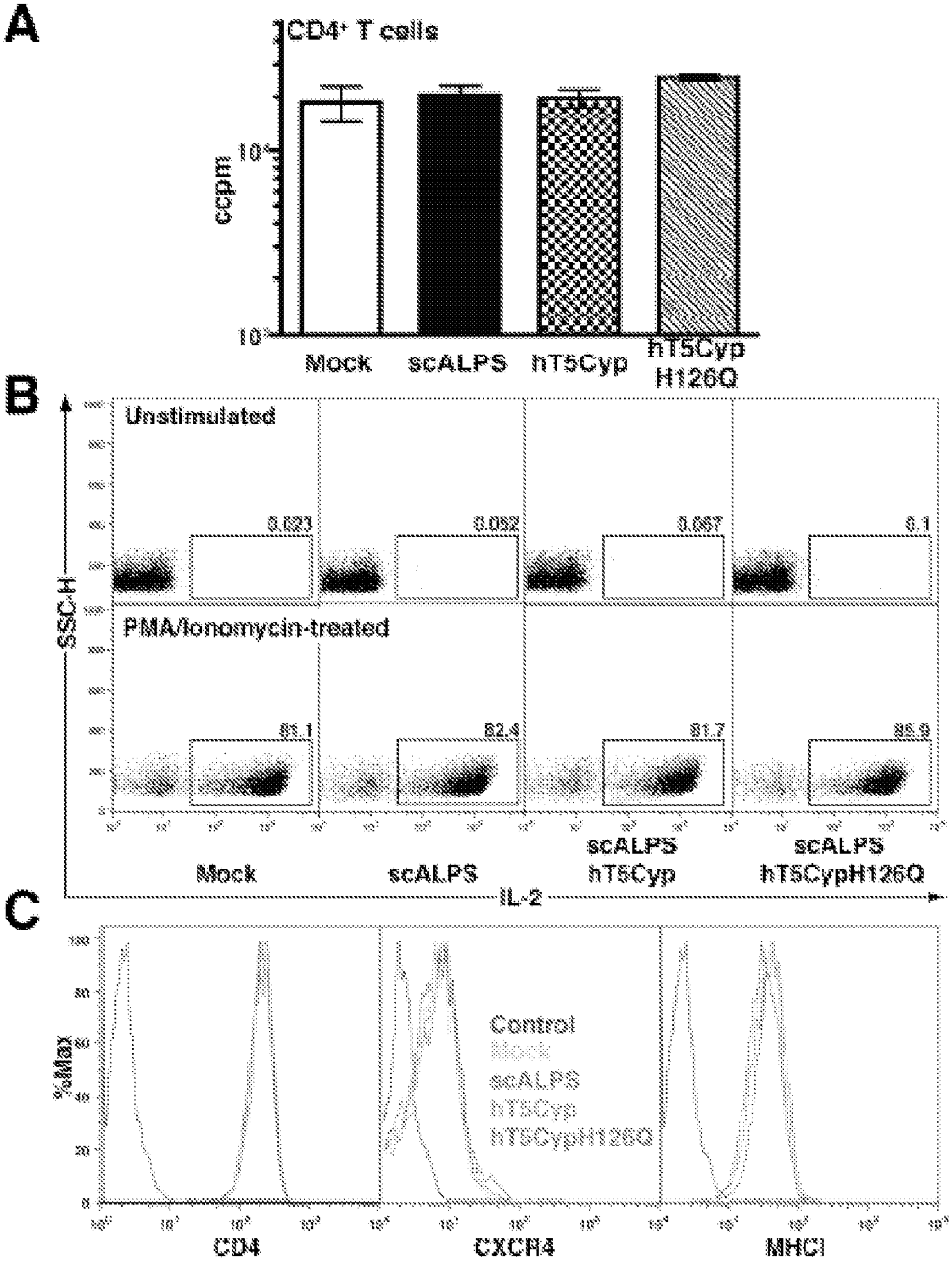
FIGS. 58A-C. Transduction of primary human CD4$^+$ T cells using a dual-promoter, lentiviral vector encoding T5Cyp and GFP does not affect basic T cell functions. (A) T5Cyp does not affect steady-state proliferation of CD4$^+$ T cells. CD4$^+$ T cells transduced with the indicated vector were sorted for GFP expression and steady-state proliferation as compared to un-transduced cells was measured using $^{3H}$Thymidine incorporation. Corrected counts per minute (ccpm, Y-axis) were measured 24 hours after addition of $^{3H}$Thymidine (for each condition, n=4). (B) IL-2 production in scALPS-transduced CD4$^+$ T cells. IL-2 production (X-axis) in proliferating un-transduced CD4$^+$ T cells and CD4$^+$ T cells transduced with indicated scALPS vectors was analyzed by flow cytometry following stimulation with PMA and ionomycin. (C) Cell-surface marker expression on scALPS-transduced CD4$^+$ T cells. The expression of the indicated cell surface markers (X-axis) was assessed in proliferating un-transduced CD4$^+$ T cells and CD4$^+$ T cells transduced with indicated scALPS vectors by flow cytometry.

It is essential that any gene therapy candidate is not toxic to cells and does not perturb host cell function. One potential mode of toxicity would be the elimination of transduced cells in vivo following expression of a foreign protein (Riddell et al., 1996). hT5 was fused to hCypA in order to minimize non-human sequences in the fusion protein (FIG. 1-3). Since hT5Cyp is an extremely efficient HIV-1 inhibitor and acts at an early point in the viral life cycle, integration of viral cDNA into the host genome is diminished. With it, the production of viral proteins is reduced and could lead to improved survival of infected cells and maintenance of a more intact memory repertoire. Aside from antigenicity, hT5Cyp expression should not perturb host cell function. Transduction of scAPLS vectors coding for hT5Cyp did not affect proliferation, expression of cell surface markers, or cytokine production of transduced $CD4^+$ T cells compared to untransduced cells (FIG. 58). At the same time, T5 isoforms form heteromultimers and hT5Cyp may thus affect endogenous T5$\alpha$ function. Indeed, expression of hT5Cyp in Jurkat T cells moderately attenuated the N-MLV restriction activity of endogenous hT5$\alpha$ (FIG. 46C).

Figure 59:
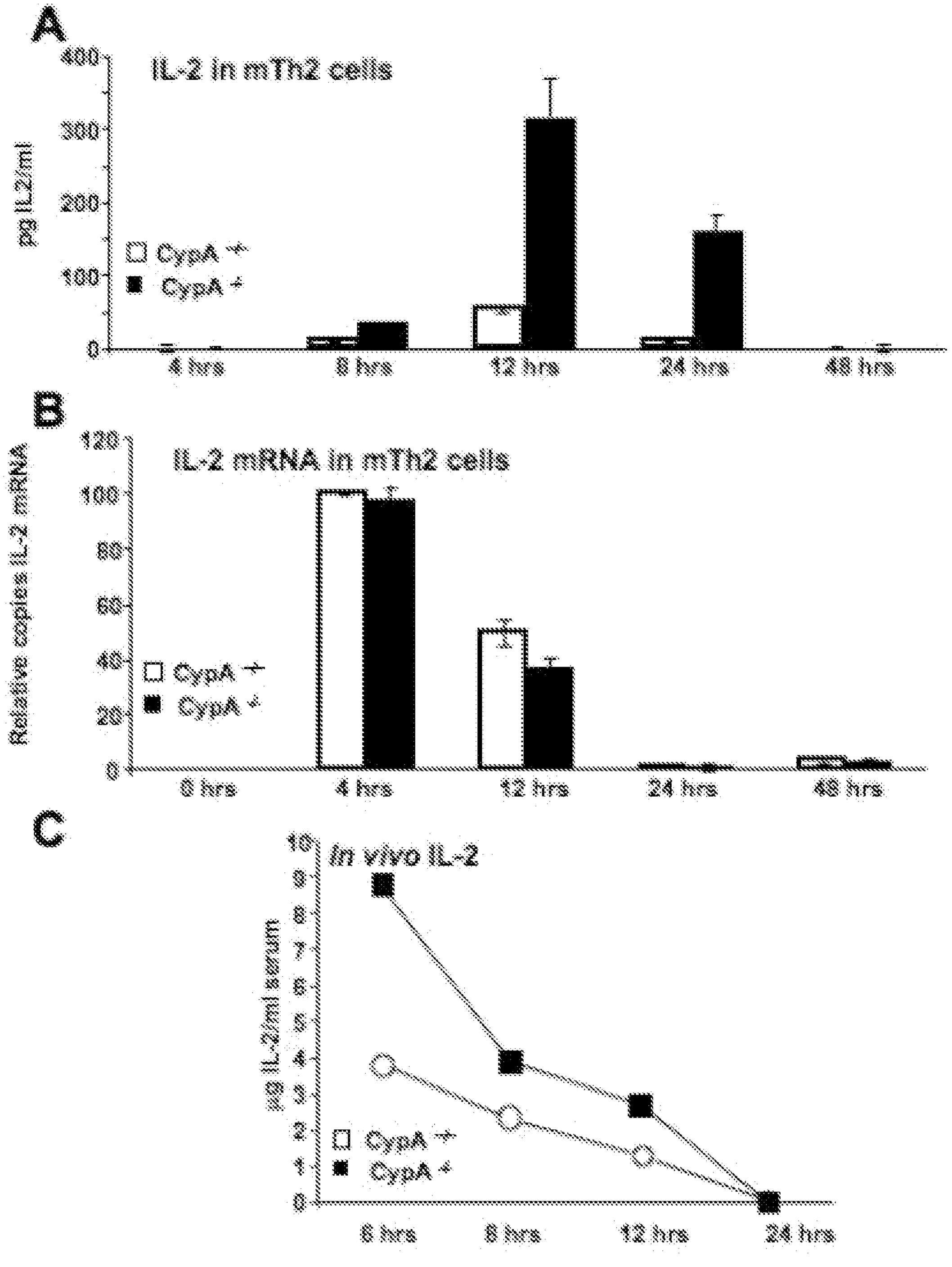
FIGS. 59A-C. (A) In vitro differentiated Th2 memory cells from wildtype and CypA$^{-/-}$ mice were restimulated using plate-bound αCD3 and αCD28 antibodies. Supernatants were collected at given time points and assayed for IL-2 by ELISA. (B) The same cells as in (A) were assayed for IL-2 mRNA content by quantitative RT-PCR at given time points. Results as shown as IL-2/HPRT mRNA ratios. (C) Mice were injected intraperitoneally with αCD3 antibody and biotinylated αIL-2 detection antibody. Serum IL-2 levels were assayed by ELISA at given time points.

For the study of CypA in $CD4^+$ T cells the $CypA^{-/-}$ mouse was used (Colgan et al., 2000). One finding in memory Th2 cells was that CypA regulates IL-2 production post-transcriptionally. Thus $CypA^{-/-}$ mTh2 cells overproduced IL-2 by ELISA without a proportional increase in IL-2 mRNA (FIG. 59). Moreover, $CypA^{-/-}$ mice were confirmed to have elevated serum levels of IL-2 compared to wildtype littermates (FIG. 59). Whether control of IL-2 production by the peptidyl prolyl isomerase CypA occurs at the level of translation or secretion remains to be elucidated. Since CypA controls the activity of the tec kinase itk, which is involved in activation-induced rearrangement of the actin cytoskeleton, CypA could control localization and amount of IL-2 secretion (Labno et al., 2003). Pulse-chase experiments as well as cytokine capture assays can provide insights into a potential control of IL-2 secretion by CypA. Alternatively, CypA could regulate translation of IL-2 mRNA. Polyribosome fractionation and assessment of IL-2 association with polyribosomes in the presence and absence of CypA should provide insights into a potential effect of CypA on polysome loading of IL-2 mRNA.

Another peptidyl-prolyl isomerase, Pin 1 is involved in post-transcriptional regulation of cytokine production by mRNA stabilization (Shen et al., 2005). GM-CSF, like many postranscriptionally regulated cytokine and proto-oncogene mRNAs is regulated through AU-rich elements (AREs) in the 3'UTR. AREs are responsible for both mRNA degradation though association with tristetraproline (TTP) as well as translational silencing through recruitment T-cell internal antigen (TIA) (Anderson et al., 2004). Pin-1 associates with an mRNA-regulating protein at the ARE and recruits GM-CSF mRNA, modulating mRNA levels dependent on signaling events (Shen et al., 2005). IL-2 also contains an ARE in its 3'-UTR and it is possible that CypA orchestrates ARE-dependent modulation of either IL-2 mRNA stability (which should have appeared in quantitative RT-PCR, FIG. 59) or translation.

Figure 60:
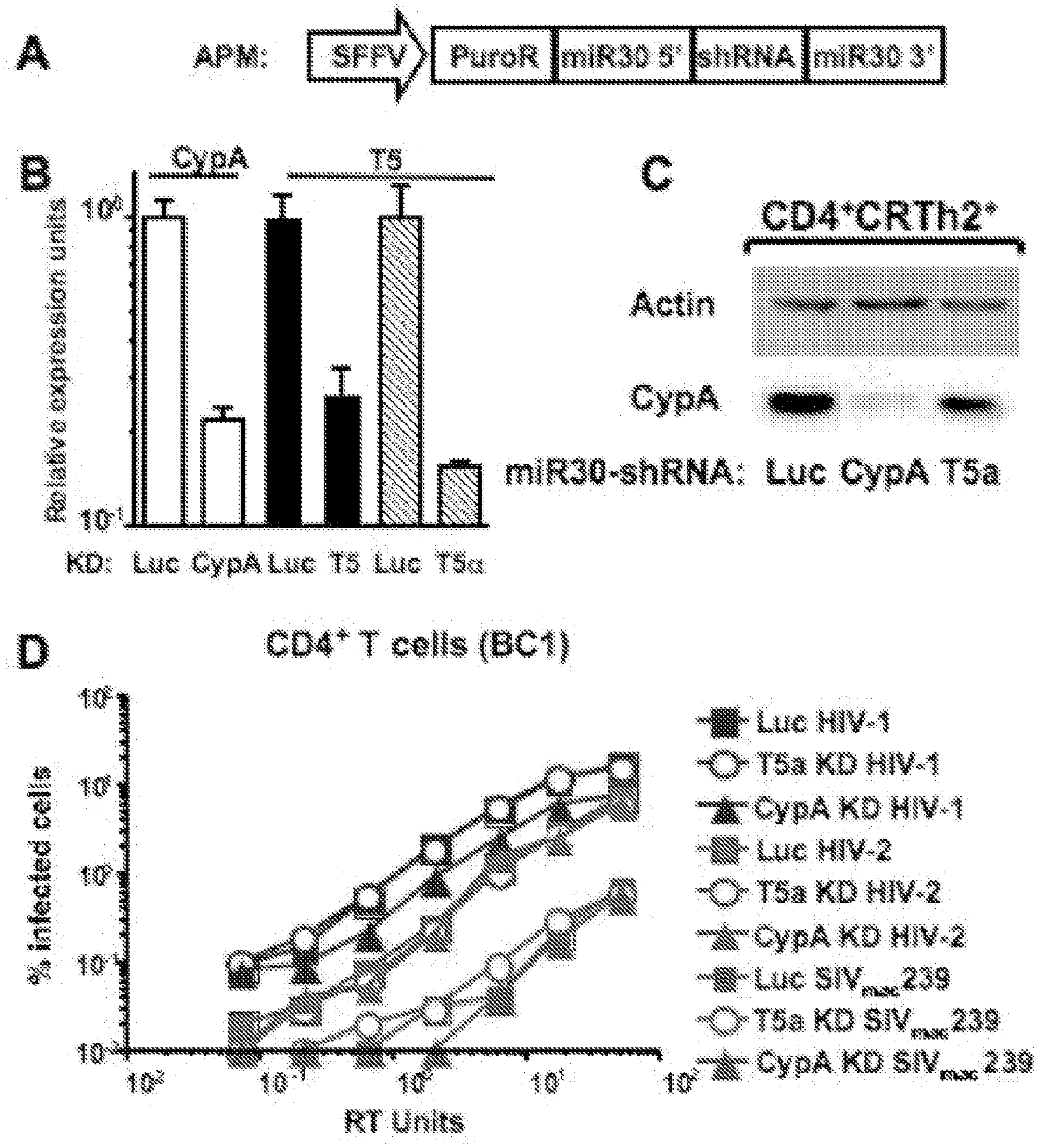
FIGS. 60A-D. (A) Schematic of APM lentiviral vector used to deliver shRNAs targeting CypA and T5 to hCD4$^+$ T cells. (B) CD4$^+$ T cells were stably transduced with APM coding for CypA, T5, and luciferase (Luc) control shRNAs. Following puromycin selection, relative expression of CypA, T5, and T5α in transduced CD4$^+$ T cells was measured by quantitative RT-PCR. (C) CD4$^+$CrTh2$^+$ human memory Th2 cells were stably transduced and selected as in (A). CypA expression in transduced Th2 cells was assessed by western blot. (D) CypA, T5, and Luc KD CD4$^+$ T cells were challenged with increasing doses (X-axis) of HIV-1, HIV-2, $SIV_{mac}$239 GFP vectors. The percentage of infected cells (Y-axis) was assessed 72 hours post-infection by flow cytometry.

To confirm whether CypA had similar effects in human $CD4^+$ T cells, a lentiviral vector, APM, for the efficient delivery and processing of a shRNA targeting CypA, was designed. APM contains a pol II promoter driving expression puromycin-N-acetyltransferase followed by the target-specific shRNA embedded within a miR-30 sequence (Stegmeier et al., 2005). APM was used to knockdown expression of CypA and of T5 (see below) in side-by-side experiments. APM transduces primary $CD4^+$ T cells efficiently and allows for puromycin selection of transduced cells resulting in effective knockdown of target genes by quantitative RT-PCR and Western blot (FIG. 60, A-C). To confirm functional CypA KD in human $CD4^+$ T cells, HIV-1, SIV, and HIV-2 infection of these cells was assessed in the presence or absence of CypA KD. In human $CD4^+$ T cells, analogous to previous observations in Jurkat T cell lines, disruption of CypA expression leads to a reduction in HIV-1 infection without any effects on HIV-2 or SIV infection. Disruption of T5, in contrast had no effect on infection with HIV-1, HIV-2, or SIV (FIG. 60D).

Figure 61:
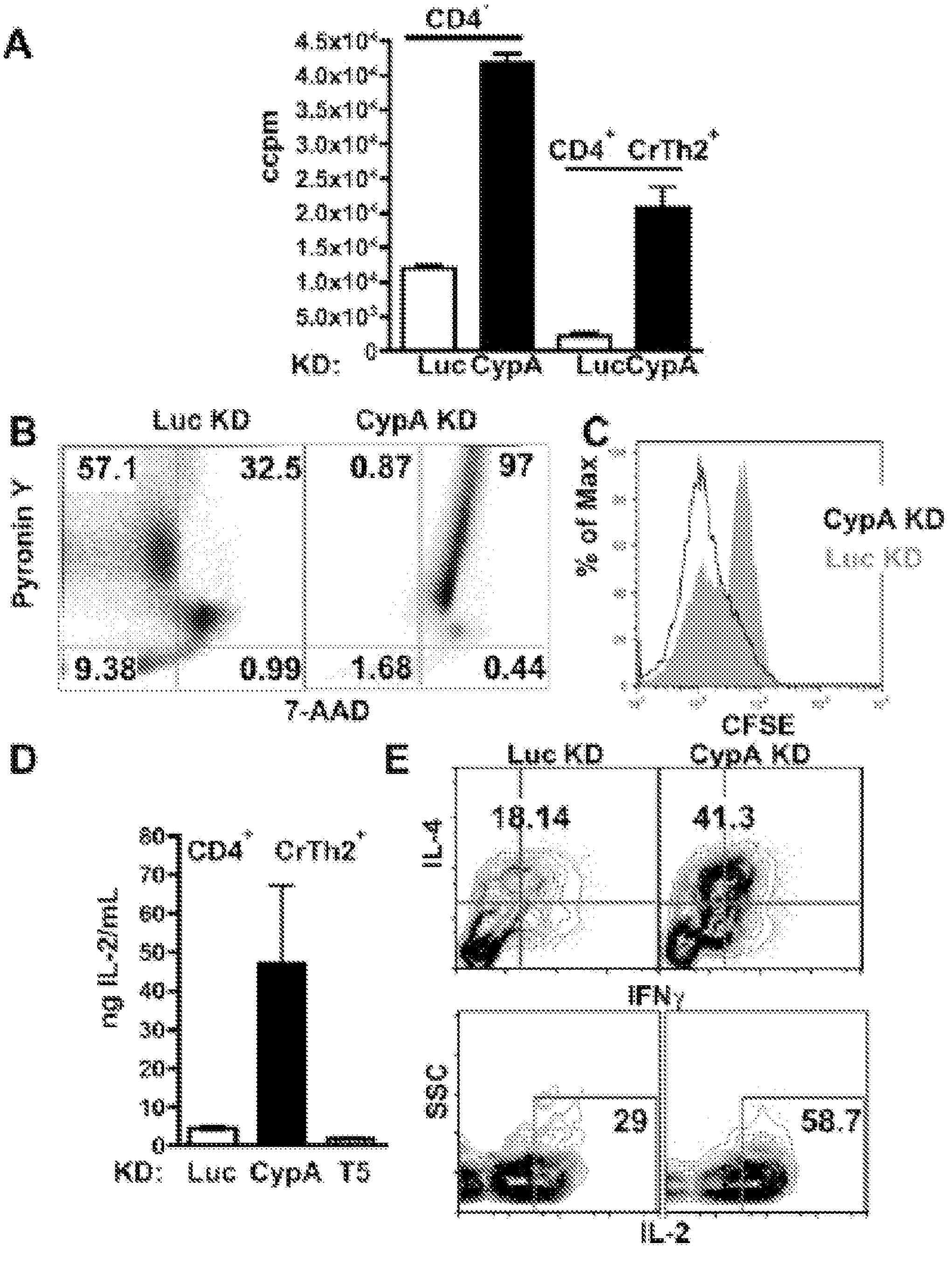
FIGS. 61A-E. (A) Proliferation in CypA KD T cells. CD4$^+$ T and CD4$^+$CrTh2$^+$ cells were stably transduced with CypA KD and Luc KD APM. Following puromycin selection, proliferation was measured using $^{3H}$Thymidine incorporation. Corrected counts per minute (ccpm, Y-axis) were measured 24 hours after addition of $^{3H}$Thymidine (for each condition, n=4). (B) CypA (right panel) and Luc KD (left panel) CD4$^+$ T cells proliferating at steady state were stained with Pyronin-Y (Y-axis) for RNA content and 7-AAD (X-axis) for DNA content and analyzed by flow cytometry. (C) CypA (open histogram) and Luc KD (grey histogram) CD4$^+$ T cells proliferating at steady state were stained with CFSE and assayed by flow cytometry 48 hours later. (D) Steady state CypA, T5, and Luc KD memory Th2 cells were assessed for IL-2 production by ELISA. (E) IL-4, IFNγ, and IL-2 (bottom panel, X-axis) in proliferating CypA and Luc KD $CD4^+$ T cells was analyzed by flow cytometry following stimulation with PMA and ionomycin.
Figure 62:
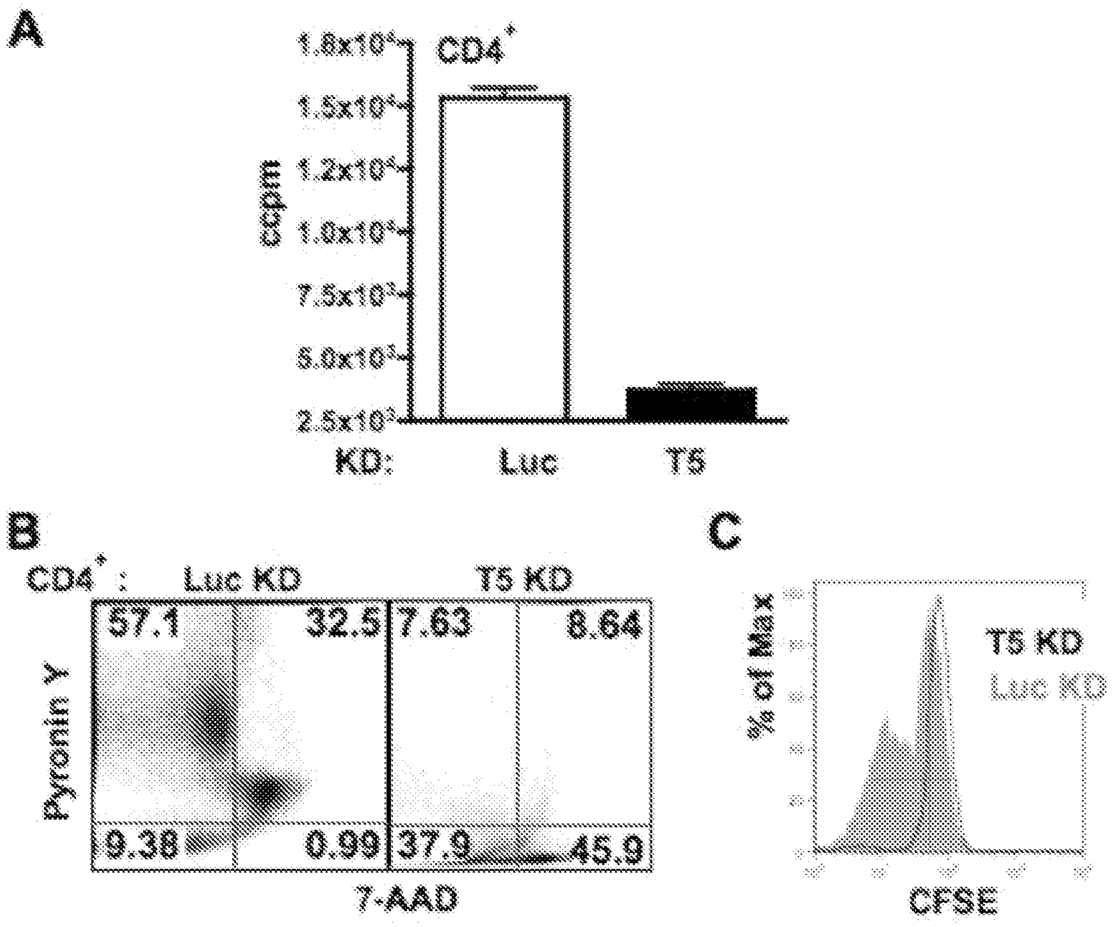
FIGS. 62A-C. (A) Proliferation in T5 KD T cells. $CD4^+$ T cells were stably transduced with APM coding for T5 and Luc shRNAs. Following puromycin selection, steady-state proliferation was measured using $^{3H}$Thymidine incorporation. Corrected counts per minute (ccpm, Y-axis) were measured 24 hours after addition of $^{3H}$Thymidine (for each condition, n=4). (B) T5 (right panel) and Luc KD (left panel) $CD4^+$ T cells proliferating at steady state were stained with Pyronin-Y (Y-axis) for RNA content and 7-AAD (X-axis) for DNA content and analyzed by flow cytometry. (C) T5 (open histogram) and Luc KD (grey histogram) $CD4^+$ T cells proliferating at steady state were stained with CFSE and assayed by flow cytometry 48 hours later.

The most impressive phenotype of CypA KD $CD4^+$ T cells is enhanced proliferation compared to Luc KD control. Restimulated CypA KD Th2 memory cells (Messi et al., 2003), incorporate thymidine almost 10-fold more efficiently and lead to more rapid CFSE dilution in steady state than Luc KD controls (FIG. 61). The proliferation phenotype in CypA KD cells is more prominent in human cells than in mouse Th2 cells (Colgan et al., 2004). Enhanced proliferation is further confirmed by rapidly cycling CypA KD $CD4^+$ T cells concentrated in the G2/M/S phase of the cell cycle, while control cells had an expected distribution for moderately fast cycling cells (FIG. 61). Whether the unchecked proliferation observed in CypA KD cells is due to loss of itk control (Colgan et al., 2004) could be assessed by expression of itk mutants unable to bind CypA ($itk_{P287G}$) or lacking kinase activity ($itk_{K390R}$) in CypA KD and Luc KD $CD4^+$ T cells. $Itk_{P287G}$-expressing Luc KD $CD4^+$ T cells should then have the same phenotype as CypA $KD^+$ T cells. Following PMA/Ionomycin stimulation, CypA KD $CD4^+$ T cells produce more than 2-fold higher levels of IL-2 and IL-4 by intracellular cytokine stain (FIG. 61E). Similarly, memory Th2 cells produce more than 10-fold higher levels of IL-2 by ELISA in the absence of stimulation (FIG. 61D). Whether CypA has effects on transcription or is regulating post-transcriptional control of cytokine production in human $CD4^+$ T cells remains to be elucidated.

Since mice do not have T5, its function has to be directly assessed in human $CD4^+$ T cells. T5α KD $CD4^+$ T cells exhibited cell cycle arrest much earlier than their Luc KD counterparts. This is reflected in 5-fold lower steady-state proliferation by thymidine incorporation and failure of CFSE dilution. Upon cell cycle analysis, the majority of cells were either in $G_0$ or dead; technically complicating the characterization of T5α KD $CD4^+$ T cells. A more thorough analysis has to be undertaken to distinguish cell cycle arrest and subsequent death by neglect from increased apoptosis or AICD in the absence of T5α. Upon restimulation of T5α KD $CD4^+$ T cells, growth kinetics are at first similar to Luc KD T cells without evidence for an increased number of $PI^+$ cells. One week later, however, the proliferation defect becomes apparent. There were no striking differences in cytokine production or activation marker expression between T5α KD and Luc KD $CD4^+$ T cells.

The closest murine relative of T5α is TRIM30α (T30α). By targeting TAB2,3 for degradation, T30α disassembles the TAB2/TAB3/TAK1 complex required for TLR4 signaling to NFκB (Shi et al., 2008). Whether T5α KD has an analogous effect on TLR4 signaling in $CD4^+$ T cells and what the exact protein expression profiles and functions of TLRs are in these cells, remains to be elucidated. T cell receptor triggering itself, however, activates NFκB via the TAK1 complex (Wan et al., 2006). Should T5α, akin to T30α, disrupt this signaling downstream of the T cell receptor, a defect in T cell proliferation in the absence of T5α is not surprising. Furthermore, the effect would be potentiated by the fact that TAK1 activates signaling to both MAPKs and NFκB. TAK1 is essential for T cell development as well as for the survival and cytokine-driven proliferation of effector T cells (Wan et al., 2006). Intriguingly, peripheral T cells from $TAK1^{-/-}$ mice have a similar reduced proliferation and survival phenotype as hT5α KD $CD4^+$ T cells. The data presented here indicate that T5α coordinates essential T cell functions. Since hT5Cyp may have the potential to interfere with endogenous T5α, a thorough understanding of its function is required.

Example 3

Assessment of hT5Cyp Effects on HIV-1 Infection In Vivo

Monkey Models for Lentiviral Infection

A major hurdle to the study of HIV-1 pathogenicity and therapy is the paucity of adequate animal models. HIV-1 infection is almost exclusively restricted to humans, where it is the primary cause of AIDS (Barre-Sinoussi et al., 1983). HIV-1 can also replicate in chimpanzees, the apes from which HIV-1 originated by zoonotic transmission of SIVcpz to humans (Gao et al., 1999), as well as gibbon apes (Ambrose et al., 2007). In chimpanzees, HIV-1 establishes a long-term chronic infection accompanied by seroconversion and establishment of cellular and humoral immune responses, but rarely causes an AIDS-like syndrome (Ambrose et al., 2007; Fultz et al., 1989; Novembre et al., 1997). Furthermore, the use of chimpanzees for experimental purposes has become increasingly undesirable first and foremost for ethical reasons (Goodall, 1995). Secondarily, from a practical standpoint, maintenance of chimpanzees is prohibitively expensive and data output will be limited by long experimental duration and small cohort sizes (Nath et al., 2000).

In most new world monkeys, the CD4 receptor and CCR5 co-receptor do not support HIV-1 entry and thus replication (Kunstman et al., 2003; LaBonte et al., 2002). Even in the case of the old world monkeys, however, whose CD4 and CCR5 surface receptors allow for HIV-1 entry (Kunstman et al., 2003), viral replication is blocked by restriction factors such as TRIM5 (T5) and APOBEC3G (A3G). At the same time, most African monkey species harbor the HIV-related SIVs. While SIV-infection leads to high viral replication coupled with acute depletion of mucosal T cells, it seems to be a well-tolerated and non-progressive infection in natural hosts, in contrast to HIV-1 in humans (Pandrea et al., 2008). The major difference between non-pathogenic infection and pathogenic infection seems to be the degree of immune activation during the chronic phase of infection (Pandrea et al., 2008). Systemically, the chronic immune activation observed during HIV-1 infection results in part from destruction of the mucosal barrier allowing for translocation of microbial products to the peritoneum (Brenchley et al., 2006). On a cellular level, HIV-1 Nef, in contrast to SIV Nef fails to suppress T-cell activation, again leading to high-level immune activation associated with morbidity in infected individuals (Schindler et al., 2006).

While SIV-infection in its natural host is non-pathogenic, infection of Asian monkeys with SIVs derived from African hosts, leads to a rapid and fatal immune suppression with symptoms highly reminiscent of AIDS in humans (Letvin et al., 1985). To date, infection of rhesus macaques with $SIV_{mac}$ or modified $SIV_{mac}$ has thus become the most widespread animal model to approximate HIV-1 infection in the human host as well as for assessment of candidate antivirals (Ambrose et al., 2007). In this model, immunity against SIV-infection was obtained using vaccination with an attenuated Nef-deleted SIV prior to challenge with high-dose, pathogenic $SIV_{mac}251$ (Daniel et al., 1992). Notwithstanding failures in the vaccine field, this study is an essential reminder that protective immunity against a lentivirus is possible in primates and may encourage a new approach to vaccine development. Furthermore, in some long-term nonprogressors with low viral loads and stable $CD4^+$ T cell counts, HIV strains with mutations and deletions in the Nef gene were detected (Kirchhoff et al., 1995).

Despite similarities in genomic organization and pathogenic potential between the closely-related HIV-1 and $SIV_{mac}$, they are distinct viruses with substantial differences in genomic sequence, accessory genes, and progression of infection. A similar distinction has to be made between immune responses in the closely-related *Macacca* genus and *Homo sapiens*. The sequence dissimilarities between HIV-1 and SIV partly limit the usefulness of the SIV animal model for study of antivirals. Neutralizing antibodies produced in humans and monkeys will differ as the env sequences governing these responses differ (Ambrose et al., 2007). Sequence dissimilarities provide the same consideration for cytotoxic T cell responses. HIV-1 contains the accessory gene vpu which, absent in SIV, counteracts tetherin-mediated restriction of HIV-1 (Wolf and Goff, 2008). SIV, on the other hand contains the accessory protein vpx, which, while absent in HIV-1, increases HIV-1 infection in human DCs and macrophages in trans (Goujon et al., 2007). $SIV_{mac}$ and HIV-1 also exhibit differences in the course of infection. The decline in immune function of SIV-infected macaques takes 1-3 years on average; a process requiring an average 10 years in HIV-1 infected individuals (Brown et al., 2007). Infected macaques can fail to mount immune responses to $SIV_{mac}$, leading to a severe AIDS-like disease and death within 6 months post-infection (Brown et al., 2007). This represents a reduction in the duration of the chronic phase of infection; a phase which deserves particular scrutiny since it is when most differences between a pathogenic and non-pathogenic SIV infection are apparent (Pandrea et al., 2008).

To minimize shortcomings based on genomic differences of HIV and SIV in the macaque animal model, SIV-HIV chimeric viruses were generated. The first SHIV was a $SIV_{mac}$ containing tat, rev, vpu, and env from HIV-1 (Shibata et al., 1991). After SHIV was shown to be infectious in rhesus macaques ever more sophisticated CXCR4- and CCR5-tropic versions have emerged, culminating in simian-tropic HIV-1 (Ambrose et al., 2007; Hatziioannou et al., 2006). stHIV-1 incorporates the recent understanding that dominant intracellular restriction factors determine lentiviral tropism. RhT5α targets HIV-1 but not SIV CA. Similarly, SIV but not HIV-1 vif blocks lentiviral restriction by A3G in simian cells. By substituting HIV-1 CA and vif with their SIV counterparts, a chimeric virus (stHIV-1) was generated that has the highest sequence homology with HIV-1 to date. After tissue-culture adaptation, stHIV-1 is able to replicate in rhesus macaque cells at similar levels as SIV. Once stHIV-1 infection is successfully established in monkeys, stHIV-1 could provide a significant improvement of the SIV animal model (Hatziioannou et al., 2006). Despite the unquestionable value of the SIV/SHIV monkey model coupled with recent advances like stHIV-1, CA-sequences differ between the two lentiviruses, and CA-variation governs the ability to infect non-dividing cells (Yamashita et al., 2007), with potential effects on immune responses to stHIV-1 in monkeys. An ideal model would allow for direct testing of HIV-1. The discovery of a macaque T5Cyp that does not block HIV-1 infection and is encoded for by the Mamu7 allele in rhesus macaques raises the possibility that Mamu7 homozygous animals may be infectible with HIV-1 (Wilson et al., 2008).

Mouse Models for HIV-1 Infection

A different approach has been to “humanize” small animal models, ideally providing high-throughput systems for the study of HIV-1 pathogenesis, immunity, and antivirals in vivo. Rodents do not allow for HIV-1 replication partly because mouse homologs of required cellular co-factors do not support HIV-1 replication. This provides blocks at multiple steps of the viral life cycle (Goldstein, 2008). A direct approach to overcome this problem in the context of a pre-existing functional immune system is the creation of rodents transgenic for the required human homologs. Thus, the introduction of the human CD4 receptor and CCR5 co-receptor for HIV-1 into rats (Keppler et al., 2002) and mice (Zhang et al., 2008b) allowed for efficient viral entry and reverse transcription. In rats, this approach led to low-level plasma viremia as well as evidence of viral cDNA in thymus and spleen up to 6 months post infection (Keppler et al., 2002). This model was further used in proof-of-principle experiments showing that antivirals known to affect entry (enfuvirtide) or RT (efavirenz) inhibited HIV-1 infection as measured by quantification of viral cDNA and 2-LTR circles in rat splenocytes 4 days post-infection, while a semen-derived amyloid fibril (SEVI) shown to enhance HIV-1 infection in culture, had the same effect in vivo (Goffinet et al., 2007; Goldstein, 2008; Munch et al., 2007).

Generation of hCD4/hCCR5 transgenic mice highlights a further block to HIV-1 replication: murine Cyclin T1 (CycT1) does not support efficient tat-mediated transactivation of HIV-1 transcription (Zhang et al., 2008b). To overcome this block, hCycT1/hCD4/hCCR5 mice were bred. In $hCD4^+$ T cells from transgenic hCycT1/hCD4/hCCR5 mice, HIV-1 undergoes reverse transcription and nuclear import efficiently, but proviral integration is deficient. Intriguingly, secondary TCR-activation of primary murine T cells in culture during the first 12-24 hours post-infection relieved the block to proviral integration; an effect potentiated by treatment with cyclosporine A (Zhang et al., 2008b). Gag processing and virion budding remains defective in hCycT/hCD4/hCCR5 transgenic T cells, leading to significant reduction in the release of infectious progeny compared to infected human cells (Zhang et al., 1996). This model provides valuable insights both into the requirements for HIV-1 replication and reveals distinct steps at which species-specific restriction factors may act.

An alternative to mouse modification is modification of viral tropism. One group has attempted to adapt HIV-1 to mice by replacing HIV-1 env with the envelope glycoprotein from ecotropic murine leukemia virus resulting in the chimeric virus EcoHIV-1 (Potash et al., 2005). Viral cDNA can be found in the spleen and brain of infected mice which can even mount an antibody response against tat and gag (Potash et al., 2005). In the absence of documented plasma viremia and $CD4^+$ T cell destruction, however, it is unclear whether infection of mice with EcoHIV-1 is self-limiting or productive since this model does not address species-specific post-entry blocks to HIV-1 replication.

To circumvent the HIV-1 entry defect into murine cells, mice transgenic for infectious provirus under the control of a CD4 promoter/enhancer cassette were generated. Depending on level of transgene expression, these mice developed a rapidly progressing AIDS-like syndrome leading to very early death and thus limiting the utility of this model to study effects of chronic HIV-1 infection (Hanna et al., 1998a). Another approach was the generation of HIV-1 provirus (under the control of the HIV-1 LTR) and hCycT1 (under the control of a CD4 promoter/enhancer cassette) double transgenic mice (Sun et al., 2006). This method limits tat-expression to murine $CD4^+$ T cells, dendritic cells, and myeloid cells (monocytes, macrophages, microglia); increasing HIV-1 transcription and production in these targets. There was evidence for production of infectious HIV-1 by $CD4^+$ cells in all organs examined and a gradual depletion of peripheral $CD4^+$ T cells over the course of one year (Goldstein, 2008; Sun et al., 2006). HIV-1 production in myeloid cells was more than eight-fold higher than in $CD4^+$ T cells, indicating a T-cell specific block to viral replication. The HIV-1 provirus/hCyc T transgenic model for pathogenesis may be further improved once the T-cell specific block to HIV-1 replication is identified and alleviated (Sun et al., 2006).

Rather than studying the in vivo effects of an entire integrated HIV-1 provirus, some have focused on the pathogenic effects of single viral genes in transgenic mice. The discovery that nef is a major determinant for HIV-1 pathogenicity was made during the generation of mice transgenic for mutant HIV-1 proviruses. Severe AIDS-like disease affecting multiple organs and leading to early death occurred only in mice transgenic for HIV-1 proviruses with intact nef (Hanna et al., 1998b). Furthermore, mice transgenic for nef under the control of the CDR promoter show aberrant T cell activation, impaired $CD4^+$ T cell development in the thymus, and both central and peripheral $CD4^+$ T cell depletion (Skowronski et al., 1993). A similar approach showed that gp120 in isolation has the capacity to cause CNS damage in transgenic mice (Toggas et al., 1994). When placed under the glial fibrillary acidic protein (GFAP) promoter, gp120 expression was limited to astrocytes and targeted to the CNS of transgenic mice. Dependent on expression level, it caused reactive astrocytosis, dendrite damage, synapse destruction, and loss of neuronal subpopulations reminiscent of the neurological complications observed in HIV-1 infected patients (Toggas et al., 1994). These studies demonstrate how such a “reductionist” approach can lead to valuable insights regarding the pathogenic potential of single HIV-1 elements in vivo.

Humanized Mouse Models for HIV-1 Infection

The ideal remains to study the interaction of HIV-1 with the human immune system in vivo. To this end, immuno-compromised mice have been reconstituted with human immune cells that support HIV-1 infection in vivo. The first such model took advantage of the CB17-Prkdc$^{scid}$ (SCID) mouse. SCID mice contain a spontaneous autosomal mutation in the DNA-dependent protein kinase (DNA-PK) required for successful completion of VDJ recombination during the rearrangement of lymphocyte antigen receptors (Blunt et al., 1996; Bosma et al., 1983). This defect results is the absence of mature, functional B and T cells in SCID mice, allowing for their reconstitution with human PBMCs (huPBL-SCID mice) (Mosier et al., 1988); human fetal hematopoietic tissues (SCID-hu thy/liv mice) (McCune et al., 1988); and human bone marrow cells (Lapidot et al., 1992). It was not long before these models were tested for support of productive HIV-1 infection (Mosier et al., 1991; Namikawa et al., 1988). The huPBL-SCID model allows for evidence of infection using both cell-free HIV-1 as well as infected T cell blasts with apparent depletion of CD4 T cells in vivo. Infectious virus could be recovered through culture from the spleen, peripheral blood, and lymph nodes of infected mice (Mosier et al., 1991). In the huPBL-SCID model, however, human T cells are CCR5 memory cells aberrantly activated in the xenogeneic background and experimental duration is limited by the appearance of xGVHD symptoms within two-months post-transplant (Koyanagi et al., 2008) Recently, the SCIDhu Thy/Liv model has been validated as a high-fidelity model for preclinical drug-testing since HIV-1 infected SCIDhu Thy/Liv mice have comparable responses to four classes of licensed antiretrovirals at equivalent dosages used in humans (Stoddart et al., 2007). Notwithstanding such applications of humanized SCID mice, utility of these models is limited by low levels of human cell engraftment, especially in the T cell compartment in the huPBL-SCID mouse, a failure to mount primary immune responses, and limited distribution of human cells in the SCIDhu thy/liv mouse (Manz, 2007; Wege et al., 2008).

In the recipient mouse, the degree of both adaptive and innate immune deficiency correlates with the success of immune reconstitution using human cells. The SCID mouse is suboptimal in both categories. The scid-mutation is "leaky" in up to 20% of young mice, allowing for spontaneous development of mature B and T cells (Bosma et al., 1988). Additionally, mice have high numbers of host-derived NK cells combined with enhanced innate immune activation (Shultz et al., 2007). The scid-mutation also causes a defect in DNA repair leading to radiosensitive mice with short life spans (Fulop and Phillips, 1990). The generation of NOD/SCID mice significantly improved engraftment of human cells due to the synergistic effects of the scid-mutation on lymphoid development combined with NOD-specific defects in innate immune function, including defects in macrophage and NK cell activity (Shultz et al., 1995). Adoptive transfer of human PBMCs into NOD/SCID mice leads to 5-10 fold higher reconstitution than seen in SCID mice although reconstitution of the T cell compartment remained deficient in this model (Hesselton et al., 1995). HIV-1 replication in hPBL-NOD/SCID mice was observed in the spleens of >80% infected mice at much higher levels of plasma viremia (>1 ng p25/ml plasma) than in infected huPBL-SCID mice (Koyanagi et al., 2008). Unfortunately, expression of an endogenous retrovirus (Emv30) located on chromosome 11 leads to spontaneous development of thymomas in NOD/SCID mice and limits their life span (Shultz et al., 1995).

Despite this shortcoming, one NOD/SCID model deserves special mention as it supports high-level human cell engraftment and reconstitution of a functional human immune system. The bone marrow/liver/thymus (BLT) mouse is a NOD/SCID-based model in which tissue from fetal thymus and liver is transplanted beneath the kidney capsule of adult mice. Three weeks later mice are conditioned with sublethal irradiation and transplanted with autologous fetal CD34$^+$ hematopoietic stem and progenitor cells (HSCs) (Melkus et al., 2006). High-level engraftment (20-40%) of functional human cells is observed in peripheral blood and reconstitution encompasses human B and T cells with appropriate subsets as well as monocytes and DCs, 4-8 weeks after CD34$^+$ HSC transfer. Human T cells in the mouse have a broad Vβ repertoire and can mount MHC-restricted, antigen-specific immune responses to EBV infection (Melkus et al., 2006). Human DCs were also functional in BLT mice since inoculation of mice with the TSST-1 superantigen led to the selective expansion of Vβ2$^+$ T cells and elaboration of inflammatory cytokines as well as transient upregulation of activation/maturation markers in splenic DCs (Melkus et al., 2006).

The mucosa of BLT mice is successfully reconstituted with multi-subset human immune cells. Systemic infection could be established though intrarectal HIV-1 inoculation, and led to a depletion of CD4$^+$ T cells in the mesenteric lymph node as well as depletion of T cells located in the lamia propria of the gut; analogous to the course of infection in humans. Moreover, three of four infected mice mounted antibody responses against gp120 and p24 (Denton et al., 2008). These studies were extended to show that systemic infection could be initiated through intravaginal HIV-1 inoculation, with resulting T cell depletion in the gut-associated lymphoid tissues. Furthermore, topical antiviral prophylaxis protected 5/5 mice from vaginal HIV-1 transmission in a proof-of-principle experiment showing the utility of the BLT model for preclinical evaluation of microbicides and antiretrovirals in HIV-1 prophylaxis (Sun et al., 2007). Despite these outstanding results, the surgical intervention required for generation of the BLT-model is not trivial. So far, this model is not a high-throughput solution for multi-center, preclinical drug testing.

The generation of recombination-activating gene (RAG1 and 2) knockout mice eliminated the problems of leakiness and radiosensitivity observed with SCID-mice, while retaining the drawbacks of host NK cell activity and innate immune activation (Mombaerts et al., 1992; Shinkai et al., 1992). While gradual improvements in humanized mouse models continued over the next decade, T cell development remained elusive. A major breakthrough came with inhibition of NK cell activity by disruption of IL-2 signaling. Thus, using anti-mIL-2Rβ antibodies in pretransplantation conditioning regimens increased de novo thymopoiesis (Kerre et al., 2002). A further improvement was the genetic disruption of NK cell activity through deletion or truncation of the mIL-2Rγ chain (Manz, 2007). The mIL-2Rγ chain is required for high affinity binding of IL-2, IL-4, IL-7, IL-9, IL-15, and IL-21 to their receptor complexes and for subsequent signaling events. Mutations in the human IL-2Rγ chain are responsible for X-linked SCID (Sugamura et al., 1996). When the NOD/SCID and Rag2$^{-/-}$ were crossed to IL-2Rγ$^{-/-}$ mice, yielding NOD/SCIDIl2rg$^{-/-}$ and NOG mice (Ishikawa et al., 2005; Ito et al., 2002; Shultz et al., 2005) as well as Rag2$^{-/-}\gamma_c^{-/-}$ mice (Gimeno et al., 2004; Traggiai et al., 2004), respectively, a major breakthrough in the field of humanized mice was achieved.

Also, a hPBL-NOG mouse model was validated for preclinical drug testing in a proof-of-principle experiment where a CCR5 antagonist blocked protected $CD4^+$ from depletion following HIV-1 infection and >200-fold reduced viral load (Nakata et al., 2005). Adoptive transfer of hPBMCs into the NOG mouse represents an improvement over the huPBL-SCID model. Human cell engraftment even in peripheral blood (<40% $CD45^+$) is consistently higher and allows for a higher level of viremia (up to $10^6$ copies proviral DNA/$10^5$ $CD4^+$ T cells); which is both more similar to what is observed in patients during acute viremia and also allows for longitudinal monitoring of HIV-1 infection without the need for sacrificing mice (Nakata et al., 2005). As with the hPBL-SCID model, the experimental duration is limited due to the potential development of xGVHD.

The major benefit of these new mouse models is consistent and robust de novo T cell development following transplant of Rag2$^{-/-}\gamma_c^{-/-}$ or NOD/SCIDIl2rg$^{-/-}$ and NOG mice with hHSCs. These strains lack B, T, and functional NK cells without any apparent tumor susceptibility or life-span reduction (Manz, 2007). Optimal results are achieved with transplantation of $CD34^+$ HSCs into the liver of sublethally-irradiated newborn mice. Targeting human HSCs to the site of perinatal hematopoiesis in newborns leads to T cell development in mouse strains that do not support human T cell development well in adults (Wege et al., 2008). Both strains allow for differentiation and maintenance (>6 months) of a human hemato-lymphoid system (HHLS) with robust reconstitution of the lymphoid compartment including multiple T cell subsets ($CD4^+$ and $CD8^+$ T cells with broad Vβ distribution, as well as Foxp3$^+$CD25$^+$ regulatory T cells), B cells (including $CD5^+$ B cells), and NK cells; reconstitution of cDCs and IPC; and with some erythroid, and myeloid reconstitution (mono-myeloid cells, RBCs and platelets) (Ishikawa et al., 2005; Manz, 2007; Traggiai et al., 2004). Immune-reconstitution leads to formation and structural organization of the major primary and secondary lymphoid organs absent or hypotrophic in non-reconstituted mice (Manz, 2007). EBV-infected HHLS-Rag2$^{-/-}\gamma_c^{-/-}$ mice showed evidence of EBV infection in B cells of spleen, lymph node, and bone marrow by PCR, and elaborated appropriate T cells responses with CD4:CD8 ratio inversion and control of LMP$^+$ B cell proliferation in vivo. With high-dose EBV infection, however, human-hemato-lymphoid-system (HHLS)-Rag2$^{-/-}\gamma_c^{-/-}$ mice failed to control proliferation of LMP$^+$ B cells (Traggiai et al., 2004).

Upon HIV-1 infection with either CCR5- or CXCR4-tropic HIV-1, HHLS-Rag2$^{-/-}\gamma_c^{-/-}$ mice peak viral loads ($10^5$-$10^6$ copies viral RNA/ml plasma) were observed 2-4 weeks post-infection. As in humans, viremia stabilized at lower levels and was detectable throughout the course of analysis (190 days) (Baenziger et al., 2006). Infectious virus could be retrieved from mice by co-culture of cells from infected organs with human lymphocytes. CXCR4-tropic HIV-1 infected $CD3^+$ T cells in thymus, spleen, lymph nodes, and peripheral blood while CCR5-tropic HIV-1 was excluded from the thymus as few thymocytes express CCR5. Consistent with this distribution, CD4 depletion was observed in infected organs and was particularly dramatic for CXCR4-tropic strains. Less than 10% of the mice were able to mount α-p24 antibody responses and HIV-1 specific T cell responses were absent as assayed by in vitro IFNγ production upon restimulation. This limits the utility of the HHLS-Rag2$^{-/-}\gamma_c^{-/-}$ model in HIV-1 immunity and vaccine study (Baenziger et al., 2006). Similar results were obtained for HIV-1 infection of NOG mice, with long-term viremia at levels comparable to infection in patients, gradual CD4:CD8 ratio reversal, and elaboration of α-p24 and α-gp120 antibodies in a minority of infected animals combined with a failure to demonstrate cellular immune responses to HIV-1 infection (Watanabe et al., 2007).

Most groups do not report significant restoration of GALT or consistent establishment of long-term, systemic HIV-1 infection via the rectal or vaginal routes in HHLS-Rag2$^{-/-}\gamma_c^{-/-}$ mice (Goldstein, 2008; Hofer et al., 2008), although better results may be obtained by reconstituting with $CD34^+$ cells of fetal rather than cord blood origin (Berges et al., 2008). Rag2$^{-/-}\gamma_c^{-/-}$ mice breed well, with litter-sizes between 6-11 animals, and have long life-spans in specified pathogen-free environments. Generation of HHLS-Rag2$^{-/-}\gamma_c^{-/-}$ mice is straightforward with consistent engraftment of human cells (90% of mice have >5-10% h$CD45^+$ cells in PB) (Goldstein, 2008). The limitation on numbers of mice in a single study is the availability of hHSCs. Thus, the HHLS-Rag2$^{-/-}\gamma_c^{-/-}$ mouse is a valuable and straight-forward model for the study of HIV-1 pathogenesis and antivirals.

Establishing the Rag2$^{-/-}\gamma_c^{-/-}$ Mouse Model for HIV-1 Infection

Figure 63:
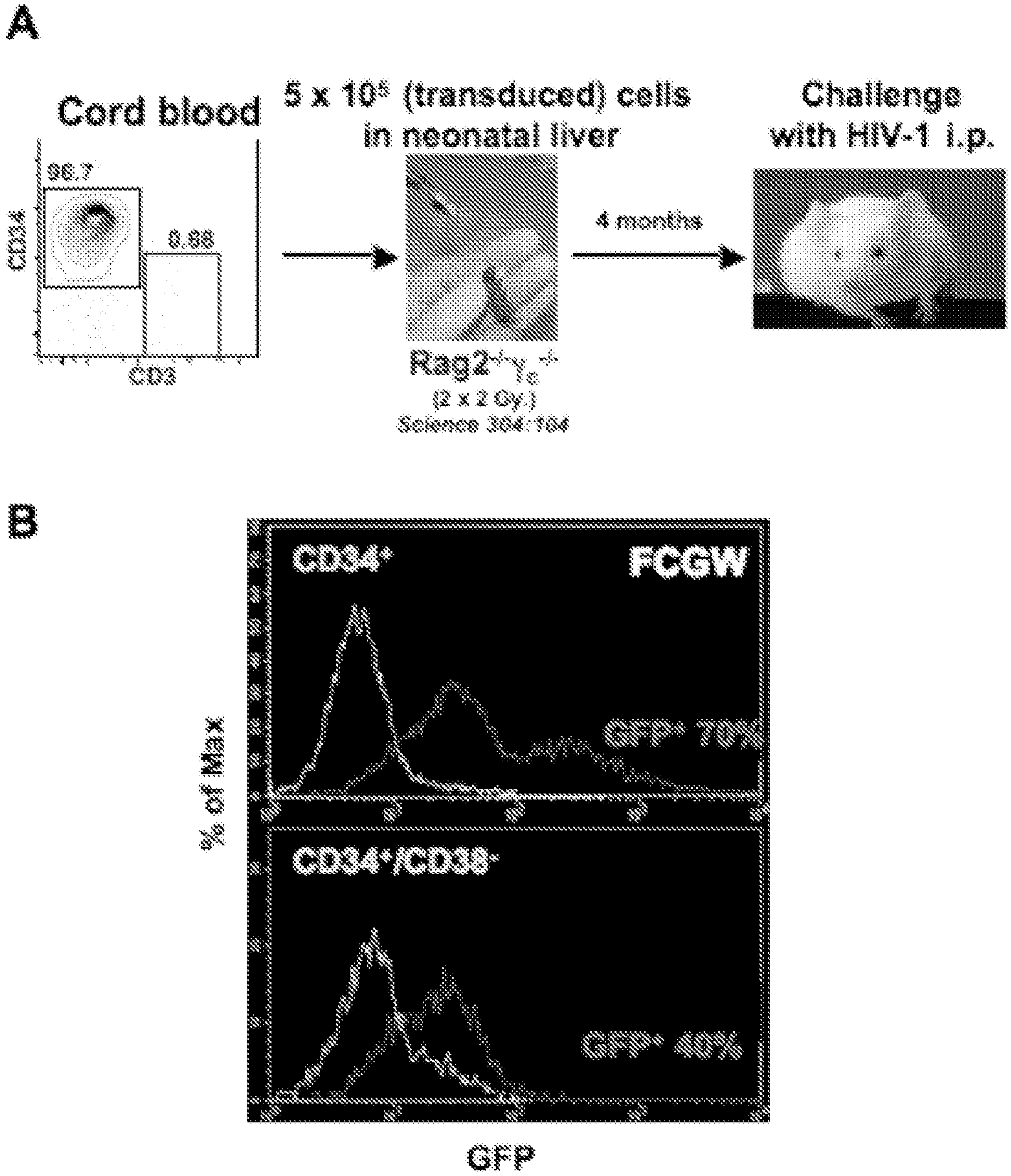
FIGS. 63A-B. (A) Schematic describing generation of HHLS-$Rag2^{-/-}\gamma_c^{-/-}$ mice. $CD34^+$ cells are enriched from cord blood. Following optional transduction, >$5\times10^5$ $CD34^+$ cells are injected intrahepatically into newborn $Rag2^{-/-}\gamma_c^{-/-}$ mice preconditioned with sublethal irradiation. Engraftment of $hCD45^+$ cells in peripheral blood is assessed 2-4 months post-transplant, and if satisfactory, mice are infected with HIV-1 by intraperitoneal (i.p.) injection. (B) GFP expression (X-axis) in $CD34^+$ (top panel) and $CD34^+CD38^-$ cells 48 hours following optimized transduction of freshly-thawed $CD34^+$ cells with FCGW (hCypA promoter driving GFP expression).

HIV-1 infection spreads from cell to cell at high titer in complex lymphoid tissues with a specific hierarchy of T cell destruction and distinct kinetics in vivo (Douek et al., 2003). If considering hT5Cyp as potential HIV-1 therapy, in vitro assays remain incomplete surrogates to in vivo testing. Therefore, studies were designed to assess the ability of hT5Cyp to protect $CD4^+$ T cells from HIV-1 infection in human hemato-lymphoid system (HHLS) mice. This mouse model takes advantage of the lack of functional B, T, and NK cells in Rag2$^{-/-}\gamma_c^{-/-}$ mice and allows for improved engraftment of xenografts as well de novo intrathymic generation of human T cells (Baenziger et al., 2008; Mazurier et al., 1999). Briefly, $CD34^+$ hematopoietic stem and progenitor cells are enriched from cord blood of healthy donors by MACS and transplanted intrahepatically into irradiated, newborn Rag2$^{-/-}\gamma_c^{-/-}$ mice (FIG. 63A). 2-4 months post-transplant, reconstitution of peripheral blood is assessed by flow cytometry, and mice with more that 5% h$CD45^+$ cells in peripheral blood are infected intraperitoneally (i.p.) with HIV-1 (FIG. 63A). In order to assesses the anti-HIV-1 efficacy of hT5Cyp in this model, $CD34^+$ cells are transduced with lentiviral vectors coding for hT5Cyp and ideally a reporter such as GFP prior to transplant into Rag2$^{-/-}\gamma_c^{-/-}$ neonates.

An optimal transduction of $CD34^+$ cells using a lentiviral vector in which the hCypA promoter drives GFP synthesis is shown in FIG. 63B. Transduction here was performed in media containing serum replacement in the absence of cytokines and GFP expression was monitored 48 hours later. 70% of $CD34^+$ T cells were GFP$^+$ and 40% of $CD34^+CD38^-$ cells believed to contain a higher proportion of hematopoietic stem cells are GFP$^+$ ex vivo (FIG. 63B).

Figure 64:
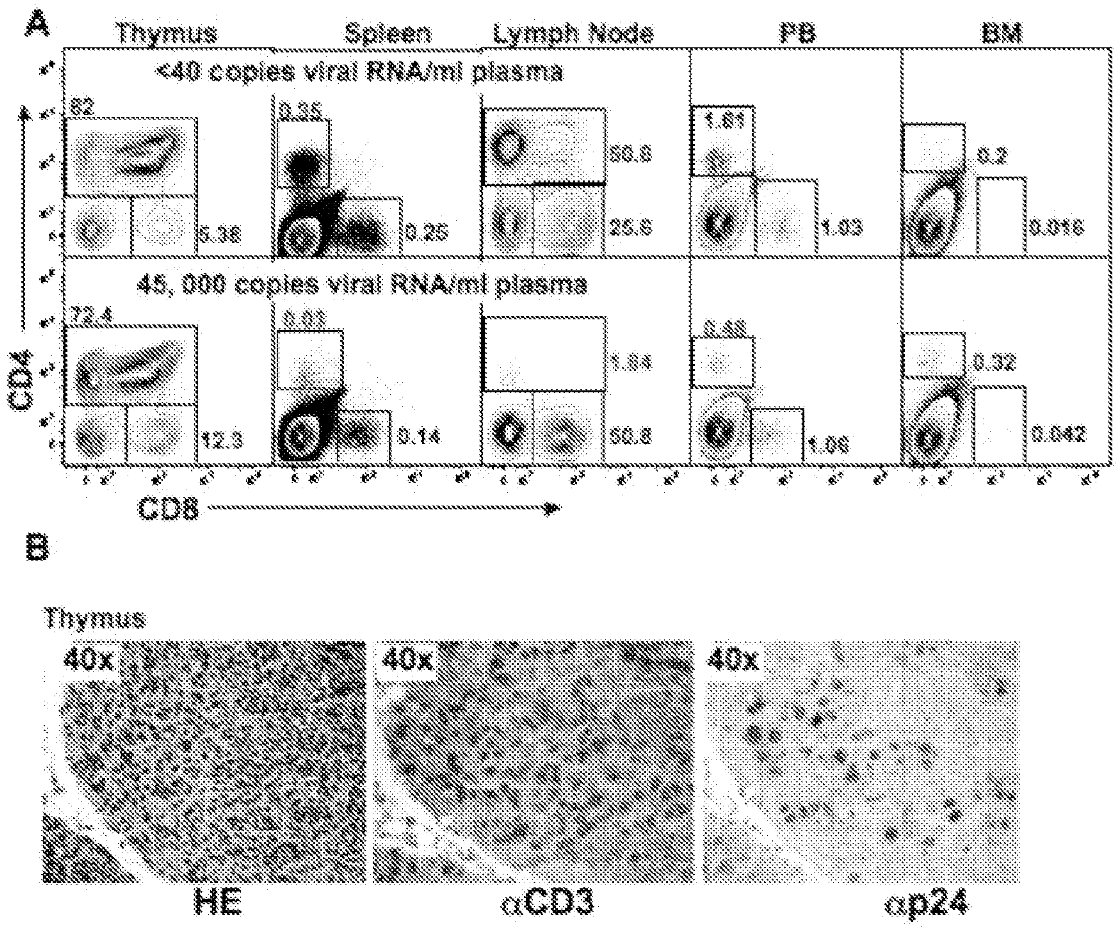
FIGS. 64A-B. HIV-1 infection in HHLS-$Rag2^{-/-}\gamma_c^{-/-}$ mice. (A) HHLS-$Rag2^{-/-}\gamma_c^{-/-}$ mice were generated and mock-infected with HIV-$1_{\Delta Nef}$ (top panel) or infected with HIV-$1_{NL4\text{-}3}$ (bottom panel) 10 weeks post-transplant. Four weeks post-infection, mice were sacrificed, and single cell suspensions from indicated organs were analyzed for presence of $CD4^+$ (Y-axis) and $CD8^+$ (X-axis) T cells. Viral load in plasma from these mice was determined. (B) Representative CD3- and p24-stained paraffin-embedded tissue sections of thymus are shown. Engraftment of CD3 human T cells in the thymus is robust and p24 staining is observed.

When untransduced $CD34^+$ cells are used to reconstitute newborn Rag2$^{-/-}\gamma_c^{-/-}$ mice and the resulting HHLS-mice are infected with HIV-1 eight weeks later, there is a striking depletion of $CD4^+$ T cells four weeks post-infection (FIG. 64A). This is most visible in the mesenteric lymph node, with a 28-fold reduction in $CD4^+$ T cells and a two-fold increase in $CD8^+$ T cells in infected mice compared to mice infected with a Nef-deleted virus that fails to replicate in vivo (FIG. 64A). Similarly, both in the peripheral blood as well as in the spleen of infected mice, there is a 3- and 10-fold reduction in $CD4^+$ T cells, respectively, although CD8 T cell levels remain constant (FIG. 64A). In the infected mouse, it is of note that in organs consisting almost entirely of lymphocytes such as the thymus and lymph node, a consistent 2-fold increase in $CD8^+$ T cells is observed, potentially as a reaction to infection (FIG. 64A). As can be seen by p24-staining of tissue sections from the infected thymus, infection of T cells was clearly established and is confirmed by a viral load of 45,000 copies viral RNA/ml plasma (FIG. 64A, B).

Optimizing Transduction of $CD34^+$ Cells

Once the HHLS-mouse model for HIV-1 infection was established, the next step was high-level transduction of $CD34^+$ cells with lentiviral vectors carrying hT5Cyp and a GFP reporter, coupled with efficient reconstitution of the T cell compartment in mice transplanted with transduced cells. While a number of groups report transduction efficiencies equivalent to ours in cultured $CD34^+$ cells (FIG. 63B), often in the presence of the early-acting cytokines TPO, SCF, and Flt3L, little is published on the reconstitution of $Rag2^{-/-}\gamma_c^{-/-}$ mice with transduced $CD34^+$ cells. One group has successfully knocked down the tumor suppressor p53 as well as the transcription factor SpiB in HHLS-mice (Gimeno et al., 2004; Schotte et al., 2004). Here, lentiviral vectors were used in which a pol III promoter drives expression of the shRNA and a pol II promoter the GFP reporter to transduce $CD34^+$ cells of fetal origin, which show both superior transduction efficiencies and reconstitution capacities compared to $CD34^+$ cells derived from cord blood.

Experiments were designed to express an exogenous protein with an unknown effect on hematopoiesis and immune system development in $CD34^+$ cells and to track transduced cells and their progeny in vivo. Transduction optimization experiments were carried out. As can be seen in Table 2 many factors affect transduction efficiency in $CD34^+$ cells including promoter choice, insert size, and envelope glycoprotein used for pseudotyping. The highest GFP-expression in transduced $CD34^+$ cells is consistently observed with a lentiviral vector in which the hCypA promoter drives GFP expression (FCGW) with up to 70% $GFP^+$ cells at 48 hours post-transduction (Table 2, FIG. 63B).

TABLE 2

| Transduction of $CD34^+$ cells | | | | | | |
|---|---|---|---|---|---|---|
| Vector | Envelope | Promoter | Insert Size (bp) | IRES-GFP | % $GFP^+$ (Average) | Repeats |
| FCGW[a] | VSVG | hCypA | 700 | – | 49.4 | N = 6 |
| FSGW[a] | VSVG | SFFV | 700 | – | 15.2 | N = 1 |
| FCGW | VSVG | hCypA | 2200 | – | 13.9[b] | N = 3 |
| FCGW | VSVG | hCypA | 2200 | – | 14.2[b] | N = 3 |
| cAPLS | VSVG | hCypA | 700 | – | 11.6 | N = 2 |
| scALPS[3c] | VSVG | SFFV/hCypA | 1500/700 | – | 8.9[c] | N = 2 |
| scAPLS[c] | VSVG | SFFV/hCypA | 1500/700 | – | 9.0[c] | N = 2 |
| FCGW[d] | RD114/TR[1] | hCypA | 700 | – | 8.5[d] | N = 1 |
| BiD[2] | VSVG | PGK/mCMV | 0/700 | – | 6.2 | N = 2 |
| sAPLS | VSVG | SFFV | 700 | – | 6.1 | N = 2 |
| BiD[2] | VSVG | PGK/mCMV | 3000/700 | – | 3.1 | N = 2 |
| APLS-IRES | VSVG | SFFV | 1500 | + | 1.9[e] | N = 1 |
| APLS-IRES | RD114/TR | SFFV | 1500 | + | 1.2[e] | N = 1 |

[a]FCGW and FSGW are FUGW[4] with the ubiquitin promoter replaced by the hCypA and SFFV promoters, respectively

[b]GFP-hT5Cyp fusion proteins were cloned into FCW; fluorescence intensity was low

[c]scAPLS was used for further studies

[d]FCGW was pseudotyped with RD114/TR[1]; when VSVG was used side-by-side, 74% of $CD34^+$ cells were $GFP^+$ at 72 hours post-transduction

[e]GFP fluorescence intensity was low

[1]Sandrin, V., et al. Lentiviral vectors pseudotyped with a modified RD114 envelope glycoprotein show increased stability in sera and augmented transduction of primary lymphocytes and CD34+ cells derived from human and nonhuman primates. *Blood* 100, 823-832 (2002).

[2]Amendola, M., Venneri, M. A., Biffi, A., Vigna, E. & Naldini, L. Coordinate dual-gene transgenesis by lentiviral vectors carrying synthetic bidirectional promoters. *Nature biotechnology* 23, 108-116 (2005).

[3]Pertel, C. & Luban, J. Unpublished. (2008).

[4]Lois, C., Hong, E. J., Pease, S., Brown, E. J. & Baltimore, D. Germline transmission and tissue-specific expression of transgenes delivered by lentiviral vectors. *Science* (New York, N.Y 295, 868-872 (2002).

Three approaches were compared for the ability to track transduced cells bearing hT5Cyp in vivo: using lentiviral vectors with an IRES driving GFP-synthesis, using hT5Cyp proteins with GFP fused at the N-terminus, and using scAPLS, a dual-promoter vector described previously (Table 2). While lentiviral vectors coding for GFP-hT5Cyp fusion proteins allow for adequate transduction efficiencies, GFP fluorescence intensity is low in this context, precluding efficient tracking in vivo (Table 2). As previously seen with transduction of primary $CD4^+$ T cells, lentiviral vectors coding for an IRES to drive GFP synthesis lead to inefficient GFP synthesis and extremely weak fluorescence intensity post-transduction (Table 2). The best combination of percentage of $GFP^+$ cells and GFP fluorescence intensity in $CD34^+$ cells was obtained using scAPLS, which also efficiently transduces $hCD4^+$ T cells (Table 2, FIG. 66A; left, pre-transplant panels). scAPLS was therefore chosen to test hT5Cyp in HHLS-mice. Additionally, BiD, another dual-promoter lentiviral vector employing the mCMV and PGK promoters (Amendola et al., 2005) was tested. Since the percentage of $GFP^+$ cells was lower post-transduction than with scAPLS and since transduction of $hCD4^+$ T cells using BiD was inefficient (Example 2), this vector was not used in experiments requiring target gene expression in T cells (Table 2).

Since high transduction efficiencies should lead to improved in vivo models, efforts were undertaken to optimize $CD34^+$ transduction. The application of spin-infection, the coating of plates with retronectin prior to transduction, or the use of polybrene during transduction had little and inconsistent effects on the percentage of $GFP^+$ cells in transduced $CD34^+$ cells. The pre-incubation of monocyte-derived DCs cells with SIV virus like particles (VLPs) has been shown to increase their transduction by more than 10-fold; an effect dependent on the SIV accessory protein Vpx (Goujon et al., 2006; Goujon et al., 2007). Similarly, pre-incubation of $CD34^+$ cells with SIV VLPs consistently led to a 2-fold increase in transduction efficiency (FIG. 65A).

The HHLS-mouse can be used as a model for evaluation of candidate gene-therapies, if development and maturation of transduced T cell progeny derived from transduced $CD34^+$ precursors is successful in vivo. BiD-transduced or FCGW-transduced $CD34^+$ cells from donor-identical cord blood were used to transplant newborn $Rag2^{-/-}\gamma_c^{-/-}$ littermates (FIG. 65B,C). Mice were analyzed 12 weeks later, with 6% and 8.9% of total $CD45^+$ lymphocytes in the bone marrow $GFP^+$ for BiD and FCGW-transduced $CD34^+$ input cells, respectively; a proportion equivalent to initial transduction efficiency (FIG. 65B,C). Since the majority of human $CD45^+$ lymphocytes in the HHLS-mouse bone marrow are $CD19^+$ B cells, similar results are obtained for B-cells with 6.6% and 9.2% of $CD19^+$ B cells $GFP^+$ for BiD and FCGW transduction, respectively (FIG. 65B,C; right panels). In the thymus, however, where the majority of $CD45^+$ human lymphocytes are T cells, there is no evidence for $GFP^+$ T cells, even when FCGW was used to transduce input $CD34^+$ cells (FIG. 65B,C; left panels). Similarly, $GFP^+$ T cells were not detected in the peripheral blood of these mice or in spleen, bone marrow, or lymph nodes.

hT5Cyp Reduces Viral Load in HHLS-Mice Challenged With HIV-1

Figure 65:
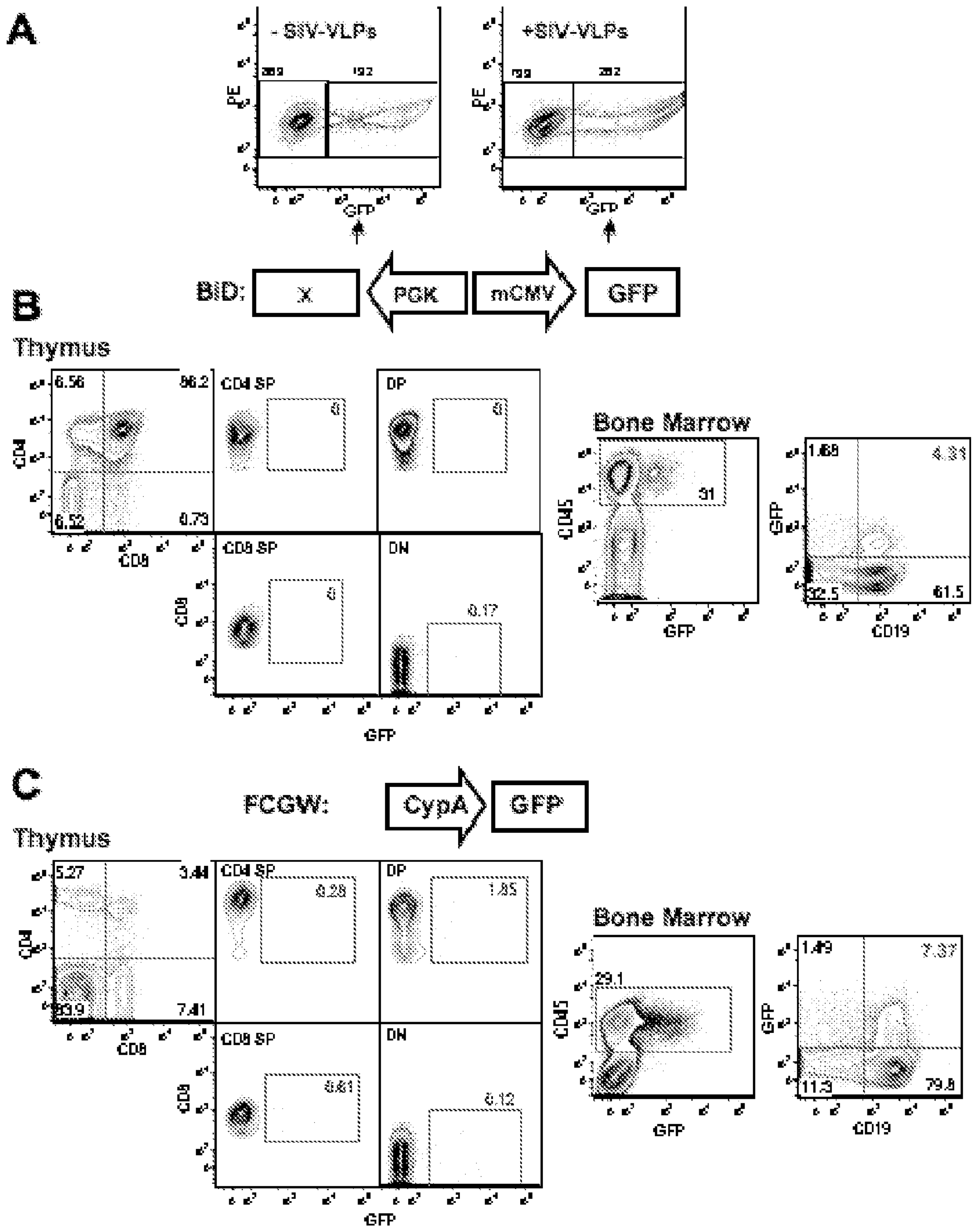
FIGS. 65A-C. (A) SIV-VLPs enhance $CD34^+$ HSC transduction. Donor-identical $CD34^+$ cells were transduced with FCGW following mock pretreatment (left panel) or pretreatment with SIV-VLPs (right panel). The percentage of $GFP^+$ (X-axis) cells was determined 72 hours post-transduction. (B) HHLS-$Rag2^{-/-}\gamma_c^{-/-}$ mice were generated using $CD34^+$ cells transduced with BID, a dual-promoter vector in which the mCMV promoter drives GFP expression (see schematic). Mice were sacrificed 12 weeks post-transplant and the percentage of $GFP^+$ cells in the thymus (left panel) and bone marrow (right panel) was determined by flow cytometry. (C) HHLS-$Rag2^{-/-}\gamma_c^{-/-}$ mice were generated using $CD34^+$ cells transduced with FCGW, a lentiviral vector in which the hCypA promoter drives GFP expression (see schematic). Mice were sacrificed after 12 weeks and analyzed as in (B).
Figure 66:
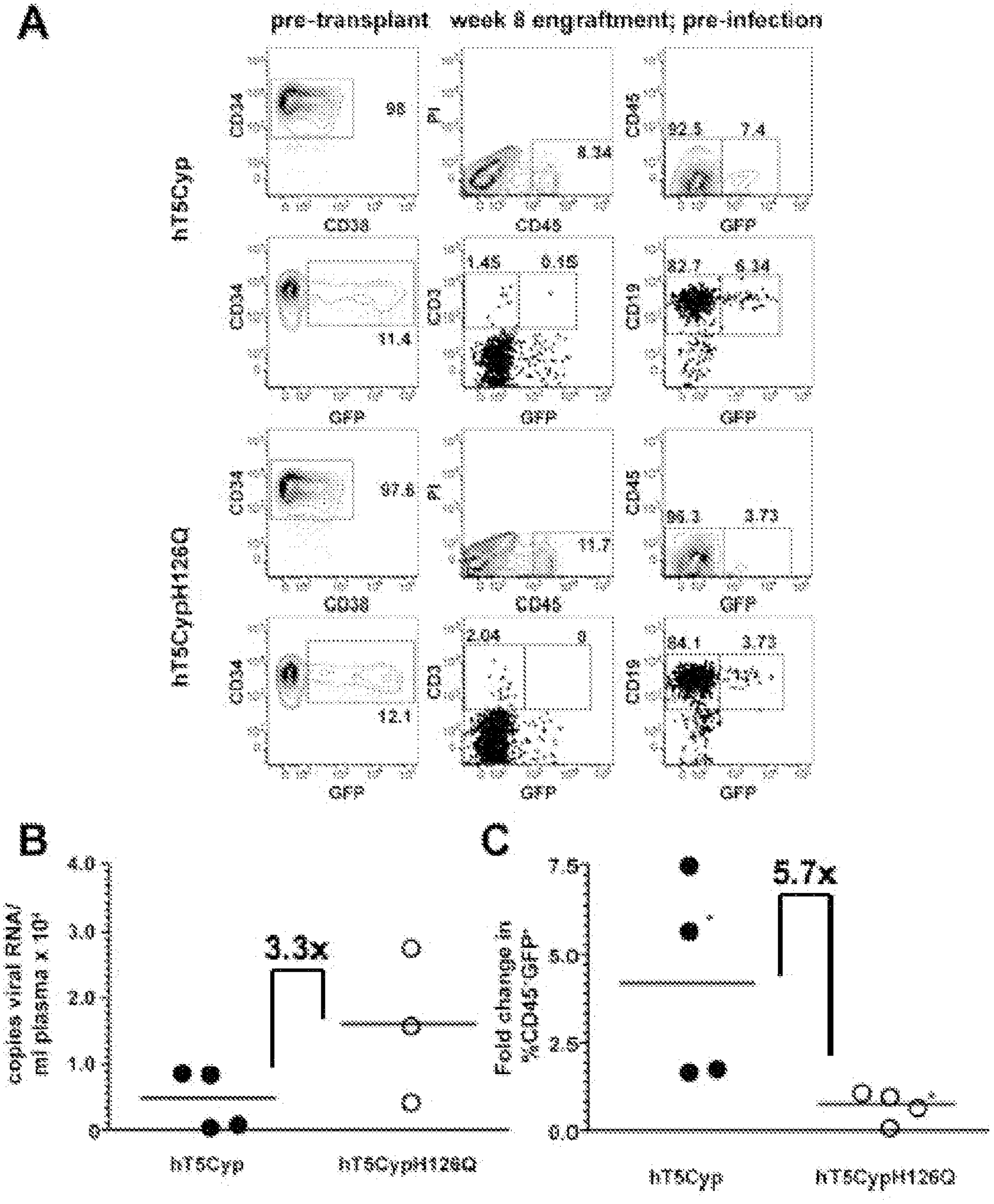
FIGS. 66A-C. hT5Cyp reduces viral load in HIV-1 infected HHLS-$Rag2^{-/-}\gamma_c^{-/-}$ mice. (A) HHLS-$Rag2^{-/-}\gamma_c^{-/-}$ were generated using $CD34^+$ cells stably transduced with scAPLS-hT5Cyp or scAPLS-hT5CypH126Q.~12% of $CD34^+$ cells were $GFP^+$ 72 hours post-transplant in vitro (left panels). Human cell engraftment in peripheral blood 8 weeks post-transplant and transgene expression in $CD45^+$ human lymphocytes, $CD3^+$ T cells, and $CD19^+$ B cells was analyzed by flow cytometry. (B) Viral load was determined in plasma of infected mice at 24 days post-infection. (C) Change in transgene (GFP) expression in $CD45^+$ cells was compared pre- and post-infection by flow cytometry.

Despite the results obtained for T cells in HHLS-mice transplanted with transduced $CD34^+$ cells, hT5Cyp was tested in the HHSL-mouse model. Donor-identical $CD34^+$ cells were transduced with scAPLS coding for hT5Cyp (FIG. 66A, top panel, pre-transplant) or the non-restricting hT5CypH126Q (FIG. 66, bottom panel, pre-transplant) and transplanted into newborn $Rag2^{-/-}\gamma_c^{-/-}$ littermates. An aliquot of cells was maintained in culture with the subsequent addition of SCF, TPO, and Flt3L, and assessed for GFP-expression 72 hours post-transduction. Transduction efficiency for hT5Cyp- and hT5CypH126Q-scALPS as measured by GFP-expression was equivalent at 11.4% and 12.4% $GFP^+$, respectively (FIG. 66A). Eight weeks post-transplant mice were analyzed by flow cytometry for peripheral blood engraftment, and mice containing between 1.3% and 24% $hCD45^+$ of nucleated cells in the peripheral blood were infected i.p. with HIV-1 (Table 3). As observed for mice reconstituted with BiD or FCGW-transduced $CD34^+$ cells, $GFP^+$ cells were found almost exclusively in the B-cell compartment with a somewhat lower proportion of $GFP^+$ cells than the original transduction efficiency reported for the $CD34^+$ cells. Again, $CD3^+$ T cells were not $GFP^+$ (Table 3, representative plots FIG. 66A). At 25 days post-infection there was a 3.3-fold reduction in plasma viral load when mice were reconstituted with hT5Cyp-transduced $CD34^+$ cells (Table 3, FIG. 66B). Similarly, there seemed to be a selection for $GFP^+CD45^+$ cells in the peripheral blood of mice reconstituted with hT5Cyp-transduced $CD34^+$ cells (Table 3, FIG. 65C), although no increase in $GFP^+CD3^+$ T cells was observed either in the peripheral blood or in the thymus post-infection (Table 3).

TABLE 3 hT5Cyp effects in HIV-1 infected HHLS-$Rag2^{-/-}\gamma_c^{-/-}$ mice

| | Pre-infection Peripheral Blood (% nuc. cells) | | | | | | | Post-infection Peripheral Blood (% nuc. cells) | | | | | | | Viral load (copies |
|---|---|---|---|---|---|---|---|---|---|---|---|---|---|---|---|
| | CD45 | | | $GFP^-$ | | $GFP^+$ | | CD45 | | | $GFP^-$ | | $GFP^+$ | | RNA/ml |
| Mouse | 45 | $GFP^-$ | $GFP^+$ | CD19 | CD3 | CD19 | CD3 | 45 | $GFP^-$ | $GFP^+$ | CD19 | CD3 | CD19 | CD3 | plasma) |
| hT5Cyp-1 | 1.3 | 100 | 0 | 41.8 | 0 | 0 | 0 | 0.81 | 94.3 | 5.71 | 13.6 | 8.51 | 100 | LC[b] | 660 |
| hT5Cyp-2[a] | 13.9 | 97 | 2.97 | 89.1 | 1.79 | 96.9 | 0 | 6.07 | 94.7 | 5.34 | 96.1 | 0.19 | 96.7 | 0 | 1062 |
| hT5Cyp-3 | 5.8 | 99.5 | 0.52 | 64 | 1.05 | 80 | 0 | 1.06 | 96.1 | 3.95 | 78.1 | 12 | 88.9 | LC[b] | 8612 |
| hT5Cyp-4 | 24.3 | 98.1 | 1.85 | 87.7 | 3.11 | 95.2 | 0 | 11.2 | 96.6 | 3.3 | 88.1 | 7.13 | 90.9 | 0 | 8620 |
| H126Q-1 | 28.9 | 99.7 | 0.35 | 88 | 2.69 | 100 | LC[b] | 27.3 | 99.6 | 0.41 | 83.2 | 10.6 | 70 | 33.3 | 15966 |
| H126Q-2 | 10.1 | 100 | 0 | 86.4 | 1.84 | 0 | 0 | 5.28 | 99 | 1 | 87.8 | 6.34 | 20 | 20 | 4353 |
| H126Q-3[a] | 9.04 | 92.6 | 7.41 | 89.3 | 1.57 | 98 | 1.96 | 1.88 | 94.7 | 5.26 | 86.9 | 14.5 | 100 | 0 | 27789 |
| H126Q-4 | 23.7 | 98.1 | 1.9 | 83.2 | 4.32 | 100 | 0 | 10.6 | 99.8 | 0.23 | 88.4 | 8.55 | 100 | 0 | ND[c] |

CD45 values are given as percent of nucleated cells. $GFP^+$ and $GFP^-$ are determined as percent $CD45^+$ cells.

CD19 and CD3 are described as percentage of $CD45^+GFP^-$ or $CD45^+GFP^+$ cells.

[a]Pre-infection cytometry profiles are shown in FIG. 66A

[b]LC indicates low cell count precluding reliable determination of percentage

[c]ND = not determined

Establishment of a $hCD4^+$-$Rag2^{-/-}\gamma_c^{-/-}$ Mouse Model for HIV-1 Infection To test the ability of hT5Cyp to protect $CD4^+$ T cells against HIV-1 infection in vivo, an experimental model was established in which human $CD4^+$ T cells were adoptively transferred into $Rag2^{-/-}\gamma_c^{-/-}$ mice. Clodronate liposomes were used to deplete macrophages and 6-10 week-old mice were conditioned with sublethal irradiation prior to transplant of human cells (van Rijn et al., 2003). Since activated human T cells will eventually cause xGVHD in this mouse model, resting and activated PBMC as well activated, purified $CD4^+$ T cells were titrated at 1, 5, and $10\times10^6$ cells/mouse (FIG. 67A). While as little as $1\times10^6$ resting PBMC lead to more than 60% reconstitution of peripheral blood with human $CD45^+$ lymphocytes, a similar result was obtained with $5\times10^6$ $CD4^+$ T cells (FIG. 67B,D). Peripheral blood engraftment was low at 6 days post-transplant and peaked by 21 days, at which point the percentage of human cells in the peripheral blood seemed to plateau (FIG. 67B). Despite the unexplained death of one mouse three days after transplant of $1\times10^6$ activated $CD4^+$ T cells, transplant of higher cell numbers generally seemed to lead to earlier development of GVHD-related symptoms and death (FIG. 67C). The longest survival observed in this setting was between 54 and 60 days post-transplant (FIG. 67C). When purified $CD4^+$ T cells were used to reconstitute $Rag2^{-/-}\gamma_c^{-/-}$ mice, the very low levels of $CD8^+$ and $CD4^+CD8^+$ cells in the input seem to have an expansion advantage. The appearance of $CD8^+$ and $CD4^+CD8^+$ cells was repeatedly observed in mice reconstituted with $CD4^+$ T cells enriched from PBMC, even when $CD8^+$ cells were specifically sorted out by FACS (FIG. 67D).

hT5Cyp Protects Against HIV-1 Infection in Vivo

Figure 68:
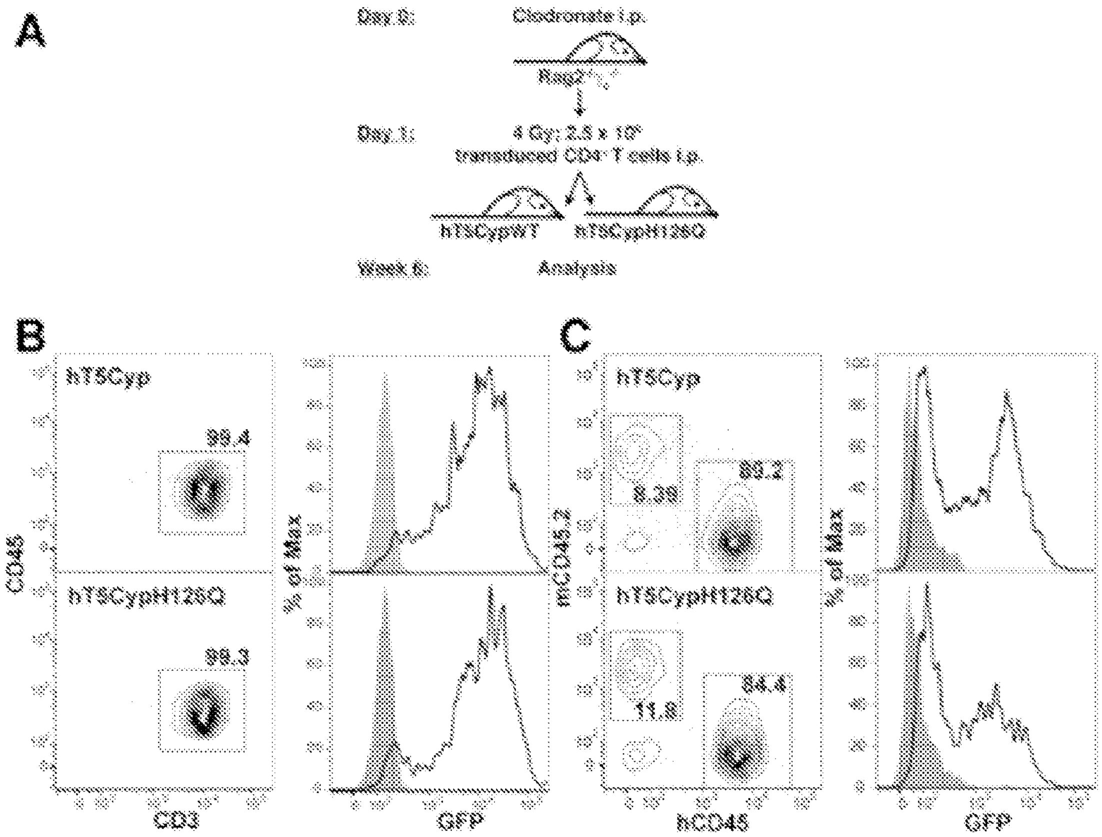
FIGS. 68A-C. (A) Experimental design for adoptive transfer of transduced $CD4^+$ T cells into $Rag2^{-/-}\gamma_c^{-/-}$ mice. 6-10 week old $Rag2^{-/-}\gamma_c^{-/-}$ mice were engrafted with GFP-sorted scALPS-transduced $CD4^+$ T cells expressing either hT5Cyp or hT5Cyph126Q. (B) A representative plot of input cells is shown (left panel). Grey histograms represent GFP-expression (X-axis) in un-transduced, donor identical $CD^+$ T cells, open histograms represent scAPLS-transduced cells. (C) Mice were sacrificed 6 weeks post-transplant and analyzed for human cell engraftment and transgene expression. Single cell suspensions of thymus were analyzed for presence of recipient-derived $CD45^+$ mouse cells (mCD45.2, x-axis) and donor derived $hCD45^+$ lymphocytes (X-axis). GFP expression (X-axis) in $mCD45.2^+$ cells (grey histogram) and $hCD45^+$ (open histogram) cells is shown.

To evaluate the anti-HIV-1 activity of hT5Cyp in this model, $CD4^+$ T cells were transduced with the hT5Cyp or hT5CypH126Q vectors and sorted for GFP-expression (FIG. 68C). Age-matched, 6-10 week-old $Rag2^{-/-}\gamma_c^{-/-}$ mice were conditioned with clodronate and sublethal irradiation (van Rijn et al., 2003), and injected intraperitoneally with $2.5\times10^6$ transduced $CD4^+$ T cells (FIG. 68A,B). In uninfected mice, engraftment efficiency was not altered by hT5Cyp or hT5CypH126Q (FIG. 68D). While over 90% of input cells were $GFP^+$, 6 weeks post-transplant it was apparent that GFP expression was down-modulated in a proportion of cells, consistently yielding a $GFP^{hi}$ and a $GFP^{lo}$ population of human $CD4^+$ T cells in mice (FIG. 68D).

To determine if hT5Cyp protected $hCD4^+$ T cells against HIV-1 in vivo, mice were infected with HIV-1 four days after adoptive transfer of the transduced $CD4^+$ T cells (FIG. 68A). When mice received hTSCyp-transduced $CD4^+$ T cells, mean peripheral blood $CD4^+$ cells constituted 6% (+/−2.87%) (FIG. 69B, Table 4) two weeks post-infection. This was 34-fold higher than the percentage $CD4^+$ cells (mean 0.18%, +/−0.04%) observed in mice transplanted with hTSCypH126Q-transduced $CD4^+$ T cells, a difference that was statistically significant (p=0.0002, n=10 hTSCyp, n=8 hTSCypH126Q) (FIG. 69B, Table 4). In this model, mice were infected with HIV-1 as cells are still expanding rapidly in the mouse (FIG. 65B). HIV-1 infection thus precludes T cell expansion in mice engrafted with hTSCypH126Q-expressing $CD4^+$ T cells. While this model reveals a 34-fold protective effect of hTSCyp on $CD4^+$ T cell survival, some cells are still productively infected with HIV-1 in the context of hTSCyp. Given the large difference in overall $CD4^+$ numbers between mice transplanted with hTSCyp- and those transplanted with hTSCypH126Q-expressing $CD4^+$ T cells, an effect of hTSCyp on absolute viral load was not observed in the absence of correction for $CD4^+$ T cell numbers (Table 4).

TABLE 4 hT5Cyp protects T cells from HIV-1 infection in vivo

| Mouse | | | Peripheral Blood (2 wks. postinfection) | | Viral load | Viral load |
|---|---|---|---|---|---|---|
| # | Donor (A or B) | hT5Cyp | CD45[a] | CD4[a,b] | (copies RNA/ml) | (Corrected for CD4 count) |
| 1A | | wt | 2.12 | 1.89 | 492800 | 260305 |
| 2A | | wt | 1.16 | 1.1 | 27826 | 25410 |
| 3A | | wt | 1.08 | 1 | 103208 | 101231 |
| 4A | | wt | 0.47 | 0.44 | 46007 | 104916 |
| 5A | | wt | 0.24 | 0.33 | 43551 | 192227 |
| 6B | | wt | 1.64 | 1.56 | 251320 | 159325 |
| 7B | | wt | 2.75 | 2.7 | 66416 | 24321 |
| 8B | | wt | 7.86 | 7.7 | 358800 | 47206 |
| 9B | | wt | 15.6 | 15.1 | 566835 | 37382 |
| 10B | | wt | 28.9 | 28.3 | 3811676 | 134446 |
| 11A | | H126Q | 0.17 | 0.15 | 13228 | 29396 |
| 12A[c] | | H126Q | 0.09[c] | 0.09 | LE[c] | LE[c] |
| 13A | | H126Q | 0.1 | 0.1 | 64465 | 644650 |
| 14A | | H126Q | 0.17 | 0.14 | 92330 | 659500 |
| 15B | | H126Q | 0.22 | 0.20 | 4755 | 23775 |
| 16B | | H126Q | 0.12 | 0.12 | 17811 | 148425 |
| 17B | | H126Q | 0.54 | 0.46 | 26520 | 57652 |
| 18B | | H126Q | 0.19 | 0.16 | 15314 | 95713 |

[a]CD45 values were determined as percentage of nucleated cells. CD4 was calculated to represent percentage of total nucleated cells. T cell protection is plotted in FIG. 69A

[b]All cells were $GFP^+$; with a $GFP^{hi}$ and $GFP^{lo}$ population. Representative profiles are in FIG. 68D.

[c]Mouse 12A had low engraftment (LE) and viral load below detection (<40) at week 2; at week 4 the viral load was at 7604 copies viral RNA/ml plasma.

To determine if hT5Cyp reduced absolute viral load in vivo, mice were infected with HIV-1 two weeks after adoptive transfer of the transduced $CD4^+$ T cells into $Rag2^{-/-}\gamma_c^{-/-}$ mice (FIG. 68B). The timing of HIV-1 infection was changed to allow for a stabilization of engraftment prior to assessment of viral replication. Mice transplanted with hT5Cyp-expressing $CD4^+$ T cells had a mean viral load of $1.6\times10^5$ (+/−$1.1\times10^5$) compared to $1.5\times10^6$ (+/−$6.9\times10^5$) copies viral RNA/ml plasma in mice transplanted with hT5CypH126Q-expressing $CD4^+$ T cells (FIG. 69B, Table 5). This 9-fold reduction in mean viral load in mice engrafted with hT5Cyp-expressing $CD4^+$ T cells was statistically significant (p=0.005; n=8 hT5Cyp, n=8 hT5CypH126Q) (FIG. 69B, Table 5). Taken together, these results from the peripheral blood indicate that hT5Cyp inhibits HIV-1 replication and protects against HIV-1-associated destruction of $CD4^+$ T cells in vivo (FIG. 69A,B; Tables 4 and 5).

TABLE 5 hT5Cyp reduces viral loads in vivo

| Mouse | | Viral | Peripheral Blood (pre-infection) | | Peripheral Blood (post-infection) | | Viral load (copies RNA/ml |
|---|---|---|---|---|---|---|---|
| #, donor | T5Cyp | tropism | CD45 | CD4 | CD45 | CD4 | plasma)[d] |
| 1C | wt | X4 | 2.02 | 1.9 | 0.67 | 0.66 | 40[c] |
| 2C[b] | wt | X4[b] | 3.64 | 3.3 | 1.93 | 1.90 | 938000 |
| 3D[a] | wt | X4[a] | 1.22 | 1.2 | NE | NE | 42402 |
| 4C | wt | R5 | 0.58 | 0.5 | 1.11 | 0.86 | 5824 |
| 5C | wt | R5 | 1.64 | 1.5 | 0.65 | 0.61 | 18900 |
| 6E | wt | R5 | 3.83 | 3.8 | 0.28 | 0.26 | 173067 |
| 7E | wt | R5 | 0.88 | 0.7 | 0.05 | 0.04 | 52436 |
| 8E | wt | R5 | 1.69 | 1.6 | 0.23 | 0.22 | 72067 |
| 9C | H126Q | X4 | 5.38 | 5.2 | 1.14 | 1.08 | 10000000[c] |
| 10C[b] | H126Q | X4[b] | 6.62 | 6.0 | 3.21 | 3.14 | 5160000 |
| 11D[a] | H126Q | X4[a] | 1.2 | 1.1 | NE | NE | 297500 |
| 12C | H126Q | R5 | 3.9 | 2.8 | 11 | 10.32 | 3906000 |
| 12C | H126Q | R5 | 0.2 | 0.2 | 1 | 0.95 | 95077 |
| 14E | H126Q | R5 | 9.58 | 8.6 | 0.02 | 0.02 | 251458 |

TABLE 5-continued hT5Cyp reduces viral loads in vivo

| Mouse | | Viral | Peripheral Blood (pre-infection) | | Peripheral Blood (post-infection) | | Viral load (copies RNA/ml |
|---|---|---|---|---|---|---|---|
| #, donor | T5Cyp | tropism | CD45 | CD4 | CD45 | CD4 | plasma)[d] |
| 15E | H126Q | R5 | 4.34 | 2.0 | 0.18 | 0.16 | 244916 |
| 16E | H126Q | R5 | 16.8 | 8.0 | 0.11 | 0.10 | 782286 |

CD45 values are given as percent of nucleated cells, CD4 values are calculated as percent of nucleated cells
[a]Pathology and intracellular p24 stain of thymus in FIG. 69C, E
[b]CD4-downregulation shown in FIG. 69D
[c]40 is below and 10000000 is above range of the assay
[d]Viral loads shown in FIG. 69B;
[e]When CD45-count was not determined (ND), human CD4 counts are of total lymphocytes (by FSC and SSC in lymph node and Thymus). NE = no engraftment, ND = not determined, NL = no lymph node, LE = low engraftment Further evidence for the in vivo effects of hT5Cyp was sought by examining lymphoid organs of HIV-1-infected mice. Single-cell suspensions were analyzed for the human T cell marker CD3 (which, unlike CD4, is not downregulated by HIV-1), the hT5Cyp vector reporter GFP, and HIV-1 p24 antigen. Few if any of the hT5Cyp-transduced human T cells in thymi or mesenteric lymph nodes of HIV-1-infected mice were $p24^+$, as compared with 1.5-5% of the cells transduced with hT5CypH126Q (FIG. 69C). HIV-1 down-regulates cell-surface expression of CD4 (Chen et al., 1996). Consistent with inhibition of productive infection in T cells, hT5Cyp prevented the down-regulation of cell surface CD4 in thymi and lymph nodes of mice infected with CXCR4-tropic or CCR5-tropic HIV-1, respectively (FIG. 69D, FIG. 70B). Finally, tissue sections of thymi were directly examined for human T cells (using anti-CD3 antibody) and HIV-1 p24 antigen. The engraftment of $CD4^+$ T cells transduced with hT5Cyp and hTSCypH126Q was similar (FIG. 69E). Intense p24 staining was observed in tissue sections from animals engrafted with hTSCypH126Q-transduced $CD4^+$ T cells but not in tissues from mice engrafted with $CD4^+$ T cells transduced with hT5Cyp (FIG. 69E, α-p24 stain). These experiments show that hT5Cyp prevented productive HIV-1 infection in vivo.

Due to lack of B, T, and NK cells, $Rag2^{-/-}\gamma_c^{-/-}$ do not have peripheral lymph nodes (Goldman et al., 1998). Lack of lymphocytes in these mice precludes migration of lymph node inducer cells into the lymph node anlage, leading to the degradation of the anlage within the first week of life (Coles et al., 2006). Transfer of mouse peripheral lymph node cells into 4 day old $Rag2^{-/-}\gamma_c^{-/-}$ leads to complete recovery of inguinal lymph nodes. The equivalent experiment performed in 4-week old mice fails to recover peripheral lymph nodes (Coles et al., 2006). When transferring transduced $hCD4^+$ T cells into 6-10 week old $Rag2^{-/-}\gamma_c^{-/-}$ the presence of peripheral lymph nodes was occasionally observed at 4-6 weeks post-transplant. An example is shown in FIG. 70A. These results are consistent with the lymph node anlage remaining intact well into adulthood.

Mice were reconstituted with hT5Cyp- or hT5CypH126Q-expressing $CD4^+$ T cells and infected two weeks later with CCR5-tropic HIV-1. When mice were reconstituted with hT5Cyp-expressing $CD4^+$ T cells, both mesenteric (MLN) and peripheral (PLN) lymph nodes showed $GFP^{hi}$ and $GFP^{lo}$ populations of $hCD4^+$ cells (FIG. 70B). Additionally, there was little evidence of CD4 downregulation in either PLN or MLN upon HIV-1 infection (FIG. 70B). In contrast, MLN and PLN of HIV-1 infected mice reconstituted with hT5CypH126Q-expressing $CD4^+$ T cells showed CD4 down-regulation (FIG. 70B). In the MLN of mice reconstituted with hT5CypH126Q only the $GFP^{lo}$ $CD45^+$ lymphocyte population persists in contrast to mice reconstituted with hT5Cyp. This is consistent with a selection for $GFP^+$ cells during HIV-1 infection in the context of restrictive hT5Cyp but not of the permissive hT5CypH126Q (FIG. 70B). The MLNs are closest to the site of HIV-1 infection (i.p), while the PLNs are further away. In the same mice where a selection against $GFP^+$ hT5CypH126Q-expressing cells is observed in the MLN, the PLN contains both $GFP^{hi}$ and $GFP^{lo}$ human lymphocytes at comparable proportions to the MLN and PLN of mice transplanted with hT5Cyp-expressing cells (FIG. 70B). These data are consistent with delayed kinetics of HIV-1 infection in PLNs.

Few if any of the hT5Cyp-transduced human T cells in MLN or PLN of HIV-1-infected mice were $p24^+$, as compared with 1.7-3.6% of the cells transduced with hT5CypH126Q (FIG. 70C). CD3 downregulation is observed in $p24^+$ cells here as HIV-$1_{NL4-3}$ was modified to express the $SIV_{mac}239$ Nef which inhibits T cell activation (FIG. 70C) in contrast to the isogenic virus containing HIV-1 Nef (FIG. 69C) (Schindler et al., 2006). Tissue sections of MLNs were directly examined for human T cells (using anti-CD3 antibody) and HIV-1 p24 antigen. The engraftment of $CD4^+$ T cells transduced with hT5Cyp and hT5CypH126Q was similar (FIG. 70D). Intense p24 staining was observed in tissue sections from animals engrafted with hT5CypH126Q-transduced $CD4^+$ T cells but not in tissues from mice engrafted with $CD4^+$ T cells transduced with hT5Cyp (FIG. 6D, α-p24 stain). Again, hT5Cyp prevented productive HIV-1 infection in vivo.

hT5Cyp Protects $CD4^+$ T Upon Infection with Cell-Associated Virus in Vivo

The previous experiments showed that $CD4^+$ T cells were protected from HIV-1 infection in vivo when mice were reconstituted with cells that had all been transduced with the hT5Cyp vector. Furthermore, the previous infections were initiated with cell-free HIV-1. Example 2 shows that cell-associated virus initially overcomes hT5Cyp-mediated restriction. Therefore, hT5Cyp anti-HIV-1 efficacy was evaluated in a more complex model. Mice were transplanted with $5\times10^6$ $CD4^+$ T cells previously transduced with scALPS-hT5Cyp or hT5CypH126Q. Cells were over 80% transduced as measured by GFP expression at the time of transplant and were not sorted further. Untransduced ($GFP^-$) $CD4^+$ cells from the same donor were cultured side by side and infected with CXCR4-tropic HIV-1 prior to infection of reconstituted mice. 4 days after transplant, mice were infected with $2.5\times10^6$ $CD4^+$ T cells that were <1% $p24^+$ (FIG. 71A). Peripheral blood was analyzed one, two, and three weeks after infection and mice were sacrificed three weeks after infection (FIG. 71A). Mice that had been transplanted with hT5Cyp-expressing cells had a 9.7-fold reduction in mean viral load one week post-infection (peak level of infection) and a 4.3-fold reduction at two weeks post-infection compared to mice transplanted with hT5CypH126Q-expressing cells (FIG. 71B).

There was a 3.7-fold protection of total $CD3^+$ T cell numbers in the thymus in the context of hT5Cyp ($2\times10^7$ $CD3^+$ T cells hT5Cyp thymus, n=2; $5.4\times10^6$ $CD3^+$ T cells hT5CypH126Q thymus, n=2). T cell protection was also apparent in the peripheral blood, where a higher degree of $CD4^+$ T cell depletion occurred in mice transplanted with hT5CypH126Q-expressing cells compared to hT5Cyp-expressing cells (FIG. 71C). For hT5Cyp-expressing cells, $CD4^+$ T cell numbers did not decline beyond 40% of initial levels three weeks post-infection, while hT5CypH126Q-expressing cells declined as low as 1% of initial levels (FIG. 71C). In mice that had received hT5Cyp-transduced $CD4^+$ T cells, few (0.9%) of the total human T cells in the infected thymus were $p24^+$, as compared with 6.5% of the cells in mice that received hT5CypH126Q-transduced cells (FIG. 71D). Next $GFP^{hi}$ and $GFP^{neg/lo}$ CD3' cell populations were analyzed in infected thymi for presence of p24. These populations represent transduced cells ($GFP^{hi}$) and untransduced cells or transduced cells that downmodulated GFP-expression) ($GFP^{neg/lo}$). In thymi of animals reconstituted with hT5CypH126Q-transduced $CD4^+$ T cells both GFP populations showed significant p24 staining (15.2% for $GFP^{neg/lo}$ and 4.4% for $GFP^{hi}$) cells (FIG. 71D). The reduced percentage of $p24^+$ cells observed here is likely due to reduced infectability of previously transduced cells. For hT5Cyp-transduced $CD4^+$ T cells, few of the $GFP^{hi}$ cells are $p24^+$, while 3.2% of the $GFP^{neg/lo}$ cells are $p24^+$, indicating a preferential HIV-1 infection of cells lacking hT5Cyp (FIG. 71D). Data shown are representative of two thymi in each group.

Discussion

Figure 69:
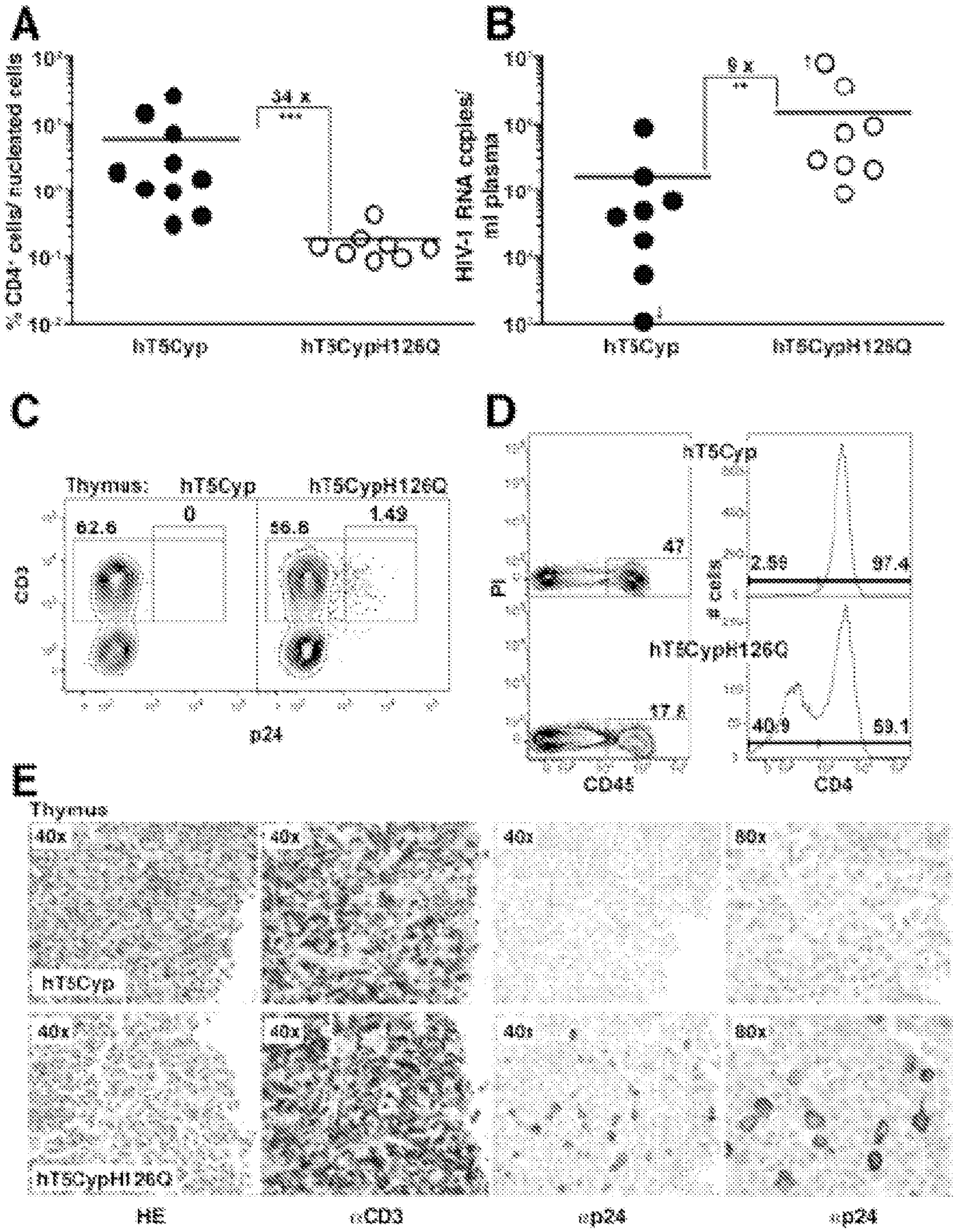
FIGS. 69A-E. hT5Cyp protects $CD4^+$ T cells from HIV-1 infection in vivo. (A) hT5Cyp prolongs $CD4^+$ T cell-survival in vivo. 6-10 week old $Rag2^{-/-}\gamma_c^{-/-}$ mice were engrafted with GFP-sorted scALPS-transduced $CD4^+$ T cells expressing either hT5Cyp or hT5Cyph126Q. Mice were infected 5 days after adoptive $CD4^+$ T cell transfer with CXCR4-tropic HIV-$1_{NL4\text{-}3}$ and analyzed for presence of $hCD4^+$ T cells (Y-axis) at 2 weeks post-infection. Individual mice are shown and fold-difference in mean peripheral blood $CD4^+$ lymphocyte engraftment (red bar) is indicated above the bracket. (*p=0.0002, Mann-Whitney test). (B) hT5Cyp reduces viral burden in vivo. $Rag2^{-/-}\gamma_c^{-/-}$ mice were engrafted with transduced $CD4^+$ T cells were infected 2 weeks after adoptive $CD4^+$ T cell transfer with CXCR4-tropic HIV-$1_{NL4\text{-}3}$. Plasma viral load was determined at 4 weeks post-infection. Individual mice are shown and fold-difference in viral load (red bar) is indicated above the bracket. (p=0.005, Mann-Whitney test). (C,D,E) hT5Cyp protects $CD4^+$ from productive HIV-1 infection in lymphoid organs. Age-matched $Rag2^{-/-}\gamma_c^{-/-}$ mice transplanted with $CD4^+$ T cells expressing either hT5Cyp or hT5Cyph126Q were infected with CXCR4-tropic HIV-$1_{NL4\text{-}3}$ 2 weeks after adoptive transfer of $CD4^+$ T cells. Single-cell suspensions of thymi were analyzed 14 days post-infection for $p24^+$ (X-axis) $CD3^+$ (Y-axis) T cells (C) or CD4-downregulation (X-axis) (D). Representative CD3- and p24-stained paraffin-embedded tissue sections of thymus are shown. While engraftment of $CD3^+$ human T cells is similar in thymi of mice transplanted with either hT5Cyp– (top panel) or hT5CypH126Q-expressing $CD4^+$ T cells (bottom panel), rare and weaker p24 staining is observed in organs from mice transplanted with hT5Cyp-$CD4^+$ T cells as compared to those transplanted with hT5CypH126Q-$CD4^+$ T cells (E).
Figure 70:
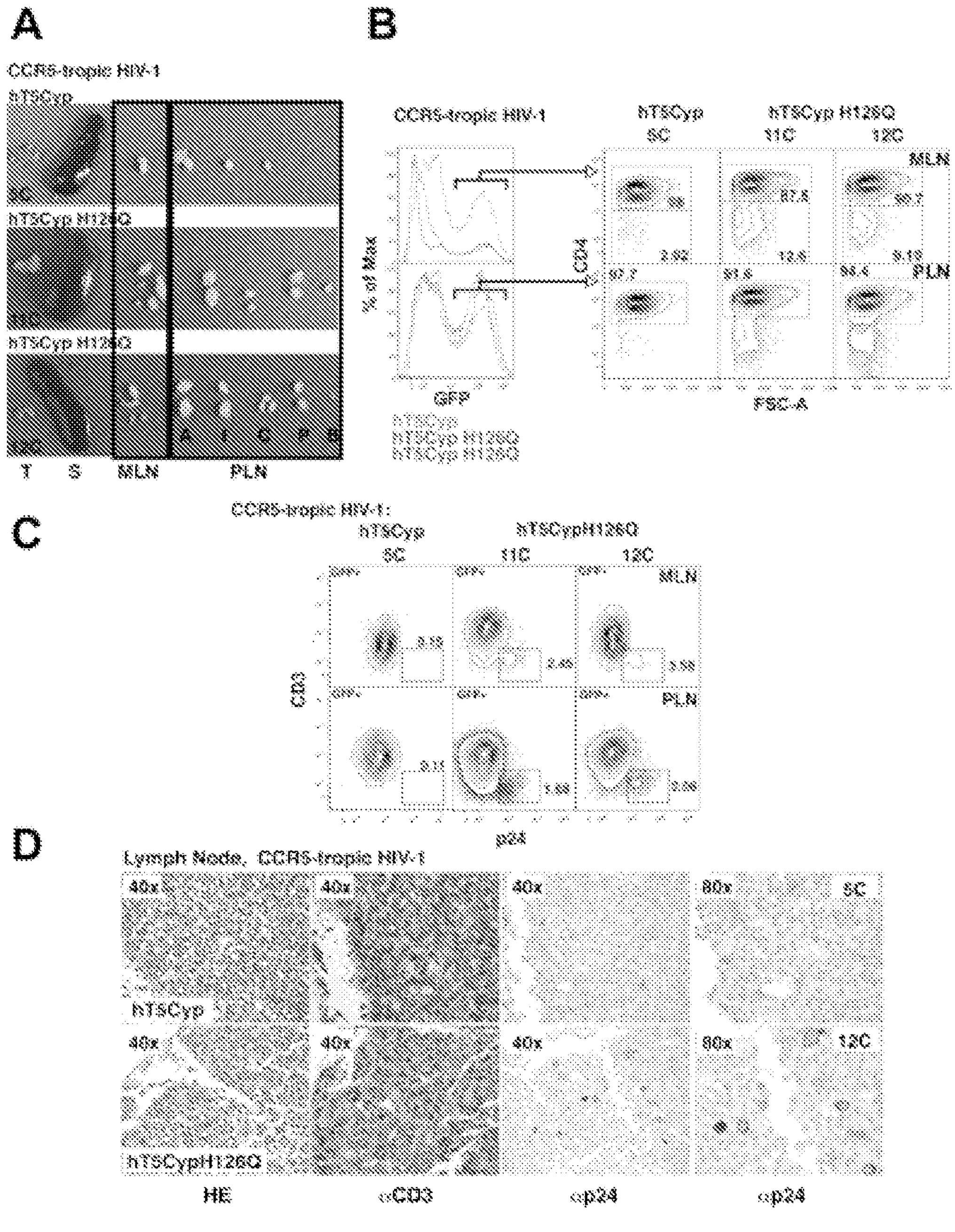
FIGS. 70A-D. hT5Cyp protects $CD4^+$ T cells from HIV-1 infection in vivo. (A) Lymphoid organs from $Rag2^{-/-}\gamma_c^{-/-}$ mice engrafted with transduced $CD4^+$ T cells are shown 4 weeks after infection with CCR5-tropic HIV-1. T=thymus, S=spleen, MLN=mesenteric lymph node, PLN=peripheral lymph node, A=axillary, I=inguinal, C=cervical, P=popliteal, B=brachial (B,C,D) hT5Cyp protects $CD4^+$ from productive HIV-1 infection in lymphoid organs. Single cell suspensions from MLN and PLN of mice infected with CCR5-tropic HIV-1 were analyzed for GFP transgene expression (B, left panel, X-axis), CD4 downregulation (B, right panel, Y-axis), and presence of $p24^+$ (X-axis) $CD3^+$ (Y-axis) cells (C). Representative CD3- and p24-stained paraffin-embedded tissue sections of mesenteric lymph node are shown. While engraftment of $CD3^+$ human T cells is similar in MLN of mice transplanted with either hT5Cyp– (top panel) or hT5CypH126Q-expressing $CD4^+$ T cells (bottom panel), rare and weaker p24 staining is observed in organs from mice transplanted with hT5Cyp-$CD4^+$ T cells as compared to those transplanted with hT5CypH126Q-$CD4^+$ T cells (D).
Figure 71:
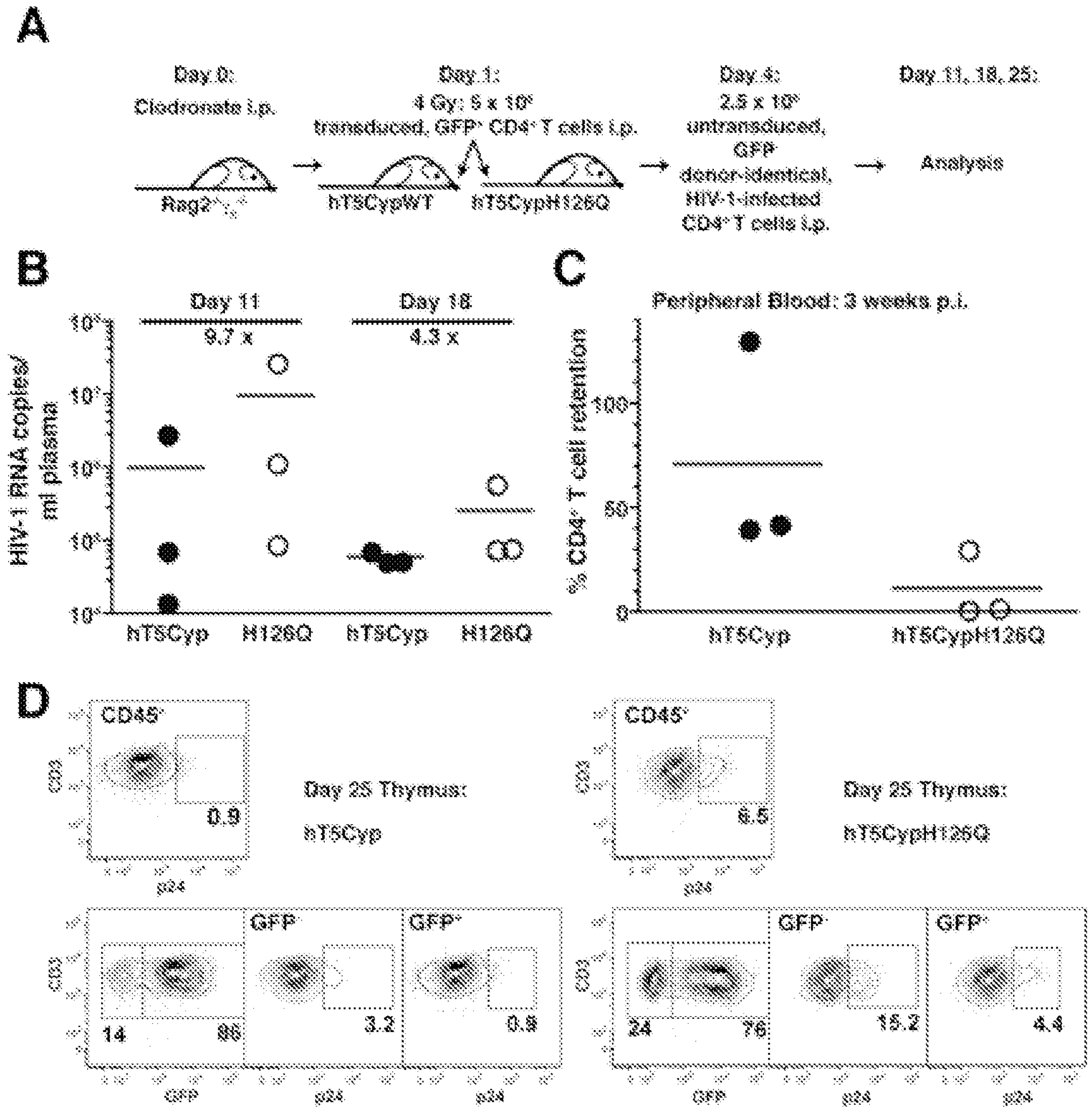
FIGS. 71A-D. (A) Experimental design for adoptive transfer of transduced $CD4^+$ T cells and in vivo challenge with cell-associated HIV-1 in $Rag2^{-/-}\gamma_c^{-/-}$ mice. Gy=Gray; i.p.=intraperitoneal injection. (B) hT5Cyp reduces viral burden in vivo. 6-10 week old $Rag2^{-/-}\gamma_c^{-/-}$ mice were engrafted with GFP-sorted scALPS-transduced $CD4^+$ T cells expressing either hT5Cyp or hTSCyph126Q. Mice were infected 5 days after adoptive $CD4^+$ T cell transfer with autologous, untransduced, HIV-1 infected cells. Plasma viral load (Y-axis) was assessed at indicated times post-infection. (C) hT5Cyp prolongs $CD4^+$ T cell-survival in vivo. $CD4^+$ T cell retention (Y-axis) was assessed as the percentage of $CD4^+$ T cells in peripheral blood at 24 days compared to 11 days post-infection. (D) Single cell suspensions of thymuses from mice that received hT5Cyp- or hTSCypH126Q-expressing $CD4^+$ T cells were analyzed for p24-, CD3-, and GFP-expression by flow cytometry.

The $hCD4^+$-$Rag2\gamma_c^{-/-}$ mouse developed here proved a robust model for assessing inhibition of HIV-1 infection and $CD4^+$ T cell protection by lentiviral transduction with hT5Cyp (FIGS. 69, 70, 71). Due to aberrant T cell activation in the xenogeneic context and eventual development of xGVHD symptoms in $hCD4^+$-$Rag2\gamma_c^{-/-}$ mice, this model is limited to assessment of hT5Cyp efficacy in the context of acute HIV-1 infection. Furthermore, in the absence of an intact innate and adaptive immune system, immune responses to HIV-1 cannot be assessed in $hCD4^+$-$Rag2\gamma_c^{-/-}$ mice. Similarly, this model will not reveal any antigenic potential hT5Cyp itself may have. Humanized mouse models to date do not elicit sufficiently robust and consistent primary immune responses to address this question. One pre-clinical approach could be screening the frequency of hT5Cyp-reactive cells in the average human T cell repertoire.

A new model with 100% infection rate and greatly improved T cell reconstitution has been developed allowing for excellent viral replication compared to the preceding huPBL-SCID models for HIV-1 infection (Mosier et al., 1991). Given that these observations are some of the highest viral loads reported, this model may prove robust enough to study infection with primary isolates and mutant viruses which replicate less efficiently in tissue culture than the lab-adapted, wildtype HIV-1 strains.

Cell-to-cell spread of HIV-1 in lymphoid organs is a major method of HIV-1 transmission in $hCD4^+$-$Rag2\gamma_c^{-/-}$ mice (Haase, 1999). Nonetheless, T5Cyp leads to an impressive T cell protection and a reduction in viral loads in these animals. These data support the validity of a T5-based HIV-1 therapy approach. While it takes a much more potent T5 than $hT5\alpha_{R323-332}$ to control cell-to-cell spread of HIV-1 (Richardson et al., 2008), hT5Cyp not only accomplishes this in vitro (FIG. 52) but also in an in vivo model (FIGS. 69,70).

To render the model more physiologically relevant, infection with cell-associated virus was initiated in mice transplanted with transduced $CD4^+$ T cells. This leads to HIV-1 infection in mice that now have mixed transduced and untransduced T cell populations, establishing a constant reservoir of $CD4^+$ cells permissive to HIV-1 infection. Despite this rigorous set-up, mice containing hT5Cyp-expressing T cells showed protection of $CD4^+$ T cells with a concomitant reduction in viral load (FIG. 71). Analysis of infected cells in the thymus showed a significant overall reduction in $p24^+$ T cells in mice that received hT5Cyp-transduced T cells. This reduction in $p24^+$ cells was not only apparent in $GFP^+$, transduced T cells but also in $GFP^-$, untransduced cells, implying a potential effect of hT5Cyp on bystander cells. Consistent with bystander protection, while mice that received hT5Cyp-transplanted cells, had a three-fold increase in total numbers of $CD3^+$ T cells in the thymus, they had a >3.3-fold reduction in total numbers of $GFP^-$ $p24^+$ cells compared to mice that received hT5CypH126Q-transplanted cells; likely due simply to lower levels of circulating virus (FIG. 71). This in vivo "competition" model can be expanded to allow for the assessment of $CD4^+$ and $CD8^+$ T cell engraftment as well as some limited B cell engraftment (van Rijn et al., 2003), by infecting mice transplanted with transduced $CD4^+$ T cells with HIV-1 infected PBMCs from the same donor.

Figure 67:
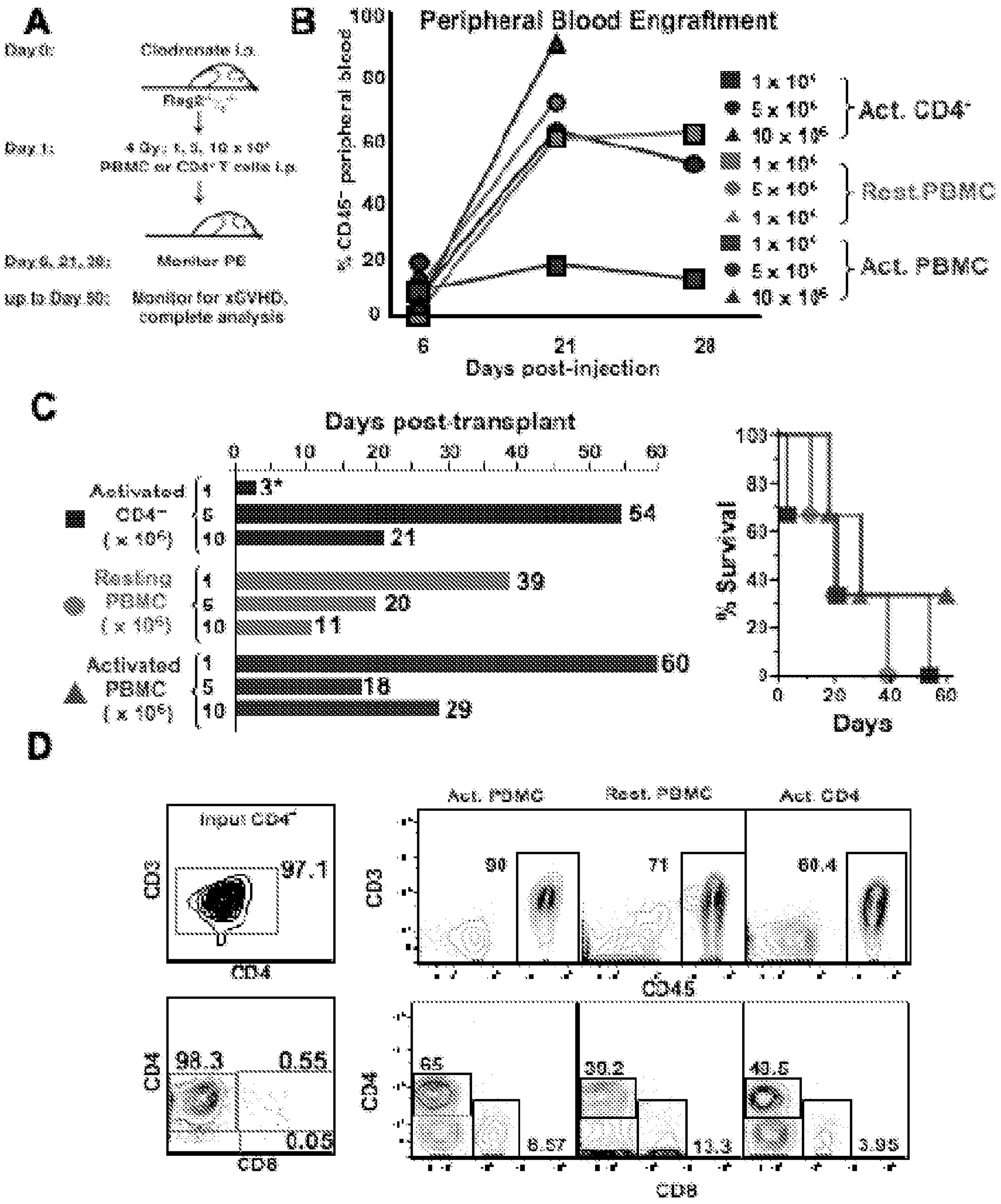
FIGS. 67A-D. Establishment of a hCD4-$Rag2^{-/-}\gamma_c^{-/-}$ mouse model. (A) Experimental design for adoptive transfer of PBMC or $CD4^+$ T cells into $Rag2^{-/-}\gamma_c^{-/-}$ mice. Gy=Gray; i.p.=intraperitoneal injection. (B) Titration of human PBMC and $CD4^+$ T cells adoptively transferred to $Rag2^{-/-}\gamma_c^{-/-}$. Engraftment of $CD45^+$ cells (Y-axis) in the peripheral blood was assessed by flow cytometry on indicated days post-transfer (X-axis). (C) Survival of $Rag2^{-/-}\gamma_c^{-/-}$ mice after transfer of human PBMC or $CD4^+$ T cells. Mice were sacrificed upon the appearance of severe GvHD symptoms. (D) Left panel shows a representative plot of input $CD4^+$ T cells following enrichment from PBMCs. Right panel shows engraftment of human lymphocytes in peripheral blood 21 days following transfer of PBMCs or $CD4^+$ T cells to pre-conditioned mice.

Since mouse availability is the only limiting factor, the $hCD4^+$-$Rag2\gamma_c^{-/-}$ model for HIV-1 infection is straightforward and allows for initiation of infection using cell-free and cell-associated virus. The model could easily be adapted to a hPBL-$Rag2\gamma_c^{-/-}$ model, as total PBMCs engraft even more efficiently in $Rag2\gamma_c^{-/-}$ mice than transduced $CD4^+$ T cells (FIG. 67). Furthermore, analysis points to presence of human T cells in the gut of $hCD4^+$-$Rag2\gamma_c^{-/-}$ mice, potentially allowing for mucosal initiation of systemic HIV-1 infection. $hCD4^+$-$Rag2\gamma_c^{-/-}$ mice were invaluable for our preclinical assessment of hT5Cyp as a candidate anti-HIV-1 gene therapy.

While, hT5Cyp had no effect on proliferation, cell-surface-marker expression, and IL-2 production of transduced $CD4^+$ T cells in culture (FIG. 46A, 58), endogenous T5α functions may be interfered with by formation of heteromultimers (FIG. 46B, 62). hT5Cyp is a new protein with unknown potential effects on hematopoiesis, immune cell development, and effector functions. hT5Cyp effects on T cell differentiation could be directly assessed in vitro by culturing $CD34^+$ cells transduced with scAPLS-hT5Cyp and scAPLS-hT5CypH126 with OP-9 stromal cells expressing delta-like ligand 1 (OP9-DL-1) in the presence of Flt3L and IL-7 (La Motte-Mohs et al., 2005). This co-culture system allows for the gradual accumulation first of $CD4^+$ single-positive T cells followed by $CD4^+CD8^+$ double-positive T cells by 24 days of co-culture. In vitro-differentiated T cells have some effector function as they upregulate activation markers following stimulation with αCD3 and αCD28 antibodies. Since scAPLS allows tracking of transduced cells by GFP expression, this system would allow for detecting possible effects of hT5Cyp on T cell development. Furthermore, addressing whether HIV-1 resistant T cells can be generated from hT5Cyp-transduced $CD34^+$ HSCs would be a valuable in vitro proof of principle experiment.

To study T5Cyp-mediated inhibition of HIV-1 in the HHLS-$Rag2\gamma_c^{-/-}$ mouse model directly, two obstacles were overcome: efficient transduction of $CD34^+$ HSCs and efficient differentiation of transduced $CD34^+$ cells into T cells in vivo. $CD34^+$ HSCs are naturally resistant to HIV-1 infection despite expression of CD4 and CXCR4 due to restriction by $p21^{Waf/Cip1/Sdf1}$, a cyclin-dependent-kinase inhibitor that complexes with HIV-1 integrase and inhibits proviral integration (Zhang et al., 2007). With entry into the cell-cycle and subsequent expansion and differentiation, p21-expression is downregulated allowing for improved lentiviral transduction. Furthermore, high proteasome activity in HSCs restricts HIV-1 post-entry (Santoni de Sio et al., 2006). Early-acting cytokines (SCF, Flt3L, TPO) are often used in short-term $CD34^+$ cell culture to increase transduction efficiency partly by reducing proteasome activity. This effect that can be further enhanced by the addition of proteasome inhibitors to yield transgene expression in ~75% of cells (Santoni de Sio et al., 2006). It is unclear what effect such ex vivo HSC manipulation has on multilineage engraftment potential, specifically regarding T cell development, as cells were only assayed in the adult NOD/SCID repopulation assay (Santoni de Sio et al., 2006). While many groups add polybrene or pre-coat plates with retronectin to enhance CD34+ HSC transduction efficiency, no consistent improvement in transduction efficiency was observed using these methods. However, a >2-fold enhancement of transduction efficiency was consistently observed by treating target cells with SIV viral-like particles (VLPs) prior to transduction. SIV VLPs have been shown to enhance transduction of DCs more than 10-fold due to the presence of the SIV accessory protein Vpx (Goujon et al., 2006; Goujon et al., 2007). Vpx may affect HIV-1 restriction mechanisms found in CD34+ HSCs such as p21 and proteasome activation without a requirement for cytokine stimulation and entry into cell cycle. The semen-derived enhancer of HIV-1 infection (SEVI) has also shown up to 10-fold enhancement of CD34+ HSC transduction efficiency in preliminary experiments.

In the absence of a proliferation advantage such as disruption of p53 (Gimeno et al., 2004), reliable transgene expression in T cells derived from transduced CD34+ in vivo is rare. This is independent of hT5Cyp expression as three different lentiviral vectors coding only for GFP were used to transduce CD34+ HSCs and all failed to yield GFP+ thymocytes despite generation of GFP+ B cells and DCs (FIG. 65). Notwithstanding, hT5Cyp reduced viral load more than 3-fold in HIV-infected HHLS-Rag2$\gamma_c^{-/-}$ mice transplanted with hT5Cyp-transduced CD34+ cells (FIG. 66). Based on T cell depletion kinetics observed in prior experiments, the mice were sacrificed 24 days post-infection. On the other hand, a longer duration of infection may have allowed for visible selection of GFP+ T cells.

T cell fate and differentiation in HHLS-Rag2$^{-/-}\gamma_c^{-/-}$ mice may be easily perturbed by any form of ex vivo HSC-manipulation, despite the unquestionably superior de novo thymopoeisis compared to previous humanized mouse models (Manz, 2007). Sorting cells based on transgene expression prior to transplant would ensure that the majority of immune-reconstituting cells are transduced and may thus enforce development of transduced T cells. A problem arising with use of CD34+ HSCs derived from cord blood is a small sample size with <1×10$^6$ cells enriched from one donor on average. Transplantation of less than 1×10$^5$ cells/animal is undesirable, and reconstitution efficiency is proportional to the dose of transplanted CD34+ HSCs. This precludes ex vivo selection of cells based on transgene expression.

An alternative is in vivo selection using lentiviral vectors expressing the MGMT$_{P140K}$ selection marker or safer adaptations thereof targeted for clinical applications. MGMT is a methytransferase that repairs DNA damage caused by DNA alkylating agents (e.g. BCNU, used clinically as anti-cancer chemotherapy). Since HSCs contain little endogenous MGMT, they are exceptionally susceptible to elimination by alkylating agents. The MGMT$_{P140K}$-variant is particularly useful, as it is resistant to small molecule-inhibitors (e.g. BG) of endogenous MGMT while still protecting from DNA damage caused by BCNU (Schambach et al., 2006). Transduction of hHSCs with lentiviral vectors coding for MGMT$_{P140K}$ allowed for efficient reconstitution of BG/BCNU-conditioned NOD/SCID mice observed after two rounds of subsequent selection. Human cells comprised >20% of cells in the bone marrow and over 99% of CFCs contained provirus as compared to 11% in controls without BG/BCNU treatment (Zielske et al., 2003). This system has not been tested in newborn HHLS-Rag2$^{-/-}\gamma_c^{-/-}$ mice. In vivo selection of MGMT$_{P140K}$-transduced cells in HHLS-Rag2$^{-/-}\gamma_c$ may allow for multilineage engraftment of transduced immune cells, including high level of transgene expression in the T cell compartment, as selection results in a pure population of transduced HSCs in vivo.

A stable and inexhaustible source of isogenic CD34+ cells would allow for in vitro manipulation prior to transplant, larger experimental cohorts, and increased experimental consistency. Directing in vitro differentiation of genetically modified human embryonic stem cells (hESCs) to hematopoietic precursors (HSCs) would revolutionize gene therapy approaches. hESCs are immortal, pluripotent cells with considerable genetic manipulability in stark contrast to HSCs. Limited hematopoietic potential in vivo has been demonstrated for hESC-derived HSCs upon direct injection into mouse bone marrow, but engraftment into adult NOD/SCID mice was very low, engrafted cells failed to migrate to target tissue, and T cell development was deficient (Wang et al., 2005). T cell development is rescued by priming hESC-derived HSCs transduced with GFP-lentivectors on OP9-DL1 before injection into the SCID-hu thy/liv. Over 90% of ES-derived thymocytes obtained by this method were GFP+ (Galic et al., 2006). Given the SCID-hu model used here, it is unclear whether these cells would have the capability for multilineage reconstitution of immunocompromised mice, in addition to reconstitution of the T cell compartment. To address this, OP9-DL1-primed hESC-derived HSCs should be used to reconstitute newborn Rag2$^{-/-}\gamma_c$ or NOG mice.

In a proof of principle experiment, sickle-cell anemia was cured in mice by reprogramming autologous tail fibroblasts into induced pluripotent cells (iPSs), genetic modification through homologs recombination of iPSs, and immune-reconstitution of lethally irradiated mice with "cured" iPSs (Hanna et al., 2007). Ex vivo culture of CD34+ HSCs combined with OP9-DL1 priming towards T cells would allow for repeated transduction opportunities and higher efficiencies, provided culture conditions allowing for maintenance of multilineage engraftment potential are established. If conditions allowing for true hematopoietic stem cell-expansion combined with T cell priming could be established, transduced cells may even be sorted prior to transgene expression.

While reconstitution of a functional human T cell compartment in prior humanized mouse models is yet unsuccessful, de novo thymopoiesis, the ability to generate specific primary T cell responses to EBV infection, as well as the elaboration of T-cell dependent antibody responses to tetanus toxoid observed in HHLS-Rag2$^{-/-}\gamma_c^{-/-}$ mice have been major advances (Traggiai et al., 2004). Given the lack of human MHC in the HHLS-Rag2$^{-/-}\gamma_c^{-/-}$ thymus, how does positive and negative T cell selection enabling these immune responses occur? Under normal developmental conditions positive selection is preferentially driven by cortical thymic epithelial cells (Palmer, 2003) while both epithelial cells and HSC-derived DCs are involved in negative selection. Since no human epithelial cells, but both murine and human DCs were found in the HHLS-Rag2$^{-/-}\gamma_c^{-/-}$ thymus, positive selection should occur on mouse epithelial cells, while negative selection can occur on both mouse and human cells (Baenziger et al., 2008). This would limit positive selection to mouse MHC only, and negative selection to both human and mouse MHC. Under certain circumstances, however, positive selection can also take place on cells of hematopoietic origin (here human DCs) (Shizuru et al., 2000; Zinkernagel and Althage, 1999). The empirical situation is the following: in mixed lymphocyte reactions, human T cells from HHLS-Rag2$^{-/-}\gamma_c^{-/-}$ lymph nodes and spleen react most strongly to allogeneic hDCs and weakly to allogeneic mDCs (Baenziger et al., 2008; Traggiai et al., 2004). Cytotoxic activity against allogeneic human cells is blocked by anti-human MHC antibodies (Ishikawa et al., 2005; Manz, 2007). At the same time, specific T cell responses to influenza infection are only observed in the context of mouse MHC (Legrand et al., 2006; Manz, 2007). In the midst of this complicated situation, HHLS-Rag2$^{-/-}\gamma_c^{-/-}$ mice do not mount robust, specific T cell responses to HIV-1 infection (Baenziger et al., 2006). A specific concern for analysis of HIV-1 infection in HHLS-Rag2$^{-/-}\gamma_c^{-/-}$ mice is that peripheral T cells isolated from HHLS-Rag2$^{-/-}\gamma_c^{-/-}$ mice and transferred into "empty" Rag2$^{-/-}\gamma_c^{-/-}$ mice do not undergo homeostatic expansion (Legrand et al., 2006). Combined with high peripheral T cell turnover and a lack of long-term T cell maintenance in HHLS-Rag2$^{-/-}\gamma_c^{-/-}$ mice, disturbed T cell homeostasis may potentially mask immune responses to HIV-1.

Given improvements, the HHLS-Rag2$^{-/-}\gamma_c^{-/-}$ mouse holds great promise as a straightforward and efficient small animal model for multiple human plagues including HIV, HTLV, EBV, Hepatitis C, and Malaria (Goldstein, 2008). Concerted multicenter efforts funded by the Bill and Melinda Gates foundation are focused on improving reconstitution and functional immunity in HHLS-Rag2$^{-/-}\gamma_c^{-/-}$ mice as well as standardizing model generation and evaluation with the ultimate goal of creating a standard, pre-clinical, HIV-1 vaccine model. The approach is to further humanize the Rag2$^{-/-}$ $\gamma_c^{-/-}$ mouse through introduction of human MHCs, and human cytokines relevant to human hemato-lymphoid development (both cross-species reactive and species-restricted cytokines) (Manz, 2007). It is believed that these modifications will lead to better engraftment, development, homing, and effector function of immune cells in second generation HHLS-Rag2$^{-/-}\gamma_c^{-/-}$ mice.

An improved HHLS-Rag2$^{-/-}\gamma_c^{-/-}$ mouse model would allow assessment long-term hT5Cyp-mediated protection from HIV-1 infection and the potential for viral resistance emerging in vivo. Furthermore, it could be used to assess if hT5Cyp would enable an improved anti-HIV immune response and may help establish what characterizes a successful anti-HIV-1 response in human cells. If second-generation HHLS-Rag2$^{-/-}\gamma_c^{-/-}$ mice develop peripheral lymph nodes in a more consistent manner than observed, cell-to-cell spread of HIV-1 in the presence or absence of restriction factors like hT5Cyp could be visualized by live imaging in vivo.

Example 4

HIV-1 Inhibition by TRIM5-Cyclophilin Fusion Proteins Engineered of Human Components Design of hT5Cyp Fusions with Potent Anti-HIV-1 Activity A cryptic splice acceptor at the AoT5Cyp fusion junction results in the synthesis of 12 amino acids derived from the CypA 5'UTR[3]. An equivalent human fusion protein cannot be engineered due to lack of sequence homology in the CypA 5'UTR. The goal was to generate hT5Cyp using components normally expressed in human cells. Consequently, hT5-direct-Cyp was engineered with hCypA fused to a position in the linear sequence of hT5 analogous to that of the AoT5Cyp retrotransposition event (FIG. 1*a*). Since the 12 amino acids encoded by the AoCypA 5'UTR might be an essential spacer between the AoT5 and AoCypA moieties, sequences from the hT5α, γ, and δ isoforms, and a synthetic 12 amino acid spacer were used to generate linkers of similar length and character: hT5-α-Cyp, hT5-γ-Cyp, hT5-δ-Cyp, and hT5(SGG)$_4$Cyp (FIG. 1*a*). Jurkat T cells stably expressing the indicated hT5Cyp fusions were challenged with serial dilutions of an HIV-1-GFP vector. hT5(SGG)$_4$Cyp restricted HIV-1 comparably to AoT5Cyp but none of the other constructs exhibited detectable HIV-1 restriction activity (FIG. 1*a*).

Next, hCypA was fused at 10 different positions along the length of hT5α (FIG. 1*b*). Of the hT5Cyp constructs tested for HIV-1 restriction activity in Jurkat T cells and THP-1 monocytes, three had activity comparable to AoT5Cyp, one (hT5-T369-Cyp) was moderately restrictive, while another (hT5-M284-Cyp) exhibited variable restriction activity based on cell-type (FIG. 1*c*). hT5-S322-Cyp, consistently the strongest HIV-1-inhibitor, became the focus of subsequent experiments, and is referred to herein as hT5Cyp. hT5Cyps also restricted HIV-1 in promonocytic U937 cells, the CEM-SS, SUP-T1, and H9 T cell lines, and the 293T embryonic kidney cell line. Like AoT5Cyp[5], hT5Cyp blocked the accumulation of viral cDNA after acute infection, as measured by quantitative PCR.

Structural Requirements for hT5Cyp-Mediated HIV-1 Restriction Activity

Despite the apparent modularity of TRIM5[9-12], most hT5Cyp fusions lacked anti-HIV-1 activity. Steady-state protein level in stably-transduced Jurkat T cells did not correlate with restriction activity: AoT5Cyp and restrictive hT5Cyp fusions were undetectable by immunoblot while some inactive hT5Cyps were highly expressed. To increase the possibility of detection, hT5Cyp proteins were expressed as triple-FLAG-tagged fusions by plasmid transfection of 293T cells. Anti-FLAG immunoprecipitates were probed in immunoblots with anti-CypA antibody. Two fusions with no detectable restriction activity, hT5-M244-Cyp and hT5-T302-Cyp, were expressed at high-level, whereas fusions with potent anti-HIV-1 activity, hT5-A331-Cyp and AoT5Cyp, were expressed at low-level (FIG. 2*a*). Again, restriction activity did not correlate with protein level.

Lack of activity could result from failure to bind HIV-1 CA. Glutathione S-transferase (GST)-CA fusion protein was used to test CA-binding activity of hT5Cyp proteins produced in 293T cells. Among hT5Cyp fusions with no anti-HIV-1 activity, hT5-T302-Cyp bound HIV-1 CA as well as the potently restrictive hT5-S322-Cyp (FIG. 2*b*). Specificity of binding was demonstrated by blocking interaction with the competitive inhibitor cyclosporine A (CsA) (FIG. 2*b*). Thus, the ability to bind CA was required but not sufficient for restriction activity.

To visualize the sites of CypA linkage to hT5, a three-dimensional model of the T5α PRYSPRY domain was generated using coordinates from three homologues (FIG. 2*c*). hT5Cyp fusions with anti-HIV-1 activity clustered near the main specificity determinant for HIV-1 restriction activityl[11,12,17]; a proposed protein interaction surface[18,19] (FIG. 2*c*). No inactive hT5Cyp proteins mapped to this region (FIG. 2*c*). Visualization of hT5Cyp fusions by immunofluorescence showed that AoT5Cyp and all three hT5Cyps with potent anti-HIV-1 activity formed distinct cytoplasmic bodies (FIG. 2*d*). Diffuse cytoplasmic staining was observed for hT5Cyp fusions that lacked restriction activity. Taken together, these results demonstrate strict conformational requirements for antiviral activity that are determined by the site of CypA fusion and revealed by the ability of the fusion proteins to form cytoplasmic bodies.

hT5Cyp Restriction Activity Depends on Both the hCypA and hT5 Components

AoT5Cyp restricts HIV-1$_{NL4-3}$, HIV-2$_{ROD}$, SIV$_{AGM}$tan, and FIV$_{PET}$, all viruses encoding a CA that binds CypA[3,5,13,14,20-22]. To evaluate whether hT5Cyp blocked infection by these lentiviruses, stable cell lines were generated using CRFK cells, feline fibroblasts that lack endogenous T5. AoT5Cyp and hT5Cyp restricted all four lentiviruses (FIG.

3*a-d*). CypA does not bind to $SIV_{MAC}251$ CA and neither AoT5Cyp nor hT5Cyp restrict this virus (FIG. 3*e*).

To confirm that hT5Cyps have the same CA-binding requirements as AoT5Cyp, the CRFK cell lines were challenged with HIV-1-G89V, a CA mutant that disrupts interaction with CypA[3]. Both AoT5Cyp and hT5Cyp failed to restrict HIV-1-G89V (FIG. 4*a*). The H126Q mutation in CypA also disrupts the CA-CypA interaction[23] and hT5Cyp bearing the H126Q mutation in its CypA domain had no detectable anti-HIV-1 restriction activity (FIG. 4*b*). Finally, cyclosporine, a competitive inhibitor of the CypA-CA interaction[14], abrogated HIV-1 restriction by AoT5Cyp and hT5Cyp (FIG. 4*c*). A previous study searched the database for CA-variants circulating in HIV-1-infected people that are resistant to cyclosporine and to AoT5Cyp-mediated HIV-1-restriction[24]. Though V86P/H87Q/I91V/M96I HIV-1 was indeed resistant to cyclosporine, both hT5Cyp and AoT5Cyp blocked infection by viruses bearing this sequence as efficiently as standard HIV-1 clones (FIG. 4*d*).

To assess the contribution of the T5 domain to T5Cyp-mediated restriction, CRFK cell lines expressing AoT5Cyp or hT5Cyp were treated with arsenic trioxide ($As_2O_3$). This drug was previously shown to inhibit T5-mediated restriction[25]. AoT5Cyp and hT5Cyp restriction activity was blocked to the same extent by $As_2O_3$ (FIG. 4*e*). These results show that, with respect to CA-recognition by the CypA domain, and effector function by the T5 domain, AoT5Cyp and hT5Cyp behave nearly identically.

hT5Cyp Eliminates Spreading Infection of HIV-1

Jurkat T cells stably transduced with T5-expression vectors were infected with replication-competent HIV-1. No HIV-1 replication was detected in cells transduced with hT5Cyp or AoT5Cyp for the two-month observation period (FIG. 5*a, b*). The same result was obtained 8 separate times, despite initiation of infection with a wide-range of HIV-1 inocula. HIV-1 replication in cells transduced with hT5Cyp bearing a mutation that blocks binding to HIV-1 CA (CypA-H126Q, see FIG. 4*c* and ref. 23), was as rapid as in cells transduced with empty vector (FIG. 5*a, b*).

In contrast to hT5α, rhT5α potently restricts HIV-1[2]. Chimeric T5 protein in which the PRYSPRY specificity determinant from the rhesus orthologue replaces the corresponding human residues (hT5α-R323-332[10,11]), or even in which a single, critical amino acid was substituted (R332P[12,26]), exhibit HIV-1 restriction activity approaching that of rhT5α. Since these molecules are nearly identical to the human protein it has been proposed that they may have therapeutic utility[10,12,26,27]. As previously reported, hT5α-R323-332 and hT5α-R332P caused moderate inhibition of HIV-1 transduction in single-cycle infection, each behaving similarly to the other, though neither was as potent as hT5Cyp or AoT5Cyp. When the effect of hT5αR332P was tested in a spreading infection, there was a delay in the peak of HIV-1 that was inversely proportional to initial viral dose, but in contrast to hT5Cyp or AoT5Cyp, it failed to prevent HIV-1 infection (FIG. 5*a, b*).

hT5Cyp-mediated restriction of HIV-1 in primary human $CD4^+$ T cells and macrophages was assessed next. To identify cells transduced with T5, a bicistronic lentiviral vector was used that directs synthesis of GFP from an internal ribosome entry site. These vectors failed to generate GFP in primary $CD4^+$ T cells (FIG. 5*d*). Better results were obtained when a vector was engineered using two promoters, one from the SFFV LTR and the other from the hCypA gene (FIG. 5*c, d*). Primary $CD4^+$ T cells transduced with dual-promoter vectors bearing hT5Cyp were sorted based on GFP-expression. Transduced cells proliferated at the same rate as untransduced cells, produced comparable amounts of IL-2 upon stimulation, and expressed the same level of cell-surface CD4, CXCR4, and MHC I.

$CD4^+$ T cells were transduced with dual-promoter vectors encoding either hT5Cyp or the non-restrictive hT5CypH126Q. Cells were sorted based on GFP-expression and then challenged with replication-competent, CXCR4-tropic, $HIV\text{-}1_{NL4\text{-}3}$. Viral replication in hT5CypH126Q-transduced cells peaked on day 12 and infection was not established in hT5Cyp-transduced cells (FIG. 5*e*). The same hT5Cyp-mediated block to infection was observed with primary isolate $HIV\text{-}1_{DH12}$. Monocyte-derived macrophages were also transduced with vectors encoding hT5Cyp or hT5CypH126Q and sorted based on GFP-expression. Cells were infected with $HIV\text{-}1_{NL4\text{-}3}$, modified to be CCR5-tropic, or with primary isolate $HIV\text{-}1_{132W}$. As with the $CD4^+$ T cells, macrophages transduced with hT5Cyp were resistant to HIV-1 infection (FIG. 5*f*).

hT5Cyp Confers Selective Advantage to $CD4^+$ T Cells Challenged with HIV-1

The previous experiments showed that HIV-1 infection is blocked when all cells in the culture have been transduced with the hT5Cyp vector. Next, anti-HIV-1 efficacy was evaluated under suboptimal conditions, in which <25% of cells were transduced with hT5Cyp. In the absence of HIV-1 infection, the percent transduced cells persisting in the culture over the course of a month was equivalent for hT5Cyp and hT5CypH126Q. In the face of HIV-1 infection, the hT5CypH126Q cells declined to <10% of the cells in the culture. hT5Cyp cells, in contrast, had a distinct advantage, expanding to 75% of the cells in the population (FIG. 5*g*). The survival advantage was most likely due to the antiviral activity of hT5Cyp since HIV-1 replication was also reduced in cultures containing hT5Cyp cells. Thus, even when a minority of cells are transduced in culture conditions where HIV-1 can spread directly from cell-to-cell, hT5Cyp is potent enough to block HIV-1 infection.

hT5Cyp Protects Against HIV-1 Infection in Vivo

To test the ability of hT5Cyp to protect against HIV-1 infection in vivo, an experimental model was established in which human $CD4^+$ T cells were adoptively transferred into $Rag2^{-/-}\gamma_c^{-/-}$ mice. Due to a lack of functional B, T, and NK cells, this mouse strain does not reject xenografts[28]. $CD4^+$ T cells were transduced with the hT5Cyp or hT5CypH126Q vectors and sorted for GFP-expression. Age-matched, 6-10 week-old $Rag2^{-/-}\gamma_c^{-/-}$ mice were conditioned with clodronate and sublethal irradiation[29], and injected intraperitoneally with $2.5\times10^6$ transduced $CD4^+$ T cells (FIG. 6*a*) One week post-transplant, peripheral blood engraftment was assessed by measuring the percentages of CD45, CD4, and GFP-positive cells. Engraftment efficiency was not altered by hT5Cyp or hT5CypH126Q.

To determine if hT5Cyp protected $hCD4^+$ T cells against HIV-1 in vivo, mice were infected with HIV-1 after adoptive transfer of the transduced $CD4^+$ T cells. Since HIV-1 down-regulates cell-surface expression of CD4[30], CD45 was used to assess the percentage of human cells in the peripheral blood four weeks post-infection with HIV-1. When mice received hT5Cyp-transduced $CD4^+$ T cells, mean peripheral blood $CD45^+$ cells constituted 6.7% (FIG. 6*b*). This was 15-fold higher than the percentage $CD45^+$ cells (mean 0.45%) observed in mice transplanted with hT5CypH126Q-transduced $CD4^+$ T cells, a difference that was statistically significant (p=0.0037, n=9 hT5Cyp, n=8 hT5CypH126Q) (FIG. 6*b*). Mice engrafted with hT5Cyp-expressing $CD4^+$ T cells had a 22-fold reduction in mean viral load compared to mice engrafted with hT5CypH126Q-expressing $CD4^+$ T cells (p=0.03; n=5 hT5Cyp, n=4 hT5CypH126Q). Taken together, these results from the peripheral blood indicate that hT5Cyp inhibits HIV-1 replication and protects against HIV-1-associated destruction of $CD4^+$ T cells in vivo.

Further evidence for the in vivo effects of hT5Cyp was sought by examining lymphoid organs of HIV-1-infected mice. Single-cell suspensions were analyzed for the human T cell marker CD3 (which, unlike CD4, is not downregulated by HIV-1), the hT5Cyp vector reporter GFP, and HIV-1 p24 antigen. Few if any of the hT5Cyp-transduced human T cells in thymi or mesenteric lymph nodes of HIV-1-infected mice were $p24^+$, as compared with 3-5% of the cells transduced with hT5CypH126Q (FIG. 6*c*). Consistent with this inhibition of productively infected T cells, hT5Cyp prevented the down-regulation of cell surface CD4, both in thymi and in mesenteric lymph nodes of mice infected with CXCR4-tropic or CCR5-tropic HIV-1, respectively (FIG. 6*d*).

Finally, tissue sections of thymi and mesenteric lymph nodes were directly examined for human T cells (using anti-CD3 antibody) and HIV-1 p24 antigen. The engraftment of $CD4^+$ T cells transduced with hT5Cyp and hT5CypH126Q was similar (FIG. 6*e*). Intense p24 staining was observed in tissue sections from animals engrafted with hT5CypH126Q-transduced $CD4^+$ T cells but not in tissues from mice engrafted with $CD4^+$ T cells transduced with hT5Cyp (FIG. 6*e*, α-p24 stain). These experiments show that hT5Cyp prevented productive HIV-1 infection in vivo.

Discussion

Anti-HIV-1 gene therapy approaches have followed two main strategies: either modification of host-cell factors required for viral replication or inhibition of essential viral elements[1]. Here, a third approach was adopted: the exploitation of natural inhibitors that evolved over millions of years in primates in response to retroviral attack[10-12,26]. The potent block to HIV-1 observed with AoT5Cyp inspired the design of a human equivalent, hT5Cyp, that robustly blocks HIV-1 in vitro and in vivo. The strict structural requirements for engineering a functional hT5Cyp emphasize the remarkable nature of the fusion gene that was generated by retrotransposition in New World owl monkeys[3]. As it turns out, a distinct T5Cyp fusion gene was generated by an independent retrotransposition event in Old World macaques. In this case, restriction activity was detected against HIV-2 and FIV, but not against HIV-1[31]. The convergent evolution of T5Cyp fusion proteins with distinct retroviral specificities indicates a strong selection for these potent restriction factors. While the specific force behind selection remains to be elucidated for individual T5 orthologues, in each case the selective pressure is likely to have been a retrovirus[11].

Since T5α and T5Cyp are modular proteins, it was expected that the engineering of a restrictive hT5Cyp would be trivial. Surprisingly, only three of 13 hT5Cyp fusions inhibited HIV-1 comparably to AoT5Cyp. No correlation was observed between protein levels and antiviral activity, and CA-binding activity was not sufficient to restrict HIV-1 (FIG. 2*a,b*). Structural modeling showed that anti-HIV-1 activity was observed when hCypA was fused at the apex of the hT5α PRYSPRY domain (FIG. 2*c*). Analysis of nonsynonymous mutations indicates that this region undergoes some of the strongest selective pressure in the primate lineage and functional experiments pinpoint it as a specificity determinant for CA recognition[11,12,32]. CypA fusion to this site may have antiviral activity because this apical loop is uniquely situated for coordinating CA recognition and effector domains of T5. Correlation between restriction activity and the ability of hT5Cyp fusion proteins to form cytoplasmic bodies suggests that activity requires particular spatial constraints or association with unknown cofactors.

Optimal gene therapy candidates should provide high efficacy and low antigenicity. Hematopoietic progenitors transduced with rhesus macaque T5α or human-rhesus T5α chimeras differentiate into HIV-1-resistant macrophages and T cells[27,33]. These proteins, however, are potentially antigenic, which could lead to the elimination of modified cells in vivo[16]. By substituting only critical amino acids within the hT5α PRYSPRY domain one can reduce the risk of antigenicity but this also decreases anti-HIV-1 efficacy (hT5αR332P; FIG. 5*a,b*). hT5Cyp potently inhibits HIV-1 and, being composed of human components, is of low antigenic potential.

Figure 4:
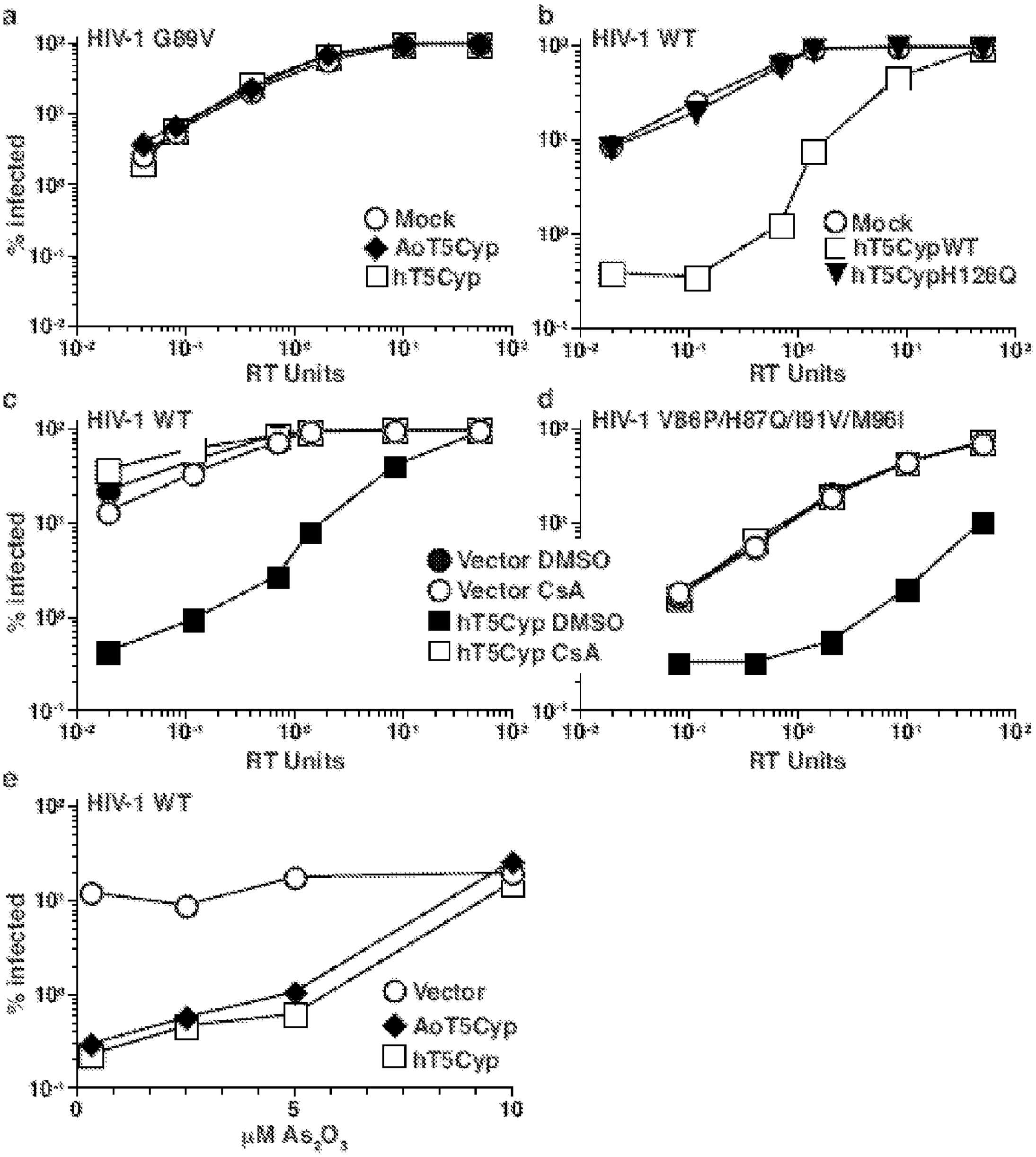
FIGS. 4*a*-4*e*. T5 and CypA components each make essential contributions to T5Cyp restriction activity. (a-c) Disruption of the CA-CypA interaction by the G89V mutation in HIV-1 CA (a), the H126Q mutation in CypA (b), or the competitive inhibitor cyclosporine (CsA) at 2.5 μM (c), blocks HIV-1 restriction activity in CRFK cells stably expressing the indicated T5 proteins or controls. Cells were challenged with increasing amounts (X-axis) of HIV-1 GFP vector bearing the G89V mutation in CA (a) or wild-type HIV-1 GFP vector (b, c). (d) Introduction of a naturally-occurring quadruple mutation flanking the CA-CypA binding site in HIV-1 CA does not abrogate hT5Cyp-mediated restriction of HIV-1. CRFK cells stably expressing T5Cyp or control were infected with increasing amounts (X-axis) of an HIV-1 GFP vector containing the V86P/H87Q/I91V/M96I mutation in CA. (e) Disruption of T5 by $As_2O_3$ blocks HIV-1 restriction activity by T5Cyp. CRFK cells stably expressing the indicated T5Cyp were infected with HIV-1 GFP vector in the presence of increasing amounts of $As_2O_3$ (X-axis). In each case (a-e) the percentage of $GFP^+$ cells was measured by flow cytometry 48 hrs post-infection (Y-axis).
Figure 5:
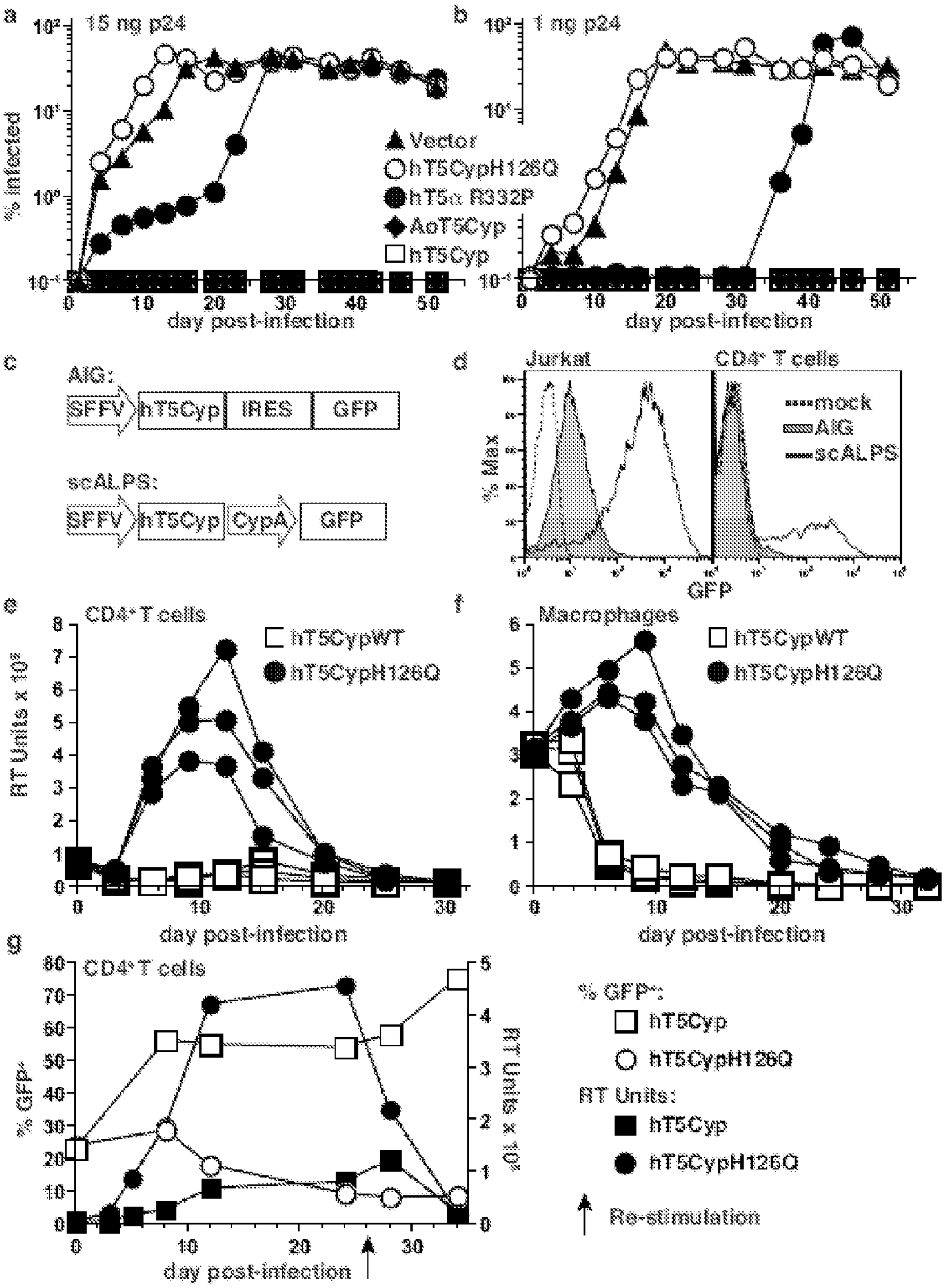
FIGS. 5*a*-5*g*. hT5Cyp potently blocks replication-competent HIV-1. (a, b) Jurkat T cells expressing the indicated proteins were infected with HIV-$1_{NL4-3-GFP-IRES-Nef}$, 15 ng p24/$10^6$ cells (a) or 1 ng p24/$10^6$ cells (b) and the percentage of infected cells was recorded. (c) Design of bicistronic (AIG) and dual promoter (scALPS) lentiviral vectors. (d) GFP expression by flow cytometry 48 hrs after transduction of Jurkat T cells (left) or primary $CD4^+$ T cells (right) with the indicated vectors. (e) hT5Cyp inhibits HIV-1 in primary human $CD4^+$ T cells. $CD4^+$ T cells transduced with scALPS encoding the indicated hT5Cyp proteins were sorted for GFP, infected with HIV-$1_{NL4-3}$, and supernatant RT activity was measured. Triplicate spreading infection for one representative donor of four is shown. (f) hT5Cyp inhibits HIV-1 in monocyte-derived macrophages. $CD14^+$ monocytes differentiated with GM-CSF were transduced, sorted for GFP, and challenged with HIV-$1_{NL4-3}$ as in (e) except that the viral envelope was modified to be CCR5-tropic. (g) Selective advantage of hT5Cyp-bearing $CD4^+$ T cells in the presence of HIV-1. $CD4^+$ T cells were transduced with scALPS encoding the indicated T5Cyp proteins. Cultures containing 23% $GFP^+$ cells were challenged with 15 ng/$10^6$ cells HIV-$1_{NL4-3}$ and monitored for percentage $GFP^+$ cells (left Y-axis, open symbols). Supernatant RT activity was measured (right Y-axis, filled symbols). Cultures were re-stimulated using allogeneic-PBMC, IL-2, and PHA on day 26 post-infection (arrow).

HIV-1 rev, tat, and gag[1,34], as well as the HIV-1 co-receptor CCR5[35,36], have been targeted by various means including siRNAs[1,34] and zinc-finger endonucleases[36]. With either approach there are concerns regarding toxicity[34], off-target effects[35], and viral resistance[1,34]. For siRNA approaches, escape mutants arise readily, since single point mutations are sufficient to escape the siRNA-mediated blocks to HIV-1 replication[34]. CCR5 disruption could select for CCR5-independent viruses[37] and is not without consequence, as the CCR5Δ32 allele is a risk factor for symptomatic West Nile Virus infection[38].

hT5Cyp is a broadly acting, anti-lentiviral agent that blocks CCR5- and CXCR4-tropic HIV-1 clones and primary isolates, as well as some HIV-2, Sly, and FIV clones (FIGS. 4 and 5). T5 isoforms form hetero-multimers and hT5Cyp might interfere with endogenous hT5α function[39]. However, no significant decrease in hT5α-mediated restriction of N-MLV, and no alteration in cell surface markers or cytokine secretion, was observed in hT5Cyp-transduced cells. hT5Cyp-resistant viruses were not detected, perhaps due to the potency of the antiviral activity and the fact that hT5Cyp blocks HIV-1 prior to reverse transcription. hT5Cyp additionally blocked a natural HIV-1 CA variant reported to be resistant to AoT5Cyp[24] (FIG. 4*d*). These results suggest that, if hT5Cyp were utilized as anti-HIV-1 gene therapy in people, viral resistance would not emerge and host cell function would remain intact.

Figure 6:
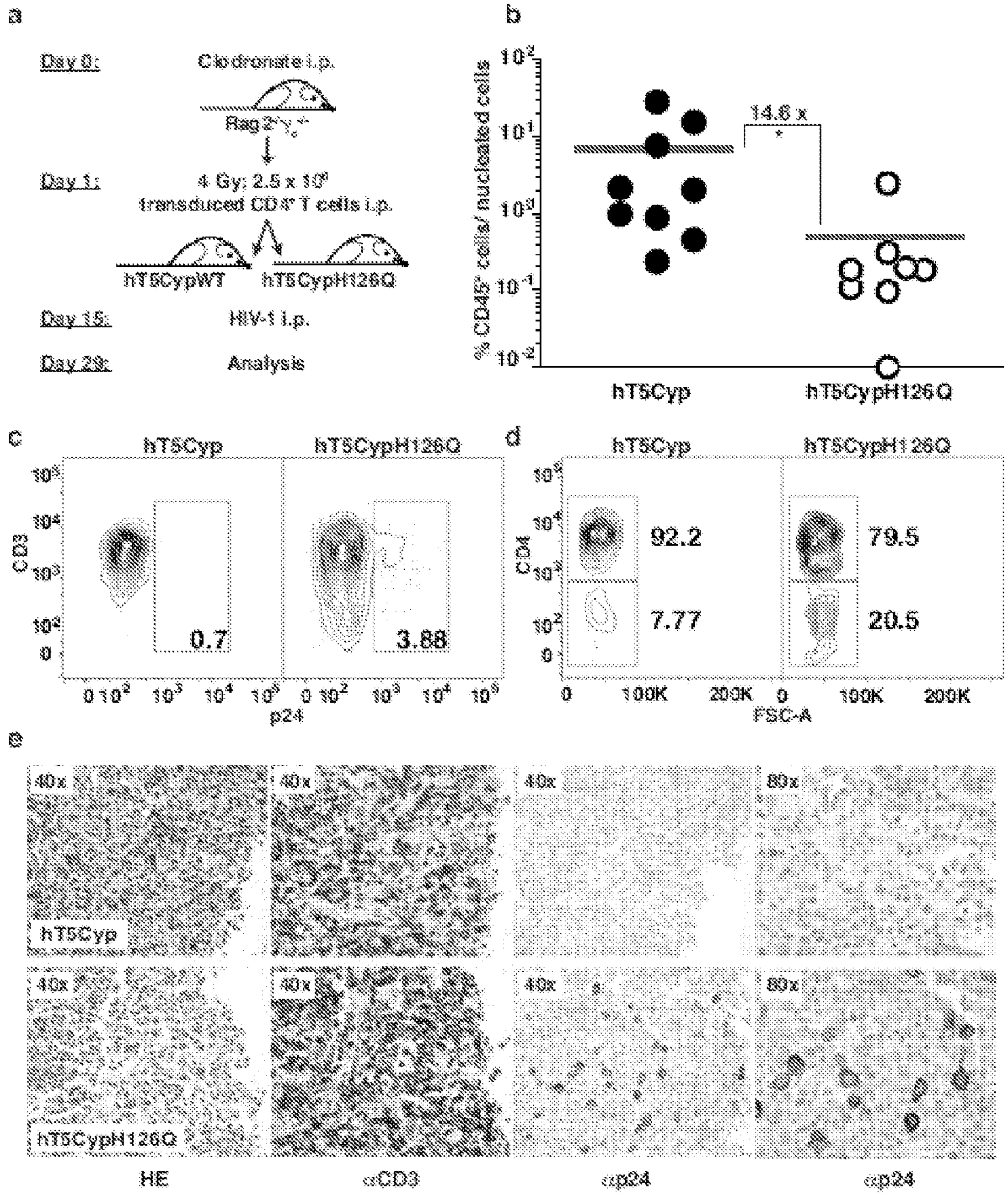
FIGS. 6*a*-6*e*. hT5Cyp protects $CD4^+$ T cells from HIV-1 infection in vivo. (a) Experimental design for adoptive transfer of transduced $CD4^+$ T cells and in vivo HIV-1 challenge in $Rag2^{-/-}\gamma_c^{-/-}$ mice. Gy=Gray; i.p.=intraperitoneal injection. (b) hT5Cyp prolongs $CD4^+$ T cell-survival in vivo. 6-10 week old $Rag2^{-/-}\gamma^{-/-}$ mice were engrafted with GFP-sorted scALPS-transduced $CD4^+$ T cells expressing either hT5Cyp or hT5Cyph126Q. Mice were infected 5 days after adoptive $CD4^+$ T cell transfer with CXCR4-tropic HIV-$1_{NL4-3}$ and analyzed for presence of $hCD45^+$ lymphocytes (Y-axis) at 4 weeks post-infection. Individual mice are shown and fold-difference in mean peripheral blood $CD45^+$ lymphocyte engraftment (red bar) is indicated above the bracket. (*p=0.0037, Mann-Whitney test) (c, d, e) hT5Cyp protects $CD4^+$ from productive HIV-1 infection in lymphoid organs. Age-matched $Rag2^{-/-}\gamma^{-/-}$ mice transplanted with $CD4^+$ T cells expressing either hT5Cyp or hT5Cyph126Q were infected with CXCR4-tropic HIV-$1_{NL4-3}$ 2 weeks after adoptive transfer of $CD4^+$ T cells. Single-cell suspensions of thymi were analyzed 14 days post-infection for $p24^+$ (X-axis) CD3' (Y-axis) T cells (c) or CD4-downregulation (Y-axis) (d). Representative CD3- and p24-stained paraffin-embedded tissue sections of thymus are shown. While engraftment of $CD3^+$ human T cells is similar in thymi of mice transplanted with either hT5Cyp– (top panel) or hT5CypH126Q-expressing $CD4^+$ T cells (bottom panel), rare and weaker p24 staining is observed in organs from mice transplanted with hT5Cyp-$CD4^+$ T cells as compared to those transplanted with hT5CypH126Q-$CD4^+$ T cells (e). (c,d,e) Representative results from three sets of experiments are shown.

The evaluation of HIV-1 therapies is limited by a lack of adequate animal models for HIV-1 replication and pathogenesis. The $hCD4^+$-$Rag2^{-/-}\gamma_c^{-/-}$ mouse developed here proved to be a robust model for assessing inhibition of HIV-1 infection and $CD4^+$ T cell protection by lentiviral transduction with hT5Cyp (FIG. 6). Autotransfusion of ex vivo expanded $CD4^+$ T cells is of clinical benefit to HIV-1-infected people). Thus, given that hT5Cyp-transduced $CD4^+$ cells can be expanded in vitro and in vivo (FIGS. 5 and 6), and that these cells exhibit a selective advantage during HIV-1 infection (FIG. 5*g*), one would expect an impressive effect of hT5Cyp-transduction on autologous $CD4^+$ T cell gene therapy in the clinical setting. $CD34^+$ hematopoietic stem cells transduced with state-of-the-art lentiviral vectors (see FIG. 5*c* and ref[41]) achieve long-term engraftment of $Rag2^{-/-}\gamma_c^{-/-}$ mice, but transgene expression in the mature $CD4^+$ T cells that develop within these animals has not been consistently detected. With improved transduction methods it will be exciting to examine the effect of stem cell transduction with hT5Cyp on subsequent immune cell development and HIV-1 infection within one of the humanized mouse models currently under development[42].

Example 5

HIV-1 Inhibition by Humanized TRIMCyp

TRIM5α is a host factor in humans and other primates that blocks retroviral infection in a capsid (CA)-specific manner. Binding to CA requires the C-terminal PRYSPRY domain. Uniquely in owl monkeys, the PRYSPRY domain of TRIM5 is replaced by the HIV-1 CA-binding protein cyclophilin A (CypA). The resulting TRIMCyp fusion protein potently blocks HIV-1 infection (Nature 430:569). Experiments were designed to engineer a potent anti-HIV-1 fusion protein in which human CypA was fused to human TRIM5 (hTRIMCyp). Of 14 fusion proteins, five had HIV-1 restriction activity comparable to that of owl monkey TRIMCyp; the other 9 lacked detectable HIV-1 restriction activity. The site of the CypA fusions was visualized on a three-dimensional model of the TRIM5 PRYSPRY domain. hTRIMCyps with restriction activity were found to have the CypA moiety fused to the putative CA interaction face of the protein. Functional hTRIMCyps exhibited strong restriction activity in multiple cell types, and against FIV and SIVAGMtan, two other viruses known to be restricted by owl monkey TRIMCyp. hTRIMCyp restriction activity was disrupted by As203 and by factors that disrupt the hTRIMCyp-CA interaction, including cyclosporine, CA mutant G89V, or CypA mutant H126Q. In ongoing experiments, viruses capable of escaping hTRIMCyp-mediated restriction are being sought, and hTRIMCyp is being tested for restriction activity in primary human cells and in a humanized mouse model for HIV-1 infection.

Figure 7:
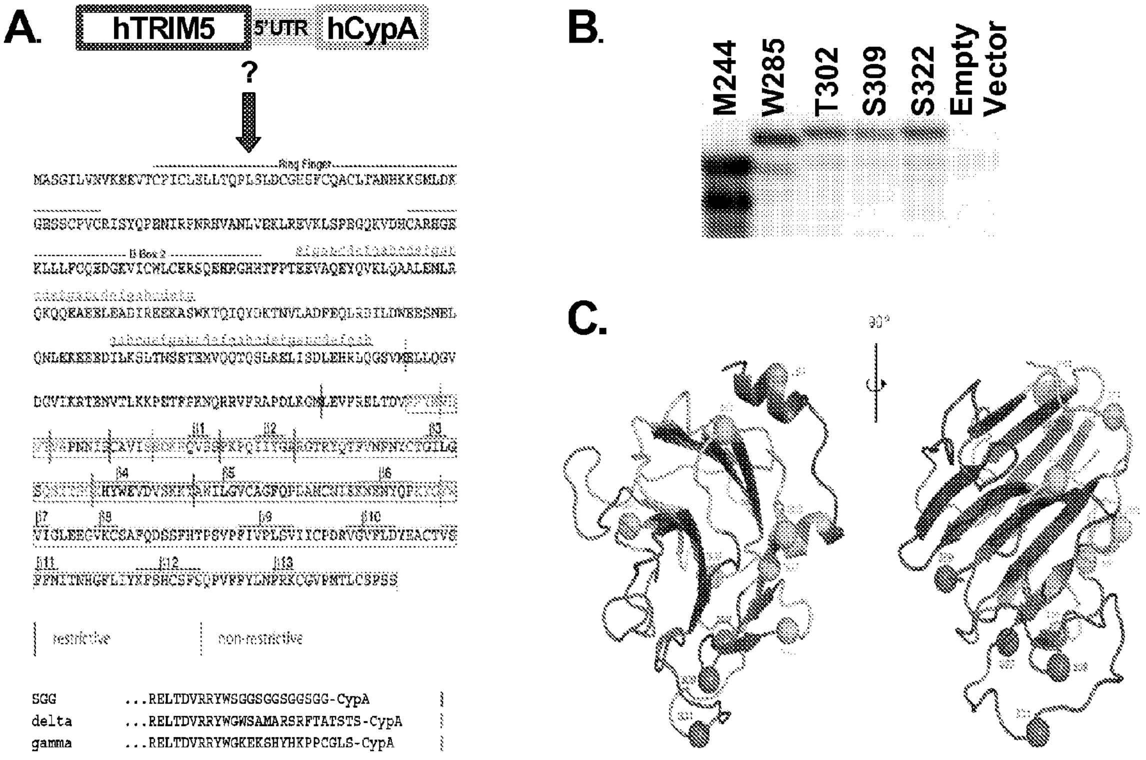
FIGS. 7A-7C. hTRIMCyp Fusion proteins and superimposition of site of fusion onto 3-D Model of TRIM5 PRYSPRY domain (SEQ ID NOs: 134-137).

FIG. 7A shows the site of fusion of human CypA to human TRIM5 generating hTRIMCyps. Fusions restricting HIV-1 are depicted in red, those without restriction activity are in green. As shown in FIG. 7B, hTRIMCyps were fused to an N-terminal 3×FLAG tag, transfected into HEK 293T cells, immuno-precipitated with an anti-FLAG antibody, and probed in western blot with an anti-CypA antibody. All nomenclature is TRIM5 AA to which CypA is fused as described for FIG. 7. FIG. 7C shows superimposition of site of hTRIMCyp fusion onto a 3-D model of the TRIM5 PRYSPRY domain. Red=restricts HIV-1, green=does not restrict HIV-1.

Figure 8:
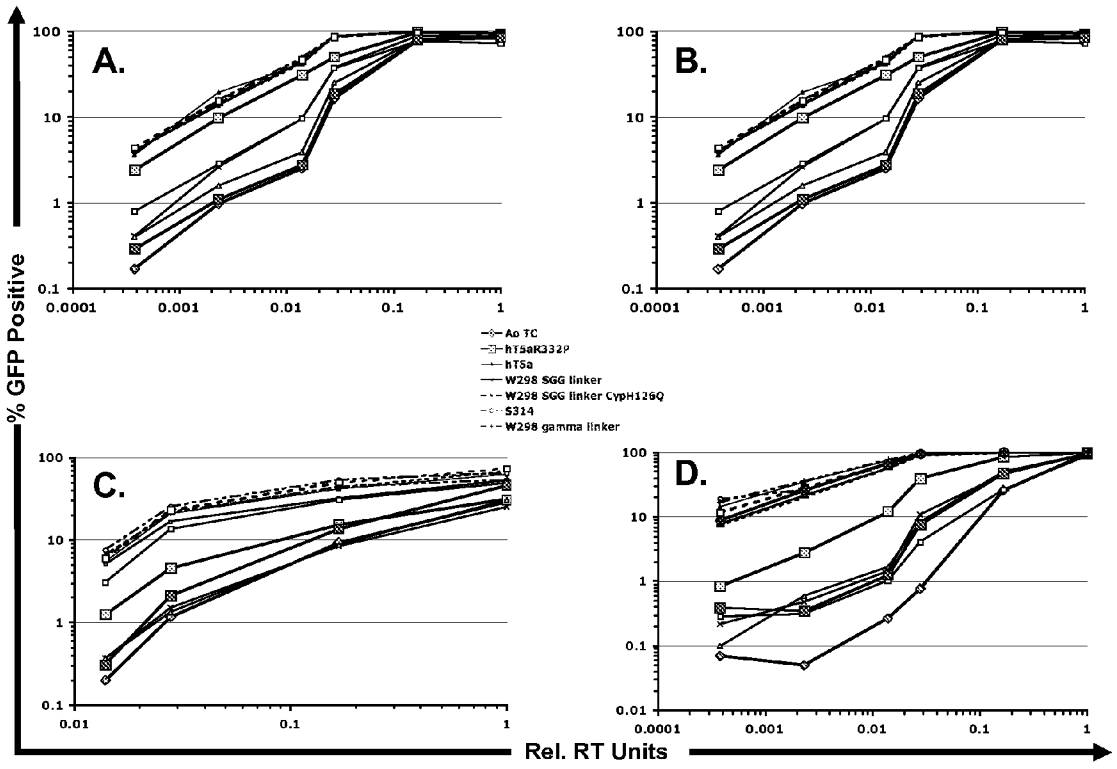
FIGS. 8A-8D. hTRIMCyp fusions and HIV-1 restriction in multiple cell lines FIG. 9A-9C. hTRIMCyp fusions and restriction of multiple lentiviruses FIGS. 10A-10C. CA-binding by the CypA-moiety of hTRIMCyp is required for HIV-1 restriction FIG. 11. hTRIMCyp restriction of NL4-3 in spreading infection FIGS. 12A-12B. HIV-1 mouse model and transduction of hHSCs FIG. 13. Human TRIM5alpha mRNA (SEQ ID NO:1) (*Homo sapiens* tripartite motif-containing 5 (TRIM5) mRNA, transcript variant alpha). GenBank Accession No. NM_033034.

Cells (Jurkat T cells (FIG. 8A), THP-1 cells (FIG. 8B), PMA-matured THP-1 cells (FIG. 8C), and CRFK cells (FIG. 8D) were transduced with indicated TRIMCyp fusion proteins, selected with puromycin, and challenged after 48 hrs. with an HIV-1 vector carrying the GFP gene. Infected cells were counted by flow cytometry. All data presented are representative of three experiments.

Figure 9:
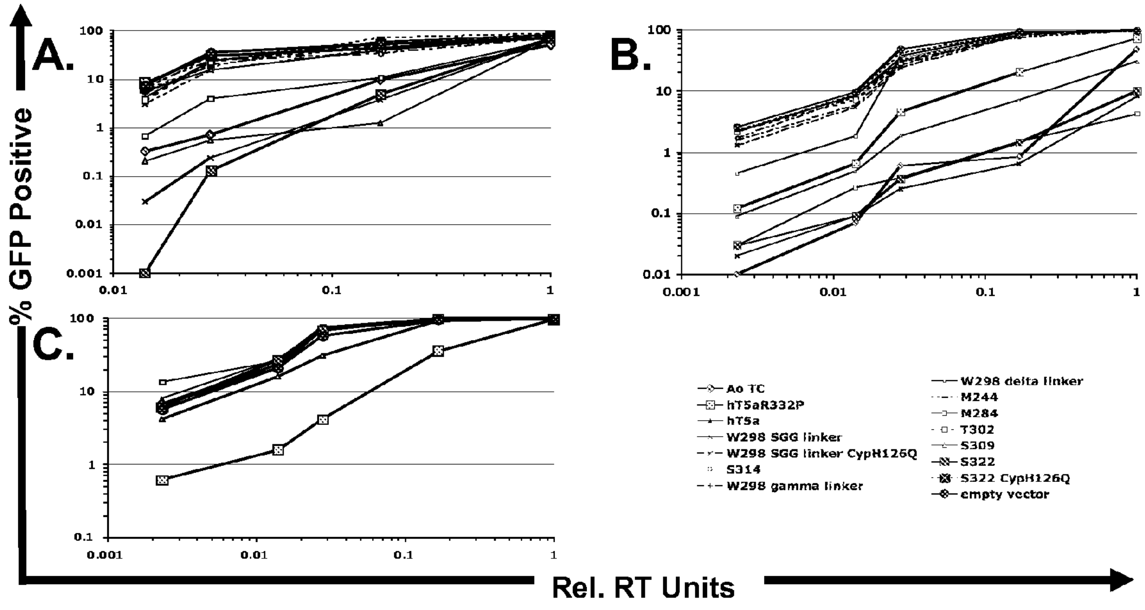

CRFK cell lines expressing TRIMCyp fusion proteins were challenged with FIV (FIG. 9A), SIVAGMtant (FIG. 9B), and SIVmac239 (FIG. 9C) vectors carrying the GFP gene. Infected cells were counted by flow cytometry. Lentiviruses restricted by Ao TRIMCyp are also restricted by hTRIMCyp.

Figure 10:
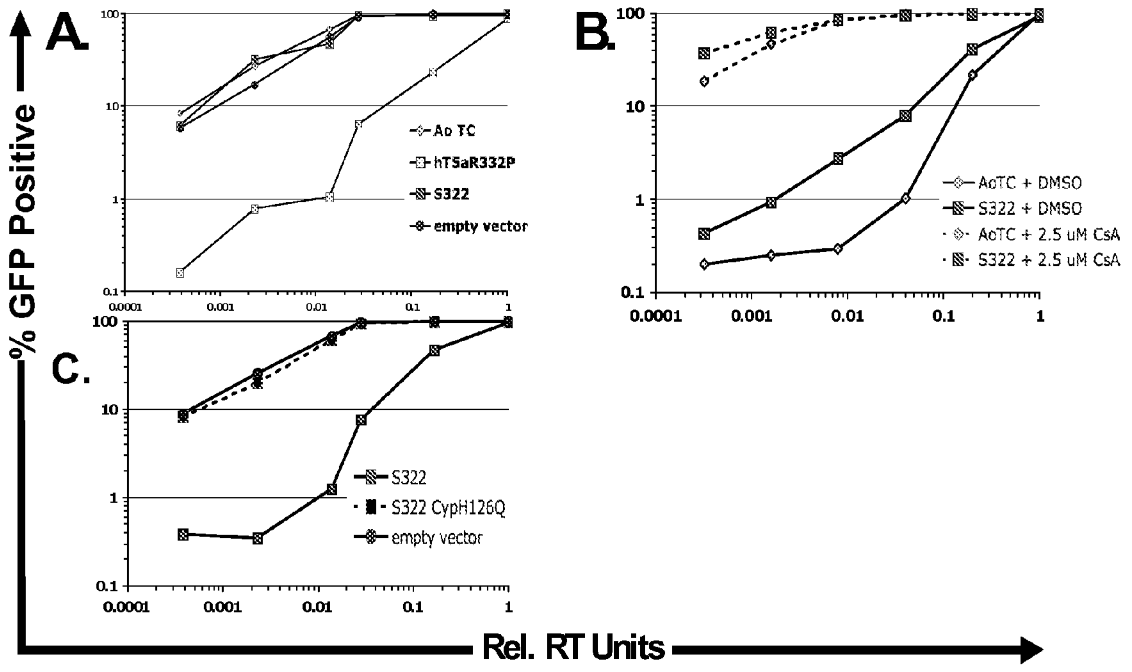
Figure 11:
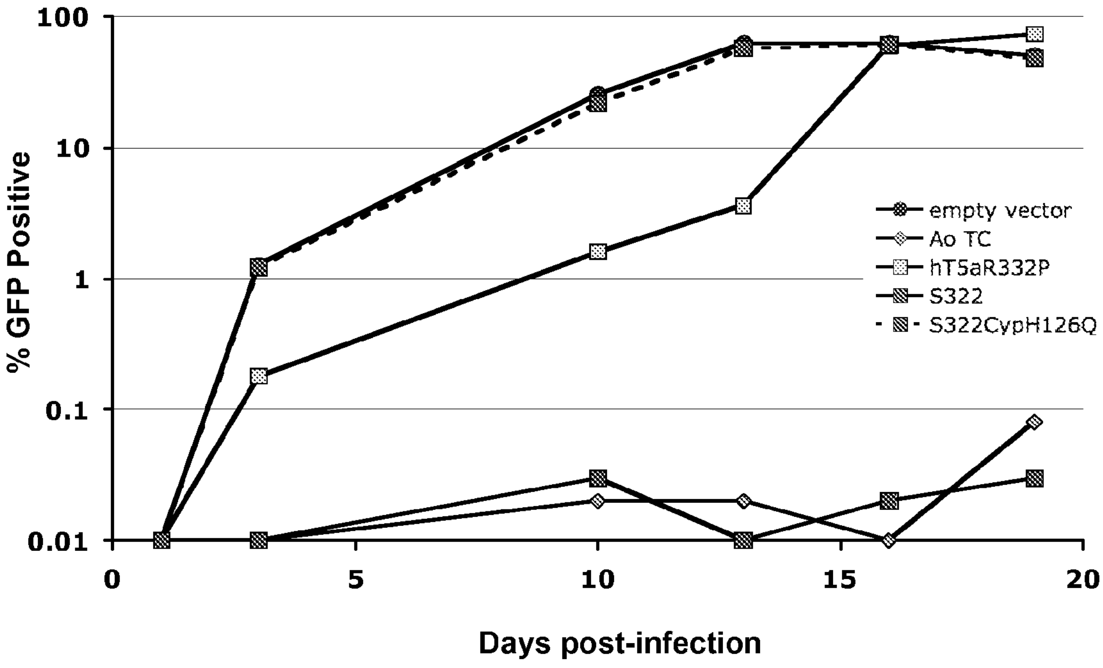

As shown in FIG. 10A, G89V mutation in CA abrogates HIV-1 restriction by TRIMCyp in CRFK cell lines. FIG. 10B shows disruption of the CA-TRIMCyp interaction with Cyclosporine abrogates HIV-1 restriction in CRFK cell lines. FIG. 10C shows the H126Q mutation in the CypA moiety of TRIMCyp abrogates the CA-TRIMCyp interaction and HIV-1 restriction in CRFK cell lines.

Jurkat T cell lines expressing the indicated proteins were infected with NL4-3 GFP IRES nef virus. Infection was monitored at given time points using flow cytometry, and results are presented in FIG. 11.

Figure 12:
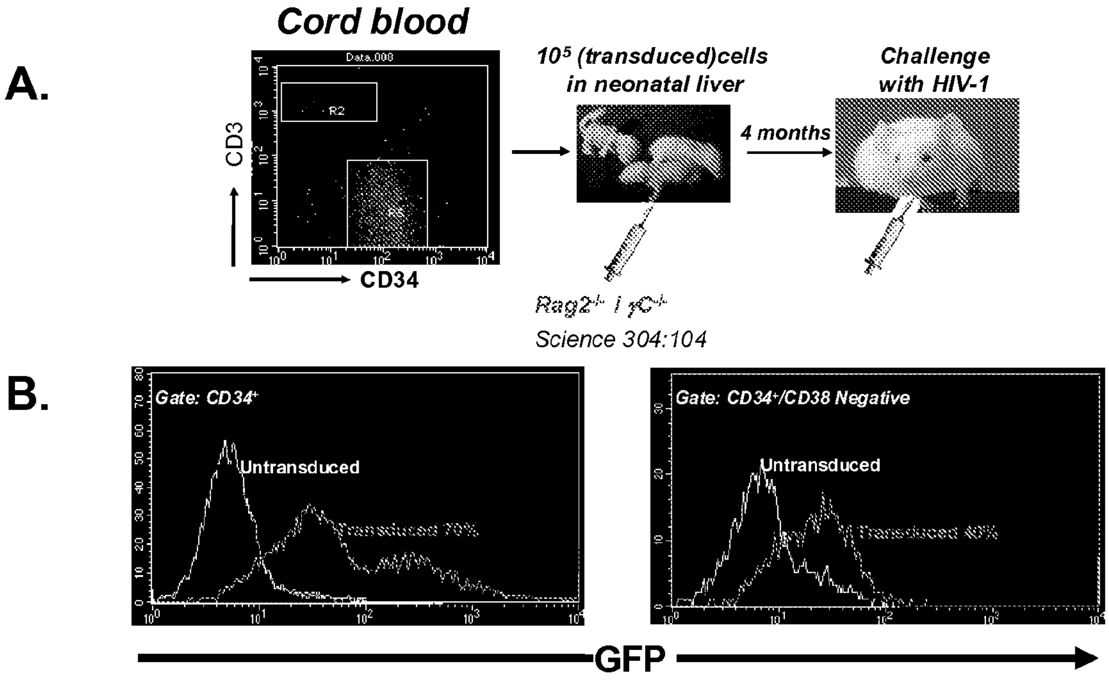

A description of a humanized mouse model for HIV-1 infection is shown in FIG. 12A. hHSC-transduction efficiency using a SIN HIV-1 vector carrying the GFP gene is shown in FIG. 12B.

Example 6

Human T5Cyp is Superior to TRIM5α Human/Rhesus Chimera and Non-Chimeric Rhesus TRIM5α

The anti-HIV-1 activity of human T5Cyp was directly compared to other TRIM5α proteins known in the art. Stremlau et al. (J Virol 79:3139-3145 (2005)) describe anti-HIV-1 activity of chimeric TRIM5α proteins. The chimerae were generated by inserting selected amino acid sequences of rhesus monkey TRIM5α into the sequence of human TRIM5α or vice versa. Stremlau et al. (Nature 427:848-53 (2004)) describe cloning of full length rhesus monkey TRIM5α and its anti-HIV-1 activity. Sayah et al. (Nature 430:569-73 (2004)) describe cloning of the *Aotus* (owl monkey) T5Cyp protein and its anti-HIV-1 activity.

Figure 22:
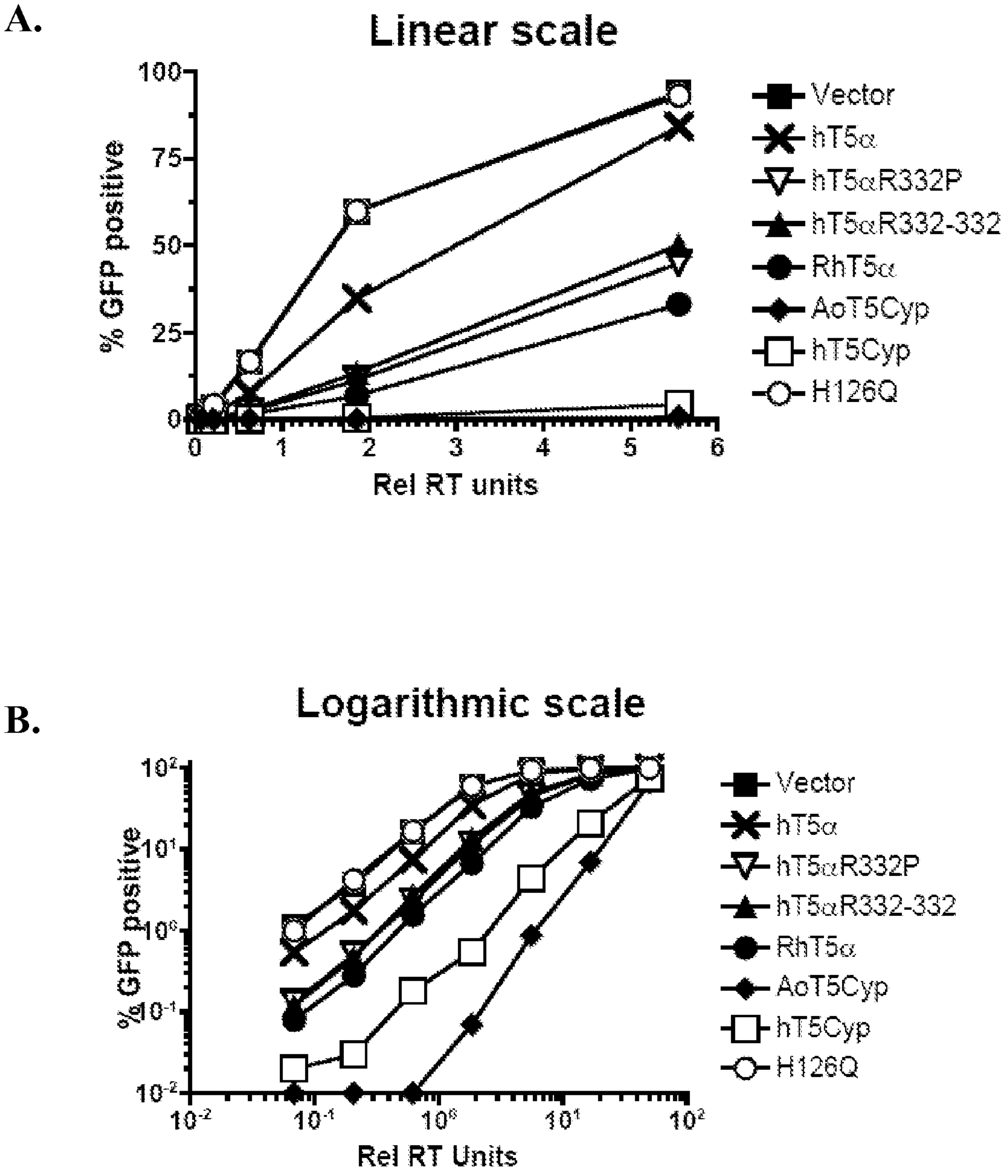
FIGS. 22A-22B. Comparison of anti-HIV-1 activity of proteins as determined by single cycle HIV-1 infection in CRFK cells. Experimental data is displayed in a linear scale (a) and logarithmic scale (b). Note that hT5Cyp has superior anti-HIV-1 activity compared to full-length rhesus monkey TRIM5α (RhT5α) and a human/rhesus monkey chimera TRIM5α (hT5αR323-332). See Example 6.
Figure 23:
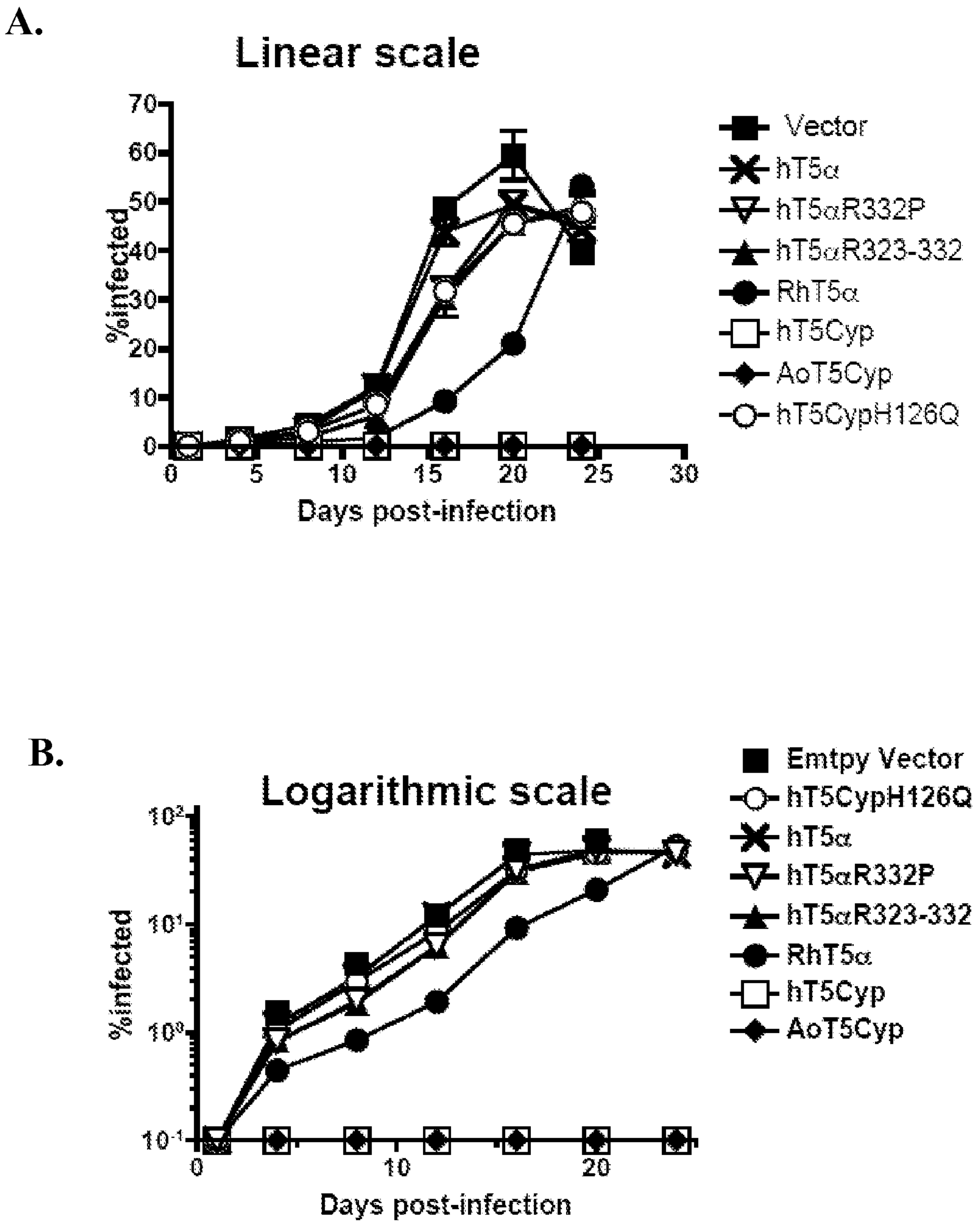
FIGS. 23A-23B. Comparison the effect on spreading of HIV-1 infection in Jurkat cells (24 days). Experimental data is displayed in a linear scale (a) and logarithmic scale (b). Note that hT5Cyp has superior anti-HIV-1 activity compared to full-length rhesus monkey TRIM5α (RhT5α) and a human/rhesus monkey chimera TRIM5α (hT5αR323-332). See Example 6.

Anti-HIV-1 activity was assessed by single cycle HIV-1 infection of CRFK feline kidney cells expressing anti-HIV-1 proteins known in the art, the human T5Cyp fusion, and controls (FIG. 22). Anti-HIV-1 activity was also assessed by determining the effect on spreading HIV-1 infection in Jurkat cells (FIG. 23). Notably, in both assays, hT5Cyp has significantly greater anti-HIV-1 activity than a chimeric human/rhesus monkey TRIM5α (hT5αR323-332) and greater activity than full length rhesus monkey TRIM5α. Indeed, the anti-HIV-1 activity of hT5Cyp is comparable to the activity of owl monkey T5Cyp (AoT5Cyp). The comparisons show that the human T5Cyp fusion protein has superior anti-HIV-1 activity compared to the TRIM5α chimera and the nonchimeric full length rhesus monkey TRIM5α.

Example 7

Methods

The following are examples of methods that can be used in the described embodiments:

Plasmids.

Most HIV-1 plasmids and vectors have been described previously (Berthoux et al., 2004). pNL4-3 contains a complete infectious HIV-1 provirus. pNL4-3-R5 bears the V3 loop of the CCR5-tropic 92TH014-2 HIV-1 strain (Papkalla et al., 2002). To generate pNL4-3-GFP-IRES-Nef, enhanced green fluorescent protein (eGFP) and the ECMV (encephalomyocarditis virus) IRES (internal ribosome entry site) were inserted upstream of nef pNLΔenvGFP is pNL4-3 with an env-inactivating mutation and eGFP in place of nef. CSGW is an HIV-1 vector expressing eGFP under the control of the spleen focus forming virus (SFFV) promoter. pFUPI, was engineered from pFUW (Lois et al., 2002) and uses the ubiquitin promoter to drive expression of a puromycin resistance cassette followed by ECMV IRES-T5. pAIG uses the SFFV promoter to drive expression of T5 followed by IRES-eGFP. In pscALPS, the SFFV promoter drives expression of T5 and the human CypA promoter drives expression of eGFP. For three-component vector production, HIV-1 gag and pol were expressed using either psPAX2, p8.9NΔSB, p8.9NΔSB-G89V, or p8.9NΔSB-V86P/H87Q/I91V/M96I. p8.9NΔSB-V86P/H87Q/I91V/M96I is p8.9NΔSB with the V86P/H87Q/I91V/M96I mutation (Chatterji et al., 2005) introduced in CA. $SIV_{mac}251$ vectors were produced using GAE1.0 and the packaging vector SIV3+ (Mangeot et al., 2002). $SIV_{AGM}$tan and HIV-$2_{ROD}$ vectors each have an env-deletion and eGFP in place of nef (Diaz-Griffero et al., 2006b). FIV vectors were produced using the genomic vector pGINSIN and the packaging vector pFP93 (Saenz et al., 2005). All lentiviral vectors were pseudotyped using the vesicular stomatitis virus glycoprotein (VSV-G). For biochemistry, hT5Cyps were cloned into the p3xFLAG-CMV-7.1 expression vector (Sigma) and HIV-1 CA was expressed as a GST-fusion using the EF1α promoter.

Cells.

293T human embryonic kidney cells and CRFK feline kidney cells were maintained in DMEM supplemented with 10% fetal bovine serum (FBS) and glutamax (Invitrogen). Jurkat E6-1, H9, CEM-SS, and SUP-T1 T cell leukemia/lymphoma cell lines, U937 promonocytic lymphoma, and THP-1 monocytic leukemia cells were grown in RPMI-1640 with 10% FBS and glutamax (Invitrogen). $CD4^+$ T cells were enriched from PBMCs (>99% $CD4^+$) using positive selection magnetic beads (Miltenyi Biotec) and stimulated for 24 hrs on multisorb 96-well plates (Nunc) coated with 2 μg/ml anti-CD3 and 2 μg/ml anti-CD28 antibodies (BD Biosciences) in RPMI with 10% FBS, glutamax (Invitrogen) and 20 IU/ml hIL-2. When indicated and in preparation for adoptive transfer to mice, $CD4^+$ T cells were stimulated using allogeneic-PBMCs irradiated at 50 Gy in the presence of 20 IU/ml IL-2 and phytohemagglutinin (PHA) at 1 μg/ml. Cells were washed and replated 24 hrs prior to viral transduction. $CD14^+$ monocytes were enriched from PBMCs (>99% $CD14^+$) using positive selection magnetic beads (Miltenyi Biotec). $CD14^+$ monocytes were resuspended in complete RPMI supplemented with 50 ng/ml recombinant human GM-CSF (Leukomax, Novartis) at $1\times10^6$ cells/ml. $2\times10^6$ were plated in each well of a 6-well plate (Nunc) and allowed to differentiate into macrophages for 10 days before transduction. Transduction of human macrophages was performed as follows: cells were pretreated for three hours with SIV VLPs (50% per volume, made with SIV3+ vector and pMD2.G at 7:1 ratio) prior to viral transduction. For both $CD4^+$ T cells and monocyte-derived macrophages, cells were sorted for GFP expression by FACS 72 hours post-transduction.

Drugs.

All chemicals were obtained from Sigma unless otherwise noted. Puromycin was used at 1 μM. Cyclosporine (CsA) (Bedford Laboratories) was diluted to 10 mM in dimethyl sulfoxide (DMSO) and then further to 2.5 μM in tissue culture media. Arsenic trioxide ($As_2O_3$) was made at 100 mM in 1N sodium hydroxide (NaOH) and then further diluted to 1 mM in phosphate buffered saline (PBS). pH was adjusted to 7.5 with hydrochloric acid and stored at 4° C.

Virus Production.

Vectors and viruses were produced by transfection of 293T cells using Lipofectamine 2000 (Invitrogen). Two-part vectors were produced by co-transfection of viral genome and VSV-G plasmids at a ratio of 7:1. Three-part vectors were produced by co-transfection of viral genome, gag-pol, and VSV-G plasmids at a ratio of 4:3:1. Infectious viruses were produced by transfection of 90% confluent 293T cells in a T75 flask (Nunc) with 40 μg of pNL4-3, pNL4-3-R5, or pNL4-3-GFP-IRES-Nef. Supernatants containing viruses and vectors were cleared by 400×g centrifugation, filtered (0.45 μm; Pall Acrodisc), tested for exogenous RT activity (Sayah et al., 2004) titered on Jurkat E6 cells in single cycle assay (Sayah et al., 2004) and stored at −80° C. When indicated, the content of viral p24 antigen was quantified by an HIV-1 p24 enzyme-linked immunoabsorbent assay kit (NIH ARRRP).

Infections.

$2\times10^4$ adherent cells/well or $8\times10^4$ suspension cells/well were plated in 48-well plates (Nunc) for challenge with single-cycle GFP reporter vectors that were titered as indicated. GFP synthesis was assessed by flow cytometry 48 hrs post-infection. For spreading infection, $10^6$ Jurkat cells were infected with 1 to 15 ng p24/$10^6$ cells of HIV-$1_{NL4-3-GFP-IRES-Nef}$. Cells were split every 3 days, fixed in 0.5% paraformaldehyde/PBS, and assayed for GFP synthesis by flow cytometry. For infection of $10^6$ primary $CD4^+$ T cells or macrophages, 15 ng p24/$10^6$ cells of a CXCR4- or CCR5-tropic HIV-$1_{NL4-3}$ stock was used, and infection was monitored by assessing the accumulation of RT activity in the supernatant (Sayah et al., 2004). FACSCalibur, Cellquest Pro (Becton Dickinson), and FlowJo software (Treestar, Inc.) were used to record and analyze fluorescence. 1-$5\times10^5$ events were acquired for analysis.

Western Blotting and Immunoprecipitation Assays.

To detect hT5Cyp, $5\times10^6$ 293T cells were transfected with 20 μg of each 3×FLAG-hT5Cyp plasmid using Lipofectamine 2000 (Invitrogen). Cells were lysed at 48 hrs in Triton lysis buffer (50 mM Tris-HCL pH 7.4, 150 mM NaCL, 1% Triton X-100, with Complete Mini protease inhibitor cocktail (Roche)), cleared at 15,000×g for 5 minutes, incubated 4 hours at 4° C. with 2 μg/ml anti-FLAG M2 monoclonal antibody (Sigma), and then incubated 1 hour at 4° C. with 20 μl of protein G-sepharose beads (GE-Amersham). The beads were washed 3 times with 1 mL Triton Lysis Buffer, and 20 μl immunoprecipitate was subjected to SDS-PAGE on a 12% gel, transferred to a PVDF membrane, and immunoblotted with rabbit polyclonal antibody to CypA (Biomol).

For co-immunoprecipitation of hT5Cyp with HIV-1 CA, $5\times10^6$ 293T cells were co-transfected as above with 20 μg p3xFLAG hT5Cyp and 20 μg of pEF1-GST-CA. At 48 hrs cells were lysed with RIPA Buffer (50 mM Tris-HCl pH 8.0, 150 mM NaCl, 1% IGEPAL CA-630, 0.1% SDS, 0.5% sodium deoxycholate, with Complete Mini protease inhibitor cocktail (Roche)) and accelerated at 15,000×g for 5 min. Lysate was divided into two equal parts and incubated on ice for 30 minutes with 20 μM CsA/DMSO or an equivalent volume of DMSO for 30 minutes. Lysates were incubated with 30 μl glutathione-sepharose beads (GE-Amersham) for 1 hour at 4° C. Beads were washed three times with RIPA buffer. Proteins were subjected to SDS-PAGE and immunoblotting with rabbit polyclonal anti-CypA antibody (Biomol) and goat polyclonal anti-HIV-1 CA (NCI).

Structural Model of the hT5α PRYSPRY Domain.

StruPro was used to superimpose and align the crystal structures for PRYSPRY-19q13.4.1 (Protein Data Bank (PDB) entry 2FBE; residue range 11 to 184 of chain A), GUSTAVUS (PDB entry 2FNJ; residue range 35 to 83 and 88 to 233 of chain A), and TRIM21 (PDB entry 21WG; residue range 2 to 182 of chain B), using an alpha carbon cutoff distance of 3.5 Å. ClustalX was used to combine the hT5α sequence with the structural alignments. A ClustalW sequence-based multiple alignment of 10 characteristic psi-BLAST hits of all three aforementioned sequences was used to localize insertions. A secondary structure prediction of hT5α obtained with NPS@ was used to manually correct the model. The final alignment was then fed into the model and loop optimization procedures of Modeller 8v2, using 2FBE, 2FNJ, and 21WG as templates. 100 models were built and evaluated for stereochemical quality with PROCHECK. Pictures of the single best model were generated with PyMol v0.98.

Immunofluorescence Microscopy.

CRFK cells stably expressing wild-type AoT5Cyp or hT5Cyp fusion proteins were grown on glass coverslips. Cells were fixed at 25° C. for 10 min with 3.7% formaldehyde in PBS and permeabilized on ice for 2 min with 2% Triton-X100 in 0.1% sodium citrate. After quenching with 0.1 M glycine in PBS at 25° C. for 10 min, cells were blocked for 30 min at 25° C. with 10% fetal bovine serum and 0.1% Tween-20 in PBS, before overnight incubation with goat polyclonal anti-TRIM5 (AbCam) and mouse monoclonal anti-tubulin (SIGMA) antibodies. After extensive washing in PBS, cells were sequentially incubated with donkey-Alexa Fluor 488-anti-goat and goat-Alexa Fluor 594 anti-mouse secondary antibodies (Invitrogen) for 1 hr at 25° C. in the dark. Finally coverslips were mounted in Vectashield with DAPI (Vector laboratories). Cells were visualized with a 63×1.4 NA Leica HCX Planapochromat oil immersion objective using an inverted Leica DMI 6000 CS microscope fitted with a TCS SP5 laser scanning confocal microscope system. Images from individual 3-dimensional stacks were subjected to noise reduction using the Leica LCS software (Leica Microsystems) and subjected to maximum intensity projection using the MetaMorph software (Universal Imaging Corp).

Mice.

Rag2$^{-/-}\gamma_c^{-/-}$ mice on a BALB/c background (provided by M. Ito; Central Institute for Experimental Animals, Kawasaki, Japan) were bred and maintained under specific pathogen-free conditions in accordance with the guidelines of the animal facility at the Institute for Research in Biomedicine. CL2 MBP (clodronate) was from Roche Diagnostics (Mannheim, Germany). Preparation of liposomes containing CL2 MBP was done as described previously (Van Rooijen and Sanders, 1994). 6-10 week-old mice received 100 ul of clodronate liposomes intraperitoneally (i.p.) 24 hours prior to irradiation using a single sublethal dose of 4.0 Gray (Gy) from a Cesium 137 source (Biobeam 8000, STS GmbH, Braunschweig, Germany) at 3.75 Gy/min. 4 hrs post-irradiation, mice were transplanted with 2.5×10$^5$ hCD4$^+$ T cells expressing hT5Cyp or control hT5CypH126Q in 100 μl PBS i.p. Mice were infected with CXCR4- or CCR5-tropic HIV-1$_{NL4-3}$, as previously described (Baenziger et al., 2006), either 5 or 14 days post-transplant and analyzed 2 or 4 weeks post-infection. CD4$^+$ T cell engraftment and maintenance in mice was measured by flow cytometry. To obtain peripheral blood cells and plasma, mice were bled from the retro-orbital venous sinus under anesthesia and red blood cells were lysed. When sacrificed, single cell suspensions from organs were prepared. For FACS analysis monoclonal antibodies against the following antigens were used: CD3 (UCHT1), CD4 (13B8.2), CD8 (B9.11), p24 (clone KC57) (all Immunotech/Beckman Coulter, Marseille, France), CD45 (HI30) (Caltag, Burlingame, Calif.). Intracellular staining for p24 was performed on single cell suspensions from mesenteric lymph nodes and thymus following staining with anti-CD3 antibody. Cells were washed, permeabilized, and fixed by treatment with BD Cytofix/Cytoperm (BD Pharmingen) and stained with anti-p24 antibody in BD Permwash solution (BD Pharmingen) following the manufacturer's instructions. Plasma HIV RNA concentrations were determined by Cobas Amplicor RT-PCR assay (Roche Diagnostics, Basel, Switzerland). Immunohistochemical stainings were performed as previously described (Baenziger et al., 2006). To assess non-specific binding, tissue from untransplanted and uninfected transplanted mice was stained as controls.

Proliferation of hT5Cyp-Expressing Primary Human CD4 T Cells.

Activated, scAPLS-transduced primary human CD4$^+$ T cells were maintained in culture for 6 days. 1×10$^5$ cells were transferred in triplicate into 96-well flat-bottom microplates (Falcon) and labeled for 18 h with 1 Ci of $^{[3H]}$thymidine (GE-Amersham). The DNA-incorporated radioactivity was measured by liquid scintillation counting. Data were expressed as mean corrected counts per minute (ccpm) of quadruplicate cultures.

Staining for Intracellular IL-2.

IL-2 producing capacity of hT5Cyp-expressing primary human T cells was assessed after stimulation for 6 h with 100 nM PMA and 1 μg/ml Ionomycin (Sigma-Aldrich). Brefeldin A (Sigma-Aldrich) was added at 10 μg/ml during the last 4 h of stimulation. Cells were washed, permeabilized, and fixed by treatment with BD Cytofix/Cytoperm and stained with anti-IL-2 antibody (5344.111) in BD Permwash solution following the manufacturer's instructions (all reagents BD/Pharmingen).

Staining for Cell Surface Markers.

The following antibodies were used for cell surface stains of primary CD4$^+$ T cells: α-CD4 (RPA-T4), α-CXCR4 (12G5), and α-MHC I (HLA A, B, C) (G46-2.6) (all from BD-Pharmingen).

Infections.

CD4$^+$ T cells and monocyte-derived macrophages were infected with low passage derivatives of primary isolates HIV-1$_{DH12}$ and HIV-1$_{132W}$, respectively. CD4$^+$ T cells and monocyte-derived macrophages had been previously transduced with T5Cyp- and T5CypH126Q scALPS and sorted for GFP expression. Infection was monitored by assessing the accumulation of RT activity in the supernatant at the indicated day post-infection, at which point CD4$^+$ cells were split and macrophages were fed as required.

Real-Time RT-PCR.

Total RNA was extracted from 5×10$^6$ CD4$^+$ T cells using the RNeasy Plus Mini kit (Qiagen). RNA was treated with RNase-free DNase I (Ambion) and reverse transcribed using the SuperScript™ III First-Strand Synthesis System (Invitrogen). qPCR was performed with the Applied Biosystems 7900HT system, using Taqman Gene Expression or Power SYBR green PCR master mixes (Applied Biosystems). Each experimental condition was performed in triplicate and data analyzed using the SDS software, version 2.2.2 (Applied Biosystems).

qPCR for HIV-1 DNA.

Total cellular DNA was extracted from 2×10$^6$ Jurkat T cells using the DNeasy Blood and Tissue kit (Qiagen). qPCR was performed with the Applied Biosystems 7900HT system, using 250 ng total DNA and Taqman Gene Expression master mix (Applied Biosystems). Each experimental condition was performed in triplicate and data analyzed using the SDS software, version 2.2.2 (Applied Biosystems).

Statistical Analysis.

Significant differences between groups was calculated using the Mann-Whitney U test. P-values<0.05 were considered significant.

Primers and Sequences:

```
Human TRIM5α (AY625000)
Primers used to clone hT5α, hT5α_R332P, hT5α_R322-332:
hTRIM5a XbaI 5'
                                                   (SEQ ID NO: 36)
ccctctagagccaccATGGCTTCTGGAATCCTGGTTA

hTRIM5a NotI 3'
                                                   (SEQ ID NO: 37)
aaaagcggccgcTCAAGAGCTTGGTGAGCACAGAGT
Cloned into pcDNA3.1 (-), sequenced, sub-cloned into scALPS-puro Xba-Pme/Pme.
```

-continued

RhTRIM5α (NM 001032910)
Primers used to clone RhTRIM5α:
RhTRIM5a XbaI 5'

(SEQ ID NO: 38)
ccctctagagccaccATGGCTTCTGGAATCCTGCTTA

RhTRIM5a HpaI 3'

(SEQ ID NO: 39)
aaaagttaacTCAAGAGCTTGGTGAGCACA
Cloned into pcDNA3.1 (-) Xba-Hpa/EcoRV, sequenced, sub-cloned into scALPS-puro Xba-Pme/Pme AoTRIMCyp (AY646198):
AoTRIM5Cyp XbaI 5'

(SEQ ID NO: 40)
ccctctagagccaccATGGTCAACCCCACCGTGTT

AoTRIM5Cyp BamH1 3'

(SEQ ID NO: 41)
AaaaggatccTTATTAGAGTTGTCCACAGTCAGC hTRIMCyp:
External primers:
hTRIM5Cyp XbaI 5'

(SEQ ID NO: 42)
ccctctagagccaccATGGCTTCTGGAATCCTGGTTA hTRIM5Cyp BamH1 3'

(SEQ ID NO: 43)
aaaaggatccTTATTCGAGTTGTCCACAGTC

Internal primers (nested PCR):
M244:

(SEQ ID NO: 44)
CGGCTGCAGGGGTCAGTGATGGTCAACCCCACCGTGTTC (SEQ ID NO: 45)
GAACACGGTGGGGTTGACCATCACTGACCCCTGCAGCCG

M284:

(SEQ ID NO: 46)
GCTCCTGATCTGAAAGGAATGGTCAACCCCACCGTGTTC (SEQ ID NO: 47)
GAACACGGTGGGGTTGACCATTCCTTTCAGATCAGGAGC

T302:

(SEQ ID NO: 48)
CGCTACTGGGTTGATGTGACAGTCAACCCCACCGTGTTC (SEQ ID NO: 49)
GAACACGGTGGGGTTGACTGTCACATCAACCCAGTAGC

S309:

(SEQ ID NO: 50)
GTGGCTCCAAACAACATTTCAGTCAACCCCACCGTGTTC (SEQ ID NO: 51)
GAACACGGTGGGGTTGACTGAAATGTTGTTTGGAGCCAC

S322 (=hT5Cyp):

(SEQ ID NO: 52)
CAAGTGAGCTCTGTCAACCCCACCGTGTTC (SEQ ID NO: 53)
GGGGTTGACAGAGCTCACTTGTCTCTTATCTTCAG

A331:

(SEQ ID NO: 54)
CCACAGATAATATATGGGGCAGTCAACCCCACCGTGTTCTTC (SEQ ID NO: 55)
CACGGTGGGGTTGACTGCCCCATATATTATCTGTGGTTTCG

G357:

(SEQ ID NO: 56)
GCTCTCAAAGTATCACATCAGGGGTCAACCCCACCGTGTTCTTC (SEQ ID NO: 57)
GAAGAACACGGTGGGGTTGACCCCTGATGTGATACTTTGAGAGC

-continued

T369:

(SEQ ID NO: 58)
GAGGTAGACGTGTCCAAGAAAACTGTCAACCCCACCGTGTTCTTC (SEQ ID NO: 59)
GAAGAACACGGTGGGGTTGACAGTTTTCTTGGACACGTCTACCTC

G398:

(SEQ ID NO: 60)
GAAAATTATCAACCTAAATACGGCGTCAACCCCACCGTGTTCTTC (SEQ ID NO: 61)
GAAGAACACGGTGGGGTTGACGCCGTATTTAGGTTGATAATTTTC

AoT5Cyp, hT5Cyp, and hT5CypH126Q were cloned into FUPI Xba/Bam and sequenced; then sublconed from FUPI into scALPS-puro Xba-Hpa/Pme Target sequences for APM KD vector:
CypA (3'UTR)

(SEQ ID NO: 62)
Ctggattgcagagttaagttta

TRIM5 (CDS) "T2"

(SEQ ID NO: 63)
tgccaagcatgcctcactgcaa

TRIM5alpha(3'UTR) "T8"

(SEQ ID NO: 64)
tcgtgtgataattgttcaccaa

Primers used to clone V86P/H87Q/I91V/M96I CA into p8.9ΔNS:
Spe R:

(SEQ ID NO: 65)
gggtactagtagttcctg

Notl F:

(SEQ ID NO: 66)
ggggcggccgctggtgagagatgggtgcgagagcgtc

Sequence of hT5Cyp:

(SEQ ID NO: 7)
ATGGCTTCTGGAATCCTGGTTAATGTAAAGGAGGAGGTGACCTGCCCCATCTGCCTGGAACTCCTGACACAACCCC
TGAGCCTGGACTGCGGCCACAGCTTCTGCCAAGCATGCCTCACTGCAAACCACAAGAAGTCCATGCTAGACAAAGG
AGAGAGTAGCTGCCCTGTGTGCCGGATCAGTTACCAGCCTGAGAACATACGGCCTAATCGGCATGTAGCCAACATA
GTGGAGAAGCTCAGGGAGGTCAAGTTGAGCCCAGAGGGGCAGAAAGTTGATCATTGTGCACGCCATGGAGAGAAAC
TTCTACTCTTCTGTCAGGAGGACGGGAAGGTCATTTGCTGGCTTTGTGAGCGGTCTCAGGAGCACCGTGGTCACCA
CACGTTCCTCACAGAGGAGGTTGCCCGGGAGTACCAAGTGAAGCTCCAGGCAGCTCTGGAGATGCTGAGGCAGAAG
CAGCAGGAAGCTGAAGAGTTGGAAGCTGACATCAGAGAAGAGAAAGCTTCCTGGAAGACTCAAATACAGTATGACA
AAACCAACGTCTTGGCAGATTTTGAGCAACTGAGAGACATCCTGGACTGGGAGGAGAGCAATGAGCTGCAAAACCT
GGAGAAGGAGGAGGAAGACATTCTGAAAAGCCTTACGAACTCTGAAACTGAGATGGTGCAGCAGACCCAGTCCCTG
AGAGAGCTCATCTCAGATCTGGAGCATCGGCTGCAGGGGTCAGTGATGGAGCTGCTTCAGGGTGTGGATGGCGTCA
TAAAAAGGACGGAGAACGTGACCTTGAAGAAGCCAGAAACTTTTCCAAAAAATCAAAGGAGAGTGTTTCGAGCTCC
TGATCTGAAAGGAATGCTAGAAGTGTTTAGAGAGCTGACAGATGTCCGACGCTACTGGGTTGATGTGACAGTGGCT
CCAAACAACATTTCATGTGCTGTCATTTCTGAAGATAAGAGACAAGTGAGCTCTGTCAACCCCACCGTGTTCTTCG
ACATTGCCGTCGACGGCGAGCCCTTGGGCCGCGTCTCCTTTGAGCTGTTTGCAGACAAGGTCCCAAAGACAGCAGA
AAATTTTCGTGCTCTGAGCACTGGAGAGAAAGGATTTGGTTATAAGGGTTCCTGCTTTCACAGAATTATTCCAGGG
TTTATGTGTCAGGGTGGTGACTTCACACGCCATAATGGCACTGGTGGCAAGTCCATCTATGGGGAGAAATTTGAAG
ATGAGAACTTCATCCTAAAGCATACGGGTCCTGGCATCTTATCGATGGCAAATGCTGGACCCAACACAAATGGTTC
CCAGTTTTTCATCTGCACTGCCAAGACTGAGTGGTTGGATGGCAAGCATGTGGTGTTTGGCAAAGTGAAAGAAGGC
ATGAATATTGTGGAGGCGATGGAGCGCTTTGGGTCCAGGAATGGCAAGACCAGCAAGAAGATCACCATTGCTGACT
GTGGACAACTCGAATAA

SYBR Green qRT-PCR primers
18s rRNA RT 5'

(SEQ ID NO: 67)
CGGCTACCACATCCAAGGAA 18s rRNA RT 3'

(SEQ ID NO: 68)
GCTGGAATTACCGCGGCT

ZsGreen1 RT 5'

(SEQ ID NO: 69)
CCCCGTGATGAAGAAGATGA

ZsGreen1 RT 3'

(SEQ ID NO: 70)
GTCAGCTTGTGCTGGATGAA

-continued hTC-L RT 5'
(SEQ ID NO: 71)
CTGGGTTGATGTGACAGTGG hTC-L RT 3'
(SEQ ID NO: 72)
TCTGCTGTCTTTGGGACCTT Taqman probes
18s rRNA fwd
(SEQ ID NO: 73)
CGGCTACCACATCCAAGGAA 18s rRNA rev
(SEQ ID NO: 74)
GCTGGAATTACCGCGGCT 18s rRNA probe
(SEQ ID NO: 75)
5-(FAM)-TGCTGGCACCAGACTTGCCCTC-(TAMRA)-3'

CypA
Assay ID: Hs99999904_ml (Applied Biosystems)

TRIMS (all isoforms)
Assay ID: Hs01552558_ml (Applied Biosystems)

TRIM5alpha (specific)
Assay ID: Hs01552552_gl (Applied Biosystems)

HIV-1 products qPCR
Mitochondrial forward primer (MH533)
(SEQ ID NO: 76)
ACCCACTCCCTCTTAGCCAATATT Mitochondrial reverse primer (MH534)
(SEQ ID NO: 77)
GTAGGGCTAGGCCCACCG Mitochondrial probe (mito-probe)
(SEQ ID NO: 78)
5'-(TET)-CTAGTCTTTGCCGCCTGCGAAGCA-(TAMRA)-3'

J1 RT forward
(SEQ ID NO: 79)
acaagctagtaccagttgagccagataag

J2 RT reverse
(SEQ ID NO: 80)
gccgtgcgcgcttcagcaagc

RT probe (LRT-P)
(SEQ ID NO: 81)
5'-(FAM)-CAGTGGCGCCCGAACAGGGA-(TAMRA)-3'

2-LTR forward (MH535)
(SEQ ID NO: 82)
AACTAGGGAACCCACTGCTTAAG

2-LTR reverse (MH536)
(SEQ ID NO: 83)
TCCACAGATCAAGGATATCTTGTC

2-LTR probe (MH603)
(SEQ ID NO: 84)
5'-(FAM)-ACACTACTTGAAGCACTCAAGGCAAGCTTT-(TAMRA)-3'

Alu forward (MH535)
(SEQ ID NO: 85)
AACTAGGGAACCCACTGCTTAAG

Alu reverse (SB704)
(SEQ ID NO: 86)
TGCTGGGATTACAGGCGTGAG

Alu probe (MH603)
(SEQ ID NO: 87)
5'-(FAM)-ACACTACTTGAAGCACTCAAGGCAAGCTTT-(TAMRA)-3'.

Example 8

Potent Inhibition of HIV-1 by TRIM5-Cyclophilin Fusion Proteins Engineered from Human Components Abstract: New World monkeys of the genus *Aotus* synthesize a TRIM5-cyclophilin A fusion protein (AoT5Cyp) that potently blocks HIV-1 infection. We attempted to generate an HIV-1 inhibitor modeled after AoT5Cyp by fusing human CypA to hT5 (hT5Cyp). Of 13 constructs, only three had significant HIV-1-inhibitory activity. Activity required capsid-binding by hCypA and correlated with hCypA linkage to the hT5α capsid-specificity determinant and the ability to form cytoplasmic bodies. CXCR4- and CCR5-tropic HIV-1 clones and primary isolates were inhibited by hT5Cyp, as were HIV-$2_{ROD}$, $SIV_{AGM}$tan, $FIV_{PET}$, and a circulating HIV-1 isolate previously reported as AoT5Cyp-resistant. Anti-HIV-1 activity of hT5Cyp was surprisingly better than that of the well-characterized rhesus T5α, especially in T cells. hT5Cyp blocked HIV-1 infection of primary $CD4^+$ T cells and macrophages, and conferred a survival advantage to these cells without disruption of host cell function. Extensive attempts to elicit HIV-1 resistant to hT5Cyp were unsuccessful. Finally, $Rag2^{-/-}\gamma_c^{-/-}$ mice were engrafted with $hCD4^+$ T cells that had been transduced by optimized lentiviral vectors bearing hT5Cyp; upon challenge with HIV-1, hT5Cyp decreased viremia and productive infection in lymphoid organs and preserved $hCD4^+$ T cells. Thus, hT5Cyp is an extraordinarily robust inhibitor of HIV-1 replication and a promising anti-HIV-1 gene therapy candidate.

Introduction:

Over 60 million people have been infected with HIV-1 and nearly half of these people have died as a consequence of this infection (1). Despite the discovery of HIV-1 25 years ago, it continues to kill several million people each year. In theory, the clearest path to the elimination of the HIV-1 pandemic would be an effective, anti-HIV-1 vaccine. In practice, the virus has proven to be an elusive target for the immune system (2, 3). Combination antiviral therapy potently suppresses HIV-1 replication and resultant disease, but these treatments are plagued with complications and they do not eliminate the virus.

The difficulties of controlling HIV-1 have stimulated thinking about alternatives to conventional vaccination or life-long pharmacotherapy. Among these creative possibilities are anti-HIV-1 gene therapy (4, 5). Ideally, gene therapy should potently suppress HIV-1 replication without eliciting viral resistance. While all steps of the viral life cycle are potential gene therapy targets, blocking the virus before reverse transcription (RT) would preclude the genetic diversity that permits emergence of viral resistance. Additionally, targeting the virus before HIV-1 cDNA is ligated into host chromosomal DNA would prevent the virus from becoming a heritable genetic element in that cellular lineage. The discovery that certain TRIM5 (T5) orthologues inhibit HIV-1 infection immediately after the virus enters otherwise susceptible cells (6-9) raised the prospect that these host factors might be exploited in HIV-1 gene therapy.

The α-isoform of TRIM5 (T5α) contains a C-terminal PRYSPRY domain that is required for T5α binding to the capsid (CA) of restriction-sensitive retroviruses (10, 11). The specificity of the PRYSPRY-CA interaction determines which retrovirus a given T5α orthologue inhibits (12). While human T5α (hT5α) weakly blocks HIV-1, it potently blocks N-tropic murine leukemia virus (N-MLV). In contrast, rhesus T5α (rhT5α) inhibits HIV-1, but N-MLV only weakly. The specificity of retroviral restriction and the modular nature of the T5 components are further demonstrated by the enhanced HIV-1 restriction activity that results when the hT5α PRYSPRY domain is replaced with that from rhT5α (13-16). Furthermore, anti-HIV-1 activity is observed when other TRIM family members (17) or even the murine anti-retroviral factor Fv1 (18) are fused to an HIV-1 CA-binding protein.

The T5 gene in the New World owl monkey (genus *Aotus*) is unusual. It resulted from retrotransposition of the cyclophilin A (CypA) cDNA into intron 7 (7, 19). CypA is a CA-binding protein (20) and the *Aotus* TRIM5Cyp fusion (AoT5Cyp) prevents HIV-1 infection (7, 19). AoT5Cyp has several properties that make it appealing for gene therapy. It potently inhibits HIV-1 infection when expressed in human cells (7, 19), acting on the virus within minutes of entry (8, 9). Furthermore, AoT5Cyp is the only TRIM5 allele in 10 *Aotus* species (21), indicating that cells bearing AoT5Cyp retain functionality. One drawback of AoT5Cyp is that it is not a human protein and if employed as gene therapy it might elicit an immune response (22). Here we engineered fully human TRIM5-cyclophilin A fusion proteins (hT5Cyp) exhibiting HIV-1 restriction activity comparable to AoT5Cyp and possessing all the properties desired of anti-HIV-1 gene therapy.

Results: Design of hT5Cyp Fusions with Potent Anti-HIV-1 Activity.

Our goal was to generate a hT5Cyp fusion modeled after AoT5Cyp using only human components. A cryptic splice acceptor at the AoT5Cyp fusion junction results in the synthesis of 12 amino acids derived from the CypA 5'UTR (7). An equivalent human fusion cannot be engineered due to lack of sequence homology in the CypA 5'UTR. Sequences from T5γ and T56, of similar length and character to the AoT5Cyp 5'UTR, were included at the T5-CypA junction, but these failed to result in proteins with anti-HIV-1 activity. hCypA was then fused directly to hT5α at 11 different positions along its linear sequence, eliminating subsequent hT5α sequence and resulting in hT5Cyp fusions consisting entirely of components expressed in human cells (FIG. 24A). Each hT5Cyp fusion was engineered into a bicistronic lentiviral vector (FUPI, FIG. 32A). Vector stocks generated for each construct were shown to have equivalent titers and then used to generate stable cell lines.

Figure 32:
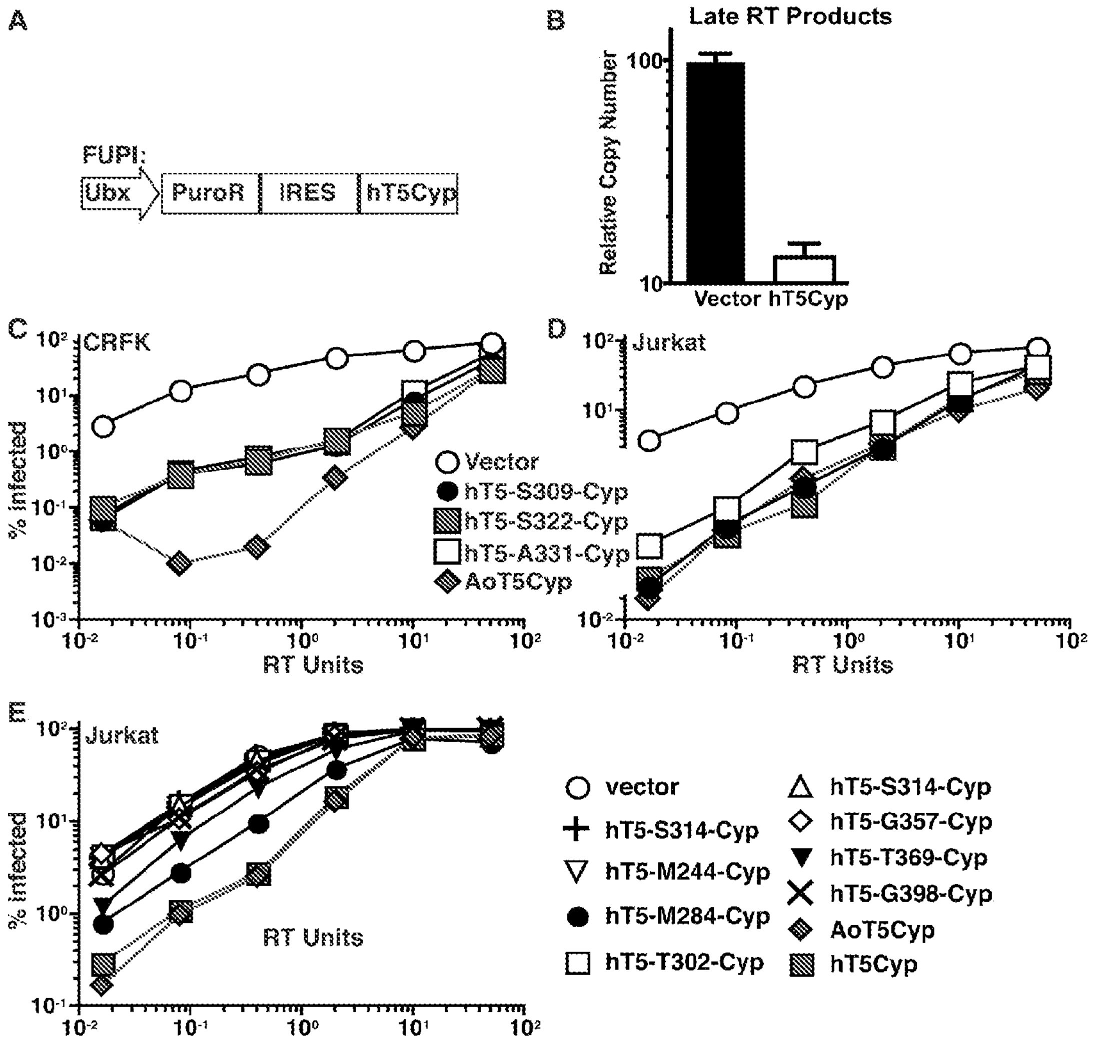
FIG. 32A-32E. HIV-1 restriction activity of different hT5Cyp fusion proteins. (A) Design of a bicistronic lentiviral vector, FUPI, used to establish T5-expressing cell lines. Ubx=ubiquitin promoter, PuroR=puromycin N-acetyltransferase, IRES=internal ribosome entry site. (B) Total cellular DNA was purified from HIV-1 vector-infected Jurkat T cell lines. Late RT products were quantified by PCR. DNA was normalized to mitochondrial DNA content. (C, D) Comparison of restrictive T5Cyp fusions in CRFK (C) and Jurkat (D) cells. (E) Comparison of all designed fusions with reduced anti-HIV-1 activity to restrictive T5Cyp and AoT5Cyp in Jurkat T cells. In all cases, cells were transduced with FUPI encoding puromycin-resistance and the indicated T5Cyp fusion proteins. Pools of puromycin-resistant cells were infected with increasing amounts of an HIV-1 GFP vector (left to right on X-axis). The percentage of GFP+ positive cells (Y-axis) was determined 48 hrs later.

Pools of Jurkat or THP-1 cells, each bearing a different hT5Cyp construct, were tested for restriction activity against a single-cycle, HIV-1-GFP vector. Among the hT5Cyp constructs, three had activity comparable to AoT5Cyp. See representative data in FIG. 24B for hT5-S322-Cyp. This fusion was used in all subsequent experiments and will be referred to as simply hT5Cyp. Data for all of the fusion constructs is shown in FIG. 32. hT5Cyp also restricted HIV-1 in promonocytic U937 cells, the CEM-SS, SUP-T1, and H9 T cell lines, and the 293T embryonic kidney cell line. Like AoT5Cyp (9), hT5Cyp blocked viral cDNA accumulation after acute infection, as measured by quantitative PCR (FIG. 32B).

Structural Requirements for hT5Cyp-Mediated HIV-1 Restriction Activity.

Figure 25:
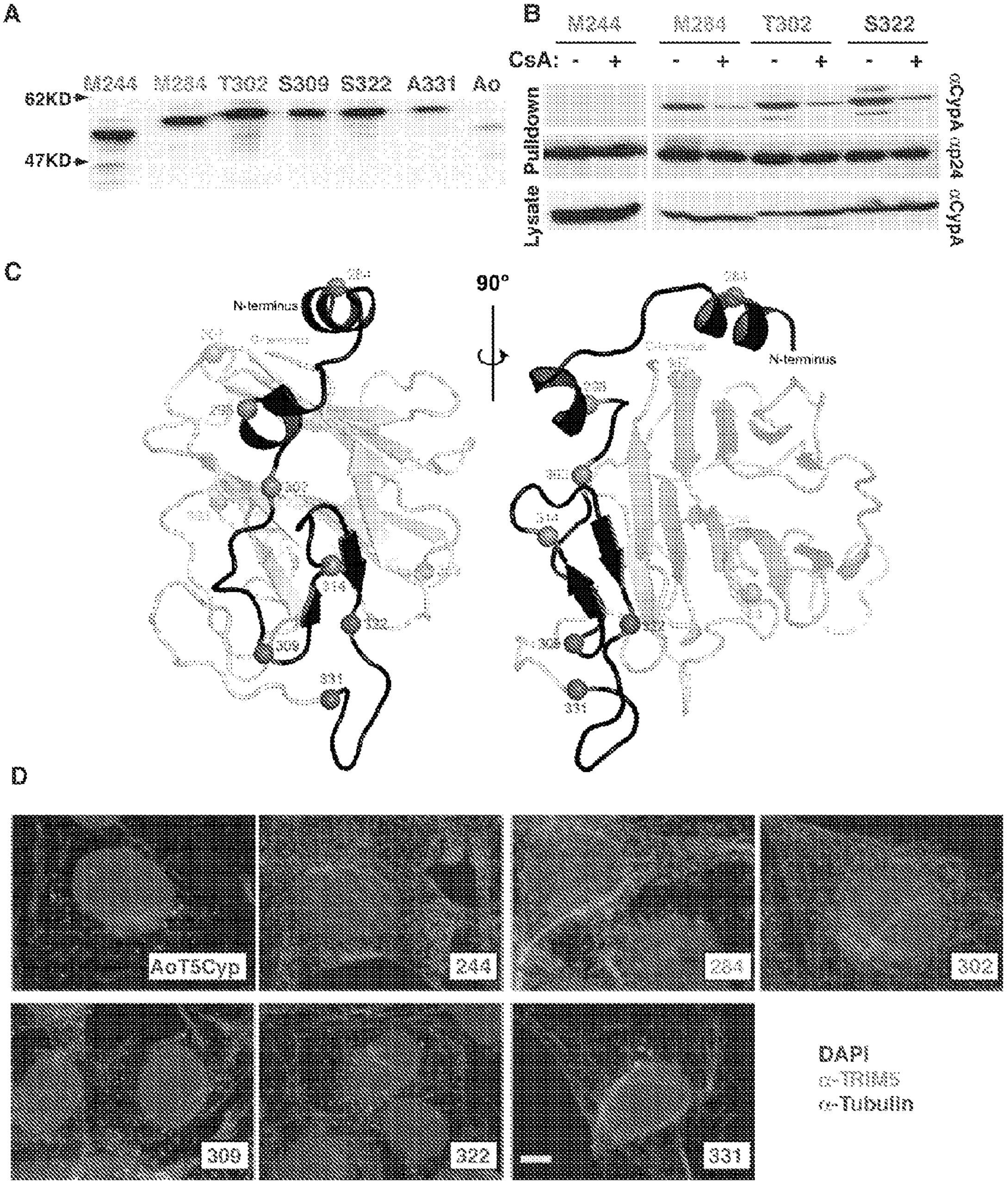
FIG. 25A-25D. HIV-1 restriction activity correlates with CypA fusion to the T5α specificity determinant and the ability to form cytoplasmic bodies. (A) Expression of hT5-Cyp fusion proteins. FLAG-hT5Cyp fusion proteins synthesized in 293T cells were immunoprecipitated and immunoblotted with anti-CypA antibodies. (B) HIV-1 CA binding activity of hT5Cyp fusion proteins. FLAG-hT5Cyp and GST-CA fusion proteins were co-expressed in 293T cells, pulled out on glutathione-sepharose beads in the presence or absence of 20 μM CsA, and immunoblotted with anti-CypA and anti-p24-CA antibodies. (C) Model of the PRYSPRY domain of human T5α based on crystal structures of PRYSPRY, GUSTAVUS and TRIM21. Two ribbon representations showing the position of hCypA fusions (spheres) to the hT5α PRYSPRY domain. The grey transparent ribbon indicates regions of the model that would be replaced by CypA in hT5-S331-Cyp. (D) Restrictive T5Cyp fusion proteins form discrete puncta in the cytoplasm. Indirect immunofluorescence images of CRFK cells stably expressing the indicated T5Cyp fusions. Fixed samples were stained with anti-T5 antibody (green) and anti-tubulin antibody (red), followed by counter-stain with DAPI (blue) to visualize the nuclear DNA. For each color, one individual stack of 20 0.35 μm optical sections was acquired and subjected to maximum intensity projection along the optical axis. Images represent three-color overlays. Bar: 5 μm. All panels are color-coded for restriction phenotype: red, restrictive; green, permissive; orange, variably restrictive.

Despite the apparent modularity of TRIM5 (13-16), most hT5Cyp fusions lacked anti-HIV-1 activity. Steady-state protein level in stably-transduced Jurkat T cells did not correlate with restriction activity: AoT5Cyp and restrictive hT5Cyp fusions were undetectable by immunoblot while some inactive mutants were highly expressed. To increase the possibility of detection, hT5Cyp proteins were expressed as triple-FLAG-tagged fusions by plasmid transfection of 293T cells. Anti-FLAG immunoprecipitates were probed in immunoblots with anti-CypA antibody. Two fusions with no detectable restriction activity, hT5-M244-Cyp and hT5-T302-Cyp, were expressed at high-level, whereas fusions with potent anti-HIV-1 activity, were variably expressed at moderate to high-level (hT5-S309-Cyp and hT5-S322-Cyp) or at low-level (hT5-A331-Cyp and AoT5Cyp) (FIG. 25A). Again, restriction activity did not correlate with protein level.

Lack of activity could result from failure to bind HIV-1 CA. Glutathione S-transferase (GST)-CA fusion protein was used to test CA-binding activity of hT5Cyp proteins produced in 293T cells. Among hT5Cyp fusions with no anti-HIV-1 activity, hT5-T302-Cyp bound HIV-1 CA as well as the potently restrictive hT5-S322-Cyp (FIG. 25B). As described for the HIV-1 CA-CypA interaction (20), specificity of binding was demonstrated by blocking the interaction using the competitive inhibitor cyclosporine A (FIG. 25B). Thus, CA-binding was necessary but not sufficient for restriction activity.

To visualize the sites of CypA linkage to hT5, a three-dimensional model of the T5α PRYSPRY domain was generated using coordinates from three homologues (FIG. 25C). hT5Cyp fusions with anti-HIV-1 activity clustered near a putative, protein interaction surface (23, 24) (FIG. 25C, red spheres), the main specificity determinant for HIV-1 restriction activity (15, 16, 25). No inactive hT5Cyp proteins mapped to this region (FIG. 25C, green spheres). Indirect immunofluorescence showed that AoT5Cyp and all three hT5Cyps with potent anti-HIV-1 activity formed distinct cytoplasmic bodies (FIG. 25D). In contrast, diffuse cytoplasmic staining was observed for hT5Cyp fusions that lacked restriction activity. These results suggest that there are conformational requirements for antiviral activity, determined by the site of CypA fusion and revealed by the ability to form cytoplasmic bodies.

hT5Cyp Restriction Activity Depends on Both the hCypA and hT5 Components.

Figure 26:
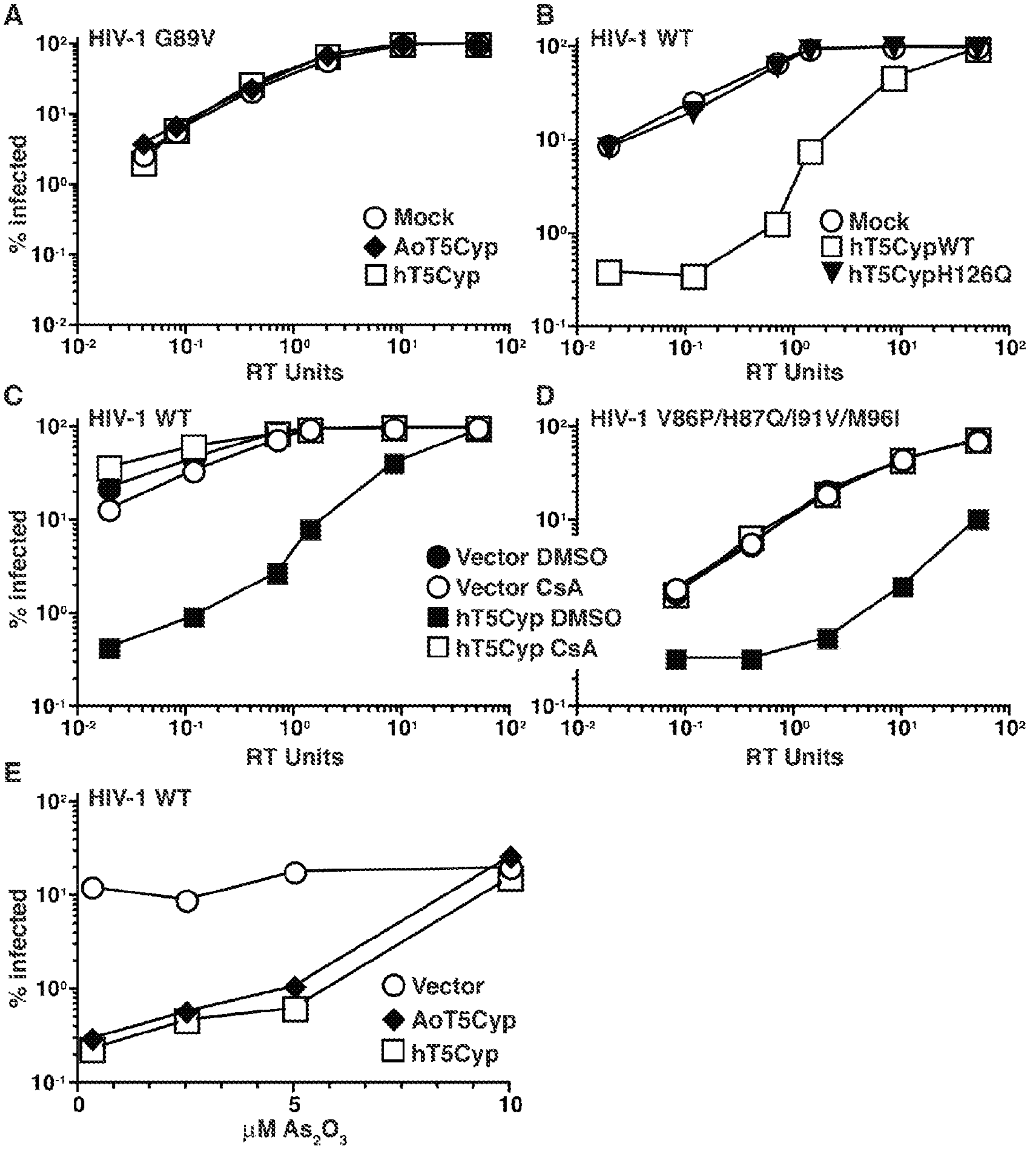
FIG. 26A-26E. T5 and CypA components each make essential contributions to T5Cyp restriction activity. (A-C) Disruption of the CA-CypA interaction by the G89V mutation in HIV-1 CA (A), the H126Q mutation in CypA (B), or the competitive inhibitor cyclosporine (CsA) at 2.5 μM (C), blocks HIV-1 restriction activity in CRFK cells stably expressing the indicated T5 proteins or controls. Cells were challenged with increasing amounts (X-axis) of HIV-1-GFP single-cycle vector bearing the G89V mutation in CA (A) or wild-type HIV-1 GFP vector (B, C). (D) Introduction of a naturally-occurring quadruple mutation flanking the CA-CypA binding site in HIV-1 CA does not abrogate hT5Cyp-mediated restriction of HIV-1. CRFK cells stably expressing T5Cyp or control were infected with increasing amounts (X-axis) of an HIV-1 GFP vector containing the V86P/H87Q/I91V/M96I mutation in CA. (E) Disruption of T5 by $As_2O_3$ blocks HIV-1 restriction activity by T5Cyp. CRFK cells stably expressing the indicated T5Cyp were infected with HIV-1 GFP vector in the presence of increasing amounts of $As_2O_3$ (X-axis). In each case (A-E) the percentage of $GFP^+$ cells was measured by flow cytometry 48 hrs post-infection (Y-axis).
Figure 33:
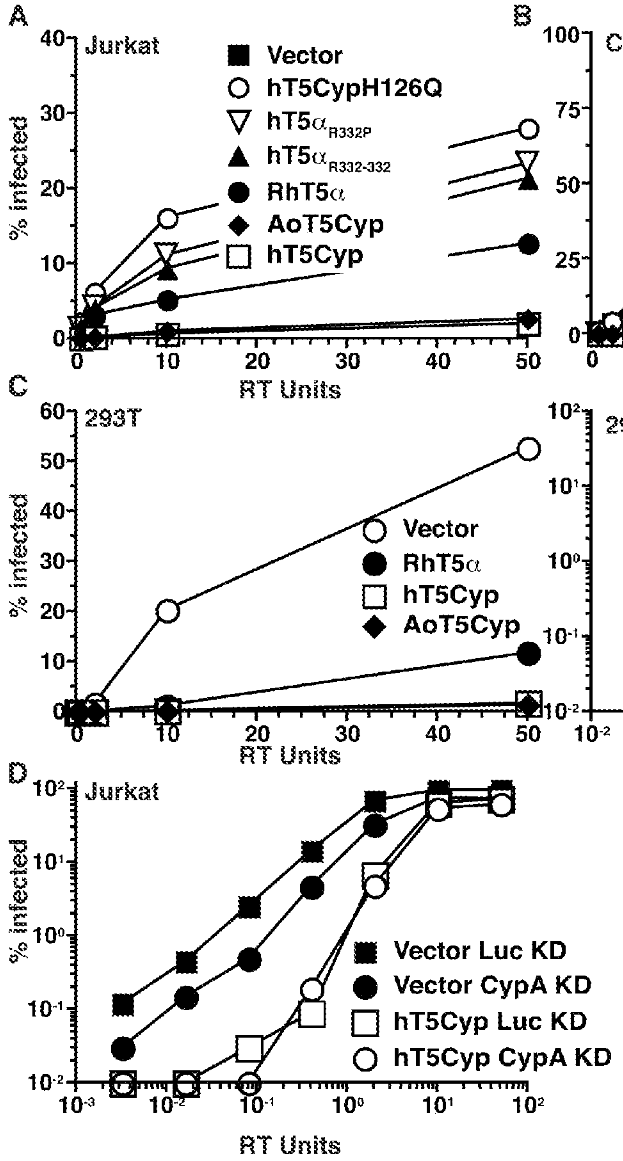
FIG. 33A-33D. HIV-1 restriction activity of different T5 proteins. (A, B) Comparison of T5-mediated restriction of HIV-1 vectors in Jurkat (A), CRFK (B), and 293T (C; left panel linear scale, right panel logarithmic scale) cells. (D) hT5Cyp restriction activity in Jurkat T cells stably transduced with lentiviral vectors coding for shRNAs targeting either cyclophilin A (CypA) or luciferase (Luc). In all cases, cells were transduced with vectors encoding puromycin-resistance and the indicated T5Cyp fusion proteins. Pools of puromycin-resistant cells were infected with increasing amounts of an HIV-1 GFP vector (left to right on X-axis). The percentage of $GFP^+$ positive cells (Y-axis) was determined 48 hrs later.

CypA is an abundant protein with potential to inhibit hT5Cyp activity by competing for CA-binding. The magnitude restriction of a single-cycle HIV-1-GFP vector by hT5Cyp was unaffected by CypA (FIG. 33D), as determined in Jurkat T cells with a stable knockdown of endogenous CypA (26). To confirm that hT5Cyps have the same CA-binding requirements as AoT5Cyp, stable hT5Cyp lines were generated using CRFK, a feline fibroblast that lacks endogenous T5. These cells were challenged with a single-cycle, HIV-1-GFP vector, containing a mutation in CA (G89V) that disrupts interaction with CypA (7). As expected, HIV-1-G89V was less fit than wild-type HIV-1, but neither AoT5Cyp nor hT5Cyp restricted this virus (FIG. 26A). The CA-CypA interaction is also disrupted by the CypA-H126Q mutation (27) and hT5Cyp bearing the H126Q mutation in its CypA domain had no detectable anti-HIV-1 restriction activity (FIG. 26B). Cyclosporine, a competitive inhibitor of the CypA-CA interaction (20), abrogated HIV-1 restriction by AoT5Cyp and hT5Cyp (FIG. 26C). HIV-1-V86P/H87Q/I91V/M96I, a CA-variant circulating in HIV-1-infected people, is reported to be resistant to cyclosporine and to AoT5Cyp-mediated HIV-1-restriction (28). Though HIV-1-V86P/H87Q/I91V/M96I was indeed resistant to cyclosporine, hT5Cyp blocked infection by single-cycle vectors bearing this CA variation (FIG. 26D).

To assess the contribution of the T5 domain to T5Cyp-mediated restriction, CRFK cell lines expressing AoT5Cyp or hT5Cyp were treated with arsenic trioxide ($As_2O_3$). This drug was previously shown to inhibit T5-mediated restriction (29). AoT5Cyp and hT5Cyp restriction activity was blocked to the same extent by $As_2O_3$ (FIG. 26E).

AoT5Cyp restricts HIV-$1_{NL4-3}$, HIV-$2_{ROD}$, $SIV_{AGM}$tan, and $FIV_{PET}$, all viruses encoding a CA that binds CypA (7, 9, 19, 20, 30-32). AoT5Cyp and hT5Cyp restricted single-cycle GFP-vectors derived from all four of these lentiviruses (FIG. 27A-D). CypA does not bind to $SIV_{MAC}$251 CA and neither AoT5Cyp nor hT5Cyp restricted a $SIV_{MAC}$251 GFP vector (FIG. 27E). These results show that, with respect to CA-recognition by the CypA domain, and effector function by the T5 domain, AoT5Cyp and hT5Cyp behave similarly.

hT5Cyp is More Potent than rhT5α.

In contrast to hT5α, the T5α orthologue from rhesus monkeys (rhT5α) potently restricts HIV-1 (6). Chimeric proteins in which critical residues from the rhT5α-PRYSPRY domain replace corresponding residues in the human orthologue exhibit HIV-1 restriction activity approaching that of rhT5α (14-16, 33, 34). These human-rhesus chimeras have been proposed as anti-HIV-1 gene-therapy candidates. Since potency is an essential consideration for any anti-HIV-1 therapy, hT5Cyp was compared side-by-side with the most promising human-rhesus chimeras. $hT5\alpha_{R332P}$ (16, 33) and $hT5\alpha_{rh323-332}$ (14, 15) transgenes, stably expressed in CRFK cells, inhibited single-cycle HIV-1 vectors ~10-fold, approaching the anti-HIV-1 activity of rhT5α (FIG. 28A and FIG. 33B). hT5Cyp, however, restricted HIV-1 almost 10-fold more potently than even rhT5α (FIG. 28A and FIG. 33B). In stable Jurkat T cell lines, the relative potency of hT5Cyp, and AoT5Cyp, was even more impressive (FIG. 28B and FIG. 33A). Similar results were obtained in 293T cells stably expressing the indicated T5 proteins (FIG. 33C).

hT5Cyp Eliminates HIV-1 Spreading Infection.

Jurkat T cells stably transduced with T5-expression vectors were infected with replication-competent HIV-1. $hT5\alpha_{R332P}$ and $hT5\alpha_{rh323-332}$ had minimal effect on the kinetics of HIV-1 infection (FIG. 28C). rhT5α delayed the HIV-1 replication peak by 8 days (FIG. 28C). In contrast, HIV-1 replication was not detected in cells transduced with hT5Cyp or AoT5Cyp for the two-month observation period (FIGS. 28C and D). HIV-1 replication in cells transduced with hT5Cyp bearing a mutation that blocks binding to HIV-1 CA (CypA-H126Q, see ref. (27)), was as rapid as in cells transduced with empty vector (FIGS. 28C and D). In the interest of identifying HIV-1 mutations that confer resistance to hT5Cyp, HIV-1 infection was initiated on 10 separate occasions, over a range of infectious doses, in co-culture of hT5Cyp-expressing and untransduced cells, and by direct transfection of infectious HIV-1 proviral DNA into hT5Cyp-expressing Jurkat cells; no evidence of HIV-1 spreading infection was detected in the presence of hT5Cyp.

New Lentiviral Vectors Bearing hT5Cyp Block HIV-1 Infection of Primary Cells.

hT5Cyp-mediated restriction of HIV-1 in primary human $CD4^+$ T cells and macrophages was assessed next. To identify cells transduced with hT5Cyp, attempts were made to use a bicistronic lentiviral vector that directs synthesis of GFP from an internal ribosome entry site (AIG in FIG. 29A). These vectors failed to generate GFP in primary $CD4^+$ T cells (FIG. 29B). Better results were obtained when a vector was engineered that bears two promoters, one from the SFFV LTR and the other from the hCypA gene (scALPS in FIGS. 29A and B). Co-synthesis of two reporter genes, GFP and dsRED, within primary $CD4^+$ T cells transduced with scALPS, was confirmed by flow cytometry (FIG. 34).

Figure 34:
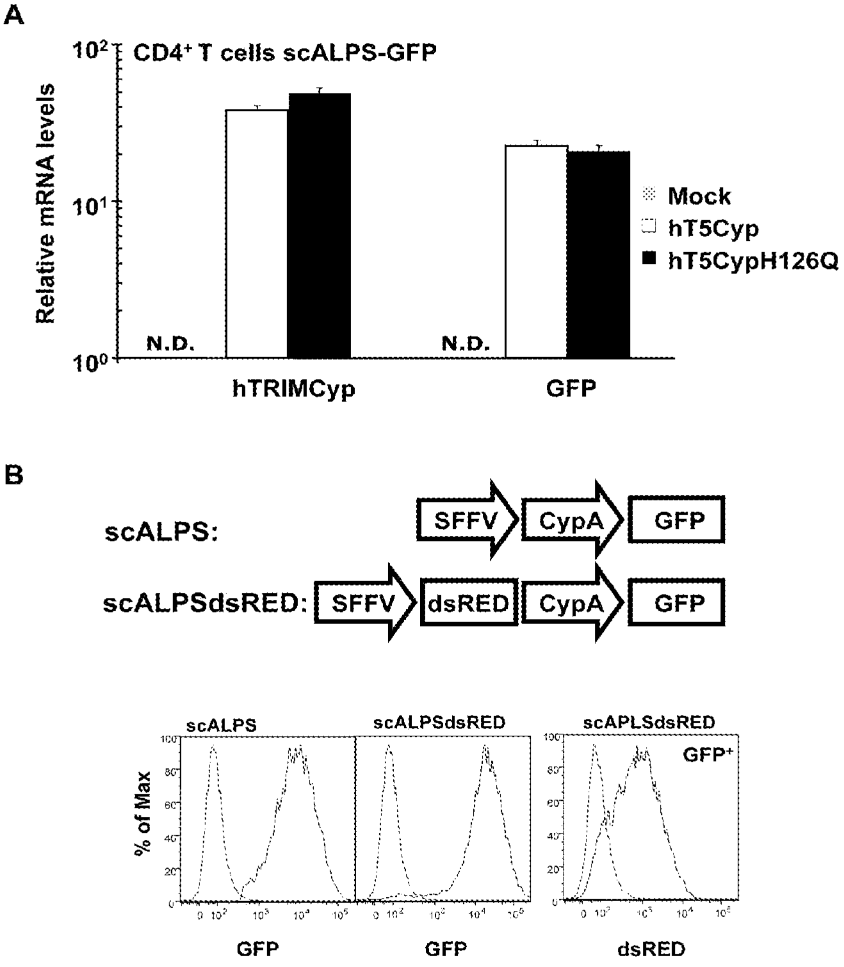
FIG. 34A-34B. Transgene expression in T cells transduced with dual promoter Vectors. (A) Quantitative RT-PCR for GFP and hT5Cyp wt or hT5CypH126Q mRNA expression normalized by 18S RNA expression 48 hours after transduction of primary $CD4^+$ T cells with scAPLS dual promoter vectors. N.D.=not detected (B) Schematic of dual promoter vectors (scAPLS and scAPLSdsRed) used to transduce Jurkat T cells (top panel). Transgene expression in transduced Jurkat T cells (bottom panel).
Figure 35:
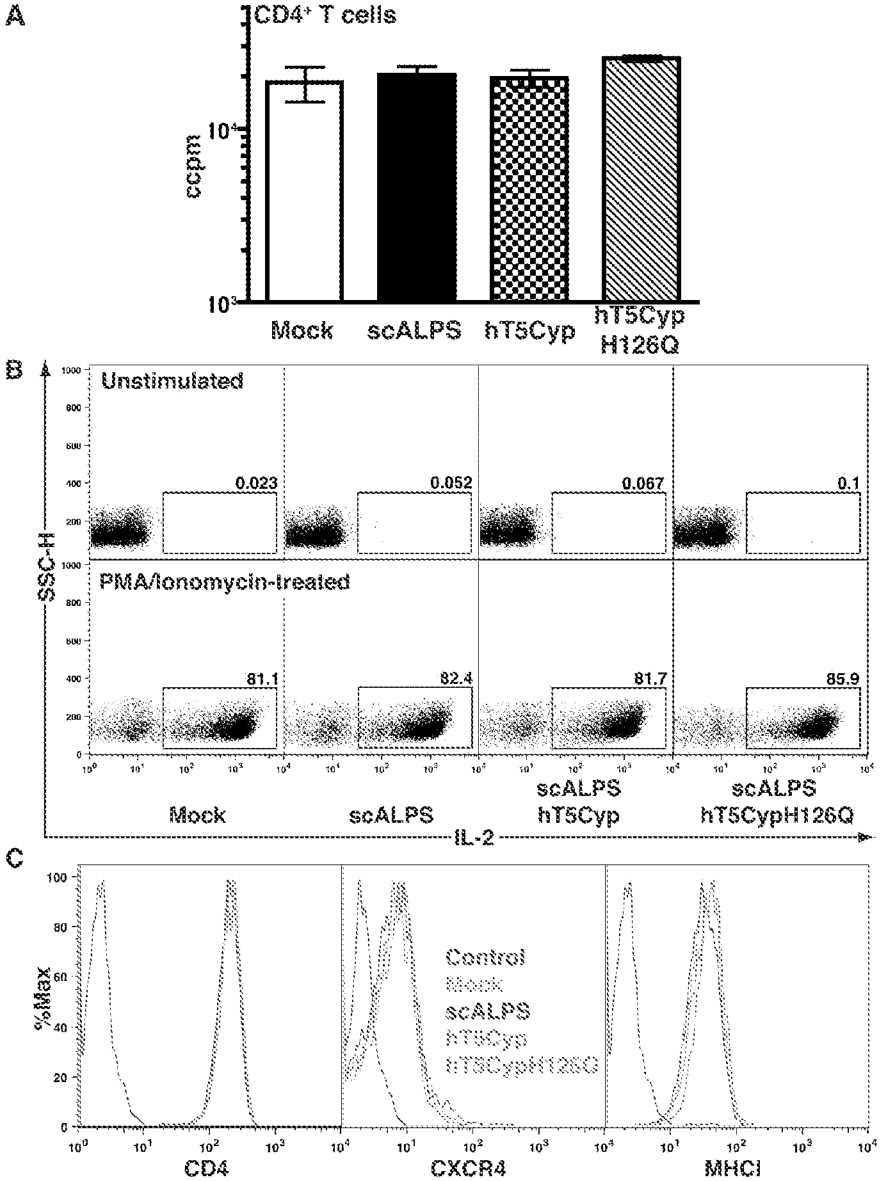
FIG. 35A-C. Transduction of primary human CD4+ T cells using a dual promoter, lentiviral vector encoding T5Cyp and GFP does not affect basic T cell functions. (A) T5Cyp does not affect steady-state proliferation of $CD4^+$ T cells. $CD4^+$ T cells transduced with the indicated vector were sorted for GFP expression and steady-state proliferation as compared to un-transduced cells was measured using $^{3H}$Thymidine incorporation. Corrected counts per minute (ccpm, Y-axis) were measured 24 hours after addition of $^{3H}$Thymidine (for each condition, n=3). (B) IL-2 production in scALPS-transduced $CD4^+$ T cells. IL-2 production (X-axis) in proliferating un-transduced $CD4^+$ T cells and $CD4^+$ T cells transduced with indicated scALPS vectors was analyzed by flow cytometry following stimulation with PMA and ionomycin. (C) Cell-surface marker expression on scALPS-transduced $CD4^+$ T cells. The expression of the indicated cell surface markers (X-axis) was assessed in proliferating un-transduced $CD4^+$ T cells and $CD4^+$ T cells transduced with indicated scALPS vectors by flow cytometry.

Primary $CD4^+$ T cells transduced with dual-promoter vectors bearing hT5Cyp or the non-restrictive hT5CypH126Q were sorted based on GFP-expression and expression of the transgenes was confirmed by real-time RT-PCR (FIG. 34). Transduced cells proliferated at the same rate as untransduced cells, produced comparable amounts of IL-2 upon stimulation, and expressed the same level of cell-surface CD4, CXCR4, and MHC I (FIG. 35). Upon challenge with replication-competent, CXCR4-tropic HIV-$1_{NL4-3}$, viral replication in hT5CypH126Q-transduced cells peaked on day 12 and infection was not established in hT5Cyp-transduced cells (FIG. 29C). The same hT5Cyp-mediated block to infection was observed with a primary isolate of HIV-1 (FIG. 29D). Monocyte-derived macrophages were also transduced with vectors encoding hT5Cyp or hT5CypH126Q and sorted based on GFP-expression. Cells were infected with HIV-$1_{NL4-3}$, modified to be CCR5-tropic, at a high multiplicity of infection (MOI=2). Upon decay of input virus, macrophages transduced with hT5Cyp were clearly resistant to HIV-1 infection (FIG. 29E). Furthermore, macrophages transduced with hT5Cyp-encoding vectors were resistant to a primary isolate of HIV-1 (FIG. 29F).

hT5Cyp Confers Selective Advantage to $CD4^+$ T Cells Challenged with HIV-1.

Figure 36:
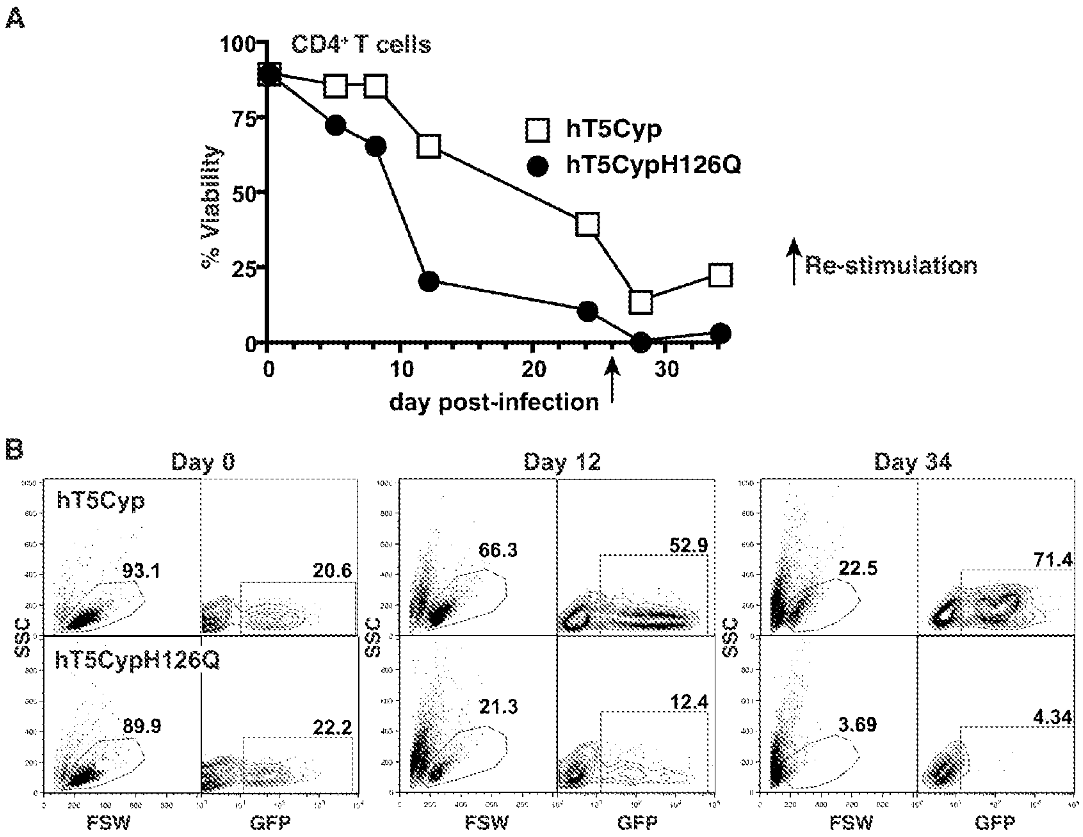
FIG. 36A-36B. hT5Cyp enhances viability of CD4+ T cells in mixed cultures infected with HIV-1. (A) CD4+ T cells were transduced with scAPLS encoding the indicated hT5Cyp proteins. Cultures containing 23% GFP+ cells (same as in FIG. 29G) were challenged with 15 ng p24/106 cells HIV-1NL4-3 and monitored for % viable cells by forward and side scatter profiles (Y-axis) on the indicated day post-infection (X-axis). Representative flow cytometry plots showing viability (left panels) and % GFP+ cells (right panels) at three time points are shown in (B).

The previous experiments showed that HIV-1 infection is blocked when all cells in the culture have been transduced with the hT5Cyp vector. Next we evaluated anti-HIV-1 efficacy under suboptimal conditions, in which <25% of cells were transduced with hT5Cyp. In the absence of HIV-1 infection, the percent transduced cells persisting in the culture over the course of a month was equivalent for hT5Cyp and hT5CypH126Q; in the face of HIV-1 infection, the hT5CypH126Q cells declined to <10% of the cells in the culture (FIG. 29G). hT5Cyp cells, in contrast, had a distinct advantage, expanding to 75% of the cells in the population (FIG. 29G). This selective advantage was mirrored in prolonged cell viability within the cultures transduced with hT5Cyp-coding vector compared to those transduced with hT5CypH126Q-expressing vector (FIG. 36). The survival advantage was most likely due to the antiviral activity of hT5Cyp, since HIV-1 replication was reduced in cultures containing hT5Cyp cells (FIG. 29G). Thus, even when a minority of cells are transduced in culture conditions where HIV-1 can spread directly from cell-to-cell, hT5Cyp is potent enough to block HIV-1 infection.

hT5Cyp Protects Against HIV-1 Infection In Vivo.

Figure 30:
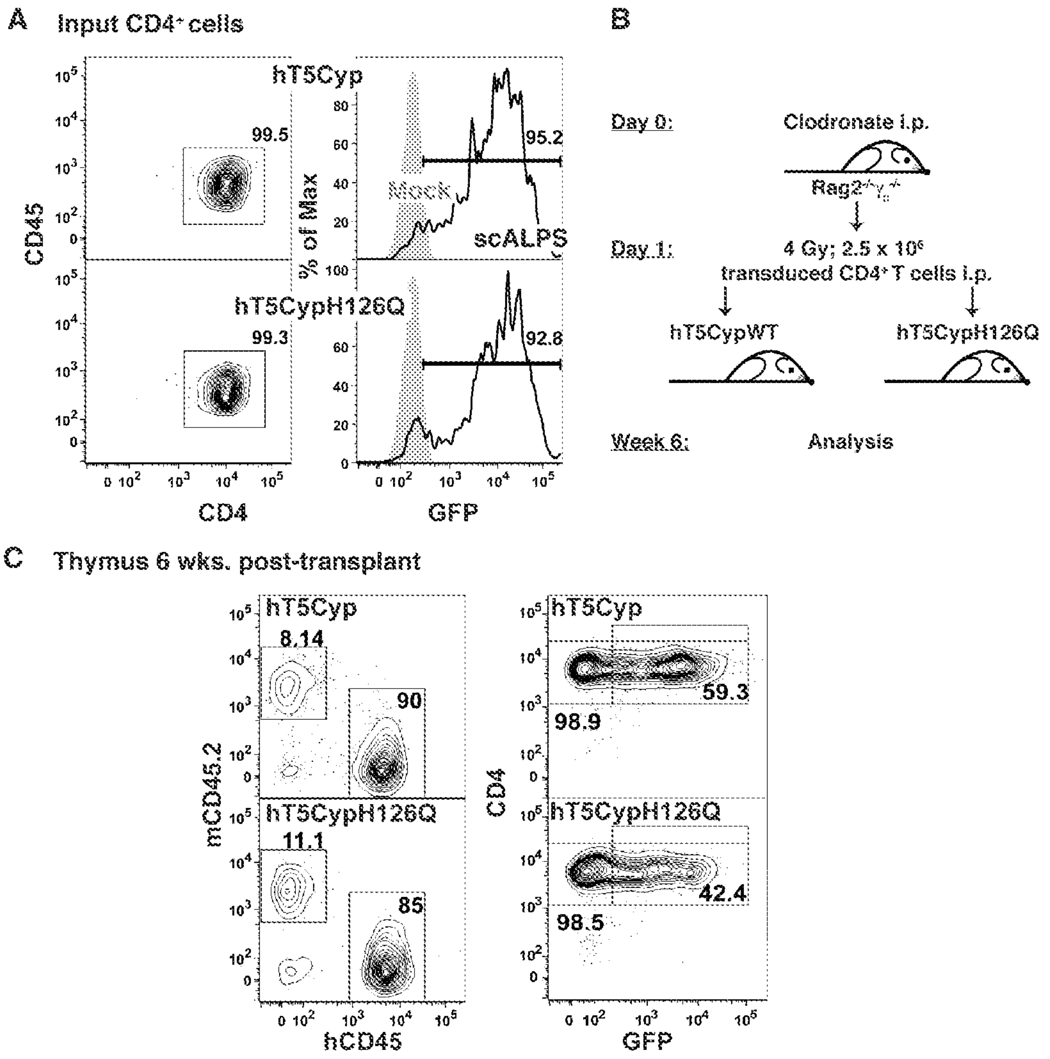
FIG. 30A-30C. Adoptive transfer of hT5Cyp-transduced hCD4 cells into $Rag2^{-/-}\gamma_c^{-/-}$ mice. Human peripheral blood $CD4^+$ T cells transduced with lentiviral vector scALPS bearing either hT5Cyp or hT5CypH126Q were sorted for GFP and injected into 6-10 wk old $Rag2^{-/-}\gamma_c^{-/-}$ mice. The experimental design is shown schematically in (A). (B) Flow cytometric analysis of the transduced, sorted cells prior to adoptive transfer. The left panel shows that nearly all cells are $hCD4^+$. The x-axis of the right panel shows GFP fluorescence in transduced cells (open histograms, scALPS) or in untransduced, donor-identical $CD4^+$ T cells (grey histogram, Mock). (C) 6 weeks post-transplant, single cell suspensions of thymus were analyzed for human cell engraftment and transgene expression. The left panel shows recipient-derived $CD45^+$ mouse cells (mCD45.2, Y-axis) and donor derived $hCD45^+$ cells (X-axis). The right panel shows CD4 and GFP signals for the $hCD45^+$ cells (right panels). In (A) and (C), the numbers indicate the percentage of cells within the indicated gates.
Figure 37:
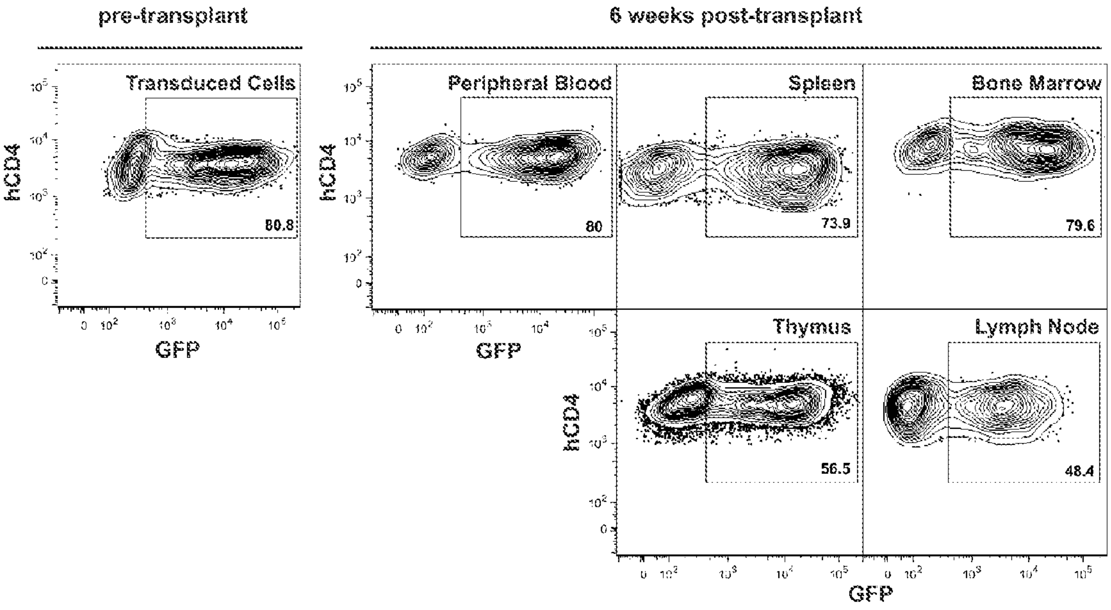
FIG. 37. In vivo GFP expression in hCD4+ T cells 6 weeks posttransplant. 6-10 week old $Rag2^{-/-}\gamma_c^{-/-}$ mice were engrafted with GFP-sorted scAPLS-transduced $CD4^+$ T cells (left panel). Indicated organs were analyzed for GFP expression 6 weeks post-transplant (right panel). Gates denote the percentage of $GFP^+$ cells in the $hCD4^+$ population. Data from one representative mouse are shown.

To test the ability of hT5Cyp to protect against HIV-1 infection in vivo, two approaches analogous to those used in human gene therapy strategies were taken. In one experimental model, human $CD4^+$ T cells were adoptively transferred into $Rag2^{-/-}\gamma_c^{-/-}$ mice. This mouse strain lacks B, T, and NK cells and does not reject xenografts (35). $CD4^+$ T cells were transduced with the hT5Cyp or hT5CypH126Q vectors and sorted for GFP-expression, leading to a >93% purity of $GFP^+$ input cells (FIG. 30A). Age-matched, 6-10 week-old $Rag2^{-/-}\gamma_c^{-/-}$ mice were conditioned with clodronate and sublethal irradiation (36), and injected intraperitoneally with $2.5\times10^6$ transduced $CD4^+$ T cells (FIG. 30B). Two and six weeks post-transplant, peripheral blood engraftment was assessed by measuring the percentages of human $CD45^+CD4^+GFP^+$ cells. 50 to 90% were $GFP^+$ at both time points (2 weeks mean+/−SEM: hT5Cyp 81.9%+/−4.5, n=8, hT5CypH126Q 73.4%+/−4.4, n=8; six weeks mean+/−SEM: hT5Cyp 76.1+/−6.0, n=8, hT5CypH126Q 76.8+/−1.56, n=8), indicating that GFP-percentages remained stable and engraftment efficiency was not altered by hT5Cyp or hT5CypH126Q. Similar to peripheral blood, percentages of engraftment and GFP+ cells did not differ in lymphoid organs between the two constructs used (FIG. 30C). However, we consistently observed that GFP expression was higher in peripheral blood, bone marrow and spleen, compared to somewhat lower levels of GFP expression in thymus and mesenteric lymph nodes (FIG. 37). The reasons for this are unclear. One can speculate that a) the minor fraction of T cells that were GFP-low/negative and thus non-transduced at transfer (<10%, FIG. 30A) have different biologic properties (e.g. better homing capacity to lymphoid organs as thymus and lymph nodes) compared to GFP+ cells; or that b) GFP expression correlates with activation status of transduced, initially GFP+ cells, with metabolically less active cells expressing lower levels or lacking GFP expression in thymus and mesenteric lymph nodes, an issue that needs to be clarified in further studies.

To assess the effect of hT5Cyp in vivo, mice were infected with HIV-1 after adoptive transfer of transduced $CD4^+$ T cells. When mice received hT5Cyp-transduced $CD4^+$ T cells, two weeks after HIV-1 infection the $CD4^+$ cells constituted 6% (+/−2.87%) of mean nucleated peripheral blood cells (FIG. 31A). This was 34-fold higher than the percentage of $CD4^+$ cells (mean 0.18%+/−0.04%) observed in mice transplanted with hT5CypH126Q-transduced $CD4^+$ T cells, a difference that was statistically significant (p=0.0002, n=10 hT5Cyp, n=8 hT5CypH126Q; FIG. 31A). A nine-fold reduction in mean plasma viral load was observed when mice engrafted with hT5Cyp-expressing $CD4^+$ cells were compared to mice engrafted with hT5CypH126Q-expressing $CD4^+$ T cells (p=0.005; n=8 hT5Cyp, n=8 hT5CypH126Q) (FIG. 31B). These results indicate that hT5Cyp inhibits HIV-1 replication and protects against HIV-1-associated destruction of $CD4^+$ T cells in vivo.

Further evidence for the in vivo effects of hT5Cyp was sought by examining lymphoid organs of mice infected with HIV-1. Three weeks post-transplant, single-cell suspensions were analyzed for the human T cell marker CD3, the hT5Cyp vector reporter GFP, and HIV-1 p24 antigen. Few if any hT5Cyp-transduced human T cells isolated from thymus or lymph node of HIV-1-infected mice were $p24^+$, as compared with 1.5-6.5% of the cells transduced with hT5CypH126Q (FIG. 31C). Consistent with fewer productively infected T cells, down-regulation of cell-surface CD4 was not observed with hT5Cyp-bearing cells (37), either in thymus or mesenteric lymph node of mice infected with CXCR4-tropic or CCR5-tropic HIV-1 (FIG. 31D).

Figure 38:
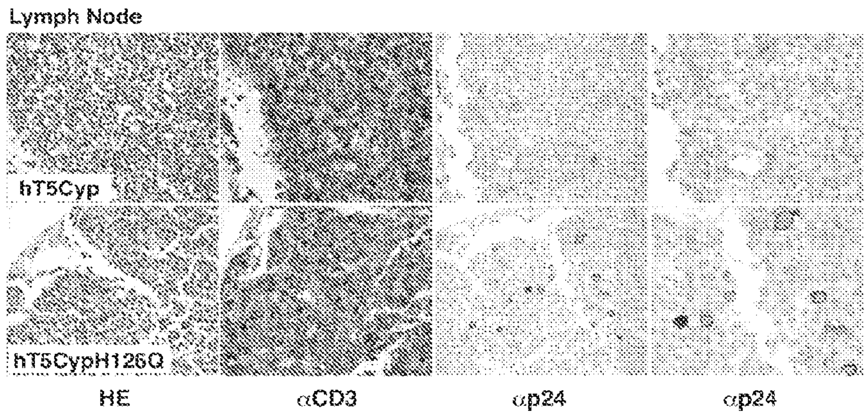
FIG. 38. hT5Cyp protects T cells from HIV-1 infection in vivo. 6-10 week old $Rag2^{-/-}\gamma_c^{-/-}$ mice were engrafted with GFP-sorted scAPLS-transduced $CD4^+$ T cells expressing either hT5Cyp or hT5CypH126Q. Mice were infected with HIV-1NL4-3 two weeks after transplant. Representative CD3- and p24-stained paraffin-embedded tissue sections of mesenteric lymph nodes are shown. While engraftment of $CD3^+$ human T cells is similar in lymph nodes of mice transplanted with either hT5Cyp– (top panel) or hT5CypH126Q-expressing (bottom panel) T cells, rare and weaker p24 staining is observed in lymph nodes from mice transplanted with hT5Cyp-CD4$^+$ T cells (top panel) as compared to those transplanted with hT5CypH126Q-CD4$^+$ T cells (bottom panel).

Tissue sections of thymus and mesenteric lymph node were directly examined for human $CD3^+$ T cells and HIV-1 p24 antigen. The engraftment of the $CD4^+$ T cells transduced with hT5Cyp and hT5CypH126Q was similar (FIG. 31E, α-CD3). Following HIV-1 infection, intense p24 staining was observed in thymic tissue sections from animals engrafted with hT5CypH126Q-transduced $CD4^+$ T cells but not in tissues from mice engrafted with $CD4^+$ T cells transduced with hT5Cyp (FIG. 31E, α-p24). Similar results were obtained for tissue sections from mesenteric lymph nodes (FIG. 38). These experiments show that hT5Cyp significantly reduced or prevented productive HIV-1 infection in vivo. Given these findings, we speculate that most of the human T cells in the thymus and lymph node were indeed transduced, although levels of GFP expression were lower compared to blood, bone marrow, and spleen CD4+ cells.

In the second in vivo approach to study the effects of hT5Cyp on HIV-1 replication, $CD34^+$ hematopoietic progenitor cells transduced with vectors bearing hT5Cyp or hT5CypH126Q were transplanted into pre-conditioned neonatal $Rag2^{-/-}\gamma_c^{-/-}$ mice (38) leading to B and T cell reconstitution in peripheral blood at 8 weeks post-transplant. The percentage of $GFP^+$ cells among the $CD45^+$ lymphocytes and CD $19^+$ B cells that developed in the mice was similar to the percent $GFP^+$ cells among the input $CD34^+$ cells, but development of $GFP^+$ $CD4^+$ T cells was rarely observed (FIG. 39A). Nonetheless, mice with $hCD45^+$ cells in peripheral blood were challenged with HIV-1. 25 days post-infection, mean viremia was reduced >4-fold in mice reconstituted with $CD34^+$ cells bearing hT5Cyp compared to the hT5CypH126Q control (FIG. 39B; n=4 hT5Cyp, n=3 hT5CypH126Q). Moreover, while peripheral blood engraftment of $hCD45^+$ remained unchanged or declined over the 25 days of HIV-1 infection, $GFP^+CD45^+$ cells selectively expanded in the context of hT5Cyp but not of hT5CypH126Q (FIG. 39C).

Discussion:

Anti-HIV-1 gene therapies have generally modified host-cell factors required for viral replication or inhibited essential viral elements (4). Here, a third approach was adopted: the exploitation of natural inhibitors that evolved over millions of years in primates in response to retroviral attack (14-16, 33). The potent block to HIV-1 observed with AoT5Cyp inspired the design of a human equivalent, hT5Cyp, that robustly blocks HIV-1 in vitro and in vivo. As it turns out, a distinct T5Cyp fusion gene was generated by an independent retrotransposition event in Old World macaques. In this case, restriction activity was detected against HIV-2 and FIV, but not against HIV-1 (39-43). The convergent evolution of T5Cyp fusion proteins with distinct retroviral specificities indicates a strong selection for these potent restriction factors. While the specific force behind selection remains to be elucidated for individual T5 orthologues, in each case the selective pressure is likely to have been a retrovirus (15).

Since T5α and T5Cyp are modular proteins, it was expected that the engineering of a restrictive hT5Cyp would not be difficult. Surprisingly, only three of 13 hT5Cyp fusions inhibited HIV-1 comparably to AoT5Cyp. No correlation was observed between protein levels and antiviral activity, and CA-binding activity was not sufficient to restrict HIV-1 (FIGS. 25A and B). Anti-HIV-1 activity was observed when hCypA was fused at the apex of the hT5α PRYSPRY domain in the structural model (FIG. 25C). Analysis of nonsynonymous mutations indicates that this region undergoes some of the strongest selective pressure in the primate lineage and functional experiments pinpoint it as a specificity determinant for CA recognition (15, 16, 44). CypA fusion to this site may have antiviral activity because this apical loop is uniquely situated for coordinating CA recognition and effector domains of T5. Correlation between restriction activity and the ability of hT5Cyp fusion proteins to form cytoplasmic bodies suggests that activity requires particular spatial constraints or association with unknown cofactors. The strict structural requirements for engineering a functional hT5Cyp emphasize the remarkable nature of the fusion gene that was generated by retrotransposition in New World owl monkeys (7).

Figure 28:
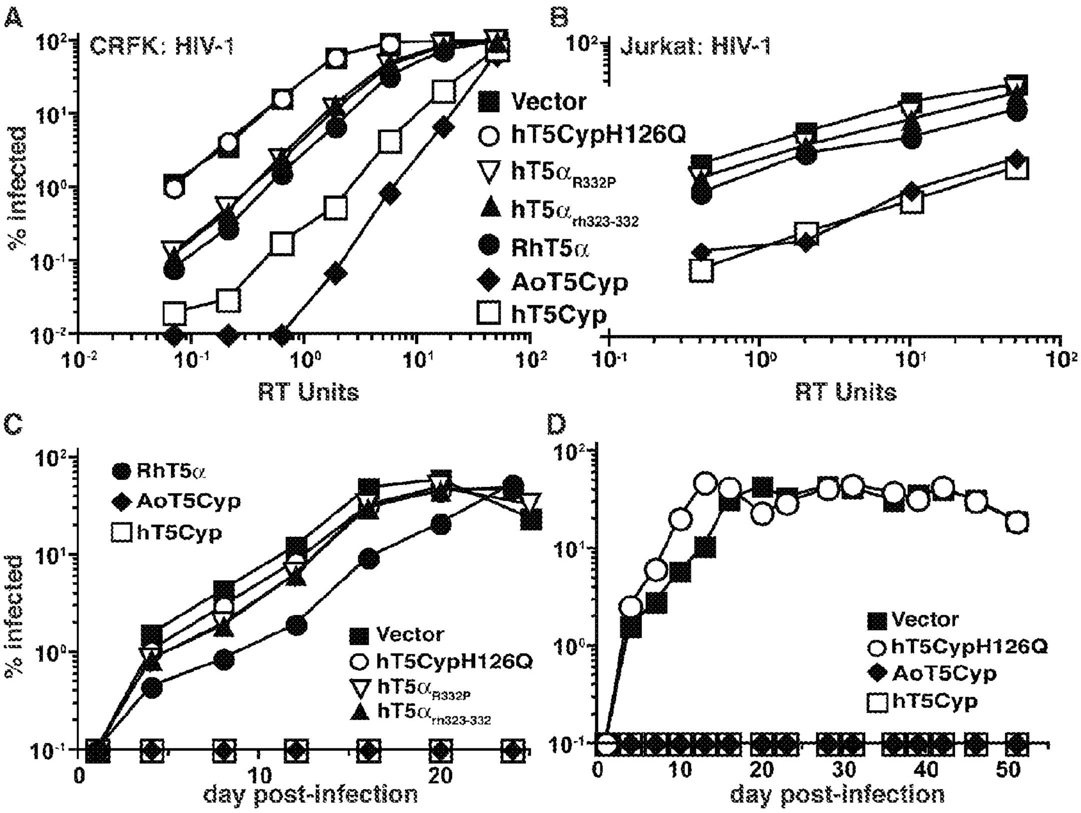
FIG. 28A-D. The anti-HIV-1 activity of hTSCyp is superior to that of rhT5α. CRFK (A) and Jurkat T cells (B) were transduced with lentiviral vectors encoding the indicated T5 proteins and a puromycin-resistance cassette. Pools of puromycin-resistant cells were infected with increasing amounts of a single-cycle HIV-1-GFP vector (left to right on X-axis). The percentage of $GFP^+$ positive cells (Y-axis) was determined 48 hrs later. (C and D) As in (A) and (B), Jurkat T cells were transduced with the indicated vectors and challenged with HIV-$1_{NL4-3-GFP-IRES-Nef}$. The percentage of infected cells was determined by flow cytometry.

Optimal gene therapy candidates should provide high efficacy and low antigenicity. Hematopoietic progenitors transduced with rhesus macaque T5α or human-rhesus T5α chimeras differentiate into HIV-1-resistant macrophages and T cells (34, 45). These proteins, however, are potentially antigenic, which could lead to the elimination of modified cells in vivo (22). Nonetheless, efforts have been taken to minimize potential sources of antigenicity. By substituting only critical amino acids within the hT5α PRYSPRY domain ($hT5\alpha_{R332P}$, $hT5\alpha_{rh332-332}$) one can reduce the risk of antigenicity, but this also decreases anti-HIV-1 efficacy (FIG. 28). hT5Cyp is the most potent HIV-1 inhibitor of the T5 proteins we compared, including rhT5α, in both single-cycle and spreading infections of human T cells with HIV-1 (FIG. 28). This difference in activity might be due to the apparently higher CA-affinity of the Cyp domain of hT5Cyp (46). In addition to its superior potency, hT5Cyp is composed of human components with no amino acids derived from non-human orthologues. Despite having a novel fusion junction, hT5Cyp is likely to have the lowest antigenic potential among these T5-based gene therapies.

Figure 27:
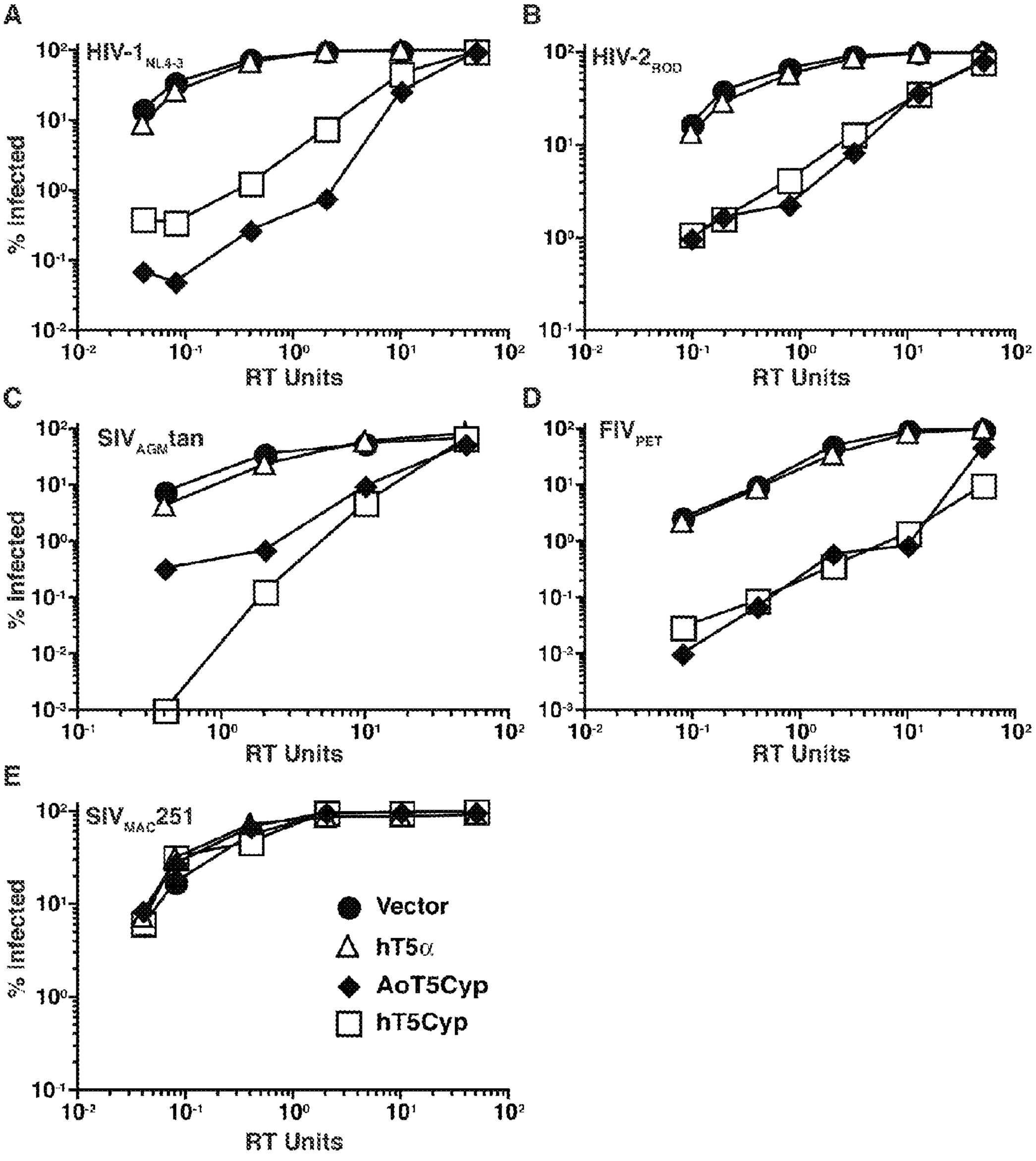
FIG. 27A-27E. T5Cyp potently restricts lentiviruses that encode Capsid with CypA-binding activity. CRFK cells stably expressing the indicated T5 proteins were transduced with increasing amounts (X-axis) of single-cycle GFP vectors derived from HIV-$1_{NL4-3}$ (A), HIV-$2_{ROD}$ (B), $SIV_{AGM}$tan (C), $FIV_{PET}$ (D), or $SIV_{MAC}$251 (E). The percentage of $GFP^+$ positive cells (Y-axis) was determined 48 hrs later.
Figure 29:
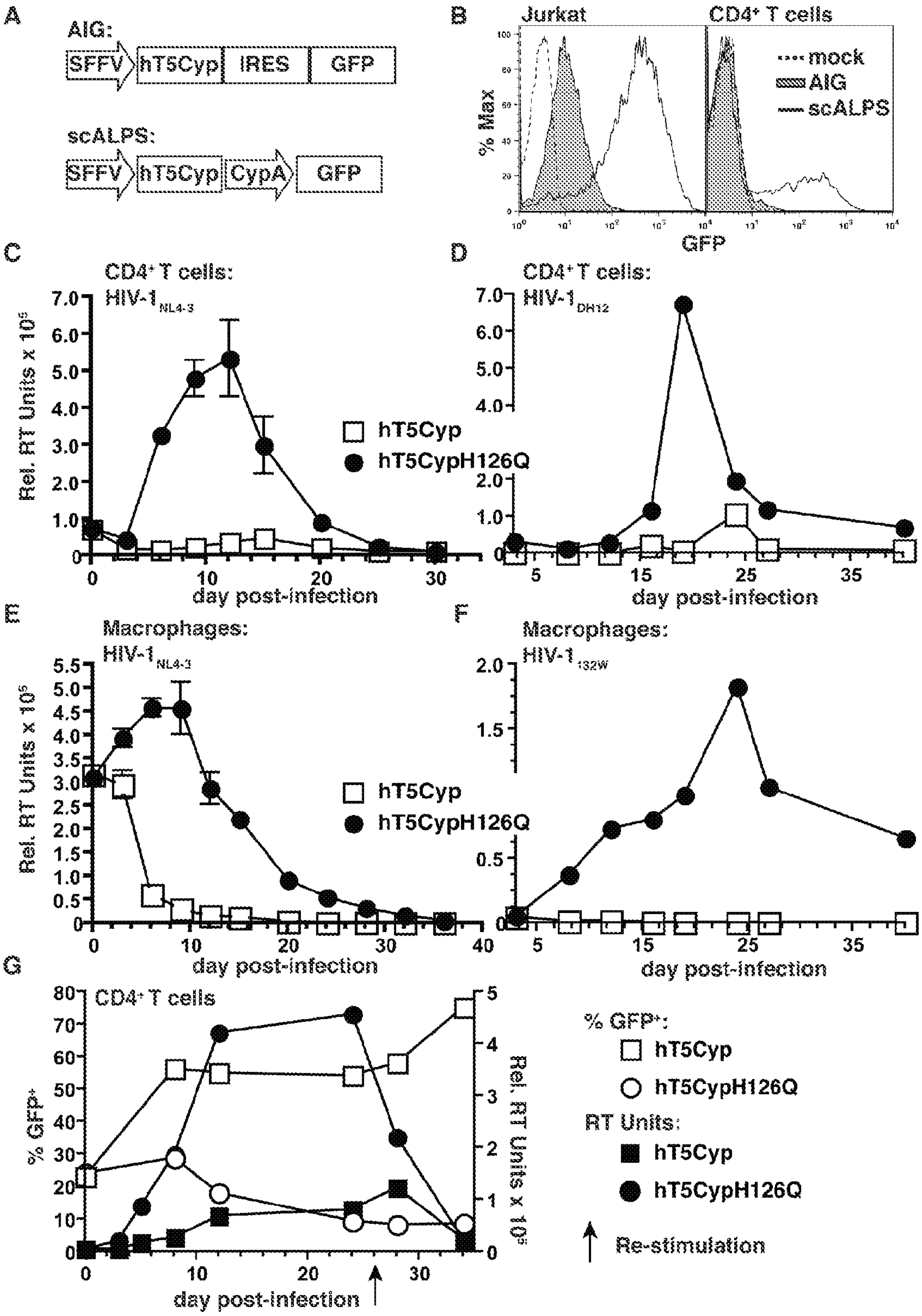
FIG. 29A-G. New lentiviral vectors bearing hTSCyp potently block replication-competent HIV-1 in primary cells. (A) Design of conventional bicistronic (AIG) and new dual-promoter (scALPS) lentiviral vectors. (B) 48 hrs after transduction with the indicated vectors, Jurkat T cells (left) or primary $hCD4^+$ T cells (right) were analyzed by flow cytometry for GFP. (C and D) Primary human $CD4^+$ T cells transduced with scALPS encoding the indicated hT5Cyp proteins were sorted for GFP and infected with lab clone HIV-$1_{NL4-3}$, (C) or primary isolate HIV-1DH12 (D) and RT activity in the supernatant was measured. Triplicate spreading infection for one representative donor of four is shown. (E and F) Human macrophages generated from GM-CSF-treated, $CD14^+$ monocytes were transduced with the indicated vectors, sorted for GFP, and challenged with modified HIV-$1_{NL4-3}$ bearing a CCR5-tropic Env (E) or primary isolate HIV-$1_{132W}$(F). Infection was monitored as in (C) and (D). Error bars in (C) and (E) represent +/− standard error of the mean, N=3. (G) hT5Cyp-bearing $CD4^+$ T cells exhibit a selective advantage after challenge with HIV-1. $CD4^+$ T cells were transduced with scALPS encoding the indicated T5Cyp proteins. Cultures containing 23% $GFP^+$ cells were challenged with 15 ng/$10^6$ cells HIV-$1_{NL4-3}$ and monitored for percentage $GFP^+$ cells (left Y-axis, open symbols). Supernatant RT activity was measured (right Y-axis, filled symbols). Cultures were re-stimulated using allogeneic-PBMC, IL-2, and PHA on day 26 post-infection (arrow).

HIV-1 rev, tat, and gag (4, 47, 51), as well as the HIV-1 co-receptor CCR5 (48-50), have been targeted by various means including siRNAs (4, 50, 51) and zinc-finger endonucleases (49). With either approach there are concerns regarding toxicity (51), off-target effects (48), and viral resistance (4, 51). Transdominant revM10 proteins, have been tested in patients without reducing viremia (47). Furthermore, revM10-resistant HIV-1 strains were observed in vitro (52). Similarly, for siRNA approaches, escape mutants arise readily, since single nucleotide changes are sufficient to escape the siRNA-mediated blocks to HIV-1 replication (51). CCR5 disruption, one of the most promising approaches to date, could select for CCR5-independent viruses (53) and is not without consequence, as the CCR5Δ32 allele is a risk factor for fatal West Nile Virus infection (54).

hT5Cyp is a broadly acting, anti-lentiviral agent that blocks CCR5- and CXCR4-tropic HIV-1 clones and primary isolates, as well as some HIV-2, SIV, and FIV clones (FIGS. 27 and 29). T5 isoforms form hetero-multimers and hT5Cyp might interfere with endogenous hT5α function (55). However, no significant decrease in hT5α-mediated restriction of N-MLV, and no alteration in cell surface markers or cytokine secretion, was observed in hT5Cyp-transduced cells (FIG. 35). Despite extensive efforts to identify hT5Cyp-resistant viruses none were detected, perhaps due to the potency of the antiviral activity and the fact that hT5Cyp blocks HIV-1 prior to reverse transcription, thus precluding the generation of the genetic diversity required for emergence of resistance. hT5Cyp additionally blocked a natural HIV-1 CA variant reported to be resistant to AoT5Cyp (28) (FIG. 26D). These results suggest that, if hT5Cyp were utilized as anti-HIV-1 gene therapy in people, viral resistance would not emerge readily and host cell function would remain intact.

Figure 31:
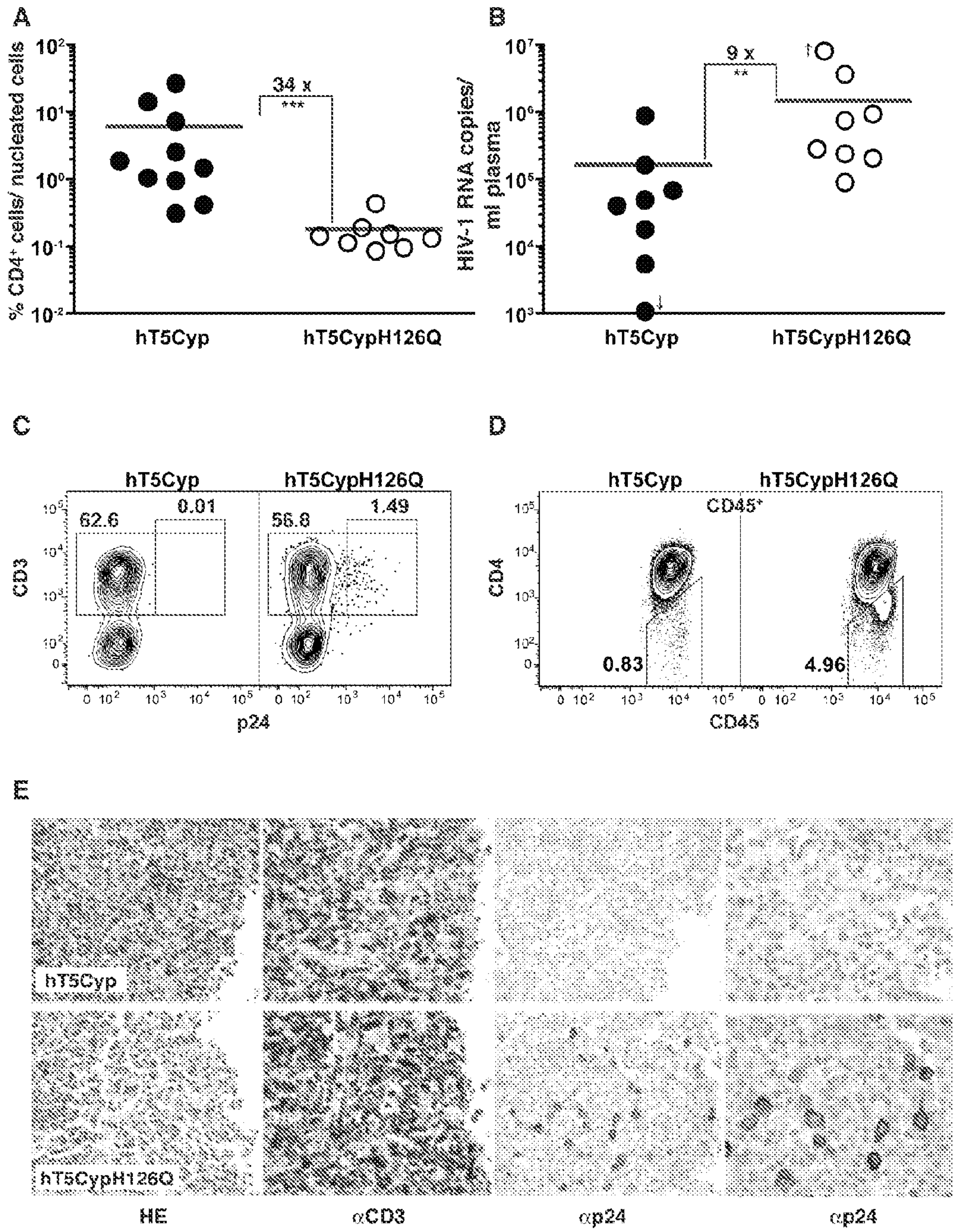
FIG. 31A-31E. hT5Cyp inhibits HIV-1 in a humanized mouse model. 6-10 week old $Rag2^{-/-}\gamma_c^{-/-}$ mice were engrafted with GFP-sorted scALPS-transduced $CD4^+$ T cells expressing either hT5Cyp or hT5CypH126Q. (A) 5 days after engraftment, mice were challenged with HIV-$1_{NL4-3}$. The percentage $hCD4^+$ T cells among all nucleated cells in the peripheral blood of individual mice is shown at 2 weeks post-infection. The fold-difference for the mean is indicated (red bar, *p=0.0002, Mann-Whitney test). (B-E) 2 weeks post-engraftment, mice were infected with HIV-$1_{NL4-3}$. (B) Plasma viral load for individual mice was determined 3 wks post-infection. The fold-difference in the mean is indicated (red bar, p=0.005, Mann-Whitney test). (C) 3 wks post-infection, single-cell suspensions from thymus were analyzed by flow cytometry for p24 and hCD3 cells (C) or hCD45 and hCD4 (D). The numbers indicate the percentage of cells within the indicated gates. (E) Paraffin-embedded sections of thymus are shown, stained with hematoxylin/eosin, anti-human-CD3 or anti-p24, as indicated. (C, D, E) Representative results from three sets of experiments are shown. (E) all panels are at 40× magnification, except the two right panels which are at 80×.

The evaluation of HIV-1 therapies is limited by a lack of adequate animal models for HIV-1 replication and pathogenesis. The $hCD4^+$-$Rag2^{-/-}\gamma_c^{-/-}$ mouse developed here is a straight-forward alternative to the HIV-1 mouse models used to date (56-59). It permitted high-level HIV-1 viremia and assessment of the effect of hT5Cyp transduction on HIV-1 infection and $CD4^+$ T cell protection (FIG. 31). Autotransfusion of ex vivo expanded $CD4^+$ T cells is of clinical benefit to HIV-1-infected people (60). Human $CD4^+$ T cells can be transduced at high efficiency and expanded to $>10^9$ cells ex vivo. Given that hT5Cyp-transduced CD4 cells can be expanded in vitro and in vivo (FIGS. 29 and 30), and that these cells exhibit a selective advantage during HIV-1 infection (FIGS. 29G and 31A), there might be an impressive effect of hT5Cyp-transduction on autologous CD4 T cell gene therapy in the clinical setting.

Figure 39:
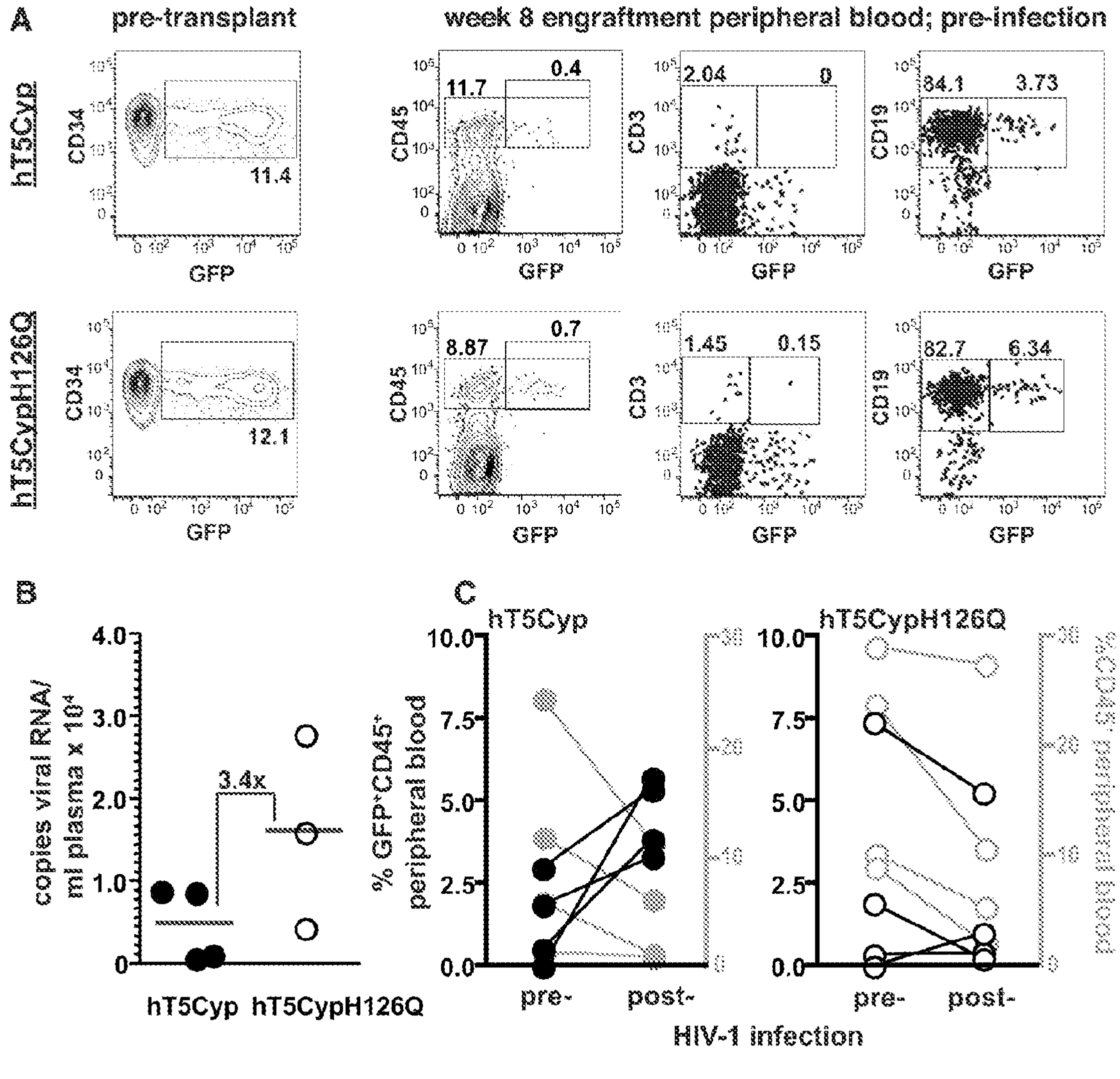
FIG. 39A-39C. hT5Cyp reduces viral load in HIV-1 infected huRag2−/−γc−/− mice. (A) huRag2$^{-/-}\gamma_c^{-/-}$ mice were generated using CD34$^+$ cells stably transduced with scAPLS-hT5Cyp or scAPLS-hT5CypH126Q.~12% of CD34$^+$ cells were GFP$^+$72 hours post-transduction in vitro (left panels). Human cell engraftment in peripheral blood and transgene expression in CD45$^+$ human lymphocytes, CD3$^+$ T cells, and CD19$^+$ B cells was analyzed by flow cytometry at eight weeks post transplant. (B) Viral load was determined in plasma of infected mice at 24 days post-infection. (C) GFP expression of CD45$^+$ cells is shown in peripheral blood pre-infection and 24 days post-infection of huRag2$^{-/-}\gamma_c^{-/-}$ with HIV-1. (left Y-axis, black symbols=% GFP$^+$ of CD45$^+$ cells; right Y-axis, grey symbols=% CD45$^+$ of nucleated cells).

$CD34^+$ hematopoietic stem cells transduced with the state-of-the-art lentiviral vectors described here and elsewhere (61) achieve long-term engraftment of $Rag2^{-/-}\gamma_c^{-/-}$ mice, but transgene expression in the mature $CD4^+$ T cells that develop within these animals has not been consistently detected. Nonetheless, hT5Cyp modestly reduced HIV-1 viremia in humanized $Rag2^{-/-}\gamma_c^{-/-}$ mice (FIG. 39). With improved transduction methods, it will be important to examine the effect of stem cell transduction with hT5Cyp on immune cell development and HIV-1 infection within one of the humanized mouse models currently under development aimed at enhancing de novo T cell development and in vivo immune function (62, 63).

Methods: Plasmids and Cloning.

Most HIV-1 plasmids and vectors have been described previously (64). pNL4-3 contains a complete infectious HIV-1 provirus. pNL4-3-R5 bears the V3 loop of the CCR5-tropic 92TH014-2 HIV-1 strain (65). To generate pNL4-3-GFP-IRES-Nef, enhanced green fluorescent protein (eGFP) and the ECMV (encephalomyocarditis virus) IRES (internal ribosome entry site) were inserted upstream of nef pNLΔenvGFP is pNL4-3 with an env-inactivating mutation and eGFP in place of nef. CSGW is an HIV-1 vector expressing eGFP under the control of the spleen focus forming virus (SFFV) promoter. pFUPI, engineered from pFUW (66), uses the ubiquitin promoter to drive expression of a puromycin resistance cassette followed by the ECMV IRES (FIG. 32A).

hT5Cyp variants were cloned by overlapping PCR using the oligonucleotides shown in Table 6. rhT5α, hT5$\alpha_{R332P}$ (16, 33) and hT5$\alpha_{rh323\text{-}332}$ (14, 15) were also obtained. All T5 constructs were cloned downstream of the IRES in FUPI. All PCR products were sequenced to eliminate unwanted mutations.

pAIG uses the SFFV promoter to drive expression of T5 followed by IRES-eGFP. In pscALPS, the SFFV promoter drives expression of T5 and the human CypA promoter drives expression of eGFP. For three-component vector production, HIV-1 gag and pol were expressed using either psPAX2, p8.9NΔSB, p8.9NΔSB-G89V, or p8.9NΔSB-V86P/H87Q/I91V/M96I. The V86P/H87Q/I91V/M96I mutation in CA (28) was obtained. SIV$_{mac}$251 vectors were produced using GAE1.0 and the packaging vector SIV3+ (67). SIV$_{AGM}$tan and HIV-2$_{ROD}$ vectors each have an env-deletion and eGFP in place of nef (9). FIV vectors were produced using the genomic vector pGINSIN and the packaging vector pFP93 (30). All lentiviral vectors were pseudotyped using the vesicular stomatitis virus glycoprotein (VSV-G). For biochemistry, hT5Cyps were cloned into the p3xFLAG-CMV-7.1 expression vector (Sigma) and HIV-1 CA was expressed as a GST-fusion using the EF1α promoter.

Cells.

293T human embryonic kidney cells and CRFK feline kidney cells were maintained in DMEM supplemented with 10% fetal bovine serum (FBS) and glutamax (Invitrogen). Jurkat E6-1, H9, CEM-SS, and SUP-T1 T cell leukemia/lymphoma cell lines, U937 promonocytic lymphoma, and THP-1 monocytic leukemia cells were grown in RPMI-1640 with 10% FBS and glutamax (Invitrogen). For creation of T5-expressing cell lines, suspension cells were transduced with $2\times10^5$ Jurkat infectious units/ml and adherent cells were transduced with $2\times10^4$ Jurkat infectious units/ml of FUPI containing the indicated T5. Jurkat infectious units were determined by serial dilutions of concomitantly-produced FUPI-GFP on Jurkat E6 cells. 48 hrs. post-transduction, cells were selected with puromycin. The different constructs were normalized to each other by comparing RT activity of the supernatants and assessing the puromycin-resistant colonies after serial dilution on HeLa cells. $CD4^+$ T cells were enriched from PBMCs (>99% $CD4^+$) using positive selection magnetic beads (Miltenyi Biotec) and stimulated for 24 hrs on multisorb 96-well plates (Nunc) coated with 2 μg/ml anti-CD3 and 2 μg/ml anti-CD28 antibodies (BD Biosciences) in RPMI with 10% FBS, glutamax (Invitrogen) and 20 IU/ml hIL-2. When indicated and in preparation for adoptive transfer to mice, $CD4^+$ T cells were stimulated using allogeneic-PBMCs irradiated at 50 Gy in the presence of 20 IU/ml IL-2 and phytohemagglutinin (PHA) at 1 μg/ml. Cells were washed and replated 24 hrs prior to viral transduction. $CD14^+$ monocytes were enriched from PBMCs (>99% $CD14^+$) using positive selection magnetic beads (Miltenyi Biotec). $CD14^+$ monocytes were resuspended in complete RPMI supplemented with 50 ng/ml recombinant human GM-CSF (Leukomax, Novartis) at $1\times10^6$ cells/ml. $2\times10^6$ were plated in each well of a 6-well plate (Nunc) and allowed to differentiate into macrophages for 10 days before transduction. Transduction of human macrophages was performed as follows: cells were pretreated for three hours with SIV VLPs (50% per volume, made with SIV3+ vector and pMD2.G at 7:1 ratio) prior to viral transduction. For both $CD4^+$ T cells and monocyte-derived macrophages, cells were sorted for GFP expression by FACS 72 hours post-transduction.

Drugs.

All chemicals were obtained from Sigma unless otherwise noted. Puromycin was used at 1 μM. Cyclosporine (CsA) (Bedford Laboratories) was diluted to 10 mM in dimethyl sulfoxide (DMSO) and then further to 2.5 μM in tissue culture media. Arsenic trioxide ($As_2O_3$) was made at 100 mM in 1N sodium hydroxide (NaOH) and then further diluted to 1 mM in phosphate buffered saline (PBS). pH was adjusted to 7.5 with hydrochloric acid and stored at 4° C.

Virus Production.

Vectors and viruses were produced by transfection of 293T cells using Lipofectamine 2000 (Invitrogen). Two-part vectors were produced by co-transfection of viral genome and VSV-G plasmids at a ratio of 7:1. Three-part vectors were produced by co-transfection of viral genome, gag-pol, and VSV-G plasmids at a ratio of 4:3:1. Infectious viruses were produced by transfection of 90% confluent 293T cells in a T75 flask (Nunc) with 40 μg of pNL4-3, pNL4-3-R5, or pNL4-3-GFP-IRES-Nef. Supernatants containing viruses and vectors were cleared by 400×g centrifugation, filtered (0.45 μm; Pall Acrodisc), tested for exogenous RT activity (7) titered on Jurkat E6 cells in single cycle assay (7) and stored at −80° C. When indicated, the content of viral p24 antigen was quantified by an HIV-1 p24 enzyme-linked immunoabsorbent assay kit (NIH AIDS Research and Reference Reagent Program, Germantown, Md.).

Infections.

$2\times10^4$ adherent cells/well or $8\times10^4$ suspension cells/well were plated in 48-well plates (Nunc) for challenge with single-cycle GFP reporter vectors that were titered as indicated. GFP synthesis was assessed by flow cytometry 48 hrs post-infection. For spreading infection, $10^6$ Jurkat cells were infected with 1 to 15 ng p24/$10^6$ cells of HIV-$1_{NL4\text{-}3\text{-}GFP\text{-}IRES\text{-}Nef}$. Cells were split every 3 days, fixed in 0.5% paraformaldehyde/PBS, and assayed for GFP synthesis by flow cytometry. $10^6$ primary $CD4^+$ T cells or macrophages were infected with 15 ng p24/$10^6$ cells of CXCR4 or CCR5-tropic HIV-$1_{NL4\text{-}3}$ stocks, or with low passage, primary isolates HIV-$1_{DH12}$ and HIV-$1_{132W}$, (Olivier Schwartz, Pasteur Institute, Paris). Infection was monitored by assessing the accumulation of RT activity in the supernatant (7). FACSCalibur, Cellquest Pro (Becton Dickinson), and FlowJo software (Treestar, Inc.) were used to record and analyze fluorescence. 1-$5\times10^5$ events were acquired for analysis.

Western Blotting and Immunoprecipitation.

To detect hT5Cyp, $5\times10^6$ 293T cells were transfected with 20 μg of each 3×FLAG-hT5Cyp plasmid using Lipofectamine 2000 (Invitrogen). Cells were lysed at 48 hrs in Triton lysis buffer (50 mM Tris-HCL pH 7.4, 150 mM NaCL, 1% Triton X-100, with Complete Mini protease inhibitor cocktail (Roche)), cleared at 15,000×g for 5 minutes, incubated 4 hours at 4° C. with 2 μg/ml anti-FLAG M2 monoclonal antibody (Sigma), and then incubated 1 hour at 4° C. with 20 μl of protein G-sepharose beads (GE-Amersham). The beads were washed 3 times with 1 mL Triton Lysis Buffer, and 20 μl immunoprecipitate was subjected to SDS- PAGE on a 12% gel, transferred to a PVDF membrane, and immunoblotted with rabbit polyclonal antibody to CypA (Biomol).

For co-immunoprecipitation of hT5Cyp with HIV-1 CA, $5\times10^6$ 293T cells were co-transfected as above with 20 μg p3xFLAG hT5Cyp and 20 μg of pEF1-GST-CA. At 48 hrs cells were lysed with RIPA Buffer (50 mM Tris-HCl pH 8.0, 150 mM NaCl, 1% IGEPAL CA-630, 0.1% SDS, 0.5% sodium deoxycholate, with Complete Mini protease inhibitor cocktail (Roche)) and accelerated at 15,000×g for 5 min. Lysate was divided into two equal parts and incubated on ice for 30 minutes with 20 μM CsA/DMSO or an equivalent volume of DMSO for 30 minutes. Lysates were incubated with 30 μl glutathione-sepharose beads (GE-Amersham) for 1 hour at 4° C. Beads were washed three times with RIPA buffer. Proteins were subjected to SDS-PAGE and immunoblotting with rabbit polyclonal anti-CypA antibody (Biomol) and goat polyclonal anti-HIV-1 CA (NCI).

Structural Model of the hT5α PRYSPRY Domain.

StruPro was used to superimpose and align the crystal structures for PRYSPRY-19q13.4.1 (Protein Data Bank (PDB) entry 2FBE; residue range 11 to 184 of chain A), GUSTAVUS (PDB entry 2FNJ; residue range 35 to 83 and 88 to 233 of chain A), and TRIM21 (PDB entry 21WG; residue range 2 to 182 of chain B), using an alpha carbon cutoff distance of 3.5 Å. ClustalX was used to combine the hT5α sequence with the structural alignments. A ClustalW sequence-based multiple alignment of 10 characteristic psi-BLAST hits of all three aforementioned sequences was used to localize insertions. A secondary structure prediction of hT5α obtained with NPS@ was used to manually correct the model. The final alignment was then fed into the model and loop optimization procedures of Modeller 8v2 (http://salilab.org/modeller), using 2FBE, 2FNJ, and 21WG as templates. 100 models were built and evaluated for stereochemical quality with PROCHECK. Pictures of the single best model were generated with PyMol v0.98.

Immunofluorescence Microscopy.

CRFK cells stably expressing wild-type AoT5Cyp or hT5Cyp fusion proteins were grown on glass coverslips. Cells were fixed at 25° C. for 10 min with 3.7% formaldehyde in PBS and permeabilized on ice for 2 min with 2% Triton-X100 in 0.1% sodium citrate. After quenching with 0.1 M glycine in PBS at 25° C. for 10 min, cells were blocked for 30 min at 25° C. with 10% fetal bovine serum and 0.1% Tween-20 in PBS, before overnight incubation with goat polyclonal anti-TRIM5 (AbCam) and mouse monoclonal anti-tubulin (SIGMA) antibodies. After extensive washing in PBS, cells were sequentially incubated with donkey-Alexa Fluor 488-anti-goat and goat-Alexa Fluor 594 anti-mouse secondary antibodies (Invitrogen) for 1 hr at 25° C. in the dark. Finally coverslips were mounted in Vectashield with DAPI (Vector laboratories). Cells were visualized with a 63×1.4 NA Leica HCX Planapochromat oil immersion objective using an inverted Leica DMI 6000 CS microscope fitted with a TCS SP5 laser scanning confocal microscope system. Images from individual 3-dimensional stacks were subjected to noise reduction using the Leica LCS software (Leica Microsystems) and subjected to maximum intensity projection using the MetaMorph software (Universal Imaging Corp).

Mice.

$Rag2^{-/-}\gamma_c^{-/-}$ mice on a BALB/c background (provided by M. Ito; Central Institute for Experimental Animals, Kawasaki, Japan) were bred and maintained under specific pathogen-free conditions in accordance with the guidelines of the animal facility at the Institute for Research in Biomedicine (Bellinzona) and the Swiss Federal Veterinary Office (Bern). Mouse experiments were reviewed and approved by the Veterinary Commission of the State of Ticino (Bellinzona, Switzerland). CL2 MBP (clodronate) was from Roche Diagnostics (Mannheim, Germany). Preparation of liposomes containing CL2 MBP was done as described previously (68). 6-10 week-old mice received 100 ul of clodronate liposomes intraperitoneally (i.p.) 24 hours prior to irradiation using a single sublethal dose of 4.0 Gray (Gy) from a Cesium 137 source (Biobeam 8000, STS GmbH, Braunschweig, Germany) at 3.75 Gy/min. 4 hrs post-irradiation, mice were transplanted with $2.5\times10^5$ $hCD4^+$ T cells expressing hT5Cyp or control hT5CypH126Q in 100 μl PBS i.p. Mice were infected with $HIV\text{-}1_{NL4\text{-}3}$, as previously described (58), either 5 or 14 days post-transplant and analyzed 2, 3, or 4 weeks post-infection. $CD4^+$ T cell engraftment and maintenance in mice was measured by flow cytometry. To obtain peripheral blood cells and plasma, mice were bled from the retro-orbital venous sinus under anesthesia and red blood cells were lysed. When sacrificed, single cell suspensions from organs were prepared. For FACS analysis monoclonal antibodies against the following antigens were used: CD3 (UCHT1), CD4 (13B8.2), CD8 (B9.11), p24 (clone KC57) (all Immunotech/Beckman Coulter, Marseille, France), CD45 (HI30) (Caltag, Burlingame, Calif.). Intracellular staining for p24 was performed on single cell suspensions from mesenteric lymph nodes and thymus following staining with anti-CD3 antibody. Cells were washed, permeabilized, and fixed by treatment with BD Cytofix/Cytoperm (BD Pharmingen) and stained with anti-p24 antibody in BD Permwash solution (BD Pharmingen) following the manufacturer's instructions. Plasma HIV RNA concentrations were determined by Cobas Amplicor RT-PCR assay (Roche Diagnostics, Basel, Switzerland). Immunohistochemical stainings were performed as previously described (58). To assess nonspecific binding, tissue from untransplanted and uninfected transplanted mice was stained as controls.

Statistical Analysis.

Significant differences between groups were calculated using the Mann-Whitney U test. P-values<0.05 were considered significant.

References for Example 8

1. Fauci, A. S. 2008. 25 years of HIV. *Nature* 453:289-290.
2. Barouch, D. H. 2008. Challenges in the development of an HIV-1 vaccine. *Nature* 455:613-619.
3. Medzhitov, R., and Littman, D. 2008. HIV immunology needs a new direction. *Nature* 455:591.
4. Strayer, D. S., et al. 2005. Current status of gene therapy strategies to treat HIV/AIDS. *Mol Ther* 11:823-842.
5. Baltimore, D. 2008. Presidential address. A global perspective on science and technology. *Science* 322:544-551.
6. Stremlau, M., et al. 2004. The cytoplasmic body component TRIM5alpha restricts HIV-1 infection in Old World monkeys. *Nature* 427:848-853.
7. Sayah, D. M., Sokolskaja, E., Berthoux, L., and Luban, J. 2004. Cyclophilin A retrotransposition into TRIM5 explains owl monkey resistance to HIV-1. *Nature* 430:569-573.
8. Perez-Caballero, D., Hatziioannou, T., Zhang, F., Cowan, S., and Bieniasz, P. D. 2005.

Restriction of human immunodeficiency virus type 1 by TRIM-CypA occurs with rapid kinetics and independently of cytoplasmic bodies, ubiquitin, and proteasome activity. *J Virol* 79:15567-15572.

9. Diaz-Griffero, F., et al. 2006. Requirements for capsid-binding and an effector function in TRIMCyp-mediated restriction of HIV-1. *Virology* 351:404-419.
10. Sebastian, S., and Luban, J. 2005. TRIM5alpha selectively binds a restriction-sensitive retroviral capsid. *Retrovirology* 2:40.
11. Stremlau, M., et al. 2006. Specific recognition and accelerated uncoating of retroviral capsids by the TRIM5alpha restriction factor. *Proc Natl Acad Sci USA* 103:5514-5519.
12. Luban, J. 2007. Cyclophilin A, TRIM5, and resistance to human immunodeficiency virus type 1 infection. *J Virol* 81:1054-1061.
13. Perez-Caballero, D., Hatziioannou, T., Yang, A., Cowan, S., and Bieniasz, P. D. 2005. Human tripartite motif 5alpha domains responsible for retrovirus restriction activity and specificity. *J Virol* 79:8969-8978.
14. Stremlau, M., Perron, M., Welikala, S., and Sodroski, J. 2005. Species-specific variation in the B30.2(SPRY) domain of TRIM5alpha determines the potency of human immunodeficiency virus restriction. *J Virol* 79:3139-3145.
15. Sawyer, S. L., Wu, L. I., Emerman, M., and Malik, H. S. 2005. Positive selection of primate TRIM5 alpha identifies a critical species-specific retroviral restriction domain. *Proc Natl Acad Sci USA* 102:2832-2837.
16. Yap, M. W., Nisole, S., and Stoye, J. P. 2005. A single amino acid change in the SPRY domain of human Trim5alpha leads to HIV-1 restriction. *Curr Biol* 15:73-78.
17. Yap, M. W., Dodding, M. P., and Stoye, J. P. 2006. Trim-cyclophilin A fusion proteins can restrict human immunodeficiency virus type 1 infection at two distinct phases in the viral life cycle. *J Virol* 80:4061-4067.
18. Schaller, T., Ylinen, L. M., Webb, B. L., Singh, S., and Towers, G. J. 2007. Fusion of cyclophilin a to fv1 enables cyclosporine-sensitive restriction of human and feline immunodeficiency viruses. *J Virol* 81:10055-10063.
19. Nisole, S., Lynch, C., Stoye, J. P., and Yap, M. W. 2004. A Trim5-cyclophilin A fusion protein found in owl monkey kidney cells can restrict HIV-1. *Proc Natl Acad Sci USA* 101:13324-13328.
20. Luban, J., Bossolt, K. L., Franke, E. K., Kalpana, G. V., and Goff, S. P. 1993. Human immunodeficiency virus type 1 Gag protein binds to cyclophilins A and B. *Cell* 73:1067-1078.
21. Ribeiro, I. P., et al. 2005. Evolution of cyclophilin A and TRIMCyp retrotransposition in New World primates. *J Virol* 79:14998-15003.
22. Riddell, S. R., et al. 1996. T-cell mediated rejection of gene-modified HIV-specific cytotoxic T lymphocytes in HIV-infected patients. *Nat Med* 2:216-223.
23. Grutter, C., et al. 2006. Structure of the PRYSPRY-domain: implications for autoinflammatory diseases. *FEBS Lett* 580:99-106.
24. Woo, J. S., et al. 2006. Structural and functional insights into the B30.2/SPRY domain. *EMBO J* 25:1353-1363.
25. Ohkura, S., Yap, M. W., Sheldon, T., and Stoye, J. P. 2006. All three variable regions of the TRIM5alpha B30.2 domain can contribute to the specificity of retrovirus restriction. *J Virol* 80:8554-8565.
26. Sokolskaja, E., Berthoux, L., and Luban, J. 2006. Cyclophilin A and TRIM5alpha independently regulate human immunodeficiency virus type 1 infectivity in human cells. *J Virol* 80:2855-2862.
27. Braaten, D., Ansari, H., and Luban, J. 1997. The hydrophobic pocket of cyclophilin is the binding site for the human immunodeficiency virus type 1 Gag polyprotein. *J Virol* 71:2107-2113.
28. Chatterji, U., et al. 2005. Naturally occurring capsid substitutions render HIV-1 cyclophilin A independent in human cells and TRIM-cyclophilin-resistant in Owl monkey cells. *J Biol Chem* 280:40293-40300.
29. Sebastian, S., Sokolskaja, E., and Luban, J. 2006. Arsenic counteracts human immunodeficiency virus type 1 restriction by various TRIM5 orthologues in a cell type-dependent manner. *J Virol* 80:2051-2054.
30. Saenz, D. T., Teo, W., Olsen, J. C., and Poeschla, E. M. 2005. Restriction of feline immunodeficiency virus by Ref1, Lv1, and primate TRIM5 alpha proteins. *J Virol* 79:15175-15188.
31. Zhang, F., Hatziioannou, T., Perez-Caballero, D., Derse, D., and Bieniasz, P. D. 2006. Antiretroviral potential of human tripartite motif-5 and related proteins. *Virology* 353:396-409.
32. Lin, T. Y., and Emerman, M. 2006. Cyclophilin A interacts with diverse lentiviral capsids. *Retrovirology* 3:70.
33. Li, Y., Li, X., Stremlau, M., Lee, M., and Sodroski, J. 2006. Removal of arginine 332 allows human TRIM5alpha to bind human immunodeficiency virus capsids and to restrict infection. *J Virol* 80:6738-6744.
34. Anderson, J., and Akkina, R. 2008. Human immunodeficiency virus type 1 restriction by human-rhesus chimeric tripartite motif 5alpha (TRIM 5alpha) in CD34(+) cell-derived macrophages in vitro and in T cells in vivo in severe combined immunodeficient (SCID-hu) mice transplanted with human fetal tissue. *Hum Gene Ther* 19:217-228.
35. Mazurier, F., et al. 1999. A novel immunodeficient mouse model—RAG2 x common cytokine receptor gamma chain double mutants—requiring exogenous cytokine administration for human hematopoietic stem cell engraftment. *J Interferon Cytokine Res* 19:533-541.
36. van Rijn, R. S., et al. 2003. A new xenograft model for graft-versus-host disease by intravenous transfer of human peripheral blood mononuclear cells in RAG2−/− gammac−/− double-mutant mice. *Blood* 102:2522-2531.
37. Chen, B. K., Gandhi, R. T., and Baltimore, D. 1996. CD4 down-modulation during infection of human T cells with human immunodeficiency virus type 1 involves independent activities of vpu, env, and nef. *J Virol* 70:6044-6053.
38. Traggiai, E., et al. 2004. Development of a human adaptive immune system in cord blood cell-transplanted mice. *Science* 304:104-107.
39. Liao, C. H., Kuang, Y. Q., Liu, H. L., Zheng, Y. T., and Su, B. 2007. A novel fusion gene, TRIM5-Cyclophilin A in the pig-tailed macaque determines its susceptibility to HIV-1 infection. *Aids* 21 Suppl 8:S19-26.
40. Virgen, C. A., Kratovac, Z., Bieniasz, P. D., and Hatziioannou, T. 2008. Independent genesis of chimeric TRIM5-cyclophilin proteins in two primate species. *Proc Natl Acad Sci USA* 105:3563-3568.
41. Wilson, S. J., et al. 2008. Independent evolution of an antiviral TRIMCyp in rhesus macaques. *Proc Natl Acad Sci USA* 105:3557-3562.
42. Brennan, G., Kozyrev, Y., and Hu, S. L. 2008. TRIMCyp expression in Old World primates *Macaca nemestrina* and *Macaca fascicularis*. *Proc Natl Acad Sci USA* 105:3569-3574.
43. Newman, R. M., et al. 2008. Evolution of a TRIM5-CypA splice isoform in old world monkeys. *PLoS Pathog* 4:e1000003.
44. Song, B., et al. 2005. The B30.2(SPRY) domain of the retroviral restriction factor TRIM5 alpha exhibits lineage-specific length and sequence variation in primates. *J Virol* 79:6111-6121.

45. Anderson, J., and Akkina, R. 2005. TRIM5alpharh expression restricts HIV-1 infection in lentiviral vector-transduced CD34+-cell-derived macrophages. *Mol Ther* 12:687-696.

46. Li, X., and Sodroski, J. 2008. The TRIM5alpha B-box 2 domain promotes cooperative binding to the retroviral capsid by mediating higher-order self-association. *J Virol* 82:11495-11502.

47. Ranga, U., et al. 1998. Enhanced T cell engraftment after retroviral delivery of an antiviral gene in HIV-infected individuals. *Proc Natl Acad Sci USA* 95:1201-1206.

48. An, D. S., et al. 2007. Stable reduction of CCR5 by RNAi through hematopoietic stem cell transplant in non-human primates. *Proc Natl Acad Sci USA* 104:13110-13115.

49. Perez, E. E., et al. 2008. Establishment of HIV-1 resistance in CD4(+) T cells by genome editing using zinc-finger nucleases. *Nat Biotechnol* 26:808-816.

50. Kumar, P., et al. 2008. T cell-specific siRNA delivery suppresses HIV-1 infection in humanized mice. *Cell* 134: 577-586.

51. Boden, D., Pusch, O., and Ramratnam, B. 2007. Overcoming HIV-1 resistance to RNA interference. *Front Biosci* 12:3104-3116.

52. Hamm, T. E., Rekosh, D., and Hammarskjold, M. L. 1999. Selection and characterization of human immunodeficiency virus type 1 mutants that are resistant to inhibition by the transdominant negative RevM10 protein. *J Virol* 73:5741-5747.

53. Taylor, B. M., et al. 2008. An alteration of human immunodeficiency virus gp41 leads to reduced CCR5 dependence and CD4 independence. *J Virol* 82:5460-5471.

54. Glass, W. G., et al. 2006. CCR5 deficiency increases risk of symptomatic West Nile virus infection. *J Exp Med* 203: 35-40.

55. Berthoux, L., Sebastian, S., Sayah, D. M., and Luban, J. 2005. Disruption of human TRIM5alpha antiviral activity by nonhuman primate orthologues. *J Virol* 79:7883-7888.

56. Mosier, D. E., et al. 1991. Human immunodeficiency virus infection of human-PBL-SCID mice. *Science* 251: 791-794.

57. Namikawa, R., Kaneshima, H., Lieberman, M., Weissman, I. L., and McCune, J. M. 1988. Infection of the SCID-hu mouse by HIV-1. *Science* 242:1684-1686.

58. Baenziger, S., et al. 2006. Disseminated and sustained HIV infection in CD34+ cord blood cell-transplanted Rag2−/−gamma c−/− mice. *Proc Natl Acad Sci USA* 103: 15951-15956.

59. Nakata, H., et al. 2005. Potent anti-R5 human immunodeficiency virus type 1 effects of a CCR5 antagonist, AK602/ONO4128/GW873140, in a novel human peripheral blood mononuclear cell nonobese diabetic-SCID, interleukin-2 receptor gamma-chain-knocked-out AIDS mouse model. *J Virol* 79:2087-2096.

60. Levine, B. L., et al. 2002. Adoptive transfer of costimulated CD4+ T cells induces expansion of peripheral T cells and decreased CCR5 expression in HIV infection. *Nat Med* 8:47-53.

61. Amendola, M., Venneri, M. A., Biffi, A., Vigna, E., and Naldini, L. 2005. Coordinate dual-gene transgenesis by lentiviral vectors carrying synthetic bidirectional promoters. *Nat Biotechnol* 23:108-116.

62. Goldstein, H. 2008. Summary of presentations at the NIH/NIAID New Humanized Rodent Models 2007 Workshop. *AIDS Res Ther* 5:3.

63. Manz, M. G. 2007. Human-hemato-lymphoid-system mice: opportunities and challenges. *Immunity* 26:537-541.

64. Berthoux, L., Sebastian, S., Sokolskaja, E., and Luban, J. 2004. Lv1 inhibition of human immunodeficiency virus type 1 is counteracted by factors that stimulate synthesis or nuclear translocation of viral cDNA. *J Virol* 78:11739-11750.

65. Papkalla, A., Munch, J., Otto, C., and Kirchhoff, F. 2002. Nef enhances human immunodeficiency virus type 1 infectivity and replication independently of viral coreceptor tropism. *J Virol* 76:8455-8459.

66. Lois, C., Hong, E. J., Pease, S., Brown, E. J., and Baltimore, D. 2002. Germline transmission and tissue-specific expression of transgenes delivered by lentiviral vectors. *Science* 295:868-872.

67. Mangeot, P. E., et al. 2002. High levels of transduction of human dendritic cells with optimized SIV vectors. *Mol Ther* 5:283-290.

68. Van Rooijen, N., and Sanders, A. 1994. Liposome mediated depletion of macrophages: mechanism of action, preparation of liposomes and applications. *J Immunol Methods* 174:83-93.

Example 9

Methods Describing FIGS. 32-39

Proliferation of hT5Cyp-Expressing Primary Human CD4 T Cells.

Activated, scAPLS-transduced primary human $CD4^+$ T cells were maintained in culture for 6 days. $1\times10^5$ cells were transferred in triplicate into 96-well flat-bottom microplates (Falcon) and labelled for 18 h with 1 Ci of $^{[3H]}$thymidine (GE-Amersham). The DNA-incorporated radioactivity was measured by liquid scintillation counting. Data were expressed as mean corrected counts per minute (ccpm) of quadruplicate cultures.

Staining for Intracellular IL-2.

IL-2 producing capacity of hT5Cyp-expressing primary human T cells was assessed after stimulation for 6 h with 100 nM PMA and 1 μg/ml Ionomycin (Sigma-Aldrich). Brefeldin A (Sigma-Aldrich) was added at 10 μg/ml during the last 4 h of stimulation. Cells were washed, permeabilized, and fixed by treatment with BD Cytofix/Cytoperm and stained with anti-IL-2 antibody (5344.111) in BD Permwash solution following the manufacturer's instructions (all reagents BD/Pharmingen).

Staining for Cell Surface Markers.

The following antibodies were used for cell surface stains of primary $CD4^+$ T cells: α-CD4 (RPA-T4), α-CXCR4 (12G5), and α-MHC I (HLA A, B, C) (G46-2.6) (all from BD-Pharmingen).

Real-Time RT-PCR.

Total RNA was extracted from $5\times10^6$ $CD4^+$ T cells using the RNeasy Plus Mini kit (Qiagen). RNA was treated with RNase-free DNase I (Ambion) and reverse transcribed using the Superscript™ III First-Strand Synthesis System (Invitrogen). qPCR was performed with the Applied Biosystems 7900HT system, using Taqman Gene Expression or Power SYBR green PCR master mixes (Applied Biosystems). Each experimental condition was performed in triplicate and data analyzed using the SDS software, version 2.2.2 (Applied Biosystems). Following primers were used: for 18S RNA 5': CGGCTACCACATCCAAGGAA (SEQ ID NO:88), 18S RNA 3': GCTGGAATTACCGCGGCT (SEQ ID NO:89), GFP 5': CCCCGTGATGAAGAAGATGA (SEQ ID NO:90), GFP 3': GTCAGCTTGTGCTGGATGAA (SEQ ID NO:91), hT5Cyp 5': CTGGGTTGATGTGACAGTGG (SEQ ID NO:92), hT5Cyp 3': TCTGCTGTCTTTGGGACCTT (SEQ ID NO:93).

qPCR for HIV-1 DNA.

Total cellular DNA was extracted from $2\times10^6$ Jurkat T cells using the DNeasy Blood and Tissue kit (Qiagen). qPCR was performed with the Applied Biosystems 7900HT system, using 250 ng total DNA and Taqman Gene Expression master mix (Applied Biosystems). Each experimental condition was performed in triplicate and data analyzed using the SDS software, version 2.2.2 (Applied Biosystems).

Following primers were used:

```
Mitochondrial forward primer (MH533):
                                        (SEQ ID NO: 94)
ACCCACTCCCTCTTAGCCAATATT,

Mitochondrial reverse primer (MH534):
                                        (SEQ ID NO: 95)
GTAGGGCTAGGCCCACCG,

Mitochondrial probe (mito-probe):
                                        (SEQ ID NO: 96)
5'-(TET)-CTAGTCTTTGCCGCCTGCGAAGCA-(TAMRA)-3',

J1 RT forward:
                                        (SEQ ID NO: 97)
ACAAGCTAGTACCAGTTGAGCCAGATAAG,

J2 RT reverse:
                                        (SEQ ID NO: 98)
GCCGTGCGCGCTTCAGCAAGC,

RT probe (LRT-P):
                                        (SEQ ID NO: 99)
5'-(FAM)-CAGTGGCGCCCGAACAGGGA-(TAMRA)-3'.
```

huRag2$^{-/-}\gamma_c^{-/-}$ Mice.

huRag2$^{-/-}\gamma_c^{-/-}$ mice were generated as previously described[1]. Briefly, fresh human cord blood was obtained with parent written informed consent from healthy full-term newborns (Department of Gynecology and Obstetrics, Ospedale San Giovanni, Bellinzona). CD34$^+$ cells were enriched from fresh cord blood to >95% purity (with less than 0.1% CD3$^+$ T cells) and frozen until newborn mice were available for transplant. Traggiai, E., et al. Development of a human adaptive immune system in cord blood cell-transplanted mice. *Science* (New York, N. Y 304, 104-107 (2004). Prior to transplant, CD34$^+$ cells were thawed and resuspended in RPMI with serum replacement (StemCell Technologies). Transduction of human CD34$^+$ cells was performed as follows: cells were pretreated for three hours with SIV VLPs (50% per volume, made with SIV3+ vector and pMD2.G at 7:1 ratio) prior to viral transduction of three hours duration using concentrated scAPLS vectors coding for either hT5Cyp or hT5CypH126Q. Cells were then washed in PBS and injected into newborn, conditioned Rag2$^{-/-}\gamma_c^{-/-}$ mice as previously described. Traggiai, E., et al. Mice were infected with HIV-1 by intraperitoneal injection as previously described. Baenziger, S., et al. Disseminated and sustained HIV infection in CD34+ cord blood cell-transplanted Rag2–/–gamma c–/– mice. *Proceedings of the National Academy of Sciences of the United States of America* 103, 15951-15956 (2006).

Non-limiting examples of sequences of the invention are provided below. Certain sequences not provided herein are available in the public domain. There are methods known in the art to reverse translate and obtain a nucleic acid sequence based on a known polypeptide sequence, non-limiting example is provided by the ExPASy proteomics tools available from the Swiss Institute for Bioinformatics.

DNA Sequence of a portion of hTRIM5 encoding polypeptide ending with amino acids RWY:

```
                                                        (SEQ ID NO: 18)
ATGGCTTCTGGAATCCTGGTTAATGTAAAGGAGGAGGTGACCTGCCCCATCTGCCTGGAACT

CCTGACACAACCCCTGAGCCTGGACTGCGGCCACAGCTTCTGCCAAGCATGCCTCACTGCAA

ACCACAAGAAGTCCATGCTAGACAAAGGAGAGAGTAGCTGCCCTGTGTGCCGGATCAGTTAC

CAGCCTGAGAACATACGGCCTAATCGGCATGTAGCCAACTTAGTGGAGAAGCTCAGGGAGGT

CAAGTTGAGCCCAGAGGGGCAGAAAGTTGATCATTGTGCACGCCATGGAGAGAAACTTCTAC

TCTTCTGTCAGGAGGACGGGAAGGTCATTTGCTGGCTTTGTGAGCGGTCTCAGGAGCACCGT

GGTCACCACACGTTCCCCACAGAGGAGGTTGCCCAGGAGTACCAAGTGAAGCTCCAGGCAGC

TCTGGAGATGCTGAGGCAGAAGCAGCAGGAAGCTGAAGAGTTGGAAGCTGACATCAGAGAAG

AGAAAGCTTCCTGGAAGACTCAAATACAGTATGACAAAACCAACGTCTTGGCAGATTTTGAG

CAACTGAGAGACATCCTGGACTGGGAGGAGAGCAATGAGCTGCAAAACCTGGAGAAGGAGGA

GGAAGACATTCTGAAAAGCCTTACGAACTCTGAAACTGAGATGGTGCAGCAGACCCAGTCCC

TGAGAGAGCTCATCTCAGATCTGGAGCATCGGCTGCAGGGGTCAGTGATGGAGCTGCTTCAG

GGTGTGGATGGCGTCATAAAAAGGACGGAGAACGTGACCTTGAAGAAGCCAGAAACTTTTCC

AAAAAATCAAAGGAGAGTGTTTCGAGCTCCTGATCTGAAAGGAATGCTAGAAGTGTTTAGAG

AGCTGACAGATGTCCGACGCTACTGG.
```

Amino acid sequence of a portion of hTRIM5 ending with amino acids RWY:

(SEQ ID NO: 13)
```
  1 masgilvnvk eevtcpicle lltqplsldc ghsfcqaclt anhkksmldk gesscpvcri
 61 syqpenirpn rhvanlvekl revklspegq kvdhcarhge klllfcqedg kvicwlcers
121 qehrghhtfp teevaqeyqv klqaalemlr qkqqeaeele adireekasw ktqiqydktn
181 vladfeqlrd ildweesnel qnlekeeedi lksltnsete mvqqtqslre lisdlehrlq
241 gsvmellqgv dgvikrtenv tlkkpetfpk nqrrvfrapd lkgmlevfre ltdvrryw.
```

Linkers of fusion proteins:

Linker Xn, where X is any amino acid, n=12-33 (SEQ ID NO:14). Linker Xn, where X is any amino acid, n=12 (SEQ ID NO:24), n=24 (SEQ ID NO:25), n=33 (SEQ ID NO:26).

Linker SGGSGGSGGSGG. (SEQ ID NO: 20)

Linker V D V T V A P N N I S C A V I S E D K R Q V S S P K P Q I I Y G A. (SEQ ID NO: 21)

Linker V D V T V A P N N I S. (SEQ ID NO: 22)

Linker V D V T V A P N N I S C A V I S E D K R Q V S S. (SEQ ID NO: 23)

DNA Sequence of CypA encoding polypeptide from position 2 to the end (missing the starting Met):

(SEQ ID NO: 19)
```
GTCAACCCCACCGTGTTCTTCGACATTGCCGTCGACGGCGAGCCCTTGGGCCGCGTCTCCTT
TGAGCTGTTTGCGACAAGGTCCCAAAGACAGCAGAAAATTTTCGTGCTCTGAGCACTGGAGA
GAAAGGATTTGGTTATAAGGGTTCCTGCTTTCACAGAATTATTCCAGGGTTTATGTGTCAGG
GTGGTGACTTCACACGCCATAATGGCACTGGTGGCAAGTCCATCTATGGGGAGAAATTTGAA
GATGAGAACTTCATCCTAAAGCATACGGGTCCTGGCATCTTGTCCATGGCAAATGCTGGACC
CAACACAAATGGTTCCCAGTTTTTCATCTGCACTGCCAAGACTGAGTGGTTGGATGGCAAGC
ATGTGGTGTTTGGCAAAGTGAAAGAAGGCATGAATATTGTGGAGGCCATGGAGCGCTTTGGG
TCCAGGAATGGCAAGACCAGCAAGAAGATCACCATTGCTGACTGTGGACAACTCGAATAA.
```

Amino acid sequence of CypA from position 2 to the end (missing the starting Met):

(SEQ ID NO: 15)
```
    vnptvffdi avdgeplgrv sfelfadkvp ktaenfrals tgekgfgykg scfhriipgf
 61 mcqggdftrh ngtggksiyg ekfedenfil khtgpgilsm anagpntngs qffictakte
121 wldgkhvvfg kvkegmnive amerfgsrng ktskkitiad cgqle.
```

Fusion protein between hTRIM5 (aa position 1 to 298)-linker (SGG)4-hCypA (aa position 2 to 166):

(SEQ ID NO: 17)
```
M A S G I L V N V K E E V T C P I C L E L L T Q P L S L D C G H S F C Q A C L T A N
H K K S M L D K G E S S C P V C R I S Y Q P E N I R P N R H V A N I V E K L R E V K
L S P E G Q K V D H C A R H G E K L L L F C Q E D G K V I C W L C E R S Q E H R G
H H T F L T E E V A R E Y Q V K L Q A A L E M L R Q K Q Q E A E E L E A D I R E E
K A S W K T Q I Q Y D K T N V L A D F E Q L R D I L D W E E S N E L Q N L E K E E
```

-continued

E D I L K S L T N S E T E M V Q Q T Q S L R E L I S D L E H R L Q G S V M E L L Q G

V D G V I K R T E N V T L K K P E T F P K N Q R R V F R A P D L K G M L E V F R E

L T D V R R Y WSGGSGGSGGSGGV N P T V F F D I A V D G E P L G R V S F E L F A D

K V P K T A E N F R A L S T G E K G F G Y K G S C F H R I I P G F M C Q G G D F T R

H N G T G G K S I Y G E K F E D E N F I L K H T G P G I L S M A N A G P N T N G S Q

F F I C T A K T E W L D G K H V V F G K V K E G M N I V E A M E R F G S R N G K T

S K K I T I A D C G Q L E.

Additional amino acid sequences provided by the invention:

masgilvnvk eevtcpicle lltgplsldc ghsfcqaclt anhkksmldk gesscpvcri syqpenirpn rhvanlvekl revklspegq kvdhcarhge klllfcqedg kvicwlcers qehrghhtfp teevaqeyqv klqaalemlr qkqqeaeele adireekasw ktqiqydktn vladfeqlrd ildweesnel qnlekeeedi lksltnsete mvqqtqslre lisdlehrlq gsvmellqgv dgvikrtenv tlkkpetfpk nqrrvfrapd lkgmlevfre ltdvrryw[Xn]

vnptvffdiavdgeplgrv sfelfadkvp ktaenfrals tgekgfgykg scfhriipgf mcqggdftrh ngtggksiyg ekfedenfil khtgpgilsm anagpntngs qffictakte wldgkhvvfg kvkegmnive amerfgsrng ktskkitiad cgqle where X is any amino acid, n=12-33 (SEQ ID NO: 16); n=12 (SEQ ID NO: 27); n=24 (SEQ ID NO:28); n=33 (SEQ ID NO:29); n=11 (SEQ ID NO:30).

TABLE 6

| Cloning Primers | |
|---|---|
| Name | Primer Sequence |
| External Primers hT5Cyp | |
| hT5Cyp XbaI 5' | 5'- CCCTCTAGAGCCACCATGGCTTCTGGAATCCTGGTTA-3' (SEQ ID NO: 100) |
| hT5Cyp BamHl 3' | 5'- AAAAGGATCCTTATTCGAGTTGTCCACAGTC-3' (SEQ ID NO: 101) |
| Internal Primers hT5Ccyp | |
| M244F | 5'- CGGCTGCAGGGGTCAGTGATGGTCAACCCCACCGTGTTC-3' (SEQ ID NO: 102) |
| M244R | 5'- GAACACGGTGGGGTTGACCATCACTGACCCCTGCAGCCG-3' (SEQ ID NO: 103) |
| M284F | 5'- GCTCCTGATCTGAAAGGAATGGTCAACCCCACCGTGTTC-3' (SEQ ID NO: 104) |
| M284R | 5'- GAACACGGTGGGGTTGACCATTCCTTTCAGATCAGGAGC-3' (SEQ ID NO: 105) |
| W298F | 5'- GGTGGGGTTGACCCAGTAGCGTCGGACATCTGTC-3' (SEQ ID NO: 106) |
| W298R | 5'- CGACGCTACTGGGTCAACCCCACCGTGTTC-3' (SEQ ID NO: 107) |
| T302F | 5'- CGCTACTGGGTTGATGTGACAGTCAACCCCACCGTGTTC-3' (SEQ ID NO: 108) |
| T302R | 5'- GAACACGGTGGGGTTGACTGTCACATCAACCCAGTAGC-3' (SEQ ID NO: 109) |

TABLE 6-continued

| Name | Primer Sequence |
|---|---|
| **Cloning Primers** | |
| S309F | 5'- GTGGCTCCAAACAACATTTCAGTCAACCCCACCGTGTTC-3' (SEQ ID NO: 110) |
| S309R | 5'- GAACACGGTGGGGTTGACTGAAATGTTGTTTGGAGCCAC-3' (SEQ ID NO: 111) |
| S314F | 5'- TGGGTTGATGTGACAGTGGCTCCAAACAACATTTCATGTGC TGTCATTTCGTCAACCCCACCGTG-3' (SEQ ID NO: 112) |
| S314R | 5'-GTTGACAGAAATGACAGCACATGAAATGTTGTTTGGAGCC ACTGTCACATCAACCCAGTAGCGTCGGAC-3' (SEQ ID NO: 113) |
| S322F | 5'- CAAGTGAGCTCTGTCAACCCCACCGTGTTC-3' (SEQ ID NO: 114) |
| S322R | 5'- GGGGTTGACAGAGCTCACTTGTCTCTTATCTTCAG-3' (SEQ ID NO: 115) |
| A331F | 5'- CCACAGATAATATATGGGGCAGTCAACCCCACCGTGTTCTTC-3' (SEQ ID NO: 116) |
| A331R | 5'- CACGGTGGGGTTGACTGCCCCATATATTATCTGTGGTTTCG-3' (SEQ ID NO: 117) |
| G357F | 5'- GCTCTCAAAGTATCACATCAGGGGTCAACCCCACCGTGTTCTTC-3' (SEQ ID NO: 118) |
| G357R | 5'- GAAGAACACGGTGGGGTTGACCCCTGATGTGATACTTTGAGAGC-3' (SEQ ID NO: 119) |
| T369F | 5'- GAGGTAGACGTGTCCAAGAAAACTGTCAACCCCACCGTGTTCTTC-3' (SEQ ID NO: 120) |
| T369R | 5'- GAAGAACACGGTGGGGTTGACAGTTTTCTTGGACACGTCTACCTC-3' (SEQ ID NO: 121) |
| G398F | 5'- GAAAATTATCAACCTAAATACGGCGTCAACCCCACCGTGTTCTTC-3' (SEQ ID NO: 122) |
| G398R | 5'- GAAGAACACGGTGGGGTTGACGCCGTATTTAGGTTGATAATTTTC-3' (SEQ ID NO: 123) |
| **T5α cloning primers** | |
| RhT5α XbaI 5' | 5'-CCCTCTAGAGCCACCATGGCTTCTGGAATCCTGCTTA-3' (SEQ ID NO: 124) |
| RhT5α HpaI 3' | 5'-AAAAGTTAACTCAAGAGCTTGGTGAGCACA-3' (SEQ ID NO: 125) |
| hT5α XbaI 5' | 5'-CCCTCTAGAGCCACCATGGCTTCTGGAATCCTGGTTA-3' (SEQ ID NO: 126) |
| hhT5α HpaI 3' | 5'-AAAAGTTAACTCAAGAGCTTGGTGAGCACAGAGT-3' (SEQ ID NO: 127) |

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

REFERENCES

1. Strayer, D. S., et al. Current status of gene therapy strategies to treat HIV/AIDS. *Mol Ther* 11, 823-842 (2005).
2. Stremlau, M., et al. The cytoplasmic body component TRIM5alpha restricts HIV-1 infection in Old World monkeys. *Nature* 427, 848-853 (2004).
3. Sayah, D. M., Sokolskaja, E., Berthoux, L. & Luban, J. Cyclophilin A retrotransposition into TRIM5 explains owl monkey resistance to HIV-1. *Nature* 430, 569-573 (2004).
4. Perez-Caballero, D., Hatziioannou, T., Zhang, F., Cowan, S. & Bieniasz, P. D. Restriction of human immunodeficiency virus type 1 by TRIM-CypA occurs with rapid kinetics and independently of cytoplasmic bodies, ubiquitin, and proteasome activity. *Journal of Virology* 79, 15567-15572 (2005).
5. Diaz-Griffero, F., et al. Requirements for capsid-binding and an effector function in TRIMCyp-mediated restriction of HIV-1. *Virology* 351, 404-419 (2006).

6. Sebastian, S. & Luban, J. TRIM5alpha selectively binds a restriction-sensitive retroviral capsid. *Retrovirology* 2, 40 (2005).
7. Stremlau, M., et al. Specific recognition and accelerated uncoating of retroviral capsids by the TRIM5alpha restriction factor. *Proc Natl Acad Sci* 103, 5514-5519 (2006).
8. Luban, J. Cyclophilin A, TRIM5, and resistance to human immunodeficiency virus type 1 infection. *Journal of Virology* 81, 1054-1061 (2007).
9. Perez-Caballero, D., Hatziioannou, T., Yang, A., Cowan, S. & Bieniasz, P. D. Human tripartite motif 5alpha domains responsible for retrovirus restriction activity and specificity. *Journal of Virology* 79, 8969-8978 (2005).
10. Stremlau, M., Perron, M., Welikala, S. & Sodroski, J. Species-specific variation in the B30.2(SPRY) domain of TRIM5alpha determines the potency of human immunodeficiency virus restriction. *Journal of Virology* 79, 3139-3145 (2005).
11. Sawyer, S. L., Wu, L. I., Emerman, M. & Malik, H. S. Positive selection of primate TRIM5 alpha identifies a critical species-specific retroviral restriction domain. *Proc Natl Acad Sci* 102, 2832-2837 (2005).
12. Yap, M. W., Nisole, S. & Stoye, J. P. A single amino acid change in the SPRY domain of human Trim5alpha leads to HIV-1 restriction. *Curr Biol* 15, 73-78 (2005).
13. Nisole, S., Lynch, C., Stoye, J. P. & Yap, M. W. A Trim5-cyclophilin A fusion protein found in owl monkey kidney cells can restrict HIV-1. *Proc Natl Acad Sci* 101, 13324-13328 (2004).
14. Luban, J., Bossolt, K. L., Franke, E. K., Kalpana, G. V. & Goff, S. P. Human immunodeficiency virus type 1 Gag protein binds to cyclophilins A and B. *Cell* 73, 1067-1078 (1993).
15. Ribeiro, I. P., et al. Evolution of cyclophilin A and TRIMCyp retrotransposition in New World primates. *Journal of Virology* 79, 14998-15003 (2005).
16. Riddell, S. R., et al. T-cell mediated rejection of gene-modified HIV-specific cytotoxic T lymphocytes in HIV-infected patients. *Nature Medicine* 2, 216-223 (1996).
17. Ohkura, S., Yap, M. W., Sheldon, T. & Stoye, J. P. All three variable regions of the TRIM5alpha B30.2 domain can contribute to the specificity of retrovirus restriction. *Journal of Virology* 80, 8554-8565 (2006).
18. Grutter, C., et al. Structure of the PRYSPRY-domain: implications for autoinflammatory diseases. *FEBS Lett* 580, 99-106 (2006).
19. Woo, J. S., et al. Structural and functional insights into the B30.2/SPRY domain. *EMBO J* 25, 1353-1363 (2006).
20. Saenz, D. T., Teo, W., Olsen, J. C. & Poeschla, E. M. Restriction of feline immunodeficiency virus by Ref1, Lv1, and primate TRIM5 alpha proteins. *Journal of Virology* 79, 15175-15188 (2005).
21. Zhang, F., Hatziioannou, T., Perez-Caballero, D., Derse, D. & Bieniasz, P. D. Antiretroviral potential of human tripartite motif-5 and related proteins. *Virology* 353, 396-409 (2006).
22. Lin, T. Y. & Emerman, M. Cyclophilin A interacts with diverse lentiviral capsids. *Retrovirology* 3, 70 (2006).
23. Braaten, D., Ansari, H. & Luban, J. The hydrophobic pocket of cyclophilin is the binding site for the human immunodeficiency virus type 1 Gag polyprotein. *Journal of Virology* 71, 2107-2113 (1997).
24. Chatterji, U., et al. Naturally occurring capsid substitutions render HIV-1 cyclophilin A independent in human cells and TRIM-cyclophilin-resistant in Owl monkey cells. *J Biol Chem* 280, 40293-40300 (2005).
25. Sebastian, S., Sokolskaja, E. & Luban, J. Arsenic counteracts human immunodeficiency virus type 1 restriction by various TRIM5 orthologues in a cell type-dependent manner. *Journal of Virology* 80, 2051-2054 (2006).
26. Li, Y., Li, X., Stremlau, M., Lee, M. & Sodroski, J. Removal of arginine 332 allows human TRIM5 alpha to bind human immunodeficiency virus capsids and to restrict infection. *Journal of Virology* 80, 6738-6744 (2006).
27. Anderson, J. & Akkina, R. Human immunodeficiency virus type 1 restriction by human-rhesus chimeric tripartite motif 5alpha (TRIM 5alpha) in CD34(+) cell-derived macrophages in vitro and in T cells in vivo in severe combined immunodeficient (SCID-hu) mice transplanted with human fetal tissue. *Human Gene Therapy* 19, 217-228 (2008).
28. Mazurier, F., et al. A novel immunodeficient mouse model—RAG2 x common cytokine receptor gamma chain double mutants—requiring exogenous cytokine administration for human hematopoietic stem cell engraftment. *J Interferon Cytokine Res* 19, 533-541 (1999).
29. van Rijn, R. S., et al. A new xenograft model for graft-versus-host disease by intravenous transfer of human peripheral blood mononuclear cells in RAG2−/− gammac−/− double-mutant mice. *Blood* 102, 2522-2531 (2003).
30. Chen, B. K., Gandhi, R. T. & Baltimore, D. CD4 down-modulation during infection of human T cells with human immunodeficiency virus type 1 involves independent activities of vpu, env, and nef. *Journal of Virology* 70, 6044-6053 (1996).
31. Stoye, J. P. & Yap, M. W. Chance favors a prepared genome. *Proc Natl Acad Sci* 105, 3177-3178 (2008).
32. Song, B., et al. The B30.2(SPRY) domain of the retroviral restriction factor TRIM5alpha exhibits lineage-specific length and sequence variation in primates. *Journal of Virology* 79, 6111-6121 (2005).
33. Anderson, J. & Akkina, R. TRIM5alpharh expression restricts HIV-1 infection in lentiviral vector-transduced CD34+-cell-derived macrophages. *Mol Ther* 12, 687-696 (2005).
34. Boden, D., Pusch, O. & Ramratnam, B. Overcoming HIV-1 resistance to RNA interference. *Front Biosci* 12, 3104-3116 (2007).
35. An, D. S., et al. Stable reduction of CCR5 by RNAi through hematopoietic stem cell transplant in non-human primates. *Proc Natl Acad Sci* 104, 13110-13115 (2007).
36. Perez, E. E., et al. Establishment of HIV-1 resistance in CD4(+) T cells by genome editing using zinc-finger nucleases. *Nat Biotechnol* (2008).
37. Taylor, B. M., et al. An alteration of human immunodeficiency virus gp41 leads to reduced CCR5 dependence and CD4 independence. *Journal of Virology* 82, 5460-5471 (2008).
38. Glass, W. G., et al. CCR5 deficiency increases risk of symptomatic West Nile virus infection. *The Journal of Experimental Medicine* 203, 35-40 (2006).
39. Berthoux, L., Sebastian, S., Sayah, D. M. & Luban, J. Disruption of human TRIM5 alpha antiviral activity by nonhuman primate orthologues. Journal of Virology 79, 7883-7888 (2005).
40. Levine, B. L., et al. Adoptive transfer of costimulated CD4+ T cells induces expansion of peripheral T cells and decreased CCR5 expression in HIV infection. *Nature Medicine* 8, 47-53 (2002).
41. Amendola, M., Venneri, M. A., Biffi, A., Vigna, E. & Naldini, L. Coordinate dual-gene transgenesis by lentiviral vectors carrying synthetic bidirectional promoters. *Nat Biotechnol* 23, 108-116 (2005).

42. Goldstein, H. Summary of presentations at the NIH/NIAID New Humanized Rodent Models 2007 Workshop. *AIDS Research and Therapy* 5, 3 (2008).

43. Berthoux, L., Sebastian, S., Sokolskaja, E. & Luban, J. Lv1 inhibition of human immunodeficiency virus type 1 is counteracted by factors that stimulate synthesis or nuclear translocation of viral cDNA. *Journal of Virology* 78, 11739-11750 (2004).

44. Papkalla, A., Munch, J., Otto, C. & Kirchhoff, F. Nef enhances human immunodeficiency virus type 1 infectivity and replication independently of viral coreceptor tropism. *Journal of Virology* 76, 8455-8459 (2002).

45. Lois, C., Hong, E. J., Pease, S., Brown, E. J. & Baltimore, D. Germline transmission and tissue-specific expression of transgenes delivered by lentiviral vectors. *Science* 295, 868-872 (2002).

46. Mangeot, P. E., et al. High levels of transduction of human dendritic cells with optimized SIV vectors. *Mol Ther* 5, 283-290 (2002).

47. Van Rooijen, N. & Sanders, A. Liposome mediated depletion of macrophages: mechanism of action, preparation of liposomes and applications. *J Immunol Methods* 174, 83-93 (1994).

48. Baenziger, S., et al. Disseminated and sustained HIV infection in CD34+ cord blood cell-transplanted Rag2−/−gamma c−/− mice. *Proc Natl Acad Sci* 103, 15951-15956 (2006).

Ambrose, Z., KewalRamani, V. N., Bieniasz, P. D., and Hatziioannou, T. (2007). HIV/AIDS: in search of an animal model. Trends in biotechnology 25, 333-337.

Amendola, M., Venneri, M. A., Biffi, A., Vigna, E., and Naldini, L. (2005). Coordinate dual-gene transgenesis by lentiviral vectors carrying synthetic bidirectional promoters. Nature biotechnology 23, 108-116.

An, D. S., Donahue, R. E., Kamata, M., Poon, B., Metzger, M., Mao, S. H., Bonifacino, A., Krouse, A. E., Darlix, J. L., Baltimore, D., et al. (2007). Stable reduction of CCR5 by RNAi through hematopoietic stem cell transplant in nonhuman primates. Proc Natl Acad Sci USA 104, 13110-13115.

Anderson, J., and Akkina, R. (2005a). CXCR4 and CCR5 shRNA transgenic CD34+ cell derived macrophages are functionally normal and resist HIV-1 infection. Retrovirology 2, 53.

Anderson, J., and Akkina, R. (2005b). TRIM5alpharh expression restricts HIV-1 infection in lentiviral vector-transduced CD34+-cell-derived macrophages. Mol Ther 12, 687-696.

Anderson, J., and Akkina, R. (2008). Human immunodeficiency virus type 1 restriction by human-rhesus chimeric tripartite motif 5alpha (TRIM 5alpha) in CD34(+) cell-derived macrophages in vitro and in T cells in vivo in severe combined immunodeficient (SCID-hu) mice transplanted with human fetal tissue. Human gene therapy 19, 217-228.

Anderson, J., Li, M. J., Palmer, B., Remling, L., Li, S., Yam, P., Yee, J. K., Rossi, J., Zaia, J., and Akkina, R. (2007). Safety and efficacy of a lentiviral vector containing three anti-HIV genes—CCR5 ribozyme, tat-rev siRNA, and TAR decoy—in SCID-hu mouse-derived T cells. Mol Ther 15, 1182-1188.

Anderson, J. L., Campbell, E. M., Wu, X., Vandegraaff, N., Engelman, A., and Hope, T. J. (2006). Proteasome inhibition reveals that a functional preintegration complex intermediate can be generated during restriction by diverse TRIM5 proteins. J Virol 80, 9754-9760.

Anderson, P., Phillips, K., Stoecklin, G., and Kedersha, N. (2004). Post-transcriptional regulation of proinflammatory proteins. J Leukoc Biol 76, 42-47.

Arthos, J., Cicala, C., Martinelli, E., Macleod, K., Van Ryk, D., Wei, D., Xiao, Z., Veenstra, T. D., Conrad, T. P., Lempicki, R. A., et al. (2008). HIV-1 envelope protein binds to and signals through integrin alpha4beta7, the gut mucosal homing receptor for peripheral T cells. Nature immunology 9, 301-309.

Asaoka, K., Ikeda, K., Hishinuma, T., Horie-Inoue, K., Takeda, S., and Inoue, S. (2005). A retrovirus restriction factor TRIM5 alpha is transcriptionally regulated by interferons. Biochemical and biophysical research communications 338, 1950-1956.

Baenziger, S., Tussiwand, R., Schlaepfer, E., Mazzucchelli, L., Heikenwalder, M., Kurrer, M. O., Behnke, S., Frey, J., Oxenius, A., Joller, H., et al. (2006). Disseminated and sustained HIV infection in CD34+ cord blood cell-transplanted Rag2−/−gamma c−/− mice. Proc Natl Acad Sci USA 103, 15951-15956.

Baenziger, S., Ziegler, P., Mazzucchelli, L., Bronz, L., Speck, R. F., and Manz, M. G. (2008). Human T cell development and HIV infection in human hemato-lymphoid system mice. Current topics in microbiology and immunology 324, 125-131.

Barre-Sinoussi, F., Chemann, J. C., Rey, F., Nugeyre, M. T., Chamaret, S., Gruest, J., Dauguet, C., Axler-Blin, C., Vezinet-Brun, F., Rouzioux, C., et al. (1983). Isolation of a T-lymphotropic retrovirus from a patient at risk for acquired immune deficiency syndrome (AIDS). Science 220, 868-871.

Bartee, E., McCormack, A., and Fruh, K. (2006). Quantitative membrane proteomics reveals new cellular targets of viral immune modulators. PLoS pathogens 2, e107.

Bassin, R. H., Duran-Troise, G., Gerwin, B. I., and Rein, A. (1978). Abrogation of Fv-1b restriction with murine leukemia viruses inactivated by heat or by gamma irradiation. J Virol 26, 306-315.

Benit, L., De Parseval, N., Casella, J. F., Callebaut, I., Cordonnier, A., and Heidmann, T. (1997). Cloning of a new murine endogenous retrovirus, MuERV-L, with strong similarity to the human HERV-L element and with a gag coding sequence closely related to the Fv1 restriction gene. J Virol 71, 5652-5657.

Berges, B. K., Akkina, S. R., Folkvord, J. M., Connick, E., and Akkina, R. (2008). Mucosal transmission of R5 and X4 tropic HIV-1 via vaginal and rectal routes in humanized Rag2−/− gammac−/− (RAG-hu) mice. Virology 373, 342-351.

Berthoux, L., Sebastian, S., Sayah, D. M., and Luban, J. (2005a). Disruption of human TRIM5alpha antiviral activity by nonhuman primate orthologues. J Virol 79, 7883-7888.

Berthoux, L., Sebastian, S., Sokolskaja, E., and Luban, J. (2004). Lv 1 inhibition of human immunodeficiency virus type 1 is counteracted by factors that stimulate synthesis or nuclear translocation of viral cDNA. J Virol 78, 11739-11750.

Berthoux, L., Sebastian, S., Sokolskaja, E., and Luban, J. (2005b). Cyclophilin A is required for TRIM5 {alpha}-mediated resistance to HIV-1 in Old World monkey cells. Proc Natl Acad Sci USA 102, 14849-14853.

Berthoux, L., Towers, G. J., Gurer, C., Salomoni, P., Pandolfi, P. P., and Luban, J. (2003). As(2)O(3) enhances retroviral reverse transcription and counteracts Ref1 antiviral activity. J Virol 77, 3167-3180.

Besnier, C., Takeuchi, Y., and Towers, G. (2002). Restriction of lentivirus in monkeys. Proc Natl Acad Sci USA 99, 11920-11925.

Besnier, C., Ylinen, L., Strange, B., Lister, A., Takeuchi, Y., Goff, S. P., and Towers, G. J. (2003). Characterization of murine leukemia virus restriction in mammals. J Virol 77, 13403-13406.

Best, S., Le Tissier, P., Towers, G., and Stoye, J. P. (1996). Positional cloning of the mouse retrovirus restriction gene Fv1. Nature 382, 826-829.

Bishop, K. N., Bock, M., Towers, G., and Stoye, J. P. (2001). Identification of the regions of Fv1 necessary for murine leukemia virus restriction. J Virol 75, 5182-5188.

Blunt, T., Gell, D., Fox, M., Taccioli, G. E., Lehmann, A. R., Jackson, S. P., and Jeggo, P. A. (1996). Identification of a nonsense mutation in the carboxyl-terminal region of DNA-dependent protein kinase catalytic subunit in the scid mouse. Proc Natl Acad Sci USA 93, 10285-10290.

Boden, D., Pusch, O., Lee, F., Tucker, L., and Ramratnam, B. (2003). Human immunodeficiency virus type 1 escape from RNA interference. J Virol 77, 11531-11535.

Boden, D., Pusch, O., and Ramratnam, B. (2007). Overcoming HIV-1 resistance to RNA interference. Front Biosci 12, 3104-3116.

Bogerd, H. P., Doehle, B. P., Wiegand, H. L., and Cullen, B. R. (2004). A single amino acid difference in the host APOBEC3G protein controls the primate species specificity of HIV type 1 virion infectivity factor. Proc Natl Acad Sci USA 101, 3770-3774.

Boone, L. R., Innes, C. L., and Heitman, C. K. (1990). Abrogation of Fv-1 restriction by genome-deficient virions produced by a retrovirus packaging cell line. J Virol 64, 3376-3381.

Bosco, D. A., Eisenmesser, E. Z., Pochapsky, S., Sundquist, W. I., and Kern, D. (2002). Catalysis of cis/trans isomerization in native HIV-1 capsid by human cyclophilin A. Proc Natl Acad Sci USA 99, 5247-5252.

Bosma, G. C., Custer, R. P., and Bosma, M. J. (1983). A severe combined immunodeficiency mutation in the mouse. Nature 301, 527-530.

Bosma, G. C., Fried, M., Custer, R. P., Carroll, A., Gibson, D. M., and Bosma, M. J. (1988). Evidence of functional lymphocytes in some (leaky) scid mice. The Journal of experimental medicine 167, 1016-1033.

Braaten, D., Aberham, C., Franke, E. K., Yin, L., Phares, W., and Luban, J. (1996). Cyclosporine A-resistant human immunodeficiency virus type 1 mutants demonstrate that Gag encodes the functional target of cyclophilin A. J Virol 70, 5170-5176.

Braaten, D., Ansari, H., and Luban, J. (1997). The hydrophobic pocket of cyclophilin is the binding site for the human immunodeficiency virus type 1 Gag polyprotein. J Virol 71, 2107-2113.

Braaten, D., and Luban, J. (2001). Cyclophilin A regulates HIV-1 infectivity, as demonstrated by gene targeting in human T cells. The EMBO journal 20, 1300-1309.

Brass, A. L., Dykxhoorn, D. M., Benita, Y., Yan, N., Engelman, A., Xavier, R. J., Lieberman, J., and Elledge, S. J. (2008). Identification of host proteins required for HIV infection through a functional genomic screen. Science 319, 921-926.

Brenchley, J. M., Price, D. A., Schacker, T. W., Asher, T. E., Silvestri, G., Rao, S., Kazzaz, Z., Bornstein, E., Lambotte, O., Altmann, D., et al. (2006). Microbial translocation is a cause of systemic immune activation in chronic HIV infection. Nature medicine 12, 1365-1371.

Brennan, G., Kozyrev, Y., and Hu, S. L. (2008). TRIMCyp expression in Old World primates *Macaca nemestrina* and *Macaca fascicularis*. Proc Natl Acad Sci USA 105, 3569-3574.

Brown, C. R., Czapiga, M., Kabat, J., Dang, Q., Ourmanov, I., Nishimura, Y., Martin, M. A., and Hirsch, V. M. (2007). Unique pathology in simian immunodeficiency virus-infected rapid progressor macaques is consistent with a pathogenesis distinct from that of classical AIDS. J Virol 81, 5594-5606.

Bushman, F. D. (2007). Retroviral integration and human gene therapy. The Journal of clinical investigation 117, 2083-2086.

Campbell, E. M., Dodding, M. P., Yap, M. W., Wu, X., Gallois-Montbrun, S., Malim, M. H., Stoye, J. P., and Hope, T. J. (2007). TRIM5 alpha cytoplasmic bodies are highly dynamic structures. Mol Biol Cell 18, 2102-2111.

Campbell, E. M., Perez, O., Anderson, J. L., and Hope, T. J. (2008). Visualization of a proteasome-independent intermediate during restriction of HIV-1 by rhesus TRIM5alpha. The Journal of cell biology 180, 549-561.

Cavazzana-Calvo, M., Hacein-Bey, S., de Saint Basile, G., Gross, F., Yvon, E., Nusbaum, P., Selz, F., Hue, C., Certain, S., Casanova, J. L., et al. (2000). Gene therapy of human severe combined immunodeficiency (SCID)-X1 disease. Science 288, 669-672.

Chatterji, U., Bobardt, M. D., Gaskill, P., Sheeter, D., Fox, H., and Gallay, P. A. (2006). Trim5alpha accelerates degradation of cytosolic capsid associated with productive HIV-1 entry. The Journal of biological chemistry 281, 37025-37033.

Chatterji, U., Bobardt, M. D., Stanfield, R., Ptak, R. G., Pallansch, L. A., Ward, P. A., Jones, M. J., Stoddart, C. A., Scalfaro, P., Dumont, J. M., et al. (2005). Naturally occurring capsid substitutions render HIV-1 cyclophilin A independent in human cells and TRIM-cyclophilin-resistant in Owl monkey cells. The Journal of biological chemistry 280, 40293-40300.

Chen, B. K., Gandhi, R. T., and Baltimore, D. (1996). CD4 down-modulation during infection of human T cells with human immunodeficiency virus type 1 involves independent activities of vpu, env, and nef. J Virol 70, 6044-6053.

Chiu, Y. L., and Greene, W. C. (2008). The APOBEC3 cytidine deaminases: an innate defensive network opposing exogenous retroviruses and endogenous retroelements. Annual review of immunology 26, 317-353.

Chiu, Y. L., Soros, V. B., Kreisberg, J. F., Stopak, K., Yonemoto, W., and Greene, W. C. (2005). Cellular APOBEC3G restricts HIV-1 infection in resting CD4+ T cells. Nature 435, 108-114.

Chiu, Y. L., Witkowska, H. E., Hall, S. C., Santiago, M., Soros, V. B., Esnault, C., Heidmann, T., and Greene, W. C. (2006). High-molecular-mass APOBEC3G complexes restrict Alu retrotransposition. Proc Natl Acad Sci USA 103, 15588-15593.

Ciuffi, A., Diamond, T. L., Hwang, Y., Marshall, H. M., and Bushman, F. D. (2006). Modulating target site selection during human immunodeficiency virus DNA integration in vitro with an engineered tethering factor. Human gene therapy 17, 960-967.

Coles, M. C., Veiga-Fernandes, H., Foster, K. E., Norton, T., Pagakis, S. N., Seddon, B., and Kioussis, D. (2006). Role of T and NK cells and IL7/IL7r interactions during neonatal maturation of lymph nodes. Proc Natl Acad Sci USA 103, 13457-13462.

Colgan, J., Asmal, M., and Luban, J. (2000). Isolation, characterization and targeted disruption of mouse ppia: cyclophilin A is not essential for mammalian cell viability. Genomics 68, 167-178.

Colgan, J., Asmal, M., Neagu, M., Yu, B., Schneidkraut, J., Lee, Y., Sokolskaja, E., Andreotti, A., and Luban, J. (2004). Cyclophilin A regulates TCR signal strength in CD4+ T cells via a proline-directed conformational switch in Itk. Immunity 21, 189-201.

Colgan, J., Asmal, M., Yu, B., and Luban, J. (2004). Cyclophilin A-deficient Mice are Resistant to Immunosuppresion by Cyclosporine.

Cowan, S., Hatziioannou, T., Cunningham, T., Muesing, M. A., Gottlinger, H. G., and Bieniasz, P. D. (2002). Cellular inhibitors with Fv1-like activity restrict human and simian immunodeficiency virus tropism. Proc Natl Acad Sci USA 99, 11914-11919.

Daniel, M. D., Kirchhoff, F., Czajak, S. C., Sehgal, P. K., and Desrosiers, R. C. (1992). Protective effects of a live attenuated SIV vaccine with a deletion in the nef gene. Science 258, 1938-1941.

Delebecque, F., Suspene, R., Calattini, S., Casartelli, N., Saib, A., Froment, A., Wain-Hobson, S., Gessain, A., Vartanian, J. P., and Schwartz, 0. (2006). Restriction of foamy viruses by APOBEC cytidine deaminases. J Virol 80, 605-614.

Denton, P. W., Estes, J. D., Sun, Z., Othieno, F. A., Wei, B. L., Wege, A. K., Powell, D. A., Payne, D., Haase, A. T., and Garcia, J. V. (2008). Antiretroviral Pre-exposure Prophylaxis Prevents Vaginal Transmission of HIV-1 in Humanized BLT Mice. PLoS Med 5, e16.

Diaz-Griffero, F., Kar, A., Lee, M., Stremlau, M., Poeschla, E., and Sodroski, J. (2007). Comparative requirements for the restriction of retrovirus infection by TRIM5 alpha and TRIMCyp. Virology 369, 400-410.

Diaz-Griffero, F., Li, X., Javanbakht, H., Song, B., Welikala, S., Stremlau, M., and Sodroski, J. (2006a). Rapid turnover and polyubiquitylation of the retroviral restriction factor TRIM5. Virology 349, 300-315.

Diaz-Griffero, F., Vandegraaff, N., Li, Y., McGee-Estrada, K., Stremlau, M., Welikala, S., Si, Z., Engelman, A., and Sodroski, J. (2006b). Requirements for capsid-binding and an effector function in TRIMCyp-mediated restriction of HIV-1. Virology 351, 404-419.

Dimitrov, D. S., Willey, R. L., Sato, H., Chang, L. J., Blumenthal, R., and Martin, M. A. (1993). Quantitation of human immunodeficiency virus type 1 infection kinetics. J Virol 67, 2182-2190.

Dorfman, T., and Gottlinger, H. G. (1996). The human immunodeficiency virus type 1 capsid p2 domain confers sensitivity to the cyclophilin-binding drug SDZ NIM 811. J Virol 70, 5751-5757.

Douek, D. C., Picker, L. J., and Koup, R. A. (2003). T cell dynamics in HIV-1 infection. Annual review of immunology 21, 265-304.

Duran-Troise, G., Bassin, R. H., Wallace, B. F., and Rein, A. (1981). Balb/3T3 cells chronically infected with N-tropic murine leukemia virus continue to express Fv-1b restriction. Virology 112, 795-799.

Esnault, C., Heidmann, O., Delebecque, F., Dewannieux, M., Ribet, D., Hance, A. J., Heidmann, T., and Schwartz, 0. (2005). APOBEC3G cytidine deaminase inhibits retrotransposition of endogenous retroviruses. Nature 433, 430-433.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Fischer, G., Bang, H., and Mech, C. (1984). [Determination of enzymatic catalysis for the cis-trans-isomerization of peptide binding in proline-containing peptides]. Biomed Biochim Acta 43, 1101-1111.

Fisher, A. G., Ensoli, B., Ivanoff, L., Chamberlain, M., Petteway, S., Ratner, L., Gallo, R. C., and Wong-Staal, F. (1987). The sor gene of HIV-1 is required for efficient virus transmission in vitro. Science 237, 888-893.

Forshey, B. M., Shi, J., and Aiken, C. (2005). Structural requirements for recognition of the human immunodeficiency virus type 1 core during host restriction in owl monkey cells. J Virol 79, 869-875.

Forshey, B. M., von Schwedler, U., Sundquist, W. I., and Aiken, C. (2002). Formation of a human immunodeficiency virus type 1 core of optimal stability is crucial for viral replication. J Virol 76, 5667-5677.

Franke, E. K., and Luban, J. (1996). Inhibition of HIV-1 replication by cyclosporine A or related compounds correlates with the ability to disrupt the Gag-cyclophilin A interaction. Virology 222, 279-282.

Franke, E. K., Yuan, H. E., and Luban, J. (1994). Specific incorporation of cyclophilin A into HIV-1 virions. Nature 372, 359-362.

Friend, C. (1957). Cell-free transmission in adult Swiss mice of a disease having the character of a leukemia. The Journal of experimental medicine 105, 307-318.

Fulop, G. M., and Phillips, R. A. (1990). The scid mutation in mice causes a general defect in DNA repair. Nature 347, 479-482.

Fultz, P. N., McClure, H. M., Swenson, R. B., and Anderson, D. C. (1989). HIV infection of chimpanzees as a model for testing chemotherapeutics. Intervirology 30 Suppl 1, 51-58.

Galic, Z., Kitchen, S. G., Kacena, A., Subramanian, A., Burke, B., Cortado, R., and Zack, J. A. (2006). T lineage differentiation from human embryonic stem cells. Proc Natl Acad Sci USA 103, 11742-11747.

Gao, F., Bailes, E., Robertson, D. L., Chen, Y., Rodenburg, C. M., Michael, S. F., Cummins, L. B., Arthur, L. O., Peeters, M., Shaw, G. M., et al. (1999). Origin of HIV-1 in the chimpanzee Pan troglodytes troglodytes. Nature 397, 436-441.

Geraghty, R. J., Talbot, K. J., Callahan, M., Harper, W., and Panganiban, A. T. (1994). Cell type-dependence for Vpu function. Journal of medical primatology 23, 146-150.

Gimeno, R., Weijer, K., Voordouw, A., Uittenbogaart, C. H., Legrand, N., Alves, N. L., Wijnands, E., Blom, B., and Spits, H. (2004). Monitoring the effect of gene silencing by RNA interference in human CD34+ cells injected into newborn RAG2−/− gammac−/− mice: functional inactivation of p53 in developing T cells. Blood 104, 3886-3893.

Glass, W. G., McDermott, D. H., Lim, J. K., Lekhong, S., Yu, S. F., Frank, W. A., Pape, J., Cheshier, R. C., and Murphy, P. M. (2006). CCR5 deficiency increases risk of symptomatic West Nile virus infection. The Journal of experimental medicine 203, 35-40.

Goff, S. P. (2004). Retrovirus restriction factors. Molecular cell 16, 849-859.

Goffinet, C., Allespach, I., and Keppler, O. T. (2007). HIV-susceptible transgenic rats allow rapid preclinical testing of antiviral compounds targeting virus entry or reverse transcription. Proc Natl Acad Sci USA 104, 1015-1020.

Goila-Gaur, R., and Strebel, K. (2008). HIV-1 Vif, APOBEC, and intrinsic immunity. Retrovirology 5, 51.

Goldman, J. P., Blundell, M. P., Lopes, L., Kinnon, C., Di Santo, J. P., and Thrasher, A. J. (1998). Enhanced human cell engraftment in mice deficient in RAG2 and the common cytokine receptor gamma chain. British journal of haematology 103, 335-342.

Goldstein, H. (2008). Summary of presentations at the NIH/NIAID New Humanized Rodent Models 2007 Workshop. AIDS Res Ther 5, 3.

Goodall, J. (1995). Why is it unethical to use chimpanzees in the laboratory? Altern Lab Anim 23, 615-620.

Gothel, S. F., and Marahiel, M. A. (1999). Peptidyl-prolyl cis-trans isomerases, a superfamily of ubiquitous folding catalysts. Cell Mol Life Sci 55, 423-436.

Gottlinger, H. G. (2008). HIV/AIDS: virus kept on a leash. Nature 451, 406-408.

Gottlinger, H. G., Dorfman, T., Cohen, E. A., and Haseltine, W. A. (1993). Vpu protein of human immunodeficiency virus type 1 enhances the release of capsids produced by gag gene constructs of widely divergent retroviruses. Proc Natl Acad Sci USA 90, 7381-7385.

Goujon, C., Jarrosson-Wuilleme, L., Bernaud, J., Rigal, D., Darlix, J. L., and Cimarelli, A. (2006). With a little help from a friend: increasing HIV transduction of monocyte-derived dendritic cells with virion-like particles of SIV (MAC). Gene therapy 13, 991-994.

Goujon, C., Riviere, L., Jarrosson-Wuilleme, L., Bernaud, J., Rigal, D., Darlix, J. L., and Cimarelli, A. (2007). SIVSM/HIV-2 Vpx proteins promote retroviral escape from a proteasome-dependent restriction pathway present in human dendritic cells. Retrovirology 4, 2.

Grant, A. D., and De Cock, K. M. (2001). ABC of AIDS. HIV infection and AIDS in the developing world. BMJ (Clinical research ed 322, 1475-1478.

Grutter, C., Briand, C., Capitani, G., Mittl, P. R., Papin, S., Tschopp, J., and Grutter, M. G. (2006). Structure of the PRYSPRY-domain: implications for autoinflammatory diseases. FEBS Lett 580, 99-106.

Haase, A. T. (1999). Population biology of HIV-1 infection: viral and CD4+ T cell demographics and dynamics in lymphatic tissues Annual review of immunology 17, 625-656.

Hacein-Bey-Abina, S., Garrigue, A., Wang, G. P., Soulier, J., Lim, A., Morillon, E., Clappier, E., Caccavelli, L., Delabesse, E., Beldjord, K., et al. (2008). Insertional oncogenesis in 4 patients after retrovirus-mediated gene therapy of SCID-X1. The Journal of clinical investigation 118, 3132-3142.

Han, Y., Wind-Rotolo, M., Yang, H. C., Siliciano, J. D., and Siliciano, R. F. (2007). Experimental approaches to the study of HIV-1 latency. Nature reviews 5, 95-106.

Handschumacher, R. E., Harding, M. W., Rice, J., Drugge, R. J., and Speicher, D. W. (1984). Cyclophilin: a specific cytosolic binding protein for cyclosporin A. Science 226, 544-547.

Hanna, J., Wernig, M., Markoulaki, S., Sun, C. W., Meissner, A., Cassady, J. P., Beard, C., Brambrink, T., Wu, L. C., Townes, T. M., et al. (2007). Treatment of sickle cell anemia mouse model with iPS cells generated from autologous skin. Science 318, 1920-1923.

Hanna, Z., Kay, D. G., Cool, M., Jothy, S., Rebai, N., and Jolicoeur, P. (1998a). Transgenic mice expressing human immunodeficiency virus type 1 in immune cells develop a severe AIDS-like disease. J Virol 72, 121-132.

Hanna, Z., Kay, D. G., Rebai, N., Guimond, A., Jothy, S., and Jolicoeur, P. (1998b). Nef harbors a major determinant of pathogenicity for an AIDS-like disease induced by HIV-1 in transgenic mice. Cell 95, 163-175.

Harris, R. S., Bishop, K. N., Sheehy, A. M., Craig, H. M., Petersen-Mahrt, S. K., Watt, I. N., Neuberger, M. S., and Malim, M. H. (2003). DNA deamination mediates innate immunity to retroviral infection. Cell 113, 803-809.

Hartley, J. W., Rowe, W. P., and Huebner, R. J. (1970). Host-range restrictions of murine leukemia viruses in mouse embryo cell cultures. J Virol 5, 221-225.

Hatziioannou, T., Perez-Caballero, D., Yang, A., Cowan, S., and Bieniasz, P. D. (2004). Retrovirus resistance factors Ref1 and Lv1 are species-specific variants of TRIM5alpha. Proc Natl Acad Sci USA 101, 10774-10779.

Hatziioannou, T., Princiotta, M., Piatak, M., Jr., Yuan, F., Zhang, F., Lifson, J. D., and Bieniasz, P. D. (2006). Generation of simian-tropic HIV-1 by restriction factor evasion. Science 314, 95.

Hesselton, R. M., Greiner, D. L., Mordes, J. P., Rajan, T. V., Sullivan, J. L., and Shultz, L. D. (1995). High levels of human peripheral blood mononuclear cell engraftment and enhanced susceptibility to human immunodeficiency virus type 1 infection in NOD/LtSz-scid/scid mice. The Journal of infectious diseases 172, 974-982.

Himathongkham, S., and Luciw, P. A. (1996). Restriction of HIV-1 (subtype B) replication at the entry step in rhesus macaque cells. Virology 219, 485-488.

Ho, D. D., and Bieniasz, P. D. (2008). HIV-1 at 25. Cell 133, 561-565.

Hofer, U., Baenziger, S., Heikenwalder, M., Schlaepfer, E., Gehre, N., Regenass, S., Brunner, T., and Speck, R. F. (2008). RAG2−/−{gamma}c−/− mice transplanted with human cord blood CD34+ cells show low intestinal engraftment and are resistant to rectal HIV transmission. J. Virol.

Hofmann, W., Schubert, D., LaBonte, J., Munson, L., Gibson, S., Scammell, J., Ferrigno, P., and Sodroski, J. (1999). Species-specific, postentry barriers to primate immunodeficiency virus infection. J Virol 73, 10020-10028.

Howe, S. J., Mansour, M. R., Schwarzwaelder, K., Bartholomae, C., Hubank, M., Kempski, H., Brugman, M. H., Pike-Overzet, K., Chatters, S. J., de Ridder, D., et al. (2008). Insertional mutagenesis combined with acquired somatic mutations causes leukemogenesis following gene therapy of SCID-X1 patients. The Journal of clinical investigation 118, 3143-3150.

Hughes, A. L., and Yeager, M. (1998). Natural selection at major histocompatibility complex loci of vertebrates. Annual review of genetics 32, 415-435.

Isaacs, A., and Lindenmann, J. (1957). Virus interference. I. The interferon. Proceedings of the Royal Society of London Series B, Containing papers of a Biological character 147, 258-267.

Ishikawa, F., Yasukawa, M., Lyons, B., Yoshida, S., Miyamoto, T., Yoshimoto, G., Watanabe, T., Akashi, K., Shultz, L. D., and Harada, M. (2005). Development of functional human blood and immune systems in NOD/SCID/IL2 receptor {gamma} chain (null) mice. Blood 106, 1565-1573.

Ito, M., Hiramatsu, H., Kobayashi, K., Suzue, K., Kawahata, M., Hioki, K., Ueyama, Y., Koyanagi, Y., Sugamura, K., Tsuji, K., et al. (2002). NOD/SCID/gamma(c)(null) mouse: an excellent recipient mouse model for engraftment of human cells. Blood 100, 3175-3182.

Iwatani, Y., Takeuchi, H., Strebel, K., and Levin, J. G. (2006). Biochemical activities of highly purified, catalytically active human APOBEC3G: correlation with antiviral effect. J Virol 80, 5992-6002.

James, L. C., Keeble, A. H., Khan, Z., Rhodes, D. A., and Trowsdale, J. (2007). Structural basis for PRYSPRY-mediated tripartite motif (TRIM) protein function. Proc Natl Acad Sci USA 104, 6200-6205.

Jarmuz, A., Chester, A., Bayliss, J., Gisbourne, J., Dunham, I., Scott, J., and Navaratnam, N. (2002). An anthropoid-specific locus of orphan C to U RNA-editing enzymes on chromosome 22. Genomics 79, 285-296.

Javanbakht, H., Diaz-Griffero, F., Stremlau, M., Si, Z., and Sodroski, J. (2005). The contribution of RING and B-box 2 domains to retroviral restriction mediated by monkey TRIM5alpha. The Journal of biological chemistry 280, 26933-26940.

Javanbakht, H., Diaz-Griffero, F., Yuan, W., Yeung, D. F., Li, X., Song, B., and Sodroski, J. (2007). The ability of multimerized cyclophilin A to restrict retrovirus infection. Virology.

Javanbakht, H., Yuan, W., Yeung, D. F., Song, B., Diaz-Griffero, F., Li, Y., Li, X., Stremlau, M., and Sodroski, J. (2006). Characterization of TRIM5alpha trimerization and its contribution to human immunodeficiency virus capsid binding. Virology 353, 234-246.

Jolicoeur, P., and Baltimore, D. (1976). Effect of Fv-1 gene product on proviral DNA formation and integration in cells infected with murine leukemia viruses. Proc Natl Acad Sci USA 73, 2236-2240.

Jolly, C., Kashefi, K., Hollinshead, M., and Sattentau, Q. J. (2004). HIV-1 cell to cell transfer across an Env-induced, actin-dependent synapse. The Journal of experimental medicine 199, 283-293.

Kaiser, S. M., Malik, H. S., and Emerman, M. (2007). Restriction of an extinct retrovirus by the human TRIM5 alpha antiviral protein. Science 316, 1756-1758.

Kao, S., Khan, M. A., Miyagi, E., Plishka, R., Buckler-White, A., and Strebel, K. (2003). The human immunodeficiency virus type 1 Vif protein reduces intracellular expression and inhibits packaging of APOBEC3G (CEM15), a cellular inhibitor of virus infectivity. J Virol 77, 11398-11407.

Kazazian, H. H., Jr. (2004). Mobile elements: drivers of genome evolution. Science 303, 1626-1632.

Keckesova, Z., Ylinen, L. M., and Towers, G. J. (2004). The human and African green monkey TRIM5 alpha genes encode Ref1 and Lv1 retroviral restriction factor activities. Proc Natl Acad Sci USA 101, 10780-10785.

Keele, B. F., Van Heuverswyn, F., Li, Y., Bailes, E., Takehisa, J., Santiago, M. L., Bibollet-Ruche, F., Chen, Y., Wain, L. V., Liegeois, F., et al. (2006). Chimpanzee reservoirs of pandemic and nonpandemic HIV-1. Science 313, 523-526.

Keppler, O. T., Welte, F. J., Ngo, T. A., Chin, P. S., Patton, K. S., Tsou, C. L., Abbey, N. W., Sharkey, M. E., Grant, R. M., You, Y., et al. (2002). Progress toward a human CD4/CCR5 transgenic rat model for de novo infection by human immunodeficiency virus type 1. The Journal of experimental medicine 195, 719-736.

Kerre, T. C., De Smet, G., De Smedt, M., Zippelius, A., Pittet, M. J., Langerak, A. W., De Bosscher, J., Offner, F., Vandekerckhove, B., and Plum, J. (2002). Adapted NOD/SCID model supports development of phenotypically and functionally mature T cells from human umbilical cord blood CD34(+) cells. Blood 99, 1620-1626.

Kirchhoff, F., Greenough, T. C., Brettler, D. B., Sullivan, J. L., and Desrosiers, R. C. (1995). Brief report: absence of intact nef sequences in a long-term survivor with nonprogressive HIV-1 infection. The New England journal of medicine 332, 228-232.

Klimkait, T., Strebel, K., Hoggan, M. D., Martin, M. A., and Orenstein, J. M. (1990). The human immunodeficiency virus type-specific protein Vpu is required for efficient virus maturation and release. J Virol 64, 621-629.

Konig, R., Zhou, Y., Elleder, D., Diamond, T. L., Bonamy, G. M., Irelan, J. T., Chiang, C. Y., Tu, B. P., De Jesus, P. D., Lilley, C. E., et al. (2008). Global analysis of host-pathogen interactions that regulate early-stage HIV-1 replication. Cell 135, 49-60.

Kootstra, N. A., Munk, C., Tonnu, N., Landau, N. R., and Verma, I. M. (2003). Abrogation of postentry restriction of HIV-1-based lentiviral vector transduction in simian cells. Proc Natl Acad Sci USA 100, 1298-1303.

Koyanagi, Y., Tanaka, Y., Ito, M., and Yamamoto, N. (2008). Humanized mice for human retrovirus infection. Current topics in microbiology and immunology 324, 133-148.

Kozak, C. A., and Chakraborti, A. (1996). Single amino acid changes in the murine leukemia virus capsid protein gene define the target of Fv1 resistance. Virology 225, 300-305.

Kumar, P., Ban, H. S., Kim, S. S., Wu, H., Pearson, T., Greiner, D. L., Laouar, A., Yao, J., Haridas, V., Habiro, K., et al. (2008). T cell-specific siRNA delivery suppresses HIV-1 infection in humanized mice. Cell 134, 577-586.

Kunstman, K. J., Puffer, B., Korber, B. T., Kuiken, C., Smith, U. R., Kunstman, J., Stanton, J., Agy, M., Shibata, R., Yoder, A. D., et al. (2003). Structure and function of CC-chemokine receptor 5 homologues derived from representative primate species and subspecies of the taxonomic suborders Prosimii and Anthropoidea. J Virol 77, 12310-12318.

La Motte-Mohs, R. N., Herer, E., and Zuniga-Pflucker, J. C. (2005). Induction of T-cell development from human cord blood hematopoietic stem cells by Delta-like 1 in vitro. Blood 105, 1431-1439.

Labno, C. M., Lewis, C. M., You, D., Leung, D. W., Takesono, A., Kamberos, N., Seth, A., Finkelstein, L. D., Rosen, M. K., Schwartzberg, P. L., et al. (2003). Itk functions to control actin polymerization at the immune synapse through localized activation of Cdc42 and WASP. Curr Biol 13, 1619-1624.

LaBonte, J. A., Babcock, G. J., Patel, T., and Sodroski, J. (2002). Blockade of HIV-1 infection of New World monkey cells occurs primarily at the stage of virus entry. The Journal of experimental medicine 196, 431-445.

Lapidot, T., Pflumio, F., Doedens, M., Murdoch, B., Williams, D. E., and Dick, J. E. (1992). Cytokine stimulation of multilineage hematopoiesis from immature human cells engrafted in SCID mice. Science 255, 1137-1141.

Lee, Y. N., and Bieniasz, P. D. (2007). Reconstitution of an infectious human endogenous retrovirus. PLoS pathogens 3, e10.

Lee, Y. N., Malim, M. H., and Bieniasz, P. D. (2008). Hypermutation of an ancient human retrovirus by APOBEC3G. J Virol 82, 8762-8770.

Legrand, N., Weijer, K., and Spits, H. (2006). Experimental models to study development and function of the human immune system in vivo. J Immunol 176, 2053-2058.

Letvin, N. L., Daniel, M. D., Sehgal, P. K., Desrosiers, R. C., Hunt, R. D., Waldron, L. M., MacKey, J. J., Schmidt, D. K., Chalifoux, L. V., and King, N. W. (1985). Induction of AIDS-like disease in macaque monkeys with T-cell tropic retrovirus STLV-III. Science 230, 71-73.

Levine, B. L., Bernstein, W. B., Aronson, N. E., Schlienger, K., Cotte, J., Perfetto, S., Humphries, M. J., Ratto-Kim, S., Birx, D. L., Steffens, C., et al. (2002). Adoptive transfer of costimulated CD4+ T cells induces expansion of peripheral T cells and decreased CCR5 expression in HIV infection. Nature medicine 8, 47-53.

Lewinski, M. K., Yamashita, M., Emerman, M., Ciuffi, A., Marshall, H., Crawford, G., Collins, F., Shinn, P., Leipzig, J., Hannenhalli, S., et al. (2006). Retroviral DNA integration: viral and cellular determinants of target-site selection. PLoS pathogens 2, e60.

Li, X., Li, Y., Stremlau, M., Yuan, W., Song, B., Perron, M., and Sodroski, J. (2006a). Functional replacement of the RING, B-box 2, and coiled-coil domains of tripartite motif 5alpha (TRIM5alpha) by heterologous TRIM domains. J Virol 80, 6198-6206.

Li, Y., Li, X., Stremlau, M., Lee, M., and Sodroski, J. (2006b). Removal of arginine 332 allows human TRIM5alpha to bind human immunodeficiency virus capsids and to restrict infection. J Virol 80, 6738-6744.

Lilly, F. (1967). Susceptibility to two strains of Friend leukemia virus in mice. Science 155, 461-462.

Lin, T. Y., and Emerman, M. (2006). Cyclophilin A interacts with diverse lentiviral capsids. Retrovirology 3, 70.

Liu, J., Farmer, J. D., Jr., Lane, W. S., Friedman, J., Weissman, I., and Schreiber, S. L. (1991). Calcineurin is a common target of cyclophilin-cyclosporin A and FKBP-FK506 complexes. Cell 66, 807-815.

Lois, C., Hong, E. J., Pease, S., Brown, E. J., and Baltimore, D. (2002). Germline transmission and tissue-specific expression of transgenes delivered by lentiviral vectors. Science 295, 868-872.

Lombardo, A., Genovese, P., Beausejour, C. M., Colleoni, S., Lee, Y. L., Kim, K. A., Ando, D., Urnov, F. D., Galli, C., Gregory, P. D., et al. (2007). Gene editing in human stem cells using zinc finger nucleases and integrase-defective lentiviral vector delivery. Nature biotechnology 25, 1298-1306.

Luban, J. (2007). Cyclophilin A, TRIM5, and resistance to human immunodeficiency virus type 1 infection. J Virol 81, 1054-1061.

Luban, J., Bossolt, K. L., Franke, E. K., Kalpana, G. V., and Goff, S. P. (1993). Human immunodeficiency virus type 1 Gag protein binds to cyclophilins A and B. Cell 73, 1067-1078.

Madani, N., and Kabat, D. (1998). An endogenous inhibitor of human immunodeficiency virus in human lymphocytes is overcome by the viral Vif protein. J Virol 72, 10251-10255.

Maddon, P. J., Dagleish, A. G., McDougal, J. S., Clapham, P. R., Weiss, R. A., and Axel, R. (1986). The T4 gene encodes the AIDS virus receptor and is expressed in the immune system and the brain. Cell 47, 333-348.

Maertens, G., Cherepanov, P., Pluymers, W., Busschots, K., De Clercq, E., Debyser, Z., and Engelborghs, Y. (2003). LEDGF/p75 is essential for nuclear and chromosomal targeting of HIV-1 integrase in human cells. The Journal of biological chemistry 278, 33528-33539.

Malim, M. H., Freimuth, W. W., Liu, J., Boyle, T. J., Lyerly, H. K., Cullen, B. R., and Nabel, G. J. (1992). Stable expression of transdominant Rev protein in human T cells inhibits human immunodeficiency virus replication. The Journal of experimental medicine 176, 1197-1201.

Mangeat, B., Turelli, P., Caron, G., Friedli, M., Perrin, L., and Trono, D. (2003). Broad antiretroviral defence by human APOBEC3G through lethal editing of nascent reverse transcripts. Nature 424, 99-103.

Mangeot, P. E., Duperrier, K., Negre, D., Boson, B., Rigal, D., Cosset, F. L., and Darlix, J. L. (2002). High levels of transduction of human dendritic cells with optimized SIV vectors. Mol Ther 5, 283-290.

Manz, M. G. (2007). Human-hemato-lymphoid-system mice: opportunities and challenges. Immunity 26, 537-541.

Marathe, J. G., and Wooley, D. P. (2007). Is gene therapy a good therapeutic approach for HIV-positive patients? Genet Vaccines Ther 5, 5.

Mariani, R., Chen, D., Schrofelbauer, B., Navarro, F., Konig, R., Bollman, B., Munk, C., Nymark-McMahon, H., and Landau, N. R. (2003). Species-specific exclusion of APOBEC3G from HIV-1 virions by Vif. Cell 114, 21-31.

Massiah, M. A., Simmons, B. N., Short, K. M., and Cox, T. C. (2006). Solution structure of the RBCC/TRIM B-box1 domain of human MIDI: B-box with a RING. Journal of molecular biology 358, 532-545.

Mazurier, F., Fontanellas, A., Salesse, S., Taine, L., Landriau, S., Moreau-Gaudry, F., Reiffers, J., Peault, B., Di Santo, J. P., and de Verneuil, H. (1999). A novel immunodeficient mouse model—RAG2 x common cytokine receptor gamma chain double mutants—requiring exogenous cytokine administration for human hematopoietic stem cell engraftment. J Interferon Cytokine Res 19, 533-541.

McCune, J. M., Namikawa, R., Kaneshima, H., Shultz, L. D., Lieberman, M., and Weissman, I. L. (1988). The SCID-hu mouse: murine model for the analysis of human hematolymphoid differentiation and function. Science 241, 1632-1639.

Melkus, M. W., Estes, J. D., Padgett-Thomas, A., Gatlin, J., Denton, P. W., Othieno, F. A., Wege, A. K., Haase, A. T., and Garcia, J. V. (2006). Humanized mice mount specific adaptive and innate immune responses to EBV and TSST-1. Nature medicine 12, 1316-1322.

Messi, M., Giacchetto, I., Nagata, K., Lanzavecchia, A., Natoli, G., and Sallusto, F. (2003). Memory and flexibility of cytokine gene expression as separable properties of human T(H)1 and T(H)2 lymphocytes. Nature immunology 4, 78-86.

Mische, C. C., Javanbakht, H., Song, B., Diaz-Griffero, F., Stremlau, M., Strack, B., Si, Z., and Sodroski, J. (2005). Retroviral restriction factor TRIM5alpha is a trimer. J Virol 79, 14446-14450.

Mitchell, R. S., Beitzel, B. F., Schroder, A. R., Shinn, P., Chen, H., Berry, C. C., Ecker, J. R., and Bushman, F. D. (2004). Retroviral DNA integration: ASLV, HIV, and MLV show distinct target site preferences. PLoS biology 2, E234.

Mitsuyasu, R. T., Anton, P. A., Deeks, S. G., Scadden, D. T., Connick, E., Downs, M. T., Bakker, A., Roberts, M. R., June, C. H., Jalali, S., et al. (2000). Prolonged survival and tissue trafficking following adoptive transfer of CD4zeta gene-modified autologous CD4(+) and CD8(+) T cells in human immunodeficiency virus-infected subjects. Blood 96, 785-793.

Mombaerts, P., Iacomini, J., Johnson, R. S., Herrup, K., Tonegawa, S., and Papaioannou, V. E. (1992). RAG-1-deficient mice have no mature B and T lymphocytes. Cell 68, 869-877.

Morgan, R. A., Walker, R., Carter, C. S., Natarajan, V., Tavel, J. A., Bechtel, C., Herpin, B., Muul, L., Zheng, Z., Jagannatha, S., et al. (2005). Preferential survival of CD4+ T lymphocytes engineered with anti-human immunodeficiency virus (HIV) genes in HIV-infected individuals. Human gene therapy 16, 1065-1074.

Mosier, D. E., Gulizia, R. J., Baird, S. M., and Wilson, D. B. (1988). Transfer of a functional human immune system to mice with severe combined immunodeficiency. Nature 335, 256-259.

Mosier, D. E., Gulizia, R. J., Baird, S. M., Wilson, D. B., Spector, D. H., and Spector, S. A. (1991). Human immunodeficiency virus infection of human-PBL-SCID mice. Science 251, 791-794.

Muesing, M. A., Smith, D. H., Cabradilla, C. D., Benton, C. V., Lasky, L. A., and Capon, D. J. (1985). Nucleic acid structure and expression of the human AIDS/lymphadenopathy retrovirus. Nature 313, 450-458.

Munch, J., Rucker, E., Standker, L., Adermann, K., Goffinet, C., Schindler, M., Wildum, S., Chinnadurai, R., Rajan, D., Specht, A., et al. (2007). Semen-derived amyloid fibrils drastically enhance HIV infection. Cell 131, 1059-1071.

Munk, C., Brandt, S. M., Lucero, G., and Landau, N. R. (2002). A dominant block to HIV-1 replication at reverse transcription in simian cells. Proc Natl Acad Sci USA 99, 13843-13848.

Muramatsu, M., Kinoshita, K., Fagarasan, S., Yamada, S., Shinkai, Y., and Honjo, T. (2000). Class switch recombination and hypermutation require activation-induced cytidine deaminase (AID), a potential RNA editing enzyme. Cell 102, 553-563.

Nakata, H., Maeda, K., Miyakawa, T., Shibayama, S., Matsuo, M., Takaoka, Y., Ito, M., Koyanagi, Y., and Mitsuya, H. (2005). Potent anti-R5 human immunodeficiency virus type 1 effects of a CCR5 antagonist, AK602/ONO4128/GW873140, in a novel human peripheral blood mononuclear cell nonobese diabetic-SCID, interleukin-2 receptor gamma-chain-knocked-out AIDS mouse model. J Virol 79, 2087-2096.

Namikawa, R., Kaneshima, H., Lieberman, M., Weissman, I. L., and McCune, J. M. (1988). Infection of the SCID-hu mouse by HIV-1. Science 242, 1684-1686.

Nath, B. M., Schumann, K. E., and Boyer, J. D. (2000). The chimpanzee and other non-human-primate models in HIV-1 vaccine research. Trends in microbiology 8, 426-431.

Neil, S. J., Eastman, S. W., Jouvenet, N., and Bieniasz, P. D. (2006). HIV-1 Vpu promotes release and prevents endocytosis of nascent retrovirus particles from the plasma membrane. PLoS pathogens 2, e39.

Neil, S. J., Sandrin, V., Sundquist, W. I., and Bieniasz, P. D. (2007). An interferon-alpha-induced tethering mechanism inhibits HIV-1 and Ebola virus particle release but is counteracted by the HIV-1 Vpu protein. Cell host & microbe 2, 193-203.

Neil, S. J., Zang, T., and Bieniasz, P. D. (2008). Tetherin inhibits retrovirus release and is antagonized by HIV-1 Vpu. Nature 451, 425-430.

Newman, R. M., Hall, L., Kirmaier, A., Pozzi, L. A., Pery, E., Farzan, M., O'Neil, S. P., and Johnson, W. (2008). Evolution of a TRIM5-CypA splice isoform in old world monkeys. PLoS pathogens 4, e1000003.

Newman, R. M., and Johnson, W. E. (2007). A brief history of TRIM5alpha. AIDS Rev 9, 114-125.

Nisole, S., Lynch, C., Stoye, J. P., and Yap, M. W. (2004). A Trim5-cyclophilin A fusion protein found in owl monkey kidney cells can restrict HIV-1. Proc Natl Acad Sci USA 101, 13324-13328.

Nisole, S., Stoye, J. P., and Saib, A. (2005). TRIM family proteins: retroviral restriction and antiviral defence. Nature reviews 3, 799-808.

Nomaguchi, M., Fujita, M., and Adachi, A. (2008). Role of HIV-1 Vpu protein for virus spread and pathogenesis. Microbes Infect.

Novembre, F. J., Saucier, M., Anderson, D. C., Klumpp, S. A., O'Neil, S. P., Brown, C. R., 2nd, Hart, C. E., Guenthner, P. C., Swenson, R. B., and McClure, H. M. (1997). Development of AIDS in a chimpanzee infected with human immunodeficiency virus type 1. J Virol 71, 4086-4091.

Ohkura, S., Yap, M. W., Sheldon, T., and Stoye, J. P. (2006). All three variable regions of the TRIM5alpha B30.2 domain can contribute to the specificity of retrovirus restriction. J Virol 80, 8554-8565.

Opi, S., Kao, S., Goila-Gaur, R., Khan, M. A., Miyagi, E., Takeuchi, H., and Strebel, K. (2007). Human immunodeficiency virus type 1 Vif inhibits packaging and antiviral activity of a degradation-resistant APOBEC3G variant. J Virol 81, 8236-8246.

Owens, C. M., Yang, P. C., Gottlinger, H., and Sodroski, J. (2003). Human and simian immunodeficiency virus capsid proteins are major viral determinants of early, postentry replication blocks in simian cells. J Virol 77, 726-731.

Palmer, E. (2003). Negative selection—clearing out the bad apples from the T-cell repertoire. Nat Rev Immunol 3, 383-391.

Pandrea, I., Apetrei, C., Gordon, S., Barbercheck, J., Dufour, J., Bohm, R., Sumpter, B., Rogues, P., Marx, P. A., Hirsch, V. M., et al. (2007). Paucity of CD4+CCR5+ T cells is a typical feature of natural SIV hosts. Blood 109, 1069-1076.

Pandrea, I., Sodora, D. L., Silvestri, G., and Apetrei, C. (2008). Into the wild: simian immunodeficiency virus (SIV) infection in natural hosts. Trends in immunology 29, 419-428.

Papkalla, A., Munch, J., Otto, C., and Kirchhoff, F. (2002). Nef enhances human immunodeficiency virus type 1 infectivity and replication independently of viral coreceptor tropism. J Virol 76, 8455-8459.

Perez, E. E., Wang, J., Miller, J. C., Jouvenot, Y., Kim, K. A., Liu, O., Wang, N., Lee, G., Bartsevich, V. V., Lee, Y. L., et al. (2008). Establishment of HIV-1 resistance in CD4(+) T cells by genome editing using zinc-finger nucleases. Nature biotechnology.

Perez-Caballero, D., Hatziioannou, T., Yang, A., Cowan, S., and Bieniasz, P. D. (2005a). Human tripartite motif 5alpha domains responsible for retrovirus restriction activity and specificity. J Virol 79, 8969-8978.

Perez-Caballero, D., Hatziioannou, T., Zhang, F., Cowan, S., and Bieniasz, P. D. (2005b). Restriction of human immunodeficiency virus type 1 by TRIM-CypA occurs with rapid kinetics and independently of cytoplasmic bodies, ubiquitin, and proteasome activity. J Virol 79, 15567-15572.

Perron, M. J., Stremlau, M., Lee, M., Javanbakht, H., Song, B., and Sodroski, J. (2007). The human TRIM5 alpha restriction factor mediates accelerated uncoating of the N-tropic murine leukemia virus capsid. J Virol 81, 2138-2148.

Perron, M. J., Stremlau, M., Song, B., Ulm, W., Mulligan, R. C., and Sodroski, J. (2004). TRIM5 alpha mediates the postentry block to N-tropic murine leukemia viruses in human cells. Proc Natl Acad Sci USA 101, 11827-11832.

Pichlmair, A., and Reis e Sousa, C. (2007). Innate recognition of viruses. Immunity 27, 370-383.

Pincus, T., Hartley, J. W., and Rowe, W. P. (1971a). A major genetic locus affecting resistance to infection with murine leukemia viruses. I. Tissue culture studies of naturally occurring viruses. The Journal of experimental medicine 133, 1219-1233.

Pincus, T., Hartley, J. W., and Rowe, W. P. (1975). A major genetic locus affecting resistance to infection with murine leukemia viruses. IV. Dose-response relationships in Fv-1-sensitive and resistant cell cultures. Virology 65, 333-342.

Pincus, T., Rowe, W. P., and Lilly, F. (1971b). A major genetic locus affecting resistance to infection with murine leukemia viruses. II. Apparent identity to a major locus described for resistance to friend murine leukemia virus. The Journal of experimental medicine 133, 1234-1241.

Popovic, M., Sarngadharan, M. G., Read, E., and Gallo, R. C. (1984). Detection, isolation, and continuous production of cytopathic retroviruses (HTLV-III) from patients with AIDS and pre-AIDS. Science 224, 497-500.

Potash, M. J., Chao, W., Bentsman, G., Paris, N., Saini, M., Nitkiewicz, J., Belem, P., Sharer, L., Brooks, A. I., and Volsky, D. J. (2005). A mouse model for study of systemic HIV-1 infection, antiviral immune responses, and neuroinvasiveness. Proc Natl Acad Sci USA 102, 3760-3765.

Pryciak, P. M., and Varmus, H. E. (1992). Fv-1 restriction and its effects on murine leukemia virus integration in vivo and in vitro. J Virol 66, 5959-5966.

Qi, C. F., Bonhomme, F., Buckler-White, A., Buckler, C., Orth, A., Lander, M. R., Chattopadhyay, S. K., and Morse, H. C., 3rd (1998). Molecular phylogeny of Fv1. Mamm Genome 9, 1049-1055.

Ranga, U., Woffendin, C., Verma, S., Xu, L., June, C. H., Bishop, D. K., and Nabel, G. J. (1998). Enhanced T cell engraftment after retroviral delivery of an antiviral gene in HIV-infected individuals. Proc Natl Acad Sci USA 95, 1201-1206.

Rein, A., Kashmiri, S. V., Bassin, R. H., Gerwin, B. L., and Duran-Troise, G. (1976). Phenotypic mixing between N- and B-tropic murine leukemia viruses: infectious particles with dual sensitivity to Fv-1 restriction. Cell 7, 373-379.

Reymond, A., Meroni, G., Fantozzi, A., Merla, G., Cairo, S., Luzi, L., Riganelli, D., Zanaria, E., Messali, S., Cainarca, S., et al. (2001). The tripartite motif family identifies cell compartments. The EMBO journal 20, 2140-2151.

Ribeiro, I. P., Menezes, A. N., Moreira, M. A., Bonvicino, C. R., Seuanez, H. N., and Soares, M. A. (2005). Evolution of cyclophilin A and TRIMCyp retrotransposition in New World primates. J Virol 79, 14998-15003.

Richardson, M. W., Carroll, R. G., Stremlau, M., Korokhov, N., Humeau, L. M., Silvestri, G., Sodroski, J., and Riley, J. L. (2008). Mode of Transmission Affects the Sensitivity of HIV-1 to Restriction by Rhesus TRIM5 {alpha}. J. Virol.

Riddell, S. R., Elliott, M., Lewinsohn, D. A., Gilbert, M. J., Wilson, L., Manley, S. A., Lupton, S. D., Overell, R. W., Reynolds, T. C., Corey, L., et al. (1996). T-cell mediated rejection of gene-modified HIV-specific cytotoxic T lymphocytes in HIV-infected patients. Nature medicine 2, 216-223.

Roberts, M. R., Qin, L., Zhang, D., Smith, D. H., Tran, A. C., Dull, T. J., Groopman, J. E., Capon, D. J., Byrn, R. A., and Finer, M. H. (1994). Targeting of human immunodeficiency virus-infected cells by CD8+ T lymphocytes armed with universal T-cell receptors. Blood 84, 2878-2889.

Rold, C. J., and Aiken, C. (2008). Proteasomal degradation of TRIM5 alpha during retrovirus restriction. PLoS pathogens 4, e1000074.

Ryffel, B., Woerly, G., Greiner, B., Haendler, B., Mihatsch, M. J., and Foxwell, B. M. (1991). Distribution of the cyclosporine binding protein cyclophilin in human tissues. Immunology 72, 399-404.

Saenz, D. T., Teo, W., Olsen, J. C., and Poeschla, E. M. (2005). Restriction of feline immunodeficiency virus by Ref1, Lv1, and primate TRIM5 alpha proteins. J Virol 79, 15175-15188.

Sakuma, R., Noser, J. A., Ohmine, S., and Ikeda, Y. (2007). Rhesus monkey TRIM5alpha restricts HIV-1 production through rapid degradation of viral Gag polyproteins. Nature medicine 13, 631-635.

Samuel, C. E. (2001). Antiviral actions of interferons. Clinical microbiology reviews 14, 778-809, table of contents.

Santiago, M. L., Montano, M., Benitez, R., Messer, R. J., Yonemoto, W., Chesebro, B., Hasenkrug, K. J., and Greene, W. C. (2008). Apobec3 encodes Rfv3, a gene influencing neutralizing antibody control of retrovirus infection. Science 321, 1343-1346.

Santoni de Sio, F. R., Cascio, P., Zingale, A., Gasparini, M., and Naldini, L. (2006). Proteasome activity restricts lentiviral gene transfer into hematopoietic stem cells and is down-regulated by cytokines that enhance transduction. Blood 107, 4257-4265.

Sarkar, I., Hauber, I., Hauber, J., and Buchholz, F. (2007). HIV-1 proviral DNA excision using an evolved recombinase. Science 316, 1912-1915.

Sasada, A., Takaori-Kondo, A., Shirakawa, K., Kobayashi, M., Abudu, A., Hishizawa, M., Imada, K., Tanaka, Y., and Uchiyama, T. (2005). APOBEC3G targets human T-cell leukemia virus type 1. Retrovirology 2, 32.

Sawyer, S. L., Emerman, M., and Malik, H. S. (2004). Ancient adaptive evolution of the primate antiviral DNA-editing enzyme APOBEC3G. PLoS biology 2, E275.

Sawyer, S. L., Wu, L. I., Akey, J. M., Emerman, M., and Malik, H. S. (2006). High-frequency persistence of an impaired allele of the retroviral defense gene TRIM5 alpha in humans. Curr Biol 16, 95-100.

Sawyer, S. L., Wu, L. I., Emerman, M., and Malik, H. S. (2005). Positive selection of primate TRIM5 alpha identifies a critical species-specific retroviral restriction domain. Proc Natl Acad Sci USA 102, 2832-2837.

Sayah, D. M., and Luban, J. (2004). Selection for loss of Ref1 activity in human cells releases human immunodeficiency virus type 1 from cyclophilin A dependence during infection. J Virol 78, 12066-12070.

Sayah, D. M., Sokolskaja, E., Berthoux, L., and Luban, J. (2004). Cyclophilin A retrotransposition into TRIM5 explains owl monkey resistance to HIV-1. Nature 430, 569-573.

Schaller, T., Ylinen, L. M., Webb, B. L., Singh, S., and Towers, G. J. (2007). Fusion of cyclophilin a to fv1 enables cyclosporine-sensitive restriction of human and feline immunodeficiency viruses. J Virol 81, 10055-10063.

Schambach, A., Schiedlmeier, B., Kuhlcke, K., Verstegen, M., Margison, G. P., Li, Z., Kamino, K., Bohne, J., Alexandrov, A., Hermann, F. G., et al. (2006). Towards hematopoietic stem cell-mediated protection against infection with human immunodeficiency virus. Gene therapy 13, 1037-1047.

Schindler, M., Munch, J., Kutsch, O., Li, H., Santiago, M. L., Bibollet-Ruche, F., Muller-Trutwin, M. C., Novembre, F. J., Peeters, M., Courgnaud, V., et al. (2006). Nef-mediated suppression of T cell activation was lost in a lentiviral lineage that gave rise to HIV-1. Cell 125, 1055-1067.

Schmid, F. X. (1995). Protein folding. Prolyl isomerases join the fold. Curr Biol 5, 993-994.

Schotte, R., Nagasawa, M., Weijer, K., Spits, H., and Blom, B. (2004). The ETS transcription factor Spi-B is required for human plasmacytoid dendritic cell development. The Journal of experimental medicine 200, 1503-1509.

Schrofelbauer, B., Chen, D., and Landau, N. R. (2004). A single amino acid of APOBEC3G controls its species-specific interaction with virion infectivity factor (Vif). Proc Natl Acad Sci USA 101, 3927-3932.

Schrofelbauer, B., Yu, Q., Zeitlin, S. G., and Landau, N. R. (2005). Human immunodeficiency virus type 1 Vpr induces the degradation of the UNG and SMUG uracil-DNA glycosylases. J Virol 79, 10978-10987.

Schwartz, O., Marechal, V., Friguet, B., Arenzana-Seisdedos, F., and Heard, J. M. (1998). Antiviral activity of the proteasome on incoming human immunodeficiency virus type 1. J Virol 72, 3845-3850.

Sebastian, S., and Luban, J. (2005). TRIM5alpha selectively binds a restriction-sensitive retroviral capsid. Retrovirology 2, 40.

Sebastian, S., and Luban, J. (2007). The Retroviral Restriction Factor TRIM5alpha. Curr Infect Dis Rep 9, 167-173.

Sebastian, S., Sokolskaja, E., and Luban, J. (2006). Arsenic counteracts human immunodeficiency virus type 1 restriction by various TRIM5 orthologues in a cell type-dependent manner. J Virol 80, 2051-2054.

Sheehy, A. M., Gaddis, N. C., Choi, J. D., and Malim, M. H. (2002). Isolation of a human gene that inhibits HIV-1 infection and is suppressed by the viral Vif protein. Nature 418, 646-650.

Sheehy, A. M., Gaddis, N. C., and Malim, M. H. (2003). The antiretroviral enzyme APOBEC3G is degraded by the proteasome in response to HIV-1 Vif. Nature medicine 9, 1404-1407.

Shen, Z. J., Esnault, S., and Malter, J. S. (2005). The peptidyl-prolyl isomerase Pin1 regulates the stability of granulocyte-macrophage colony-stimulating factor mRNA in activated eosinophils. Nature immunology 6, 1280-1287.

Sherer, N. M., Lehmann, M. J., Jimenez-Soto, L. F., Horensavitz, C., Pypaert, M., and Mothes, W. (2007). Retroviruses can establish filopodial bridges for efficient cell-to-cell transmission. Nature cell biology 9, 310-315.

Shi, J., and Aiken, C. (2006). Saturation of TRIM5 alpha-mediated restriction of HIV-1 infection depends on the stability of the incoming viral capsid. Virology 350, 493-500.

Shi, M., Deng, W., Bi, E., Mao, K., Ji, Y., Lin, G., Wu, X., Tao, Z., Li, Z., Cai, X., et al. (2008). TRIM30 alpha negatively regulates TLR-mediated NF-kappa B activation by targeting TAB2 and TAB3 for degradation. Nature immunology 9, 369-377.

Shibata, R., Kawamura, M., Sakai, H., Hayami, M., Ishimoto, A., and Adachi, A. (1991). Generation of a chimeric human and simian immunodeficiency virus infectious to monkey peripheral blood mononuclear cells. J Virol 65, 3514-3520.

Shinkai, Y., Rathbun, G., Lam, K. P., Oltz, E. M., Stewart, V., Mendelsohn, M., Charron, J., Datta, M., Young, F., Stall, A. M., et al. (1992). RAG-2-deficient mice lack mature lymphocytes owing to inability to initiate V(D)J rearrangement. Cell 68, 855-867.

Shizuru, J. A., Weissman, I. L., Kernoff, R., Masek, M., and Scheffold, Y. C. (2000). Purified hematopoietic stem cell grafts induce tolerance to alloantigens and can mediate positive and negative T cell selection. Proc Natl Acad Sci USA 97, 9555-9560.

Shultz, L. D., Ishikawa, F., and Greiner, D. L. (2007). Humanized mice in translational biomedical research. Nat Rev Immunol 7, 118-130.

Shultz, L. D., Lyons, B. L., Burzenski, L. M., Gott, B., Chen, X., Chaleff, S., Kotb, M., Gillies, S. D., King, M., Mangada, J., et al. (2005). Human lymphoid and myeloid cell development in NOD/LtSz-scid IL2R gamma null mice engrafted with mobilized human hemopoietic stem cells. J Immunol 174, 6477-6489.

Shultz, L. D., Schweitzer, P. A., Christianson, S. W., Gott, B., Schweitzer, I. B., Tennent, B., McKenna, S., Mobraaten, L., Rajan, T. V., Greiner, D. L., et al. (1995). Multiple defects in innate and adaptive immunologic function in NOD/LtSz-scid mice. J Immunol 154, 180-191.

Simon, J. H., Gaddis, N. C., Fouchier, R. A., and Malim, M. H. (1998a). Evidence for a newly discovered cellular anti-HIV-1 phenotype. Nature medicine 4, 1397-1400.

Simon, J. H., Miller, D. L., Fouchier, R. A., Soares, M. A., Peden, K. W., and Malim, M. H. (1998b). The regulation of primate immunodeficiency virus infectivity by Vif is cell species restricted: a role for Vif in determining virus host range and cross-species transmission. The EMBO journal 17, 1259-1267.

Simon, J. H., Southerling, T. E., Peterson, J. C., Meyer, B. E., and Malim, M. H. (1995). Complementation of vif-defective human immunodeficiency virus type 1 by primate, but not nonprimate, lentivirus vif genes. J Virol 69, 4166-4172.

Skowronski, J., Parks, D., and Mariani, R. (1993). Altered T cell activation and development in transgenic mice expressing the HIV-1 nef gene. The EMBO journal 12, 703-713.

Sokolskaja, E., Sayah, D. M., and Luban, J. (2004). Target cell cyclophilin A modulates human immunodeficiency virus type 1 infectivity. J Virol 78, 12800-12808.

Song, B., Diaz-Griffero, F., Park, D. H., Rogers, T., Stremlau, M., and Sodroski, J. (2005a). TRIM5alpha association with cytoplasmic bodies is not required for antiretroviral activity. Virology 343, 201-211.

Song, B., Gold, B., O'Huigin, C., Javanbakht, H., Li, X., Stremlau, M., Winkler, C., Dean, M., and Sodroski, J. (2005b). The B30.2(SPRY) domain of the retroviral restriction factor TRIM5alpha exhibits lineage-specific length and sequence variation in primates. J Virol 79, 6111-6121.

Soros, V. B., Yonemoto, W., and Greene, W. C. (2007). Newly synthesized APOBEC3G is incorporated into HIV virions, inhibited by HIV RNA, and subsequently activated by RNase H. PLoS pathogens 3, e15.

Sourisseau, M., Sol-Foulon, N., Porrot, F., Blanchet, F., and Schwartz, O. (2007). Inefficient human immunodeficiency virus replication in mobile lymphocytes. J Virol 81, 1000-1012.

Stegmeier, F., Hu, G., Rickles, R. J., Hannon, G. J., and Elledge, S. J. (2005). A lentiviral microRNA-based system for single-copy polymerase II-regulated RNA interference in mammalian cells. Proc Natl Acad Sci USA 102, 13212-13217.

Stetson, D. B., Ko, J. S., Heidmann, T., and Medzhitov, R. (2008). Trex1 prevents cell-intrinsic initiation of autoimmunity. Cell 134, 587-598.

Stoddart, C. A., Bales, C. A., Bare, J. C., Chkhenkeli, G., Galkina, S. A., Kinkade, A. N., Moreno, M. E., Rivera, J. M., Ronquillo, R. E., Sloan, B., et al. (2007). Validation of the SCID-hu Thy/Liv mouse model with four classes of licensed antiretrovirals. PLoS ONE 2, e655.

Stopak, K., de Noronha, C., Yonemoto, W., and Greene, W. C. (2003). HIV-1 Vif blocks the antiviral activity of APOBEC3G by impairing both its translation and intracellular stability. Molecular cell 12, 591-601.

Stopak, K. S., Chiu, Y. L., Kropp, J., Grant, R. M., and Greene, W. C. (2007). Distinct patterns of cytokine regulation of APOBEC3G expression and activity in primary lymphocytes, macrophages, and dendritic cells. The Journal of biological chemistry 282, 3539-3546.

Stoye, J. P., and Yap, M. W. (2008). Chance favors a prepared genome. Proc Natl Acad Sci USA 105, 3177-3178.

Strayer, D. S., Akkina, R., Bunnell, B. A., propulic, B., Planelles, V., Pomerantz, R. J., Rossi, J. J., and Zaia, J. A. (2005). Current status of gene therapy strategies to treat HIV/AIDS. Mol Ther 11, 823-842.

Strebel, K. (2005). APOBEC3G & HTLV-1: inhibition without deamination. Retrovirology 2, 37.

Strebel, K., Daugherty, D., Clouse, K., Cohen, D., Folks, T., and Martin, M. A. (1987). The HIV 'A' (*sor*) gene product is essential for virus infectivity. Nature 328, 728-730.

Strebel, K., Klimkait, T., Maldarelli, F., and Martin, M. A. (1989). Molecular and biochemical analysis of human immunodeficiency virus type 1 vpu protein. J Virol 63, 3784-3791.

Stremlau, M., Owens, C. M., Perron, M. J., Kiessling, M., Autissier, P., and Sodroski, J. (2004). The cytoplasmic body component TRIM5alpha restricts HIV-1 infection in Old World monkeys. Nature 427, 848-853.

Stremlau, M., Perron, M., Lee, M., Li, Y., Song, B., Javanbakht, H., Diaz-Griffero, F., Anderson, D. J., Sundquist, W. I., and Sodroski, J. (2006). Specific recognition and accelerated uncoating of retroviral capsids by the TRIM5 alpha restriction factor. Proc Natl Acad Sci USA 103, 5514-5519.

Stremlau, M., Perron, M., Welikala, S., and Sodroski, J. (2005). Species-specific variation in the B30.2(SPRY) domain of TRIM5alpha determines the potency of human immunodeficiency virus restriction. J Virol 79, 3139-3145.

Sugamura, K., Asao, H., Kondo, M., Tanaka, N., Ishii, N., Ohbo, K., Nakamura, M., and Takeshita, T. (1996). The interleukin-2 receptor gamma chain: its role in the multiple cytokine receptor complexes and T cell development in XSCID Annual review of immunology 14, 179-205.

Sun, J., Soos, T., Kewalramani, V. N., Osiecki, K., Zheng, J. H., Falkin, L., Santambrogio, L., Littman, D. R., and Goldstein, H. (2006). CD4-specific transgenic expression of human cyclin T1 markedly increases human immunodeficiency virus type 1 (HIV-1) production by CD4+ T lymphocytes and myeloid cells in mice transgenic for a provirus encoding a monocyte-tropic HIV-1 isolate. J Virol 80, 1850-1862.

Sun, Z., Denton, P. W., Estes, J. D., Othieno, F. A., Wei, B. L., Wege, A. K., Melkus, M. W., Padgett-Thomas, A., Zupancic, M., Haase, A. T., et al. (2007). Intrarectal transmission, systemic infection, and CD4+ T cell depletion in humanized mice infected with HIV-1. The Journal of experimental medicine 204, 705-714.

Szymczak, A. L., Workman, C. J., Wang, Y., Vignali, K. M., Dilioglou, S., Vanin, E. F., and Vignali, D. A. (2004). Correction of multi-gene deficiency in vivo using a single 'self-cleaving' 2A peptide-based retroviral vector. Nature biotechnology 22, 589-594.

Takaoka, A., Wang, Z., Choi, M. K., Yanai, H., Negishi, H., Ban, T., Lu, Y., Miyagishi, M., Kodama, T., Honda, K., et al. (2007). DAI (DLM-1/ZBP1) is a cytosolic DNA sensor and an activator of innate immune response. Nature 448, 501-505.

Takeda, K., Kaisho, T., and Akira, S. (2003). Toll-like receptors. Annual review of immunology 21, 335-376.

Taylor, B. M., Foulke, J. S., Flinko, R., Heredia, A., DeVico, A., and Reitz, M. (2008). An alteration of human immunodeficiency virus gp41 leads to reduced CCR5 dependence and CD4 independence. J Virol 82, 5460-5471.

Teng, B., Burant, C. F., and Davidson, N. O. (1993). Molecular cloning of an apolipoprotein B messenger RNA editing protein. Science 260, 1816-1819.

Terwilliger, E. F., Cohen, E. A., Lu, Y. C., Sodroski, J. G., and Haseltine, W. A. (1989). Functional role of human immunodeficiency virus type 1 vpu. Proc Natl Acad Sci USA 86, 5163-5167.

Tissot, C., and Mechti, N. (1995). Molecular cloning of a new interferon-induced factor that represses human immunodeficiency virus type 1 long terminal repeat expression. The Journal of biological chemistry 270, 14891-14898.

Toggas, S. M., Masliah, E., Rockenstein, E. M., Rall, G. F., Abraham, C. R., and Mucke, L. (1994). Central nervous system damage produced by expression of the HIV-1 coat protein gp120 in transgenic mice. Nature 367, 188-193.

Towers, G., Bock, M., Martin, S., Takeuchi, Y., Stoye, J. P., and Danos, O. (2000). A conserved mechanism of retrovirus restriction in mammals. Proc Natl Acad Sci USA 97, 12295-12299.

Towers, G. J., Hatziioannou, T., Cowan, S., Goff, S. P., Luban, J., and Bieniasz, P. D. (2003). Cyclophilin A modulates the sensitivity of HIV-1 to host restriction factors. Nature medicine 9, 1138-1143.

Traggiai, E., Chicha, L., Mazzucchelli, L., Bronz, L., Piffaretti, J. C., Lanzavecchia, A., and Manz, M. G. (2004). Development of a human adaptive immune system in cord blood cell-transplanted mice. Science 304, 104-107.

Turelli, P., Mangeat, B., Jost, S., Vianin, S., and Trono, D. (2004a). Inhibition of hepatitis B virus replication by APOBEC3G. Science 303, 1829.

Turelli, P., Vianin, S., and Trono, D. (2004b). The innate antiretroviral factor APOBEC3G does not affect human LINE-1 retrotransposition in a cell culture assay. The Journal of biological chemistry 279, 43371-43373.

Uchil, P. D., Quinlan, B. D., Chan, W. T., Luna, J. M., and Mothes, W. (2008). TRIM E3 ligases interfere with early and late stages of the retroviral life cycle. PLoS pathogens 4, e16.

Unutmaz, D., KewalRamani, V. N., Marmon, S., and Littman, D. R. (1999). Cytokine signals are sufficient for HIV-1 infection of resting human T lymphocytes. The Journal of experimental medicine 189, 1735-1746.

Van Damme, N., Goff, D., Katsura, C., Jorgenson, R. L., Mitchell, R., Johnson, M. C., Stephens, E. B., and Guatelli, J. (2008). The interferon-induced protein BST-2 restricts HIV-1 release and is downregulated from the cell surface by the viral Vpu protein. Cell host & microbe 3, 245-252.

van Rijn, R. S., Simonetti, E. R., Hagenbeek, A., Hogenes, M. C., de Weger, R. A., Canninga-van Dijk, M. R., Weijer, K., Spits, H., Storm, G., van Bloois, L., et al. (2003). A new xenograft model for graft-versus-host disease by intravenous transfer of human peripheral blood mononuclear cells in RAG2−/− gammac−/− double-mutant mice. Blood 102, 2522-2531.

Van Rooijen, N., and Sanders, A. (1994). Liposome mediated depletion of macrophages: mechanism of action, preparation of liposomes and applications. J Immunol Methods 174, 83-93.

Varthakavi, V., Heimann-Nichols, E., Smith, R. M., Sun, Y., Bram, R. J., Ali, S., Rose, J., Ding, L., and Spearman, P. (2008). Identification of calcium-modulating cyclophilin ligand as a human host restriction to HIV-1 release overcome by Vpu. Nature medicine 14, 641-647.

Varthakavi, V., Smith, R. M., Bour, S. P., Strebel, K., and Spearman, P. (2003). Viral protein U counteracts a human host cell restriction that inhibits HIV-1 particle production. Proc Natl Acad Sci USA 100, 15154-15159.

Virgen, C. A., Kratovac, Z., Bieniasz, P. D., and Hatziioannou, T. (2008). Independent genesis of chimeric TRIM5-cyclophilin proteins in two primate species. Proc Natl Acad Sci USA 105, 3563-3568.

Vocero-Akbani, A. M., Heyden, N. V., Lissy, N. A., Ratner, L., and Dowdy, S. F. (1999). Killing HIV-infected cells by transduction with an HIV protease-activated caspase-3 protein. Nature medicine 5, 29-33.

von Laer, D., Hasselmann, S., and Hasselmann, K. (2006a). Gene therapy for HIV infection: what does it need to make it work? J Gene Med 8, 658-667.

von Laer, D., Hasselmann, S., and Hasselmann, K. (2006b). Impact of gene-modified T cells on HIV infection dynamics. J Theor Biol 238, 60-77.

Walker, R. E., Bechtel, C. M., Natarajan, V., Baseler, M., Hege, K. M., Metcalf, J. A., Stevens, R., Hazen, A., Blaese, R. M., Chen, C. C., et al. (2000). Long-term in vivo survival of receptor-modified syngeneic T cells in patients with human immunodeficiency virus infection. Blood 96, 467-474.

Wan, Y. Y., Chi, H., Xie, M., Schneider, M. D., and Flavell, R. A. (2006). The kinase TAK1 integrates antigen and cytokine receptor signaling for T cell development, survival and function. Nature immunology 7, 851-858.

Wang, L., Menendez, P., Shojaei, F., Li, L., Mazurier, F., Dick, J. E., Cerdan, C., Levac, K., and Bhatia, M. (2005). Generation of hematopoietic repopulating cells from human embryonic stem cells independent of ectopic HOXB4 expression. The Journal of experimental medicine 201, 1603-1614.

Watanabe, S., Terashima, K., Ohta, S., Horibata, S., Yajima, M., Shiozawa, Y., Dewan, M. Z., Yu, Z., Ito, M., Mario, T., et al. (2007). Hematopoietic stem cell-engrafted NOD/SCID/IL2Rgamma null mice develop human lymphoid systems and induce long-lasting HIV-1 infection with specific humoral immune responses. Blood 109, 212-218.

Watashi, K., Khan, M., Yedavalli, V. R., Yeung, M. L., Strebel, K., and Jeang, K. T. (2008). Human immunodeficiency virus-1 replication and regulation of APOBEC3G by peptidyl prolyl isomerase Pin1. J. Virol.

Wege, A. K., Melkus, M. W., Denton, P. W., Estes, J. D., and Garcia, J. V. (2008). Functional and phenotypic characterization of the humanized BLT mouse model. Current topics in microbiology and immunology 324, 149-165.

Wilson, S. J., Webb, B. L., Ylinen, L. M., Verschoor, E., Heeney, J. L., and Towers, G. J. (2008). Independent evolution of an antiviral TRIMCyp in rhesus macaques. Proc Natl Acad Sci USA 105, 3557-3562.

Wolf, D., and Goff, S. P. (2008). Host Restriction Factors Blocking Retroviral Replication. Annual review of genetics.

Woo, J. S., 1 mm, J. H., Min, C. K., Kim, K. J., Cha, S. S., and Oh, B. H. (2006). Structural and functional insights into the B30.2/SPRY domain. The EMBO journal 25, 1353-1363.

Wu, X., Anderson, J. L., Campbell, E. M., Joseph, A. M., and Hope, T. J. (2006). Proteasome inhibitors uncouple rhesus TRIM5 alpha restriction of HIV-1 reverse transcription and infection. Proc Natl Acad Sci USA 103, 7465-7470.

Wu, X., Li, Y., Crise, B., and Burgess, S. M. (2003). Transcription start regions in the human genome are favored targets for MLV integration. Science 300, 1749-1751.

Xu, L., Yang, L., Moitra, P. K., Hashimoto, K., Rallabhandi, P., Kaul, S., Meroni, G., Jensen, J. P., Weissman, A. M., and D'Arpa, P. (2003). BTBD1 and BTBD2 colocalize to cytoplasmic bodies with the RBCC/tripartite motif protein, TRIM5delta. Exp Cell Res 288, 84-93.

Yamashita, M., Perez, O., Hope, T. J., and Emerman, M. (2007). Evidence for direct involvement of the capsid protein in HIV infection of nondividing cells. PLoS pathogens 3, 1502-1510.

Yang, B., Chen, K., Zhang, C., Huang, S., and Zhang, H. (2007). Virion-associated uracil DNA glycosylase-2 and apurinic/apyrimidinic endonuclease are involved in the degradation of APOBEC3G-edited nascent HIV-1 DNA. The Journal of biological chemistry 282, 11667-11675.

Yang, L., Bailey, L., Baltimore, D., and Wang, P. (2006). Targeting lentiviral vectors to specific cell types in vivo. Proc Natl Acad Sci USA 103, 11479-11484.

Yap, M. W., Dodding, M. P., and Stoye, J. P. (2006). Trim-cyclophilin A fusion proteins can restrict human immunodeficiency virus type 1 infection at two distinct phases in the viral life cycle. J Virol 80, 4061-4067.

Yap, M. W., Mortuza, G. B., Taylor, I. A., and Stoye, J. P. (2007). The design of artificial retroviral restriction factors. Virology 365, 302-314.

Yap, M. W., Nisole, S., Lynch, C., and Stoye, J. P. (2004). Trim5alpha protein restricts both HIV-1 and murine leukemia virus. Proc Natl Acad Sci USA 101, 10786-10791.

Yap, M. W., Nisole, S., and Stoye, J. P. (2005). A single amino acid change in the SPRY domain of human Trim5alpha leads to HIV-1 restriction. Curr Biol 15, 73-78.

Yin, L., Braaten, D., and Luban, J. (1998). Human immunodeficiency virus type 1 replication is modulated by host cyclophilin A expression levels. J Virol 72, 6430-6436.

Yoneyama, M., Kikuchi, M., Matsumoto, K., Imaizumi, T., Miyagishi, M., Taira, K., Foy, E., Loo, Y. M., Gale, M., Jr., Akira, S., et al. (2005). Shared and unique functions of the DExD/H-box helicases RIG-I, MDA5, and LGP2 in antiviral innate immunity. J Immunol 175, 2851-2858.

Yu, Q., Konig, R., Pillai, S., Chiles, K., Kearney, M., Palmer, S., Richman, D., Coffin, J. M., and Landau, N. R. (2004). Single-strand specificity of APOBEC3G accounts for minus-strand deamination of the HIV genome. Nature structural & molecular biology 11, 435-442.

Yu, X., Yu, Y., Liu, B., Luo, K., Kong, W., Mao, P., and Yu, X. F. (2003). Induction of APOBEC3G ubiquitination and degradation by an HIV-1 Vif-Cul5-SCF complex. Science 302, 1056-1060.

Zennou, V., Perez-Caballero, D., Gottlinger, H., and Bieniasz, P. D. (2004). APOBEC3G incorporation into human immunodeficiency virus type 1 particles. J Virol 78, 12058-12061.

Zhang, B. W., Zimmer, G., Chen, J., Ladd, D., Li, E., Alt, F. W., Wiederrecht, G., Cryan, J., O'Neill, E. A., Seidman, C. E., et al. (1996). T cell responses in calcineurin A alpha-deficient mice. The Journal of experimental medicine 183, 413-420.

Zhang, F., Hatziioannou, T., Perez-Caballero, D., Derse, D., and Bieniasz, P. D. (2006). Antiretroviral potential of human tripartite motif-5 and related proteins. Virology 353, 396-409.

Zhang, F., Perez-Caballero, D., Hatziioannou, T., and Bieniasz, P. D. (2008a). No effect of endogenous TRIM5alpha on HIV-1 production. Nature medicine 14, 235-236; author reply 236-238.

Zhang, H., Yang, B., Pomerantz, R. J., Zhang, C., Arunachalam, S. C., and Gao, L. (2003). The cytidine deaminase CEM15 induces hypermutation in newly synthesized HIV-1 DNA. Nature 424, 94-98.

Zhang, J., Scadden, D. T., and Crumpacker, C. S. (2007). Primitive hematopoietic cells resist HIV-1 infection via p21. The Journal of clinical investigation 117, 473-481.

Zhang, J. X., Diehl, G. E., and Littman, D. R. (2008b). Relief of preintegration inhibition and characterization of additional blocks for HIV replication in primary mouse T cells. PLoS ONE 3, e2035.

Zielske, S. P., Reese, J. S., Lingas, K. T., Donze, J. R., and Gerson, S. L. (2003). In vivo selection of MGMT (P140K) lentivirus-transduced human NOD/SCID repopulating cells without pretransplant irradiation conditioning. The Journal of clinical investigation 112, 1561-1570.

Zinkernagel, R. M., and Althage, A. (1999). On the role of thymic epithelium vs. bone marrow-derived cells in repertoire selection of T cells. Proc Natl Acad Sci USA 96, 8092-8097.

What is claimed is:

1. A nucleic acid which comprises a sequence selected from the group consisting of SEQ ID NO:5, SEQ ID NO:6, SEQ ID NO:7, a variant having at least 87% identity to SEQ ID NO:5, a variant having at least 94% identity to SEQ ID NO:6, and a variant having at least 89% identity to SEQ ID NO:7.

2. A nucleic acid which comprises a sequence complementary to the nucleic acid of claim 1.

3. A nucleic acid encoding a polypeptide comprising SEQ ID NO:10, 11 or 12.

4. The nucleic acid of claim 1, encoding a human TRIM5-cyclophilin A fusion protein which comprises a polypeptide linker sequence, wherein (i) TRIM5 is located upstream of the linker sequence, so that the N-terminal amino acid of the linker sequence is attached to the C-terminal amino acid of TRIM5, and (ii) cyclophilin A is located downstream of the linker sequence, so that the C-terminal amino acid residue of the linker sequence is attached to the N-terminal amino acid residue of cyclophilin A.

5. The nucleic acid of claim 4, wherein the linker sequence comprises from about 10 to about 20 amino acids.

6. A polypeptide encoded by the nucleic acid of any of claim 1, 2, 3, 4, or 5.

7. A nucleic acid vector, which comprises the nucleic acid of any one of claim 1, 2, 3, 4, or 5.

8. A composition comprising the nucleic acid of claim 1, 2, 3, 4 or 5, and a carrier.

9. An isolated host cell comprising the nucleic acid of claim 1, 2, 3, 4, or 5.

10. The nucleic acid of claim 1, wherein the variant has at least 89%, 91%, 93%, 95%, or 99% identity to SEQ ID NO:5.

11. The nucleic acid of claim 1, wherein the variant has at least 95%, 96%, 97%, 98%, or 99% identity to SEQ ID NO:6.

12. The nucleic acid of claim 1, wherein the variant has at least 90%, 92%, 94%, 96%, or 98% identity to SEQ ID NO:7.

* * * * *